United States Patent
Liu et al.

(10) Patent No.: US 12,312,349 B2
(45) Date of Patent: *May 27, 2025

(54) APOPTOSIS-INDUCING AGENTS

(71) Applicants: Fochon Pharmaceuticals, Ltd., Chongqing (CN); Shanghai Fosun Pharmaceutical Industrial Development Co., Ltd., Shanghai (CN)

(72) Inventors: Hongbin Liu, Chongqing (CN); Yue Rong, Chongqing (CN); Huajie Zhang, Chongqing (CN); Zhifang Chen, Chongqing (CN); Rui Tan, Chongqing (CN); Chengxi He, Chongqing (CN); Zhifu Li, Chongqing (CN); Zuwen Zhou, Chongqing (CN); Haohan Tan, Chongqing (CN); Kai Ran, Chongqing (CN); Xianlong Wang, Chongqing (CN); Zongyao Zou, Chongqing (CN); Lihua Jiang, Chongqing (CN); Yanxin Liu, Chongqing (CN); Xingdong Zhao, Chongqing (CN); Weibo Wang, Moraga (CN); Jiemin Fu, Chongqing (CN)

(73) Assignees: Fochon Pharmaceuticals, Ltd., Chongqing (CN); Shanghai Fosun Pharmaceutical Industrial Development Co, , Ltd., Shanghai (CN)

( * ) Notice: Subject to any disclaimer, the term of this patent is extended or adjusted under 35 U.S.C. 154(b) by 986 days.

This patent is subject to a terminal disclaimer.

(21) Appl. No.: 17/376,963

(22) Filed: Jul. 15, 2021

(65) Prior Publication Data

US 2022/0402913 A1 Dec. 22, 2022

Related U.S. Application Data

(63) Continuation of application No. 16/603,873, filed as application No. PCT/CN2018/083268 on Apr. 17, 2018, now Pat. No. 11,091,478.

(60) Provisional application No. 62/572,417, filed on Oct. 14, 2017, provisional application No. 62/486,965, filed on Apr. 18, 2017.

(51) Int. Cl.
*C07D 471/04* (2006.01)
*C07D 519/00* (2006.01)

(52) U.S. Cl.
CPC ......... *C07D 471/04* (2013.01); *C07D 519/00* (2013.01)

(58) Field of Classification Search
CPC ................ C07D 471/04; C07D 519/00; C07D 471/14; A61P 35/00; A61P 1/00; A61P 1/18; A61P 3/10; A61P 9/10; A61P 11/00; A61P 11/06; A61P 13/08; A61P 13/12; A61P 15/18; A61P 17/00; A61P 17/06; A61P 19/02; A61P 27/02; A61P 29/00; A61P 37/00; A61P 37/06; A61K 31/5355
See application file for complete search history.

(56) References Cited

U.S. PATENT DOCUMENTS

| | | | |
|---|---|---|---|
| 8,426,422 B2 | 4/2013 | Hexamer et al. | |
| 11,091,478 B2 * | 8/2021 | Liu ..................... | C07D 471/04 |
| 2011/0124628 A1 | 5/2011 | Bruncko et al. | |
| 2012/0108590 A1 | 5/2012 | Birtalan et al. | |

FOREIGN PATENT DOCUMENTS

| | | |
|---|---|---|
| EP | 3112361 | 1/2017 |
| WO | 2002/098848 | 12/2002 |
| WO | 2006/127364 | 11/2006 |
| WO | 2010/065824 | 6/2010 |
| WO | 2010/065865 | 6/2010 |
| WO | 2010/083441 | 7/2010 |
| WO | 2010/083442 | 7/2010 |
| WO | 2010/138588 | 12/2010 |
| WO | 2011/150016 | 5/2011 |
| WO | 2011/149492 | 12/2011 |
| WO | 2012/058392 | 5/2012 |
| WO | 2014/158528 | 10/2014 |
| WO | 2017/132474 | 8/2017 |
| WO | 2018/027097 | 2/2018 |
| WO | 2018/041248 | 3/2018 |
| WO | 2018/127130 | 7/2018 |
| WO | 2019/139899 | 7/2019 |
| WO | 2019/210828 | 11/2019 |

OTHER PUBLICATIONS

Roberts et al. Targeting BCL2 with Venetoclax in Relapsed Chronic Lymphocytic Leukemia (N Engl J Med, 374;4, 311-322). (Year: 2016).*
International Preliminary Report on Patentability issued Jul. 9, 2019 in International Patent Application No. PCT/CN2018/071562. 6 pages.
International Preliminary Report on Patentability issued Oct. 22, 2019 in International Patent Application No. PCT/CN2018/083268. 8 pages.
International Search Report and Written Opinion issued Mar. 30, 2018 in International Patent Application No. PCT/CN2018/071562. 11 pages.
International Search Report and Written Opinion issued on Jul. 23, 2018 in International Patent Application No. PCT/CN2018/083268. 14 pages.

* cited by examiner

*Primary Examiner* — Matthew P Coughlin
*Assistant Examiner* — Meghan C Heasley
(74) *Attorney, Agent, or Firm* — IceMiller LLP

(57) ABSTRACT

Provided are certain Bcl-2 inhibitors, pharmaceutical compositions thereof, and methods of use thereof.

16 Claims, No Drawings

APOPTOSIS-INDUCING AGENTS

CROSS-REFERENCE TO RELATED APPLICATIONS

This application is a continuation of U.S. patent application Ser. No. 16/603,873, filed Oct. 9, 2019, which is a national stage filed under § 371 of International Application No. PCT/CN2018/083268, filed Apr. 17, 2018, which claims priority to U.S. provisional application No. 62/486,965, filed Apr. 18, 2017, and U.S. provisional application No. 62/572,417, filed Oct. 14, 2017, the disclosures of which are incorporated herein by reference in their entireties.

FIELD OF THE INVENTION

Provided are certain compounds or pharmaceutically acceptable salts thereof which can inhibit anti-apoptotic Bcl-2 family proteins and may be useful for the treatment of hyper-proliferative diseases like cancer and inflammation, or immune and autoimmune diseases.

BACKGROUND OF THE INVENTION

Hyper-proliferative diseases like cancer and inflammation are attracting the scientific community to provide therapeutic benefits. In this regard efforts have been made to identify and target specific mechanisms which play a role in proliferating the diseases.

Protein-protein interactions (PPIs) control many biological process, such as cell proliferation, growth, differentiation, signal transduction and apoptosis. Abnormal regulation of PPIs leads to different diseases. Thus, PPIs represent an important class of molecular targets for novel human therapeutics.

The B-cell lymphoma-2 (Bcl-2) family of proteins is central to the regulation of apoptosis, which is vital for proper tissue development and cellular homeostasis. Apoptosis occurs via activation of two different pathways. The extrinsic pathway, triggered by activation of the intrinsic pathway involving members of the Bcl-2 family of proteins. The Bcl-2 family protein includes anti-apoptotic proteins, such as Bcl-2, Bcl-$X_L$ and Mcl-1, and pro-apoptotic proteins, including Bid, Bim, Bad, Bak and Bax.

Anti-apoptotic Bcl-2 family members are often found to be up-regulated in cancers and are associated with stage of disease and prognosis. Therefore, Bcl-2 proteins are under investigation as potential therapeutic drug targets which include, for example, Bcl-2 and Bcl-$X_L$. Expression of Bcl-2 proteins is an independent indicator of poor prognosis in tumors including chronic lymphocytic leukemia (CLL), prostate cancer, and small cell lung cancer (SCLC). In other tumors such as colorectal cancer, Bcl-$X_L$ expression is linked to grade and stage, and in hepatocellular cancer, Bcl-$X_L$, expression is an independent marker of poorer overall and disease-free survival.

Therefore, a compound having an inhibitory activity on Bcl-2 will be useful for the prevention or treatment of cancer. In this regard, a novel class of Bcl-2 inhibitors is provided herein. Although Bcl-2 inhibitors were disclosed in the arts, e.g. WO 2011149492, many suffer from having short half-life or toxicity. Therefore, there is a need for new Bcl-2 inhibitors that have at least one advantageous property selected from potency, stability, selectivity, toxicity, pharmacodynamic and pharmacokinetic properties as an alternative for the treatment of hyper-proliferative diseases. In this regard, a novel class of Bcl-2 inhibitors is provided herein.

DISCLOSURE OF THE INVENTION

Disclosed herein are certain novel compounds, pharmaceutically acceptable salts thereof, and pharmaceutical compositions thereof, and their use as pharmaceuticals.

In one aspect, disclosed herein is a compound of formula (I):

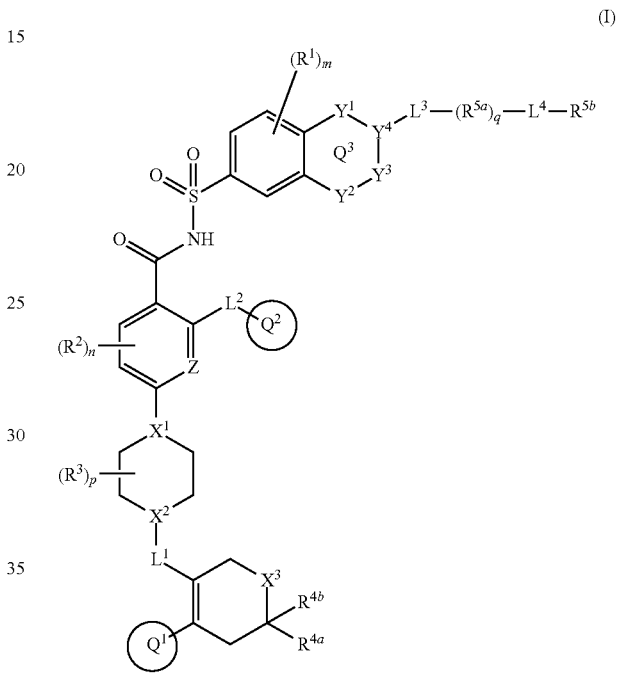

or a pharmaceutically acceptable salt thereof, wherein:
$L^1$, $L^2$, $L^3$ and $L^4$ are independently selected from —(CR$^C$R$^D$)$_u$—, —(CR$^C$R$^D$)$_u$O(CR$^C$R$^D$)$_t$—, —(CR$^C$R$^D$)$_u$NR$^A$(CR$^C$R$^{D5}$)$_t$—, —(CR$^C$R$^D$)$_u$S(CR$^C$R$^D$)$_t$—, —(CR$^C$R$^D$)$_u$C(O)(CR$^C$R$^D$)$_t$—, —(CR$^C$R$^D$)$_u$C(=NR$^E$)(CR$^C$R$^D$)$_t$—, —(CR$^C$R$^D$)$_u$C(S)(CR$^C$R$^D$)$_t$—, —(CR$^C$R$^D$)$_u$C(O)O(CR$^C$R$^D$)$_t$—, —(CR$^C$R$^D$)$_u$OC(O)(CR$^C$R$^D$)$_t$—, —(CR$^C$R$^D$)$_u$C(O)NR$^A$(CR$^C$R$^D$)$_t$—, —(CR$^C$R$^D$)$_u$NR$^A$C(O)(CR$^C$R$^D$)$_t$—, —(CR$^C$R$^D$)$_u$NR$^A$C(O)NR$^B$ (CR$^C$R$^D$)$_t$—, —(CR$^C$R$^D$)$_u$C(=NR$^E$)NR$^B$(CR$^C$R$^D$)$_t$—, —(CR$^C$R$^D$)$_u$NR$^B$C(=NR$^E$)(CR$^C$R$^D$)$_t$—, —(CR$^C$R$^D$)$_u$NR$^A$C(=NR$^E$)NR$^B$(CR$^C$R$^D$)$_t$—, —(CR$^C$R$^D$)$_u$C(S)NR$^A$(CR$^C$R$^D$)$_t$—, —(CR$^C$R$^D$)$_u$NR$^A$C(S)(CR$^C$R$^D$)$_t$—, —(CR$^C$R$^D$)$_u$NR$^A$C(S)NR$^B$(CR$^C$R$^D$)$_t$—, —(CR$^C$R$^D$)$_u$S(O)$_r$(CR$^C$R$^D$)$_t$—, —(CR$^C$R$^D$)$_u$S(O)$_r$NR$^A$(CR$^C$R$^D$)$_t$—, —(CR$^{C5}$R$^{D5}$)$_u$NR$^A$S(O)$_r$(CR$^C$R$^D$)$_t$— and —(CR$^C$R$^D$)$_u$NR$^A$S(O)$_r$NR$^B$ (CR$^C$R$^D$)$_t$—;

$Q^1$ and $Q^2$ are independently selected from aryl and heteroaryl, wherein aryl and heteroaryl are each unsubstituted or substituted with at least one substituent, such as one, two, three or four substituents, independently selected from R$^X$;

$Q^3$ is selected from aryl, C$_{3-10}$ cycloalkyl, heteroaryl and heterocyclyl, wherein aryl, cycloalkyl, heteroaryl and heterocyclyl are each unsubstituted or substituted with at least one substituent, such as one, two, three or four substituents, independently selected from R$^X$;

when $Q^3$ is $C_{3-10}$ cycloalkyl, $Y^1$, $Y^2$ and $Y^3$ are independently selected from $(CR^{6a}R^{6b})_o$, wherein cycloalkyl is unsubstituted or substituted with at least one substituent independently selected from $R^X$;

when $Q^3$ is heteroaryl, $Y^1$, $Y^2$ and $Y^3$ are independently selected from a bond, C, N, O and S, wherein heteroaryl is unsubstituted or substituted with at least one or two substituents independently selected from $R^X$;

when $Q^3$ is heterocyclyl, $Y^1$, $Y^2$ and $Y^3$ are independently selected from $(CR^{6a}R^{6b})_o$, N, O and S, wherein heterocyclyl is unsubstituted or substituted with at least one substituent independently selected from $R^X$;

$X^1$ and $X^2$ are independently selected from C and N;
$X^3$ is selected from $CR^{4c}R^{4d}$ and O;
$Y^4$ is selected from C and N;
Z is selected from C and N;

each $R^1$ is independently selected from hydrogen, halogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, heteroaryl-$C_{1-4}$ alkyl, CN, $NO_2$, $-NR^{A1}R^{B1}$, $-OR^{A1}$, $-C(O)R^{A1}$, $-C(=NR^{E1})R^{A1}$, $-C(=N-OR^{B1})R^{A1}$, $-OC(O)OR^{A1}$, $-OC(O)R^{A1}$, $-C(O)NR^{A1}R^{B1}$, $-NR^{A1}C(O)R^{B1}$, $-C(=NR^{E1})NR^{A1}R^{B1}$, $-NR^{A1}C(=NR^{E1})R^{B1}$, $-OC(O)NR^{A1}R^{B1}$, $-NR^{A1}C(O)OR^{B1}$, $-NR^{A1}C(O)NR^{A1}R^{B1}$, $-NR^{A1}C(S)NR^{A1}R^{B1}$, $-NR^{A1}C(=NR^{E1})NR^{A1}R^{B1}$, $-S(O)_rR^{A1}$, $-S(O)(=NR^{E1})R^{B1}$, $-N=S(O)R^{A1}R^{B1}$, $-S(O)_2OR^{A1}$, $-OS(O)_2R^{A1}$, $-NR^{A1}S(O)_rR^{B1}$, $-NR^{A1}S(O)(=NR^{E1})R^{B1}$, $-S(O)_rNR^{A1}R^{B1}$, $-S(O)(=NR^{E1})NR^{A1}R^{B1}$, $-NR^{A1}S(O)_2NR^{A1}R^{B1}$, $-NR^{A1}S(O)(=NR^{E1})NR^{A1}R^{B1}$, $-P(O)R^{A1}R^{B1}$ and $-P(O)(OR^{A1})(OR^{B1})$, wherein alkyl, alkenyl, alkynyl, cycloalkyl, heterocyclyl, aryl and heteroaryl are each unsubstituted or substituted with at least one substituent, such as one, two, three or four substituents, independently selected from $R^X$;

each $R^2$ is independently selected from hydrogen, halogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, heteroaryl-$C_{1-4}$ alkyl, CN, $NO_2$, $-NR^{A2}R^{B2}$, $-OR^{A2}$, $-C(O)R^{A2}$, $-C(=NR^{E2})R^{A2}$, $-C(=N-OR^{B2})R^{A2}$, $-C(O)OR^{A2}$, $-OC(O)R^{A2}$, $-C(O)NR^{A2}R^{B2}$, $-NR^{A2}C(O)R^{B2}$, $-C(=NR^{E2})NR^{A2}R^{B2}$, $-NR^{A2}C(=NR^{E2})R^{B2}$, $-OC(O)NR^{A2}R^{B2}$, $-NR^{A2}C(O)OR^{B2}$, $-NR^{A2}(O)NR^{A2}R^{B2}$m $-NR^{A2}C(S)NR^{A2}R^{B2}$, $-NR^{A2}C(=NR^{E2})NR^{A2}R^{B2}$, $-S(O)_rR^{A2}$, $-S(O)(=NR^{E2})R^{B2}$, $-N=S(O)R^{A2}R^{B2}$, $-S(O)_2OR^{A2}$, $-OS(O)_2R^{A2}$, $-NR^{A2}S(O)_rR^{B2}$, $-NR^{A2}S(O)(=NR^{E2})R^{B2}$, $-S(O)_rNR^{A2}R^{B2}$, $-S(O)(=NR^{E2})NR^{A2}R^{B2}$, $-NR^{A2}S(O)_2NR^{A2}R^{B2}$, $-NR^{A2}S(O)(=NR^{E2})NR^{A2}R^{B2}$, $-P(O)R^{A2}R^{B2}$ and $-P(O)(OR^{A2}(OR^{B2})$, wherein alkyl, alkenyl, alkynyl, cycloalkyl, heterocyclyl, aryl and heteroaryl are each unsubstituted or substituted with at least one substituent, such as one, two, three or four substituents, independently selected from $R^X$;

each $R^3$ is independently selected from hydrogen, halogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$, alkyl, heteroaryl, heteroaryl-$C_{1-4}$ alkyl, CN, $NO_2$, $-NR^{A3}R^{B3}$, $-OR^{A3}$, $-C(O)R^{A3}$, $-C(=NR^{E3})R^{A3}$, $-C(=N-OR^{B3})R^{A3}$, $-C(O)OR^{A3}$, $-OC(O)R^{A3}$, $-C(O)NR^{A3}R^{B3}$, $-NR^{A3}C(O)R^{B3}$, $-C(=NR^{E3})NR^{A3}R^{B3}$, $-NR^{A3}C(=NR^{E3})R^{B3}$, $-OC(O)NR^{A3}R^{B3}$, $-NR^{A3}C(O)OR^{B3}$, $-NR^{A3}C(O)NR^{A3}R^{B3}$, $-NR^{A3}C(S)NR^{A3}R^{B3}$, $-NR^{A3}C(=NR^{E3})NR^{A3}R^{A3}$, $-S(O)_rR^{A3}$, $-S(O)(=NR^{E3})R^{B3}$, $-N=S(O)R^{A3}R^{B3}$, $-S(O)_2OR^{A3}$, $-OS(O)_2R^{A3}$, $-NR^{A3}S(O)_rR^{B3}$, $-NR^{A3}S(O)(=NR^{E3})R^{B3}$, $-S(O)_rNR^{A3}R^{B3}$, $-S(O)(=NR^{E3})NR^{A3}R^{B3}$, $-NR^{A3}S(O)_2NR^{A3}R^{B3}$, $-NR^{A3}S(O)(=NR^{E3})NR^{A3}R^{B3}$, $-P(O)R^{A3}R^{B3}$ and $-P(O)(OR^{A3})(OR^{B3})$, wherein alkyl, alkenyl, alkynyl, cycloalkyl, heterocyclyl, aryl and heteroaryl are each unsubstituted or substituted with at least one substituent, such as one, two, three or four substituents, independently selected from $R^X$;

$R^{4a}$, $R^{4b}$, $R^{4c}$ and $R^{4d}$ are independently selected from hydrogen, halogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, heteroaryl-$C_{1-4}$ alkyl, CN, $NO_2$, $-NR^{A4}R^{B4}$, $-OR^{A4}$, $-C(O)R^{A4}$, $-C(=NR^{E4})R^{A4}$, $-C(=N-OR^{B4})R^{A4}$, $-C(O)OR^{A4}$, $-OC(O)R^{A4}$, $-C(O)NR^{A4}R^{B4}$, $-NR^{A4}C(O)R^{B4}$, $-C(=NR^{E4})NR^{A4}R^{B4}$, $-NR^{A4}C(=NR^{E4})R^{B4}$, $-OC(O)NR^{A4}R^{B4}$, $-NR^{A4}C(O)OR^{B4}$, $-NR^{A4}C(O)NR^{A4}R^{B4}$, $-NR^{A4}C(S)NR^{A4}R^{B4}$, $-NR^{A4}C(=NR^{E4})NR^{A4}R^{B4}$, $-S(O)_rR^{A4}$, $-S(O)(=NR^{E4})R^{B4}$, $-N=S(O)R^{A4}R^{B4}$, $-S(O)_2OR^{A4}$, $-S(O)_2R^{A4}$, $-NR^{A4}S(O)_rR^{B4}$, $-NR^{A4}S(O)(=NR^{E4})R^{B4}$, $-S(O)_rNR^{A4}R^{B4}$, $-S(O)(=NR^{E4})NR^{A4}R^{B4}$, $-NR^{A4}S(O)_2NR^{A4}R^{B4}$, $-NR^{A4}S(O)(=NR^{E4})NR^{A4}R^{B4}$, $-P(O)R^{A4}R^{B4}$ and $-P(O)(OR^{A4}(OR^{B4})$, whereinalkyl, alkenyl, alkynyl, cycloalkyl, heterocyclyl, aryl and heteroaryl are each unsubstituted or substituted with at least one substituent, such as one, two, three or four substituents, independently selected from $R^X$;

or "$R^{4a}$ and $R^{4b}$" or "$R^{4c}$ and $R^{4d}$" together with the carbon atoms to which they are attached form a 3-7 membered ring containing 0, 1, 2 or 3 heteroatoms independently selected from oxygen, sulfur, nitrogen, and phosphorus, and optionally substituted with 1, 2 or 3 $R^X$ groups;

each $R^{5a}$ is independently selected from $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, heteroaryl-$C_{1-4}$ alkyl, wherein alkyl, alkenyl, alkynyl, cycloalkyl, heterocyclyl, aryl and heteroaryl are each unsubstituted or substituted with at least one substituent, such as one, two, three or four substituents, independently selected from $R^X$;

$R^{5b}$ is selected from hydrogen, halogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, heteroaryl-$C_{1-4}$ alkyl, CN, $NO_2$, $-NR^{A5}R^{B5}$, $-OR^{A5}$, $-C(O)R^{A5}$, $-C(=NR^{E5})R^{A5}$, $-C(=N-OR^{B5})R^{A5}$, $-C(O)OR^{A5}$, $-OC(O)R^{A5}$, $-C(O)NR^{A5}R^{B5}$, $-C(=NR^{E5})NR^{A5}R^{B5}$, $-NR^{A5}C(=NR^{E5})R^{B5}$, $-OC(O)NR^{A5}R^{B5}$, $-NR^{A5}C(O)OR^{B5}$, $-NR^{A5}C(O)NR^{A5}R^{B5}$, $-NR^{A5}C(S)NR^{A5}R^{B5}$, $-NR^{A5}C(=NR^{E5})NR^{A5}R^{B5}$, $-S(O)(=NR^{E5})R^{B5}$, $-N=S(O)R^{A5}R^{B5}$, $-S(O)_2OR^{A5}$, $-OS(O)_2R^{A5}$, $-NR^{A5}S(O)_rR^{B5}$, $-NR^{A5}S(O)(=NR^{E5})R^{B5}$, $-S(O)_rNR^{A5}R^{B5}$, $-S(O)(=NR^{E5})NR^{A5}R^{B5}$, $-NR^{A5}S(O)_2NR^{A5}R^{B5}$, $-NR^{A5}S(O)(=NR^{E5})NR^{A5}R^{B5}$, $-P(O)R^{A5}R^{B5}$ and $-P(O)(OR^{A5})(OR^{B5})$, wherein alkyl, alkenyl, alkynyl, cycloalkyl, heterocyclyl, aryl and heteroaryl are each unsubstituted or substituted with at least one substituent, such as one, two, three or four substituents, independently selected from $R^X$;

each $R^{6a}$ and $R^{6b}$ are independently selected from hydrogen, halogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, heteroaryl-$C_{1-4}$ alkyl, CN, $NO_2$, $-NR^{A6}R^{B6}$, $-OR^{A6}$, $-C(O)R^{A6}$, $-C(=NR^{E6})R^{A6}$, $-C(=N-OR^B)R^{A6}$, $-C(O)OR^{A6}$, $-OC(O)R^{A6}$, $-C(O)NR^{A6}R^{B6}$, $-NR^{A6}(O)R^{B6}$, $-C(=NR^{E6})NR^{A6}R^{B6}$, $-NR^{A6}C(=NR^{E6})R^{B6}$, $-OC(O)NR^{A6}R^{B6}$, $-NR^{A6}C(O)OR^{B6}$, $-NR^{A6}(O)NR^{A6}R^{B6}$, $-NR^{A6}C(S)NR^{A6}R^{B6}$, $-NR^{A6}C(=NR^{E6})NR^{A6}R^{B6}$, $-S(O)_rR^{A6}$, $-S(O)(=NR^{E6})R^{B6}$, $-N=S(O)R^{A6}R^{B6}$, —S(O)$_2$OR$^{A6}$, —OS(O)$_2$R$^{A6}$, —NR$^{A6}$S(O)$_r$R$^{B6}$, —NR$^{A6}$S(O)(=NR$^{E6}$)R$^{B6}$, —S(O)$_r$NR$^{A6}$R$^{B6}$, —S(O)(=NR$^{E6}$)NR$^{A6}$R$^{B6}$, —NR$^{A6}$S(O)$_2$NR$^{A6}$R$^{B6}$, —NR$^{A6}$S(O)(=NR$^{E6}$)NR$^{A6}$R$^{B6}$, —P(O)R$^{A6}$R$^{B6}$ and —P(O)(OR$^{A6}$)(OR$^{B6}$)m wherein alkyl, alkenyl, alkynyl, cycloalkyl, heterocyclyl, aryl and heteroaryl are each unsubstituted or substituted with at least one substituent, such as one, two, three or four substituents, independently selected from R$^X$;

or R$^{6a}$ and R$^{6b}$ together with the carbon atoms to which they are attached form a 3-7 membered ring containing 0, 1, 2 or 3 heteroatoms independently selected from oxygen, sulfur, nitrogen, and phosphorus, and optionally substituted with 1, 2 or 3 R$^X$ groups;

each R$^A$, R$^{A1}$, R$^{A2}$, R$^{A3}$, R$^{A4}$, R$^{A5}$, R$^{A6}$, R$^B$, R$^{B1}$, R$^{B2}$, R$^{B3}$, R$^{B4}$, R$^{B5}$ and R$^{B6}$ are independently selected from hydrogen, C$_{1-10}$ alkyl, C$_{2-10}$ alkenyl, C$_{2-10}$ alkynyl, C$_{3-10}$ cycloalkyl, C$_{3-10}$ cycloalkyl-C$_{1-4}$ alkyl, heterocyclyl, heterocyclyl-C$_{1-4}$ alkyl, aryl, aryl-C$_{1-4}$ alkyl, heteroaryl, and heteroaryl-C$_{1-4}$ alkyl, wherein alkyl, alkenyl, alkynyl, cycloalkyl, heterocyclyl, aryl and heteroaryl are each unsubstituted or substituted with at least one substituent, such as one, two, three, or four substituents, independently selected from R$^X$;

or each "R$^A$ and R$^B$," "R$^{A1}$ and R$^{B1}$," "R$^{A2}$ and R$^{B2}$," "R$^{A3}$ and R$^{B3}$", "R$^{A4}$ and R$^{B4}$," "R$^{A5}$ and R$^{B5}$" and "R$^{A6}$ and R$^{B6}$" together with the atom(s) to which they are attached form a heterocyclic ring of 4 to 12 members containing 0, 1, or 2 additional heteroatoms independently selected from oxygen, sulfur, nitrogen and phosphorus, and optionally substituted with 1, 2 or 3 R$^X$ groups;

each R$^C$ and R$^D$ are independently selected from hydrogen, halogen, C$_{1-10}$ alkyl, C$_{2-10}$ alkenyl, C$_{2-10}$ alkynyl, C$_{3-10}$ cycloalkyl, C$_{3-10}$ cycloalkyl-C$_{1-4}$ alkyl, heterocyclyl, heterocyclyl-C$_{1-4}$ alkyl, aryl, aryl-C$_{1-4}$ alkyl, heteroaryl and heteroaryl-C$_{1-4}$ alkyl, wherein alkyl, alkenyl, alkynyl, cycloalkyl, heterocyclyl, aryl and heteroaryl are each unsubstituted or substituted with at least one substituent, such as one, two, three or four substituents, independently selected from R$^X$;

or R$^C$ and R$^D$ together with the carbon atom(s) to which they are attached form a ring of 3 to 12 members containing 0, 1 or 2 heteroatoms independently selected from oxygen, sulfur and nitrogen, and optionally substituted with 1, 2 or 3 R$^X$ groups;

Each R$^E$, R$^{E1}$, R$^{E2}$, R$^{E3}$, R$^{E4}$, R$^{E5}$ and R$^{E6}$ are independently selected from hydrogen, C$_{1-10}$ alkyl, C$_{2-10}$ alkenyl, C$_{2-10}$ alkynyl, C$_{3-10}$ cycloalkyl, C$_{3-10}$ cycloalkyl-C$_{1-4}$ alkyl, heterocyclyl, heterocyclyl-C$_{1-4}$ alkyl, aryl, aryl-C$_{1-4}$ alkyl, heteroaryl, heteroaryl-C$_{1-4}$ alkyl, CN, NO$_2$, OR$^{a1}$, SR$^{a1}$, —S(O)$_r$R$^{a1}$, —C(O)R$^{a1}$, C(O)OR$^{a1}$, —C(O)NR$^{a1}$R$^{b1}$ and —S(O)$_r$NR$^{a1}$R$^{b1}$, wherein alkyl, alkenyl, alkynyl, cycloalkyl, heterocyclyl, aryl and heteroaryl are each unsubstituted or substituted with at least one substituent, such as one, two, three or four substituents, independently selected from R$^Y$;

each R$^X$ is independently selected from hydrogen, C$_{1-10}$ alkyl, C$_{2-10}$ alkenyl, C$_{2-10}$ alkynyl, C$_{3-10}$ cycloalkyl, C$_{3-10}$ cycloalkyl-C$_{1-4}$ alkyl, heterocyclyl, heterocyclyl-C$_{1-4}$ alkyl, aryl, aryl-C$_{1-4}$ alkyl, heteroaryl, heteroaryl-C$_{1-4}$ alkyl, halogen, CN, NO$_2$, —(CR$^{c1}$R$^{d1}$)$_t$NR$^{a1}$R$^{b1}$, —(CR$^{c1}$R$^{d1}$)$_t$OR$^{b1}$, —(CR$^{c1}$R$^{d1}$)$_t$C(O)R$^{a1}$, —(CR$^{c1}$R$^{d1}$)$_t$C(=NR$^{c1}$)R$^{a1}$, —(CR$^{c1}$R$^{d1}$)$_t$C(=N—OR$^{b1}$)R$^{a1}$, —(CR$^{c1}$R$^{d1}$)$_t$C(O)OR$^1$, —(CR$^{c1}$R$^{d1}$)$_t$OC(O)R$^{b1}$, —(CR$^{c1}$R$^{d1}$)$_t$C(O)NR$^{a1}$R$^{b1}$, —(CR$^{c1}$R$^{d1}$)$_t$NR$^{a1}$C(O)R$^{b1}$, —(CR$^{c1}$R$^{d1}$)$_t$C(=NR$^{c1}$)NR$^{a1}$R$^{b1}$, —(CR$^{c1}$R$^{d1}$)$_t$NR$^{a1}$C(=NR$^{c1}$)R$^{b1}$, —(CR$^{c1}$R$^{d1}$)$_t$OC(O)NR$^{a1}$R$^{b1}$, —(CR$^{c1}$R$^{d1}$)$_t$NR$^{a1}$C(O)OR$^{b1}$, —(CR$^{c1}$R$^{d1}$)$_t$NR$^{a1}$C(O)NR$^{a1}$R$^{b1}$, —(CR$^{c1}$R$^{d1}$)$_t$NR$^{a1}$C(S)NR$^{a1}$R$^{b1}$, —(CR$^{c1}$R$^{d1}$)$_t$NR$^{a1}$C(=NR$^{c1}$)NR$^{a1}$R$^{b1}$, —(CR$^{c1}$R$^{d1}$)$_t$S(O)$_r$R$^{b1}$, —(CR$^{c1}$R$^{d1}$)$_t$S(O)(=NR$^{c1}$)R$^{b1}$, —(CR$^{c1}$R$^{d1}$)$_t$N=S(O)R$^{a1}$R$^{b1}$, —(CR$^{c1}$R$^{d1}$)$_t$S(O)$_2$OR$^{b1}$, —(CR$^{c1}$R$^{d1}$)$_t$OS(O)$_2$R$^{b1}$, —(CR$^{c1}$R$^{d1}$)$_t$NR$^{a1}$S(O)$_r$R$^{b1}$, —(CR$^{c1}$R$^{d1}$)$_t$NR$^{a1}$S(O)(=NR$^{c1}$)R$^{b1}$, —(CR$^{c1}$R$^{d1}$)$_t$S(O)$_r$NR$^{a1}$R$^{b1}$, —(CR$^{c1}$R$^{d1}$)$_t$S(O)(=NR$^{c1}$)NR$^{a1}$R$^{b1}$, —(CR$^{c1}$R$^{d1}$)$_t$NR$^{a1}$S(O)$_2$NR$^{a1}$R$^{b1}$, —(CR$^{c1}$R$^{d1}$)$_t$NR$^{a1}$S(O)(=NR$^{c1}$)NR$^{a1}$R$^{b1}$, —(CR$^{c1}$R$^{d1}$)$_t$P(O)R$^{a1}$R$^{b1}$ and —(CR$^{c1}$R$^{d1}$)$_t$P(O)(OR$^{a1}$)(OR$^{b1}$), wherein alkyl, alkenyl, alkynyl, cycloalkyl, heterocyclyl, aryl and heteroaryl are each unsubstituted or substituted with at least one substituent, such as one, two, three or four substituents, independently selected from R$^Y$;

each R$^{a1}$ and each R$^{b1}$ are independently selected from hydrogen, C$_{1-10}$ alkyl, C$_{2-10}$ alkenyl, C$_{2-10}$ alkynyl, C$_{3-10}$ cycloalkyl, C$_{3-10}$ cycloalkyl-C$_{1-4}$ alkyl, heterocyclyl, heterocyclyl-C$_{1-4}$ alkyl, aryl, aryl-C$_{1-4}$ alkyl, heteroaryl and heteroaryl-C$_{1-4}$ alkyl, wherein alkyl, alkenyl, alkynyl, cycloalkyl, heterocyclyl, aryl and heteroaryl are each unsubstituted or substituted with at least one substituent, such as one, two, three or four substituents, independently selected from R$^Y$;

or R$^{a1}$ and R$^{b1}$ together with the atom(s) to which they are attached form a heterocyclic ring of 4 to 12 members containing 0, 1 or 2 additional heteroatoms independently selected from oxygen, sulfur, nitrogen and phosphorus, and optionally substituted with 1, 2 or 3 R$^Y$ groups;

each R$^{c1}$ and each R$^{d1}$ are independently selected from hydrogen, halogen, C$_{1-10}$ alkyl, C$_{2-10}$ alkenyl, C$_{2-10}$ alkynyl, C$_{3-10}$ cycloalkyl, C$_{3-10}$ cycloalkyl-C$_{1-4}$ alkyl, heterocyclyl, heterocyclyl-C$_{1-4}$ alkyl, aryl, aryl-C$_{1-4}$ alkyl, heteroaryl and heteroaryl-C$_{1-4}$ alkyl, wherein alkyl, alkenyl, alkynyl, cycloalkyl, heterocyclyl, aryl and heteroaryl are each unsubstituted or substituted with at least one substituent, such as one, two, three or four substituents, independently selected from R$^Y$;

or R$^{c1}$ and R$^{d1}$ together with the carbon atom(s) to which they are attached form a ring of 3 to 12 members containing 0, 1 or 2 heteroatoms independently selected from oxygen, sulfur and nitrogen, and optionally substituted with 1, 2 or 3 R$^Y$ groups;

each R$^{e1}$ is independently selected from hydrogen, C$_{1-10}$ alkyl, C$_{3-10}$ cycloalkyl, C$_{3-10}$ cycloalkyl-C$_{1-4}$ alkyl, CN, NO$_2$, —OR$^{a2}$, —SR$^{a2}$, —S(O)$_r$R$^{a2}$, —C(O)R$^{a2}$, —C(O)OR$^{a2}$, —S(O)$_r$NR$^{a2}$R$^{b2}$ and —C(O)NR$^{a2}$R$^{b2}$;

each R$^Y$ is independently selected from C$_{1-10}$ alkyl, C$_{2-10}$ alkenyl, C$_{2-10}$ alkynyl, C$_{3-10}$ cycloalkyl, C$_{3-10}$ cycloalkyl-C$_{1-4}$ alkyl, heterocyclyl, heterocyclyl-C$_{1-4}$ alkyl, aryl, aryl-C$_{1-4}$ alkyl, heteroaryl, heteroaryl-C$_{1-4}$ alkyl, halogen, CN, NO$_2$, —(CR$^{c2}$R$^{d2}$)$_t$NR$^{a2}$R$^{b2}$, —(CR$^{c2}$R$^{d2}$)$_t$OR$^{b2}$, —(CR$^{c2}$R$^{d2}$)$_t$C(O)R$^{a2}$, —(CR$^{c2}$R$^{d2}$)$_t$C(=NR$^{e2}$)R$^{a1}$, —(CR$^{c2}$R$^{d2}$)$_t$C(=N—OR$^{b2}$)R$^{a2}$, —(CR$^{c2}$R$^{d2}$)$_t$C(O)OR$^{b2}$, —(CR$^{c2}$R$^{d2}$)$_t$OC(O)R$^{b2}$, —(CR$^{c2}$R$^{d2}$)$_t$C(O)NR$^{a2}$R$^{b2}$, —(CR$^{c2}$R$^{d2}$)$_t$NR$^{a2}$C(O)R$^{b2}$, —(CR$^{c2}$R$^{d2}$)$_t$C(=NR$^{e2}$)NR$^{a2}$R$^{b2}$, —(CR$^{c2}$R$^{d2}$)$_t$NR$^{a2}$C(=NR$^{e2}$)R$^{b2}$, —(CR$^{c2}$R$^{d2}$)$_t$OC(O)NR$^{a2}$R$^{b2}$, —(CR$^{c2}$R$^{d2}$)$_t$NR$^{a2}$C(O)OR$^{b2}$, —(CR$^{c2}$R$^{d2}$)$_t$NR$^{a2}$C(O)NR$^{a2}$R$^{b2}$, —(CR$^{c2}$R$^{d2}$)$_t$NR$^{a2}$C(S)NR$^{a2}$R$^{b2}$, —(CR$^{c2}$R$^{d2}$)$_t$NR$^{a2}$C(=NR$^{e2}$)NR$^{a2}$R$^{b2}$, —(CR$^{c2}$R$^{d2}$)$_t$S(O)$_r$R$^{b2}$, —(CR$^{c2}$R$^{d2}$)$_t$S(O)(=NR$^{e2}$)R$^{b2}$, —(CR$^{c2}$R$^{d2}$)$_t$N=S(O)R$^{a2}$R$^{b2}$, —(CR$^{c2}$R$^{d2}$)$_t$S(O)$_2$OR$^{b2}$, —(CR$^{c2}$R$^{d2}$)$_t$OS(O)$_2$R$^{b2}$, —(CR$^{c2}$R$^{d2}$)$_t$NR$^{a2}$S(O)$_r$R$^{b2}$, —(CR$^{c2}$R$^{d2}$)$_t$NR$^{a2}$S(O)(=NR$^{e2}$)R$^{b2}$, —(CR$^{c2}$R$^{d2}$)$_t$S(O)$_r$NR$^{a2}$R$^{b2}$, —(CR$^{c2}$R$^{d2}$)$_t$S(O)(=NR$^{e2}$)NR$^{a2}$R$^{b2}$, —(CR$^{c2}$R$^{d2}$)$_t$NR$^{a2}$S(O)$_2$NR$^{a2}$R$^{b2}$, —(CR$^{c2}$R$^{d2}$)$_t$NR$^{a2}$S(O)(=NR$^{e2}$)NR$^{a2}$R$^{b2}$, —(CR$^{c2}$R$^{d2}$)$_t$P(O)R$^{a2}$R$^{b2}$ and —(CR$^{c2}$R$^{d2}$)$_t$P(O)(OR$^{a2}$)(OR$^{b2}$), wherein alkyl, alkenyl, alkynyl, cycloalkyl, heterocyclyl, aryl and heteroaryl are each unsubstituted or substituted with at least one substituent, such as one, two, three or four substituents, independently selected from OH, CN, amino, halogen, C$_{1-10}$ alkyl, C$_{2-10}$ alkenyl, C$_{2-10}$ alkynyl, C$_{3-10}$ cycloalkyl, C$_{1-10}$ alkoxy, $C_{3-10}$ cycloalkoxy, $C_{1-10}$ alkylthio, $C_{3-10}$ cycloalkylthio, $C_{1-10}$ alkylamino, $C_{3-10}$ cycloalkylamino and di($C_{1-10}$ alkyl)amino;

each $R^{a2}$ and each $R^{b2}$ are independently selected from hydrogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, $C_{1-10}$ alkoxy, $C_{3-10}$ cycloalkoxy, $C_{1-10}$ alkylthio, $C_{3-10}$ cycloalkylthio, $C_{1-10}$ alkylamino, $C_{3-10}$ cycloalkylamino, di($C_{1-10}$ alkyl)amino, heterocyclyl, heterocyclyl-$C_{1-4}$ alkyl, aryl, aryl-$C_{1-4}$ alkyl, heteroaryl and heteroaryl-$C_{1-4}$ alkyl, wherein alkyl, alkenyl, alkynyl, cycloalkyl, alkoxy, cycloalkoxy, alkylthio, cycloalkylthio, alkylamino, cycloalkylamino, heterocyclyl, aryl and heteroaryl are each unsubstituted or substituted with at least one substituent, such as one, two, three or four substituents, independently selected from halogen, CN, $C_{1-10}$ alkyl, $C_{2-10}$ alkenyl, $C_{2-10}$ alkynyl, $C_{3-10}$ cycloalkyl, OH, $C_{1-10}$ alkoxy, $C_{3-10}$ cycloalkoxy, $C_{1-10}$ alkylthio, $C_{3-10}$ cycloalkylthio, amino, $C_{1-10}$ alkylamino, $C_{3-10}$ cycloalkylamino and di($C_{1-10}$ alkyl)amino;

or $R^{a2}$ and $R^{b2}$ together with the atom(s) to which they are attached form a heterocyclic ring of 4 to 12 members containing 0, 1 or 2 additional heteroatoms independently selected from oxygen, sulfur, nitrogen and phosphorus, and optionally substituted with 1 or 2 substituents, independently selected from halogen, CN, $C_{1-10}$ alkyl, $C_{2-10}$ alkenyl, $C_{2-10}$ alkynyl, $C_{3-10}$ cycloalkyl, OH, $C_{1-10}$ alkoxy, $C_{3-10}$ cycloalkoxy, $C_{1-10}$ alkylthio, $C_{3-10}$ cycloalkylthio, amino, $C_{1-10}$ alkylamino, $C_{3-10}$ cycloalkylamino and di($C_{1-10}$ alkyl)amino;

each $R^{c2}$ and each $R^{d2}$ are independently selected from hydrogen, halogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, $C_{1-10}$ alkoxy, $C_{3-10}$ cycloalkoxy, $C_{1-10}$ alkylthio, $C_{3-10}$ cycloalkylthio, $C_{1-10}$ alkylamino, $C_{3-10}$ cycloalkylamino, di($C_{1-10}$ alkyl)amino, heterocyclyl, heterocyclyl-$C_{1-4}$ alkyl, aryl, aryl-$C_{1-4}$ alkyl, heteroaryl and heteroaryl-$C_{1-4}$ alkyl, wherein alkyl, alkenyl, alkynyl, cycloalkyl, alkoxy, cycloalkoxy, alkylthio, cycloalkylthio, alkylamino, cycloalkylamino, heterocyclyl, aryl and heteroaryl are each unsubstituted or substituted with at least one substituent, such as one, two, three or four substituents, independently selected from halogen, CN, $C_{1-10}$ alkyl, $C_{2-10}$ alkenyl, $C_{2-10}$ alkynyl, $C_{3-10}$ cycloalkyl, OH, $C_{1-10}$ alkoxy, $C_{3-10}$ cycloalkoxy, $C_{1-10}$ alkylthio, $C_{3-10}$ cycloalkylthio, amino, $C_{1-10}$ alkylamino, $C_{3-10}$ cycloalkylamino and di($C_{1-10}$ alkyl)amino;

or $R^{c2}$ and $R^{d2}$ together with the carbon atom(s) to which they are attached form a ring of 3 to 12 members containing 0, 1 or 2 heteroatoms independently selected from oxygen, sulfur and nitrogen, and optionally substituted with 1 or 2 substituents, independently selected from halogen, CN, $C_{1-10}$ alkyl, $C_{2-10}$ alkenyl, $C_{2-10}$ alkynyl, $C_{3-10}$ cycloalkyl, OH, $C_{1-10}$ alkoxy, $C_{3-10}$ cycloalkoxy, $C_{1-10}$ alkylthio, $C_{3-10}$ cycloalkylthio, amino, $C_{1-10}$ alkylamino, $C_{3-10}$ cycloalkylamino and di($C_{1-10}$ alkyl)amino;

each $R^{e2}$ is independently selected from hydrogen, CN, $NO_2$, $C_{1-10}$ alkyl, $C_{3-10}$ cycloalkyl, $C_{3-10}$ cycloalkyl-$C_{1-4}$ alkyl, $C_{1-10}$ alkoxy, $C_{3-10}$ cycloalkoxy, —C(O)$C_{1-4}$ alkyl, —C(O)$C_{3-10}$ cycloalkyl, —C(O)O$C_{1-4}$ alkyl, —C(O)O$C_{3-10}$ cycloalkyl, —C(O)N($C_{1-4}$ alkyl)$_2$, —C(O)N($C_{3-10}$ cycloalkyl)$_2$, —S(O)$_2C_{1-4}$ alkyl, —S(O)$_2C_{3-10}$ cycloalkyl, —S(O)$_2$N($C_{1-4}$ alkyl)$_2$ and —S(O)$_2$N($C_{3-10}$ cycloalkyl)$_2$;

m is selected from 0, 1, 2 and 3;
n is selected from 0, 1, 2 and 3;
o is selected from 0, 1 and 2;
p is selected from 0, 1, 2, 3 and 4;
q is selected from 0 and 1;
each r is independently selected from 0, 1 and 2;
each t is independently selected from 0, 1, 2, 3 and 4;
each u is independently selected from 0, 1, 2, 3 and 4.

In yet another aspect, the present disclosure provides pharmaceutical compositions comprising a compound of formula (I) or a pharmaceutically acceptable salt thereof and a pharmaceutically acceptable excipient.

In yet another aspect, the disclosure provides methods for modulating Bcl-2, comprising administering to a system or a subject in need thereof, a therapeutically effective amount of a compound of formula (I) or a pharmaceutically acceptable salt thereof or pharmaceutical compositions thereof, thereby modulating said Bcl-2.

In yet another aspect, disclosed is a method to treat, ameliorate or prevent a condition which responds to inhibition of Bcl-2 comprising administering to a system or subject in need of such treatment an effective amount of a compound of formula (I) or a pharmaceutically acceptable salt thereof or pharmaceutical compositions thereof, and optionally in combination with a second therapeutic agent, thereby treating said condition.

Alternatively, the present disclosure provides the use of a compound of formula (I) or a pharmaceutically acceptable salt thereof in the manufacture of a medicament for treating a condition mediated by Bcl-2. In particular embodiments, the compounds of the disclosure may be used alone or in combination with a second therapeutic agent to treat a condition mediated by Bcl-2.

Alternatively, disclosed is a compound of formula (I) or a pharmaceutically acceptable salt thereof for treating a condition mediated by Bcl-2.

Specifically, the condition herein includes but not limited to, an autoimmune disease, a transplantation disease, an infectious disease or a cell proliferative disorder.

Furthermore, the disclosure provides methods for treating a cell proliferative disorder, comprising administering to a system or subject in need of such treatment an effective amount of a compound of formula (I) or a pharmaceutically acceptable salt thereof or pharmaceutical compositions thereof, and optionally in combination with a second therapeutic agent, thereby treating said condition.

Alternatively, the present disclosure provides the use of a compound of formula (I) or a pharmaceutically acceptable salt thereof in the manufacture of a medicament for treating a cell-proliferative disorder. In particular examples, the compounds of the disclosure may be used alone or in combination with a chemotherapeutic agent to treat a cell proliferative disorder.

Specifically, the cell proliferative disorder disclosed herein includes but not limited to, lymphoma, osteosarcoma, melanoma, or a tumor of breast, renal, prostate, colorectal, thyroid, ovarian, pancreatic, neuronal, lung, uterine or gastrointestinal tumor.

In the above methods for using the compounds of the disclosure, a compound of formula (I) or a pharmaceutically acceptable salt thereof may be administered to a system comprising cells or tissues, or to a subject including a mammalian subject such as a human or animal subject.

Certain Terminology

Unless defined otherwise, all technical and scientific terms used herein have the same meaning as is commonly understood by one of skill in the art to which the claimed subject matter belongs. All patents, patent applications, published materials referred to throughout the entire disclosure herein, unless noted otherwise, are incorporated by reference in their entirety. In the event that there is a plurality of definitions for terms herein, those in this section prevail.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a", "an" and "the" include plural referents unless the context clearly dictates otherwise. It should also be noted that use of "or" means "and/or" unless stated otherwise. Furthermore, use of the term "including" as well as other forms, such as "include", "includes", and "included" is not limiting. Likewise, use of the term "comprising" as well as other forms, such as "comprise", "comprises", and "comprised" is not limiting.

[22] Definition of standard chemistry terms may be found in reference works, including Carey and Sundberg "ADVANCED ORGANIC CHEMISTRY $4^{TH}$ ED." Vols. A (2000) and B (2001), Plenum Press, New York. Unless otherwise indicated, conventional methods of mass spectroscopy, NMR, HPLC, IR and UV/V is spectroscopy and pharmacology, within the skill of the art are employed. Unless specific definitions are provided, the nomenclature employed in connection with, and the laboratory procedures and techniques of, analytical chemistry, synthetic organic chemistry, and medicinal and pharmaceutical chemistry described herein are those known in the art. Standard techniques can be used for chemical syntheses, chemical analyses, pharmaceutical preparation, formulation, and delivery, and treatment of patients. Reactions and purification techniques can be performed e.g., using kits of manufacturer's specifications or as commonly accomplished in the art or as described herein. The foregoing techniques and procedures can be generally performed of conventional methods well known in the art and as described in various general and more specific references that are cited and discussed throughout the present specification. Throughout the specification, groups and substituents thereof can be chosen by one skilled in the field to provide stable moieties and compounds.

Where substituent groups are specified by their conventional chemical formulas, written from left to right, they equally encompass the chemically identical substituents that would result from writing the structure from right to left. As a non-limiting example, $CH_2O$ is equivalent to $OCH_2$.

The term "substituted" means that a hydrogen atom is removed and replaced by a substituent. It is to be understood that substitution at a given atom is limited by valency. Throughout the definitions, the term "$C_{i-j}$" indicates a range which includes the endpoints, wherein i and j are integers and indicate the number of carbons. Examples include $C_{1-4}$, $C_{1-10}$, $C_{3-10}$, and the like.

The term "alkyl", employed alone or in combination with other terms, refers to both branched and straight-chain saturated aliphatic hydrocarbon groups having the specified number of carbon atoms. Unless otherwise specified, "alkyl" refers to $C_{1-10}$ alkyl. For example, $C_{1-6}$, as in "$C_{1-6}$ alkyl" is defined to include groups having 1, 2, 3, 4, 5, or 6 carbons in a linear or branched arrangement. For example, "$C_{1-8}$ alkyl" includes but is not limited to methyl, ethyl, n-propyl, i-propyl, n-butyl, t-butyl, i-butyl, pentyl, hexyl, heptyl, and octyl.

The term "cycloalkyl", employed alone or in combination with other terms, refers to a monocyclic or bridged hydrocarbon ring system. The monocyclic cycloalkyl is a carbocyclic ring system containing three to ten carbon atoms, zero heteroatoms and zero double bonds. Examples of monocyclic ring systems include cyclopropyl, cyclobutyl, cyclopentyl, cyclohexyl, cycloheptyl, and cyclooctyl. The monocyclic ring may contain one or two alkylene bridges, each consisting of one, two, or three carbon atoms, each linking two non-adjacent carbon atoms of the ring system. Representative examples of such bridged cycloalkyl ring systems include, but are not limited to, bicyclo[3.1.1]heptane, bicyclo[2.2.1]heptane, bicyclo[2.2. 2]octane, bicyclo[3.2.2]nonane, bicyclo[3.3.1]nonane, bicyclo[4.2.1]nonane, tricyclo[3.3.1.03,7]nonane and tricyclo[3.3.1.13,7]decane (adamantane). The monocyclic and bridged cycloalkyl can be attached to the parent molecular moiety through any substitutable atom contained within the ring system.

The term "alkenyl", employed alone or in combination with other terms, refers to a non-aromatic hydrocarbon radical, straight, branched or cyclic, containing from 2 to 10 carbon atoms and at least one carbon to carbon double bond. In some embodiments, one carbon to carbon double bond is present, and up to four non-aromatic carbon-carbon double bonds may be present. Thus, "$C_{2-6}$ alkenyl" means an alkenyl radical having from 2 to 6 carbon atoms. Alkenyl groups include but are not limited to ethenyl, propenyl, butenyl, 2-methylbutenyl and cyclohexenyl. The straight, branched or cyclic portion of the alkenyl group may contain double bonds and may be substituted if a substituted alkenyl group is indicated.

The term "alkynyl", employed alone or in combination with other terems, refers to a hydrocarbon radical straight, branched or cyclic, containing from 2 to 10 carbon atoms and at least one carbon to carbon triple bond. In some embodiments, up to three carbon-carbon triple bonds may be present. Thus, "$C_{2-6}$ alkynyl" means an alkynyl radical having from 2 to 6 carbon atoms. Alkynyl groups include but are not limited to ethynyl, propynyl, butynyl, and 3-methylbutynyl. The straight, branched or cyclic portion of the alkynyl group may contain triple bonds and may be substituted if a substituted alkynyl group is indicated.

The term "halogen" (or "halo") refers to fluorine, chlorine, bromine and iodine.

The term "alkoxy", employed alone or in combination with other terms, refers to an alkyl radical that is single bonded to an oxygen atom. The attachment point of an alkoxy radical to a molecule is through the oxygen atom. An alkoxy radical may be depicted as —O-alkyl. The term "$C_{1-10}$ alkoxy" refers to an alkoxy radical containing from one to ten carbon atoms, having straight or branched moieties. Alkoxy groups, includes but is not limited to, methoxy, ethoxy, propoxy, isopropoxy, butoxy, pentyloxy, hexyloxy, and the like.

The term "cycloalkoxy", employed alone or in combination with other terms, refers to cycloalkyl radical that is single bonded to an oxygen atom. The attachment point of a cycloalkoxy radical to a molecule is through the oxygen atom. A cycloalkoxy radical may be depicted as —O-cycloalkyl. "$C_{3-10}$ cycloalkoxy" refers to a cycloalkoxy radical containing from three to ten carbon atoms. Cycloalkoxy groups, includes but is not limited to, cyclopropoxy, cyclobutoxy, cyclopentyloxy, cyclohexyloxy, and the like.

The term "alkylthio", employed alone or in combination with other terms, refers to an alkyl radical that is single bonded to a sulfur atom. The attachment point of an alkylthio radical to a molecule is through the sulfur atom. An alkylthio radical may be depicted as —S-alkyl. The term "$C_{1-10}$ alkylthio" refers to an alkylthio radical containing from one to ten carbon atoms, having straight or branched moieties. Alkylthio groups, includes but is not limited to, methylthio, ethylthio, propylthio, isopropylthio, butylthio, hexylthio, and the like.

The term "cycloalkylthio", employed alone or in combination with other terms, refers to cycloalkyl radical that is single bonded to a sulfur atom. The attachment point of a cycloalkylthio radical to a molecule is through the sulfur atom. A cycloalkylthio radical may be depicted as —S-cycloalkyl. "$C_{3-10}$ cycloalkylthio" refers to a cycloalkylthio radical containing from three to ten carbon atoms. Cycloalkylthio groups, includes but is not limited to, cyclopropylthio, cyclobutylthio, cyclohexylthio, and the like.

The term "alkylamino", employed alone or in combination with other terms, refers to an alkyl radical that is single bonded to a nitrogen atom. The attachment point of an alkylamino radical to a molecule is through the nitrogen atom. An alkylamino radical may be depicted as —NH(alkyl). The term "$C_{1-10}$ alkylamino" refers to an alkylamino radical containing from one to ten carbon atoms, having straight or branched moieties. Alkylamino groups, includes but is not limited to, methylamino, ethylamino, propylamino, isopropylamino, butylamino, hexylamoino, and the like.

The term "cycloalkylamino", employed alone or in combination with other terms, refers to cycloalkyl radical that is single bonded to a nitrogen atom. The attachment point of a cycloalkylamino radical to a molecule is through the nitrogen atom. A cycloalkylamino radical may be depicted as —NH(cycloalkyl). "$C_{3-10}$ cycloalkylamino" refers to a cycloalkylamino radical containing from three to ten carbon atoms. Cycloalkylamino groups, includes but is not limited to, cyclopropylamino, cyclobutylamino, cyclohexylamino, and the like.

The term "di(alkyl)amino", employed alone or in combination with other terms, refers to two alkyl radicals that are single bonded to a nitrogen atom. The attachment point of an di(alkyl)amino radical to a molecule is through the nitrogen atom. A di(alkyl)amino radical may be depicted as —N(alkyl)$_2$. The term "di($C_{1-10}$ alkyl)amino" refers to a di($C_{1-10}$ alkyl)amino radical wherein the alkyl radicals each independently contains from one to ten carbon atoms, having straight or branched moieties.

The term "aryl", employed alone or in combination with other terms, encompasses: 5- and 6-membered carbocyclic aromatic rings, for example, benzene; bicyclic ring systems wherein at least one ring is carbocyclic and aromatic, for example, naphthalene, indane, and 1, 2, 3, 4-tetrahydroquinoline; and tricyclic ring systems wherein at least one ring is carbocyclic and aromatic, for example, fluorene. In cases where the aryl substituent is bicyclic or tricyclic and at least one ring is non-aromatic, it is understood that attachment is via the aromatic ring.

For example, aryl includes 5- and 6-membered carbocyclic aromatic rings fused to a 5- to 7-membered heterocyclic ring containing one or more heteroatoms selected from N, O, and S, provided that the point of attachment is at the carbocyclic aromatic ring. Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Aryl, however, does not encompass or overlap in any way with heteroaryl, separately defined below. Hence, if one or more carbocyclic aromatic rings are fused with a heterocyclic aromatic ring, the resulting ring system is heteroaryl, not aryl, as defined herein.

The term "heteroaryl", employed alone or in combination with other terms, refers to
5- to 8-membered aromatic, monocyclic rings containing one or more, for example, from 1 to 4, or, in some embodiments, from 1 to 3, heteroatoms selected from N, O and S, with the remaining ring atoms being carbon;
8- to 12-membered bicyclic rings containing one or more, for example, from 1 to 4, or, in some embodiments, from 1 to 3, heteroatoms selected from N, O and S, with the remaining ring atoms being carbon and wherein at least one heteroatom is present in an aromatic ring; and
11- to 14-membered tricyclic rings containing one or more, for example, from 1 to 4, or in some embodiments, from 1 to 3, heteroatoms selected from N, O and S, with the remaining ring atoms being carbon and wherein at least one heteroatom is present in an aromatic ring.

When the total number of S and O atoms in the heteroaryl group exceeds 1, those heteroatoms are not adjacent to one another. In some embodiments, the total number of S and O atoms in the heteroaryl group is not more than 2. In some embodiments, the total number of S and O atoms in the aromatic heterocycle is not more than 1.

Examples of heteroaryl groups include, but are not limited to, (as numbered from the linkage position assigned priority 1), 2-pyridyl, 3-pyridyl, 4-pyridyl, 2,3-pyrazinyl, 3,4-pyrazinyl, 2,4-pyrimidinyl, 3,5-pyrimidinyl, 1-pyrazolyl, 2,3-pyrazolyl, 2,4-imidazolinyl, isoxazolyl, oxazolyl, thiazolyl, thiadiazolyl, tetrazolyl, thienyl, benzothienyl, furyl, benzofuryl, benzoimidazolinyl, indolinyl, pyridizinyl, triazolyl, quinolinyl, pyrazolyl and 5,6,7,8-tetrahydroisoquinoline.

Further heteroaryl groups include but are not limited to pyrrolyl, isothiazolyl, triazinyl, pyrazinyl, pyridazinyl, indolyl, benzotriazolyl, quinoxalinyl and isoquinolinyl. As with the definition of heterocycle below, "heteroaryl" is also understood to include the N-oxide derivative of any nitrogen-containing heteroaryl.

Bivalent radicals derived from univalent heteroaryl radicals whose names end in "-yl" by removal of one hydrogen atom from the atom with the free valence are named by adding "-idene" to the name of the corresponding univalent radical, e.g., a pyridyl group with two points of attachment is a pyridylidene. Heteroaryl does not encompass or overlap with aryl as defined above.

In cases where the heteroaryl substituent is bicyclic or tricyclic and at least one ring is non-aromatic or contains no heteroatoms, it is understood that attachment is via the aromatic ring or via the heteroatom containing ring, respectively.

The term "heterocycle", employed alone or in combination with other terms, (and variations thereof such as "heterocyclic", or "heterocyclyl") broadly refers to a single aliphatic ring, usually with 3 to 12 ring atoms, containing at least 2 carbon atoms in addition to one or more, preferably one to three heteroatoms independently selected from oxygen, sulfur, nitrogen and phosphorus as well as combinations comprising at least one of the foregoing heteroatoms. Alternatively, a heterocycle as defined above may be multicyclic ring system (e.g. bicyclic) in which two or more rings may be fused or bridged or spiro together, wherein at least one such ring contains one or more heteroatoms independently selected from oxygen, sulfur, nitrogen and phosphorus.

"Heterocycle" also refers to 5- to 7-membered heterocyclic ring containing one or more heteroatoms selected from oxygen, sulfur, nitrogen and phosphorus fused with 5- and 6-membered carbocyclic aromatic ring, provided that the point of attachment is at the heterocyclic ring. The rings may be saturated or have one or more double bonds (i.e. partially unsaturated). The heterocycle can be substituted by oxo or imino, and imino can be unsubstituted or substituted. The point of the attachment may be carbon or heteroatom in the heterocyclic ring, provided that attachment results in the creation of a stable structure. When the heterocyclic ring has substituents, it is understood that the substituents may be attached to any atom in the ring, whether a heteroatom or a carbon atom, provided that a stable chemical structure results. Heterocycle does not overlap with heteroaryl.

Suitable heterocycles include, for example (as numbered from the linkage position assigned priority 1), 1-pyrrolidinyl, 2-pyrrolidinyl, 2,4-imidazolidinyl, 2,3-pyrazolidinyl, 1-piperidinyl, 2-piperidinyl, 3-piperidinyl, 4-piperidinyl, 2,5-piperazinyl. 1,4-piperazinyl and 2,3-pyridazinyl. Morpholinyl groups are also contemplated, including 2-morpholinyl and 3-morpholinyl(numbered wherein the oxygen is assigned priority 1). Substituted heterocycle also includes ring systems substituted with one or more oxo moieties, such as piperidinyl N-oxide, morpholinyl-N-oxide, 1-oxo-1-thiomorpholinyl and 1,1-dioxo-1-thiomorpholinyl. Bicyclic heterocycles include, for example:

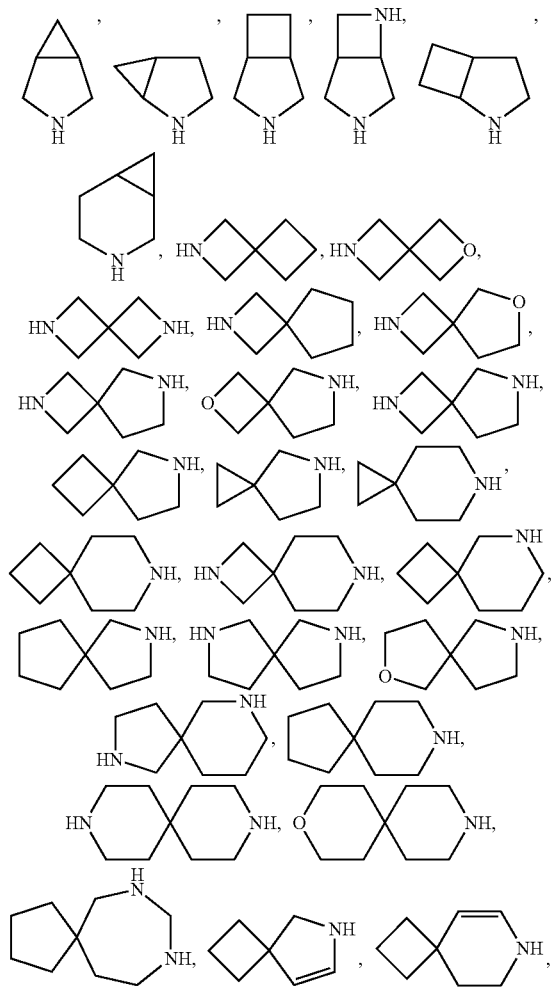

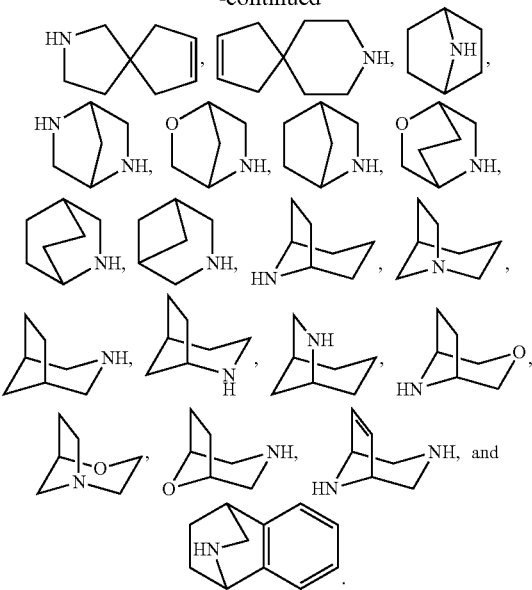

As used herein, "aryl-alkyl" refers to an alkyl moiety substituted by an aryl group. Example aryl-alkyl groups include benzyl, phenethyl and naphthylmethyl groups. In some embodiments, aryl-alkyl groups have from 7 to 20 or 7 to 11 carbon atoms. When used in the phrase "aryl-$C_{1-4}$ alkyl", the term "$C_{1-4}$" refers to the alkyl portion of the moiety and does not describe the number of atoms in the aryl portion of the moiety.

As used herein, "heterocyclyl-alkyl" refers to alkyl substituted by heterocyclyl. When used in the phrase "heterocyclyl-$C_{1-4}$ alkyl", the term "$C_{1-4}$" refers to the alkyl portion of the moiety and does not describe the number of atoms in the heterocyclyl portion of the moiety.

As used herein, "cycloalkyl-alkyl" refers to alkyl substituted by cycloalkyl. When used in the phrase "$C_{3-10}$ cycloalkyl-$C_{1-4}$ alkyl", the term "$C_{3-10}$" refers to the cycloalkyl portion of the moiety and does not describe the number of atoms in the alkyl portion of the moiety, and the term "$C_{1-4}$" refers to the alkyl portion of the moiety and does not describe the number of atoms in the cycloalkyl portion of the moiety.

As used herein, "heteroaryl-alkyl" refers to alkyl substituted by heteroaryl. When used in the phrase "heteroaryl-$C_{1-4}$ alkyl", the term "$C_{1-4}$" refers to the alkyl portion of the moiety and does not describe the number of atoms in the heteroaryl portion of the moiety.

For avoidance of doubt, reference, for example, to substitution of alkyl, cycloalkyl, heterocyclyl, aryl and/or heteroaryl refers to substitution of each of those groups individually as well as to substitutions of combinations of those groups. That is, if $R^1$ is aryl-$C_{1-4}$ alkyl, the aryl portion may be unsubstituted or substituted with at least one substituent, such as one, two, three, or four substituents, independently selected from $R^X$ and the alkyl portion may also be unsubstituted or substituted with at least one substituent, such as one, two, three, or four substituens, independently selected from $R^X$.

The term "pharmaceutically acceptable salts" refers to salts prepared from pharmaceutically acceptable non-toxic bases or acids including inorganic or organic bases and inorganic or organic acids. Salts derived from inorganic bases may be selected, for example, from aluminum, ammonium, calcium, copper, ferric, ferrous, lithium, magnesium, manganic, manganous, potassium, sodium and zinc salts. Further, for example, the pharmaceutically acceptable salts derived from inorganic bases may be selected from ammonium, calcium, magnesium, potassium and sodium salts. Salts in the solid form may exist in one or more crystal structures, and may also be in the form of hydrates. Salts derived from pharmaceutically acceptable organic non-toxic bases may be selected, for example, from salts of primary, secondary and tertiary amines, substituted amines including naturally occurring substituted amines, cyclic amines and basic ion exchange resins, such as arginine, betaine, caffeine, choline, N,N'-dibenzylethylene-diamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine and tripropylamine, tromethamine.

When the compound disclosed herein is basic, salts may be prepared using at least one pharmaceutically acceptable non-toxic acid, selected from inorganic and organic acids. Such acid may be selected, for example, from acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric and p-toluenesulfonic acids. In some embodiments, such acid may be selected, for example, from citric, hydrobromic, hydrochloric, maleic, phosphoric, sulfuric, fumaric and tartaric acids.

The terms "administration of" and or "administering" a compound or a pharmaceutically acceptable salt should be understood to mean providing a compound or a pharmaceutically acceptable salt thereof to the individual in recognized need of treatment.

The term "effective amount" means the amount of the a compound or a pharmaceutically acceptable salt that will elicit the biological or medical response of a tissue, system, animal or human that is being sought by the researcher, veterinarian, medical doctor or other clinician.

The term "composition" as used herein is intended to encompass a product comprising the specified ingredients in the specified amounts, as well as any product which results, directly or indirectly, from combination of the specified ingredients in the specified amounts. Such term in relation to a pharmaceutical composition is intended to encompass a product comprising the active ingredient (s) and the inert ingredient (s) that make up the carrier, as well as any product which results, directly or indirectly, from combination, complexation or aggregation of any two or more of the ingredients, or from dissociation of one or more of the ingredients, or from other types of reactions or interactions of one or more of the ingredients.

The term "pharmaceutically acceptable" it is meant compatible with the other ingredients of the formulation and not unacceptably deleterious to the recipient thereof.

The term "subject" as used herein in reference to individuals suffering from a disorder, a condition, and the like, encompasses mammals and non-mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs and cats; laboratory animals including rodents, such as rats, mice and guinea pigs, and the like. Examples of non-mammals include, but are not limited to, birds, fish and the like. In one embodiment of the methods and compositions provided herein, the mammal is a human.

The terms "treat," "treating" or "treatment," and other grammatical equivalents as used herein, include alleviating, abating or ameliorating a disease or condition, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition, and are intended to include prophylaxis. The terms further include achieving a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

The term "protecting group" or "Pg" refers to a substituent that can be commonly employed to block or protect a certain functionality while reacting other functional groups on the compound. For example, an "amino-protecting group" is a substituent attached to an amino group that blocks or protects the amino functionality in the compound. Suitable amino-protecting groups include but are not limited to acetyl, trifluoroacetyl, t-butoxycarbonyl (BOC), benzyloxycarbonyl (CBZ) and 9-fluorenylmethylenoxycarbonyl (Fmoc). Similarly, a "hydroxy-protecting group" refers to a substituent of a hydroxy group that blocks or protects the hydroxy functionality. Suitable protecting groups include but are not limited to acetyl and silyl. A "carboxy-protecting group" refers to a substituent of the carboxy group that blocks or protects the carboxy functionality. Common carboxy-protecting groups include —$CH_2CH_2SO_2Ph$, cyanoethyl, 2-(trimethylsilyl)ethyl, 2-(trimethylsilyl)ethoxymethyl, 2-(p-toluenesulfonyl)ethyl, 2-(p-nitrophenylsulfenyl) ethyl, 2-(diphenylphosphino)-ethyl, nitroethyl and the like. For a general description of protecting groups and their use, see T. W. Greene, Protective Groups in Organic Synthesis, *John Wiley & Sons*, New York, 1991.

The term "NH protecting group" as used herein includes, but not limited to, trichloroethoxycarbonyl, tribromoethoxycarbonyl, benzyloxycarbonyl, para-nitrobenzylcarbonyl, ortho-bromobenzyloxycarbonyl, chloroacetyl, dichloroacetyl, trichloroacetyl, trifluoroacetyl, phenylacetyl, formyl, acetyl, benzoyl, tert-amyloxycarbonyl, tert-butoxycarbonyl, para-methoxybenzyloxycarbonyl, 3,4-dimethoxybenzyloxycarbonyl, 4-(phenylazo)-benzyloxycarbonyl, 2-furfuryloxycarbonyl, diphenylmethoxycarbonyl, 1,1-dimethylpropoxy-carbonyl, isopropoxycarbonyl, phthaloyl, succinyl, alanyl, leucyl, 1-adamantyloxycarbonyl, 8-quinolyloxycarbonyl, benzyl, diphenylmethyl, triphenylmethyl, 2-nitrophenylthio, methanesulfonyl, para-toluenesulfonyl, N,N-dimethylaminomethylene, benzylidene, 2-hydroxybenzylidene, 2-hydroxy-5-chlorobenzylidene, 2-hydroxy-1-naphthylmethylene, 3-hydroxy-4-pyridylmethylene, cyclohexylidene, 2-ethoxycarbonylcyclohexylidene, 2-ethoxycarbonylcyclopentylidene, 2-acetylcyclohexylidene, 3,3-dimethyl-5-oxycyclo-hexylidene, diphenylphosphoryl, dibenzylphosphoryl, 5-methyl-2-oxo-2H-1,3-dioxol-4-yl-methyl, trimethylsilyl, triethylsilyl and triphenylsilyl.

The term "C(O)OH protecting group" as used herein includes, but not limited to, methyl, ethyl, n-propyl, isopropyl, 1,1-dimethylpropyl, n-butyl, tert-butyl, phenyl, naphthyl, benzyl, diphenylmethyl, triphenylmethyl, para-nitrobenzyl, para-methoxybenzyl, b is (para-methoxyphenyl) methyl, acetylmethyl, benzoylmethyl, para-nitrobenzoylmethyl, para-bromobenzoylmethyl, para-methanesulfonylbenzoylmethyl, 2-tetrahydropyranyl, 2-tetrahydrofuranyl, 2,2,2-trichloro-ethyl, 2-(trimethylsilyl) ethyl, acetoxymethyl, propionyloxymethyl, pivaloyloxymethyl, phthalimidomethyl, succinimidomethyl, cyclopropyl, cyclobutyl, cyclopentyl, cyclohexyl, methoxymethyl, methoxyethoxymethyl, 2-(trimethylsilyl)ethoxymethyl, benzyloxymethyl, methylthiomethyl, 2-methylthioethyl, phenylthiomethyl, 1,1-dimethyl-2-propenyl, 3-methyl-3-butenyl, allyl, trimethylsilyl, triethylsilyl, triisopropylsilyl, diethylisopropylsilyl, tert-butyldimethylsilyl, tert-butyldiphenylsilyl, diphenylmethylsilyl and tert-butylmethoxyphenylsilyl.

The term "OH or SH protecting group" as used herein includes, but not limited to, benzyloxycarbonyl, 4-nitrobenzyloxycarbonyl, 4-bromobenzyloxycarbonyl, 4-methoxybenzyloxycarbonyl, 3,4-dimethoxybenzyl oxycarbonyl, methoxycarbonyl, ethoxycarbonyl, tert-butoxycarbonyl, 1,1-dimethylpropoxycarbonyl, isopropoxycarbonyl, isobutyloxycarbonyl, diphenylmethoxycarbonyl, 2,2,2-trichloroethoxycarbonyl, 2,2,2-tribromoethoxycarbonyl, 2-(trimethylsilyl)ethoxycarbonyl, 2-(phenylsulfonyl) ethoxycarbonyl, 2-(triphenylphosphonio)ethoxycarbonyl, 2-furfuryloxycarbonyl, 1-adamantyloxycarbonyl, vinyl oxycarbonyl, allyloxycarbonyl, 4-ethoxy-1-naphthyloxycarbonyl, 8-quinolyloxycarbonyl, acetyl, formyl, chloroacetyl, dichloroacetyl, trichloroacetyl, trifluoroacetyl, methoxyacetyl, phenoxyacetyl, pivaloyl, benzoyl, methyl, tert-butyl, 2,2,2-trichloroethyl, 2-trimethylsilylethyl, 1,1-dimethyl-2-propenyl, 3-methyl-3-butenyl, allyl, benzyl(phenylmethyl), para-methoxybenzyl, 3,4-dimethoxybenzyl, diphenylmethyl, triphenylmethyl, tetrahydrofuryl, tetrahydropyranyl, tetrahydrothiopyranyl, methoxymethyl, methylthiomethyl, benzyloxymethyl, 2-methoxyethoxymethyl, 2,2,2-trichloroethoxymethyl, 2-(trimethylsilyl)ethoxymethyl, 1-ethoxyethyl, methanesulfonyl, para-toluenesulfonyl, trimethylsilyl, triethylsilyl, triisopropylsilyl, diethylisopropylsilyl, tert-butyldimethylsilyl, tert-butyldiphenylsilyl, diphenylmethylsilyl and tert-butylmethoxyphenylsilyl.

Geometric isomers may exist in the present compounds. Compounds of this invention may contain carbon-carbon double bonds or carbon-nitrogen double bonds in the E or Z configuration, wherein the term "E" represents higher order substituents on opposite sides of the carbon-carbon or carbon-nitrogen double bond and the term "Z" represents higher order substituents on the same side of the carbon-carbon or carbon-nitrogen double bond as determined by the Cahn-Ingold-Prelog Priority Rules. The compounds of this invention may also exist as a mixture of "E" and "Z" isomers. Substituents around a cycloalkyl or heterocycloalkyl are designated as being of cis or trans configuration. Furthermore, the invention contemplates the various isomers and mixtures thereof resulting from the disposal of substituents around an adamantane ring system. Two substituents around a single ring within an adamantane ring system are designated as being of Z or E relative configuration. For examples, see C. D. Jones, M. Kaselj, R. N. Salvatore, W. J. le Noble J. Org. Chem. 1998, 63, 2758-2760.

Compounds of this invention may contain asymmetrically substituted carbon atoms in the R or S configuration, in which the terms "R" and "S" are as defined by the IUPAC 1974 Recommendations for Section E, Fundamental Stereochemistry, Pure Appl. Chem. (1976) 45, 13-10. Compounds having asymmetrically substituted carbon atoms with equal amounts of R and S configurations are racemic at those carbon atoms. Atoms with an excess of one configuration over the other are assigned the configuration present in the higher amount, preferably an excess of about 85-90%, more preferably an excess of about 95-99%, and still more preferably an excess greater than about 99%. Accordingly, this invention includes racemic mixtures, relative and absolute stereoisomers, and mixtures of relative and absolute stereoisomers.

Isotope Enriched or Labeled Compounds.

Compounds of the invention can exist in isotope-labeled or -enriched form containing one or more atoms having an atomic mass or mass number different from the atomic mass or mass number most abundantly found in nature. Isotopes can be radioactive or non-radioactive isotopes. Isotopes of atoms such as hydrogen, carbon, nitrogen, phosphorous, sulfur, fluorine, chlorine and iodine include, but are not limited to, $2_H$, $3_H$, $13_C$, $14_C$, $15_N$, $^{18}O$, $^{32}P$, $^{35}S$, $^{18}F$, $^{36}Cl$ and $^{125}I$. Compounds that contain other isotopes of these and/or other atoms are within the scope of this invention.

In another embodiment, the isotope-labeled compounds contain deuterium ($^2H$), tritium ($^3H$) or $^{14}C$ isotopes. Isotope-labeled compounds of this invention can be prepared by the general methods well known to persons having ordinary skill in the art. Such isotope-labeled compounds can be conveniently prepared by carrying out the procedures disclosed in the Examples disclosed herein and Schemes by substituting a readily available isotope-labeled reagent for a non-labeled reagent. In some instances, compounds may be treated with isotope-labeled reagents to exchange a normal atom with its isotope, for example, hydrogen for deuterium can be exchanged by the action of a deuterated acid such as $D_2SO_4/D_2O$. In addition to the above, relevant procedures and intermediates are disclosed, for instance, in Lizondo, J et al, Drugs Fut, 21(11), 1116 (1996); Brickner, S J et al., J Med Chem, 39(3), 673 (1996); Mallesham, B et al, Org Lett, 5(7), 963 (2003); PCT publications WO1997010223, WO2005099353, WO1995007271, WO2006008754; U.S. Pat. Nos. 7,538,189; 7,534,814; 7,531,685; 7,528,131; 7,521,421; 7,514,068; 7,511,013; and US Patent Application Publication Nos. 20090137457; 20090131485; 20090131363; 20090118238; 20090111840; 20090105338; 20090105307; 20090105147; 20090093422; 20090088416; and 20090082471, the methods are hereby incorporated by reference.

The isotope-labeled compounds of the invention may be used as standards to determine the effectiveness of Bcl-2 inhibitors in binding assays. Isotope containing compounds have been used in pharmaceutical research to investigate the in vivo metabolic fate of the compounds by evaluation of the mechanism of action and metabolic pathway of the nonisotope-labeled parent compound (Blake et al. J. Pharm. Sci. 64, 3, 367-391 (1975)). Such metabolic studies are important in the design of safe, effective therapeutic drugs, either because the in vivo active compound administered to the patient or because the metabolites produced from the parent compound prove to be toxic or carcinogenic (Foster et al., Advances in Drug Research Vol. 14, pp. 2-36, Academic press, London, 1985; Kato et al, J. Labelled Comp. Radiopharmaceut, 36(10):927-932 (1995); Kushner et al., Can. J. Physiol. Pharmacol, 77, 79-88 (1999).

In addition, non-radio active isotope containing drugs, such as deuterated drugs called "heavy drugs" can be used for the treatment of diseases and conditions related to Bcl-2 activity. Increasing the amount of an isotope present in a compound above its natural abundance is called enrichment. Examples of the amount of enrichment include from about 0.5, 1, 2, 3, 4, 5, 6, 7, 8, 9, 10, 12, 16, 21, 25, 29, 33, 37, 42, 46, 50, 54, 58, 63, 67, 71, 75, 79, 84, 88, 92, 96, to about 100 mol %. Replacement of up to about 15% of normal atom with a heavy isotope has been effected and maintained for a period of days to weeks in mammals, including rodents and dogs, with minimal observed adverse effects (Czajka D M and Finkel A J, Ann. N.Y. Acad. Sci. 1960 84: 770; Thomson J F, Ann. New York Acad. Sci 1960 84: 736; Czakja D M et al., Am. J. Physiol. 1961 201:357). Acute replacement of as high as 15%-23% in human fluids with deuterium was found not to cause toxicity (Blagojevic N et al. in "Dosimetry & Treatment Planning for Neutron Capture Therapy", Zamenhof R, Solares G and Harling 0 Eds. 1994. Advanced Medical Publishing, Madison Wis. pp.125-134; Diabetes Metab. 23: 251 (1997)).

Stable isotope labeling of a drug can alter its physicochemical properties such as pKa and lipid solubility. These effects and alterations can affect the pharmacodynamic response of the drug molecule if the isotopic substitution affects a region involved in a ligand-receptor interaction. While some of the physical properties of a stable isotope-labeled molecule are different from those of the unlabeled one, the chemical and biological properties are the same, with one important exception: because of the increased mass of the heavy isotope, any bond involving the heavy isotope and another atom will be stronger than the same bond between the light isotope and that atom. Accordingly, the incorporation of an isotope at a site of metabolism or enzymatic transformation will slow said reactions potentially altering the pharmacokinetic profile or efficacy relative to the non-isotopic compound.

In an Embodiment (1), this invention provides to a compound of formula (I),

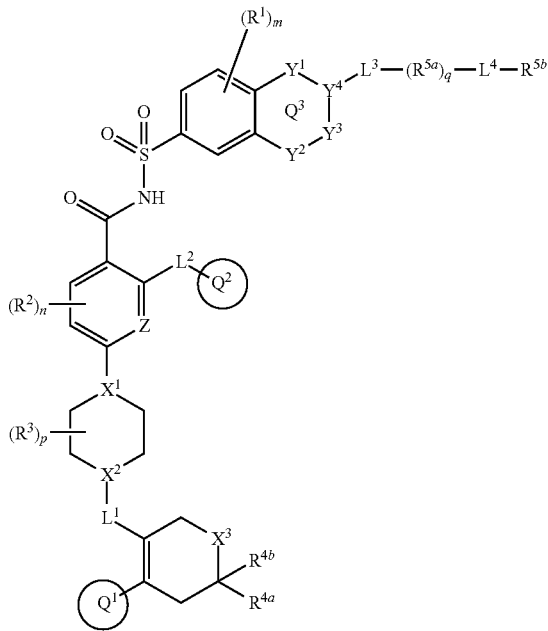

(I)

or a pharmaceutically acceptable salt thereof, wherein:

$L^1$, $L^2$, $L^3$ and $L^4$ are independently selected from $-(CR^CR^D)_u-$, $-(CR^CR^D)_uO(CR^CR^D)_t-$, $-(CR^CR^D)_u$ $NR^A(CR^CR^{D5})_t-$, $-(CR^CR^D)_uS(CR^CR^D)_t-$, $-(CR^CR^D)_uC(O)(CR^CR^D)_t-$, $-(CR^CR^D)_uC(=NR^E)(CR^CR^D)_t-$, $-(CR^CR^D)_uC(S)(CR^CR^D)_t-$, $-(CR^CR^D)_uC(O)O(CR^CR^D)_t-$, $-(CR^CR^D)_uOC(O)(CR^CR^D)_t-$, $-(CR^CR^D)_uC(O)NR^A(CR^CR^D)_t-$, $-(CR^CR^D)_uNR^AC(O)(CR^CR^D)_t-$, $-(CR^CR^D)_uNR^AC(O)NR^B(CR^CR^D)_t-$, $-(CR^CR^D)_uC(=NR^E)NR^B(CR^CR^D)_t-$, $-(CR^CR^D)_uNR^BC(=NR^E)(CR^CR^D)_t-$, $-(CR^CR^D)_uNR^AC(=NR^E)NR^B(CR^CR^D)_t-$, $-(CR^CR^D)_uC(S)NR^A(CR^CR^D)_t-$, $-(CR^CR^D)_uNR^AC(S)(CR^CR^D)_t-$, $-(CR^CR^D)_uNR^AC(S)NR^B(CR^CR^D)_t-$, $-(CR^CR^D)_uS(O)_r(CR^CR^D)_t-$, $-(CR^CR^D)_uS(O)_rNR^{A5}(CR^{C5}R^{D5})_t-$, $-(CR^{C5}R^{D5})_uNR^AS(O)_r(CR^CR^D)_t-$ and $-(CR^CR^D)_uNR^AS(O)_rNR^B(CR^CR^D)_t-$;

$Q^1$ and $Q^2$ are independently selected from aryl and heteroaryl, wherein aryl and heteroaryl are each unsubstituted or substituted with at least one substituent, such as one, two, three or four substituents, independently selected from $R^X$;

$Q^3$ is selected from aryl, $C_{3-10}$ cycloalkyl, heteroaryl and heterocyclyl, wherein aryl, cycloalkyl, heteroaryl and heterocyclyl are each unsubstituted or substituted with at least one substituent, such as one, two, three or four substituents, independently selected from $R^X$;

when $Q^3$ is $C_{3-10}$ cycloalkyl, $Y^1$, $Y^2$ and $Y^3$ are independently selected from $(CR^{6a}R^{6b})_o$, wherein cycloalkyl is unsubstituted or substituted with at least one substituent independently selected from $R^X$;

when $Q^3$ is heteroaryl, $Y^1$, $Y^2$ and $Y^3$ are independently selected from a bond, C, N, O and S, wherein heteroaryl is unsubstituted or substituted with at least one or two substituents independently selected from $R^X$;

when $Q^3$ is heterocyclyl, $Y^1$, $Y^2$ and $Y^3$ are independently selected from $(CR^{6a}R^{6b})_o$, N, O and S, wherein heterocyclyl is unsubstituted or substituted with at least one substituent independently selected from $R^X$;

$X^1$ and $X^2$ are independently selected from C and N;

$X^3$ is selected from $CR^{4c}R^{4d}$ and O;

$Y^4$ is selected from C and N;

Z is selected from C and N;

each $R^1$ is independently selected from hydrogen, halogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, heteroaryl-$C_{1-4}$ alkyl, CN, $NO_2$, $-NR^{A1}R^{B1}$, $-OR^{A1}$, $-C(O)R^{A1}$, $-C(=NR^{E1})R^{A1}$, $-C(=N-OR^{B1})R^{A1}$, $-C(O)OR^{A1}$, $-OC(O)R^{A1}$, $-C(O)NR^{A1}R^{B1}$, $-NR^{A1}C(O)R^{B1}$, $-C(=NR^{E1})NR^{A1}R^{B1}$, $-NR^{A1}C(=NR^{E1})R^{B1}$, $-OC(O)NR^{A1}R^{B1}$, $-NR^{A1}C(O)OR^{B1}$, $-NR^{A1}C(O)NR^{A1}R^{B1}$, $-NR^{A1}C(S)NR^{A1}R^{B1}$, $-NR^{A1}C(=NR^{E1})NR^{A1}R^{B1}$, $-S(O)_rR^{A1}$, $-S(O)(=NR^{E1})R^{B1}$, $-N=S(O)R^{A1}R^{B1}$, $-S(O)_2OR^{A1}$, $-OS(O)_2R^{A1}$, $-NR^{A1}S(O)_rR^{B1}$, $-NR^{A1}S(O)(=NR^{E1})R^{B1}$, $-S(O)_rNR^{A1}R^{B1}$, $-S(O)(=NR^{E1})NR^{A1}R^{B1}$, $-NR^{A1}S(O)_2NR^{A1}R^{B1}$, $-NR^{A1}S(O)(=NR^{E1})NR^{A1}R^{B1}$, $-P(O)R^{A1}R^{B1}$ and $-P(O)(OR^{A1})(OR^{B1})$, wherein alkyl, alkenyl, alkynyl, cycloalkyl, heterocyclyl, aryl and heteroaryl are each unsubstituted or substituted with at least one substituent, such as one, two, three or four substituents, independently selected from $R^X$;

each $R^2$ is independently selected from hydrogen, halogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, heteroaryl-$C_{1-4}$ alkyl, CN, $NO_2$, $-NR^{A2}R^{B2}$, $-OR^{A2}$, $-C(O)R^{A2}$, $-C(=NR^{E2})R^{A2}$, $-C(=N-OR^{B2})R^{A2}$, $-C(O)OR^{A2}$, —OC(O)R$^{A2}$, —C(O)NR$^{A2}$R$^{B2}$, —NR$^{A2}$C(O)R$^{B2}$, —C(=NR$^{E2}$)NR$^{A2}$R$^{B2}$, —NR$^{A2}$C(=NR$^{E2}$)R$^{B2}$, —OC(O)NR$^{A2}$R$^{B2}$, —NR$^{A2}$C(O)OR$^{B2}$, —NR$^{A2}$C(O)NR$^{A2}$R$^{B2}$, —NR$^{A2}$C(S)NR$^{A2}$R$^{B2}$, —NR$^{A2}$C(=NR$^{E2}$)NR$^{A2}$R$^{B2}$, —S(O)$_r$R$^{A2}$, —S(O)(=NR$^{E2}$)R$^{B2}$, —N=S(O)R$^{A2}$R$^{B2}$, —S(O)$_2$OR$^{A2}$, —OS(O)$_2$R$^{A2}$, —NR$^{A2}$S(O)$_r$R$^{B2}$, —NR$^{A2}$S(O)(=NR$^{E2}$)R$^{B2}$, —S(O)$_r$NR$^{A2}$R$^{B2}$, —S(O)(=NR$^{E2}$)NR$^{A2}$R$^{B2}$, —NR$^{A2}$S(O)$_2$NR$^{A2}$R$^{B2}$, —NR$^{A2}$S(O)(=NR$^{E2}$)NR$^{A2}$R$^{B2}$, —P(O)R$^{A2}$R$^{B2}$ and —P(O)(OR$^{A2}$)(OR$^{B2}$), wherein alkyl, alkenyl, alkynyl, cycloalkyl, heterocyclyl, aryl and heteroaryl are each unsubstituted or substituted with at least one substituent, such as one, two, three or four substituents, independently selected from R$^X$;

each R$^3$ is independently selected from hydrogen, halogen, C$_{1-10}$ alkyl, C$_{2-10}$ alkenyl, C$_{2-10}$ alkynyl, C$_{3-10}$ cycloalkyl, C$_{3-10}$ cycloalkyl-C$_{1-4}$ alkyl, heterocyclyl, heterocyclyl-C$_{1-4}$ alkyl, aryl, aryl-C$_{1-4}$ alkyl, heteroaryl, heteroaryl-C$_{1-4}$ alkyl, CN, NO$_2$, —NR$^{A3}$R$^{B3}$, —OR$^{A3}$, —C(O)R$^{A3}$, —C(=NR$^{E3}$)R$^{A3}$, —C(=N—OR$^{B3}$)R$^{A3}$, —C(O)OR$^{A3}$, —OC(O)R$^{A3}$, —C(O)NR$^{A3}$R$^{B3}$, —NR$^{A3}$C(O)R$^{B3}$, —C(=NR$^{E3}$)NR$^{A3}$R$^{B3}$, —NR$^{A3}$C(=NR$^{E3}$)R$^{B3}$, —OC(O)NR$^{A3}$R$^{B3}$, —NR$^{A3}$C(O)OR$^{B3}$, —NR$^{A3}$C(O)NR$^{A3}$R$^{B3}$, —NR$^{A3}$C(S)NR$^{A3}$R$^{B3}$, —NR$^{A3}$C(=NR$^E$)NR$^{A3}$R$^{B3}$, —S(O)$_r$R$^{A3}$, —S(O)(=NR$^{E3}$)R$^{B3}$, —N=S(O)R$^{A3}$R$^{B3}$, —S(O)$_2$OR$^{A3}$, —OS(O)$_2$R$^{A3}$, —NR$^{A3}$S(O)$_r$R$^{B3}$, —NR$^{A3}$S(O)(=NR$^{E3}$)R$^{B3}$, —S(O)$_r$NR$^{A3}$R$^{B3}$, —S(O)(=NR$^{E3}$)NR$^{A3}$R$^{B3}$, —NR$^{A3}$S(O)$_2$NR$^{A3}$R$^{B3}$, —NR$^{A3}$S(O)(=NR$^{E3}$)NR$^{A3}$R$^{B3}$, —P(O)R$^{A3}$R$^{B3}$ and —P(O)(OR$^{A3}$)(OR$^{B3}$), wherein alkyl, alkenyl, alkynyl, cycloalkyl, heterocyclyl, aryl and heteroaryl are each unsubstituted or substituted with at least one substituent, such as one, two, three or four substituents, independently selected from R$^X$;

R$^{4a}$, R$^{4b}$, R$^{4c}$ and R$^{4d}$ are independently selected from hydrogen, halogen, C$_{1-10}$ alkyl, C$_{2-10}$ alkenyl, C$_{2-10}$ alkynyl, C$_{3-10}$ cycloalkyl, C$_{3-10}$ cycloalkyl-C$_{1-4}$ alkyl, heterocyclyl, heterocyclyl-C$_{1-4}$ alkyl, aryl, aryl-C$_{1-4}$ alkyl, heteroaryl, heteroaryl-C$_{1-4}$ alkyl, CN, NO$_2$, —NR$^{A4}$R$^{B4}$, —OR$^{A4}$, —C(O)R$^{A4}$, —C(=NR$^{E4}$)R$^{A4}$, —C(=N—OR$^{B4}$)R$^{A4}$, —C(O)OR$^{A4}$, —OC(O)R$^{A4}$, —C(O)NR$^{A4}$R$^{B4}$, —NR$^{A4}$C(O)R$^{B4}$, —C(=NR$^{E4}$)NR$^{A4}$R$^{B4}$, —NR$^{A4}$C(=NR$^{E4}$)R$^{B4}$, —OC(O)NR$^{A4}$R$^{B4}$, —NR$^{A4}$C(O)OR$^{B4}$, —NR$^{A4}$C(O)NR$^{A4}$R$^{B4}$, —NR$^{A4}$C(S)NR$^{A4}$R$^{B4}$, —NR$^{A4}$C(=NR$^{E4}$)NR$^{A4}$R$^{B4}$, —S(O)$_r$R$^{A4}$, —S(O)(=NR$^{E4}$)R$^{B4}$, —N=S(O)R$^{A4}$R$^{B4}$, —S(O)$_2$OR$^{A4}$, —OS(O)$_2$R$^{A4}$, —NR$^{A4}$S(O)$_r$R$^{B4}$, —NR$^{A4}$S(O)(=NR$^{E4}$)R$^{B4}$, —S(O)$_r$NR$^{A4}$R$^{B4}$, —S(O)(=NR$^{E4}$)NR$^{A4}$R$^{B4}$, —NR$^{A4}$S(O)$_2$NR$^{A4}$R$^{B4}$, —NR$^{A4}$S(O)(=NR$^{E4}$)NR$^{A4}$R$^{B4}$, —P(O)R$^{A4}$R$^{B4}$ and —P(O)(OR$^{A4}$)(OR$^{B4}$), wherein alkyl, alkenyl, alkynyl, cycloalkyl, heterocyclyl, aryl and heteroaryl are each unsubstituted or substituted with at least one substituent, such as one, two, three or four substituents, independently selected from R$^X$;

or "R$^{4a}$ and R$^{4b}$" or "R$^{4c}$ and R$^{4d}$" together with the carbon atoms to which they are attached form a 3-7 membered ring containing 0, 1, 2 or 3 heteroatoms independently selected from oxygen, sulfur, nitrogen, and phosphorus, and optionally substituted with 1, 2 or 3 R$^X$ groups;

each R$^{5a}$ is independently selected from C$_{1-10}$ alkyl, C$_{2-10}$ alkenyl, C$_{2-10}$ alkynyl, C$_{3-10}$ cycloalkyl, C$_{3-10}$ cycloalkyl-C$_{1-4}$ alkyl, heterocyclyl, heterocyclyl-C$_{1-4}$ alkyl, aryl, aryl-C$_{1-4}$ alkyl, heteroaryl, heteroaryl-C$_{1-4}$ alkyl, wherein alkyl, alkenyl, alkynyl, cycloalkyl, heterocyclyl, aryl and heteroaryl are each unsubstituted or substituted with at least one substituent, such as one, two, three or four substituents, independently selected from R$^X$;

R$^{5b}$ is selected from hydrogen, halogen, C$_{1-10}$ alkyl, C$_{2-10}$ alkenyl, C$_{2-10}$ alkynyl, C$_{3-10}$ cycloalkyl, C$_{3-10}$ cycloalkyl-C$_{1-4}$ alkyl, heterocyclyl, heterocyclyl-C$_{1-4}$ alkyl, aryl, aryl-C$_{1-4}$ alkyl, heteroaryl, heteroaryl-C$_{1-4}$ alkyl, CN, NO$_2$, —NR$^{A5}$R$^{B5}$, —OR$^{A5}$, —C(O)R$^{A5}$, —C(=NR$^{E5}$)R$^{A5}$, —C(=N—OR$^{B5}$)R$^{A5}$, —C(O)OR$^{A5}$, —OC(O)R$^{A5}$, —C(O)NR$^{A5}$R$^{B5}$, —NR$^{A5}$C(O)R$^{B5}$, —C(=NR$^{E5}$)NR$^{A5}$R$^{B5}$, —NR$^{A5}$C(=NR$^{E5}$)R$^{B5}$, —OC(O)NR$^{A5}$R$^{B5}$, —NR$^{A5}$C(O)OR$^{B5}$, —NR$^{A5}$C(O)NR$^{A5}$R$^{B5}$, —NR$^{A5}$C(S)NR$^{A5}$R$^{B5}$, —NR$^{A5}$C(=NR$^{E5}$)NR$^{A5}$R$^{B5}$, —S(O)$_r$R$^{A5}$, —S(O)(=NR$^{E5}$)R$^{B5}$, —N=S(O)R$^{A5}$R$^{B5}$, —S(O)$_2$OR$^{A5}$, —OS(O)$_2$R$^{A5}$, —NR$^{A5}$S(O)$_r$R$^{B5}$, —NR$^{A5}$S(O)(=NR$^{E5}$)R$^{B5}$, —S(O)$_r$NR$^{A5}$R$^{B5}$, —S(O)(=NR$^{E5}$)NR$^{A5}$R$^{B5}$, —NR$^{A5}$S(O)$_2$NR$^{A5}$R$^{B5}$, —NR$^{A5}$S(O)(=NR$^{E5}$)NR$^{A5}$R$^{B5}$, —P(O)R$^{A5}$R$^{B5}$ and —P(O)(OR$^{A5}$)(OR$^{B5}$), wherein alkyl, alkenyl, alkynyl, cycloalkyl, heterocyclyl, aryl and heteroaryl are each unsubstituted or substituted with at least one substituent, such as one, two, three or four substituents, independently selected from R$^X$;

each R$^{6a}$ and R$^{6b}$ are independently selected from hydrogen, halogen, C$_{1-10}$ alkyl, C$_{2-10}$ alkenyl, C$_{2-10}$ alkynyl, C$_{3-10}$ cycloalkyl, C$_{3-10}$ cycloalkyl-C$_{1-4}$ alkyl, heterocyclyl, heterocyclyl-C$_{1-4}$ alkyl, aryl, aryl-C$_{1-4}$ alkyl, heteroaryl, heteroaryl-C$_{1-4}$ alkyl, CN, NO$_2$, —NR$^{A6}$R$^{B6}$, —OR$^{A6}$, —C(O)R$^{A6}$, —C(=NR$^{E6}$)R$^{A6}$, —C(=N—OR$^{B6}$)R$^{A6}$, —C(O)OR$^{A6}$, —OC(O)R$^{A6}$, —C(O)NR$^{A6}$R$^{B6}$, —NR$^{A6}$C(O)R$^{B6}$, —C(=NR$^{E6}$)NR$^{A6}$R$^{B6}$, —NR$^{A6}$C(=NR$^{E6}$)R$^{B6}$, —OC(O)NR$^{A6}$R$^{B6}$, —NR$^{A6}$C(O)OR$^{B6}$, —NR$^{A6}$C(O)NR$^{A6}$R$^{B6}$, —NR$^{A6}$C(S)NR$^{A6}$R$^{B6}$, —NR$^{A6}$C(=NR$^{E6}$)NR$^{A6}$R$^{B6}$, —S(O)$_r$R$^{A6}$, —S(O)(=NR$^{E6}$)R$^{B6}$, —N=S(O)R$^{A6}$R$^{B6}$, —S(O)$_2$OR$^{A6}$, —OS(O)$_2$R$^{A6}$, —NR$^{A6}$S(O)$_r$R$^{B6}$, —NR$^{A6}$S(O)(=NR$^{E6}$)R$^{B6}$, —S(O)$_r$NR$^{A6}$R$^{B6}$, —S(O)(=NR$^{E6}$)NR$^{A6}$R$^{B6}$, —NR$^{A6}$S(O)$_2$NR$^{A6}$R$^{B6}$, —NR$^{A6}$S(O)(=NR$^{E6}$)NR$^{A6}$R$^{B6}$, —P(O)R$^{A6}$R$^{B6}$ and —P(O)(OR$^{A6}$)(OR$^{B6}$), wherein alkyl, alkenyl, alkynyl, cycloalkyl, heterocyclyl, aryl and heteroaryl are each unsubstituted or substituted with at least one substituent, such as one, two, three or four substituents, independently selected from R$^X$;

or R$^{6a}$ and R$^{6b}$ together with the carbon atoms to which they are attached form a 3-7 membered ring containing 0, 1, 2 or 3 heteroatoms independently selected from oxygen, sulfur, nitrogen, and phosphorus, and optionally substituted with 1, 2 or 3 R$^X$ groups;

each R$^A$, R$^{A1}$, R$^{A2}$, R$^{A3}$, R$^{A4}$, R$^{A5}$, R$^{A6}$, R$^B$, R$^{B1}$, R$^{B2}$, R$^{B3}$, R$^{B4}$, R$^{B5}$ and R$^{B6}$ are independently selected from hydrogen, C$_{1-10}$ alkyl, C$_{2-10}$ alkenyl, C$_{2-10}$ alkynyl, C$_{3-10}$ cycloalkyl, C$_{3-10}$ cycloalkyl-C$_{1-4}$ alkyl, heterocyclyl, heterocyclyl-C$_{1-4}$ alkyl, aryl, aryl-C$_{1-4}$ alkyl, heteroaryl, and heteroaryl-C$_{1-4}$ alkyl, wherein alkyl, alkenyl, alkynyl, cycloalkyl, heterocyclyl, aryl and heteroaryl are each unsubstituted or substituted with at least one substituent, such as one, two, three, or four substituents, independently selected from R$^X$;

or each "R$^A$ and R$^B$", "R$^{A1}$ and R$^{B1}$", "R$^{A2}$ and R$^{B2}$", "R$^{A3}$ and R$^{B3}$", "R$^{A4}$ and R$^{B4}$", "R$^{A5}$ and R$^{B5}$" and "R$^{A6}$ and R$^{B6}$" together with the atom(s) to which they are attached form a heterocyclic ring of 4 to 12 members containing 0, 1, or 2 additional heteroatoms independently selected from oxygen, sulfur, nitrogen and phosphorus, and optionally substituted with 1, 2 or 3 R$^X$ groups;

each R$^C$ and R$^D$ are independently selected from hydrogen, halogen, C$_{1-10}$ alkyl, C$_{2-10}$ alkenyl, C$_{2-10}$ alkynyl, C$_{3-10}$ cycloalkyl, C$_{3-10}$ cycloalkyl-C$_{1-4}$ alkyl, heterocyclyl, heterocyclyl-C$_{1-4}$ alkyl, aryl, aryl-C$_{1-4}$ alkyl, heteroaryl and heteroaryl-C$_{1-4}$ alkyl, wherein alkyl, alkenyl, alkynyl, cycloalkyl, heterocyclyl, aryl and heteroaryl are each unsubstituted or substituted with at least one substituent, such as one, two, three or four substituents, independently selected from R$^X$;

or R$^C$ and R$^D$ together with the carbon atom(s) to which they are attached form a ring of 3 to 12 members containing 0, 1 or 2 heteroatoms independently selected from oxygen, sulfur and nitrogen, and optionally substituted with 1, 2 or 3 $R^X$ groups;

each $R^{E1}$, $R^{E2}$, $R^{E3}$, $R^{E4}$, $R^{E5}$ and $R^{E6}$ are independently selected from hydrogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, heteroaryl-$C_{1-4}$ alkyl, CN, $NO_2$, $OR^{a1}$, $SR^{a1}$, —$S(O)_rR^{a1}$, —$C(O)R^{a1}$, $C(O)OR^{a1}$, —$C(O)NR^{a1}R^{b1}$ and —$S(O)_rNR^{a1}R^{b1}$, wherein alkyl, alkenyl, alkynyl, cycloalkyl, heterocyclyl, aryl and heteroaryl are each unsubstituted or substituted with at least one substituent, such as one, two, three or four substituents, independently selected from $R^Y$;

each $R^X$ is independently selected from hydrogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, heteroaryl-$C_{1-4}$ alkyl, halogen, CN, $NO_2$, —$(CR^{c1}R^{d1})_tNR^{a1}R^{b1}$, —$(CR^{c1}R^{d1})_tOR^{b1}$, —$(CR^{c1}R^{d1})_tC(O)R^{a1}$, —$(CR^{c1}R^{d1})_tC(=NR^{c1})R^{a1}$, —$(CR^{c1}R^{d1})_tC(=N-OR^{b1})R^{a1}$, —$(CR^{c1}R^{d1})_tC(O)OR^{b1}$, —$(CR^{c1}R^{d1})_tOC(O)R^{b1}$, —$(CR^{c1}R^{d1})_tC(O)NR^{a1}R^{b1}$, —$(CR^{c1}R^{d1})_tNR^{a1}C(O)R^{b1}$, —$(CR^{c1}R^{d1})_tC(=NR^{c1})NR^{a1}R^{b1}$, —$(CR^{c1}R^{d1})_tNR^{a1}C(=NR^{c1})R^{b1}$, —$(CR^{c1}R^{d1})_tOC(O)NR^{a1}R^{b1}$, —$(CR^{c1}R^{d1})_tNR^{a1}C(O)OR^{b1}$, —$(CR^{c1}R^{d1})_tNR^{a1}C(O)NR^{a1}R^{b1}$, —$(CR^{c1}R^{d1})_tNR^{a1}C(S)NR^{a1}R^{b1}$, —$(CR^{c1}R^{d1})_tNR^{a1}C(=NR^{c1})NR^{a1}R^{b1}$, —$(CR^{c1}R^{d1})_tS(O)_rR^{b1}$, —$(CR^{c1}R^{d1})_tS(O)(=NR^{c1})R^{b1}$, —$(CR^{c1}R^{d1})_tN=S(O)R^{a1}R^{b1}$, —$(CR^{c1}R^{d1})_tS(O)_2OR^{b1}$, —$(CR^{c1}R^{d1})_tOS(O)_2R^{b1}$, —$(CR^{c1}R^{d1})_tNR^{a1}S(O)_rR^{b1}$, —$(CR^{c1}R^{d1})_tNR^{a1}S(O)(=NR^{c1})R^{b1}$, —$(CR^{c1}R^{d1})_tS(O)_rNR^{a1}R^{b1}$, —$(CR^{c1}R^{d1})_tS(O)(=NR^{c1})NR^{a1}R^{b1}$, —$(CR^{c1}R^{d1})_tNR^{a1}S(O)_2NR^{a1}R^{b1}$, —$(CR^{c1}R^{d1})_tNR^{a1}S(O)(=NR^{c1})NR^{a1}R^{b1}$, —$(CR^{c1}R^{d1})_tP(O)R^{a1}R^{b1}$ and —$(CR^{c1}R^{d1})_tP(O)(OR^{a1})(OR^{b1})$, wherein alkyl, alkenyl, alkynyl, cycloalkyl, heterocyclyl, aryl and heteroaryl are each unsubstituted or substituted with at least one substituent, such as one, two, three or four substituents, independently selected from $R^Y$;

each $R^{a1}$ and each $R^{b1}$ are independently selected from hydrogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl and heteroaryl-$C_{1-4}$ alkyl, wherein alkyl, alkenyl, alkynyl, cycloalkyl, heterocyclyl, aryl and heteroaryl are each unsubstituted or substituted with at least one substituent, such as one, two, three or four substituents, independently selected from $R^Y$;

or $R^{a1}$ and $R^{b1}$ together with the atom(s) to which they are attached form a heterocyclic ring of 4 to 12 members containing 0, 1 or 2 additional heteroatoms independently selected from oxygen, sulfur, nitrogen and phosphorus, and optionally substituted with 1, 2 or 3 $R^Y$ groups;

each $R^{c1}$ and each $R^{d1}$ are independently selected from hydrogen, halogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl and heteroaryl-$C_{1-4}$ alkyl, wherein alkyl, alkenyl, alkynyl, cycloalkyl, heterocyclyl, aryl and heteroaryl are each unsubstituted or substituted with at least one substituent, such as one, two, three or four substituents, independently selected from $R^Y$;

or $R^{c1}$ and $R^{d1}$ together with the carbon atom(s) to which they are attached form a ring of 3 to 12 members containing 0, 1 or 2 heteroatoms independently selected from oxygen, sulfur and nitrogen, and optionally substituted with 1, 2 or 3 $R^Y$ groups;

each $R^{c1}$ is independently selected from hydrogen, $C_{1-10}$ alkyl, $C_{3-10}$ cycloalkyl, $C_{3-10}$ cycloalkyl-$C_{1-4}$ alkyl, CN, $NO_2$, —$OR^{a2}$, —$SR^{a2}$, —$S(O)_rR^{a2}$, —$C(O)R^{a2}$, —$C(O)OR^{a2}$, —$S(O)_rNR^{a2}R^{b2}$ and —$C(O)NR^{a2}R^{b2}$;

each $R^Y$ is independently selected from $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, heteroaryl-$C_{1-4}$ alkyl, halogen, CN, $NO_2$, —$(CR^{c2}R^{d2})_tNR^{a2}R^{b2}$, —$(CR^{c2}R^{d2})_tOR^{b2}$, —$(CR^{c2}R^{d2})_tC(O)R^{a2}$, —$(CR^{c2}R^{d2})_tC(=NR^{e2})R^{a1}$, —$(CR^{c2}R^{d2})_tC(=N-OR^{b2})R^{a2}$, —$(CR^{c2}R^{d2})_tC(O)OR^{b2}$, —$(CR^{c2}R^{d2})_tOC(O)R^{b2}$, —$(CR^{c2}R^{d2})_tC(O)NR^{a2}R^{b2}$, —$(CR^{c2}R^{d2})_tNR^{a2}C(O)R^{b2}$, —$(CR^{c2}R^{d2})_tC(=NR^{e2})NR^{a2}R^{b2}$, —$(CR^{c2}R^{d2})_tNR^{a2}C(=NR^{e2})R^{b2}$, —$(CR^{c2}R^{d2})_tOC(O)NR^{a2}R^{b2}$, —$(CR^{c2}R^{d2})_tNR^{a2}C(O)OR^{b2}$, —$(CR^{c2}R^{d2})_tNR^{a2}C(O)NR^{a2}R^{b2}$, —$(CR^{c2}R^{d2})_tNR^{a2}C(S)NR^{a2}R^{b2}$, —$(CR^{c2}R^{d2})_tNR^{a2}C(=NR^{e2})NR^{a2}R^{b2}$, —$(CR^{c2}R^{d2})_tS(O)_rR^{b2}$, —$(CR^{c2}R^{d2})_tS(O)(=NR^{e2})R^{b2}$, —$(CR^{c2}R^{d2})_tN=S(O)R^{a2}R^{b2}$, —$(CR^{c2}R^{d2})_tS(O)_2OR^{b2}$, —$(CR^{c2}R^{d2})_tOS(O)_2R^{b2}$, —$(CR^{c2}R^{d2})_tNR^{a2}S(O)_rR^{b2}$, —$(CR^{c2}R^{d2})_tNR^{a2}S(O)(=NR^{e2})R^{b2}$, —$(CR^{c2}R^{d2})_tS(O)_rNR^{a2}R^{b2}$, —$(CR^{c2}R^{d2})_tS(O)(=NR^{e2})NR^{a2}NR^{b2}$, —$(CR^{c2}R^{d2})_tNR^{a2}S(O)_2NR^{a2}R^{b2}$, —$(CR^{c2}R^{d2})_tNR^{a2}S(O)(=NR^{e2})NR^{a2}R^{b2}$, —$(CR^{c2}R^{d2})_tP(O)R^{a2}R^{b2}$ and —$(CR^{c2}R^{d2})_tP(O)(OR^{a2})(OR^{b2})$, wherein alkyl, alkenyl, alkynyl, cycloalkyl, heterocyclyl, aryl and heteroaryl are each unsubstituted or substituted with at least one substituent, such as one, two, three or four substituents, independently selected from OH, CN, amino, halogen, $C_{1-10}$ alkyl, $C_{2-10}$ alkenyl, $C_{2-10}$ alkynyl, $C_{3-10}$ cycloalkyl, $C_{1-10}$ alkoxy, $C_{3-10}$ cycloalkoxy, $C_{1-10}$ alkylthio, $C_{3-10}$ cycloalkylthio, $C_{1-10}$ alkylamino, $C_{3-10}$ cycloalkylamino and di($C_{1-10}$ alkyl)amino;

each $R^{a2}$ and each $R^{b2}$ are independently selected from hydrogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, $C_{1-10}$ alkoxy, $C_{3-10}$ cycloalkoxy, $C_{1-10}$ alkylthio, $C_{3-10}$ cycloalkylthio, $C_{1-10}$ alkylamino, $C_{3-10}$ cycloalkylamino, di($C_{1-10}$ alkyl)amino, heterocyclyl, heterocyclyl-$C_{1-4}$ alkyl, aryl, aryl-$C_{1-4}$ alkyl, heteroaryl and heteroaryl-$C_{1-4}$ alkyl, wherein alkyl, alkenyl, alkynyl, cycloalkyl, alkoxy, cycloalkoxy, alkylthio, cycloalkylthio, alkylamino, cycloalkylamino, heterocyclyl, aryl and heteroaryl are each unsubstituted or substituted with at least one substituent, such as one, two, three or four substituents, independently selected from halogen, CN, $C_{1-10}$ alkyl, $C_{2-10}$ alkenyl, $C_{2-10}$ alkynyl, $C_{3-10}$ cycloalkyl, OH, $C_{1-10}$ alkoxy, $C_{3-10}$ cycloalkoxy, $C_{1-10}$ alkylthio, $C_{3-10}$ cycloalkylthio, amino, $C_{1-10}$ alkylamino, $C_{3-10}$ cycloalkylamino and di($C_{1-10}$ alkyl)amino;

or $R^{a2}$ and $R^{b2}$ together with the atom(s) to which they are attached form a heterocyclic ring of 4 to 12 members containing 0, 1 or 2 additional heteroatoms independently selected from oxygen, sulfur, nitrogen and phosphorus, and optionally substituted with 1 or 2 substituents, independently selected from halogen, CN, $C_{1-10}$ alkyl, $C_{2-10}$ alkenyl, $C_{2-10}$ alkynyl, $C_{3-10}$ cycloalkyl, OH, $C_{1-10}$ alkoxy, $C_{3-10}$ cycloalkoxy, $C_{1-10}$ alkylthio, $C_{3-10}$ cycloalkylthio, amino, $C_{1-10}$ alkylamino, $C_{3-10}$ cycloalkylamino and di($C_{1-10}$ alkyl)amino;

each $R^{c2}$ and each $R^{b2}$ are independently selected from hydrogen, halogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, $C_{1-10}$ alkoxy, $C_{3-10}$ cycloalkoxy, $C_{1-10}$ alkylthio, $C_{3-10}$ cycloalkylthio, $C_{1-10}$ alkylamino, $C_{3-10}$ cycloalkylamino, di($C_{1-10}$ alkyl)amino, heterocyclyl, heterocyclyl-$C_{1-4}$ alkyl, aryl, aryl-$C_{1-4}$ alkyl, heteroaryl and heteroaryl-$C_{1-4}$ alkyl, wherein alkyl, alkenyl, alkynyl, cycloalkyl, alkoxy, cycloalkoxy, alkylthio, cycloalkylthio, alkylamino, cycloalkylamino, heterocyclyl, aryl and heteroaryl are each unsubstituted or substituted with at least one substituent, such as one, two, three or four substituents, independently selected from halogen, CN, $C_{1-10}$ alkyl, $C_{2-10}$ alkenyl, $C_{2-10}$ alkynyl, $C_{3-10}$ cycloalkyl, OH, $C_{1-10}$ alkoxy, $C_{3-10}$ cycloalkoxy, $C_{1-10}$ alkylthio, $C_{3-10}$ cycloalkylthio, amino, $C_{1-10}$ alkylamino, $C_{3-10}$ cycloalkylamino and di($C_{1-10}$ alkyl)amino;

or $R^{c2}$ and $R^{d2}$ together with the carbon atom(s) to which they are attached form a ring of 3 to 12 members containing 0, 1 or 2 heteroatoms independently selected from oxygen, sulfur and nitrogen, and optionally substituted with 1 or 2 substituents, independently selected from halogen, CN, $C_{1-10}$ alkyl, $C_{2-10}$ alkenyl, $C_{2-10}$ alkynyl, $C_{3-10}$ cycloalkyl, OH, $C_{1-10}$ alkoxy, $C_{3-10}$ cycloalkoxy, $C_{1-10}$ alkylthio, $C_{3-10}$ cycloalkylthio, amino, $C_{1-10}$ alkylamino, $C_{3-10}$ cycloalkylamino and di($C_{1-10}$ alkyl)amino;

each $R^{e2}$ is independently selected from hydrogen, CN, $NO_2$, $C_{1-10}$ alkyl, $C_{3-10}$ cycloalkyl, $C_{3-10}$ cycloalkyl-$C_{1-4}$ alkyl, $C_{1-10}$ alkoxy, $C_{3-10}$ cycloalkoxy, —C(O)$C_{1-4}$ alkyl, —C(O)$C_{3-10}$ cycloalkyl, —C(O)OC$_{1-4}$ alkyl, —C(O)OC$_{3-10}$ cycloalkyl, —C(O)N($C_{1-4}$ alkyl)$_2$, —C(O)N($C_{3-10}$ cycloalkyl)$_2$, —S(O)$_2$$C_{1-4}$ alkyl, —S(O)$_2$$C_{3-10}$ cycloalkyl, —S(O)$_2$N($C_{1-4}$ alkyl)$_2$ and —S(O)$_2$N($C_{3-10}$ cycloalkyl)$_2$;

m is selected from 0, 1, 2 and 3;
n is selected from 0, 1, 2 and 3;
o is selected from 0, 1 and 2;
p is selected from 0, 1, 2, 3 and 4;
q is selected from 0 and 1;
each r is independently selected from 0, 1 and 2;
each t is independently selected from 0, 1, 2, 3 and 4;
each u is independently selected from 0, 1, 2, 3 and 4.

In another Embodiment (2), the invention provides a compound of Embodiment (1) or a pharmaceutically acceptable salt thereof, wherein $Q^1$ is aryl, wherein aryl is unsubstituted or substituted with at least one substituent independently selected from $R^X$.

In another Embodiment (3), the invention provides a compound of Embodiment (2) or a pharmaceutically acceptable salt thereof, wherein $Q^1$ is phenyl, wherein phenyl is unsubstituted or substituted with at least one substituent independently selected from $R^X$.

In another Embodiment (4), the invention provides a compound of Embodiment (3) or a pharmaceutically acceptable salt thereof, wherein $Q^1$ is phenyl, wherein phenyl is unsubstituted or substituted with at least one substituent independently selected from $C_{1-4}$ alkyl, $C_{3-6}$ cycloalkyl, halogen, CN, $CF_3$ and $OCF_3$, wherein alkyl and cycloalkyl are each unsubstituted or substituted with at least one substituent independently selected from R.

In another Embodiment (5), the invention provides a compound of Embodiment (4) or a pharmaceutically acceptable salt thereof, wherein $Q^1$ is phenyl, wherein phenyl is substituted with halogen.

In another Embodiment (6), the invention provides a compound of Embodiment (5) or a pharmaceutically acceptable salt thereof, wherein $Q^1$ is

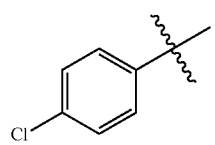

In another Embodiment (7), the invention provides a compound of Embodiment (1) or a pharmaceutically acceptable salt thereof, wherein $Q^1$ is heteroaryl, wherein heteroaryl is unsubstituted or substituted with at least one substituent independently selected from $R^X$.

In another Embodiment (8), the invention provides a compound of any one of Embodiments (1)-(7) or a pharmaceutically acceptable salt thereof, wherein $Q^2$ is aryl, wherein aryl is unsubstituted or substituted with at least one substituent independently selected from $R^X$.

In another Embodiment (9), the invention provides a compound of any one of Embodiments (1)-(7) or a pharmaceutically acceptable salt thereof, wherein $Q^2$ is heteroaryl, wherein heteroaryl is unsubstituted or substituted with at least one substituent independently selected from $R^X$.

In another Embodiment (10), the invention provides a compound of Embodiment (9) or a pharmaceutically acceptable salt thereof, wherein $Q^2$ is selected from

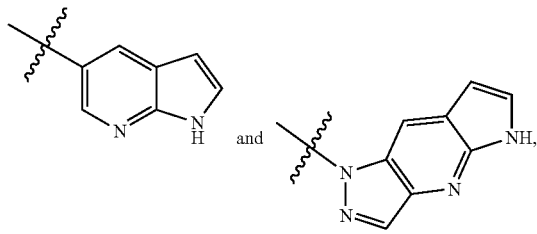 [SMILES: *c1cnc2[nH]ccc2c1 ; *n1ncc2nc3[nH]ccc3cc21]

which is unsubstituted or substituted with at least one substituent independently selected from $R^X$.

In another Embodiment (11), the invention provides a compound of any one of Embodiments (1)-(10) or a pharmaceutically acceptable salt thereof, wherein $L^1$ is —$(CR^CR^D)_u$—.

In another Embodiment (12), the invention provides a compound of Embodiment (11) or a pharmaceutically acceptable salt thereof, wherein $L^1$ is —$CH_2$—.

In another Embodiment (13), the invention provides a compound of any one of Embodiments (1)-(12) or a pharmaceutically acceptable salt thereof, wherein $L^2$ is selected from —$(CR^CR^D)_u$—, —$(CR^CR^D)_uO(CR^CR^D)_t$—, —$(CR^CR^D)_uS(CR^CR^D)_t$—, —$(CR^CR^D)_uS(O)_r(CR^CR^D)_u$—.

In another Embodiment (14), the invention provides a compound of Embodiment (13) or a pharmaceutically acceptable salt thereof, wherein $L^2$ is selected from —O—, —S—, and —S(O)$_r$—.

In another Embodiment (15), the invention provides a compound of Embodiment (14) or a pharmaceutically acceptable salt thereof, wherein $L^2$ is —O—.

In another Embodiment (16), the invention provides a compound of Embodiment (14) or a pharmaceutically acceptable salt thereof, wherein $L^2$ is —S—.

In another Embodiment (17), the invention provides a compound of Embodiment (13) or a pharmaceutically acceptable salt thereof, wherein $L^2$ is —$(CR^CR^D)_u$— and u is 0.

In another Embodiment (18), the invention provides a compound of any one of Embodiments (1)-(17) or a pharmaceutically acceptable salt thereof, wherein $X^1$ is C.

In another Embodiment (19), the invention provides a compound of any one of Embodiments (1)-(17) or a pharmaceutically acceptable salt thereof, wherein $X^1$ is N.

In another Embodiment (20), the invention provides a compound of any one of Embodiments (1)-(19) or a pharmaceutically acceptable salt thereof, wherein $X^2$ is C.

In another Embodiment (21), the invention provides a compound of any one of Embodiments (1)-(19) or a pharmaceutically acceptable salt thereof, wherein $X^2$ is N.

In another Embodiment (22), the invention provides a compound of any one of Embodiments (1)-(21) or a pharmaceutically acceptable salt thereof, wherein $X^3$ is $CR^{4a}R^{4b}$.

In another Embodiment (23), the invention provides a compound of Embodiment (22) or a pharmaceutically acceptable salt thereof, wherein $X^3$ is selected from $CH_2$ and $C(CH_3)_2$.

In another Embodiment (24), the invention provides a compound of any one of Embodiments (1)-(21) or a pharmaceutically acceptable salt thereof, wherein $X^3$ is O.

In another Embodiment (25), the invention provides a compound of Embodiment (1) or a pharmaceutically acceptable salt thereof, wherein $Q^1$ is aryl, wherein aryl is unsubstituted or substituted with at least one substituent independently selected from $R^X$;

$Q^2$ is heteroaryl, wherein heteroaryl is unsubstituted or substituted with at least one substituent independently selected from $R^X$;

$L^1$ is $—(CR^CR^D)_u—$; $L^2$ is selected from $—(CR^CR^D)_u—$, $—(CR^CR^D)_uO(CR^CR^D)_t—$, $—(CR^CR^D)_uS(CR^CR^D)_t—$, $—(CR^CR^D)_uS(O)_r(CR^CR^D)_t—$;

$X^1$ is N; $X^2$ is N; $X^3$ is $-CR^{4c}R^{4d}$; Z is C;

$R^1$ is $NO_2$ or $SO_2CF_3$; $R^2$ is hydrogen; $R^3$ is hydrogen; m is 1; n is 1; p is 1; $R^{4a}$ and $R^{4b}$ are independently selected from hydrogen and $C_{1-10}$ alkyl, wherein alkyl is unsubstituted or substituted with at least one substituent independently selected from $R^X$.

In another Embodiment (26), the invention provides a compound of Embodiment (25) or a pharmaceutically acceptable salt thereof, wherein $Q^1$ is phenyl, wherein phenyl is unsubstituted or substituted with at least one substituent independently selected from $C_{1-4}$ alkyl, $C_{3-6}$ cycloalkyl, halogen, CN, $CF_3$ and $OCF_3$;

$Q^2$ is selected from

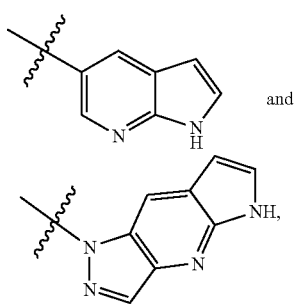

and which are each independently unsubstituted or substituted with at least one substituent independently selected from $R^X$;

$L^1$ is $—(CH_2)_u—$; $L^2$ is selected from a bond, $—O—$, $—S—$, and $—S(O)_r—$;

$X^1$ is N; $X^2$ is N; $X^3$ is selected from $—CH_2—$ and $—C(CH_3)_2$;

$R^1$ is $NO_2$;

$R^{4a}$ and $R^{4b}$ are independently selected from hydrogen and $C_{1-10}$ alkyl.

In another Embodiment (27), the invention provides a compound of Embodiment (26) or a pharmaceutically acceptable salt thereof, wherein $Q^1$ is

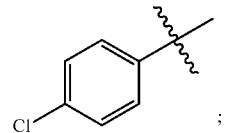 [SMILES: *c1ccc(Cl)cc1]

;

$Q^2$ is selected from

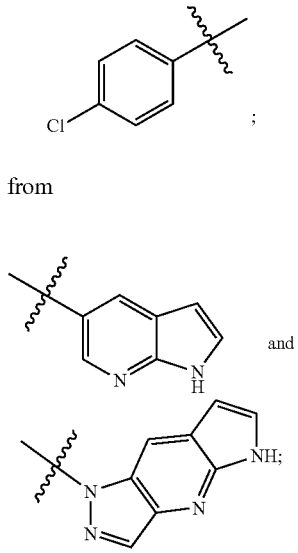

and $L^1$ is $—CH_2—$; $L^2$ is a bond or $—O—$;

$X^1$ is N; $X^2$ is N; $X^3$ is $—CH_2—$;

$R^{4a}$ and $R^{4b}$ are independently selected from hydrogen and methyl.

In another Embodiment (28), the invention provides a compound of any one of Embodiments (1)-(27) or a pharmaceutically acceptable salt thereof, wherein $Q^3$ is heterocyclyl.

In another Embodiment (29), the invention provides a compound of Embodiment (28) or a pharmaceutically acceptable salt thereof, wherein $Y^1$ is $NR^{E9}$.

In another Embodiment (30), the invention provides a compound of Embodiment (29) or a pharmaceutically acceptable salt thereof, wherein $Y^1$ is NH.

In another Embodiment (31), the invention provides a compound of Embodiment (28) or a pharmaceutically acceptable salt thereof, wherein $Y^1$ is O.

In another Embodiment (32), the invention provides a compound of Embodiment (28) or a pharmaceutically acceptable salt thereof, wherein $Y^1$ is S.

In another Embodiment (33), the invention provides a compound of any one of Embodiments (28)-(32) or a pharmaceutically acceptable salt thereof, wherein $Y^2$ is $CR^{6a}R^{6b}$.

In another Embodiment (34), the invention provides a compound of Embodiment (33) or a pharmaceutically acceptable salt thereof, wherein $Y^2$ is $CH_2$.

In another Embodiment (35), the invention provides a compound of any one of Embodiments (28)-(32) or a pharmaceutically acceptable salt thereof, wherein $Y^2$ is NH.

In another Embodiment (36), the invention provides a compound of any one of Embodiments (28)-(32), wherein $Y^2$ is 0.

In another Embodiment (37), the invention provides a compound of any one of Embodiments (28)-(32), wherein $Y^2$ is S.

In another Embodiment (38), the invention provides a compound of any one of Embodiments (28)-(37) or a pharmaceutically acceptable salt thereof, wherein $Y^3$ is selected from $(CR^{6a}R^{6b})_o$, and o is selected from 0 and 1.

In another Embodiment (39), the invention provides a compound of Embodiment (38) or a pharmaceutically acceptable salt thereof, wherein $Y^3$ is $CR^{6a}R^{6b}$.

In another Embodiment (40), the invention provides a compound of Embodiment (39) or a pharmaceutically acceptable salt thereof, wherein $R^{6a}$ and $R^{6b}$ are independently selected from hydrogen and $C_{1-10}$ alkyl.

In another Embodiment (41), the invention provides a compound of any one of Embodiments (28)-(40), wherein $Y^4$ is C.

In another Embodiment (42), the invention provides a compound of any one of Embodiments (28)-(40), wherein $Y^4$ is N.

In another Embodiment (43), the invention provides a compound of any one of Embodiments (1)-(27) or a pharmaceutically acceptable salt thereof, wherein $Q^3$ is aryl.

In another Embodiment (44), the invention provides a compound of any one of Embodiments (1)-(27) or a pharmaceutically acceptable salt thereof, wherein $Q^3$ is heteroaryl.

In another Embodiment (45), the invention provides a compound of Embodiment (44) or a pharmaceutically acceptable salt thereof, wherein $Q^3$ is

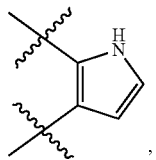 [SMILES: *c1cc[nH]c1*]

In another Embodiment (46), the invention provides a compound of any one of Embodiments (28)-(42) or a pharmaceutically acceptable salt thereof, wherein $Q^3$ is selected from

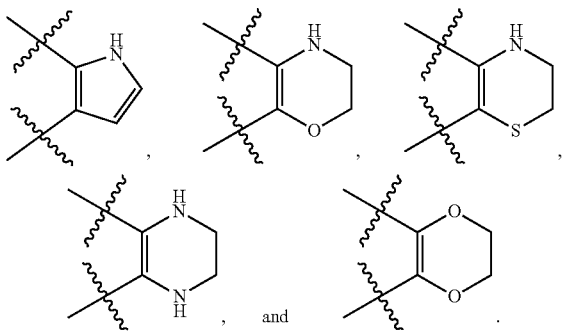

In another Embodiment (47), the invention provides a compound of any one of Embodiments (1)-(27) or a pharmaceutically acceptable salt thereof, wherein $Q^3$ is $C_{3-10}$ cycloalkyl.

In another Embodiment (48), the invention provides a compound of any one of Embodiments (1)-(47) or a pharmaceutically acceptable salt thereof, wherein Z is C.

In another Embodiment (49), the invention provides a compound of any one of Embodiments (1)-(47) or a pharmaceutically acceptable salt thereof, wherein Z is N.

In another Embodiment (50), the invention provides a compound of any one of Embodiments (1)-(49) or a pharmaceutically acceptable salt thereof, wherein $R^1$ is selected from $NO_2$ and $SO_2CF_3$, and m is 1.

In another Embodiment (51), the invention provides a compound of any one of Embodiments (1)-(50) or a pharmaceutically acceptable salt thereof, wherein $R^2$ is selected from hydrogen, halogen, $C_{1-10}$ alkyl, $C_{3-10}$ cycloalkyl, CN alkoxy, CN, $-NR^{A2}R^{B2}$, and $-OR^{A2}$.

In another Embodiment (52), the invention provides a compound of Embodiment (51) or a pharmaceutically acceptable salt thereof, wherein $R^2$ is hydrogen.

In another Embodiment (53), the invention provides a compound of any one of Embodiments (1)-(52) or a pharmaceutically acceptable salt thereof, wherein $R^3$ is selected from hydrogen, halogen, $C_{1-10}$ alkyl, $C_{3-10}$ cycloalkyl, CN, $-NR^{A3}R^{B3}$, and $-OR^{A3}$.

In another Embodiment (54), the invention provides a compound of Embodiment (53) or a pharmaceutically acceptable salt thereof, wherein $R^3$ is hydrogen.

In another Embodiment (55), the invention provides a compound of any one of Embodiments (1)-(54) or a pharmaceutically acceptable salt thereof, wherein $R^{4a}$ and $R^{4b}$ are independently selected from hydrogen and $C_{1-10}$ alkyl, wherein alkyl is unsubstituted or substituted with at least one substituent independently selected from $R^X$.

In another Embodiment (56), the invention provides a compound of Embodiment (55) or a pharmaceutically acceptable salt thereof, wherein $R^{4a}$ and $R^{4b}$ are independently selected from hydrogen and methyl.

In another Embodiment (57), the invention provides a compound of any one of Embodiments (1)-(56) or a pharmaceutically acceptable salt thereof, wherein $L^3$ is selected from $-(CR^CR^D)_u-$, $-(CR^CR^D)_uO(CR^CR^D)_t-$, $-(CR^CR^D)_uOC(O)(CR^CR^D)_t-$, $-(CR^CR^D)_uC(O)O(CR^CR^D)_t-$, $-(CR^CR^D)_uNR^AC(O)(CR^CR^D)_t-$, $-(CR^CR^D)_uC(O)NR^A(CR^CR^D)_t-$, $-(CR^CR^D)_uNR^AC(O)O(CR^CR^D)_t-$, $-(CR^CR^D)_uS(O)_r(CR^CR^D)_t-$ and $-(CR^{C5}R^{D5})_uNR^AS(O)_r(CR^CR^D)_t-$.

In another Embodiment (58), the invention provides a compound of Embodiment (57) or a pharmaceutically acceptable salt thereof, wherein u is selected from 0, 1 and 2 and t is selected from 0 and 1.

In another Embodiment (59), the invention provides a compound of Embodiment (58) or a pharmaceutically acceptable salt thereof, wherein $L^3$ is selected from a bond, $-CH_2-$, $-(CH_2)_2-$, $-CH_2O-$, $-(CH_2)_2O-$, $-(CH_2)_2OC(O)-$, $-C(O)-$, $-C(O)O-$, $-CH_2C(O)-$, $-CH_2C(O)O-$, $-CH_2OC(O)-$, $-C(O)NCH_3-$, $-CH_2NHC(O)-$, $-CH_2NHC(O)O-$, $-(CH_2)_2NHC(O)-$, $-(CH_2)_2NHC(O)O-$, $-(CH_2)_2SO_2-$, and $-CH_2NHSO_2-$.

In another Embodiment (60), the invention provides a compound of any one of Embodiments (1)-(59) or a pharmaceutically acceptable salt thereof, wherein q is selected from 0 and 1.

In another Embodiment (61), the invention provides a compound of Embodiment (60) or a pharmaceutically acceptable salt thereof, wherein q is 0.

In another Embodiment (62), the invention provides a compound of Embodiment (60) or a pharmaceutically acceptable salt thereof, wherein q is 1.

In another Embodiment (63), the invention provides a compound of any one of Embodiments (1)-(62) or a pharmaceutically acceptable salt thereof, wherein each $R^{5a}$ is independently selected from $C_{1-10}$ alkyl, $C_{3-10}$ cycloalkyl, heterocyclyl, aryl and heteroaryl, wherein alkyl, cycloalkyl and heterocyclyl are each unsubstituted or substituted with at least one substituent independently selected from $R^X$.

In another Embodiment (64), the invention provides a compound of Embodiment (63) or a pharmaceutically acceptable salt thereof, wherein $R^{5a}$ is selected from phenyl, pyridinyl,

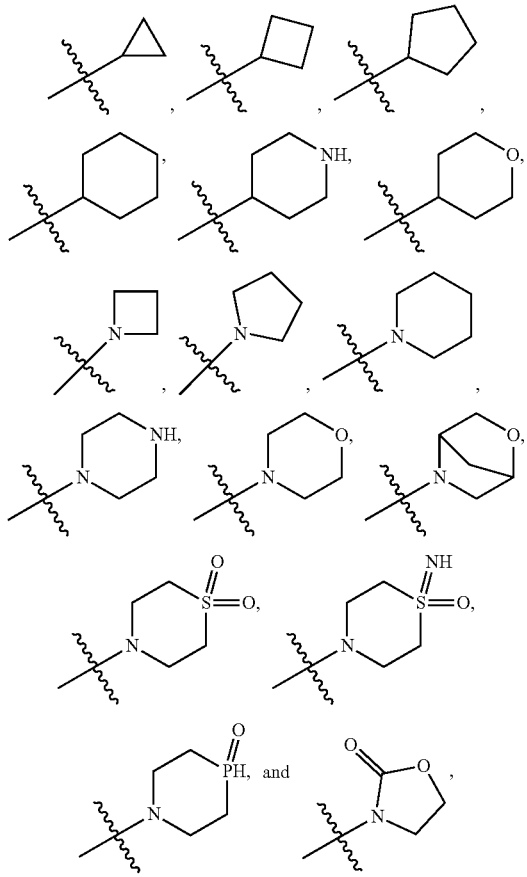

which are unsubstituted or substituted with at least one substituent independently selected from $R^X$.

In another Embodiment (65), the invention provides a compound of Embodiment (64) or a pharmaceutically acceptable salt thereof, wherein $R^{5a}$ is selected from phenyl, pyridinyl,

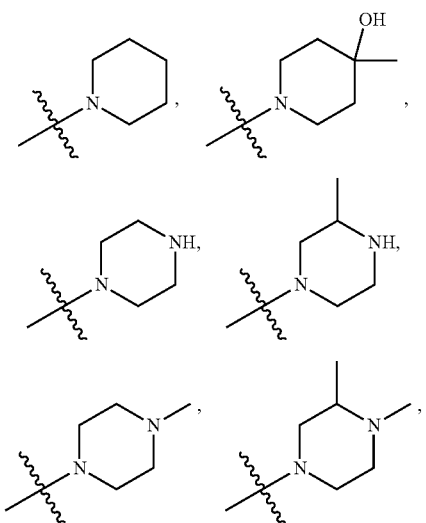

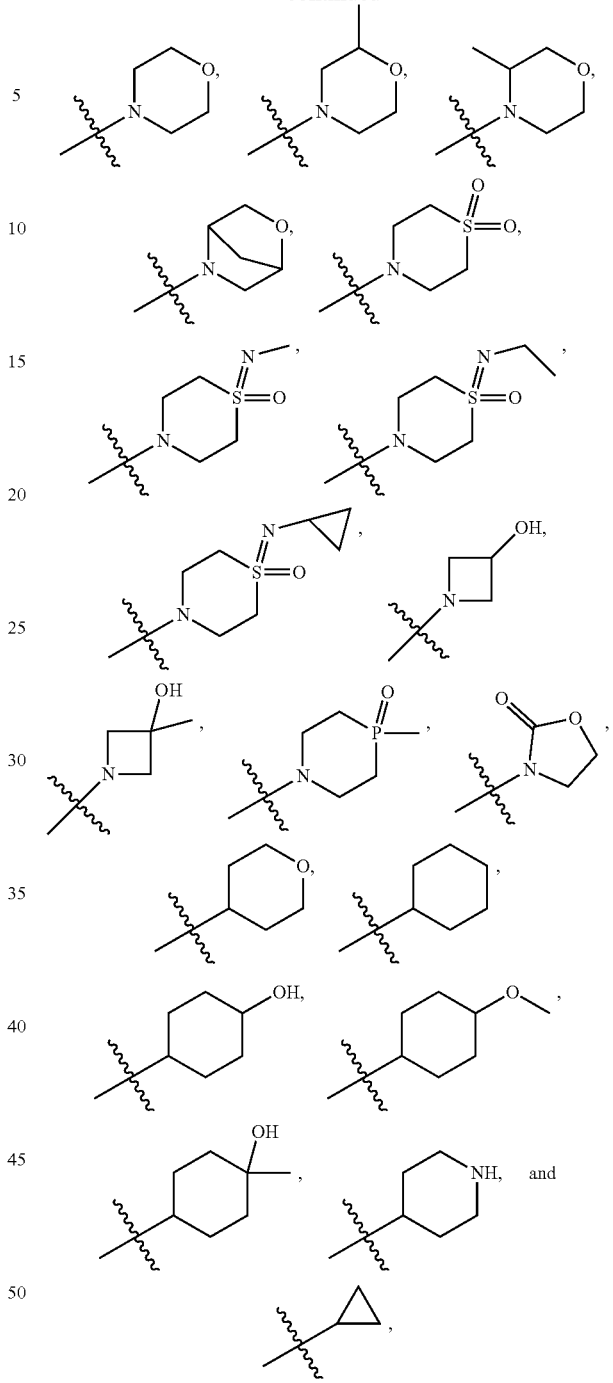

wherein phenyl and pyridinyl are unsubstituted or substituted with at least one substituent independently selected from halogen, CN, $OR^{45}$ and $—S(O)_rR^{45}$.

In another Embodiment (66), the invention provides a compound of any one of Embodiments (1)-(65) or a pharmaceutically acceptable salt thereof, wherein $L^4$ is selected from $—(CR^CR^D)_u—$ and u is selected from 0, 1 and 2.

In another Embodiment (67), the invention provides a compound of any one of Embodiments (1)-(66) or a pharmaceutically acceptable salt thereof, wherein $R^{5b}$ is selected from hydrogen, halogen, $C_{1-10}$ alkyl, $C_{3-10}$ cycloalkyl, $C_{3-10}$ heterocyclyl, CN, —OR$^{A5}$, —NR$^{A5}$R$^{B5}$, —NR$^{A5}$C(O)OR$^{B5}$, —N=S(O)R$^{A5}$R$^{B5}$, —C(O)OR$^{A5}$, —C(O)NR$^{A5}$R$^{B5}$ and —S(O)$_r$R$^{A5}$.

In another Embodiment (68), the invention provides a compound of Embodiment (67) or a pharmaceutically acceptable salt thereof, wherein R$^{5b}$ is selected from hydrogen, fluoro, methyl, ethyl, isopropyl, cyclopropyl, oxetanyl, CN, OH, —OCH$_3$, —N(CH$_3$)$_2$, —N=S(O)(CH$_3$)$_2$, —NHC(O)OCH$_3$, —C(O)CH$_3$, —C(O)C$_2$H$_5$, —C(O)-c-C$_3$H$_7$, —C(O)OCH$_3$, —C(O)OC(CH$_3$)$_3$, —C(O)N(CH$_3$)$_2$, —SOCH$_3$ and —S(O)$_2$CH$_3$.

In another Embodiment (69), the invention provides a compound of Embodiments (67) or a pharmaceutically acceptable salt thereof, wherein R$^{5b}$ is selected from —NR$^{A5}$R$^{B5}$, —N=S(O)R$^{A5}$R$^{B5}$, wherein R$^{A5}$ and R$^{B5}$ together with the atom to which they are attached form a heterocyclic ring of 4 to 12 members containing 0, 1 or 2 additional heteroatoms independently selected from oxygen, sulfur, nitrogen and phosphorus, and optionally substituted with 1, 2 or 3 R$^{X}$ groups.

In another Embodiment (70), the invention provides a compound of Embodiments (69) or a pharmaceutically acceptable salt thereof, wherein R$^{5b}$ is selected from

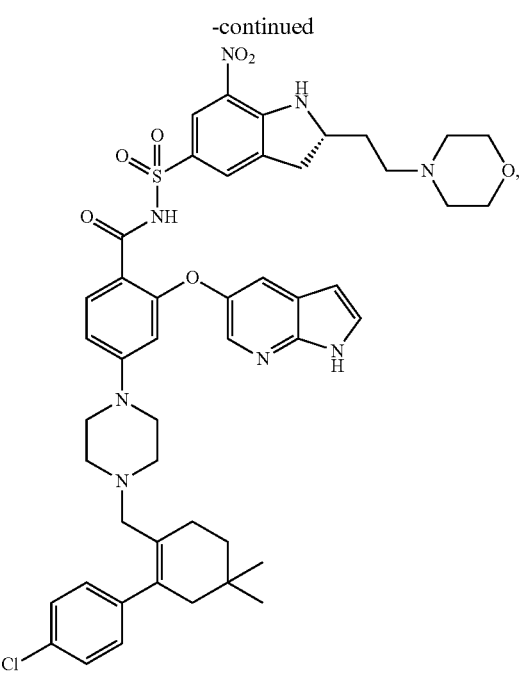

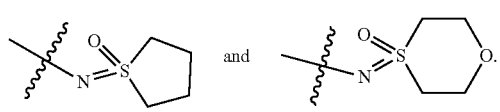 [SMILES: *N=S1(=O)CCCC1 ; "and" ; *N=S1(=O)CCOCC1]

In another Embodiment (71), the invention provides a compound selected from

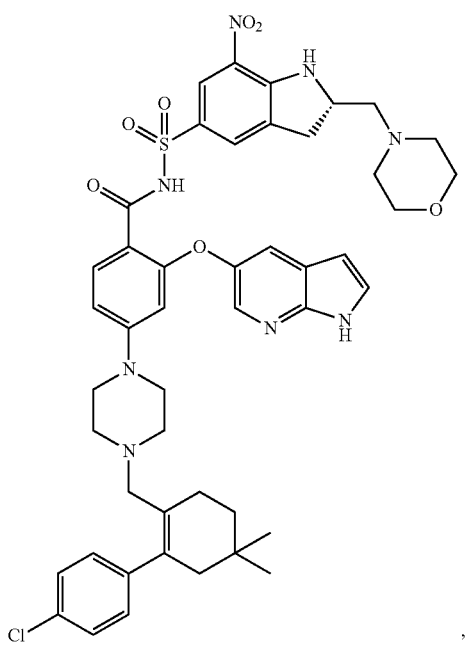

,

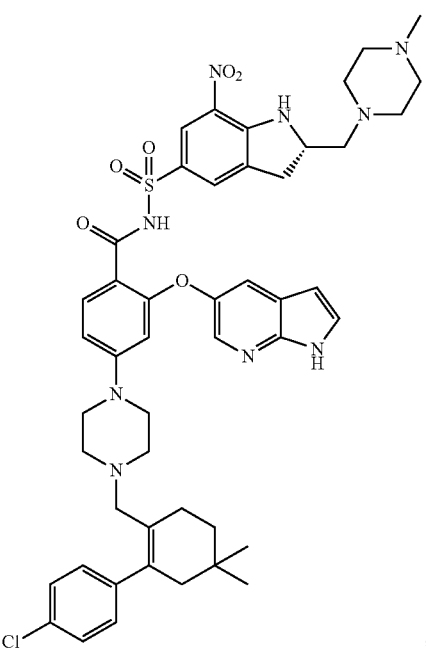

,

35
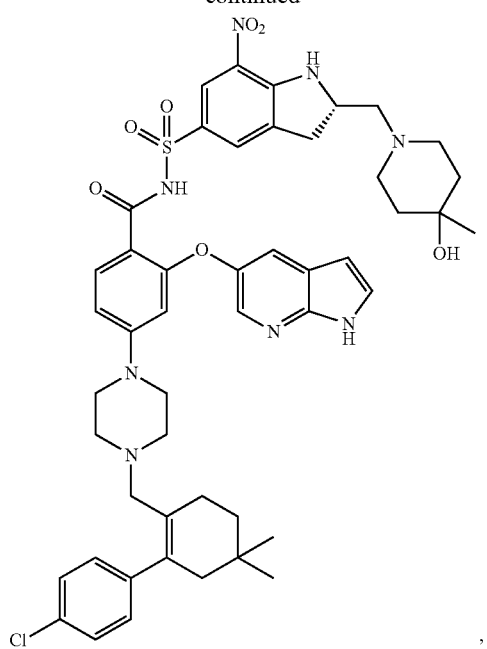
,
36
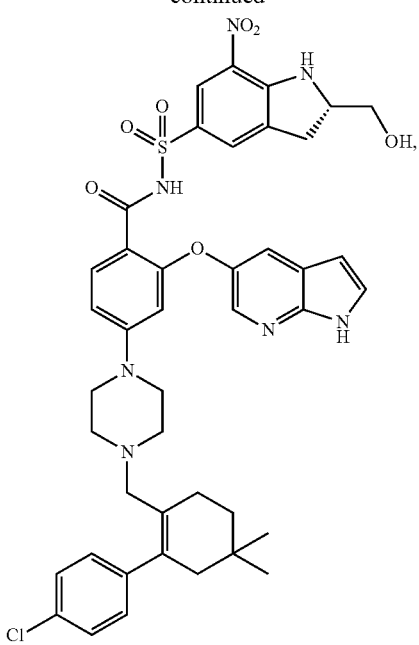
,
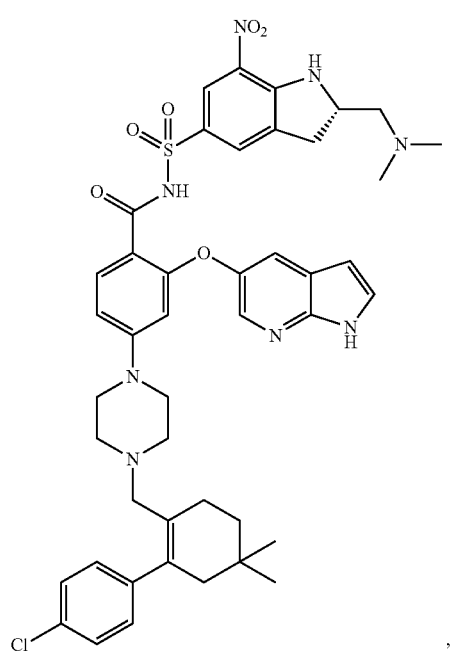
,
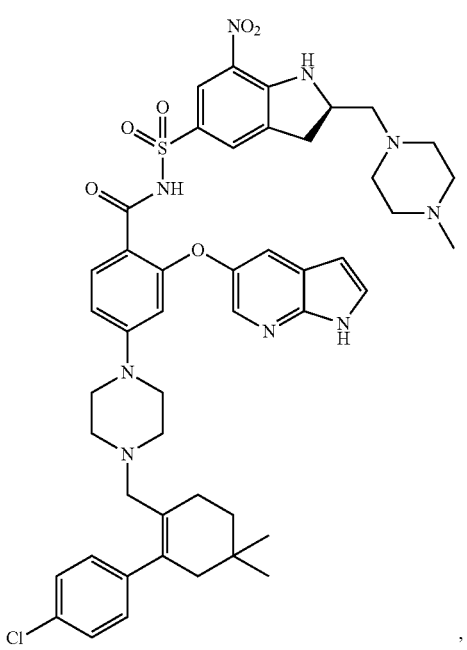
,

37
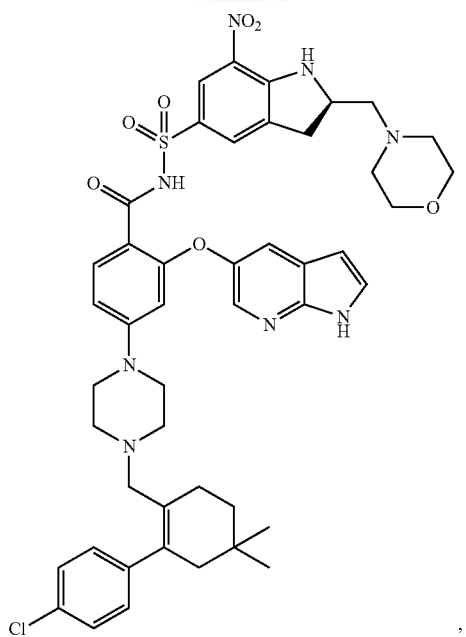
,
38
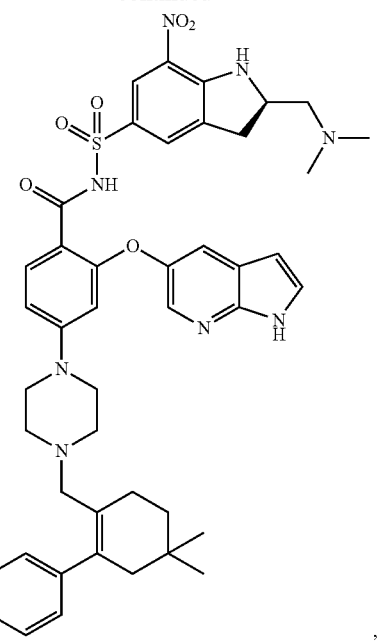
,
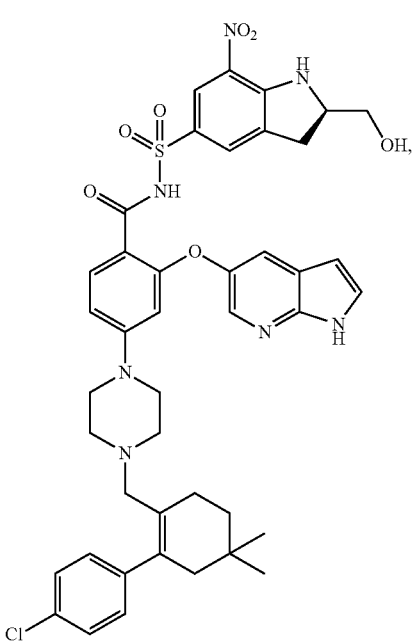
,

39
-continued
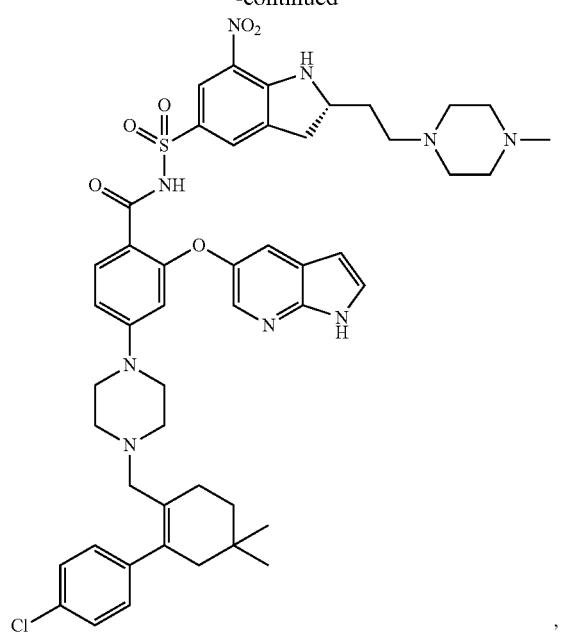
40
-continued
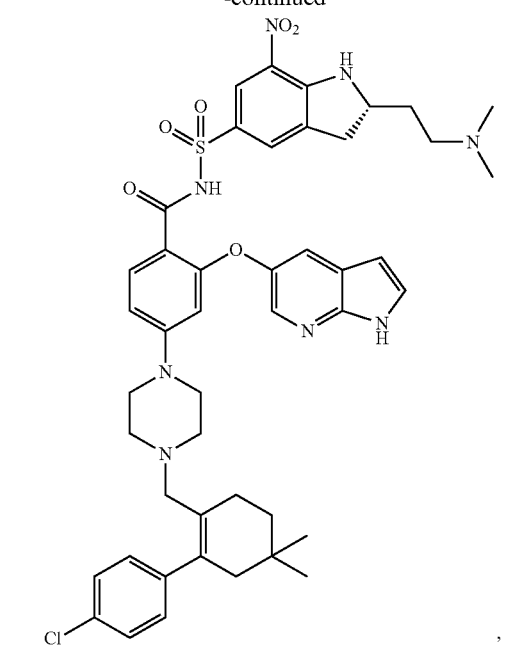
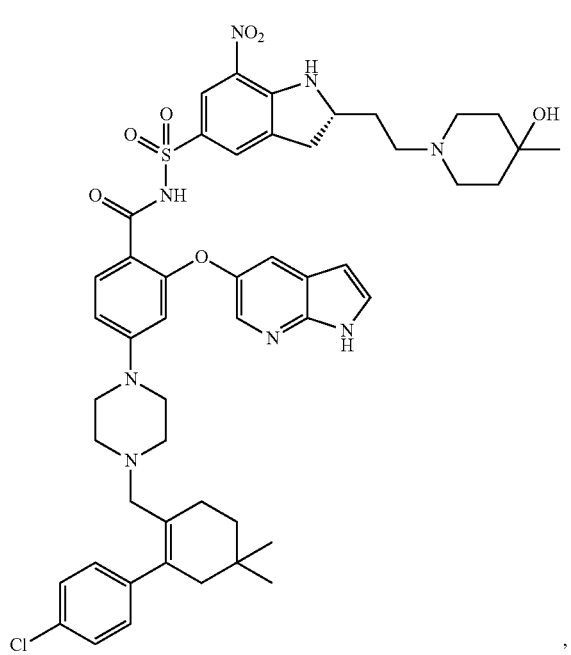
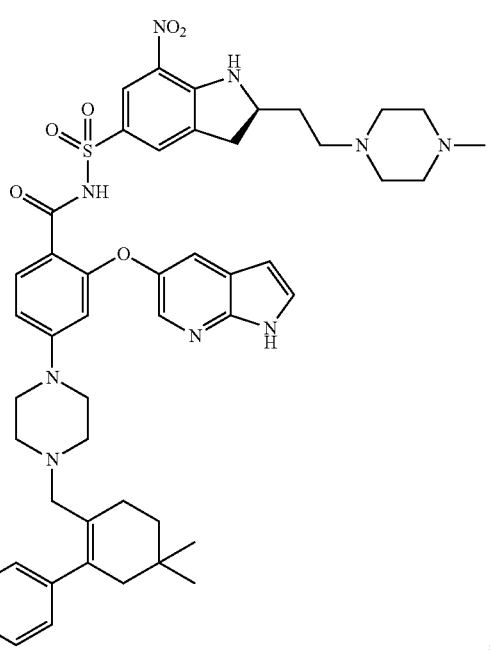

-continued
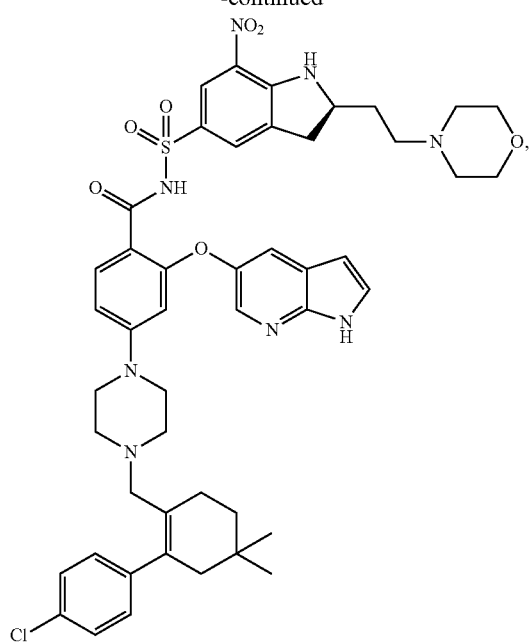
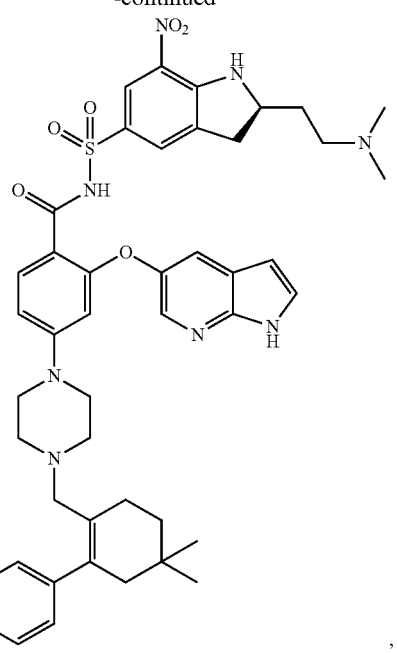
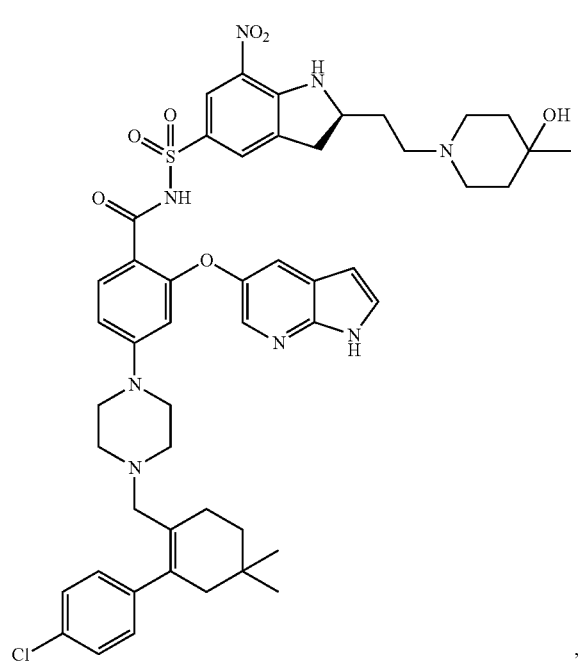
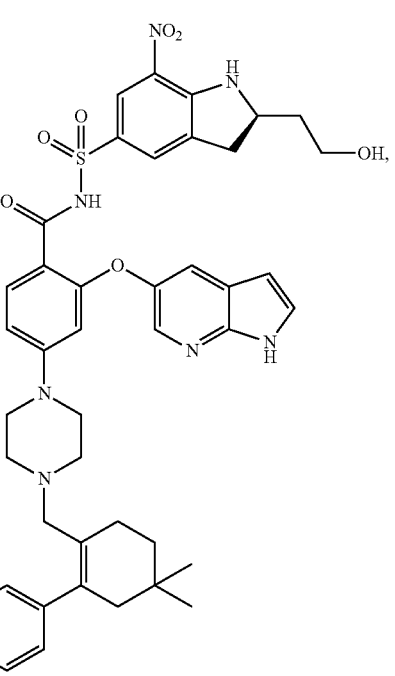

43
-continued
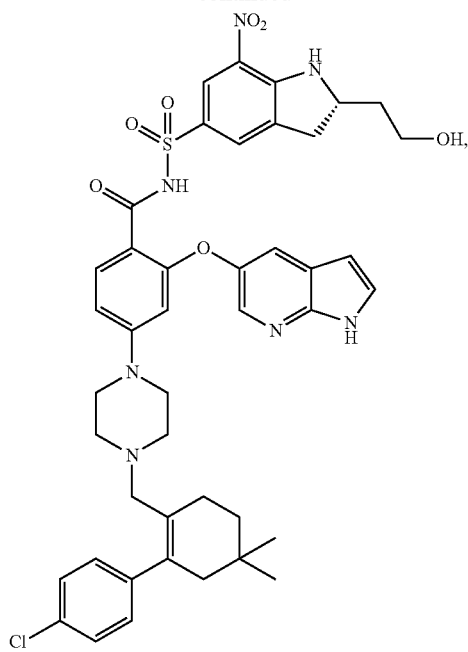
44
-continued
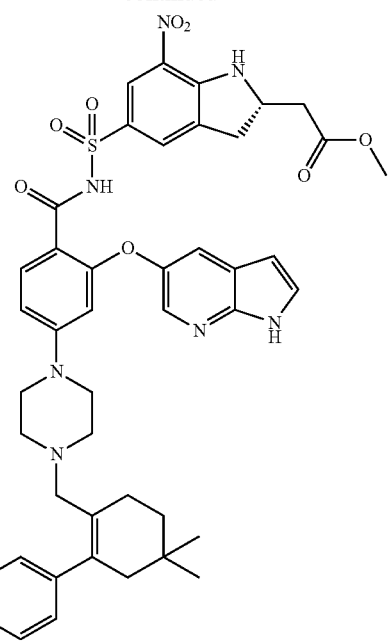
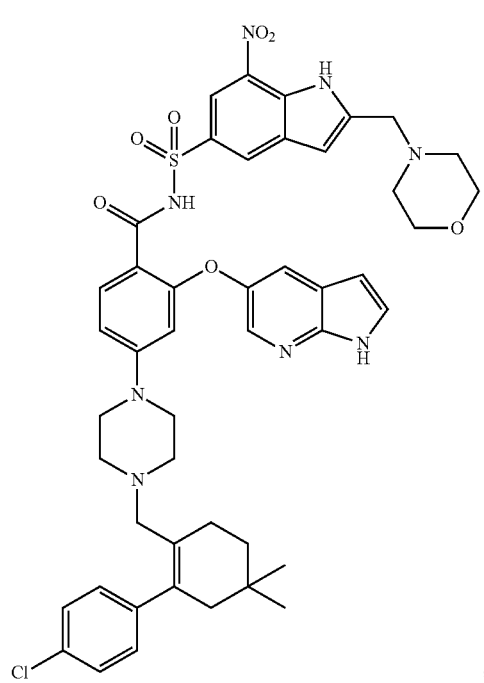
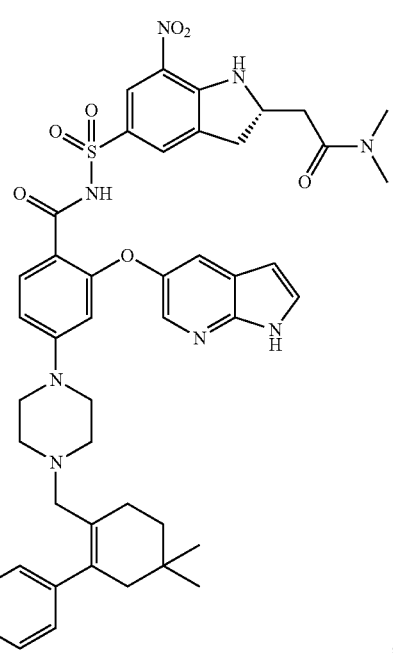

-continued
45
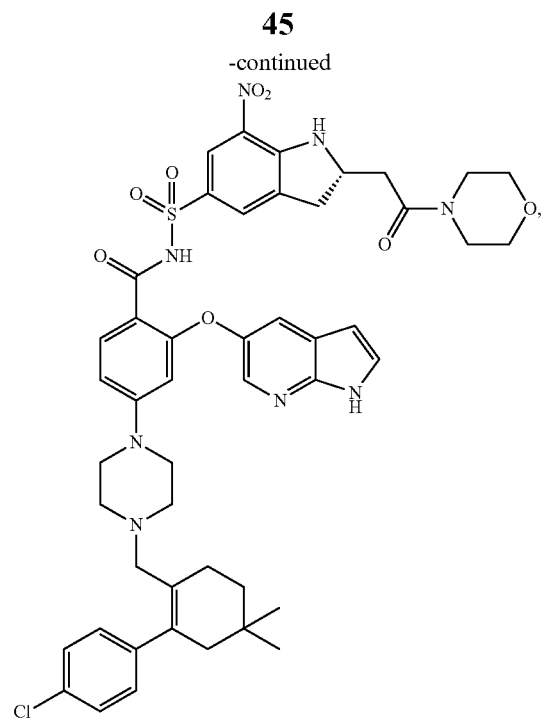
46
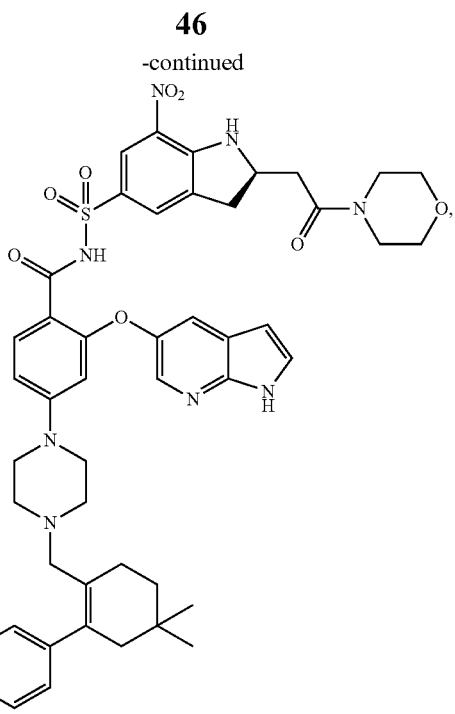

47
-continued
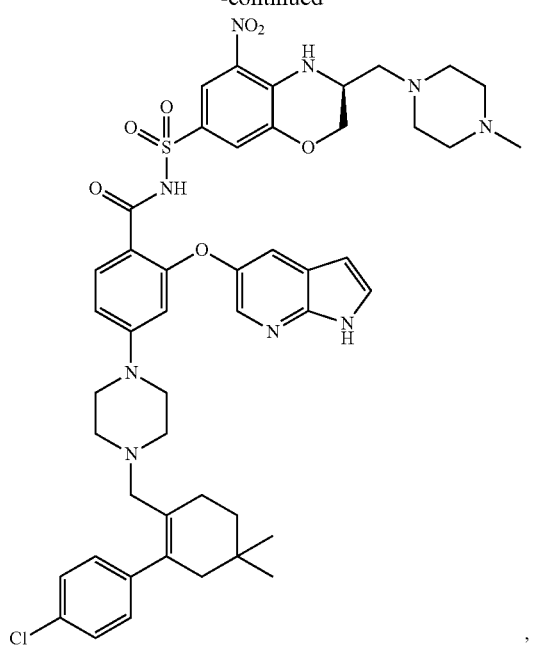
48
-continued
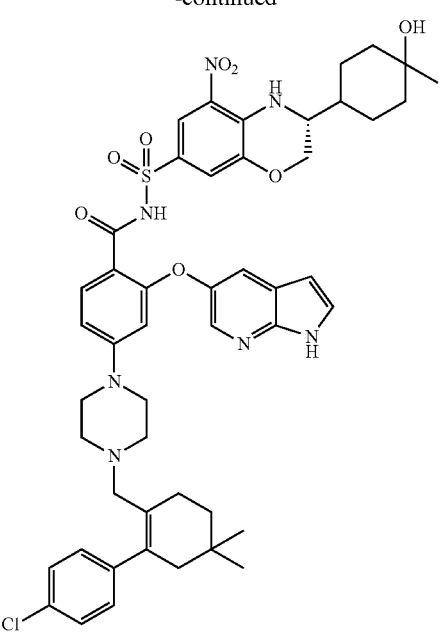
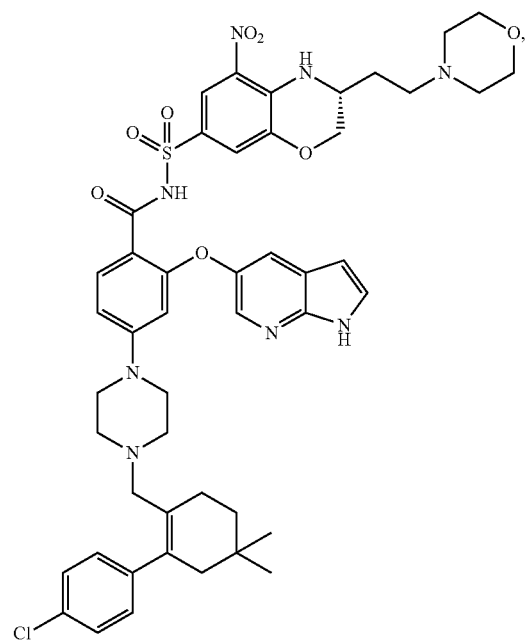
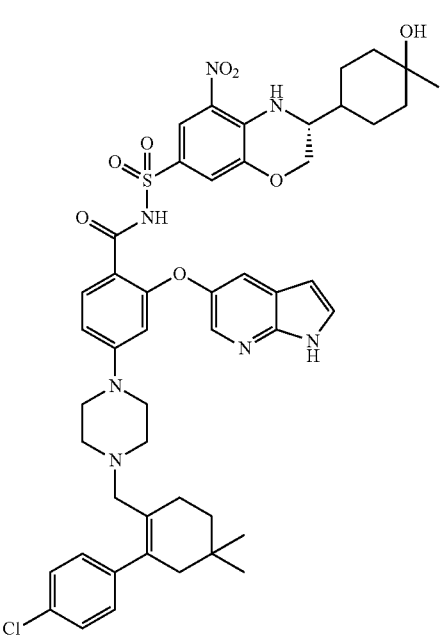

-continued
49
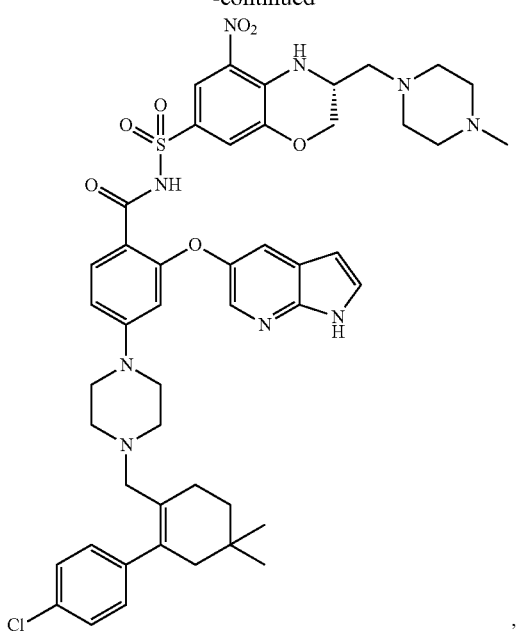
50
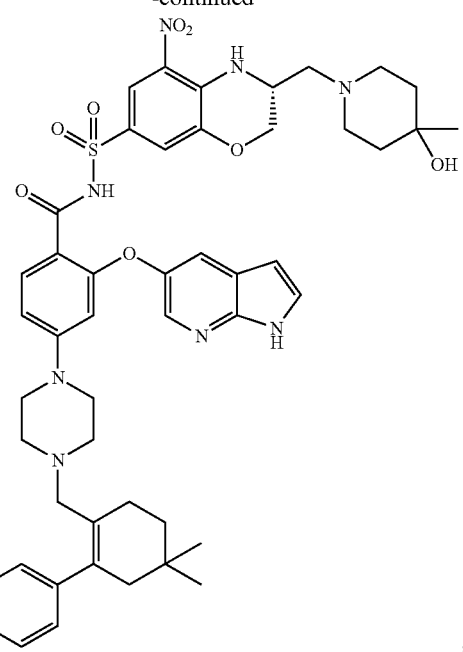
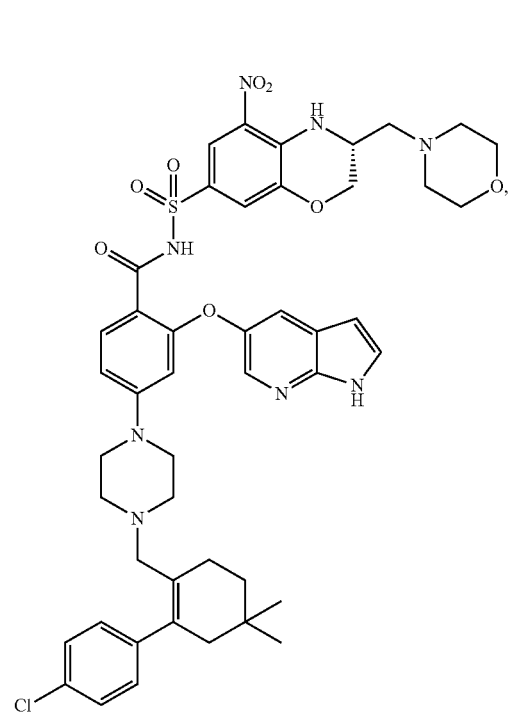
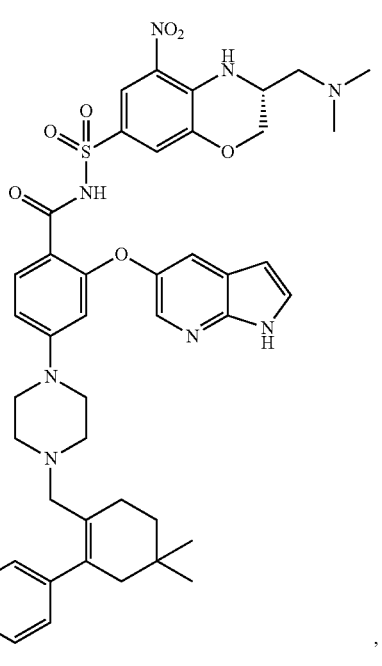

51
-continued
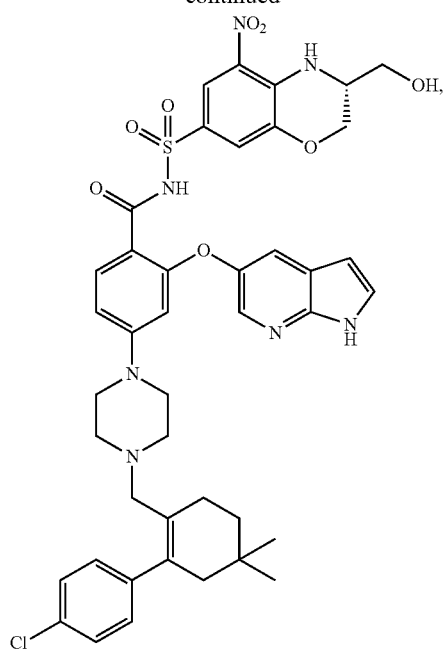
52
-continued
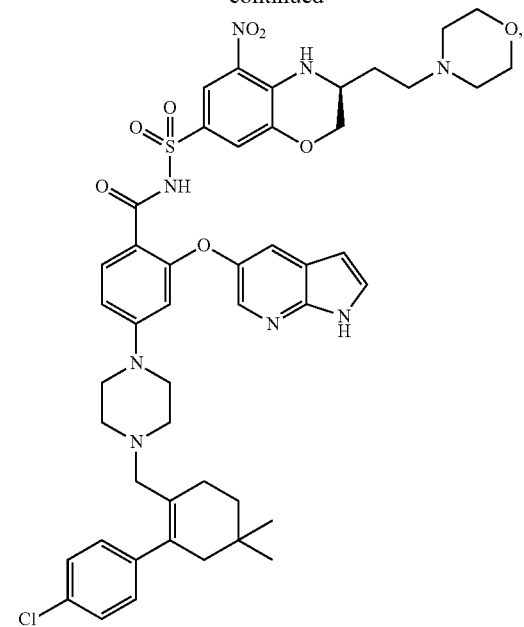
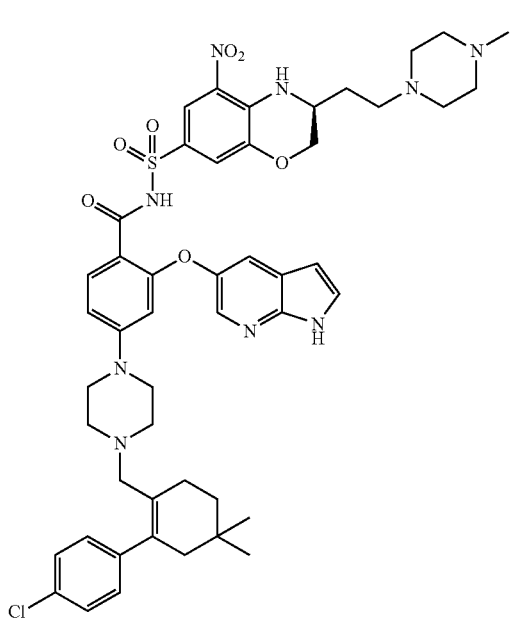
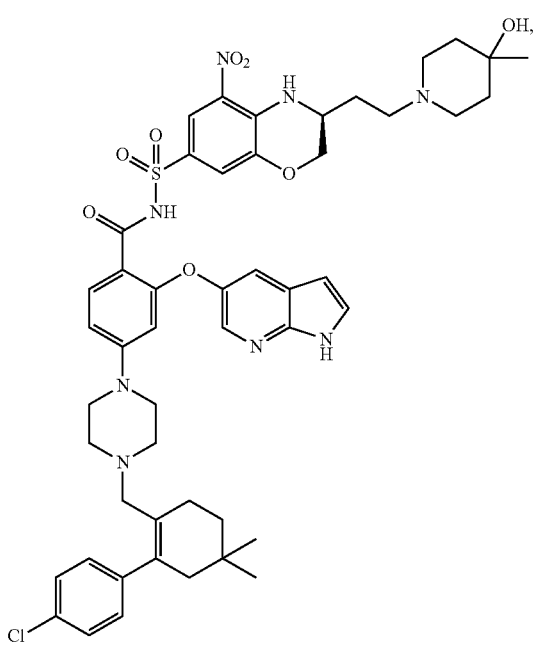

53
-continued
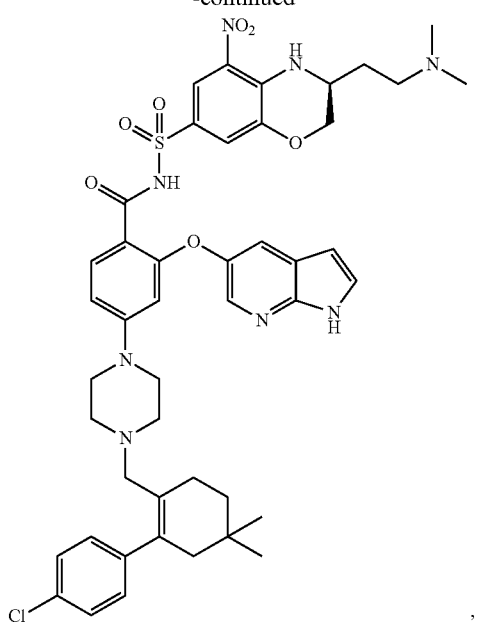
,
54
-continued
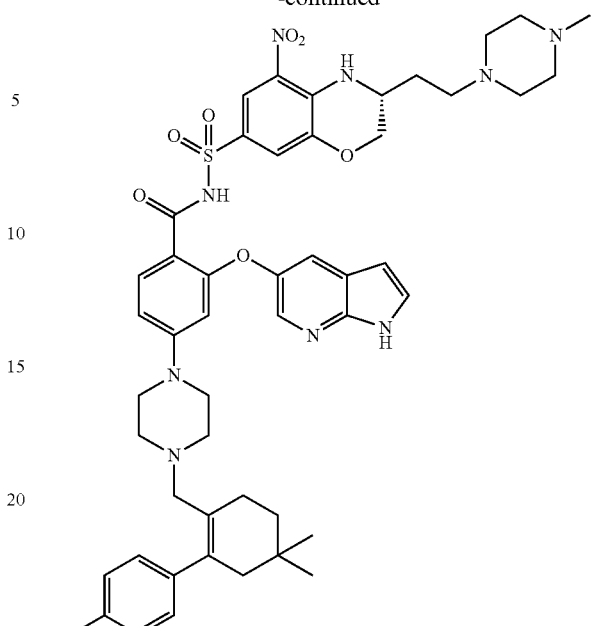
,
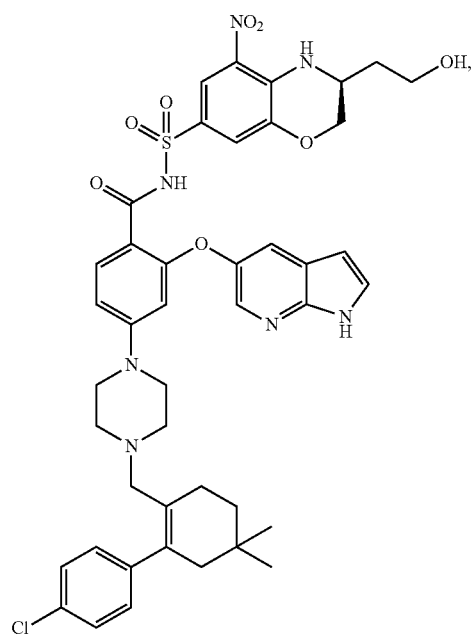
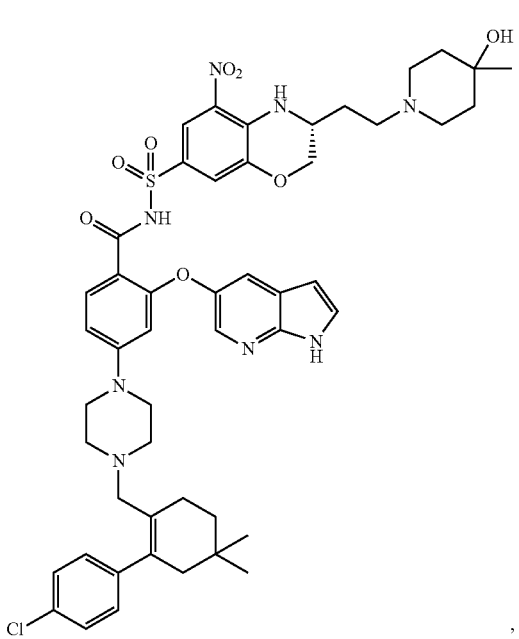

-continued
55
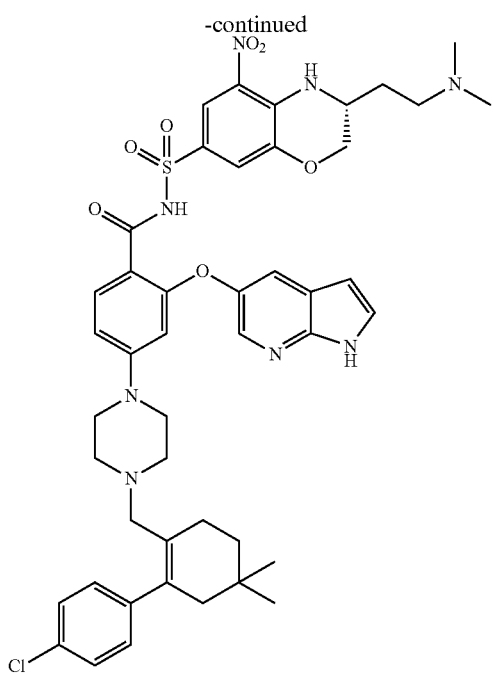
56
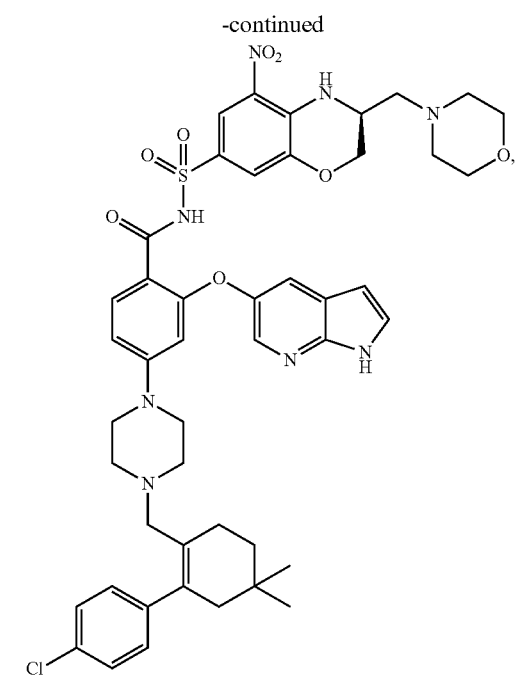
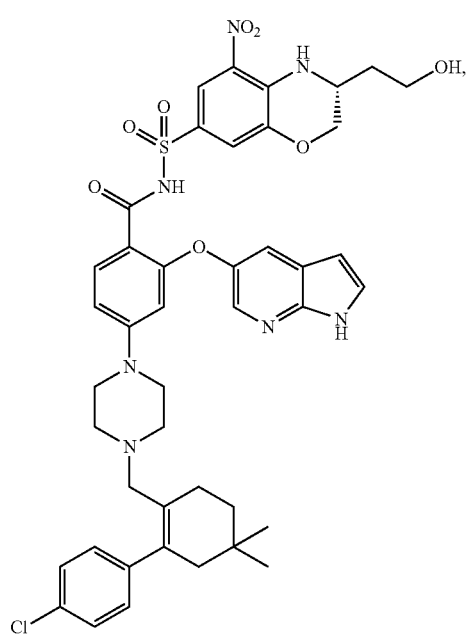
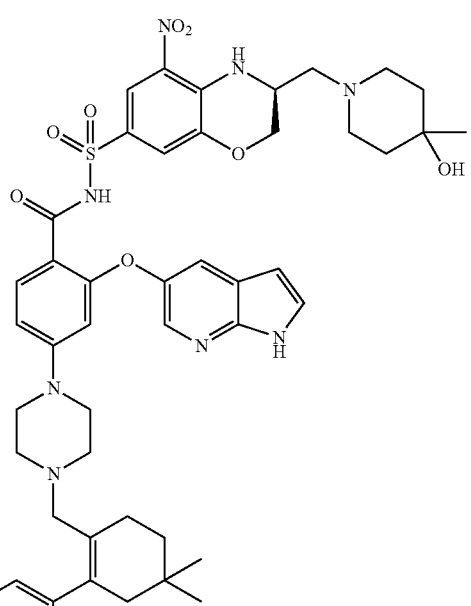

57
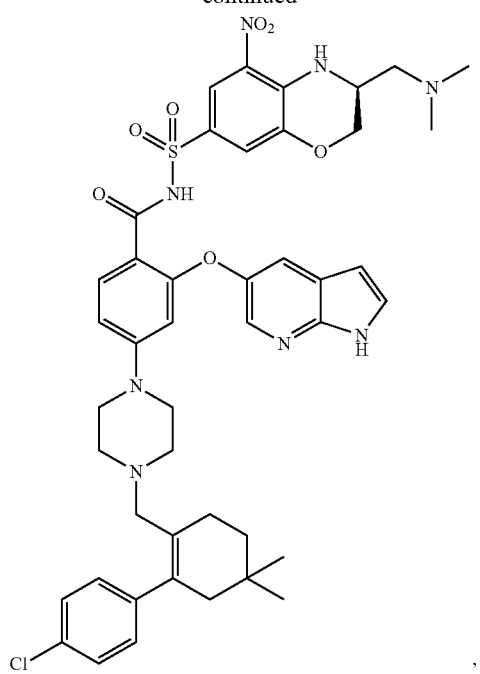
58
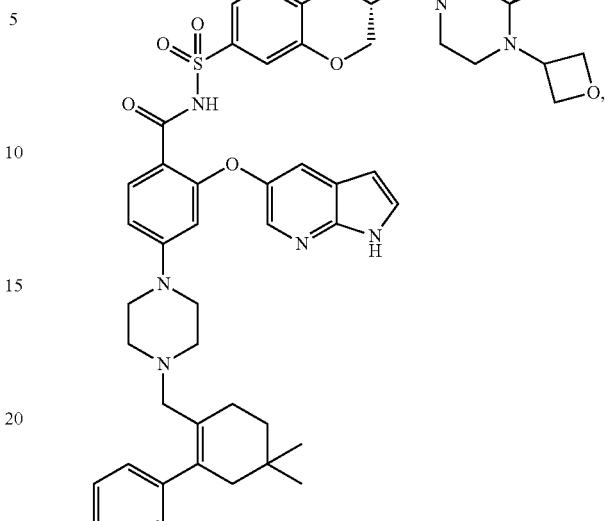
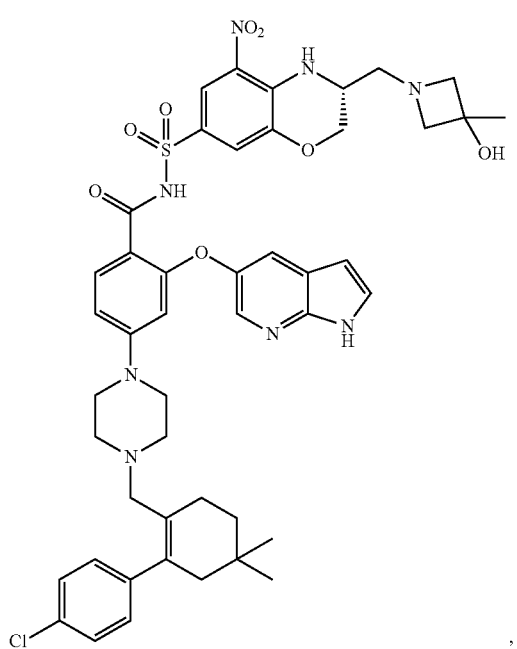
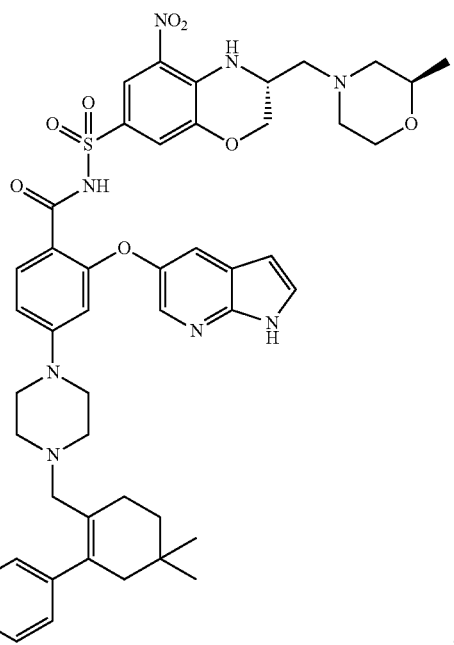

59 -continued
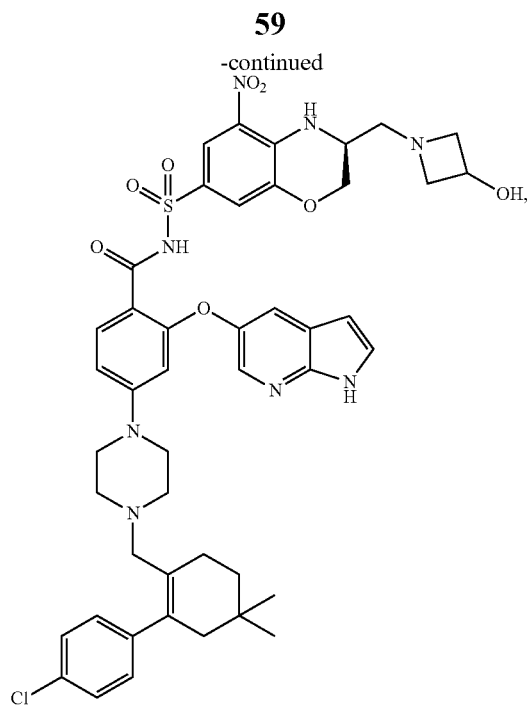
60 -continued
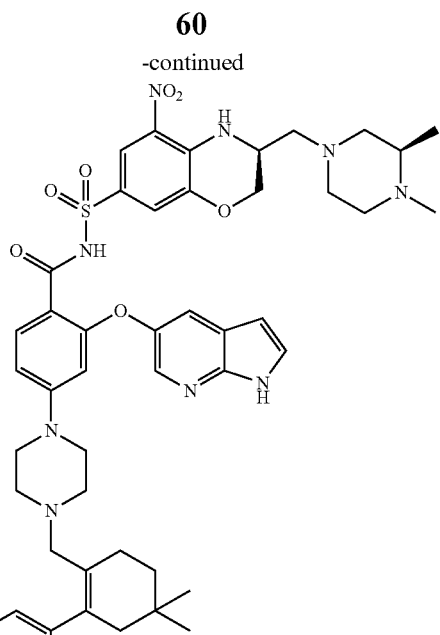
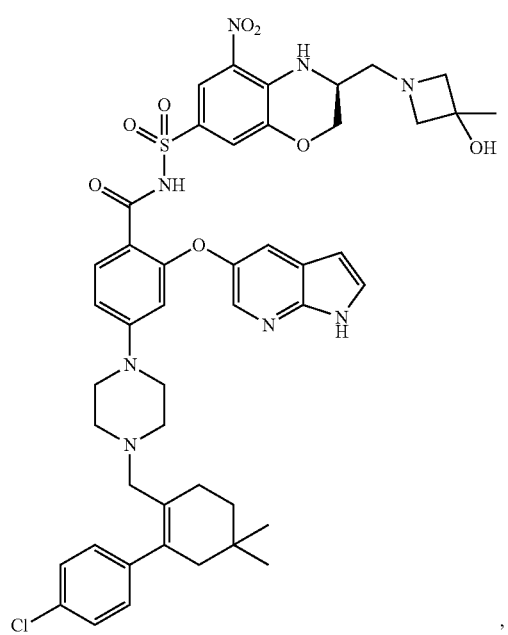
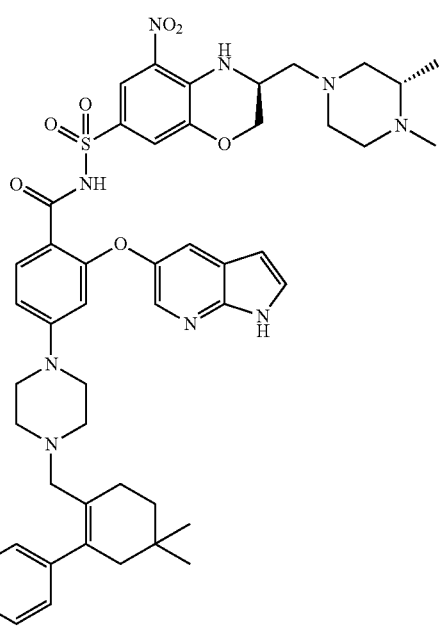

61
-continued
62
-continued
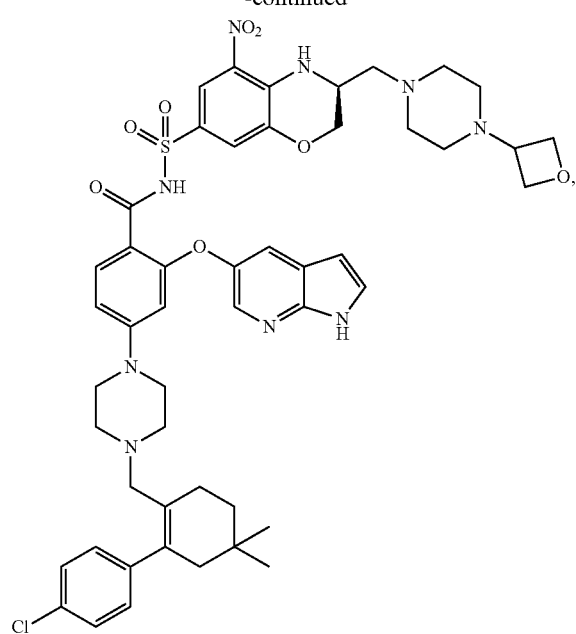
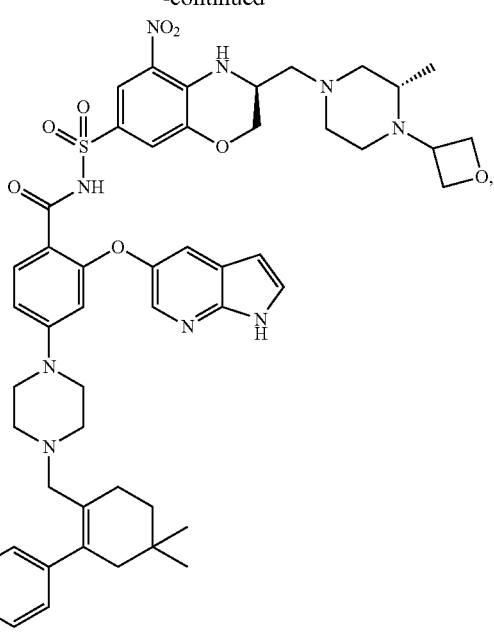

63
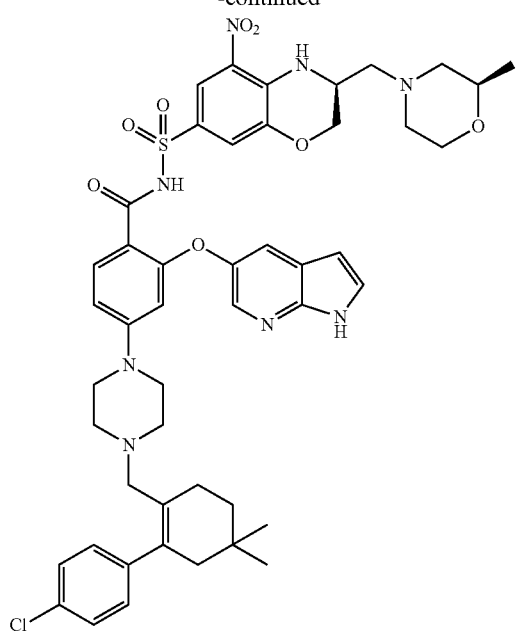
,
64
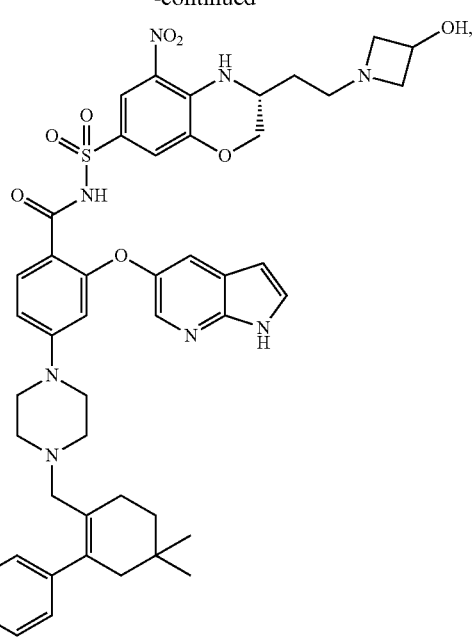
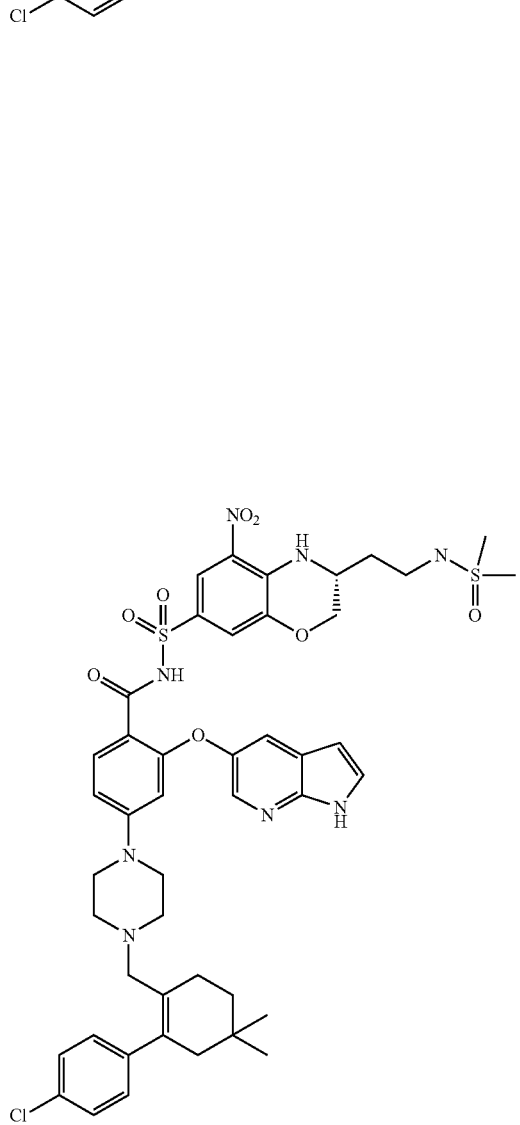
,
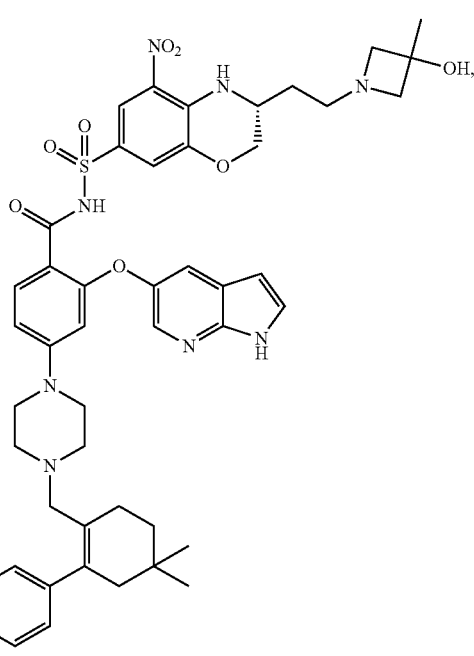
,

65
-continued
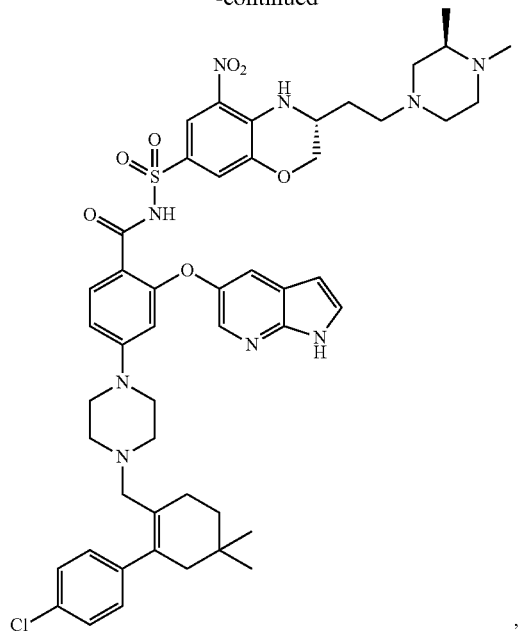
66
-continued
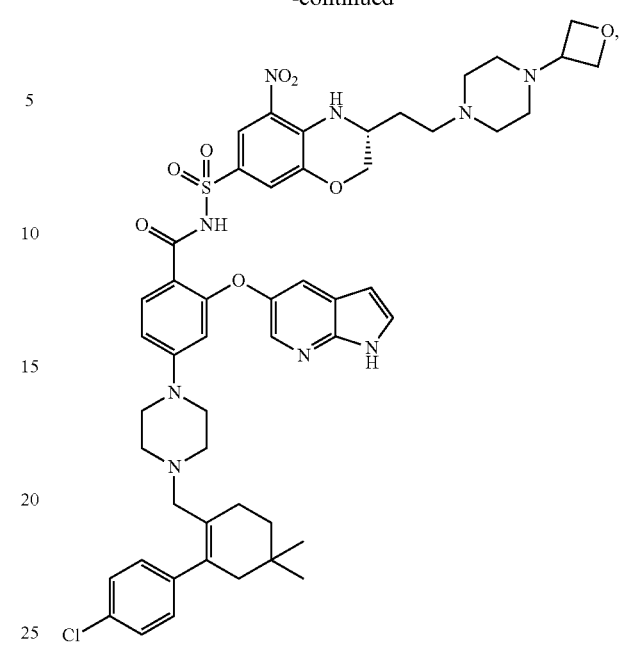
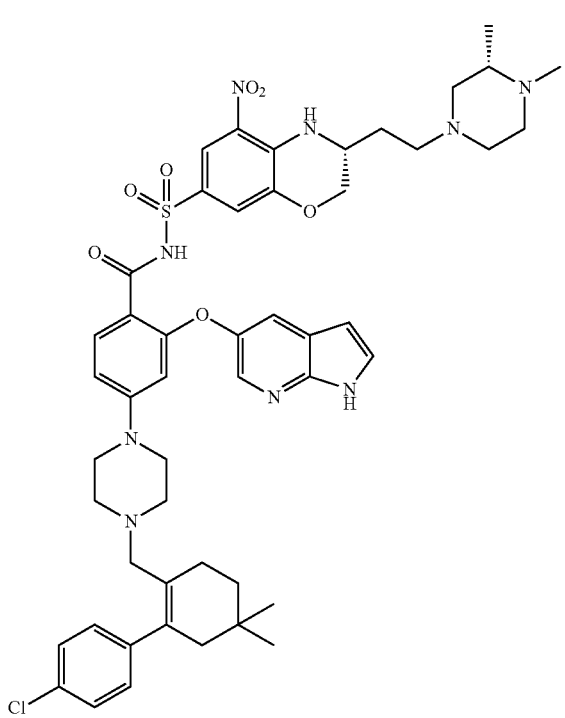
,
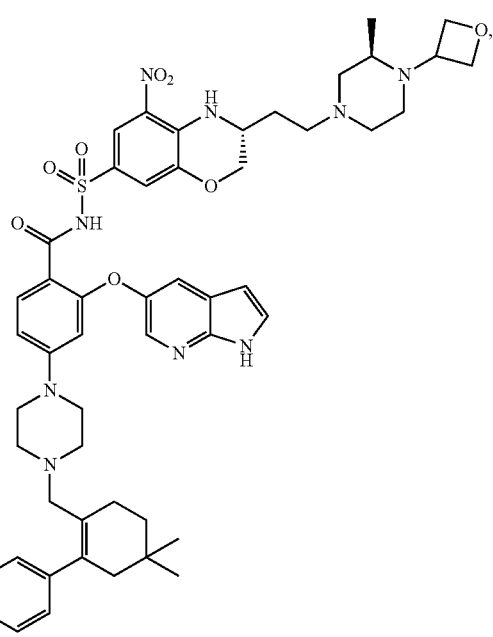
,

67
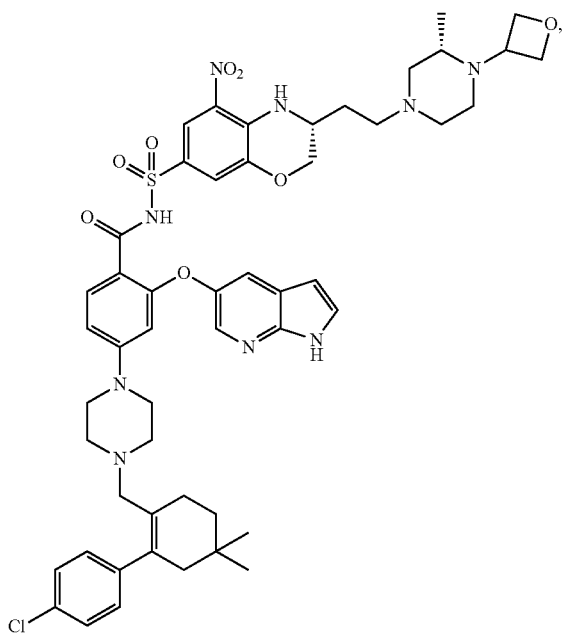
68
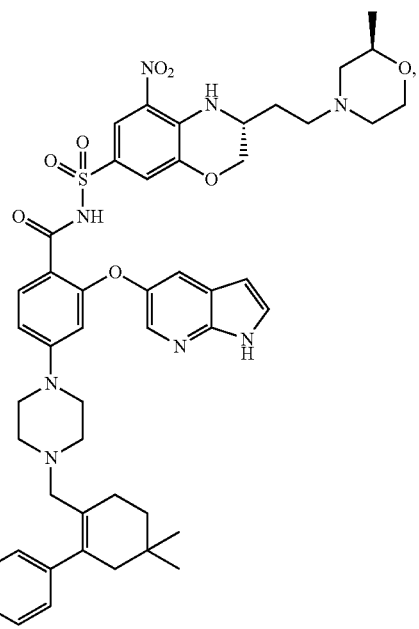

69
-continued
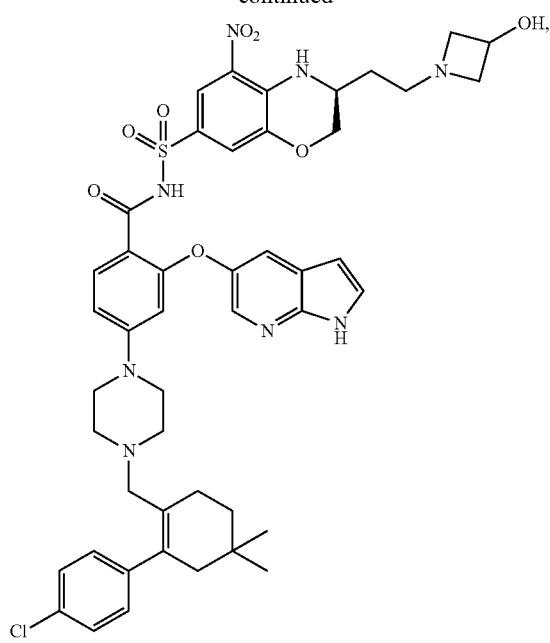
70
-continued
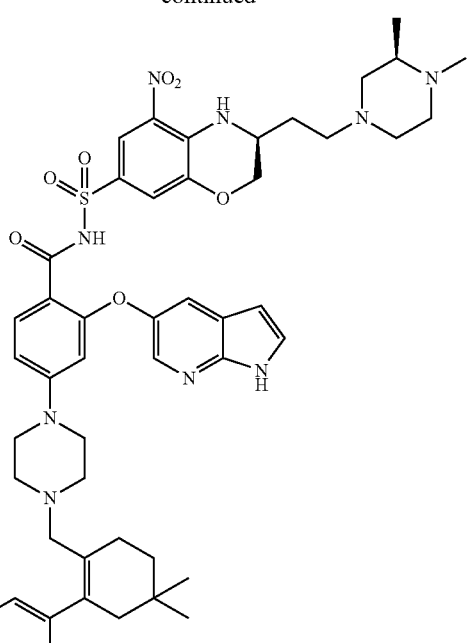
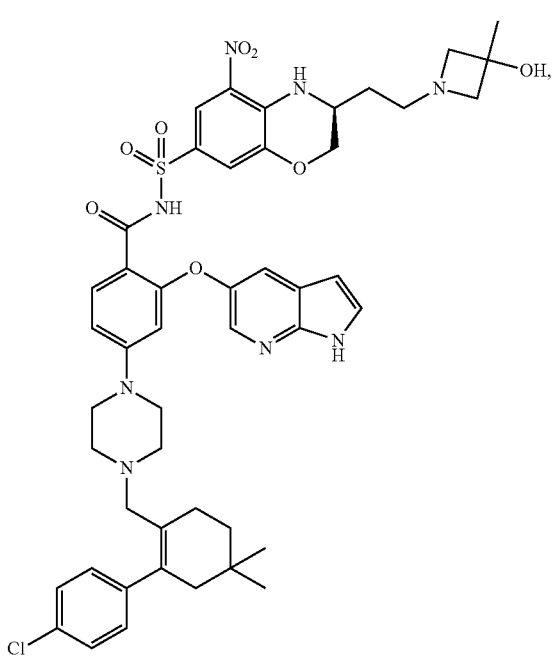
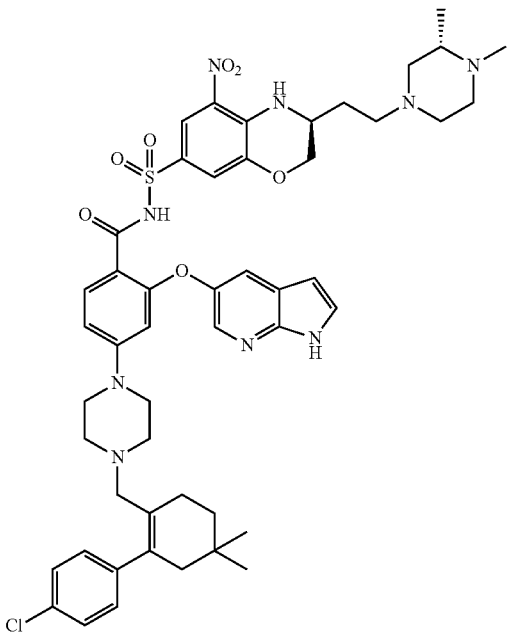

71
-continued
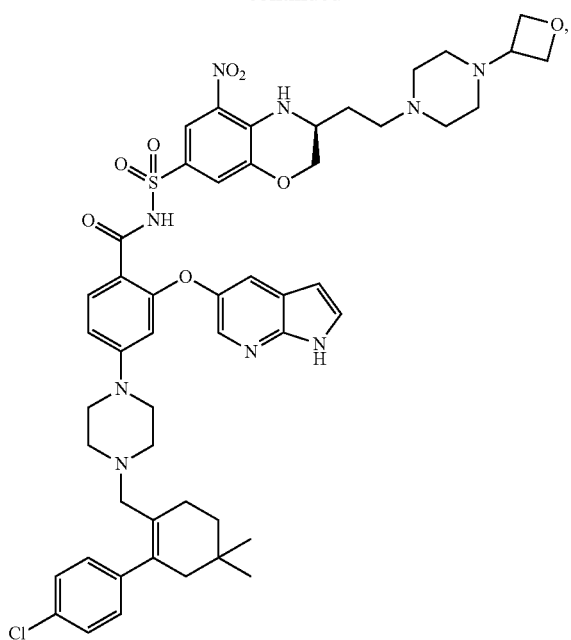
72
-continued
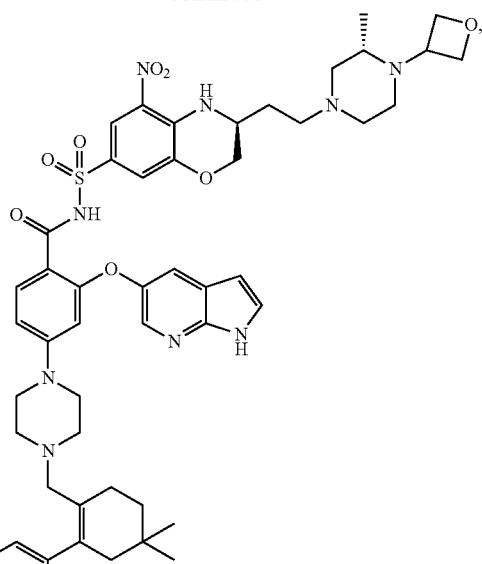

73
-continued
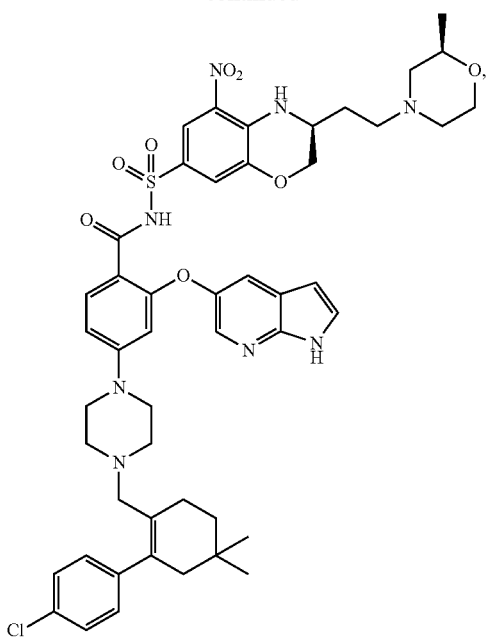
74
-continued
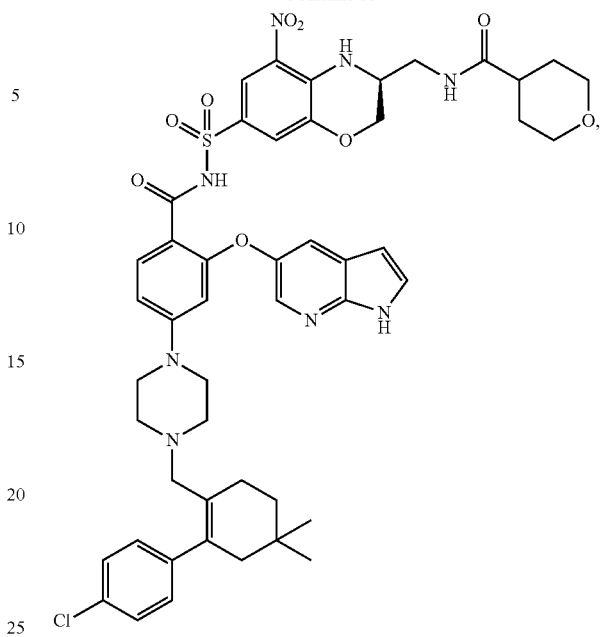

75
-continued
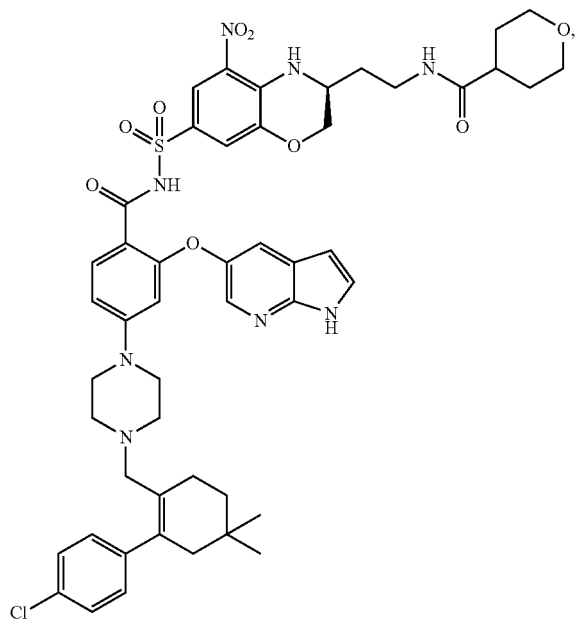
76
-continued
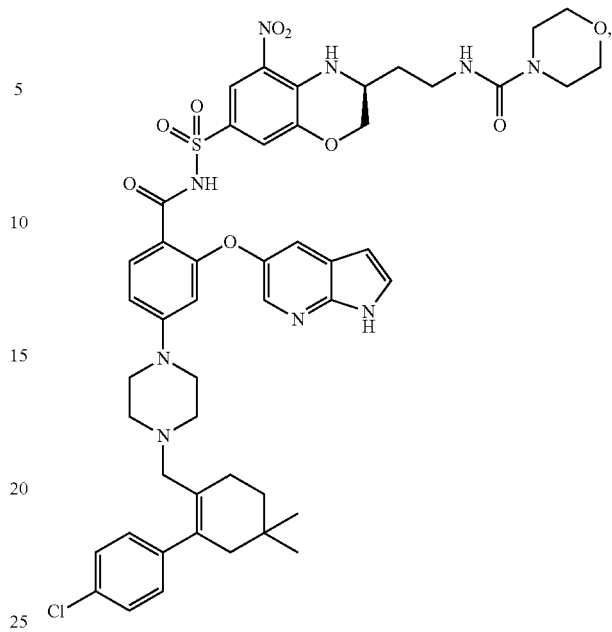
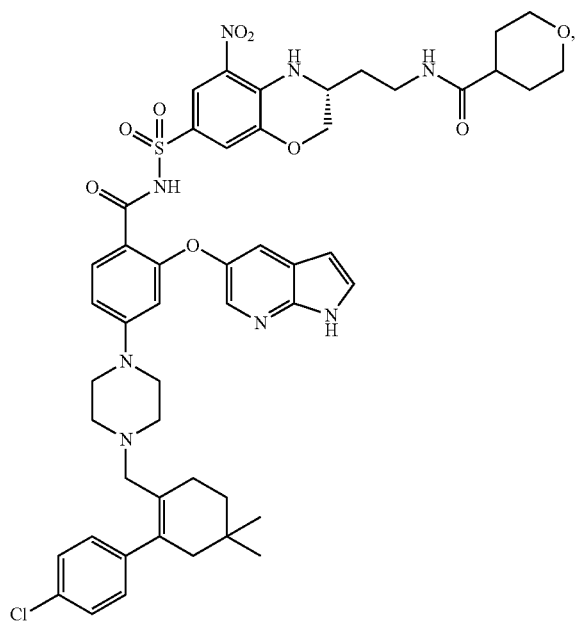
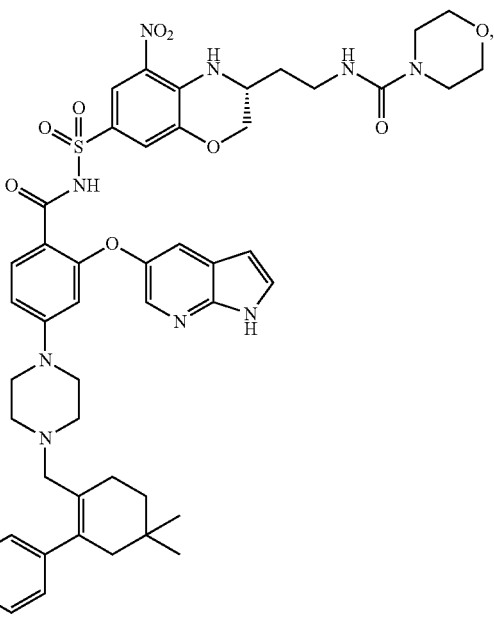

77
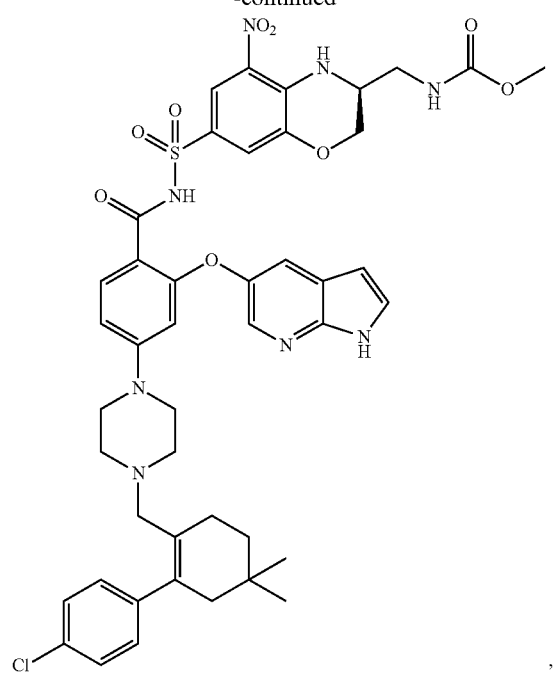
,
78
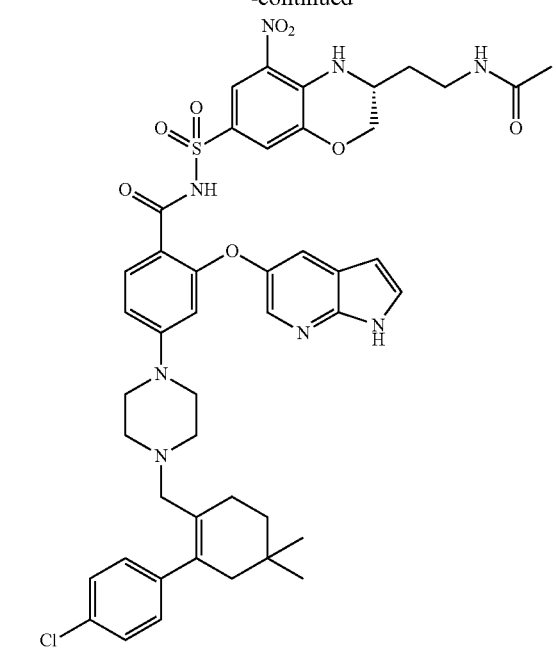
,
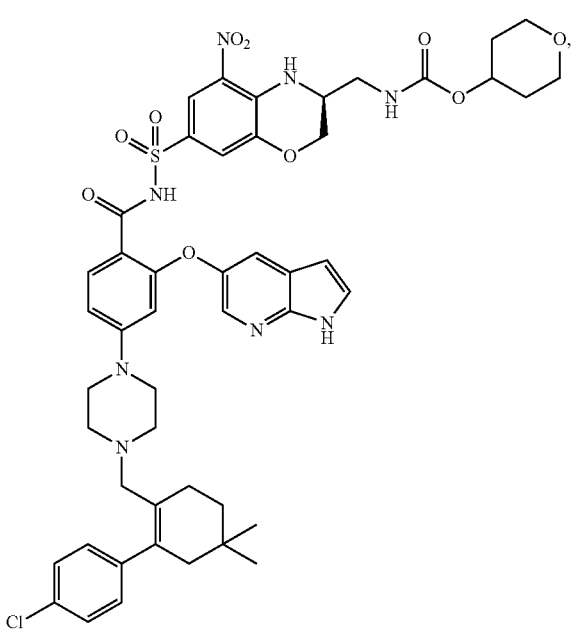
,
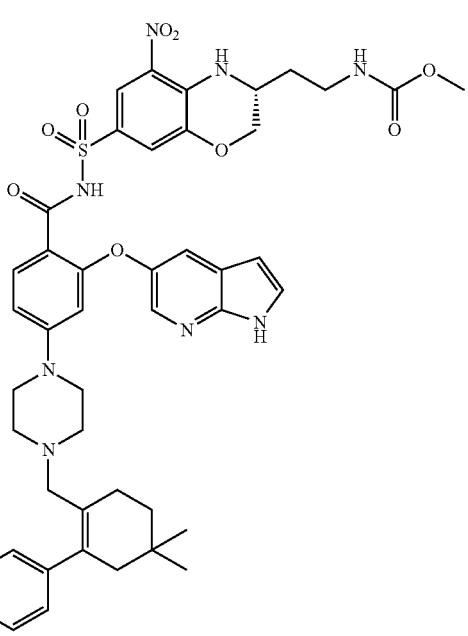
,

79
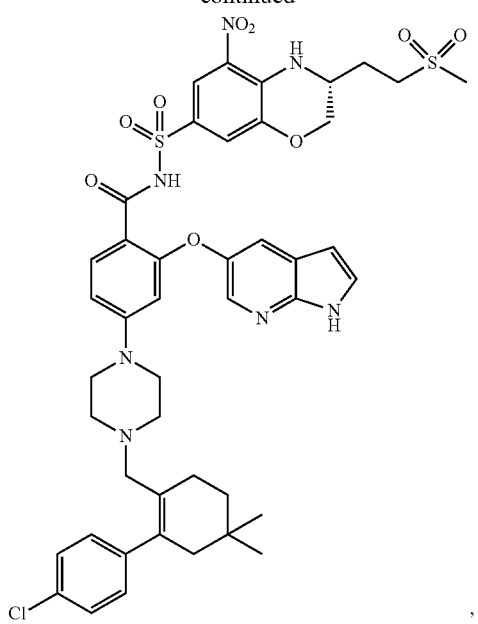
,
80
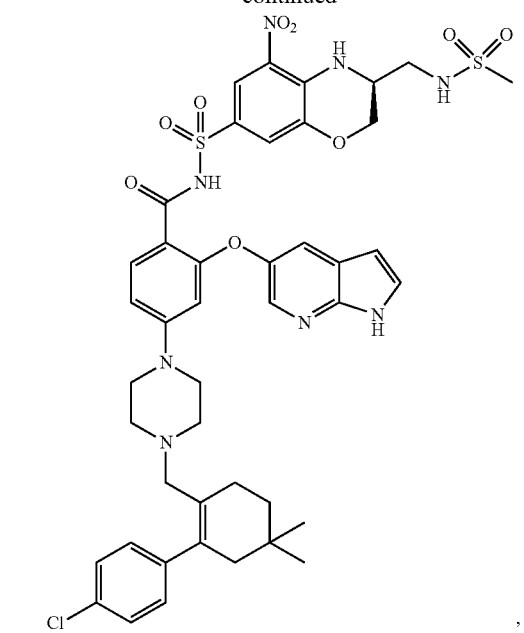
,
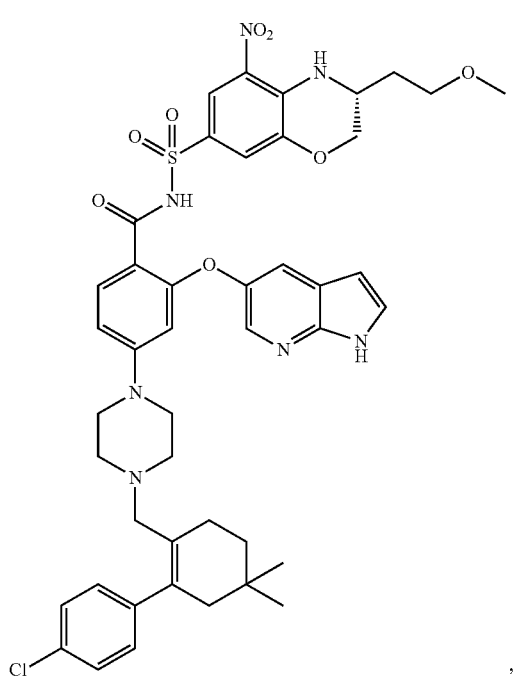
,
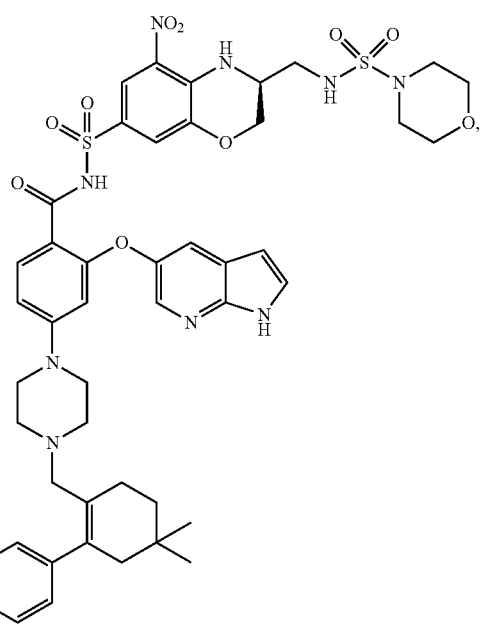
,

-continued
81
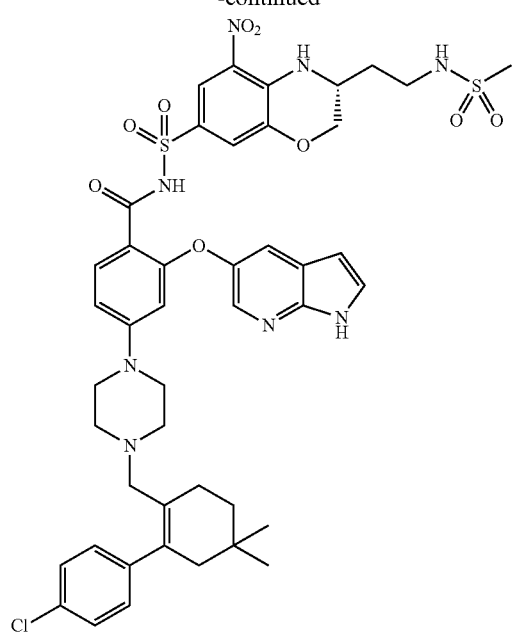
82
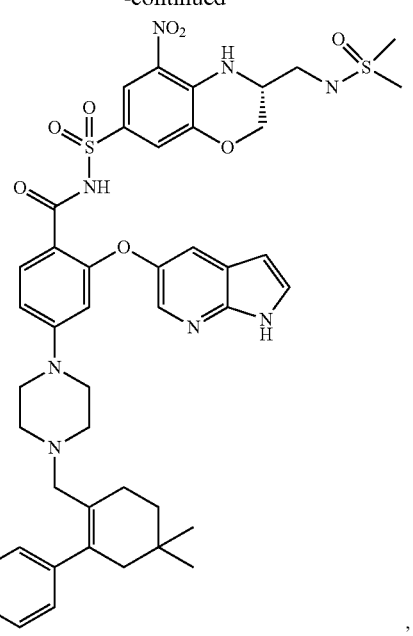
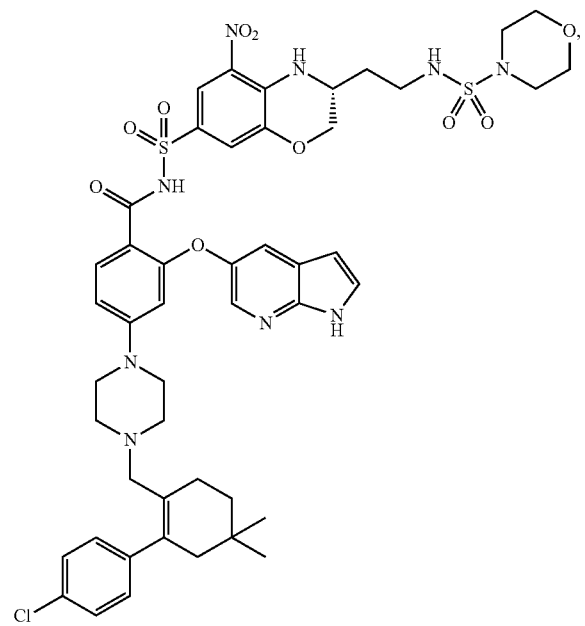
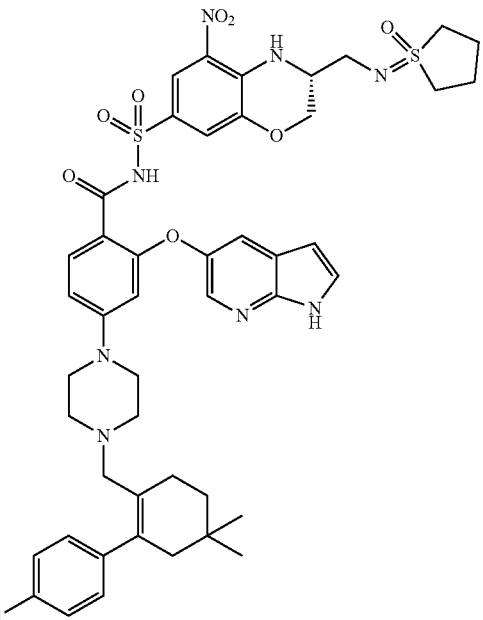

83
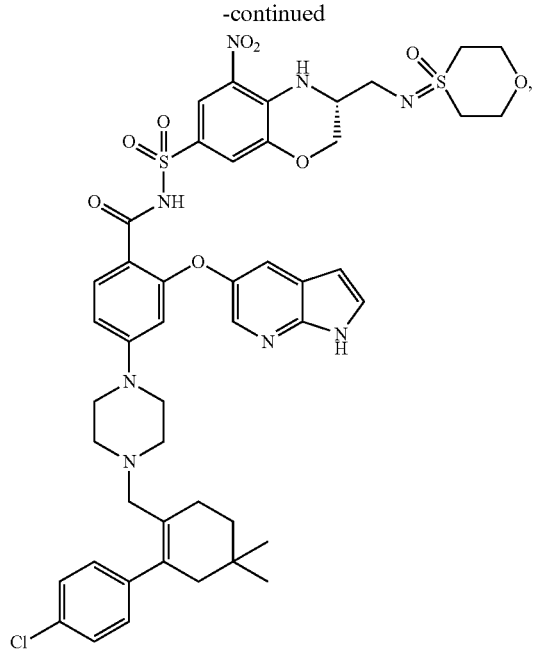
84
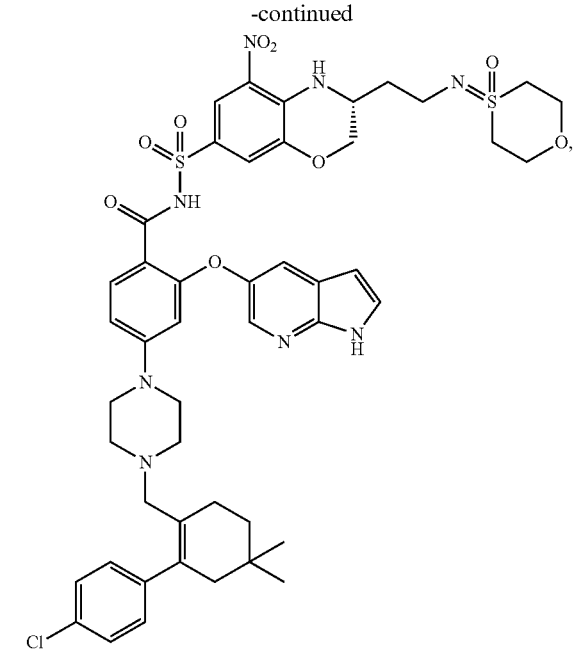
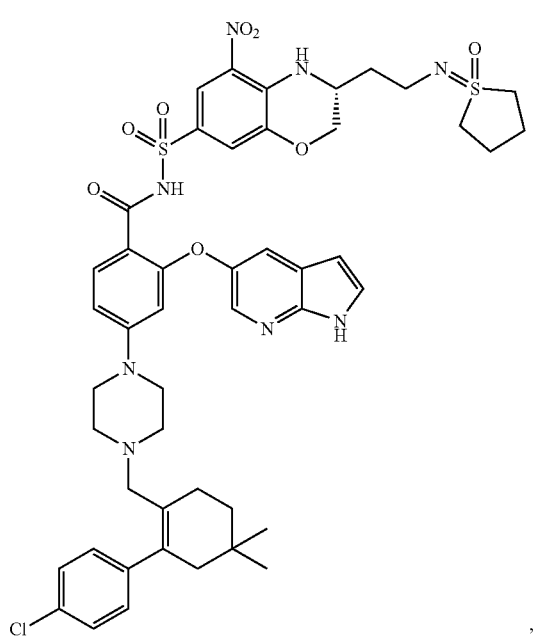
,
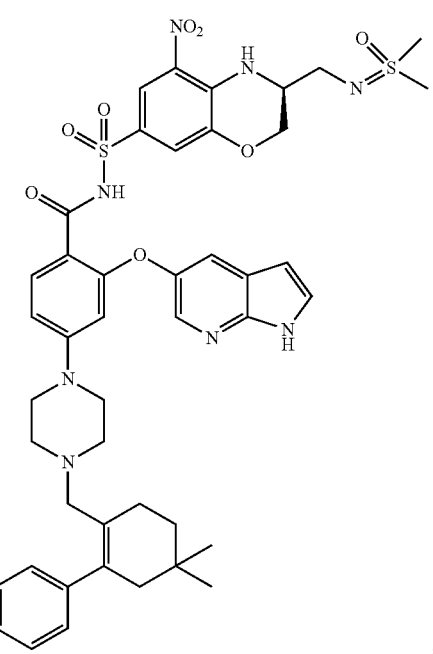
,

85
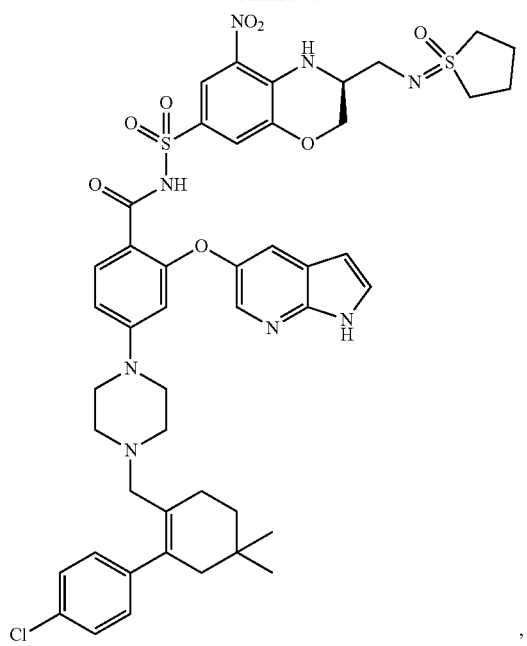
,
86
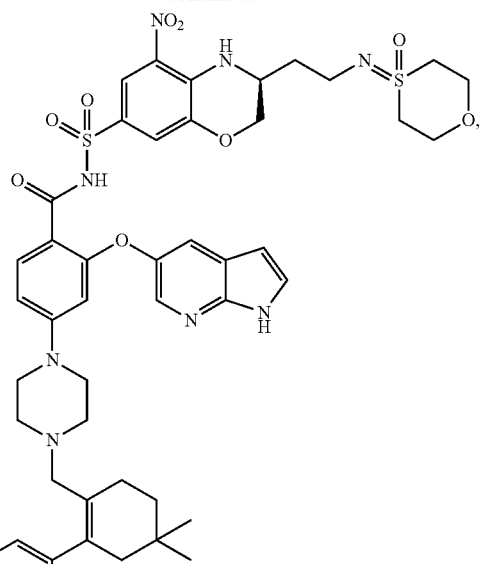
,
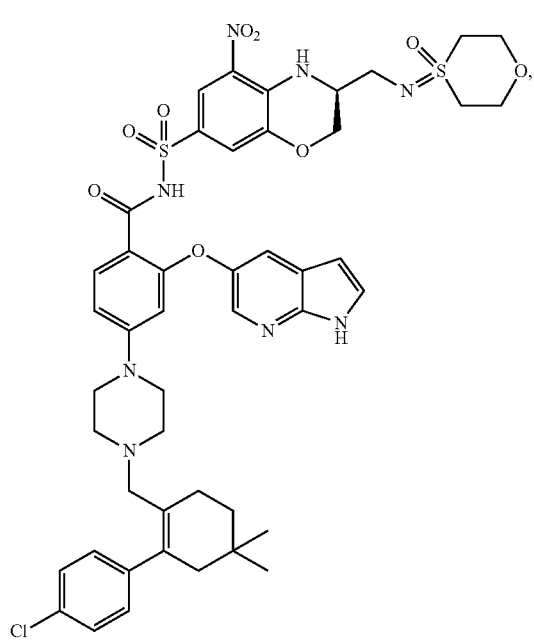
,
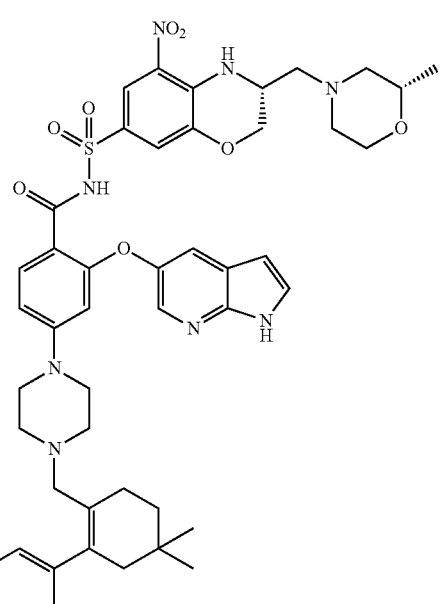
,

87
-continued
88
-continued
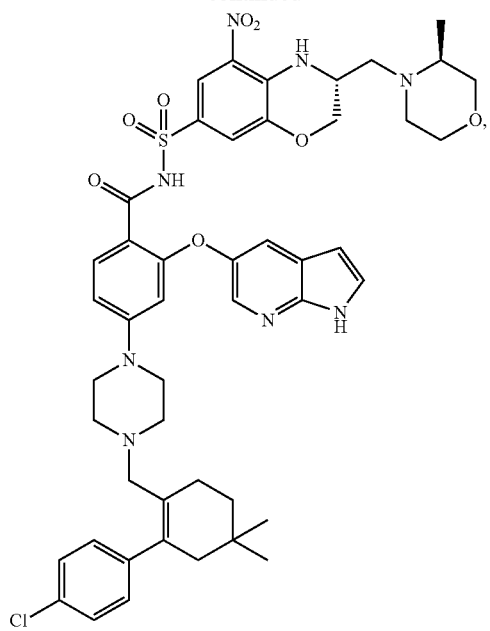
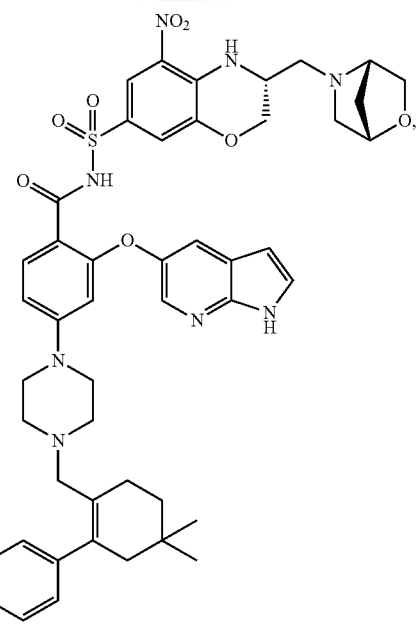

89 -continued
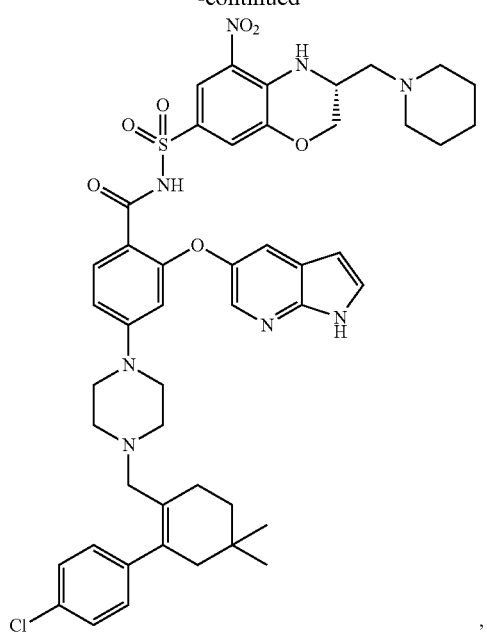
90 -continued
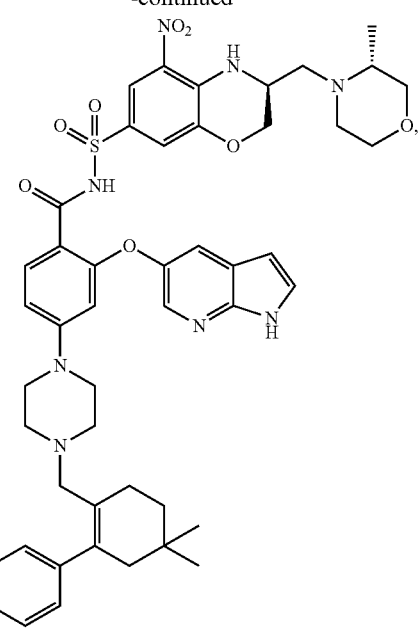
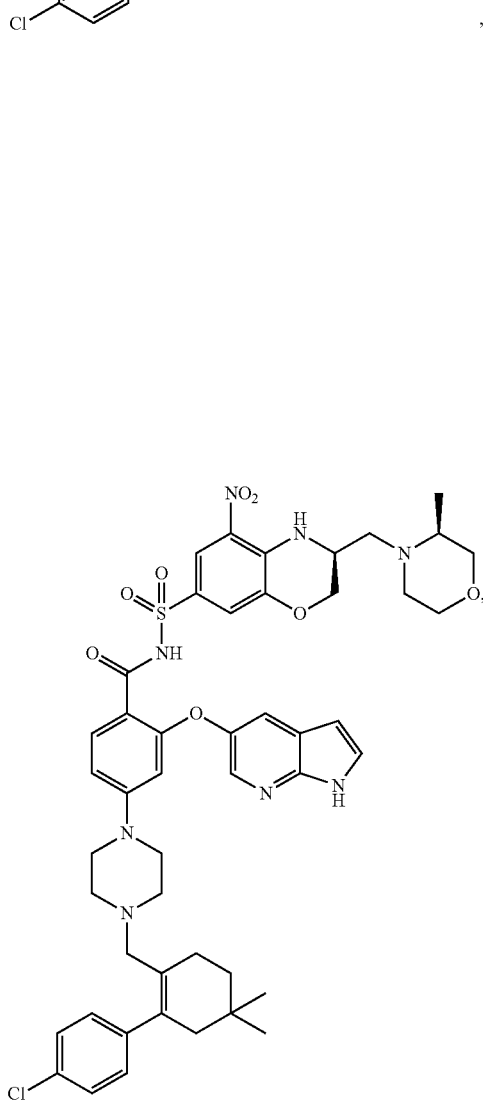
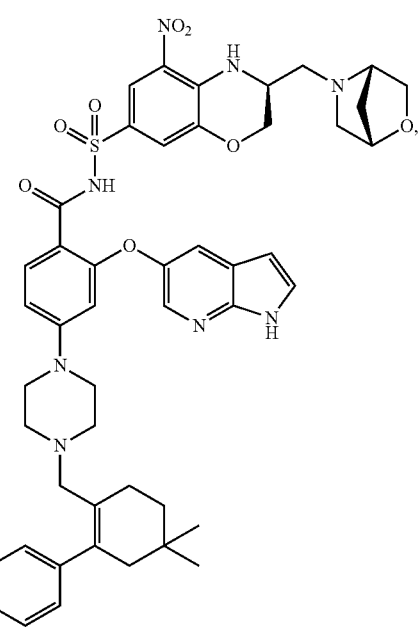

91
-continued
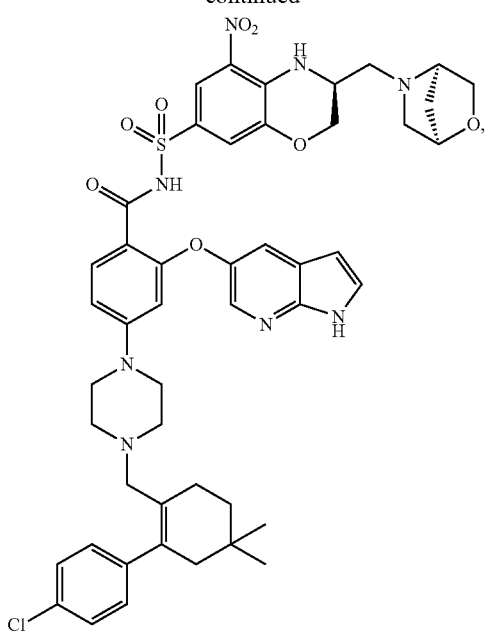
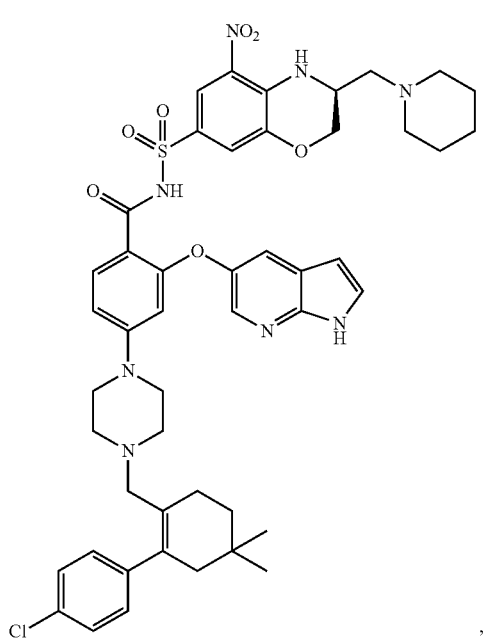
92
-continued
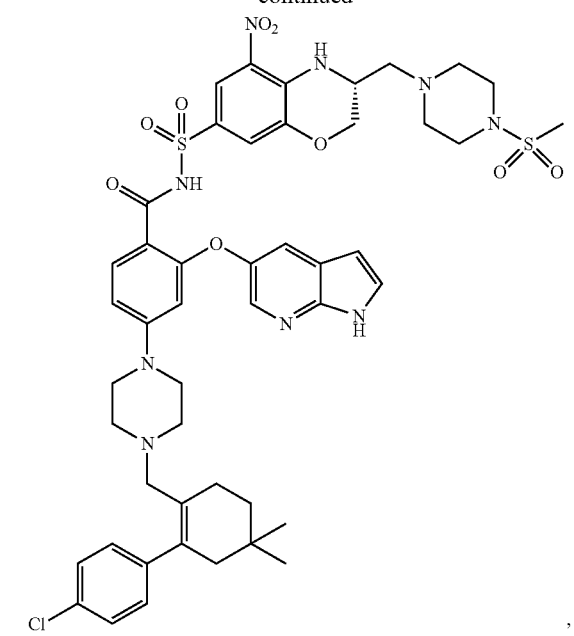
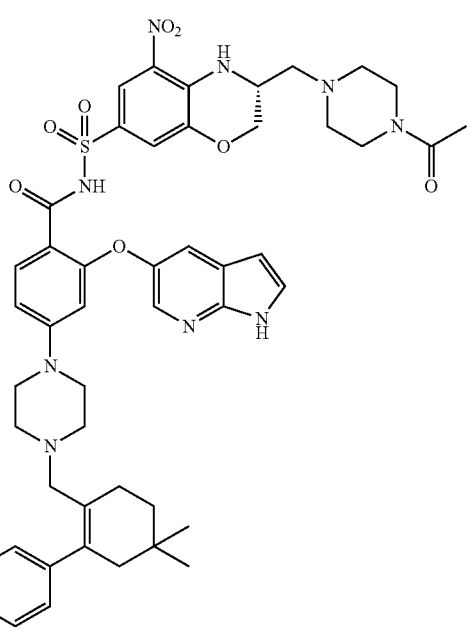

93
-continued
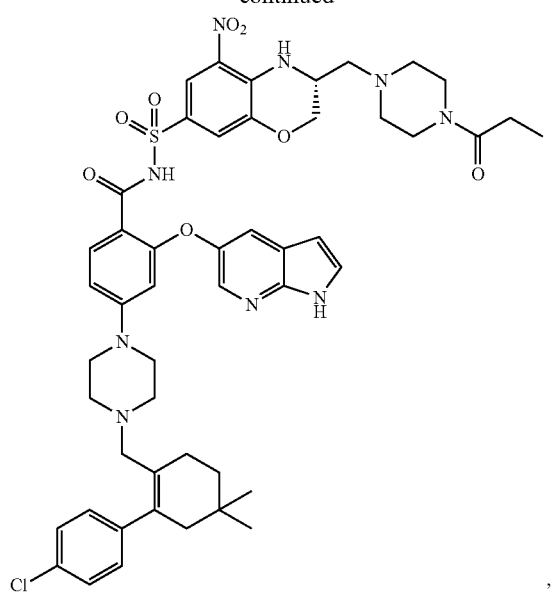
,
94
-continued
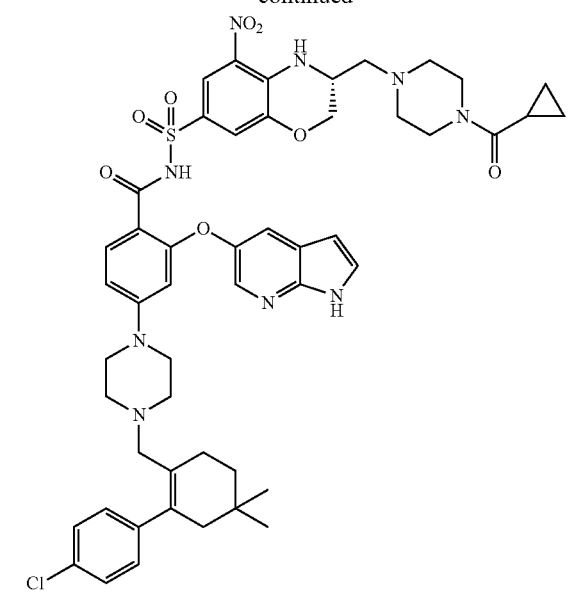
,
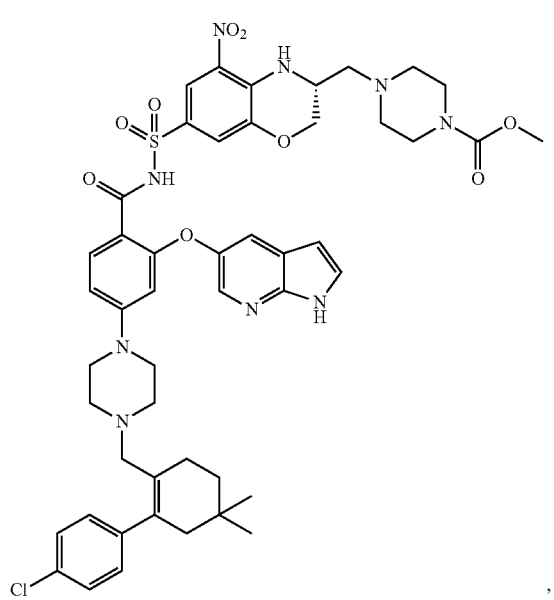
,
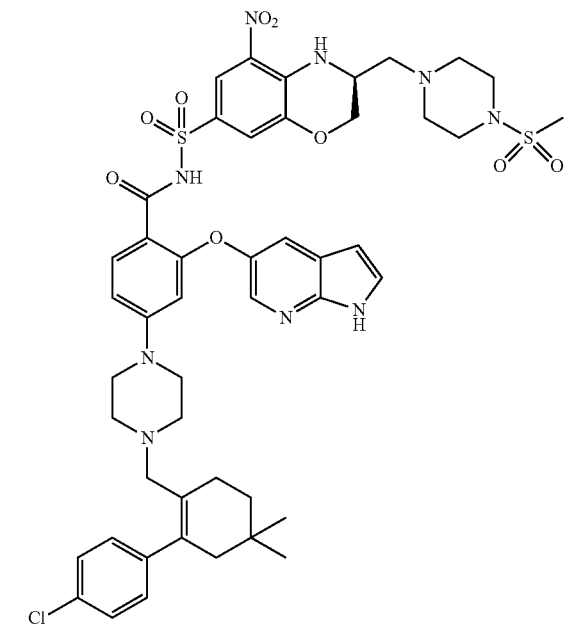
, 95
-continued
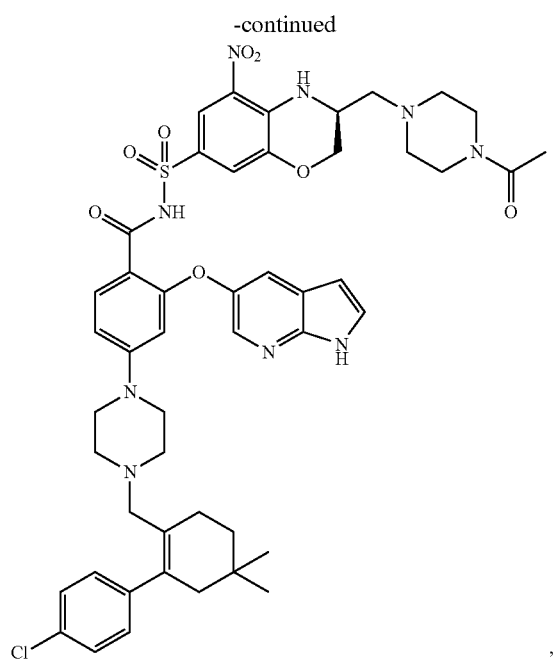
96
-continued
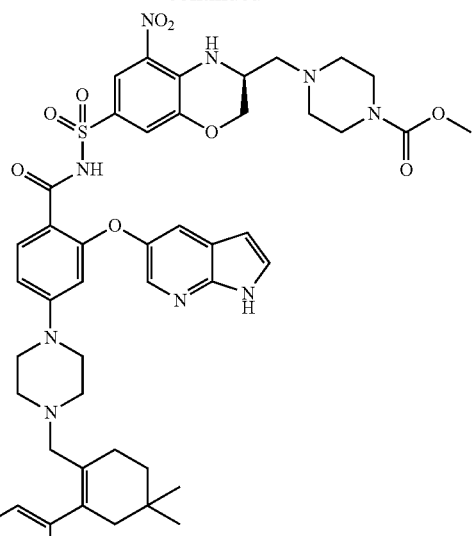
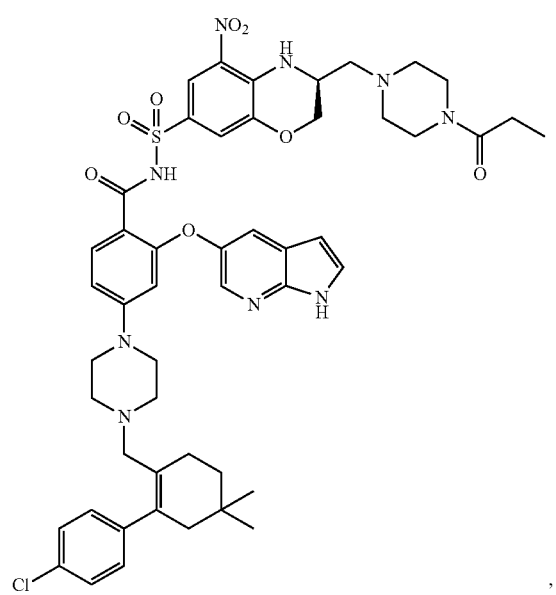
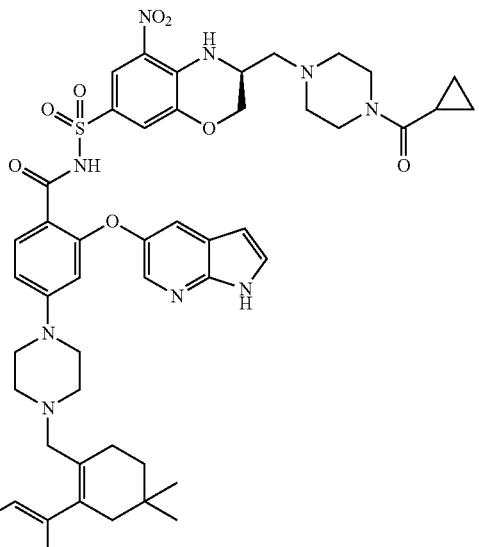

97
-continued
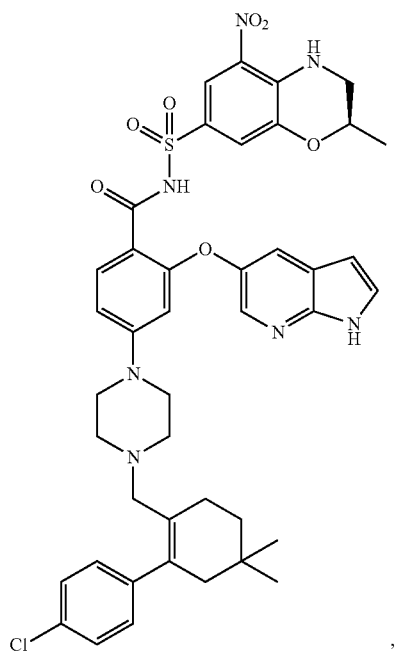
,
98
-continued
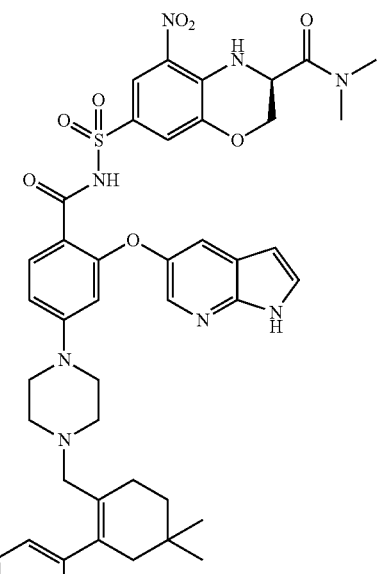
,
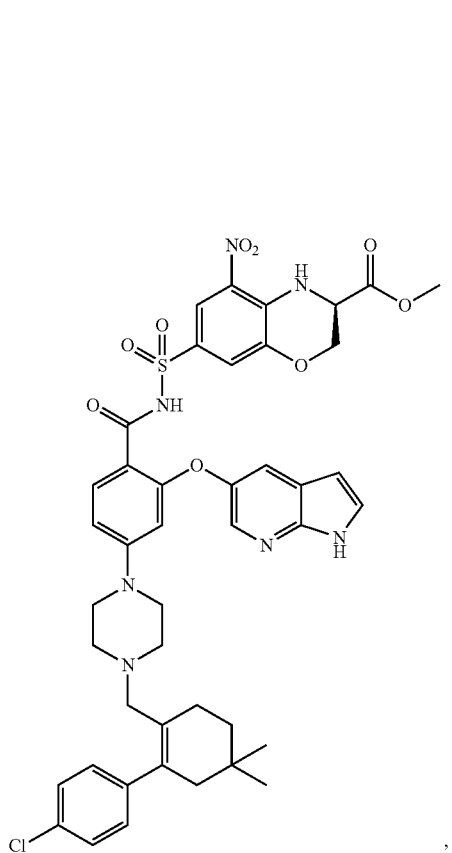
,
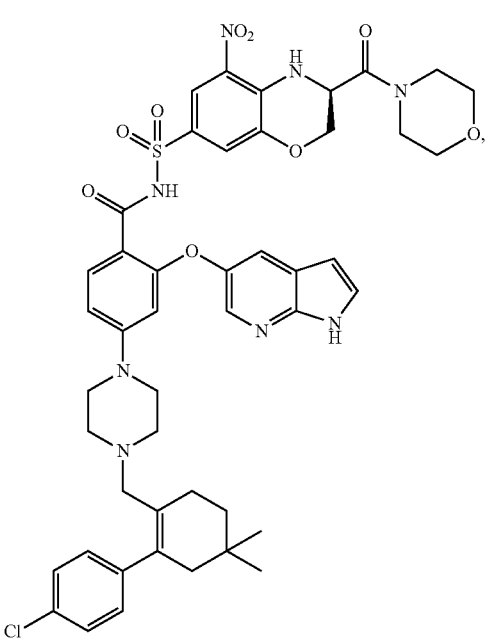
, 99
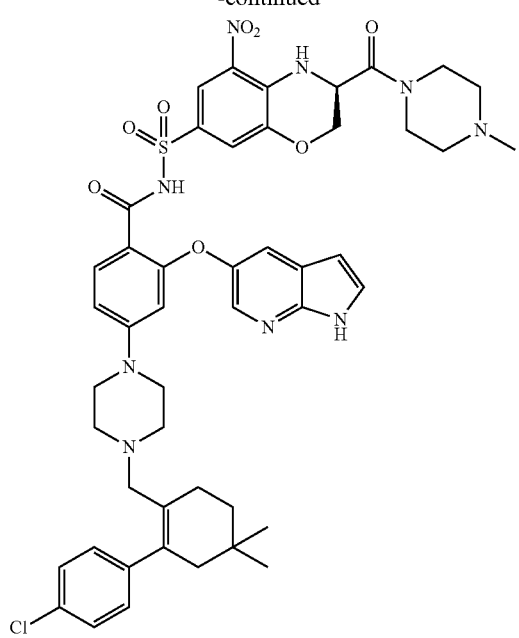
,
100
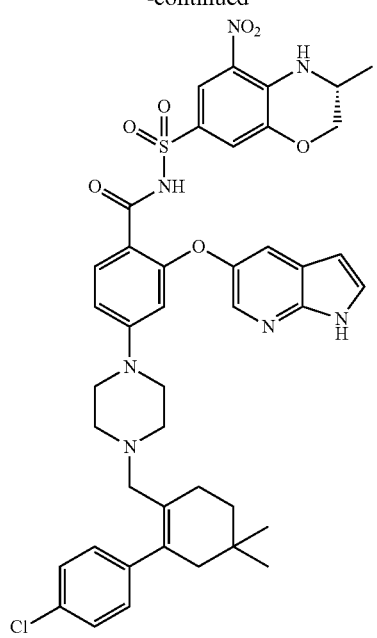
,
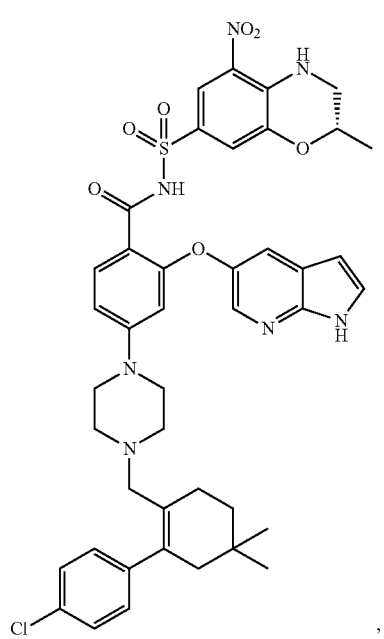
,
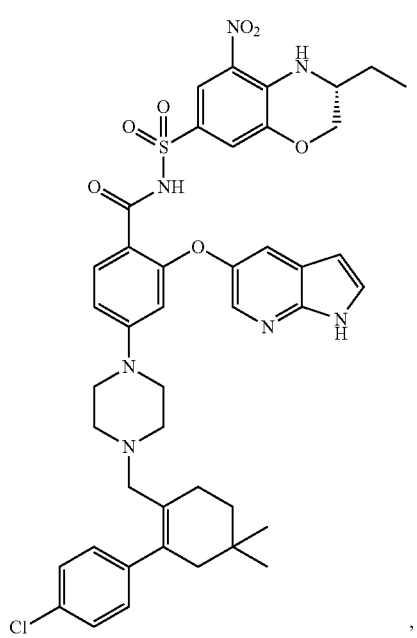
, 101
-continued
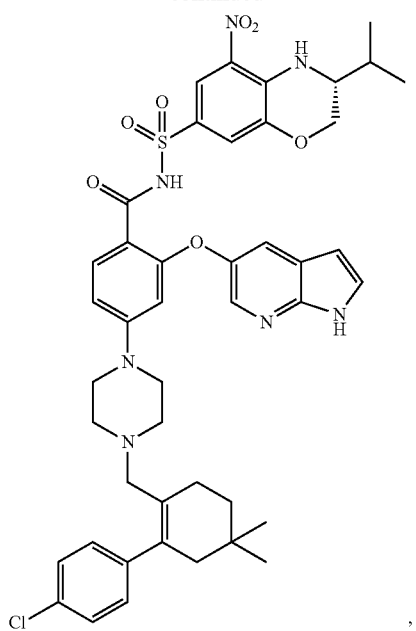
102
-continued
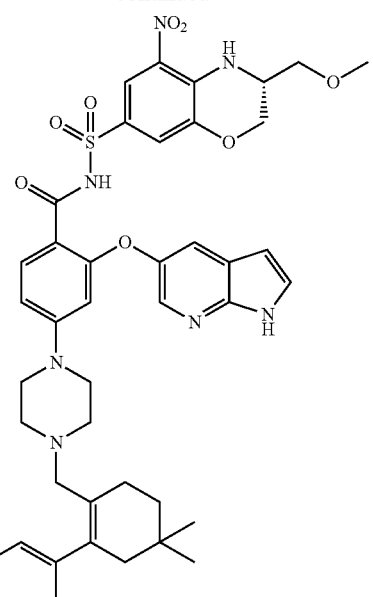
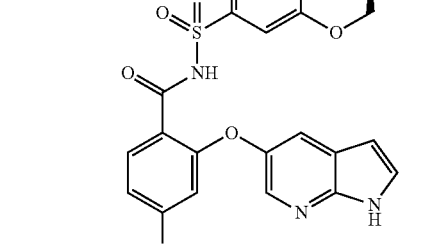
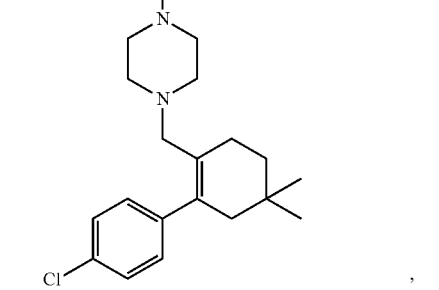

103
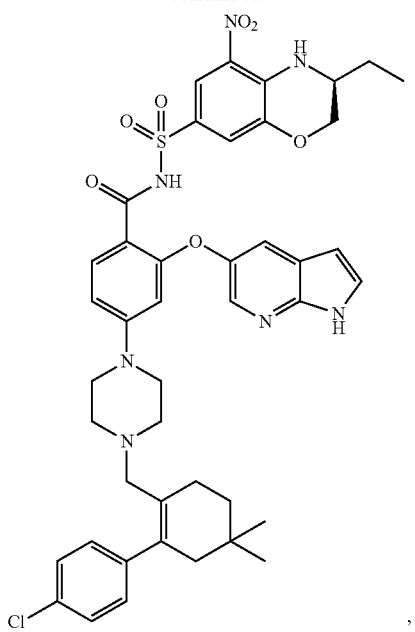
104
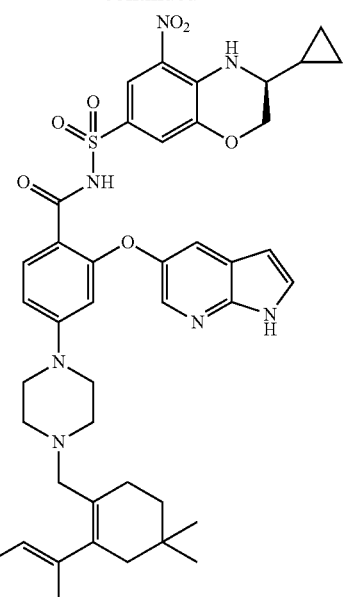
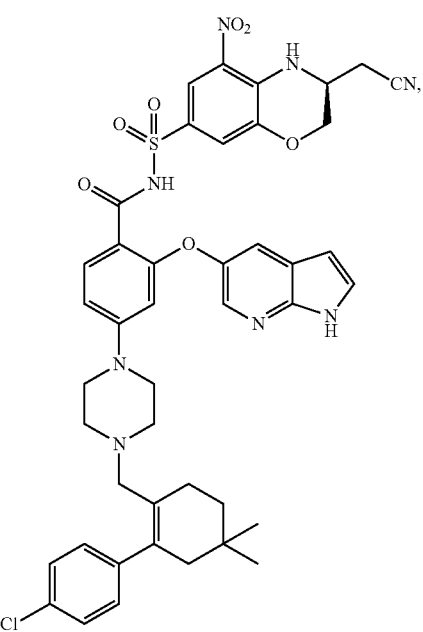

105 -continued
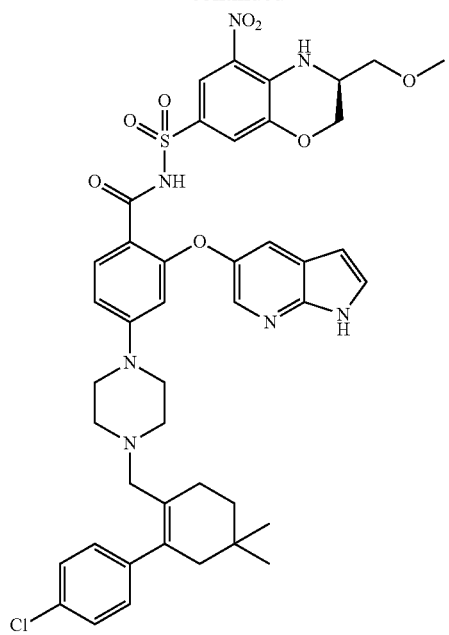
106 -continued
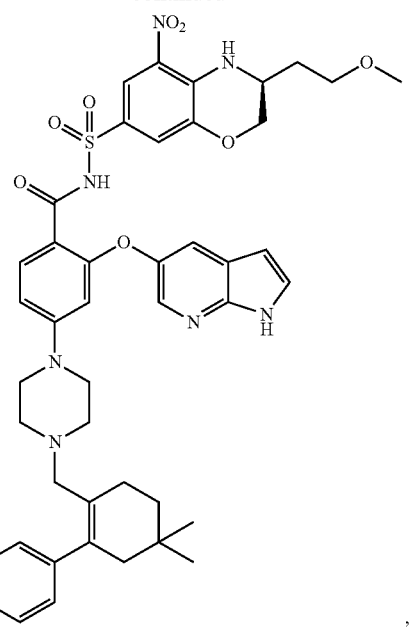

107
-continued
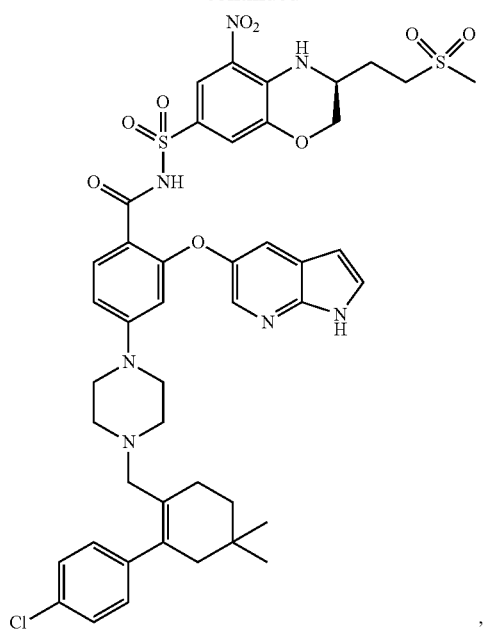
,
108
-continued
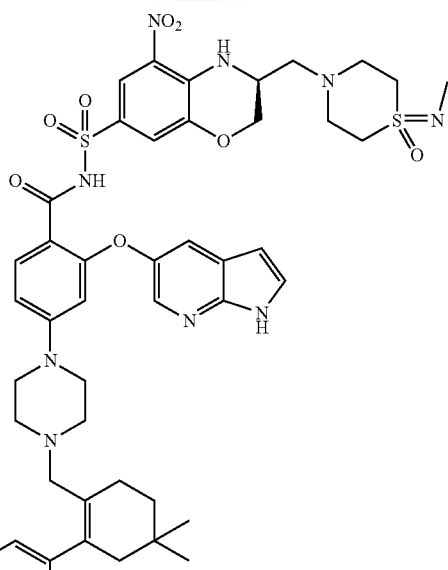
,

109
-continued
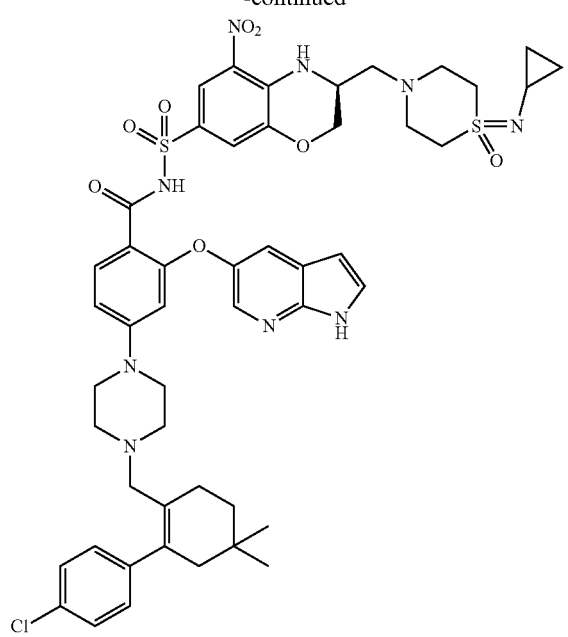
110
-continued
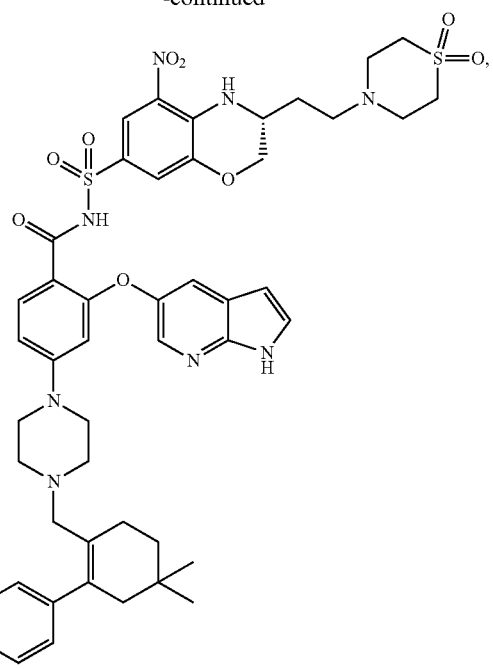
,
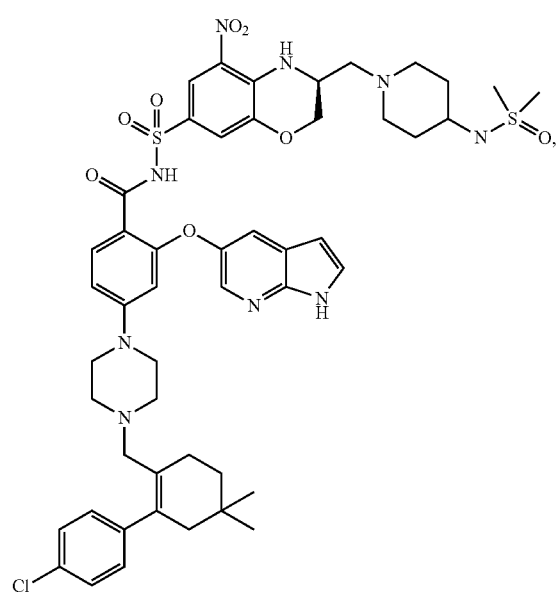
,
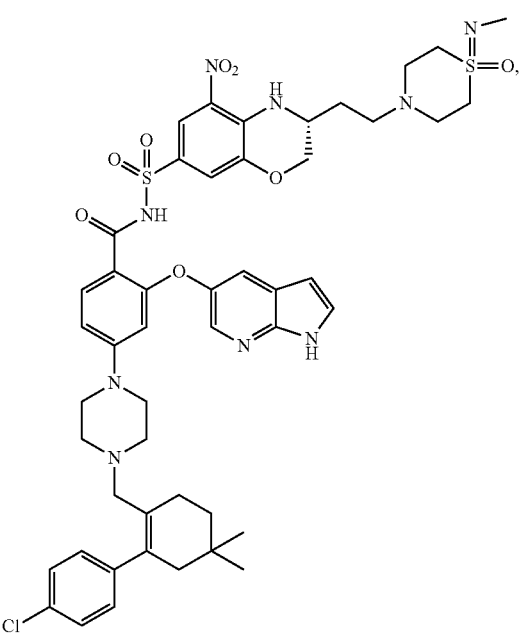

111
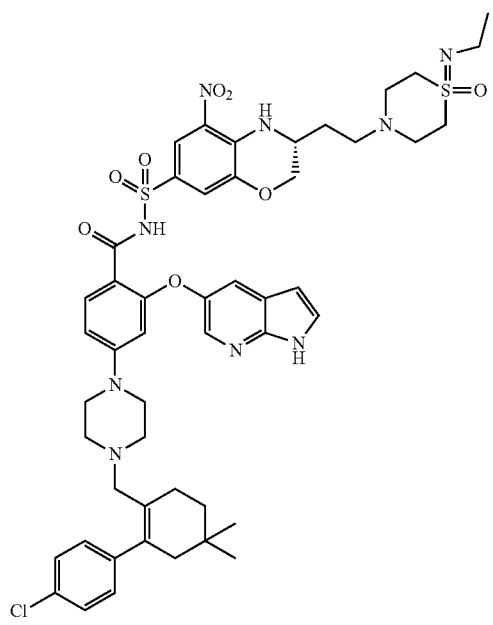
,
112
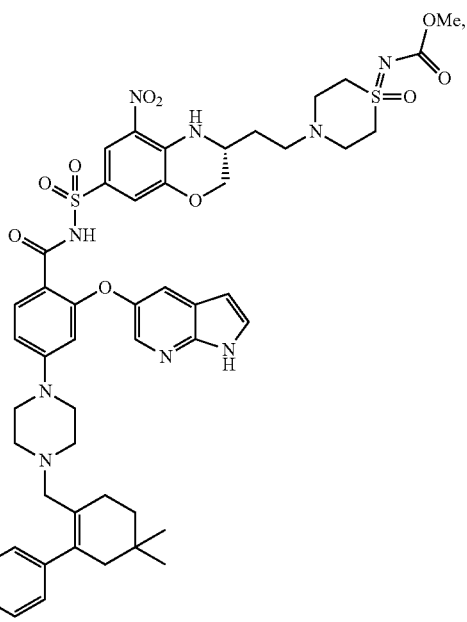
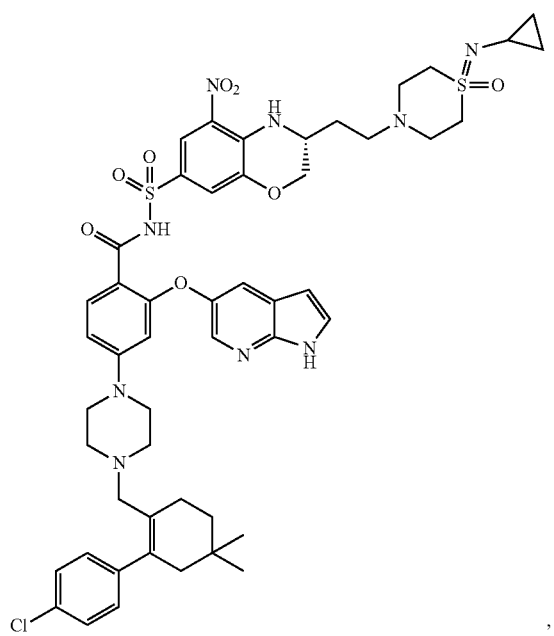
,
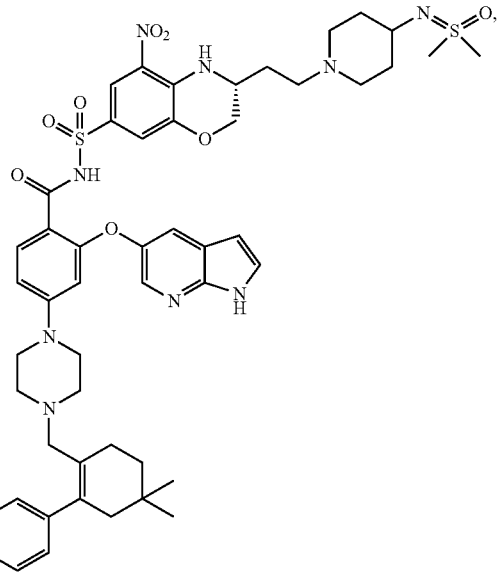
,

113
-continued
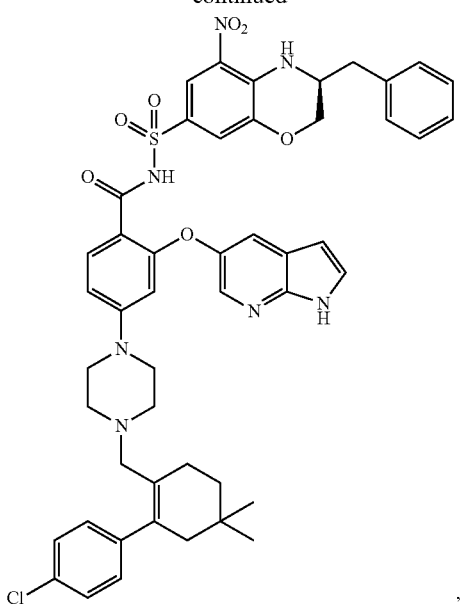
114
-continued
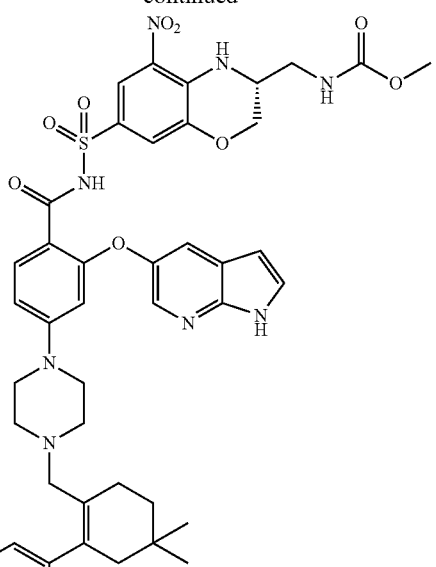
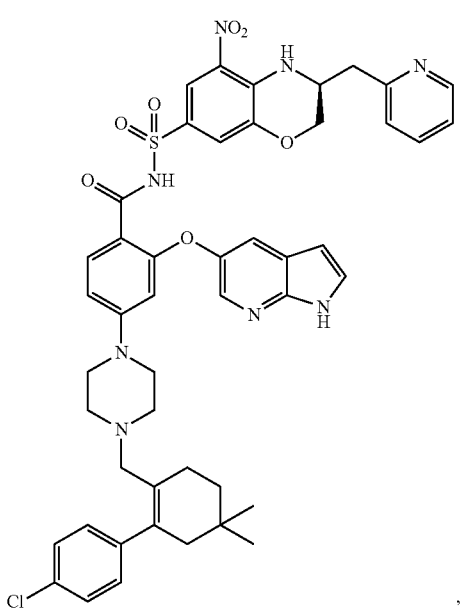

115
-continued
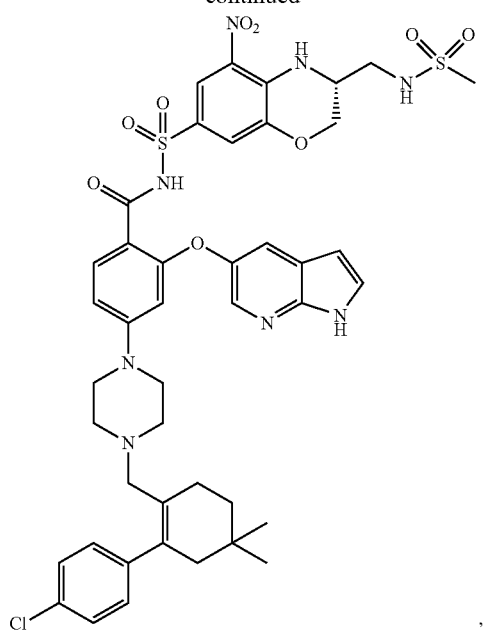
116
-continued
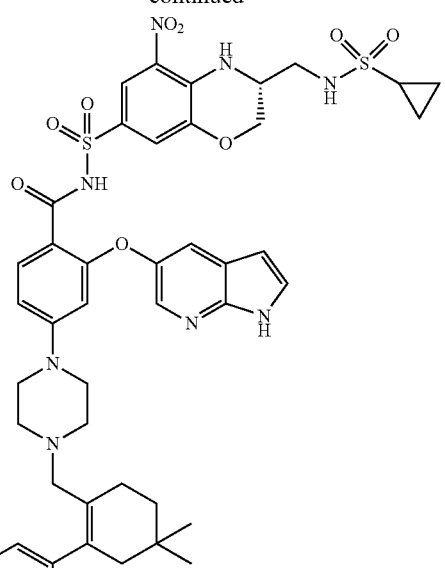

117
-continued
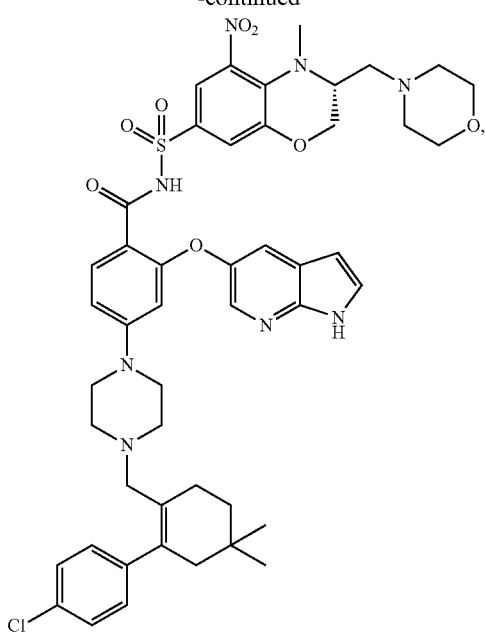
118
-continued
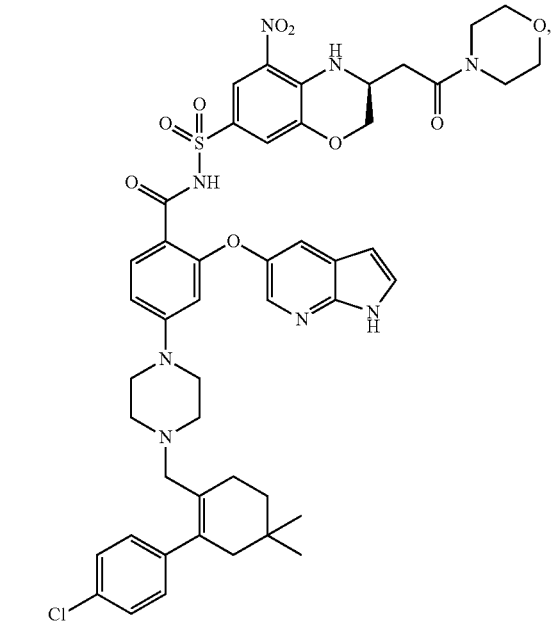
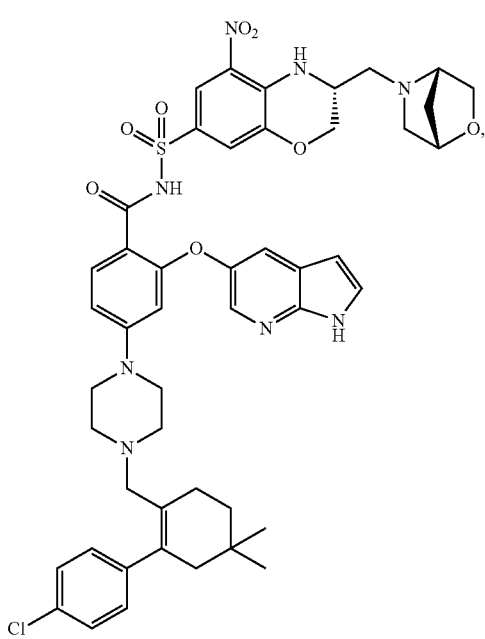
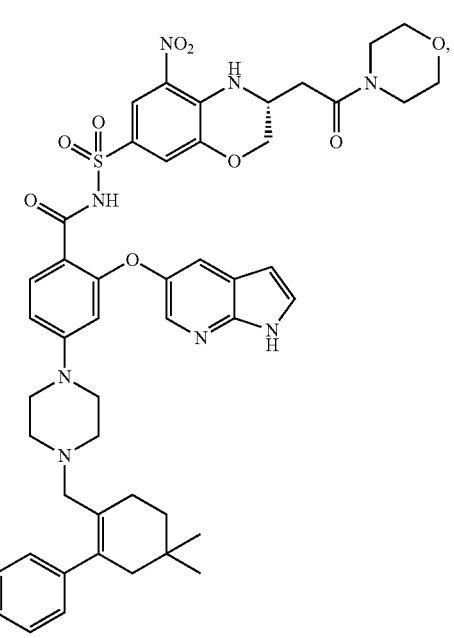

119
-continued
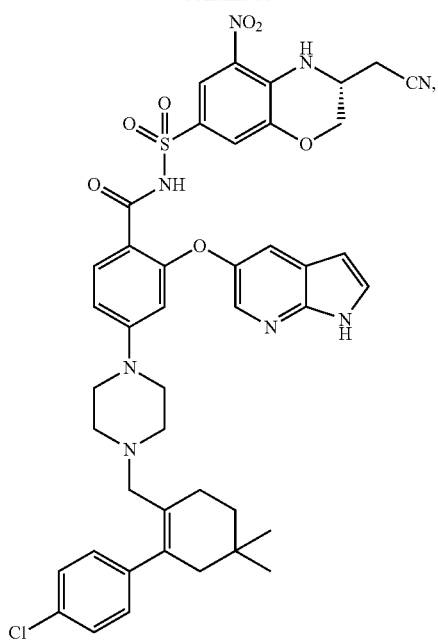
120
-continued
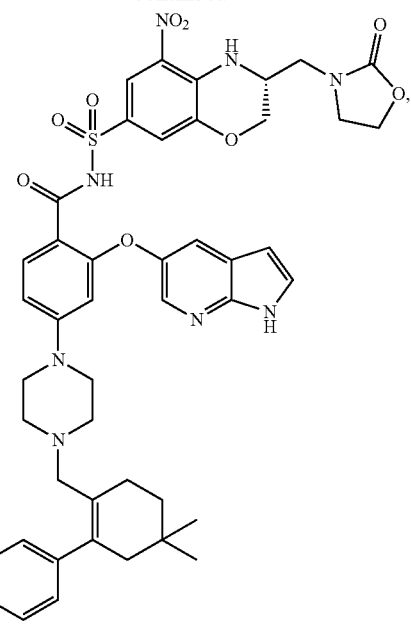
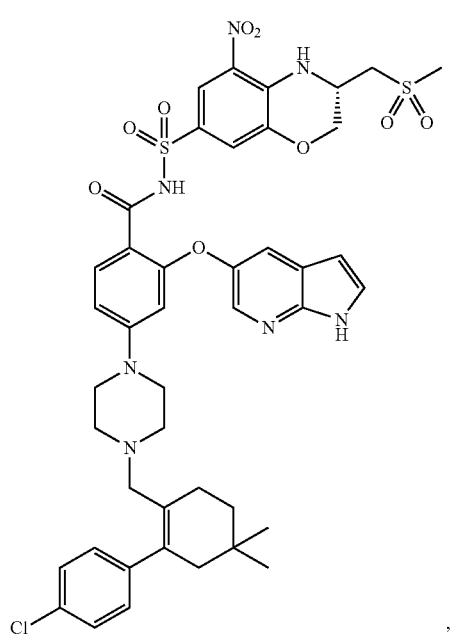
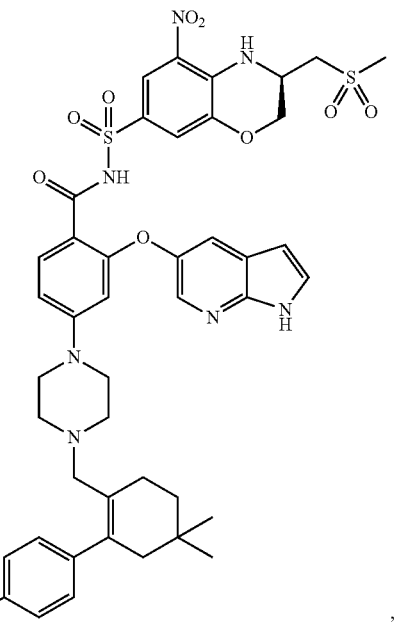

121
-continued
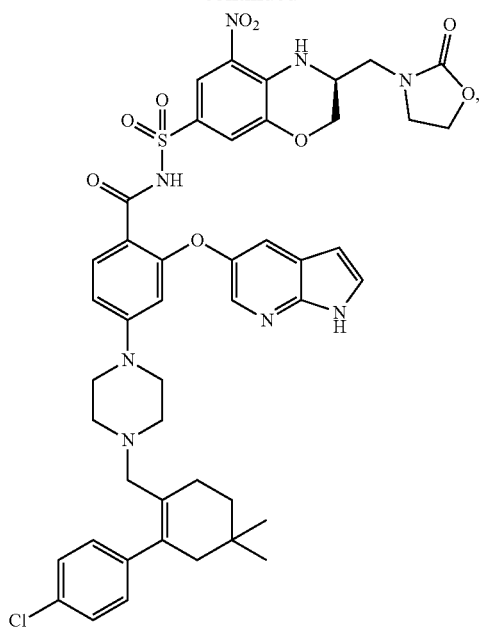
122
-continued
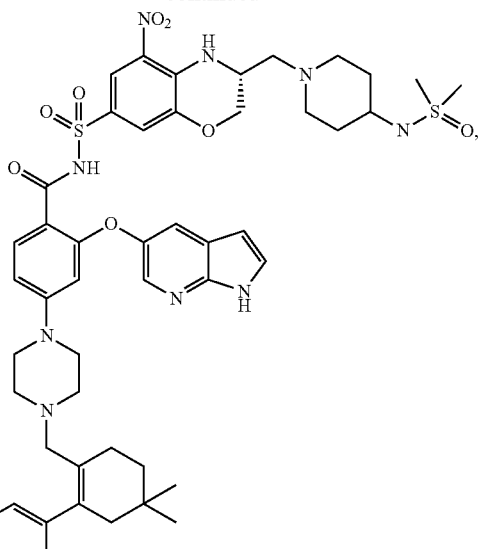
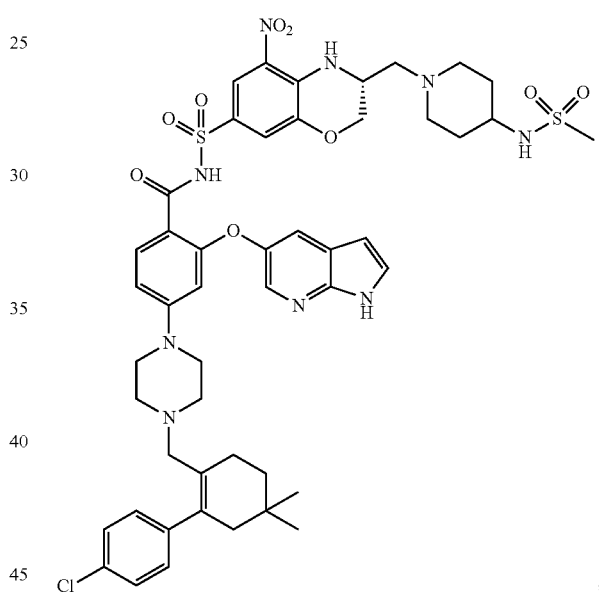
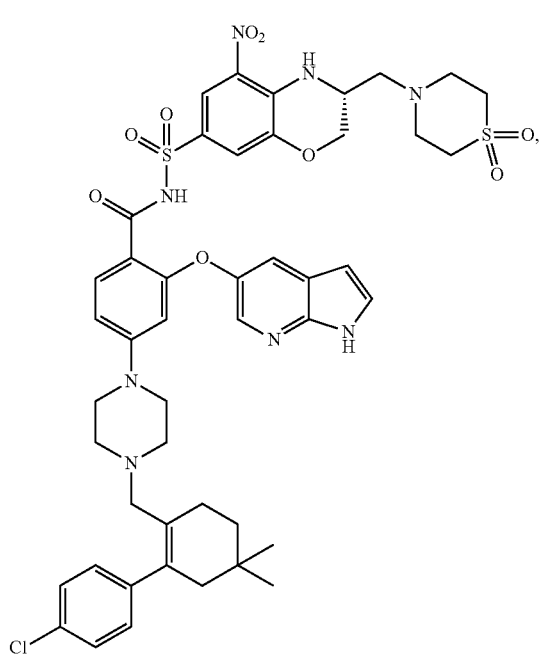

123
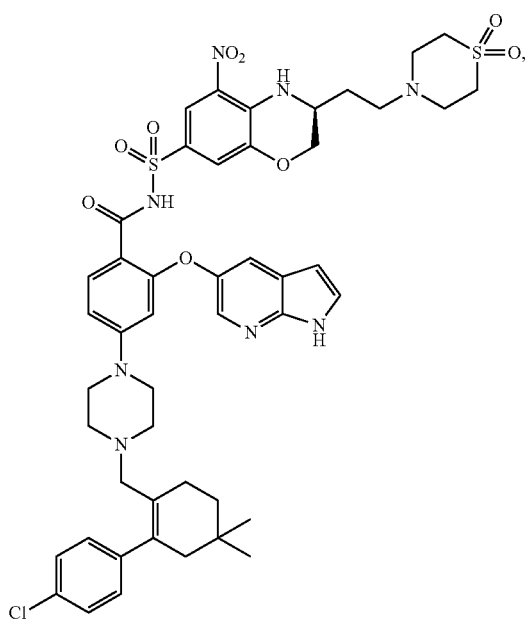
124
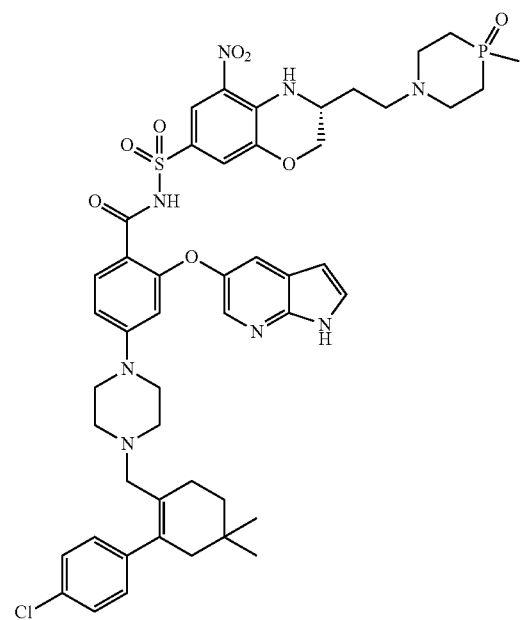

125
-continued
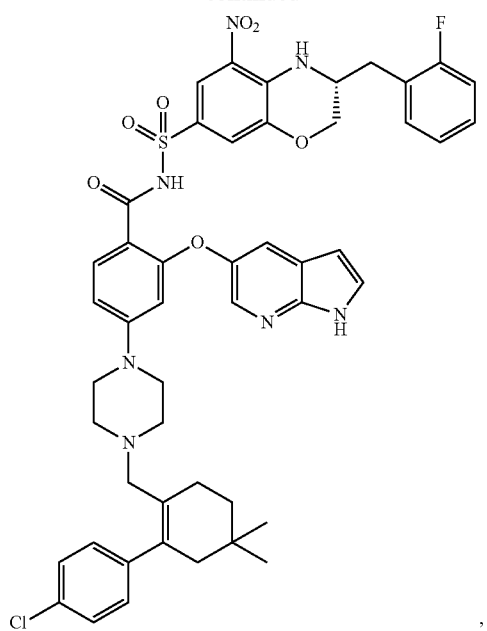
,
126
-continued
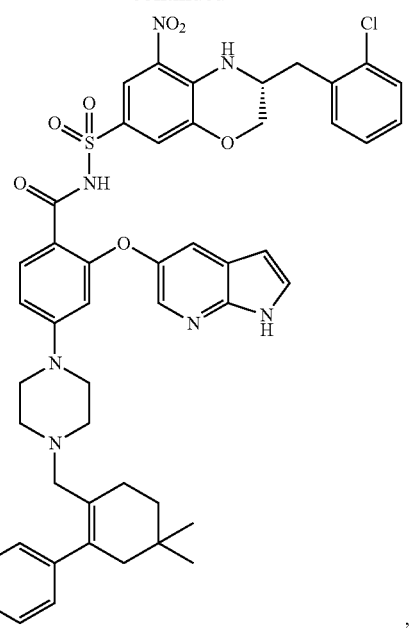
,
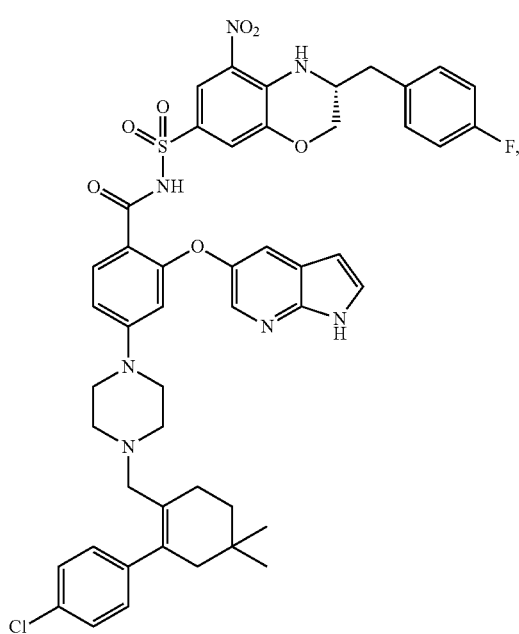
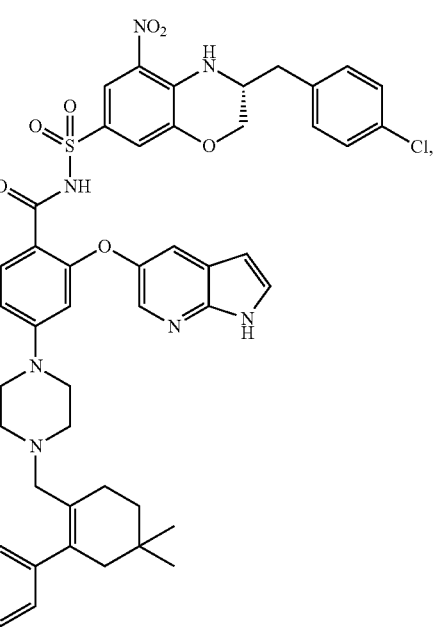

127
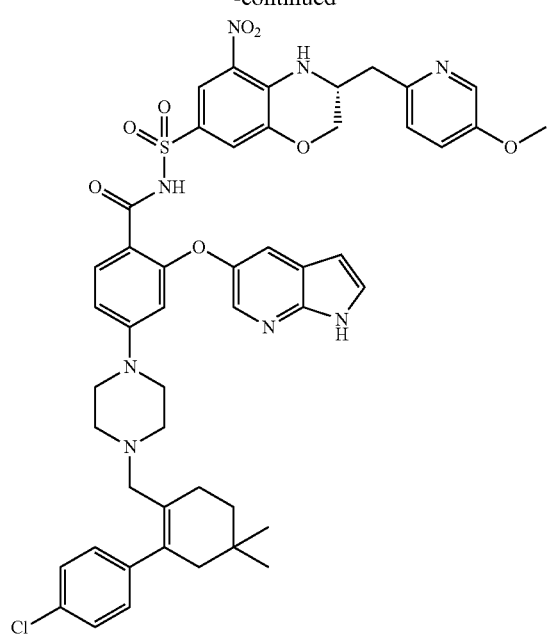
,
128
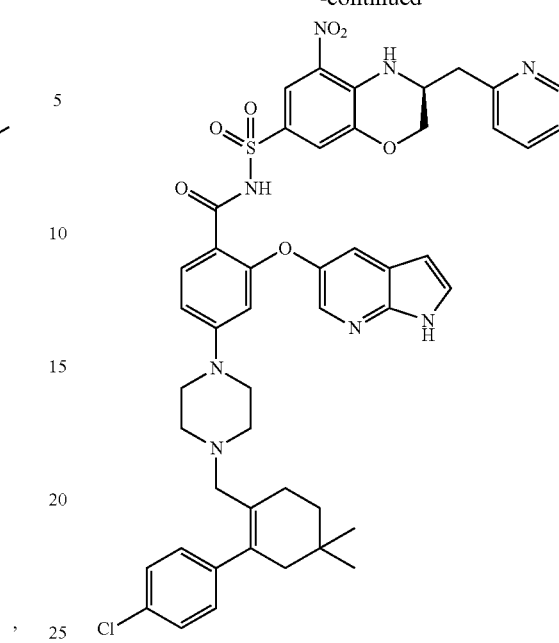
,
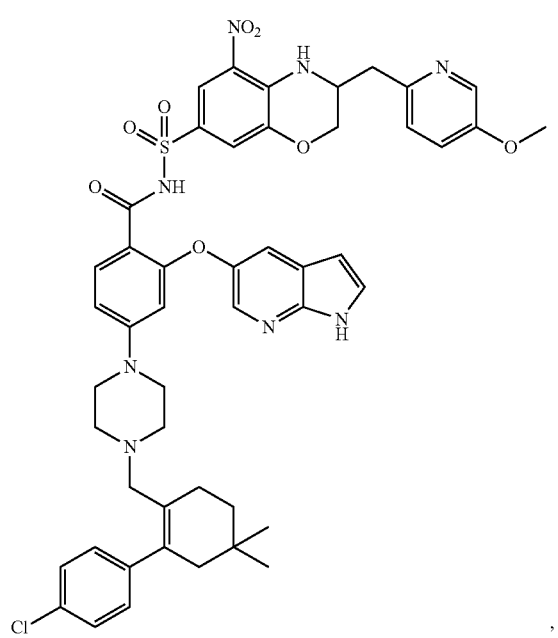
,
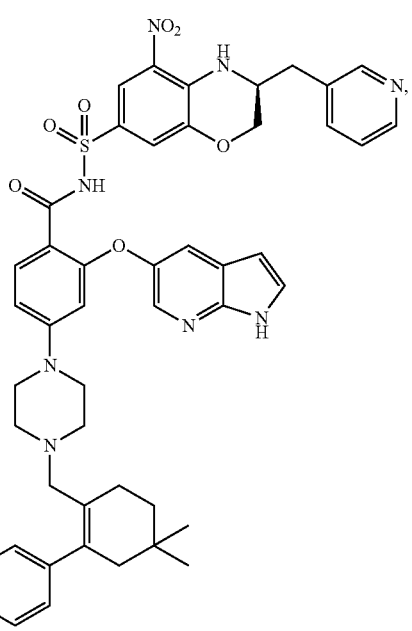
,

129
-continued
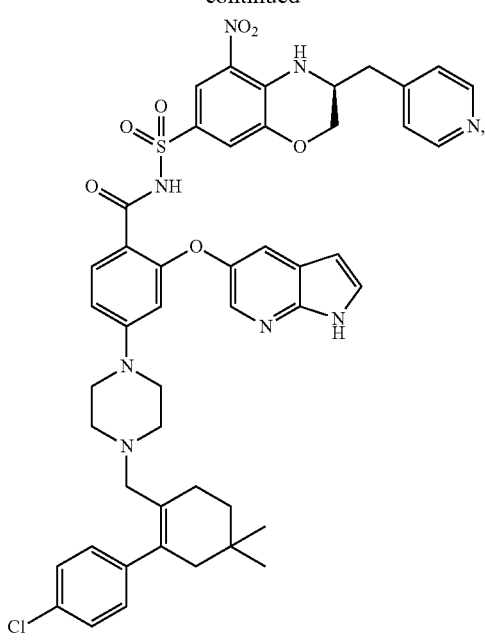
130
-continued
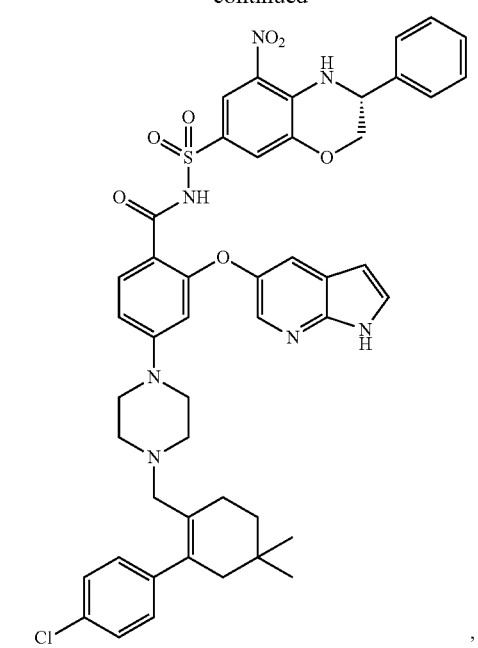
,
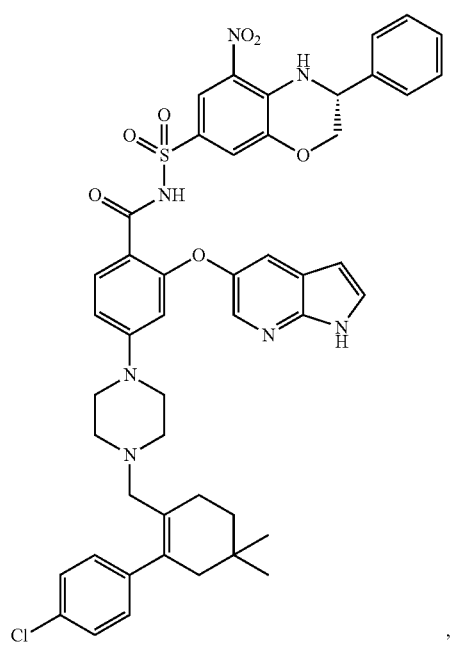
,
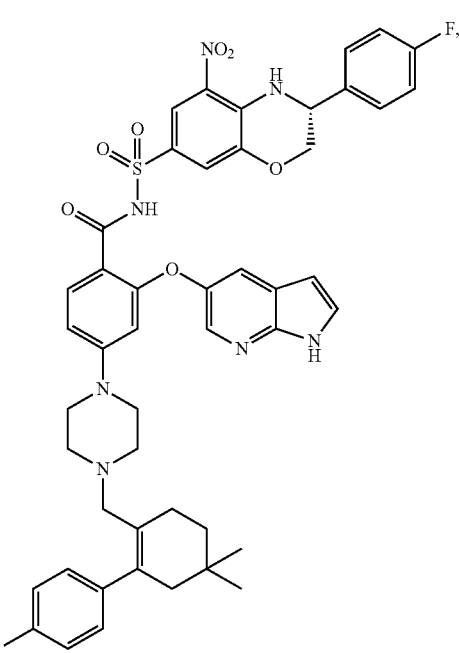

131
-continued
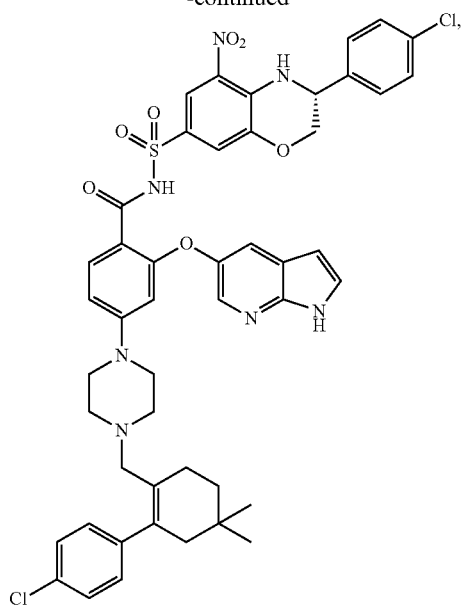
132
-continued
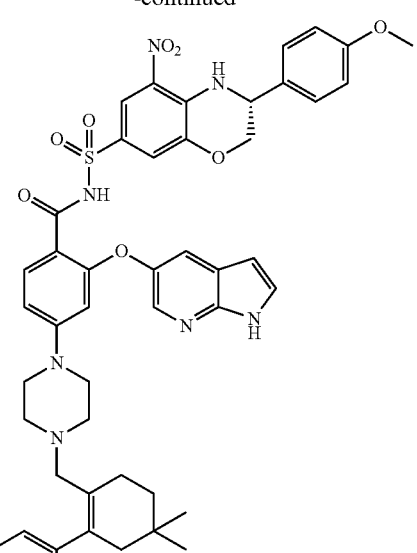
,
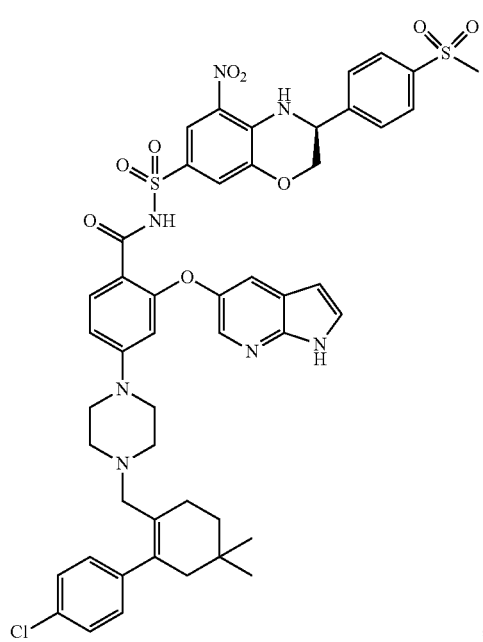
,
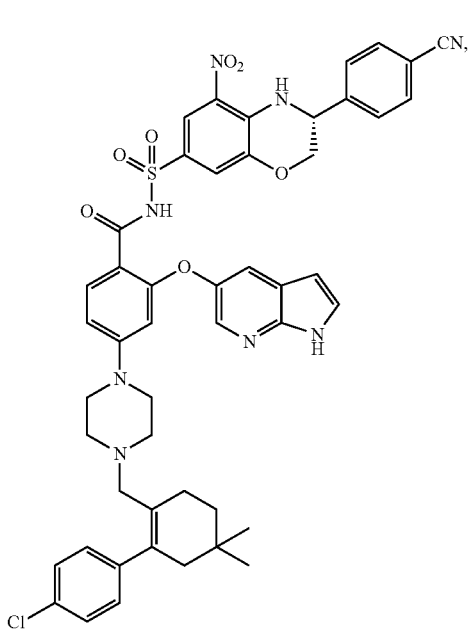

133
-continued
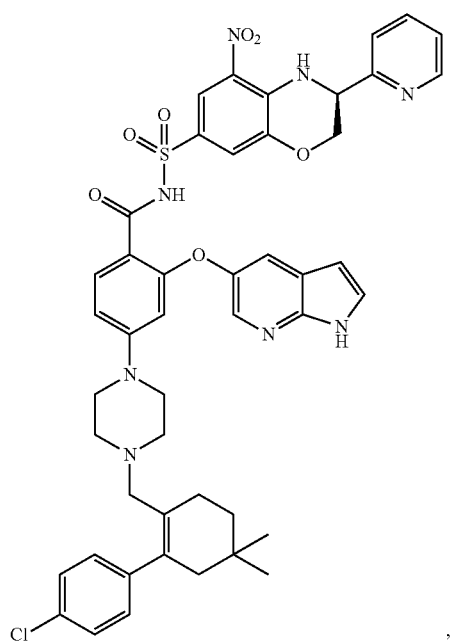
134
-continued
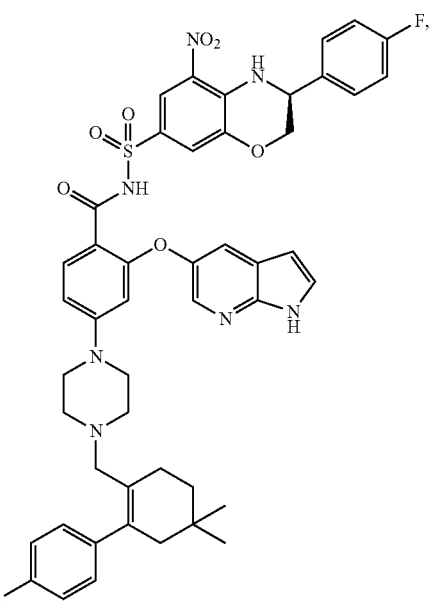
,
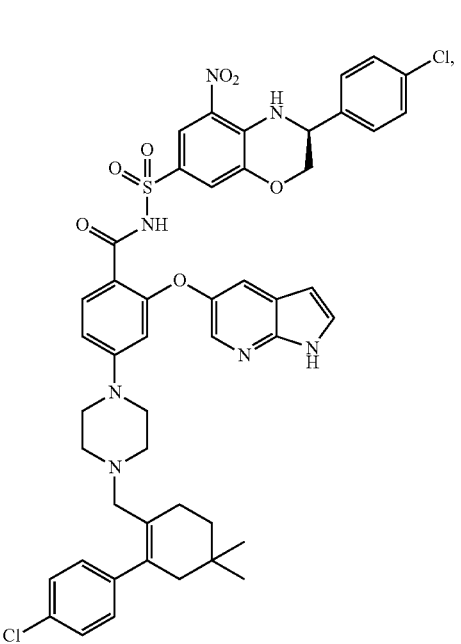
,

135
-continued
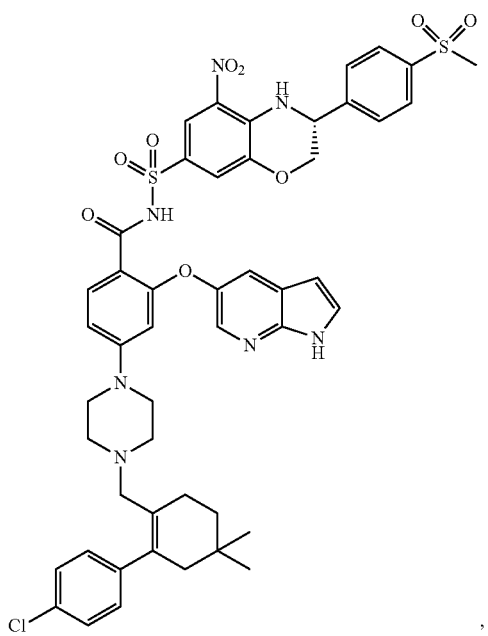
136
-continued
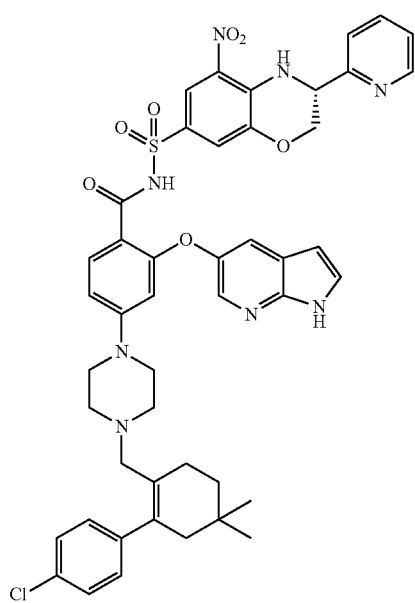
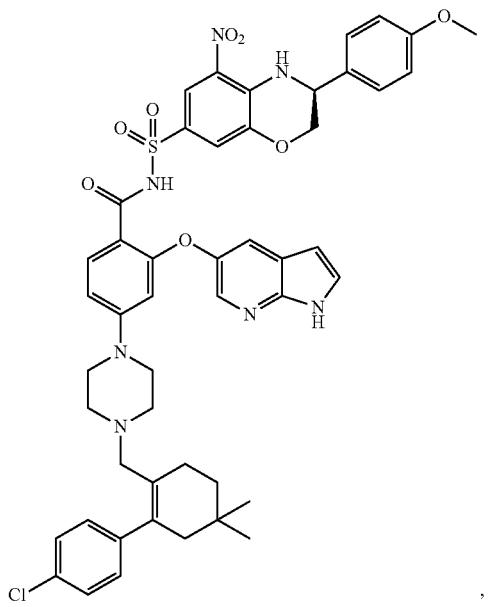
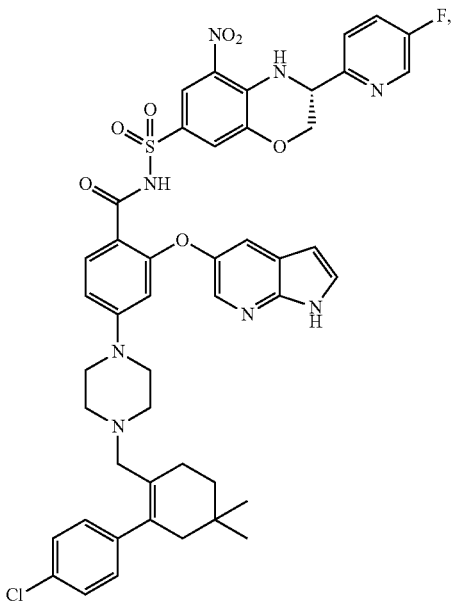

137
-continued
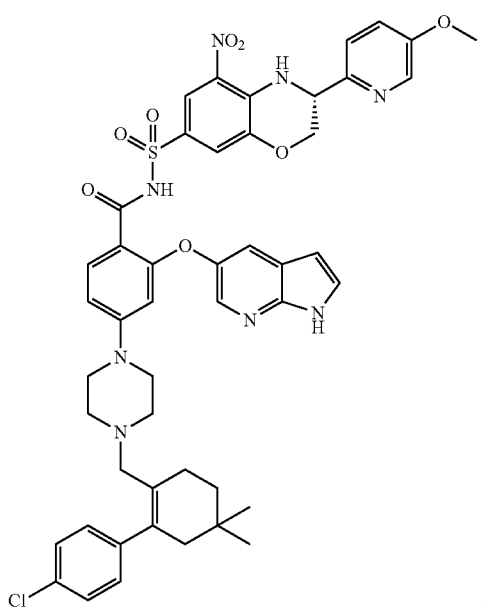
138
-continued
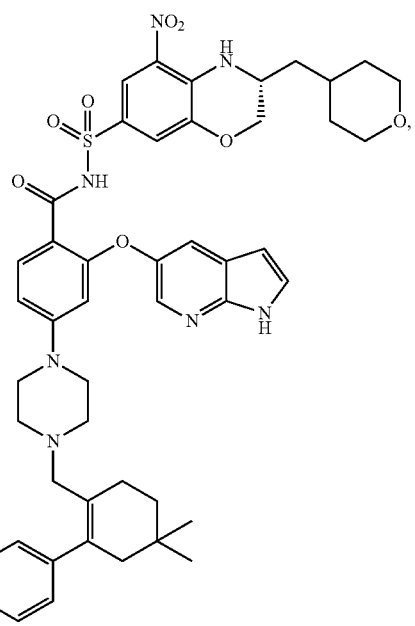

139
-continued
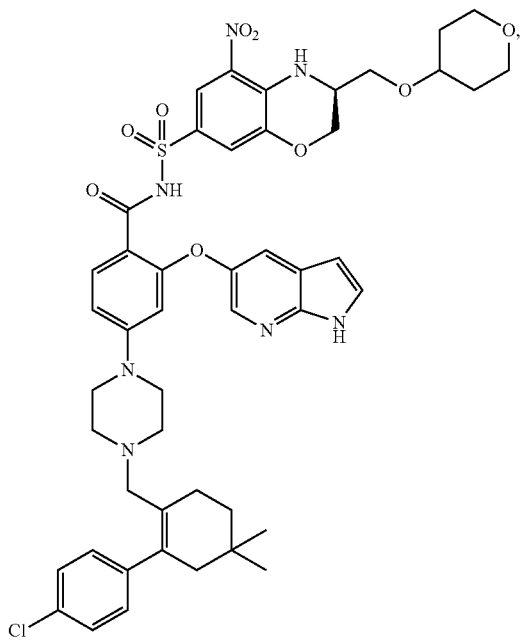
140
-continued
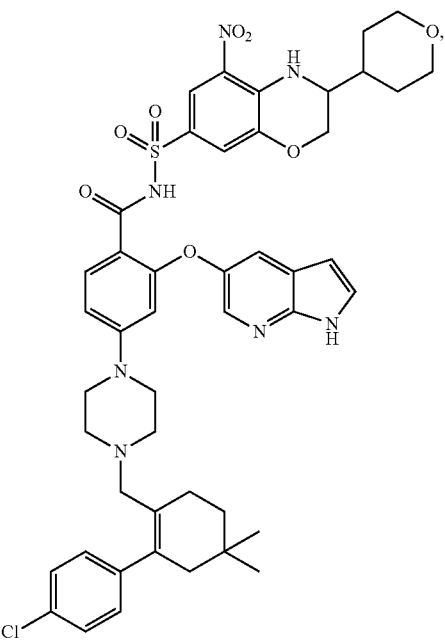
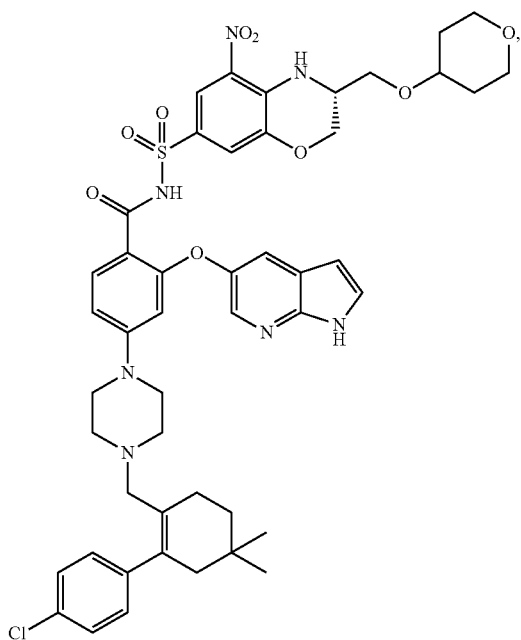
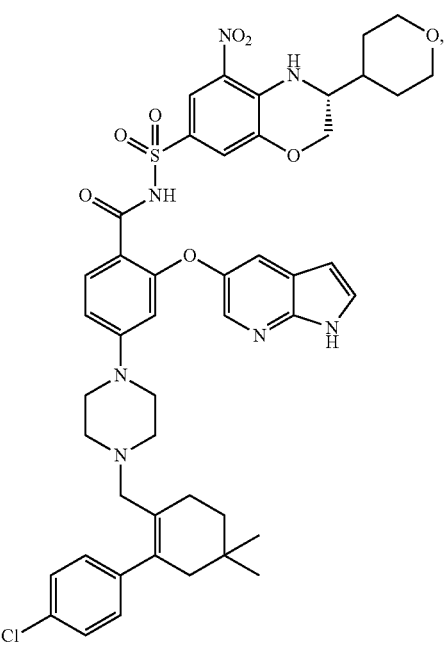

141
-continued
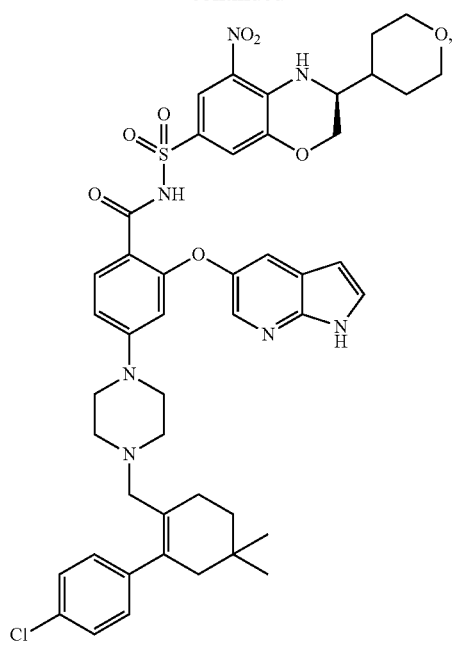
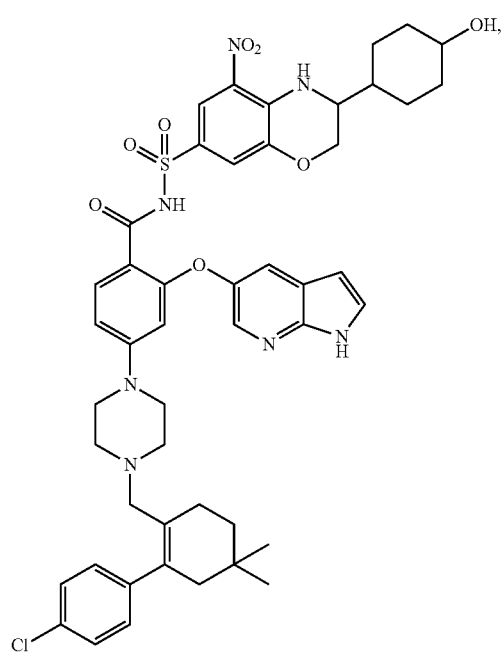
142
-continued
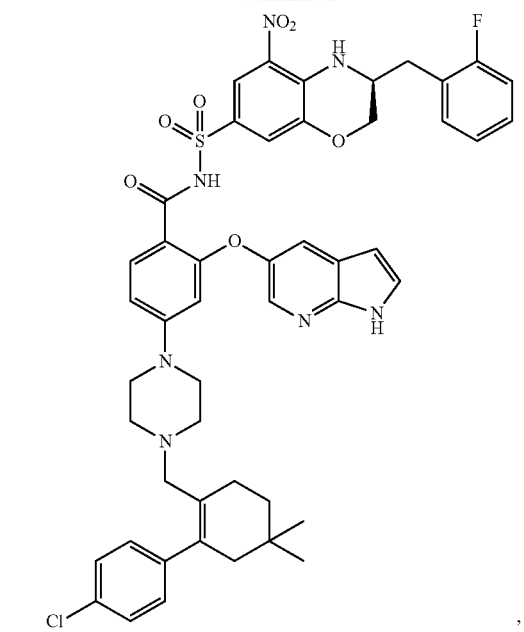
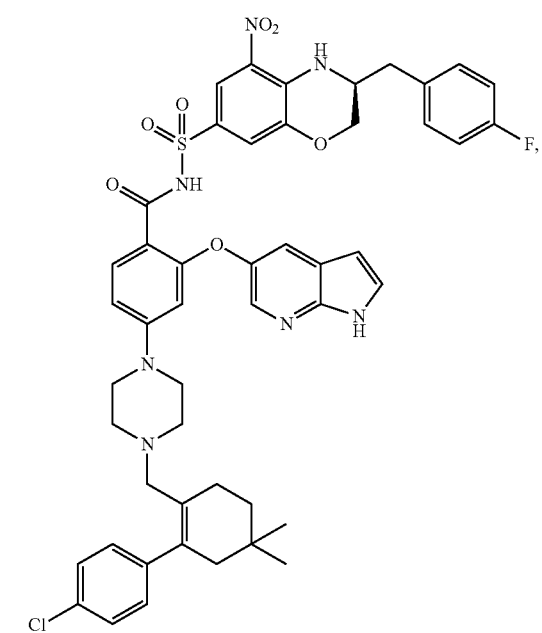

143
-continued
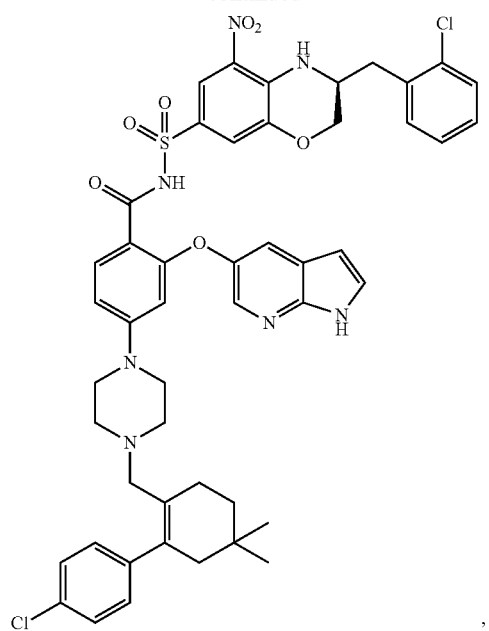
144
-continued
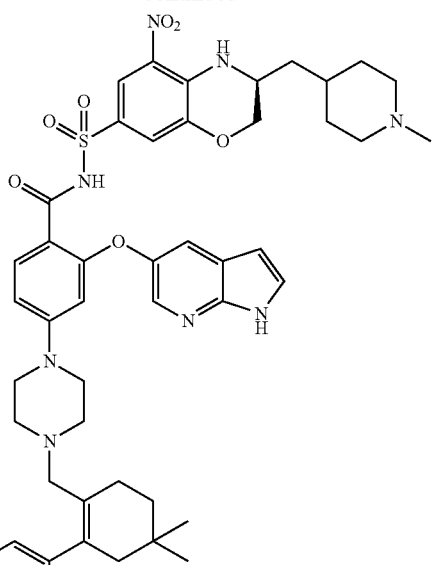

145
-continued
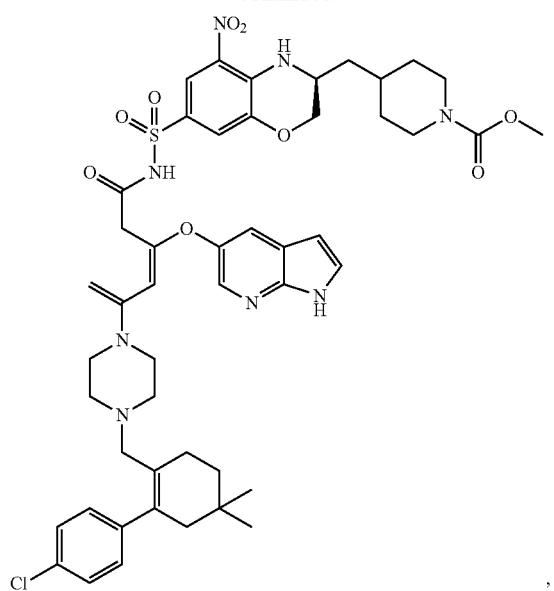
,
146
-continued
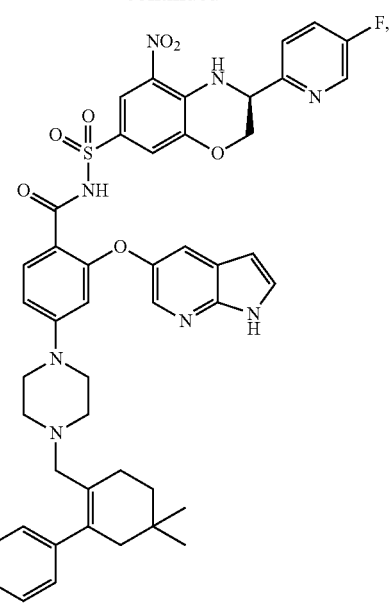
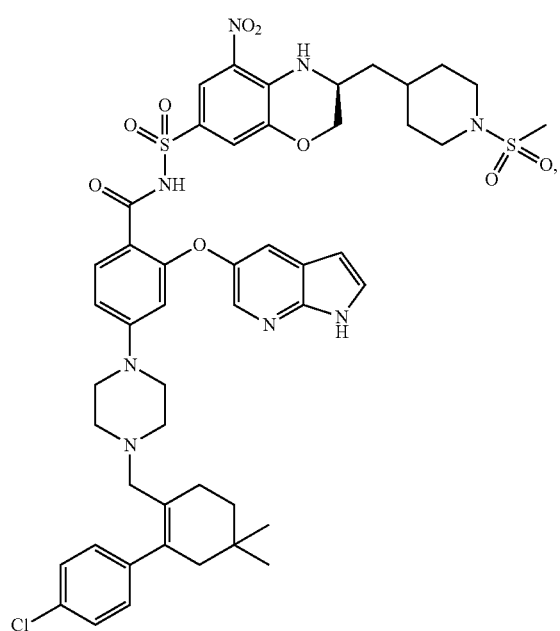
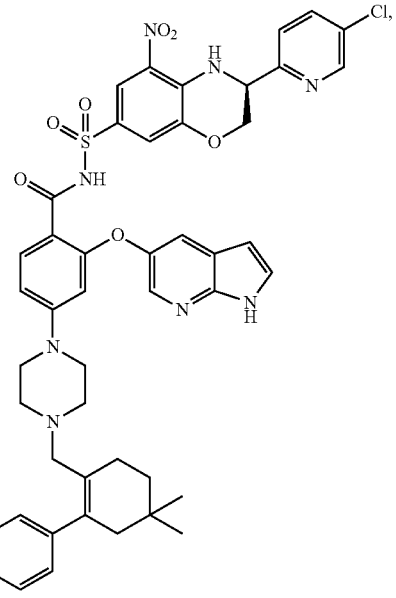

147
-continued
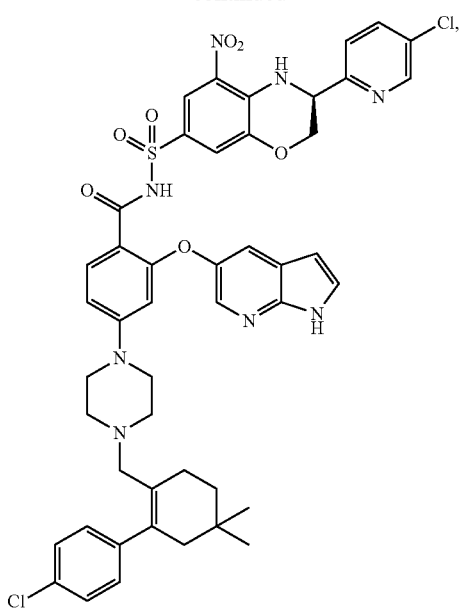
148
-continued
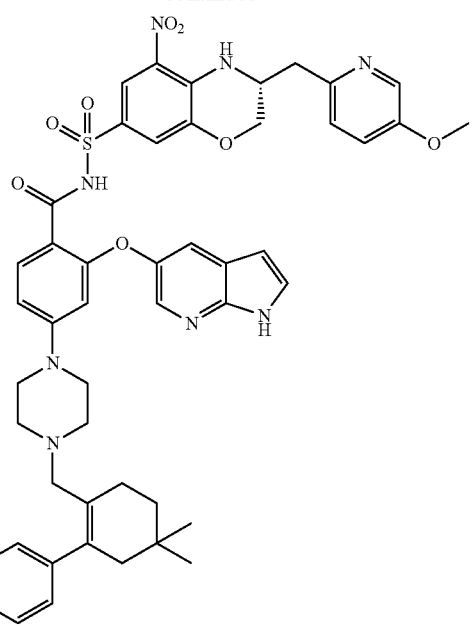
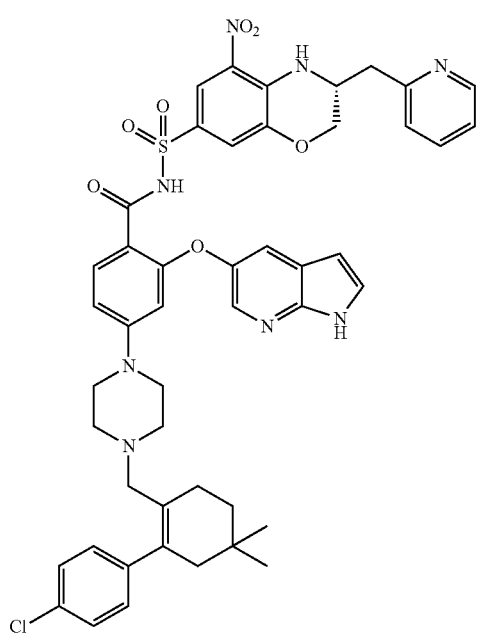
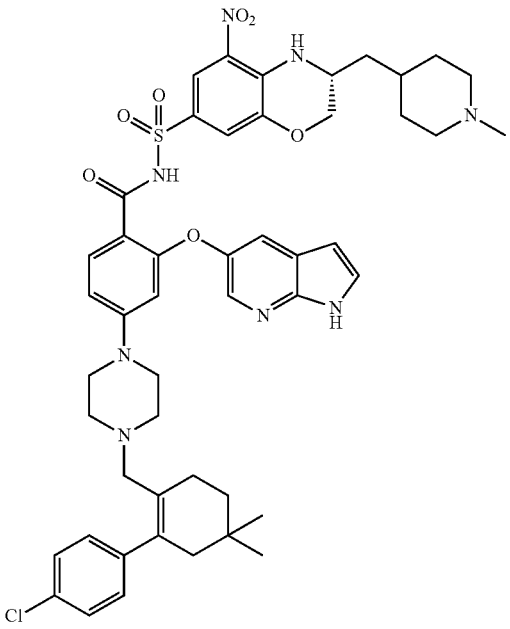

149
-continued
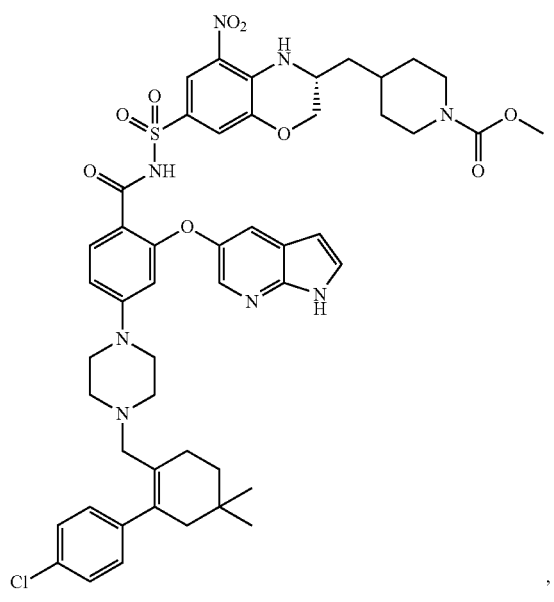
150
-continued
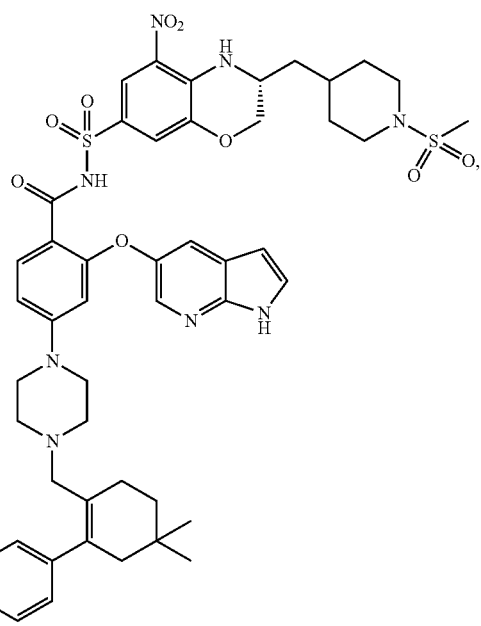
,
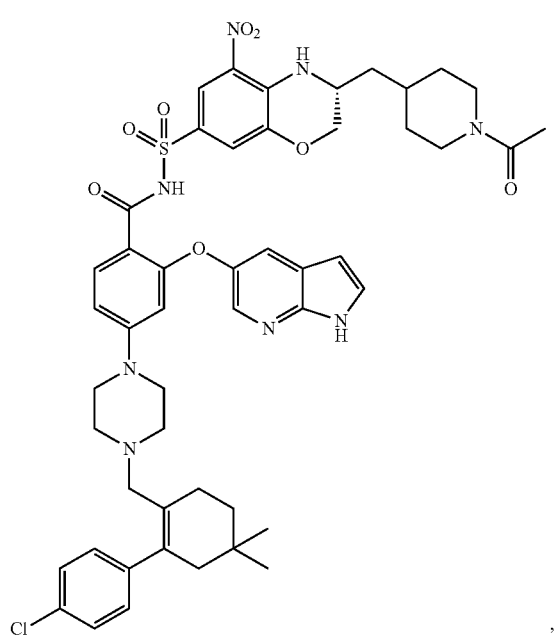
,
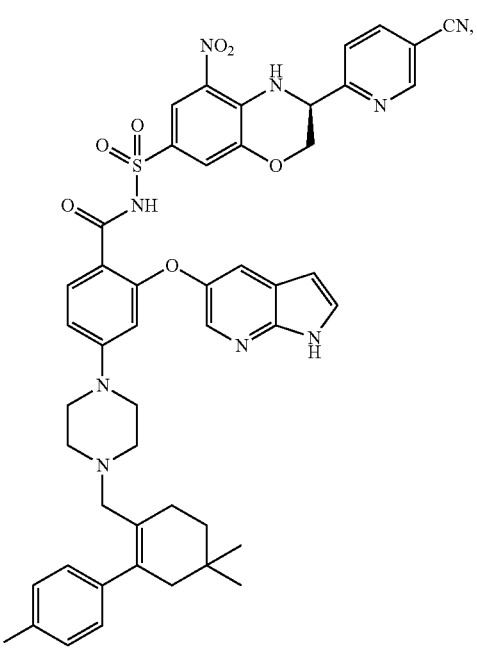
, 151
-continued
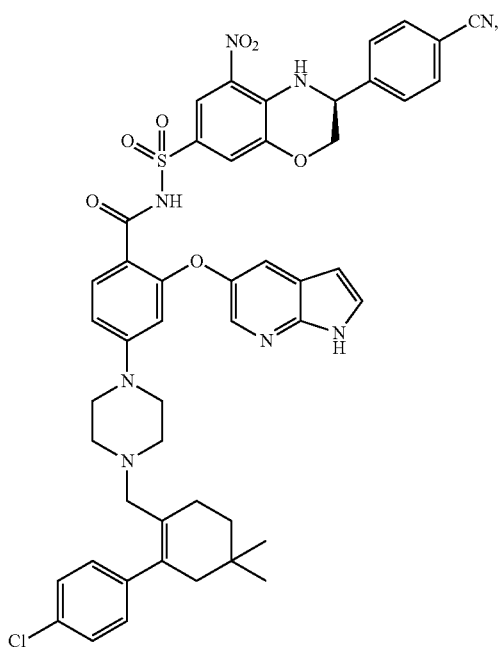
152
-continued
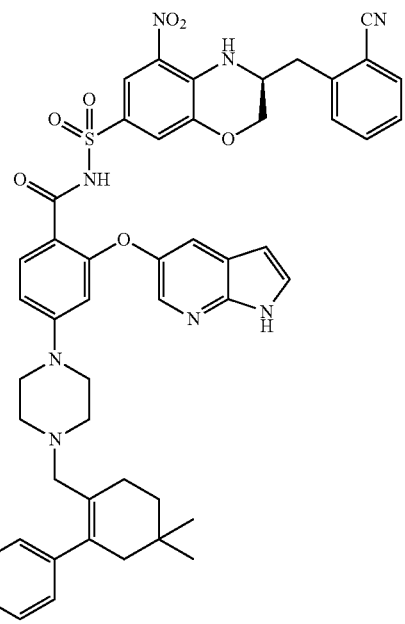
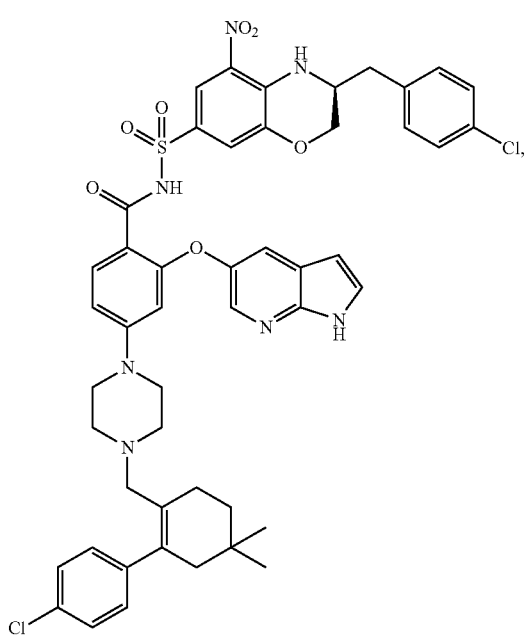
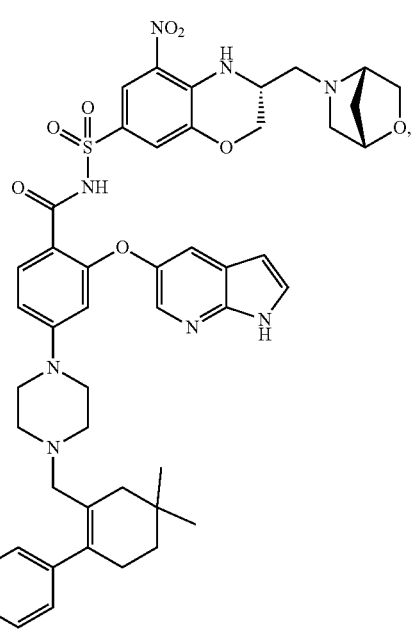

153
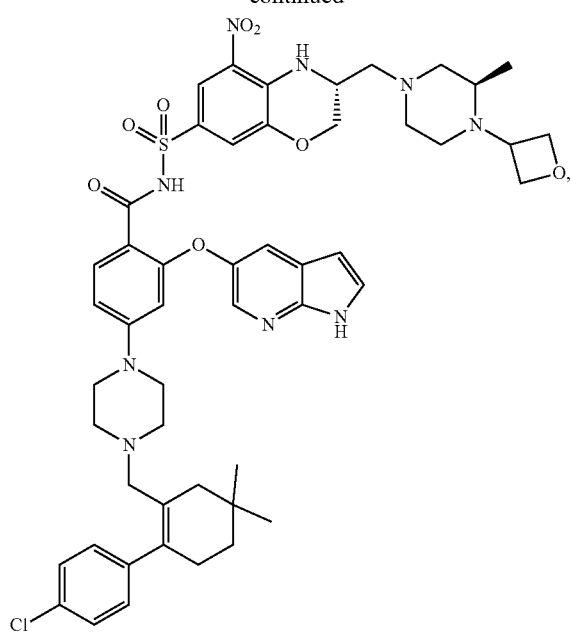
154
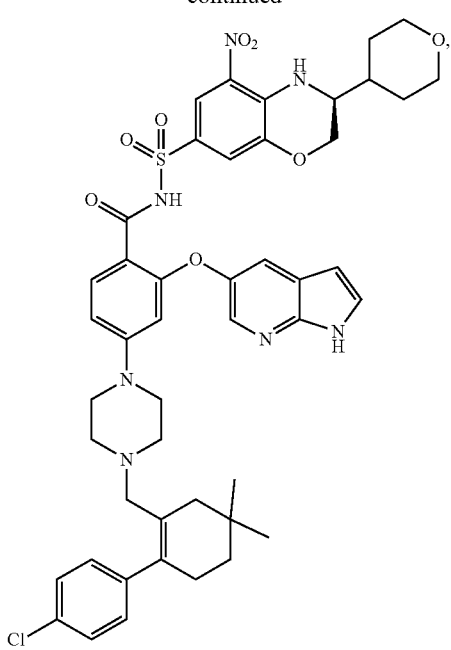
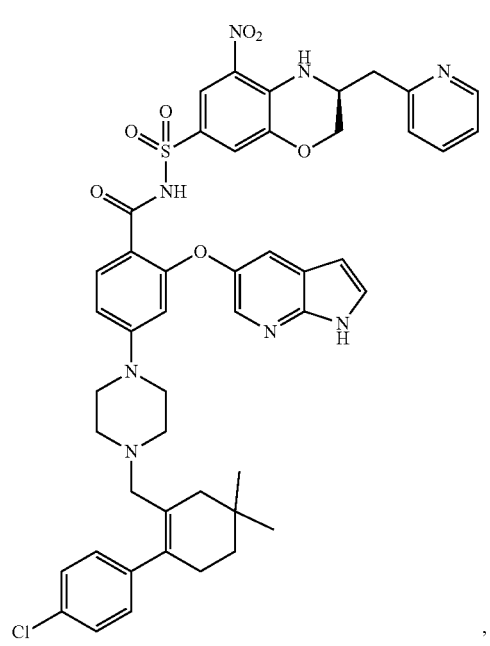
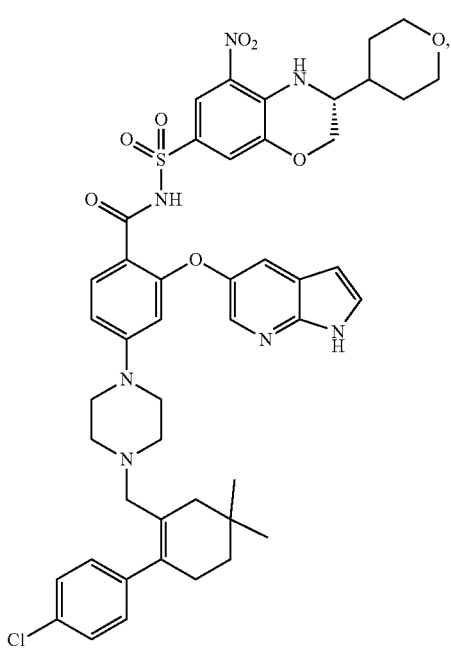

155
-continued
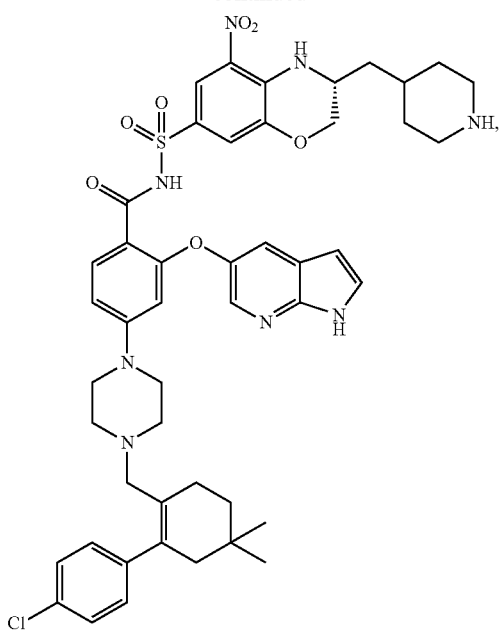
156
-continued
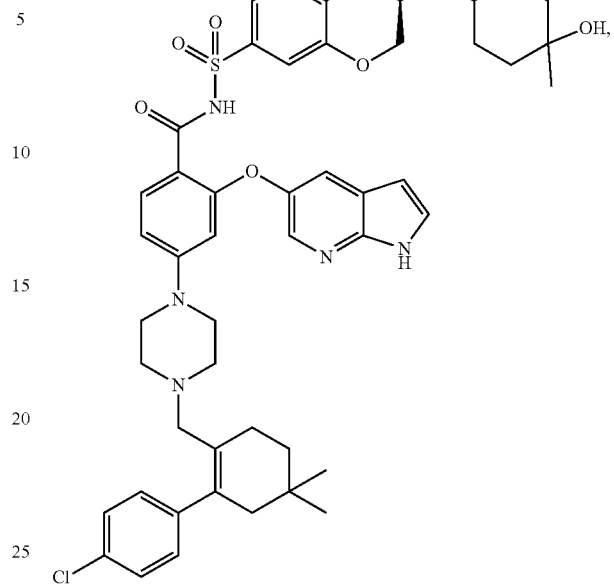
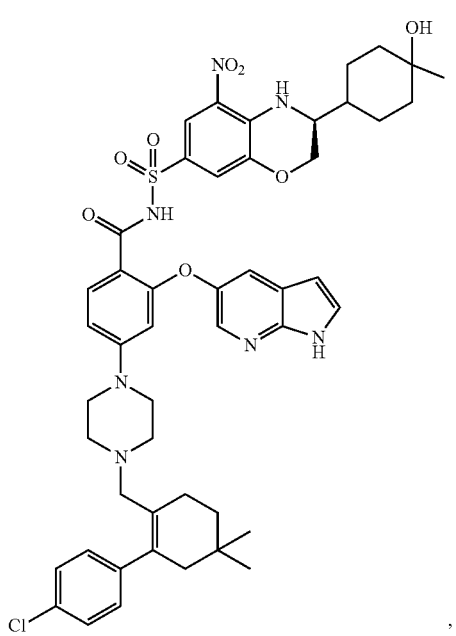
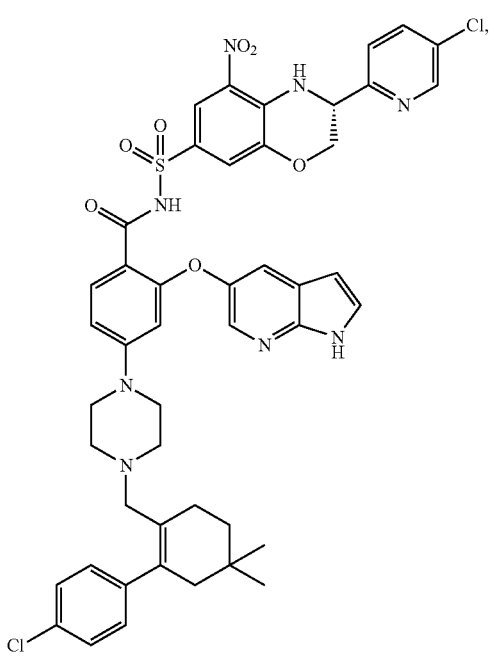

157
-continued
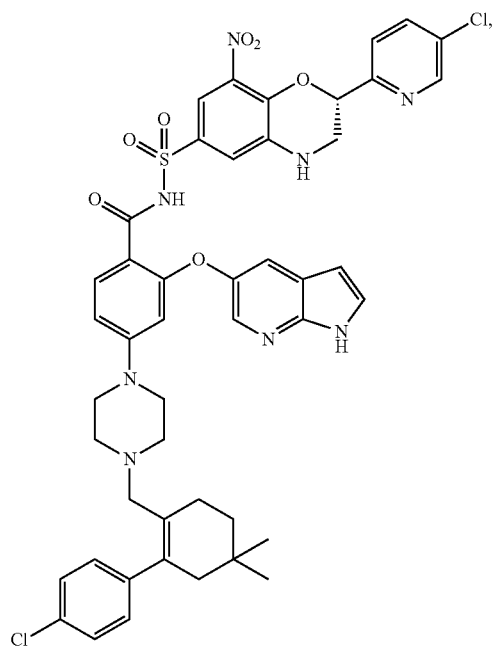
158
-continued
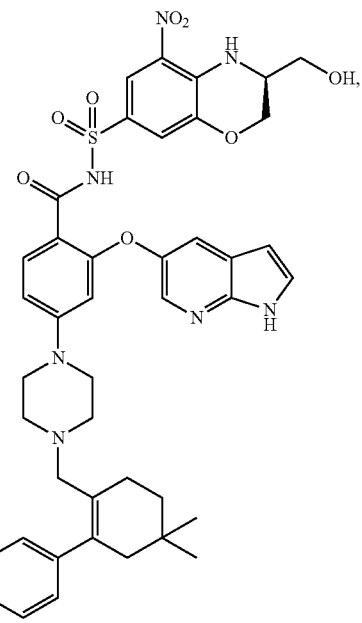
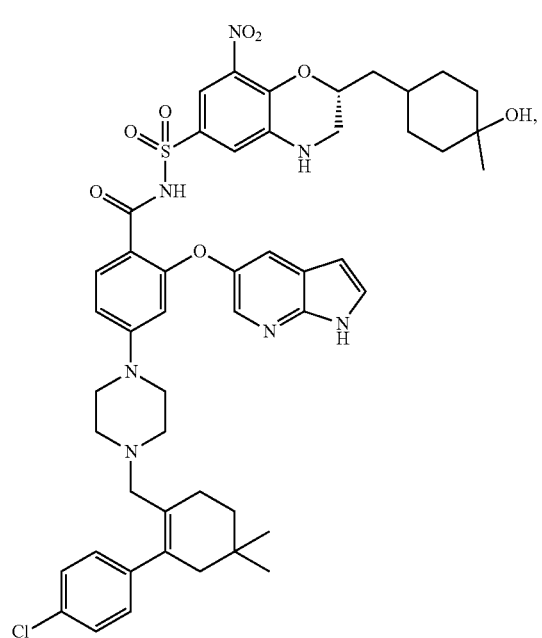
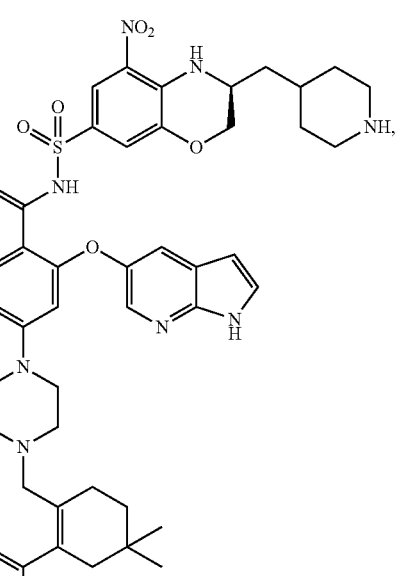

159
-continued
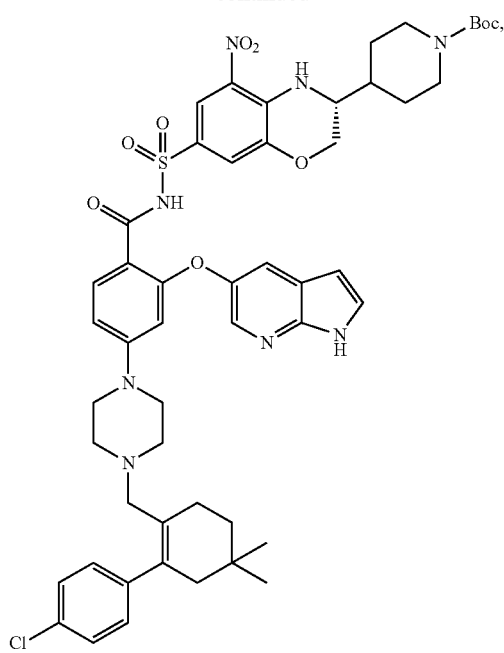
160
-continued
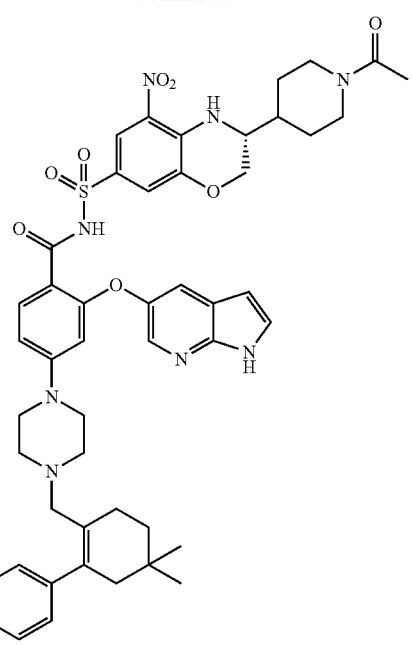
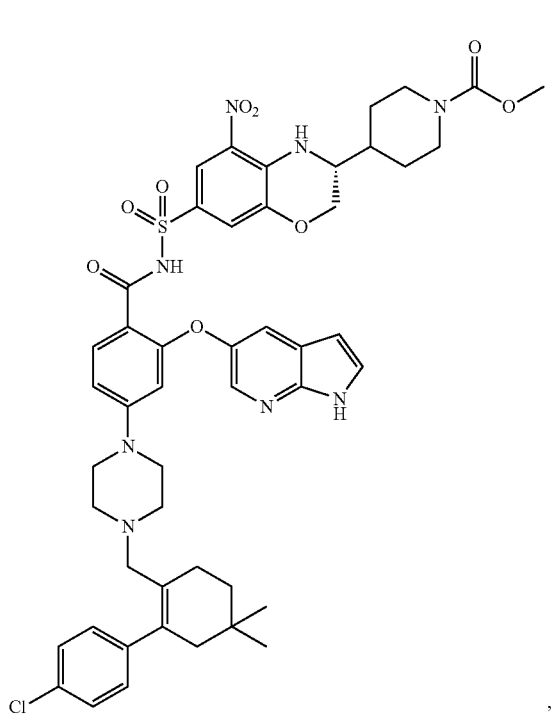
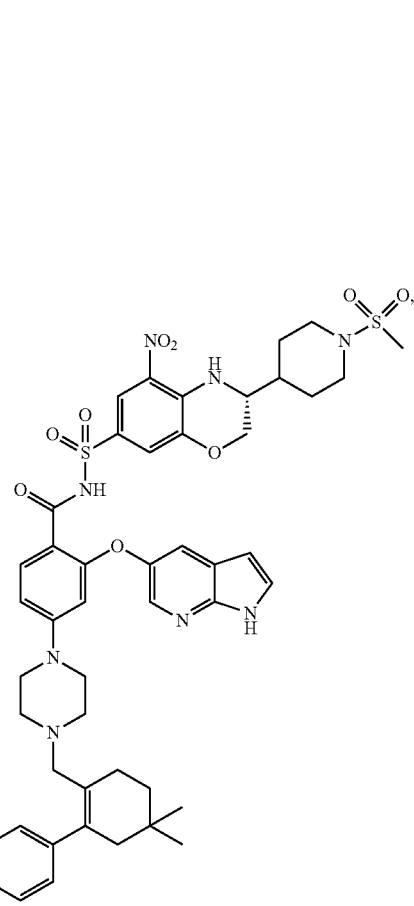

161
-continued
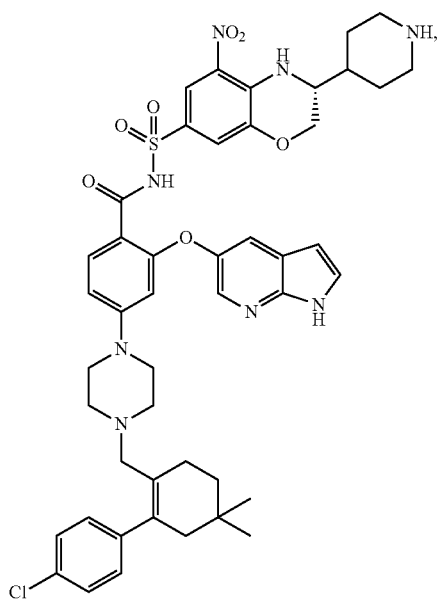
162
-continued
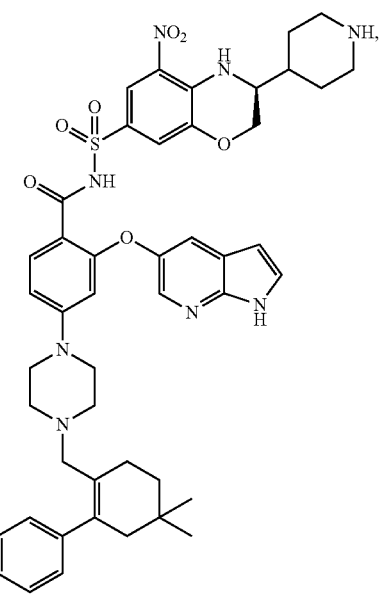
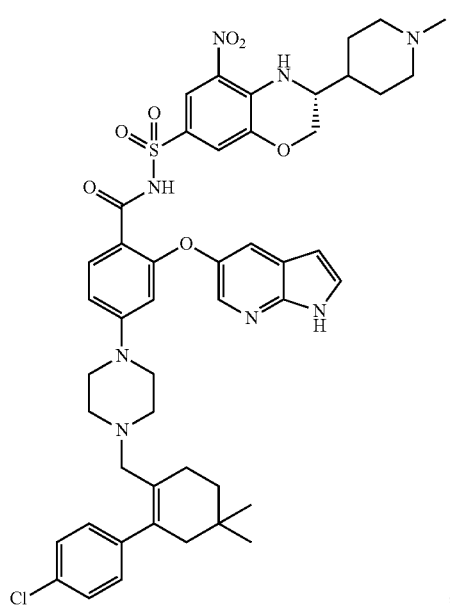
,
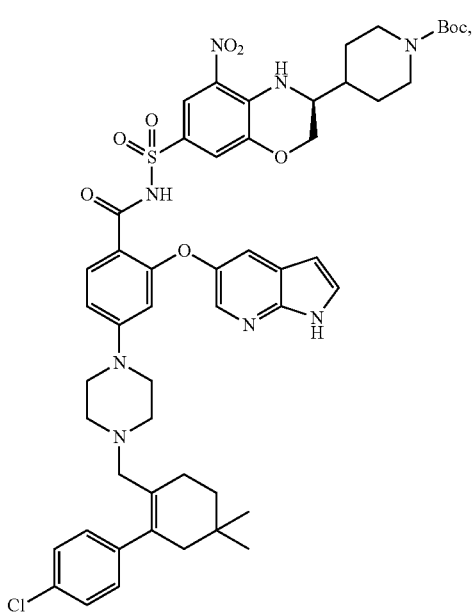

163
-continued
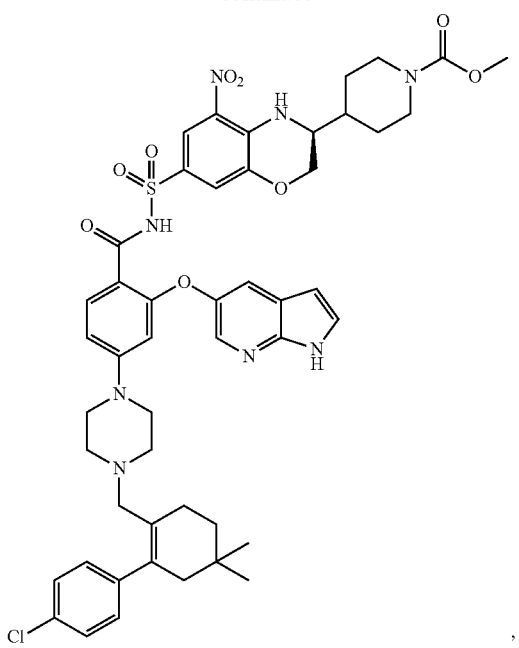
164
-continued
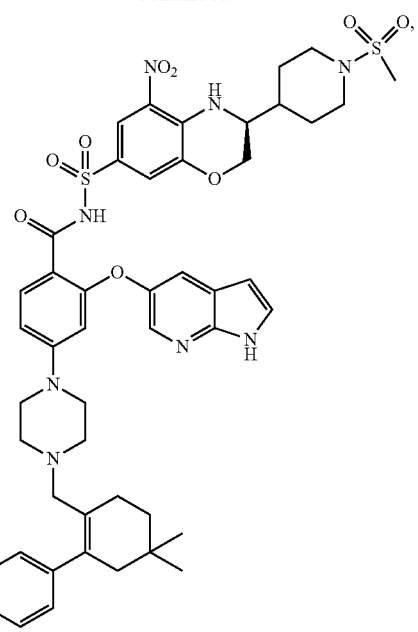

165
-continued
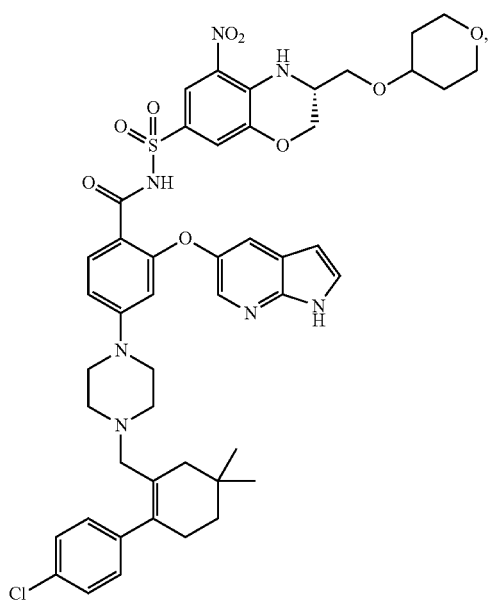
166
-continued
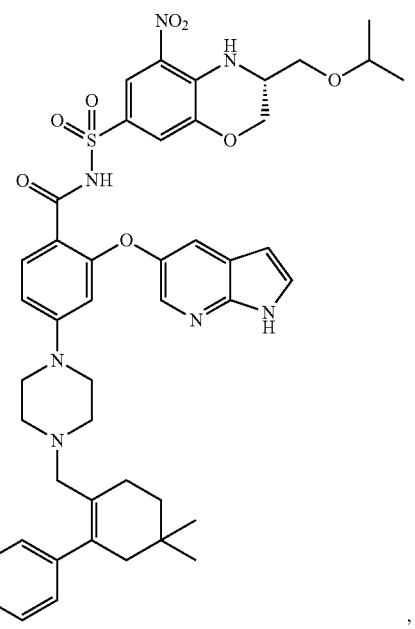
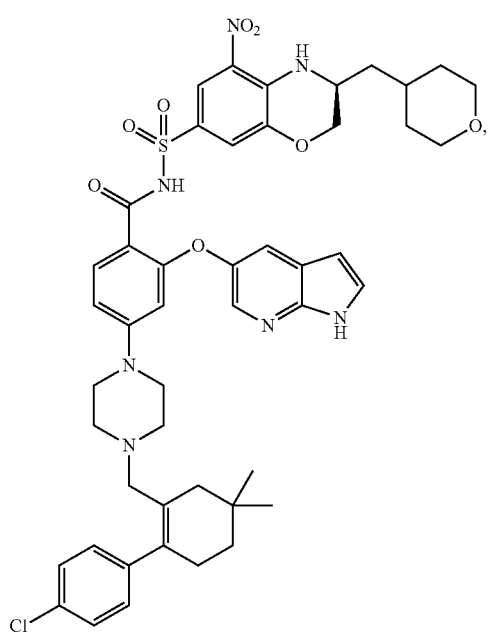

167
-continued
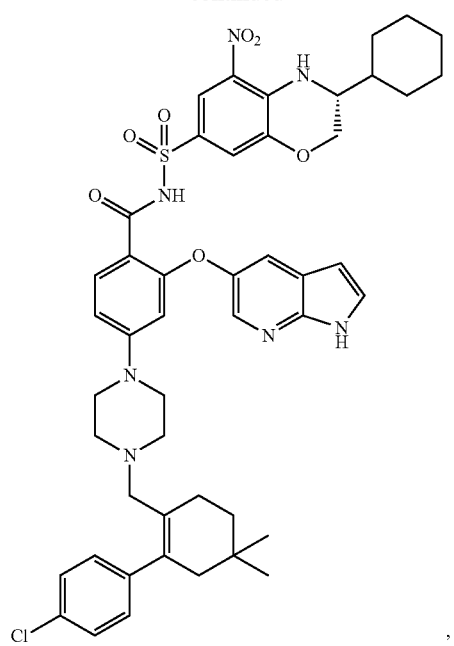
168
-continued
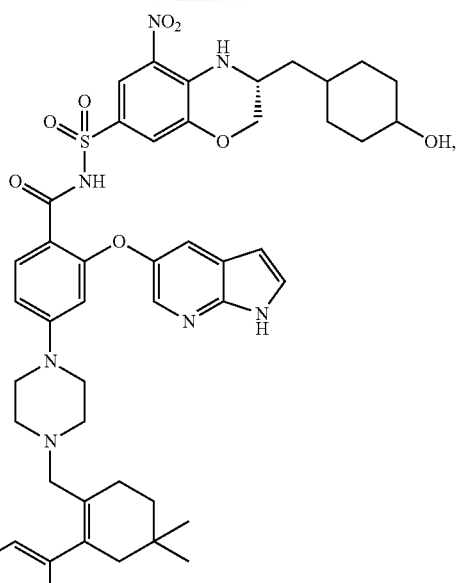
,
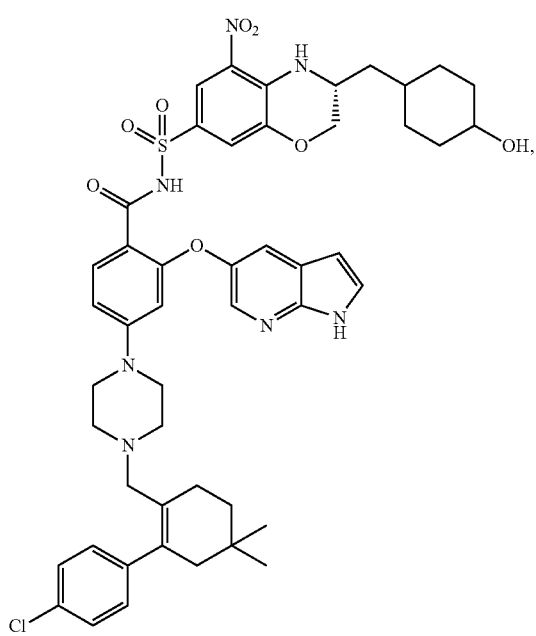
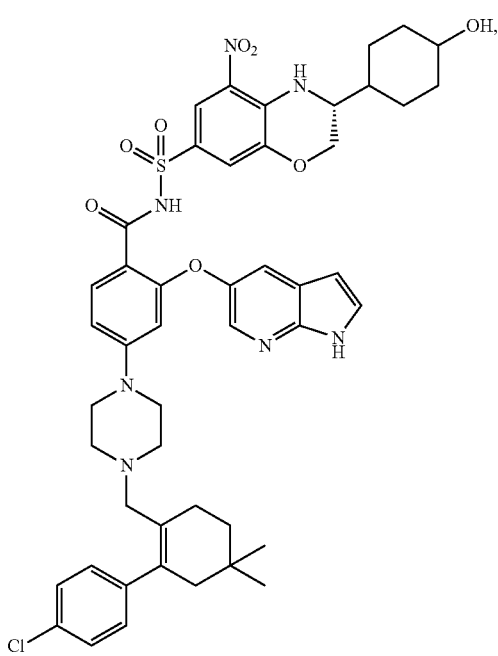

169
-continued
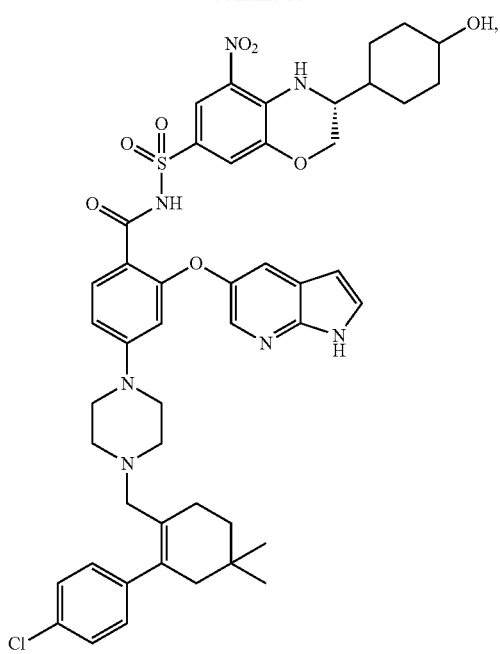
170
-continued
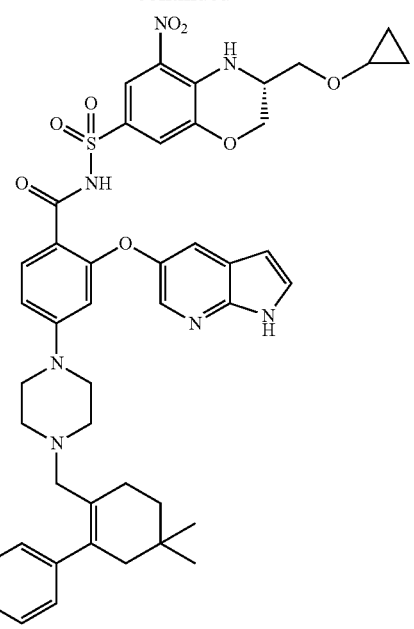
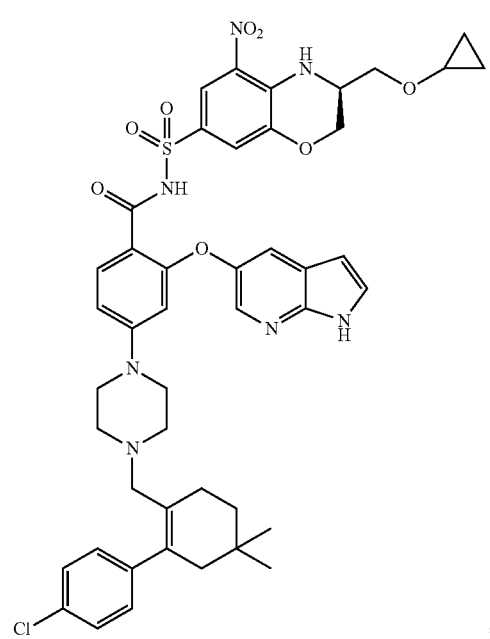
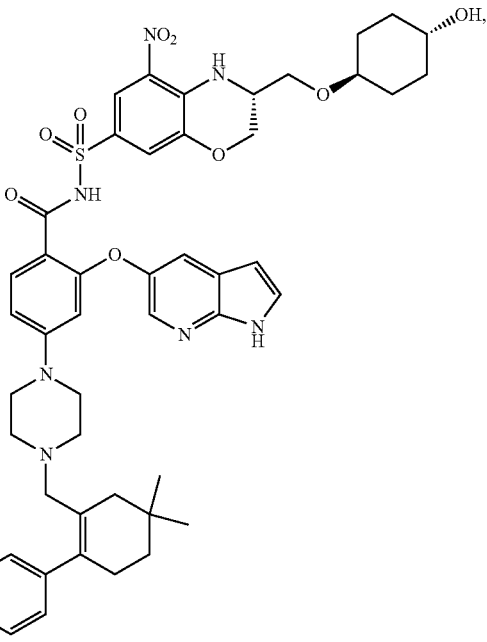

171
-continued
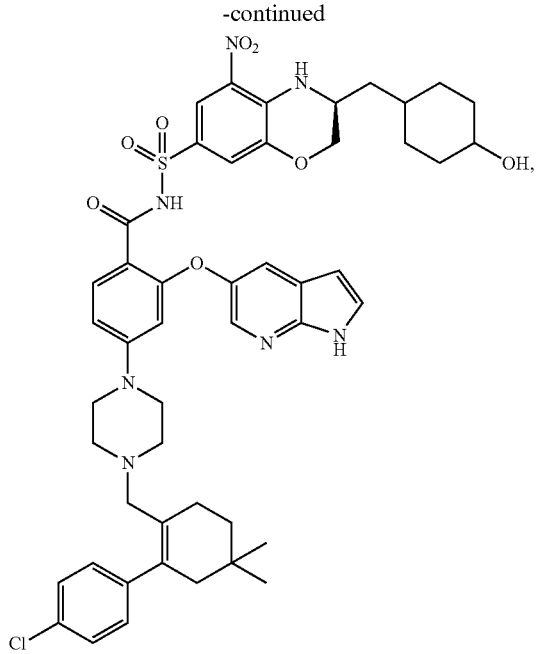
172
-continued
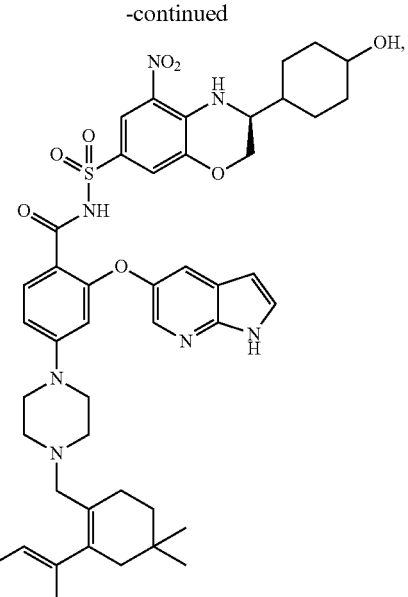
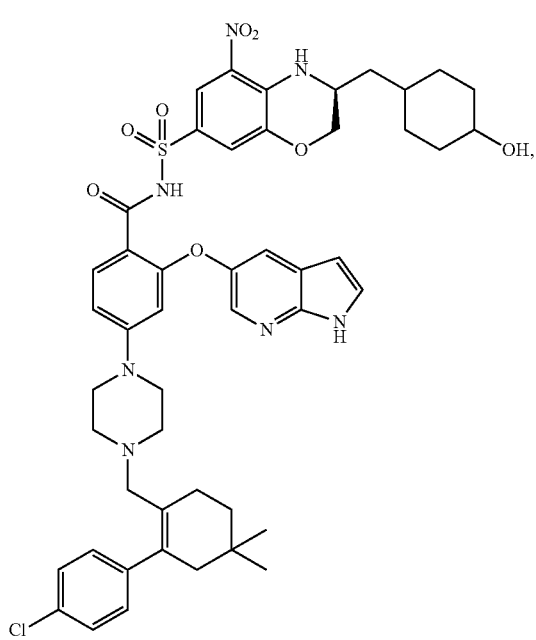
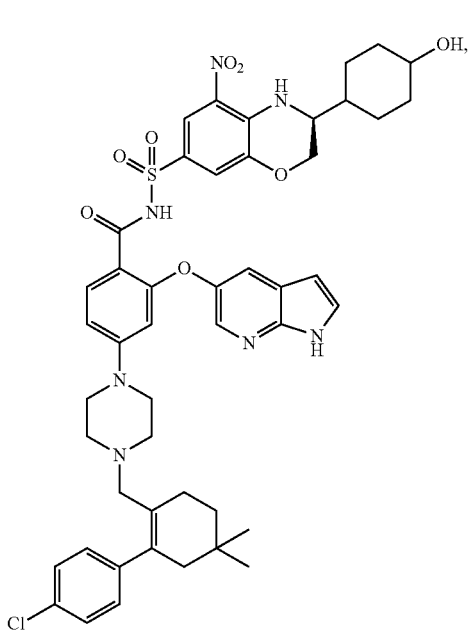

173
-continued
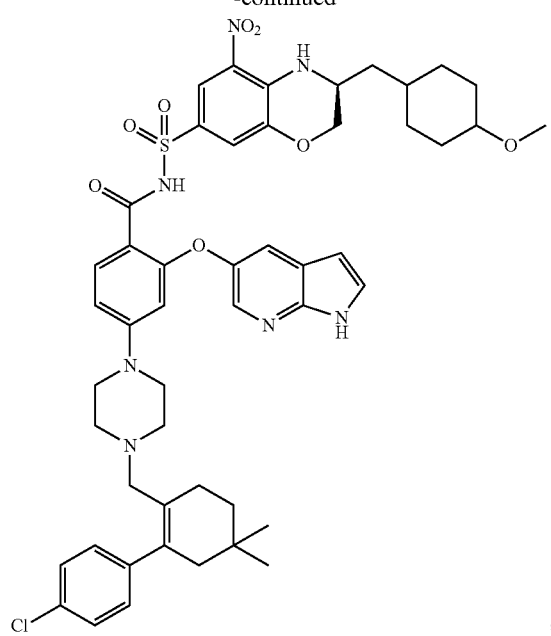
174
-continued
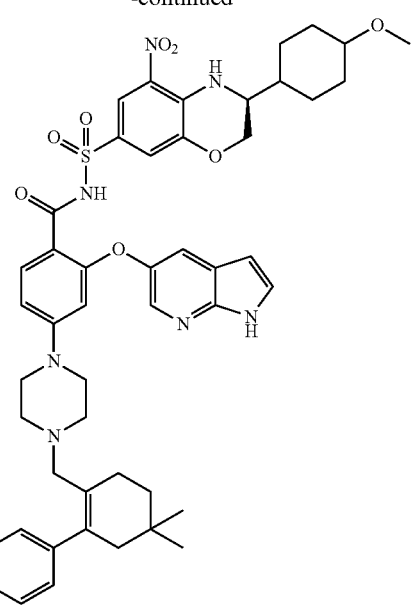
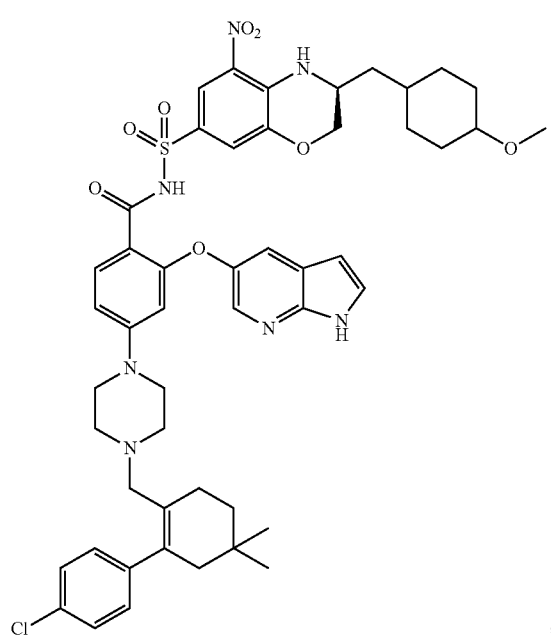

175
-continued
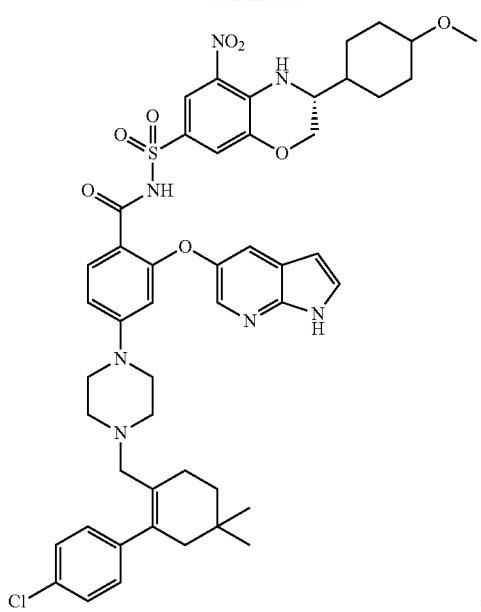
176
-continued
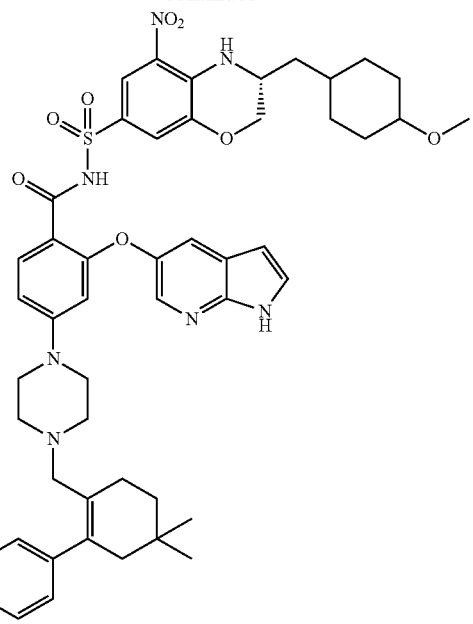

177
-continued
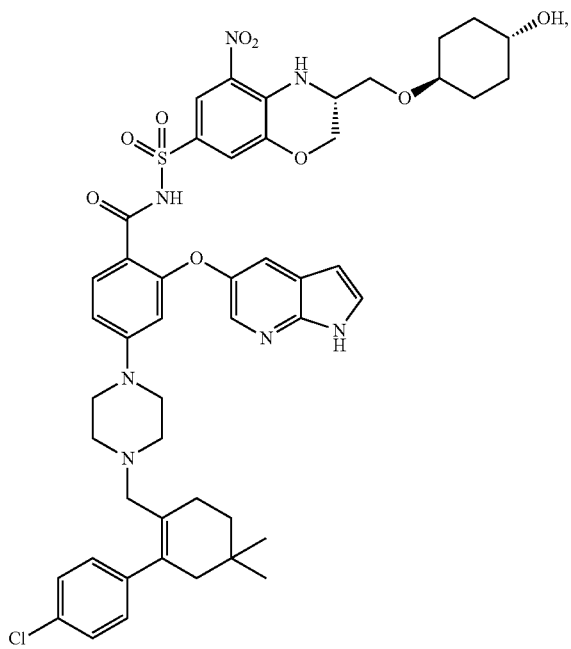
178
-continued
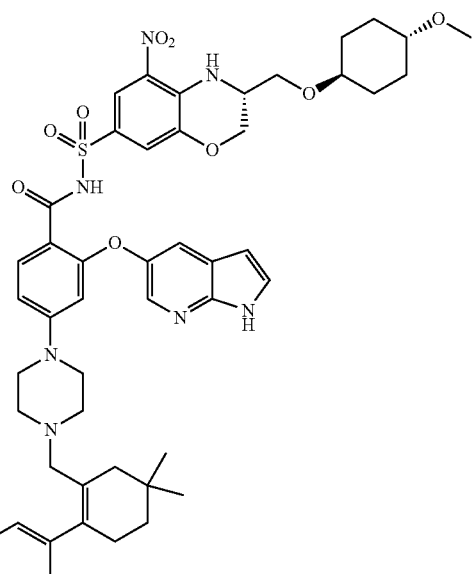
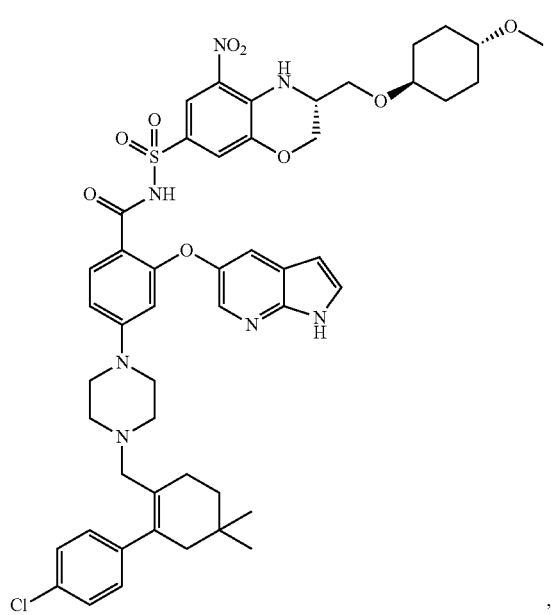
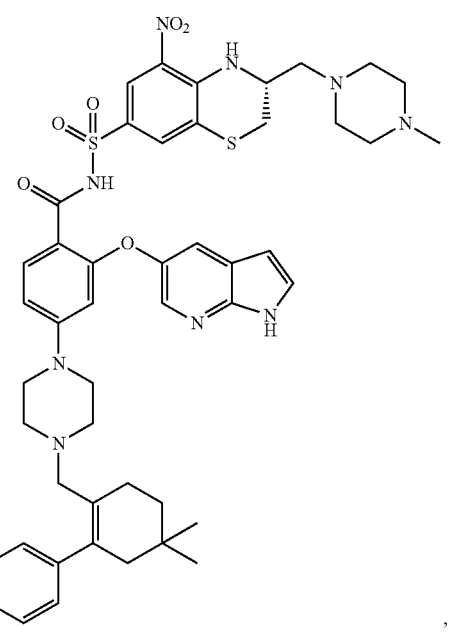

179
-continued
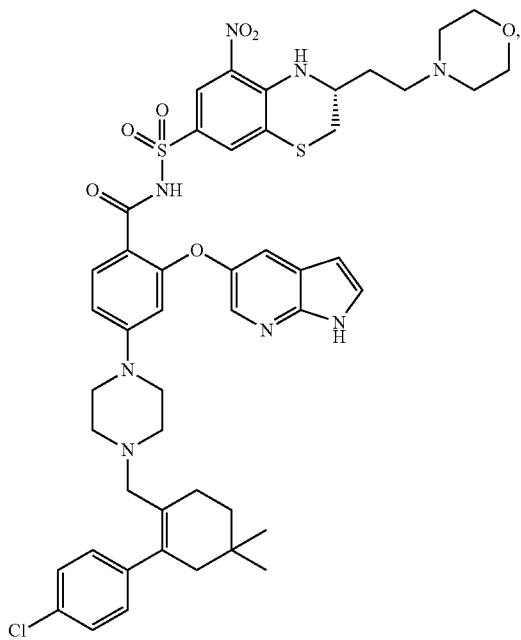
180
-continued
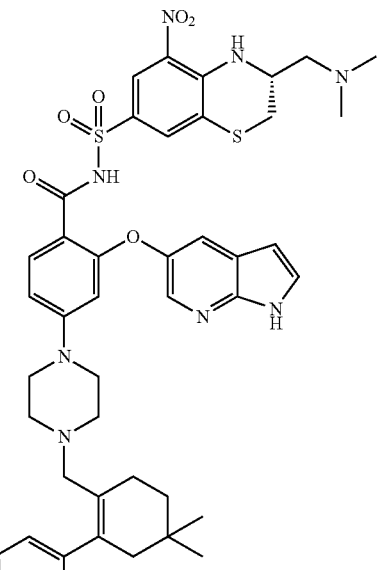
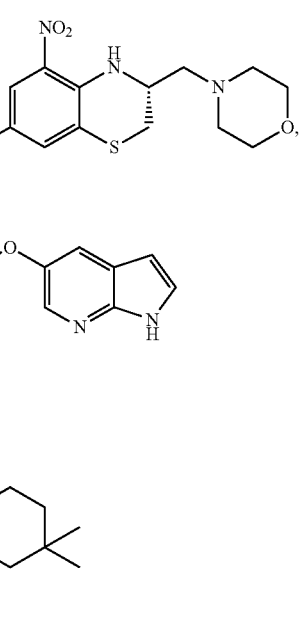
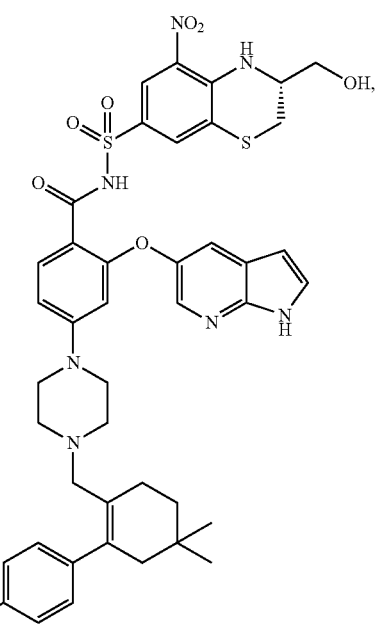

181
-continued
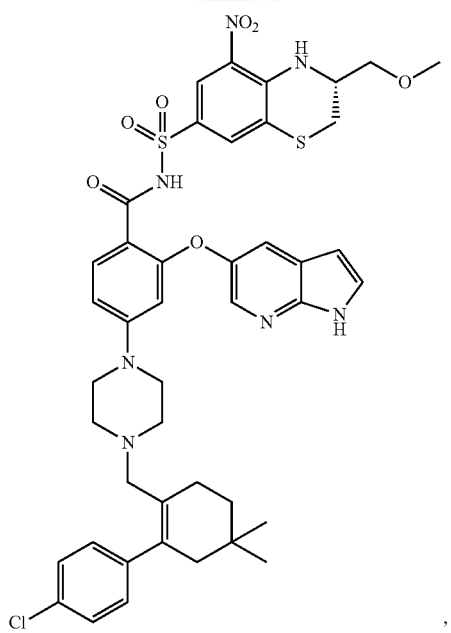
,
182
-continued
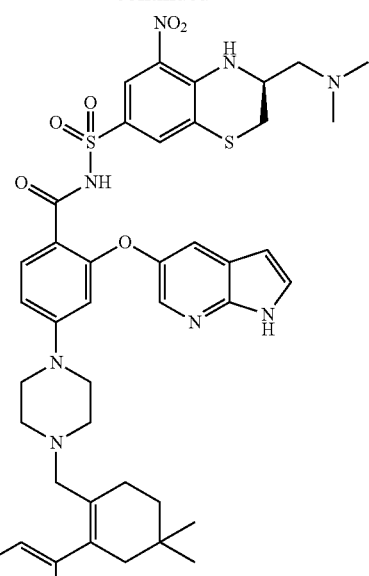
,
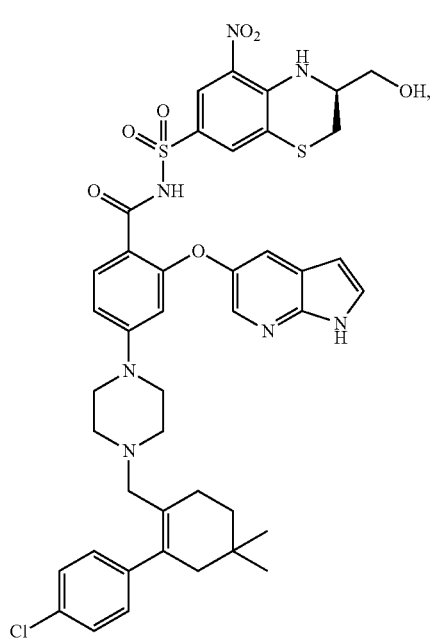
,
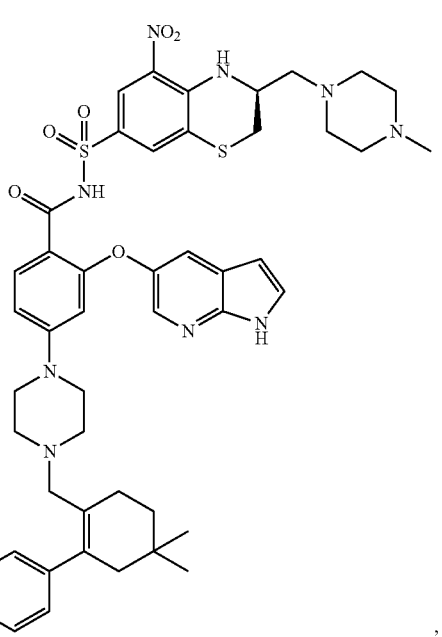
, 183
-continued
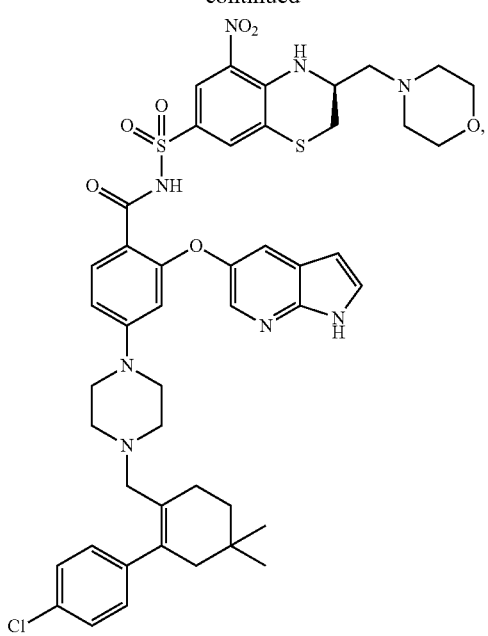
184
-continued
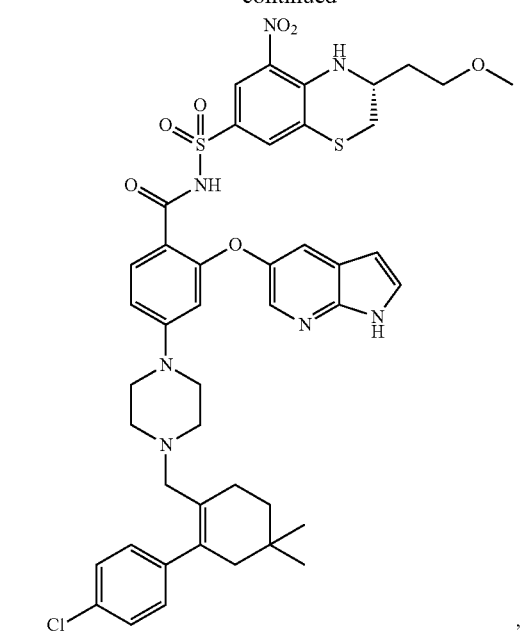
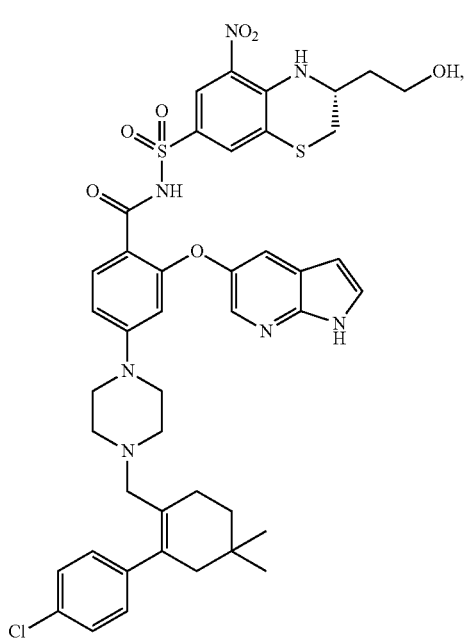
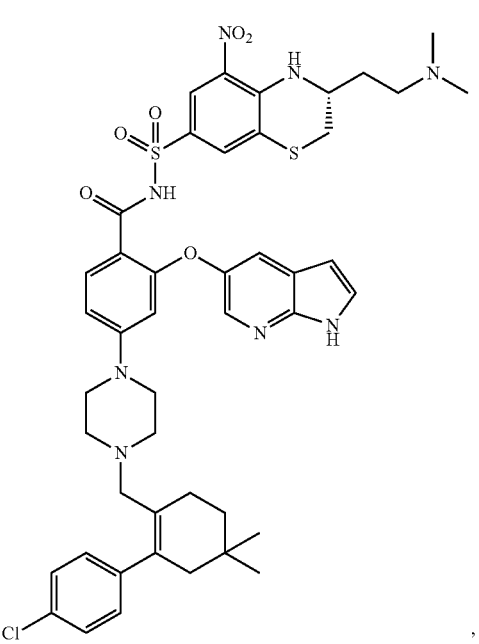

185
-continued
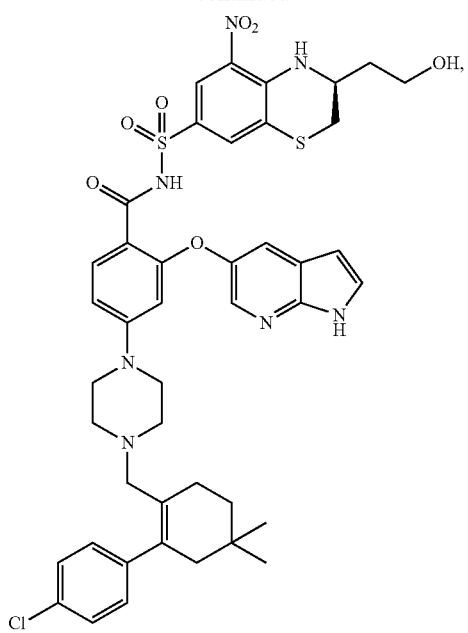
186
-continued
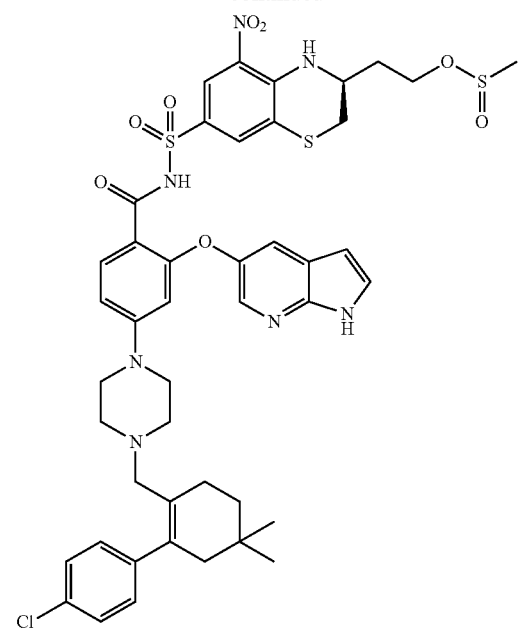
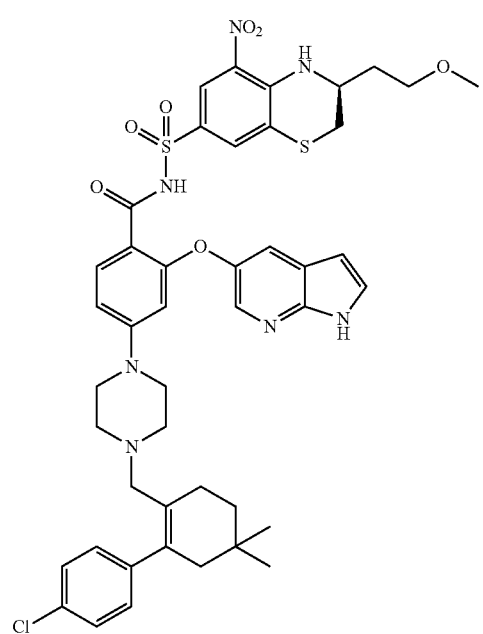
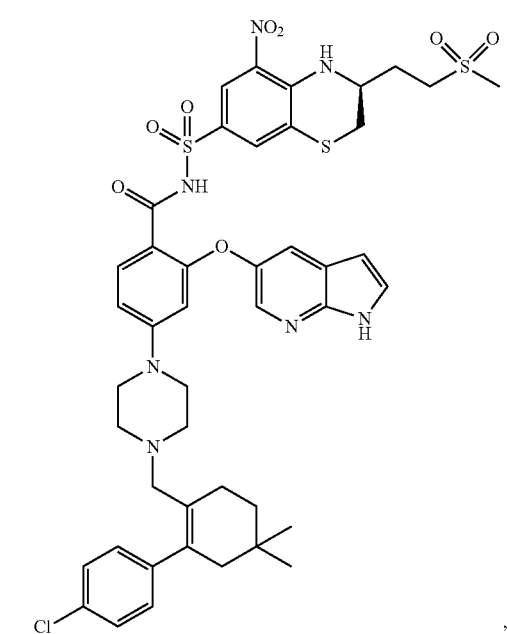

187
-continued
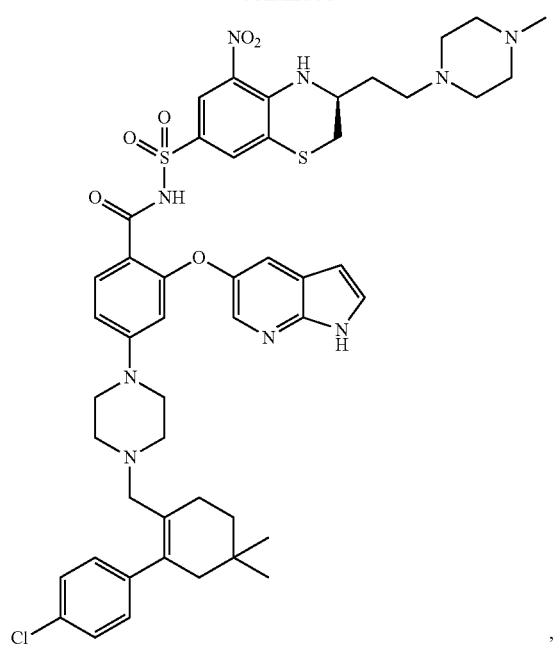
188
-continued
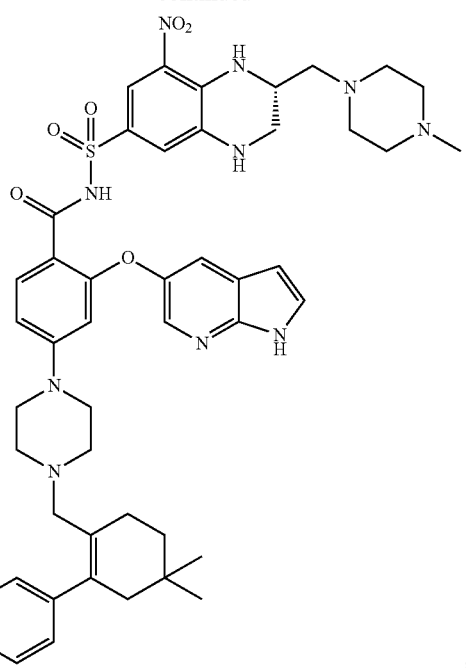

189
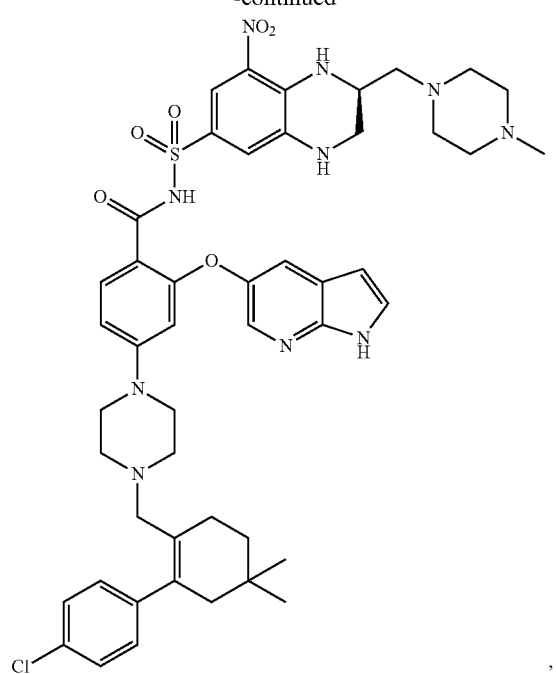
190
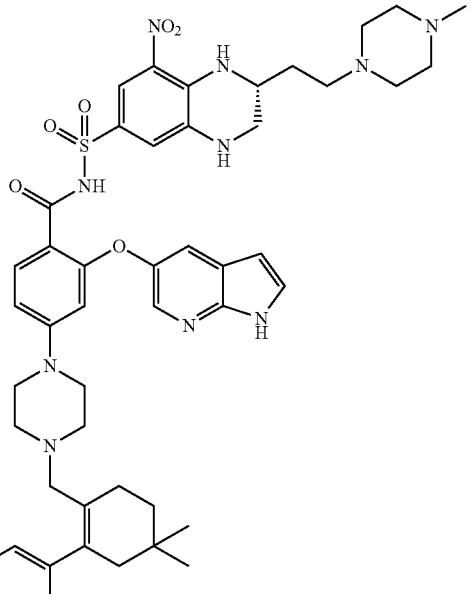
,
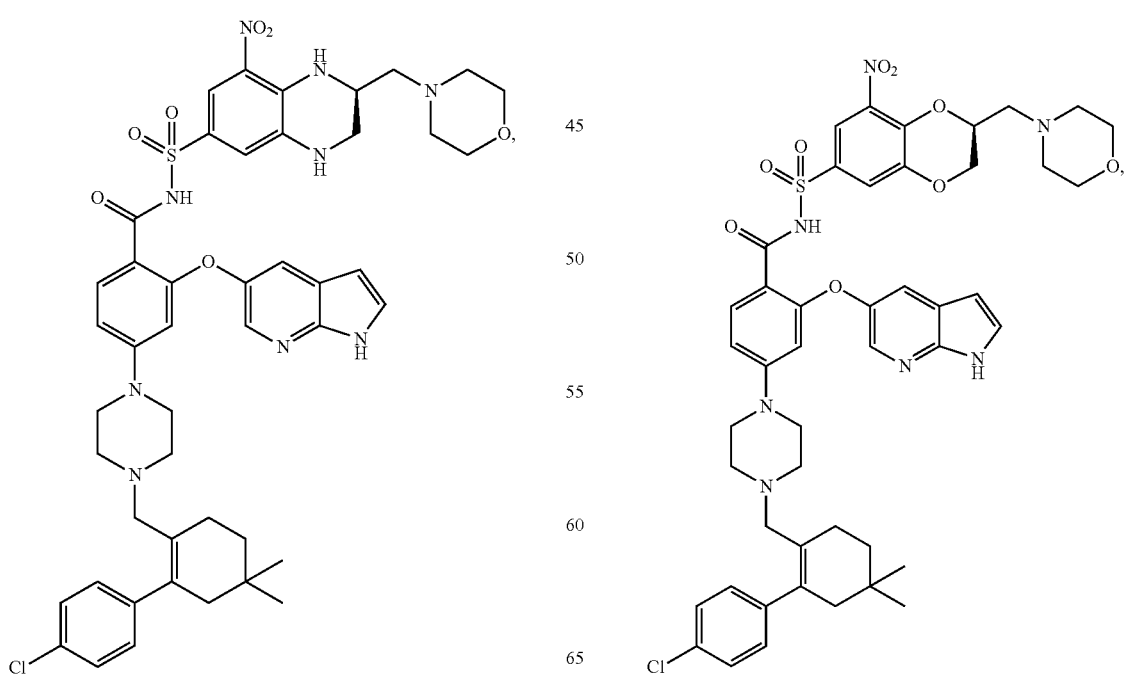

191
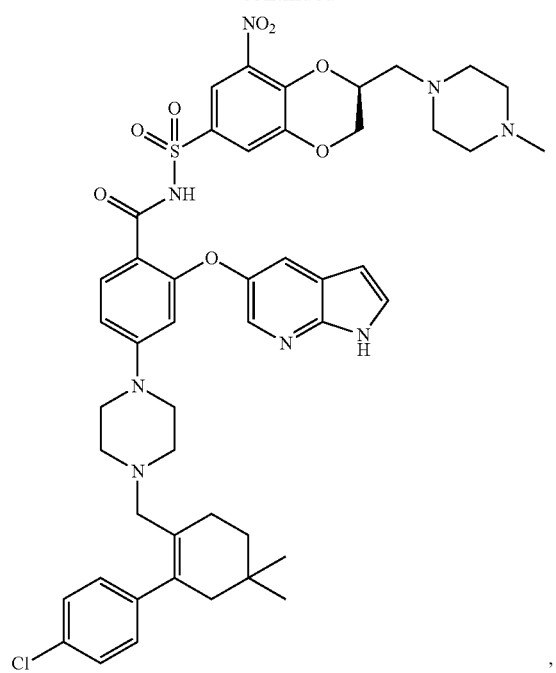
192
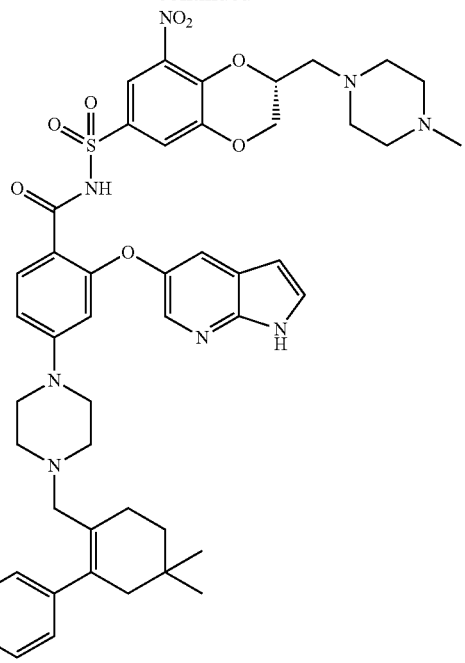
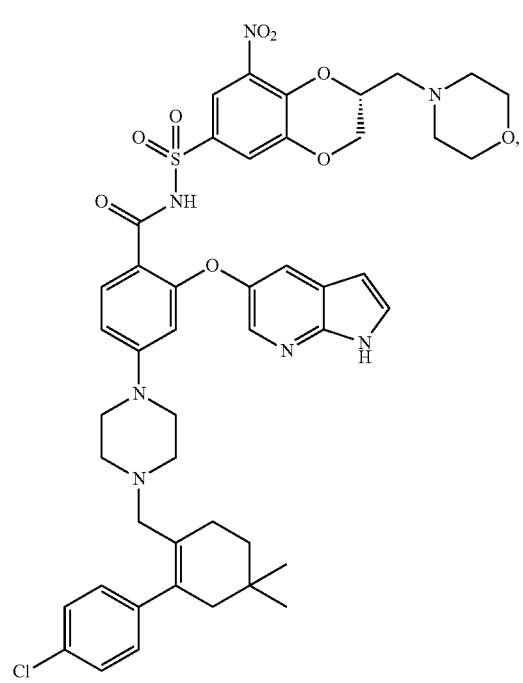
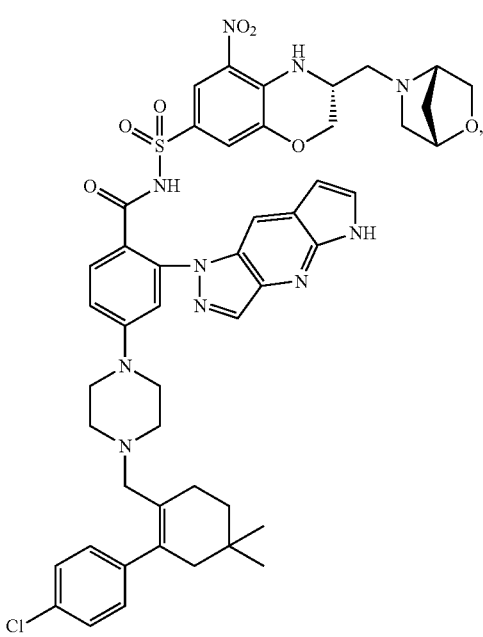

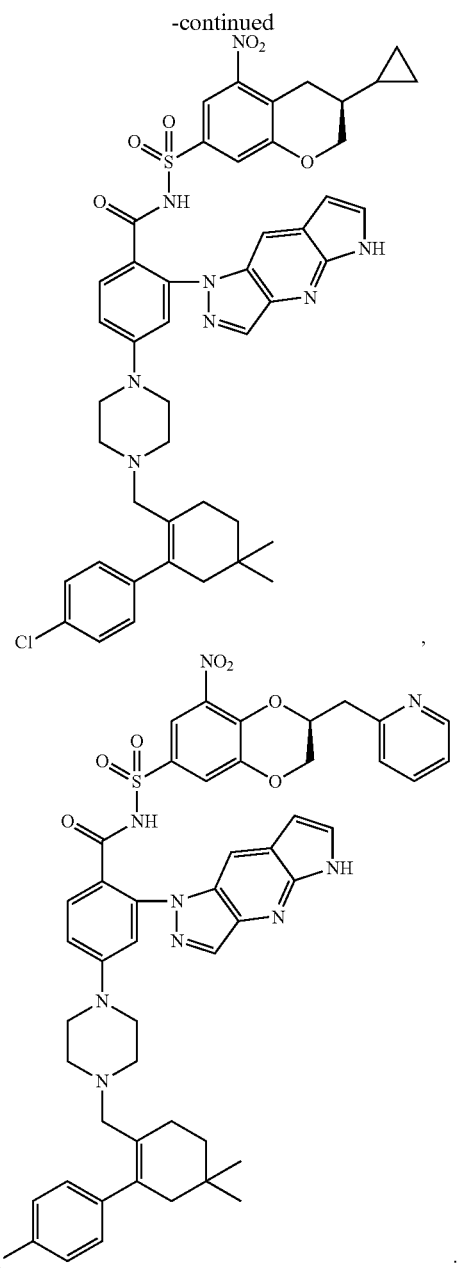

and pharmaceutically acceptable salts thereof.

In another Embodiment (71), the invention provides a pharmaceutical composition, comprising a compound of any one of Embodiments (1) to (70), or a pharmaceutically acceptable salt thereof, and at least one pharmaceutically acceptable carrier.

In another Embodiment (72), the invention provides a method of treating, ameliorating or preventing a condition, which responds to inhibition of Bcl-2, comprising administering to a subject in need of such treatment an effective amount of a compound of any one of Embodiments (1) to (70), or a pharmaceutically acceptable salt thereof, or of at least one pharmaceutical composition thereof, and optionally in combination with a second therapeutic agent.

In another Embodiment (73), the invention provides use of a compound of any one of Embodiments (1) to (70) or a pharmaceutically acceptable salt thereof in the preparation of a medicament for treating a hyper-proliferative disorder.

In yet another of its aspects, there is provided a kit comprising a compound disclosed herein, or a pharmaceutically acceptable salt thereof; and instructions which comprise one or more forms of information selected from the group consisting of indicating a disease state for which the composition is to be administered, storage information for the composition, dosing information and instructions regarding how to administer the composition. In one particular variation, the kit comprises the compound in a multiple dose form.

In still another of its aspects, there is provided an article of manufacture comprising a compound disclosed herein, or a pharmaceutically acceptable salt thereof; and packaging materials. In one variation, the packaging material comprises a container for housing the compound. In one particular variation, the container comprises a label indicating one or more members of the group consisting of a disease state for which the compound is to be administered, storage information, dosing information and/or instructions regarding how to administer the compound. In another variation, the article of manufacture comprises the compound in a multiple dose form.

In a further of its aspects, there is provided a therapeutic method comprising administering a compound disclosed herein, or a pharmaceutically acceptable salt thereof.

In another of its aspects, there is provided a method of inhibiting a Bcl-2 comprising contacting the Bcl-2 with a compound disclosed herein, or a pharmaceutically acceptable salt thereof.

In yet another of its aspects, there is provided a method of inhibiting a Bcl-2 comprising causing a compound disclosed herein, or a pharmaceutically acceptable salt thereof to be present in a subject in order to inhibit the Bcl-2 in vivo.

In a further of its aspects, there is provided a method of inhibiting Bcl-2 comprising administering a first compound to a subject that is converted in vivo to a second compound wherein the second compound inhibits the Bcl-2 in vivo, the second compound being a compound according to any one of the above embodiments and variations.

In another of its aspects, there is provided a method of treating a disease state for which a Bcl-2 possesses activity that contributes to the pathology and/or symptomology of the disease state, the method comprising causing a compound disclosed herein, or a pharmaceutically acceptable salt thereof to be present in a subject in a therapeutically effective amount for the disease state.

In a further of its aspects, there is provided a method of treating a disease state for which a Bcl-2 possesses activity that contributes to the pathology and/or symptomology of the disease state, the method comprising administering a first compound to a subject that is converted in vivo to a second compound wherein the second compound inhibits the Bcl-2 in vivo. It is noted that the compounds of the present invention may be the first or second compounds.

In one variation of each of the above methods the disease state is selected from the group consisting of cancerous hyperproliferative disorders (e.g., brain, lung, squamous cell, bladder, gastric, pancreatic, breast, head, neck, renal, kidney, ovarian, prostate, colorectal, epidermoid, esophageal, testicular, gynecological or thyroid cancer); non-cancerous hyperproliferative disorders (e.g., benign hyperplasia of the skin (e.g., psoriasis), restenosis, and benign prostatic hypertrophy (BPH)); pancreatitis; kidney disease; pain; preventing blastocyte implantation; treating diseases related to vasculogenesis or angiogenesis (e.g., tumor angiogenesis, acute and chronic inflammatory disease such as rheumatoid arthritis, atherosclerosis, inflammatory bowel disease, skin diseases such as psoriasis, exzema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer); asthma; neutrophil chemotaxis (e.g., reperfusion injury in myocardial infarction and stroke and inflammatory arthritis); septic shock;

T-cell mediated diseases where immune suppression would be of value (e.g., the prevention of organ transplant rejection, graft versus host disease, lupus erythematosus, multiple sclerosis, and rheumatoid arthritis); atherosclerosis; inhibition of keratinocyte responses to growth factor cocktails; chronic obstructive pulmonary disease (COPD) and other diseases.

In another of its aspects, there is provided a method of treating a disease state for which a mutation in the Bcl-2 gene contributes to the pathology and/or symptomology of the disease state including, for example, melanomas, lung cancer, colon cancer and other tumor types.

In still another of its aspects, the present invention relates to the use of a compound of any of the above embodiments and variations as a medicament. In yet another of its aspects, the present invention relates to the use of a compound according to any one of the above embodiments and variations in the manufacture of a medicament for inhibiting a Bcl-2.

In a further of its aspects, the present invention relates to the use of a compound according to any one of the above embodiments and variations in the manufacture of a medicament for treating a disease state for which a Bcl-2 possesses activity that contributes to the pathology and/or symptomology of the disease state.

Administration and Pharmaceutical Compositions

In general, compounds of the disclosure will be administered in therapeutically effective amounts via any of the usual and acceptable modes known in the art, either singly or in combination with one or more therapeutic agents. A therapeutically effective amount may vary widely depending on the severity of the disease, the age and relative health of the subject, the potency of the compound used and other factors known to those of ordinary skill in the art. For example, for the treatment of neoplastic diseases and immune system disorders, the required dosage will also vary depending on the mode of administration, the particular condition to be treated and the effect desired.

In general, satisfactory results are indicated to be obtained systemically at daily dosages of from about 0.001 to about 100 mg/kg per body weight, or particularly, from about 0.03 to 2.5 mg/kg per body weight. An indicated daily dosage in the larger mammal, e.g. humans, may be in the range from about 0.5 mg to about 2000 mg, or more particularly, from about 0.5 mg to about 1000 mg, conveniently administered, for example, in divided doses up to four times a day or in retard form. Suitable unit dosage forms for oral administration comprise from ca. 1 to 50 mg active ingredient.

Compounds of the disclosure may be administered as pharmaceutical compositions by any conventional route; for example, enterally, e.g., orally, e.g., in the form of tablets or capsules; parenterally, e.g., in the form of injectable solutions or suspensions; or topically, e.g., in the form of lotions, gels, ointments or creams, or in a nasal or suppository form.

Pharmaceutical compositions comprising a compound of the present disclosure in free form or in a pharmaceutically acceptable salt form in association with at least one pharmaceutically acceptable carrier or diluent may be manufactured in a conventional manner by mixing, granulating, coating, dissolving or lyophilizing processes. For example, pharmaceutical compositions comprising a compound of the disclosure in association with at least one pharmaceutical acceptable carrier or diluent may be manufactured in conventional manner by mixing with a pharmaceutically acceptable carrier or diluent. Unit dosage forms for oral administration contain, for example, from about 0.1 mg to about 500 mg of active substance.

In one embodiment, the pharmaceutical compositions are solutions of the active ingredient, including suspensions or dispersions, such as isotonic aqueous solutions. In the case of lyophilized compositions comprising the active ingredient alone or together with a carrier such as mannitol, dispersions or suspensions can be made up before use. The pharmaceutical compositions may be sterilized and/or contain adjuvants, such as preserving, stabilizing, wetting or emulsifying agents, solution promoters, salts for regulating the osmotic pressure and/or buffers. Suitable preservatives include but are not limited to antioxidants such as ascorbic acid, or microbicides, such as sorbic acid or benzoic acid. The solutions or suspensions may further comprise viscosity-increasing agents, including but not limited to, sodium carboxymethylcellulose, carboxymethylcellulose, dextran, polyvinylpyrrolidone, gelatins, or solubilizers, e.g. Tween 80 (polyoxyethylene(20)sorbitan mono-oleate).

Suspensions in oil may comprise as the oil component the vegetable, synthetic, or semi-synthetic oils customary for injection purposes. Examples include liquid fatty acid esters that contain as the acid component a long-chained fatty acid having from 8 to 22 carbon atoms, or in some embodiments, from 12 to 22 carbon atoms. Suitable liquid fatty acid esters include but are not limited to lauric acid, tridecylic acid, myristic acid, pentadecylic acid, palmitic acid, margaric acid, stearic acid, arachidic acid, behenic acid or corresponding unsaturated acids, for example oleic acid, elaidic acid, erucic acid, brassidic acid and linoleic acid, and if desired, may contain antioxidants, for example vitamin E, 3-carotene or 3,5-di-tert-butyl-hydroxytoluene. The alcohol component of these fatty acid esters may have six carbon atoms and may be monovalent or polyvalent, for example a mono-, di- or trivalent, alcohol. Suitable alcohol components include but are not limited to methanol, ethanol, propanol, butanol or pentanol or isomers thereof; glycol and glycerol.

Other suitable fatty acid esters include but are not limited ethyl-oleate, isopropyl myristate, isopropyl palmitate, LABRAFIL® M 2375, (polyoxyethylene glycerol), LABRAFIL® M 1944 CS (unsaturated polyglycolized glycerides prepared by alcoholysis of apricot kernel oil and comprising glycerides and polyethylene glycol ester), LABRASOL™ (saturated polyglycolized glycerides prepared by alcoholysis of TCM and comprising glycerides and polyethylene glycol ester; all available from GaKefosse, France), and/or MIGLYOL® 812 (triglyceride of saturated fatty acids of chain length C8 to C12 from Hüls AG, Germany), and vegetable oils such as cottonseed oil, almond oil, olive oil, castor oil, sesame oil, soybean oil, or groundnut oil.

Pharmaceutical compositions for oral administration may be obtained, for example, by combining the active ingredient with one or more solid carriers, and if desired, granulating a resulting mixture, and processing the mixture or granules by the inclusion of additional excipients, to form tablets or tablet cores.

Suitable carriers include but are not limited to fillers, such as sugars, for example lactose, saccharose, mannitol or sorbitol, cellulose preparations and/or calcium phosphates, for example tricalcium phosphate or calcium hydrogen phosphate, and also binders, such as starches, for example corn, wheat, rice or potato starch, methylcellulose, hydroxypropyl methylcellulose, sodium carboxymethylcellulose, and/or polyvinylpyrrolidone, and/or, if desired, disintegrators, such as the above-mentioned starches, carboxymethyl starch, crosslinked polyvinylpyrrolidone, alginic acid or a salt thereof, such as sodium alginate. Additional excipients include flow conditioners and lubricants, for example silicic acid, talc, stearic acid or salts thereof, such as magnesium or calcium stearate, and/or polyethylene glycol, or derivatives thereof.

Tablet cores may be provided with suitable, optionally enteric, coatings through the use of, inter alia, concentrated sugar solutions which may comprise gum arabic, talc, polyvinylpyrrolidone, polyethylene glycol and/or titanium dioxide, or coating solutions in suitable organic solvents or solvent mixtures, or, for the preparation of enteric coatings, solutions of suitable cellulose preparations, such as acetylcellulose phthalate or hydroxypropylmethylcellulose phthalate. Dyes or pigments may be added to the tablets or tablet coatings, for example for identification purposes or to indicate different doses of active ingredient.

Pharmaceutical compositions for oral administration may also include hard capsules comprising gelatin or soft-sealed capsules comprising gelatin and a plasticizer, such as glycerol or sorbitol. The hard capsules may contain the active ingredient in the form of granules, for example in admixture with fillers, such as corn starch, binders, and/or glidants, such as talc or magnesium stearate, and optionally stabilizers. In soft capsules, the active ingredient may be dissolved or suspended in suitable liquid excipients, such as fatty oils, paraffin oil or liquid polyethylene glycols or fatty acid esters of ethylene or propylene glycol, to which stabilizers and detergents, for example of the polyoxyethylene sorbitan fatty acid ester type, may also be added.

Pharmaceutical compositions suitable for rectal administration are, for example, suppositories comprising a combination of the active ingredient and a suppository base. Suitable suppository bases are, for example, natural or synthetic triglycerides, paraffin hydrocarbons, polyethylene glycols or higher alkanols.

Pharmaceutical compositions suitable for parenteral administration may comprise aqueous solutions of an active ingredient in water-soluble form, for example of a water-soluble salt, or aqueous injection suspensions that contain viscosity-increasing substances, for example sodium carboxymethylcellulose, sorbitol and/or dextran, and, if desired, stabilizers. The active ingredient, optionally together with excipients, can also be in the form of a lyophilizate and can be made into a solution before parenteral administration by the addition of suitable solvents. Solutions such as are used, for example, for parenteral administration can also be employed as infusion solutions. The manufacture of injectable preparations is usually carried out under sterile conditions, as is the filling, for example, into ampoules or vials, and the sealing of the containers.

The disclosure also provides for a pharmaceutical combinations, e.g. a kit, comprising a) a first agent which is a compound of the disclosure as disclosed herein, in free form or in pharmaceutically acceptable salt form, and b) at least one co-agent. The kit can comprise instructions for its administration.

Combination Therapies

The compounds or pharmaceutical acceptable salts of the disclosure may be administered as the sole therapy, or together with other therapeutic agent or agents.

For example, the therapeutic effectiveness of one of the compounds described herein may be enhanced by administration of an adjuvant (i.e. by itself the adjuvant may only have minimal therapeutic benefit, but in combination with another therapeutic agent, the overall therapeutic benefit to the individual is enhanced). Or, by way of example only, the benefit experienced by an individual may be increased by administering one of the compounds described herein with another therapeutic agent that also has therapeutic benefit. By way of example only, in a treatment for gout involving administration of one of the compounds described herein, increased therapeutic benefit may result by also providing the individual with another therapeutic agent for gout. Or, by way of example only, if one of the side effects experienced by an individual upon receiving one of the compounds described herein is nausea, then it may be appropriate to administer an anti-nausea agent in combination with the compound. Or, the additional therapy or therapies include, but are not limited to physiotherapy, psychotherapy, radiation therapy, application of compresses to a diseased area, rest, altered diet, and the like. Regardless of the disease, disorder or condition being treated, the overall benefit experienced by the individual may be additive of the two therapies or the individual may experience a synergistic benefit.

In the instances where the compounds described herein are administered in combination with other therapeutic agents, the compounds described herein may be administered in the same pharmaceutical composition as other therapeutic agents, or because of different physical and chemical characteristics, be administered by a different route. For example, the compounds described herein may be administered orally to generate and maintain good blood levels thereof, while the other therapeutic agent may be administered intravenously. Thus the compounds described herein may be administered concurrently, sequentially or dosed separately to other therapeutic agents.

Compounds having Formula (I) are expected to be useful when used with alkylating agents, angiogenesis inhibitors, antibodies, antimetabolites, antimitotics, antiproliferatives, antivirals, aurora kinase inhibitors, other apoptosis promoters (for example, Bcl-xL, Bcl-w and Bfl-1) inhibitors, activators of death receptor pathway, Bcr-Abl kinase inhibitors, BiTE (Bi-Specific T cell Engager) antibodies, antibody drug conjugates, biologic response modifiers, cyclin-dependent kinase inhibitors, cell cycle inhibitors, cyclooxygenase-2 inhibitors, DVDs, leukemia viral oncogene homolog (ErbB2) receptor inhibitors, growth factor inhibitors, heat shock protein (HSP)-90 inhibitors, histone deacetylase (HDAC) inhibitors, hormonal therapies, immunologicals, inhibitors of inhibitors of apoptosis proteins (IAPB), intercalating antibiotics, kinase inhibitors, kinesin inhibitors, Jak2 inhibitors, mammalian target of rapamycin inhibitors, microRNA's, mitogen-activated extracellular signal-regulated kinase inhibitors, multivalent binding proteins, non-steroidal anti-inflammatory drugs (NSAIDs), poly ADP (adenosine diphosphate)-ribose polymerase (PARP) inhibitors, platinum chemotherapeutics, polo-like kinase (Plk) inhibitors, phosphoinositide-3 kinase (PI3K) inhibitors, proteosome inhibitors, purine analogs, pyrimidine analogs, receptor tyrosine kinase inhibitors, retinoids/deltoids plant alkaloids, small inhibitory ribonucleic acids (siRNAs), topoisomerase inhibitors, ubiquitin ligase inhibitors, and the like, and in combination with one or more of these agents.

EXAMPLES

Various methods may be developed for synthesizing a compound of formula (I) or a pharmaceutically acceptable salt thereof. Representative methods for synthesizing a compound of formula (I) or a pharmaceutically acceptable salt thereof are provided in the Examples. It is noted, however, that a compound of formula (I) or a pharmaceutically acceptable salt thereof may also be synthesized by other synthetic routes that others may devise.

It will be readily recognized that certain compounds of formula (I) have atoms with linkages to other atoms that confer a particular stereochemistry to the compound (e.g., chiral centers). It is recognized that synthesis of a compound of formula (I) or a pharmaceutically acceptable salt thereof may result in the creation of mixtures of different stereoisomers (enantiomers, diastereomers). Unless a particular stereochemistry is specified, recitation of a compound is intended to encompass all of the different possible stereoisomers.

Ae compound of formula (I) can also be prepared as a pharmaceutically acceptable acid addition salt by, for example, reacting the free base form of the at least one compound with a pharmaceutically acceptable inorganic or organic acid. Alternatively, a pharmaceutically acceptable base addition salt of the at least one compound of formula (I) can be prepared by, for example, reacting the free acid form of the at least one compound with a pharmaceutically acceptable inorganic or organic base. Inorganic and organic acids and bases suitable for the preparation of the pharmaceutically acceptable salts of compounds of formula (I) are set forth in the definitions section of this Application. Alternatively, the salt forms of the compounds of formula (I) can be prepared using salts of the starting materials or intermediates.

The free acid or free base forms of the compounds of formula (I) can be prepared from the corresponding base addition salt or acid addition salt form. For example, a compound of formula (I) in an acid addition salt form can be converted to the corresponding free base thereof by treating with a suitable base (e.g., ammonium hydroxide solution, sodium hydroxide, and the like). A compound of formula (I) in a base addition salt form can be converted to the corresponding free acid thereof by, for example, treating with a suitable acid (e.g., hydrochloric acid, etc).

The N-oxides of the a compound of formula (I) or a pharmaceutically acceptable salt thereof can be prepared by methods known to those of ordinary skill in the art. For example, N-oxides can be prepared by treating an unoxidized form of the compound of formula (I) with an oxidizing agent (e.g., trifluoroperacetic acid, permaleic acid, perbenzoic acid, peracetic acid, meta-chloroperoxybenzoic acid, or the like) in a suitable inert organic solvent (e.g., a halogenated hydrocarbon such as dichloromethane) at approximately 0 to 80° C. Alternatively, the N-oxides of the compounds of formula (I) can be prepared from the N-oxide of an appropriate starting material.

Compounds of formula (I) in an unoxidized form can be prepared from N-oxides of compounds of formula (I) by, for example, treating with a reducing agent (e.g., sulfur, sulfur dioxide, triphenyl phosphine, lithium borohydride, sodium borohydride, phosphorus trichloride, tribromide, and the like) in an suitable inert organic solvent (e.g., acetonitrile, ethanol, aqueous dioxane, and the like) at 0 to 80° C.

Protected derivatives of the compounds of formula (I) can be made by methods known to those of ordinary skill in the art. A detailed description of the techniques applicable to the creation of protecting groups and their removal can be found in T. W. Greene, Protecting Groups in Organic Synthesis, 3rd edition, John Wiley & Sons, Inc. 1999.

As used herein the symbols and conventions used in these processes, schemes and examples are consistent with those used in the contemporary scientific literature, for example, the Journal of the American Chemical Society or the Journal of Biological Chemistry. Standard single-letter or three-letter abbreviations are generally used to designate amino acid residues, which are assumed to be in the L-configuration unless otherwise noted. Unless otherwise noted, all starting materials were obtained from commercial suppliers and used without further purification. For example, the following abbreviations may be used in the examples and throughout the specification: g (grams); mg (milligrams); L (liters); mL (milliliters); pt (microliters); psi (pounds per square inch); M (molar); mM (millimolar); i.v. (intravenous); Hz (Hertz); MHz (megahertz); mol (moles); mmol (millimoles); RT (room temperature); min (minutes); h (hours); mp (melting point); TLC (thin layer chromatography); Rt (retention time); RP (reverse phase); MeOH (methanol); i-PrOH (isopropanol); TEA (triethylamine); TFA (trifluoroacetic acid); TFAA (trifluoroacetic anhydride); THF (tetrahydrofuran); DMSO (dimethyl sulfoxide); EtOAc (ethyl acetate); DME (1,2-dimethoxyethane); DCM (dichloromethane); DCE (dichloroethane); DMF (N,N-dimethylformamide); DMPU (N,N'-dimethylpropyleneurea); CDI (1,1-carbonyldiimidazole); IBCF (isobutyl chloroformate); HOAc (acetic acid); HOSu (N-hydroxysuccinimide); HOBT (1-hydroxybenzotriazole); Et$_2$O (diethyl ether); EDCI (1-(3-dimethylaminopropyl)-3-ethylcarbodiimide hydrochloride); BOC (tert-butyloxycarbonyl); FMOC (9-fluorenylmethoxycarbonyl); DCC (dicyclohexylcarbodiimide); CBZ (benzyloxycarbonyl); Ac (acetyl); atm (atmosphere); TMSE (2-(trimethylsilyl)ethyl); TMS (trimethylsilyl); TIPS (triisopropylsilyl); TB S (t-butyldimethylsilyl); DMAP (4-dimethylaminopyridine); Me (methyl); OMe (methoxy); Et (ethyl); tBu (tert-butyl); HPLC (high pressure liquid chomatography); BOP (bis(2-oxo-3-oxazolidinyl)phosphinic chloride); TBAF (tetra-n-butylammonium fluoride); m-CPBA (meta-chloroperbenzoic acid).

References to ether or Et$_2$O are to diethyl ether; brine refers to a saturated aqueous solution of NaCl. Unless otherwise indicated, all temperatures are expressed in ° C. (degrees Centigrade). All reactions were conducted under an inert atmosphere at RT unless otherwise noted.

$^1$H NMR spectra were recorded on a Varian Mercury Plus 400. Chemical shifts are expressed in parts per million (ppm). Coupling constants are in units of hertz (Hz). Splitting patterns describe apparent multiplicities and are designated as s (singlet), d (doublet), t (triplet), q (quartet), m (multiplet) and br (broad).

Low-resolution mass spectra (MS) and compound purity data were acquired on a Shimadzu LC/MS single quadrapole system equipped with electrospray ionization (ESI) source, UV detector (220 and 254 nm), and evaporative light scattering detector (ELSD). Thin-layer chromatography was performed on 0.25 mm Superchemgroup silica gel plates (60F-254), visualized with UV light, 5% ethanolic phosphomolybdic acid, ninhydrin, or p-anisaldehyde solution. Flash column chromatography was performed on silica gel (200-300 mesh, Branch of Qingdao Haiyang Chemical Co.,Ltd).

Synthetic Schemes

Synthetic methods for preparing the compounds of the present invention are illustrated in the following Schemes and Examples. Starting materials are commercially available or may be made according to procedures known in the art or as illustrated herein.

The intermediates shown in the following schemes are either known in the literature or may be prepared by a variety of methods familiar to those skilled in the art.

As an illustration, one of the synthetic approach of the compounds of formula I of the present disclosure in outlined in Scheme 1. As shown in the Scheme, the compounds of formula I can be disassembled into the intermediates III and II the preparation of which is known in the literature. Coupling of carboxylic acid II with sulfonamide III via a condensation reaction leads to compounds of formula I.

Scheme 1

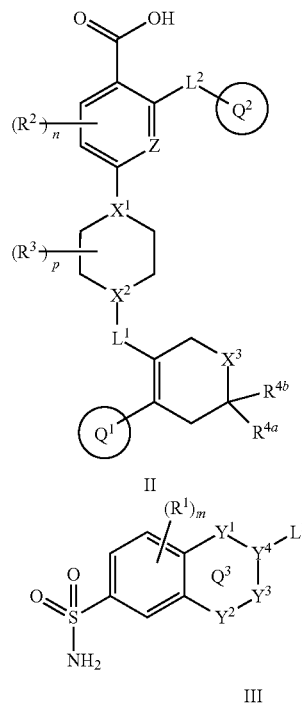

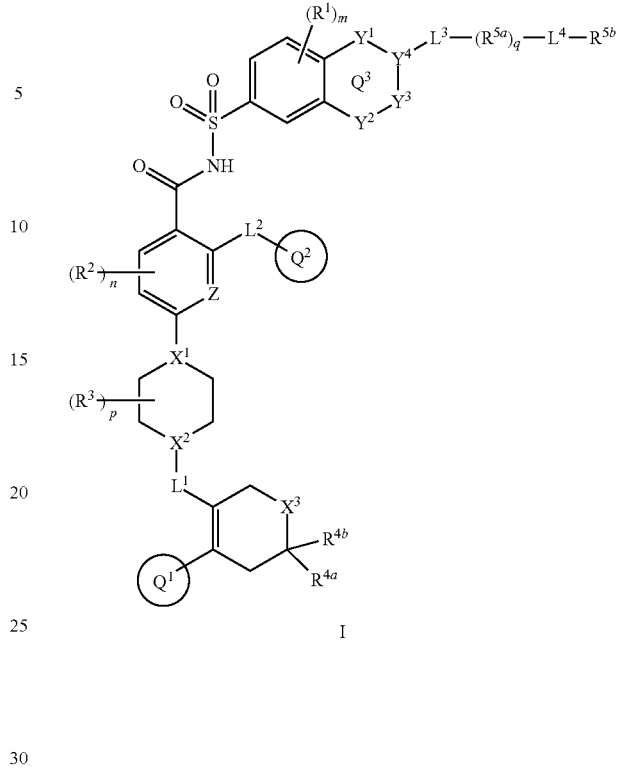

As an illustration of the preparation of intermediates of formula III, a preparation of compound IIIa is shown in Scheme 2. Starting from benzo-fused heterocycle IIIa-A, which is either commercially available or known in the literature, sulfonyl chloride IIIa-B is prepared by treating of with chlorosulfonic acid. Nitration of IIIa-B under conditions such as $HNO_3/H_2SO_4$ gives IIIa-C, which can be further converted to sulfonamide IIIa-D by reacting IIIa-C with $NH_3$. Intermediate IIIa can be obtained by the coupling of IIIa-D with IIIa-E through a substitution reaction.

Scheme 2

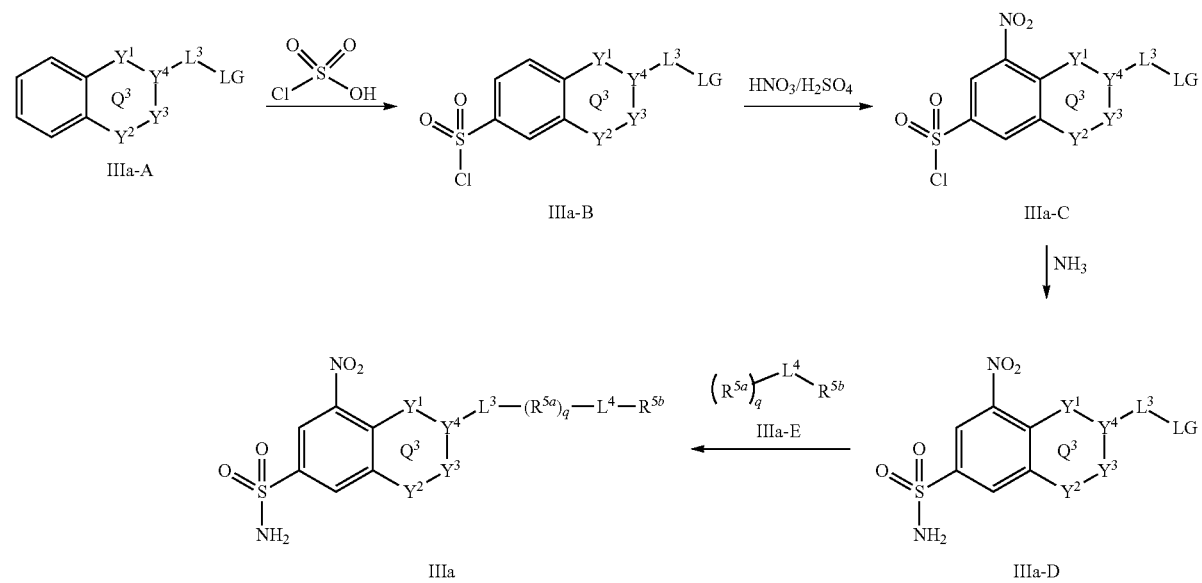

As a further illustration of the preparation of intermediates of formula III, a preparation of compound IIIb is illustrated in Scheme 3. Bromination of the commercially available IIIb-A results in IIIb-B, and then reaction of IIIb-B with IIIb-C provides Intramolecular cyclization of IIIb-D using metal catalyzed coupling conditions such as Buchwald reaction or other coupling conditions known in the literature gives IIIb-G. Alternatively intermediate IIIb-G can be obtained via a three-step sequence of mesylation of hydroxyl group of IIIb-D, SN2 reaction and intramolecular cyclization. Coupling of IIIb-G with IIIa-E leads to the desired intermediate IIIb.

Another illustration of the preparation of intermediates of formula III is shown is Scheme 4 which demonstrates preparation of compound IIIc. Starting from the commercially available IIIc-A, selective reaction of the hydroxyl group at C-3 nitrobenzene in with the commercially available IIIc-B in the presence of base provides IIIc-C. Treatment of IIIc-C with an acid such as HBr/AcOH followed by intramolecular cyclization via an etherification reaction promoted by a base results in IIIc-D. Mesylation of the hydroxyl group in into a leaving Group gives IIIc-E. Sulfonylation of IIIc-E using chlorosulfonic acid in the presence of $PCl_5$ provides IIIc-F and treatment of IIIc-F with $NH_3$ gives IIIc-G. Compounds of formula IIIc can be prepared by the coupling of the resulting with IIIa-E.

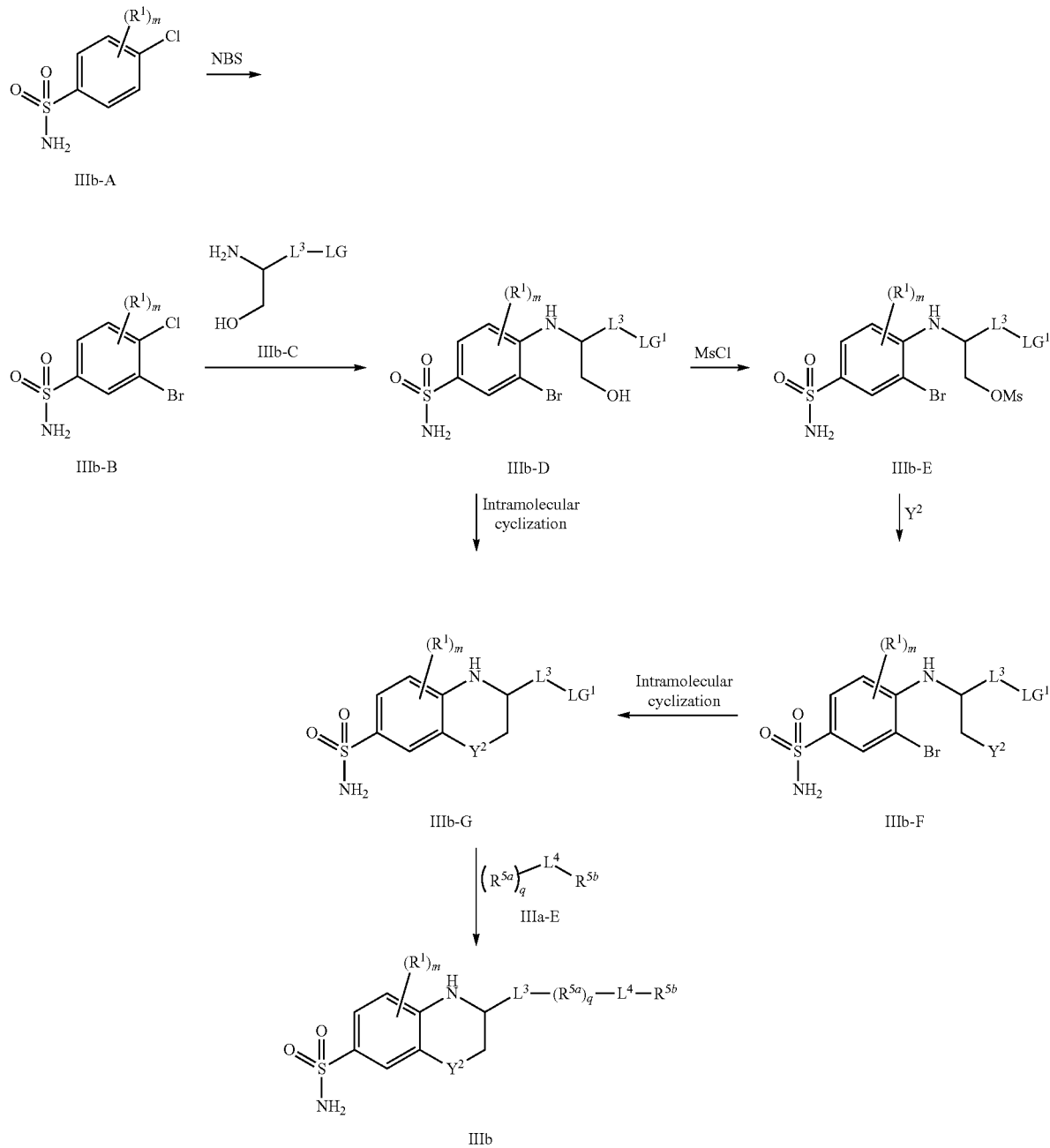

Scheme 3

Scheme 4

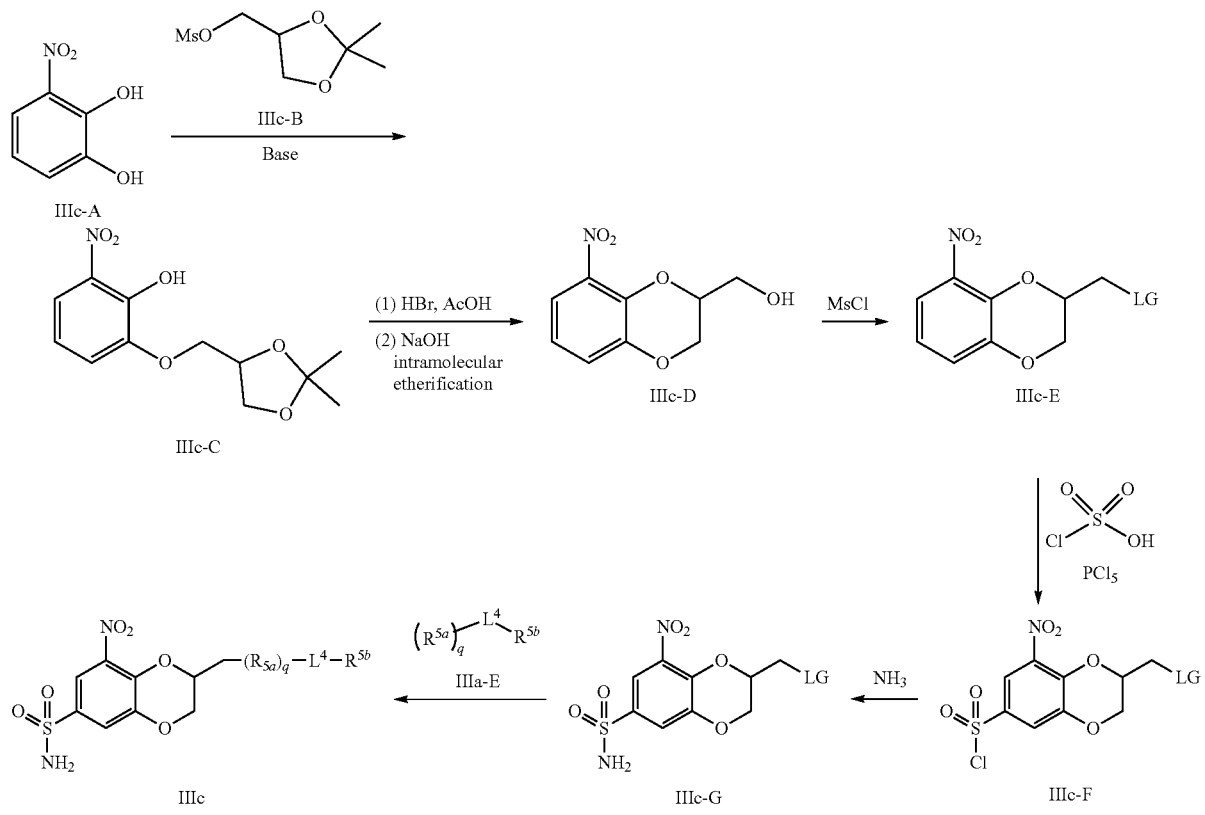

In some cases the order of carrying out the foregoing reaction schemes may be varied to facilitate the reaction or to avoid unwanted reaction products. The following examples are provided so that the invention might be more fully understood. These examples are illustrative only and should not be construed as limiting the invention in any way.

Preparation of Intermediates

Intermediate A (S)-2-(iodomethyl)-7-nitroindoline-5-sulfonamide (Intermediate A)

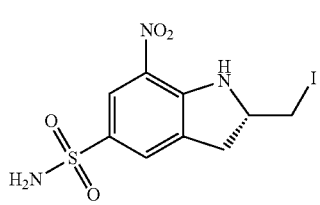

(S)-indolin-2-ylmethanol (A-1)

(S)-indolin-2-ylmethanol (A-1) was prepared according to the method described in WO2009/109364.

(S)-9,9a-dihydro-1H,3H-oxazolo[3,4-a]indol-3-one (A-2)

A mixture of (S)-indolin-2-ylmethanol (A-1) (1.63 g, 10.9 mmol) and CDI (1.78 g, 10.9 mmol) in THF (25 mL) was stirred at 60° C. for 2.5 h. The mixture was concentrated and extracted by EtOAc, the extracts were washed with brine, dried over $Na_2SO_4$ and concentrated, the residue was purified by column chromatography on silica gel eluting with PE/EtOAc (8:1~6:1) to give the title compound (S)-9,9a-dihydro-1H,3H-oxazolo[3,4-a]indol-3-one (A-2). MS-ESI (m/z): 176 [M+1]$^+$.

(S)-3-oxo-9,9a-dihydro-1H,3H-oxazolo[3,4-a]indole-7-sulfonyl chloride (A-3)

To sulfurochloridic acid (1 mL) was added (S)-9,9a-dihydro-1H,3H-oxazolo[3,4-a]indol-3-one (A-2) (0.10 g, 0.6 mmol) at 0° C. The mixture was stirred at 0° C. for 1 h and quenched by ice water (20 mL) at 0° C. The mixture was extracted by EtOAc (2×50 mL), the extracts were washed with brine (50 mL), dried over $Na_2SO_4$ and evaporated to give the crude product of (S)-3-oxo-9,9a-dihydro-1H,3H-oxazolo[3,4-a]indole-7-sulfonyl chloride (A-3), which was used for next step directly.

(S)-5-nitro-3-oxo-9,9a-dihydro-1H,3H-oxazolo[3,4-a]indole-7-sulfonyl chloride (A-4)

To a solution of (S)-3-oxo-9,9a-dihydro-1H,3H-oxazolo[3,4-a]indole-7-sulfonyl chloride (A-3) (0.05 g, 0.18 mmol)

in Con.H$_2$SO$_4$ (1 mL) was added KNO$_3$ (0.038 g, 0.36 mmol) at 0° C. The mixture was stirred at 0° C. for 1 h and quenched by ice water (20 mL) at 0° C. The mixture was extracted by EtOAc, washed with brine (15 mL), dried with Na$_2$SO$_4$. Filtered, and evaporated to give the crude product of (S)-5-nitro-3-oxo-9,9a-dihydro-1H,3H-oxazolo[3,4-a]indole-7-sulfonyl chloride (A-4), which was used for next step directly.

(S)-(7-nitro-5-sulfamoylindolin-2-yl)methyl carbamate (A-5)

A mixture of (S)-5-nitro -3-oxo-9,9a-dihydro-1H,3H-oxazolo[3,4-a]indole-7-sulfonyl chloride (A-4) (51 mg, 0.16 mmol) and NH$_3$ in MeOH (3 mL) was stirred at RT for 1 h. The mixture was concentrated to give the crude product of (S)-(7-nitro-5-sulfamoylindolin-2-yl)methyl carbamate (A-5), which was used for next step directly. MS-ESI (m/z): 315 [M−1]$^-$.

(S)-2-(hydroxymethyl)-7-nitroindoline-5-sulfonamide (A-6)

A mixture of (S)-(7-nitro-5-sulfamoylindolin-2-yl)methyl carbamate (A-5) (21 mg, 0.068 mmol) and NaOH (2 N, 0.2 mL) in MeOH (1 mL) was stirred at 50° C. for 3.5 h. The mixture was extracted with DCM, and the water phase was adjusted with 1N HCl to pH=4~5. The mixture was extracted with EtOAc (4×80 mL), the extracts were washed with brine (100 mL), dried with Na$_2$SO$_4$ and concentrated to give the crude product of (S)-2-(hydroxymethyl)-7-nitroindoline-5-sulfonamide (A-6), which was used for next step directly. MS-ESI (m/z): 272 [M−1]$^-$.

(S)-2-(iodomethyl)-7-nitroindoline-5-sulfonamide (Intermediate A)

To a solution of (S)-2-(hydroxymethyl)-7-nitroindoline-5-sulfonamide (A-6) (0.2 g, 0.73 mmol), PPh$_3$ (0.48 g, 1.83 mmol) and imidazole (0.12 g, 1.83 mmol) in CH$_3$CN (10 mL) was added I$_2$ (0.37 g, 1.46 mmol) at 0° C. for 10 min. The mixture was warmed to RT slowly and stirred at RT overnight. The reaction was quenched with saturated Na$_2$S$_2$O$_3$ aqueous solution (50 mL) and extracted with EtOAc (2×30 mL). The extracts were washed with brine (30 mL), dried with Na$_2$SO$_4$ and concentrated. The residue was purified by flash column chromatography on silica gel eluting with PE/EtOAc (4:1~2:1) to give the title compound (S)-2-(iodomethyl)-7-nitroindoline-5-sulfonamide (Intermediate A). MS-ESI (m/z): 384 [M+1]$^+$.

Intermediate B (R)-2-(iodomethyl)-7-nitroindoline-5-sulfonamide (Intermediate B)

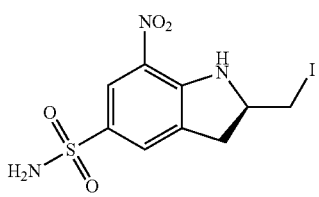

Intermediate B

The title compound (R)-2-(iodomethyl)-7-nitroindoline-5-sulfonamide (Intermediate B) was prepared according to the synthetic method of (S)-2-(iodomethyl)-7-nitroindoline-5-sulfonamide (Intermediate A) by replacing (S)-indolin-2-ylmethanol (A-1) with (R)-indolin-2-ylmethanol. MS-ESI (m/z): 384 [M+1]$^+$.

Intermediate C (R)-(5-nitro-7-sulfamoyl-3,4-dihydro-2H-benzo[b][1,4]oxazin-3-yl)methyl methanesulfonate (Intermediate C)

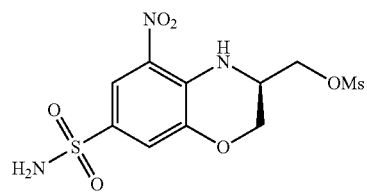

Intermediate C 3-bromo-4-chloro-5-nitrobenzenesulfonamide (C-1)

A mixture of 4-chloro-3-nitrobenzenesulfonamide (10 g, 42.5 mmol) in Con.H$_2$SO$_4$ (30 mL) was stirred at 50° C. and added NBS (11 g, 61.8 mmol) in portions. The mixture was warmed to 60° C. and stirred at 60° C. for 2 h. Then the mixture was poured into ice (200 g), after stirred for 10 min and filtered. The filtered cake was washed with water (30 mL) and evaporated to give the crude product of 3-bromo-4-chloro-5-nitrobenzenesulfonamide (C-1), which was used for next step directly. MS-ESI (m/z): 313 [M−1]$^-$.

methyl O-(tert-butyldimethylsilyl)-L-serinate (C-2)

methyl O-(tert-butyldimethylsilyl)-L-serinate (C-2) was prepared according to the method described in *Synthesis* 2009, 6, 951.

(R)-2-amino-3-((tert-butyldimethylsilyl)oxy)propan-1-ol (C-3)

(R)-2-amino-3-((tert-butyldimethylsilyl)oxy)propan-1-ol (C-3) was prepared according to the method described in *Synthesis* 2009, 6, 951.

(R)-3-bromo-4-((1-((tert-butyldimethylsilyl)oxy)-3-hydroxypropan-2-yl)amino)-5-nitrobenzenesulfonamide (C-4)

A mixture of 3-bromo-4-chloro-5-nitrobenzenesulfonamide (C-1) (2.9 g, 9.26 mmol) and (R)-2-amino-3-((tert-butyldimethylsilyl)oxy)propan-1-ol (C-3) (1.73 g, 8.44 mmol) and DIPEA (5.5 g, 42.6 mmol) in CH$_3$CN (25 mL) was stirred at 80° C. overnight. Concentrated, the residue was purified by column chromatography on silica gel eluting to give the title compound (R)-3-bromo-4-((1-((tert-butyldimethylsilyl)oxy)-3-hydroxypropan-2-yl)amino)-5-nitrobenzenesulfonamide (C-4). MS-ESI (m/z): 484 [M+1]$^+$.

(R)-3-(((tert-butyldimethylsilyl)oxy)methyl)-5-nitro-3,4-dihydro-2H-benzo[b][1, 4]oxazine-7-sulfonamide (C-5)

A mixture of (R)-3-bromo-4-((1-((tert-butyldimethylsilyl)oxy)-3-hydroxypropan-2-yl)amino)-5-nitrobenzenesulfonamide (C-4) (10 mg, 0.021 mmol), Me₄phen (2.5 mg, 0.010 mmol), CuI (4.0 mg, 0.021 mmol) and Cs₂CO₃ (10 mg, 0.032 mmol) in toluene (1.5 mL) was stirred at 105° C. for 5 h under N₂ atmosphere. The mixture was cooled to RT and concentrate. The residue was purified by column chromatography on silica gel eluting to give the title compound (R)-3-(((tert-butyldimethylsilyl)oxy)methyl)-5-nitro-3,4-dihydro-2H-benzo[b][1,4]oxazine-7-sulfonamide (C-5). MS-ESI (m/z): 404 [M+1]⁺.

(S)-3-(hydroxymethyl)-5-nitro-3,4-dihydro-2H-benzo[b][1,4]oxazine-7-sulfonamide (C-6)

A mixture of (R)-3-(((tert-butyldimethylsilyl)oxy)methyl)-5-nitro-3,4-dihydro-2H-benzo[b][1,4]oxazine-7-sulfonamide (C-5) (1.7 mg, 0.042 mmol), 2 N HCl (0.3 mL) in MeOH (1 mL) was stirred at RT for 0.5 h. The reaction was quenched by saturated NaHCO₃ aqueous solution (10 mL) and extracted with EtOAc. The organic phase was washed with brine (20 mL), dried over Na₂SO₄ and concentrated to give the crude product of (S)-3-(hydroxymethyl)-5-nitro-3,4-dihydro-2H-benzo[b][1,4]oxazine-7-sulfonamide (C-6), which was used for next step directly. MS-ESI (m/z): 290 [M+1]⁺.

(R)-(5-nitro-7-sulfamoyl-3,4-dihydro-2H-benzo[b][1,4]oxazin-3-yl)methyl methanesulfonate (Intermediate C)

To a solution of (S)-3-(hydroxymethyl)-5-nitro-3,4-dihydro-2H-benzo[b][1,4]oxazine-7-sulfonamide (C-6) (10.0 mg, 0.0346 mmol) in DCM/CH₃CN (2 mL/0.5 mL) was added MSCl (4.8 mg, 0.415 mmol) at 0° C. A solution of TEA (3.5 mg, 0.0346 mmol) in DCM was added. The mixture was stirred at 0° C. for 5 min. The reaction was quenched with saturated NaHCO₃ aqueous solution and the mixture was extracted with DCM. The organic phase was washed with brine (20 mL), dried over Na₂SO₄, and concentrated to give the crude product of (R)-(5-nitro-7-sulfamoyl-3,4-dihydro-2H-benzo[b][1,4]oxazin-3-yl)methyl methanesulfonate (Intermediate C), which was used for next step directly. MS-ESI (m/z): 368 [M+1]⁺.

Intermediate D (S)-(5-nitro-7-sulfamoyl-3,4-dihydro-2H-benzo[b][1,4]oxazin-3-yl)methyl methanesulfonate (Intermediate D)

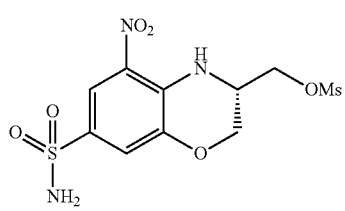

Intermediate D

The title compound (S)-(5-nitro-7-sulfamoyl-3,4-dihydro-2H-benzo[b][1,4]oxazin-3-yl)methyl methanesulfonate (Intermediate D) was prepared according to the synthetic method of (R)-(5-nitro-7-sulfamoyl-3,4-dihydro-2H-benzo[b][1,4]oxazin-3-yl)methyl methanesulfonate (Intermediate C) by replacing methyl O-(tert-butyldimethylsilyl)-L-serinate (C-2) with methyl O-(tert-butyldimethylsilyl)-D-serinate. MS-ESI (m/z): 368 [M+1]⁺.

Intermediate E (R)-3-(2-iodoethyl)-5-nitro-3,4-dihydro-2H-benzo[b][1,4]oxazine-7-sulfonamide (Intermediate E)

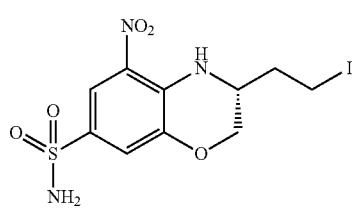

Intermediate E methyl D-homoserinate hydrochloride (E-1)

To a solution of D-homoserine (4.76 g, 40.0 mmol) in MeOH (100 mL) was added SOCl₂ (3.5 mL, 40.0 mmol) under ice-water bath. Then, the mixture was stirred at 50° C. for 1 h. Concentrated to give the crude product of methyl D-homoserinate hydrochloride (E-1), which was used for next step directly. MS-ESI (m/z): 170 [M+1]⁺.

(R)-3-bromo-4-((4-((tert-butyldimethylsilyl)oxy)-1-hydroxybutan-2-yl)amino)-5-nitrobenzenesulfonamide (E-2)

The title compound (R)-3-bromo-4-((4-((tert-butyldimethylsilyl)oxy)-1-hydroxybutan-2-yl)amino)-5-nitrobenzenesulfonamide (E-2) was prepared according to the synthetic method of (R)-3-bromo-4-((1-((tert-butyldimethylsilyl)oxy)-3-hydroxypropan-2-yl)amino)-5-nitrobenzenesulfonamide (C-4) by replacing methyl L-serinate hydrochloride with methyl D-homoserinate hydrochloride (E-1). MS-ESI (m/z): 418 [M+1]⁺.

(R)-3-(2-((tert-butyldimethylsilyl)oxy)ethyl)-5-nitro-3,4-dihydro-2H-benzo[b][1, 4]oxazine-7-sulfonamide (E-3)

The title compound (R)-3-(2-((tert-butyldimethylsilyl)oxy)ethyl)-5-nitro-3,4-dihydro-2H-benzo[b][1,4]oxazine-7-sulfonamide (E-3) was prepared according to the synthetic method of (R)-3-(((tert-butyldimethylsilyl)oxy)methyl)-5-nitro-3,4-dihydro-2H-benzo[b][1,4]oxazine-7-sulfonamide (C-5) by replacing (R)-3-bromo-4-((1-((tert-butyldimethylsilyl)oxy)-3-hydroxypropan-2-yl)amino)-5-nitrobenzenesulfonamide (C-4) with (R)-3-bromo-4-((4-((tert-butyldimethylsilyl)oxy)-1-hydroxybutan-2-yl)amino)-5-nitrobenzenesul fonamide (E-2). MS-ESI (m/z): 418 [M+1]⁺.

(R)-3-(2-hydroxyethyl)-5-nitro-3,4-dihydro-2H-benzo[b][1,4]oxazine-7-sulfona mide (E-4)

The title compound (R)-3-(2-hydroxyethyl)-5-nitro-3,4-dihydro-2H-benzo[b][1,4]oxazine-7-sulfonamide (E-4) was prepared according to the synthetic method of (S)-3-(hydroxymethyl)-5-nitro-3,4-dihydro-2H-benzo[b][1,4]oxazine-7-sulfonamide (C-6) by replacing (R)-3-(((tert-butyldimethylsilyl)oxy)methyl)-5-nitro-3,4-dihydro-2H- benzo[b][1,4]oxazine-7-sulfonamide (C-5) with (R)-3-(2-((tert-butyldimethylsilyl)oxy)ethyl)-5-nitro-3,4-dihydro-2H-benzo[b][1,4]oxazine-7-sulfonamide (E-3). MS-ESI (m/z): 304 [M+1]$^+$.

(R)-3-(2-iodoethyl)-5-nitro-3,4-dihydro-2H-benzo[b][1,4]oxazine-7-sulfonamide (Intermediate E)

The title compound (R)-3-(2-iodoethyl)-5-nitro-3,4-dihydro-2H-benzo[b][1,4]oxazine-7-sulfonamide (Intermediate E) was prepared according to the synthetic method of (S)-2-(iodomethyl)-7-nitroindoline-5-sulfonamide (Intermediate A) by replacing (S)-2-(hydroxymethyl)-7-nitroindoline-5-sulfonamide (A-6) with (R)-3-(2-hydroxyethyl)-5-nitro-3,4-dihydro-2H-benzo[b][1,4]oxazine-7-sulfonamide (E-4). MS-ESI (m/z): 414 [M+1]$^+$.

Intermediate F (S)-3-(2-iodoethyl)-5-nitro-3,4-dihydro-2H-benzo[b][1,4]oxazine-7-sulfonamide (Intermediate F)

Intermediate F

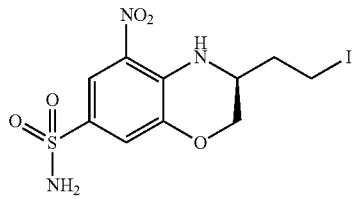

The title compound (S)-3-(2-iodoethyl)-5-nitro-3,4-dihydro-2H-benzo[b][1,4]-oxazine-7-sulfonamide (Intermediate F) was prepared according to the synthetic method of (S)-2-(iodomethyl)-7-nitroindoline-5-sulfonamide (Intermediate E) by replacing D-homoserine with L-homoserine. MS-ESI (m/z): 414 [M+1]$^+$.

Intermediate G (R)-(5-nitro-7-sulfamoyl-3,4-dihydro-2H-benzo[b][1,4]thiazin-3-yl)methyl methanesulfonate (Intermediate G)

Intermediate G

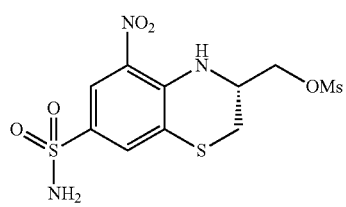

(S)-3-bromo-4-((1-((tert-butyldimethylsilyl)oxy)-3-hydroxypropan-2-yl)amino)-5-nitrobenzenesulfonamide (G-1)

The title compound (S)-3-bromo-4-((1-((tert-butyldimethylsilyl)oxy)-3-hydroxypropan-2-yl)amino)-5-nitrobenzenesulfonamide (G-1) was prepared according to the synthetic method of (R)-3-bromo-4-((1-((tert-butyldimethylsilyl)oxy)-3-hydroxypropan-2-yl)amino)-5-nitrobenzenesulfonamide (C-4) by replacing D-serinate hydrochloride with L-serinate hydrochloride. MS-ESI (m/z): 484 [M+1]$^+$.

(R)-2-((2-bromo-6-nitro-4-sulfamoylphenyl)amino)-3-((tert-butyldimethylsilyl)oxy)propyl methanesulfonate (G-2)

The title compound (R)-2-((2-bromo-6-nitro-4-sulfamoylphenyl)amino)-3-((tert-butyldimethylsilyl)oxy)propyl methanesulfonate (G-2) was prepared according to the synthetic method of (R)-(5-nitro-7-sulfamoyl-3,4-dihydro-2H-benzo[b][1,4]oxazin-3-yl)methyl methanesulfonate (Intermediate C) by replacing (S)-3-(hydroxymethyl)-5-nitro-3,4-dihydro-2H-benzo[b][1,4]oxazine-7-sulfonamide (C-6) with (S)-3-bromo-4-((1-((tert-butyldimethylsilyl)oxy)-3-hydroxypropan-2-yl)amino)-5-nitrobenzenesulfonamide (G-1). MS-ESI (m/z): 562 [M+1]$^+$.

(R)-S-(2-((2-bromo-6-nitro-4-sulfamoylphenyl)amino)-3-((tert-butyldimethylsilyl)oxy)propyl) ethanethioate (G-3)

To the solution of (R)-S-(2-((2-bromo-6-nitro-4-sulfamoylphenyl)amino)-3-((tert-butyldimethylsilyl)oxy)propyl methanesulfonate (G-2) (0.5 g, 0.89 mmol) in DMF (10 mL) was added AcSK (0.3 g, 2.6 mmol). The mixture was stirred at RT for 1 h. The reaction was quenched with water and the mixture was extracted with EtOAc (2×25 mL). The organic phase was washed with brine (20 mL), dried over Na$_2$SO$_4$, and concentrated. The residue was purified by column chromatography on silica gel eluting with EtOAc/PE (1:4) to give title compound (R)-S-(2-((2-bromo-6-nitro-4-sulfamoylphenyl)amino)-3-((tert-butyldimethylsilyl)oxy)propyl) ethanethioate (G-3). MS-ESI (m/z): 542 [M+1]$^+$.

(R)-3-bromo-4-((1-((tert-butyldimethylsilyl)oxy)-3-mercaptopropan-2-yl)amino)-5-nitrobenzenesulfonamide (G-4)

To the solution of (R)-S-(2((2-bromo-6-nitro-4-sulfamoylphenyl)amino)-3-ethanethioate (G-3) (0.3 g, 0.55 mmol) in MeOH (15 mL) was added K$_2$CO$_3$ (0.26 g, 1.88 mmol). The mixture was stirred at RT for 10 min. The reaction was quenched with water and adjusted with Con. HCl to pH=6~7. The mixture was extracted with DCM (3×25 mL). The extracts were washed with brine, dried with Na$_2$SO$_4$ and concentrated to give title compound (R)-3-bromo-4-((1-((tert-butyldimethylsilyl)oxy)-3-mercaptopropan-2-yl)amino)-5-nitrobenzenesulfonamide (G-4). MS-ESI (m/z): 500 [M+1]$^+$.

(R)-3-(((tert-butyldimethylsilyl)oxy)methyl)-5-nitro-3,4-dihydro-2H-benzo[b][1,4]thiazine-7-sulfonamide (G-5)

The title compound (R)-3-(((tert-butyldimethylsilyl)oxy)methyl)-5-nitro-3,4-dihydro-2H-benzo[b][1,4]thiazine-7-sulfonamide (G-5) was prepared according to the synthetic method of (R)-3-(((tert-butyldimethylsilyl)oxy)methyl)-5-nitro-3,4-dihydro-2H-benzo[b][1,4]oxazine-7-sulfonamide (C-5) by replacing (R)-3-bromo-4-((1-((tert-butyldimethylsilyl)oxy)-3-hydroxypropan-2-yl)amino)-5-nitrobenzenesulfonamide (C-4) with (R)-3-bromo-4-((1-((tert-butyldimethylsilyl)oxy)-3-mercaptopropan-2-yl)amino)-5-nitrobenzenesulfonamide (G-4). MS-ESI (m/z): 420 [M+1]$^+$.

(R)-3-(hydroxymethyl)-5-nitro-3,4-dihydro-2H-benzo[b][1,4]thiazine-7-sulfonamide (G-6)

The title compound (R)-3-(hydroxymethyl)-5-nitro-3,4-dihydro-2H-benzo[b][1,4]thiazine-7-sulfonamide (G-6) was prepared according to the synthetic method of (S)-3-(hydroxymethyl)-5-nitro-3,4-dihydro-2H-benzo[b][1,4]oxazine-7-sulfonamide (C-6) by replacing (R)-3-(((tert-butyldimethylsilyl)oxy)methyl)-5-nitro-3,4-dihydro-2H-benzo[b][1,4]oxazine-7-sulfonamide (C-5) with (R)-3-(((tert-butyldimethylsilyl)oxy)methyl)-5-nitro-3,4-dihydro-2H-benzo[b][1,4]thiazine-7-sulfonamide (G-5). MS-ESI (m/z): 306 [M+1]$^+$.

(R)-(5-nitro-7-sulfamoyl-3,4-dihydro-2H-benzo[b][1,4]thiazin-3-yl)methyl methanesulfonate (Intermediate G)

The title compound (R)-(5-nitro-7-sulfamoyl-3,4-dihydro-2H-benzo[b][1,4]thiazin-3-yl)methyl methanesulfonate (Intermediate G) was prepared according to the synthetic method of (R)-(5-nitro-7-sulfamoyl-3,4-dihydro-2H-benzo[b][1,4]oxazin-3-yl)methyl methanesulfonate (Intermediate C) by replacing (S)-3-(hydroxymethyl)-5-nitro-3,4-dihydro-2H-benzo[b][1,4]oxazine-7-sulfonamide (C-6) with (R)-3-(hydroxymethyl)-5-nitro-3,4-dihydro-2H-benzo[b][1,4]thiazine-7-sulfonamide (G-6). MS-ESI (m/z): 384 [M+1]$^+$.

Intermediate H (R)-2-(5-nitro-7-sulfamoyl-3,4-dihydro-2H-benzo[b][1,4]thiazin-3-yl)ethyl methanesulfonate (Intermediate H)

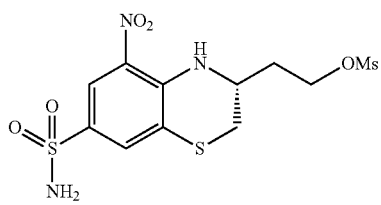

Intermediate H

The title compound (R)-2-(5-nitro-7-sulfamoyl-3,4-dihydro-2H-benzo[b][1,4]thiazin-3-yl)ethyl methanesulfonate (Intermediate H) was prepared according to the synthetic method of (R)-(5-nitro-7-sulfamoyl-3,4-dihydro-2H-benzo[b][1,4]thiazin-3-yl)methyl methanesulfonate (Intermediate G) by replacing (S)-3-bromo-4-((1-((tert-butyldimethylsilyl)oxy)-3-hydroxypropan-2-yl)amino)-5-nitrobenzenesulfonamide (G-1) with (R)-3-bromo-4-((4-((tert-butyldimethylsilyl)oxy)-1-hydroxybutan-2-yl)amino)-5-nitrobenzenesulfonamide (E-2). MS-ESI (m/z): 398 [M+1]$^+$.

Intermediate I (S)-(8-nitro-6-sulfamoyl-1,2,3,4-tetrahydroquinoxalin-2-yl)methyl methanesulfonate (Intermediate I)

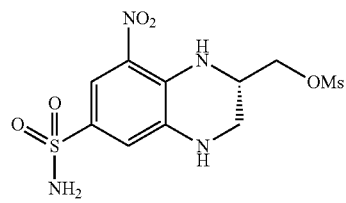

Intermediate I (S)-4-((1-azido-3-((tert-butyldimethylsilyl)oxy)propan-2-yl)amino)-3-bromo-5-nitrobenzenesulfonamide (I-1)

To the solution of (R)-2((2-bromo-6-nitro-4-sulfamoylphenyl)amino)-3-((tert-butyldimethylsilyl)oxy)propyl methanesulfonate (G-2) (30 mg, 0.0534 mmol) in DMF (1.5 mL) was added NaN$_3$ (17 mg, 0.267 mmol). The mixture was stirred at 30° C. overnight. The reaction was quenched with water and the mixture was extracted with EtOAc (2×25 mL). The organic phase was washed with brine (20 mL), dried over Na$_2$SO$_4$, and concentrated. The residue was purified by column chromatography on silica gel eluting with EtOAc/PE (1:5~1:3) to give title compound (S)-4-((1-azido-3-((tert-butyldimethylsilyl)oxy)propan-2-yl)amino)-3-bromo-5-nitrobenzenesulfonamide (I-1). MS-ESI (m/z): 509 [M+1]$^+$.

215

(S)-4-((1-amino-3-((tert-butyldimethylsilyl)oxy)propan-2-yl)amino)-3-bromo-5-nitrobenzenesulfonamide (I-2)

To a solution of (S)-4-((1-azido-3-((tert-butyldimethylsilyl)oxy)propan-2-yl)amino)-3-bromo-5-nitrobenzenesulfonamide (I-1) (0.235 g, 0.463 mmol) in H$_2$O/THF (0.125 mL/5 mL) was added PPh$_3$ (0.346 g, 1.388 mmol) under N$_2$ atmosphere. The mixture was stirred at 35° C. overnight under N$_2$ atmosphere. The reaction was quenched with water and the mixture was extracted with DCM. The organic phase was washed with brine (20 mL), dried over Na$_2$SO$_4$, and concentrated. The residue was purified by column chromatography on silica gel eluting with PE/DCM (50:1~20:1) to give title compound (S)-4-(1-amino-3-((tert-butyldimethylsilyl)oxy)propan-2-yl)amino)-3-bromo-5-nitrobenzenesulfonamide (1-2). MS-ESI (m/z): 483 [M+1]$^{30}$.

(S)-2-(((tert-butyldimethylsilyl)oxy)methyl)-8-nitro-1,2,3,4-tetrahydroquinoxaline-6-sulfonamide (I-3)

A mixture of (S)-4-((1-amino-3-((tert-butyldimethylsilyl)oxy)propan-2-yl)amino)-3-bromo-5-nitrobenzenesulfonamide (I-2) (20 mg, 0.0415 mmol), Me$_4$phen (10 mg, 0.0415 mmol), CuI (12 mg, 0.0622 mmol) and Cs$_2$CO$_3$ (20 mg, 0.0622 mmol) in dioxane (1.5 mL) was stirred at 100° C. for 5 h under N$_2$ atmosphere. The mixture was cooled to RT and concentrate. The residue was purified by column chromatography on silica gel eluting with EtOAc/PE (1:3~1:1) to give the title compound (S)-2-(((tert-butyldimethylsilyl)oxy)methyl)-8-nitro-1,2,3,4-tetrahydroquinoxaline-6-sulfonamide (I-3). MS-ESI (m/z): 403 [M+1]$^+$.

(S)-2-(hydroxymethyl)-8-nitro-1,2,3,4-tetrahydroquinoxahne-6-sulfonamide (I-4)

The title compound (S)-2-(hydroxymethyl)-8-nitro-1,2,3,4-tetrahydroquinoxaline-6-sulfonamide (I-4) was prepared according to the synthetic method of (S)-3-(hydroxymethyl)-5-nitro-3,4-dihydro-2H-benzo[b][1,4]oxazine-7-sulfonamide (C-6) by replacing (R)-3-(((tert-butyldimethylsilyl)oxy)methyl)-5-nitro-3,4-dihydro-2H-benzo[b][1,4]oxazine-7-sulfonamide (C-5) with (S)-2-(((tert-butyldimethylsilyl)oxy)methyl)-8-nitro-1,2,3,4-tetrahydroquinoxaline-6-sulfonamide (I-3). MS-ESI (m/z): 289 [M+1]$^+$.

(S)-(8-nitro-6-sulfamoyl-1,2,3,4-tetrahydroquinoxahn-2-yl)methyl methanesulfonate (Intermediate I)

The title compound (S)-(8-nitro-6-sulfamoyl-1,2,3,4-tetrahydroquinoxalin-2-yl)methyl methanesulfonate (Intermediate I) was prepared according to the synthetic method of (R)-(5-nitro-7-sulfamoyl-3,4-dihydro-2H-benzo[b][1,4]oxazin-3-yl)methyl methanesulfonate (Intermediate C) by replacing (S)-3-(hydroxymethyl)-5-nitro-3,4-dihydro-2H-benzo[b][1,4]oxazine-7-sulfonamide (C-6) with (S)-2-(hydroxymethyl)-8-nitro-1,2,3,4-tetrahydroquinoxaline-6-sulfonamide (I-4). MS-ESI (m/z): 367 [M+1]$^+$.

216

Example 1-1

(S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((2-(morphohnomethyl)-7-nitroindolin-5-yl)sulfonyl)benzamide (1-1)

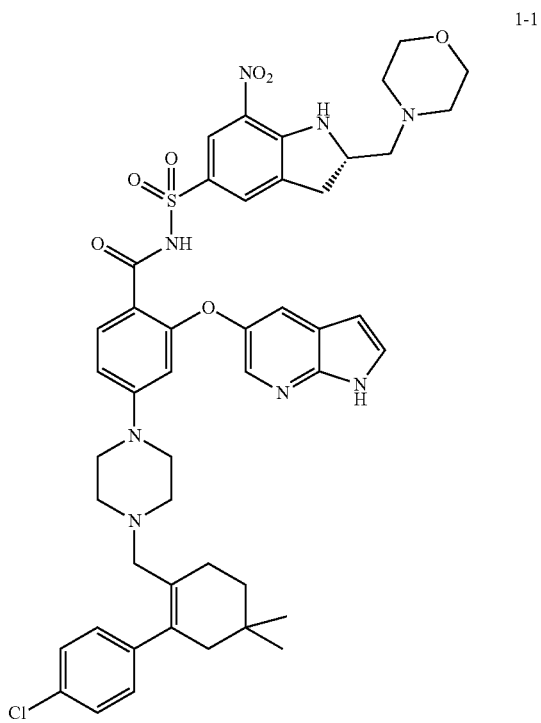 [SMILES: CC1(C)CCC(CN2CCN(c3ccc(C(=O)NS(=O)(=O)c4cc5c(c([N+](=O)[O-])c4)N[C@H](CN4CCOCC4)C5)c(Oc4cnc5[nH]ccc5c4)c3)CC2)=C(c2ccc(Cl)cc2)C1]

1-1

(S)-2-(morpholinomethyl)-7-nitroindoline-5-sulfonamide (1-1a)

A mixture of (S)-2-(iodomethyl)-7-nitroindoline-5-sulfonamide (Intermediate A) (15.3 mg, 0.04 mmol), K$_2$CO$_3$ (6.0 mg, 0.04 mmol) and morpholine (0.1 mL) in CH$_3$CN (1.5 mL) was stirred at 60° C. for 4 h. The mixture was extracted with EtOAc (2×30 mL), the extracts were washed with brine (100 mL), dried with Na$_2$SO$_4$ and concentrate. The residue was purified by preparative TLC eluting with DCM/MeOH (20:1) to give the title compound (S)-2-(morpholinomethyl)-7-nitroindoline-5-sulfonamide (1-1a). MS-ESI (m/z): 343 [M+1]$^+$.

2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)benzoic acid (1-1b)

The title compound 2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)benzoic acid (1-1b) was prepared according to the method described in US 2014/0275540, (A1). MS-ESI (m/z): 571 [M+1]$^+$.

(S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((2-(morpholinomethyl)-7-nitroindolin-5-yl)sulfonyl)benzamide (1-1)

A mixture of 2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)benzoic acid (1-1b) (0.010 g, 0.02 mmol), (S)-2-(morpholinomethyl)-7-nitroindoline-5-sulfonamide (1-1a) (6.7 mg, 0.02 mmol), EDCI (0.011 g, 0.06 mmol), Et$_3$N (6.0 mg, 0.06 mmol) and DMAP (8.0 mg, 0.06 mmol) in DCM (4 mL) was stirred at 30° C. for 20 h. The mixture was extracted by DCM (25 mL), washed with brine (15 mL), dried with Na$_2$SO$_4$ and concentrated. The residue was purified by preparative TLC eluting with DCM/MeOH (15:1) to give the title compound (S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((2-(morpholinomethyl)-7-nitroindolin-5-yl)sulfonyl)benzamide (1-1). MS-ESI (m/z): 895 [M+1]$^+$.

Example 1-2

(S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((2-(2-morpholinoethyl)-7-nitroindolin-5-yl)sulfonyl)benzamide (1-2)

1-2

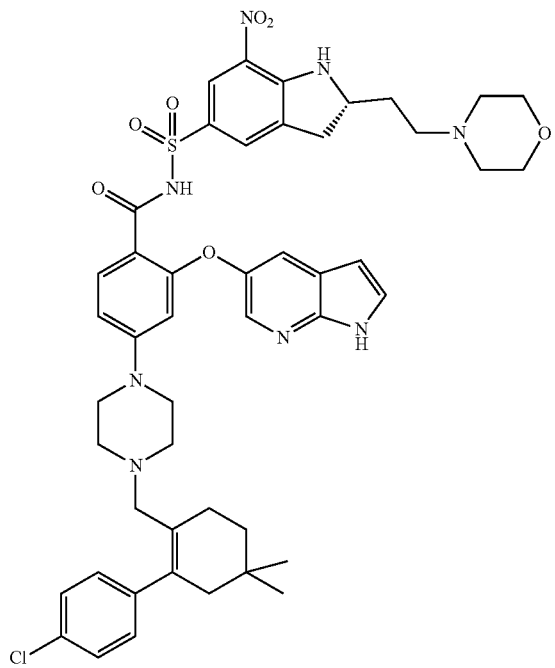

(S)-2-(cyanomethyl)-7-nitroindoline-5-sulfonamide (1-2a)

A mixture of (S)-2-(iodomethyl)-7-nitroindoline-5-sulfonamide (Intermediate A) (1.04 g, 2.72 mmol) and NaCN (160 mg, 3.26 mmol) in DMF (12 mL) was stirred at 60° C. for 3 h. The mixture was extracted by EtOAc, washed with brine, dried with Na$_2$SO$_4$, and concentrated. The residue was purified by column chromatography on silica gel eluting with DCM/MeOH (60:1~15:1) to give title compound (S)-2-(cyanomethyl)-7-nitroindoline-5-sulfonamide (1-2a). MS-ESI (m/z): 283 [M+1]$^+$.

(S)-2-(7-nitro-5-sulfamoylindolin-2-yl)acetic acid (1-2b)

A mixture of (S)-2-(cyanomethyl)-7-nitroindoline-5-sulfonamide (1-2a) (265 mg, 0.94 mmol) in Con.HCl (5 mL) was stirred at 100° C. for 2.5 h. The reaction mixture was evaporated to give the crude product of (S)-2-(7-nitro-5-sulfamoylindolin-2-yl)acetic acid (1-2b), which was used for next step directly. MS-ESI (m/z): 302 [M+1]$^{30}$.

(S)-2-(2-morpholino-2-oxoethyl)-7-nitroindoline-5-sulfonamide (1-2c)

A mixture of (S)-2-(7-nitro-5-sulfamoylindolin-2-yl)acetic acid (1-2b) (52 mg, 0.173 mmol), EDCI (66 mg, 0.35 mmol), HOBT (47 mg, 0.35 mmol), Et$_3$N (48 ml, 0.35 mmol) and morpholine (50 ml, 0.35 mmol) in DMF (1.5 mL) was stirred at 30° C. overnight, and then more EDCI (40 mg, 0.21 mmol) and HOBT (25 mg, 0.19 mmol) was added. The resulted mixture was stirred at 30° C. for 6 h. The mixture was extracted by EtOAc, washed with brine, dried with Na$_2$SO$_4$, and concentrated. The residue was purified by preparative TLC (DCM/MeOH=15:1) to give title compound (S)-2-(2-morpholino-2-oxoethyl)-7-nitroindoline-5-sulfonamide (1-2c). MS-ESI (m/z): 371 [M+1]$^+$.

(S)-2-(2-morpholinoethyl)-7-nitroindoline-5-sulfonamide (1-2d)

To a solution of (S)-2-(2-morpholino-2-oxoethyl)-7-nitroindoline-5-sulfonamide (1-2c) (18.0 mg, 0.048 mmol) in THF (1 ml) was added BH$_3$ (150 ml, 0.144 mmol) in THF at RT The mixture was stirred at RT overnight, and then, a solution of MeOH (0.5 ml) and Con.HCl (0.1 mL) was added. It was stirred at 80° C. for 3 h. The mixture was cooled to RT and adjusted with 4 N Na$_2$CO$_3$ to pH=10. The mixture was extracted with EtOAc. The extracts were washed with brine, dried with Na$_2$SO$_4$ and concentrated. The residue was purified by preparative TLC (DCM/MeOH=15:1) to give title compound (S)-2-(2-morpholinoethyl)-7-nitroindoline-5-sulfonamide (1-2d). MS-ESI (m/z): 357 [M+1]$^+$.

(S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((2-(2-morphohnoethyl)-7-nitroindolin-5-yl)sulfonyl)benzamide (1-2)

The title compound (S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((2-(2-morpholinoethyl)-7-nitroindolin-5-yl)sulfonyl)benzamide (1-2) was prepared according to the synthetic method of 1-1 by replacing (S)-2-(morpholinomethyl)-7-nitroindoline-5-sulfonamide (1-1a) with (S)-2-(2-morpholinoethyl)-7-nitroindoline-5-sulfonamide (1-2d). MS-ESI (m/z): 909 [M+1]$^+$.

Following essentially the same procedures described for Examples 1-1~1-2 or using similar synthetic methods or strategies, Examples 1-3~1-27 listed in Table 1 were prepared. The structures and names of Examples 1-3~1-27 are given in Table 1.

TABLE 1

| EXAMPLE | STRUCTURE | NAME | DATA |
| --- | --- | --- | --- |
| 1-3 | 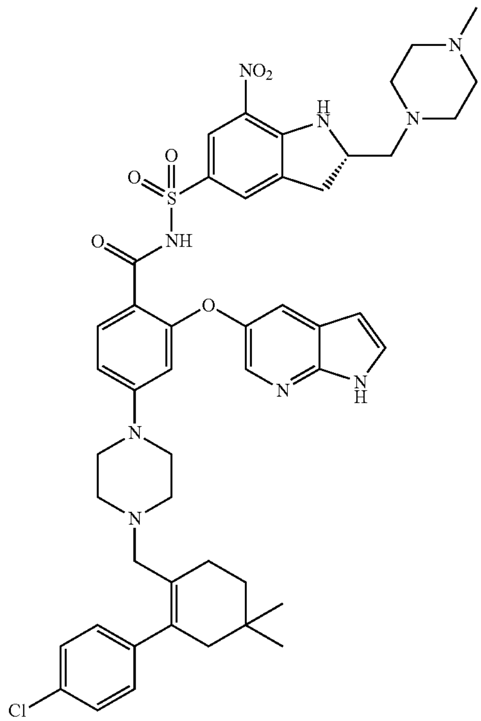 [SMILES: CN1CCN(C[C@@H]2Cc3cc(S(=O)(=O)NC(=O)c4ccc(N5CCN(CC6=C(c7ccc(Cl)cc7)CC(C)(C)CC6)CC5)cc4Oc4cnc5[nH]ccc5c4)cc([N+](=O)[O-])c3N2)CC1] | (S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((2-((4-methylpiperazin-n-2-yl)methyl)-7-nitroindolin-5-yl)sulfonyl)benzamide | MS-ESI (m/z): 908 [M + 1]+ |
| 1-4 | 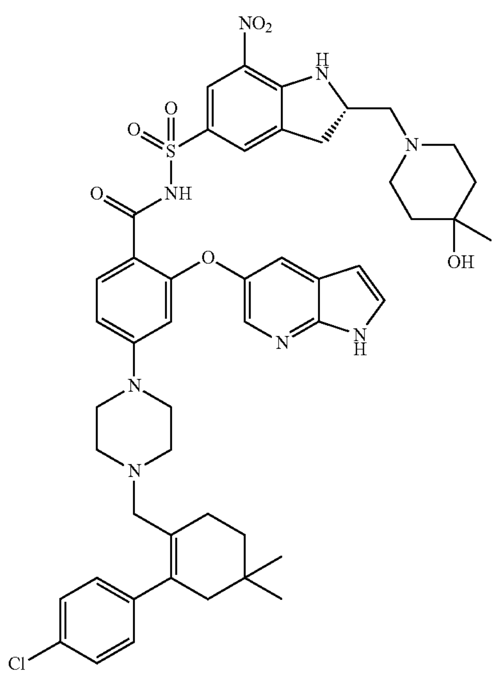 [SMILES: CC1(C)CCC(CN2CCN(c3ccc(C(=O)NS(=O)(=O)c4cc5c(c([N+](=O)[O-])c4)N[C@H](CN4CCC(C)(O)CC4)C5)c(Oc4cnc5[nH]ccc5c4)c3)CC2)=C(c2ccc(Cl)cc2)C1] | (S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((2-((4-hydroxy-4-methylpiperidin-1-yl)methyl)-7-nitroindolin-5-yl)sulfonyl)benzamide | MS-ESI (m/z): 923 [M + 1]+ |

TABLE 1-continued

| EXAMPLE | STRUCTURE | NAME | DATA |
|---|---|---|---|
| 1-5 | 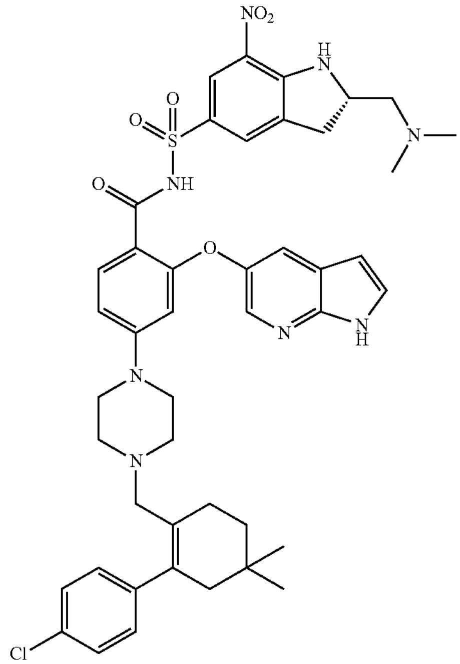 [SMILES: CN(C)C[C@@H]1Cc2cc(S(=O)(=O)NC(=O)c3ccc(N4CCN(CC5=C(c6ccc(Cl)cc6)CC(C)(C)CC5)CC4)cc3Oc3cnc4[nH]ccc4c3)cc([N+](=O)[O-])c2N1] | (S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((2-((dimethylamino)methyl)-7-nitroindolin-5-yl)sulfonyl)benzamide | MS-ESI (m/z): 853 [M + 1]+ |
| 1-6 | 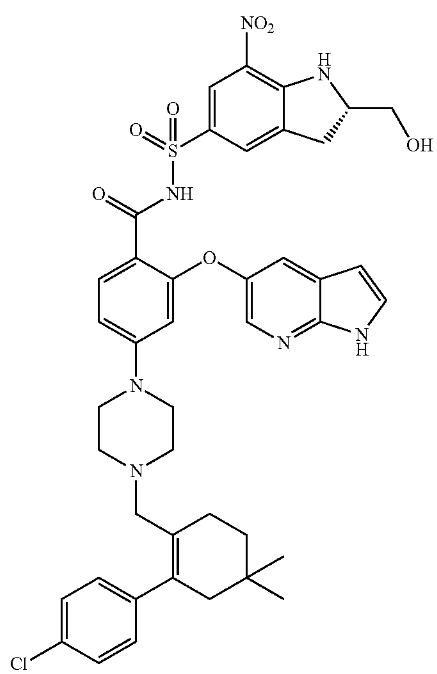 [SMILES: CC1(C)CCC(CN2CCN(c3ccc(C(=O)NS(=O)(=O)c4cc5c(c([N+](=O)[O-])c4)N[C@H](CO)C5)c(Oc4cnc5[nH]ccc5c4)c3)CC2)=C(c2ccc(Cl)cc2)C1] | (S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((2-(hydroxymethyl)-7-nitroindolin-5-yl)sulfonyl)benzamide | MS-ESI (m/z): 826 [M + 1]+ |

TABLE 1-continued

| EXAMPLE | STRUCTURE | NAME | DATA |
| --- | --- | --- | --- |
| 1-7 | 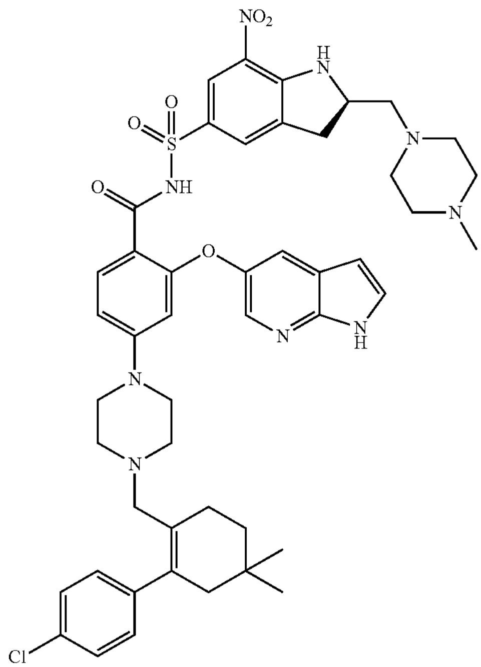 [SMILES: CN1CCN(C[C@H]2Cc3cc(S(=O)(=O)NC(=O)c4ccc(N5CCN(CC6=C(c7ccc(Cl)cc7)CC(C)(C)CC6)CC5)cc4Oc4cnc5[nH]ccc5c4)cc([N+](=O)[O-])c3N2)CC1] | (R)-2-((1H-pyrrolo[2,3-b]pyridin-5-yl)oxy)-4-(4-((4'-chloro-5,5-dimethyl-3,4,5,6-tetra-hydro-[1,1'-biphenyl]-2-yl)methyl)piperazin-1-yl)-N-((2-(((4-methylpiperazin-1-yl)methyl)-7-nitroindolin-5-yl)sulfonyl)benzamide | MS-ESI (m/z): 908 [M + 1]⁺ |
| 1-8 | 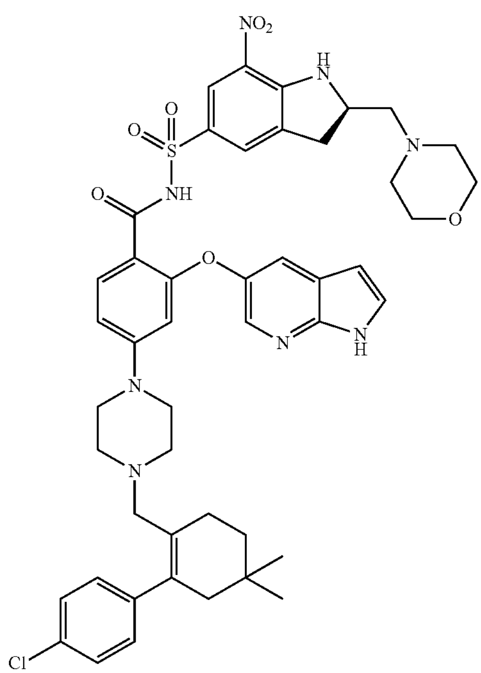 [SMILES: CC1(C)CCC(CN2CCN(c3ccc(C(=O)NS(=O)(=O)c4cc5c(c([N+](=O)[O-])c4)N[C@@H](CN4CCOCC4)C5)c(Oc4cnc5[nH]ccc5c4)c3)CC2)=C(c2ccc(Cl)cc2)C1] | (R)-2-((1H-pyrrolo[2,3-b]pyridin-5-yl)oxy)-4-(4-((4'-chloro-5,5-dimethyl-3,4,5,6-tetra-hydro-[1,1'-biphenyl]-2-yl)methyl)piperazin-1-yl)-N-((2-(morpholinomethyl)-7-nitroindolin-5-yl)sulfonyl)benzamide | MS-ESI (m/z): 895 [M + 1]⁺ |

TABLE 1-continued

| EXAMPLE | STRUCTURE | NAME | DATA |
|---|---|---|---|
| 1-9 | 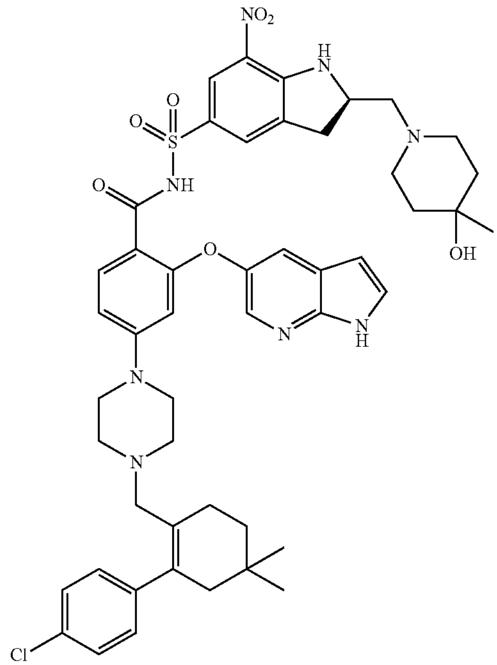 [SMILES: CC1(C)CCC(CN2CCN(c3ccc(C(=O)NS(=O)(=O)c4cc5c(c([N+](=O)[O-])c4)N[C@@H](CN4CCC(C)(O)CC4)C5)c(Oc4cnc5[nH]ccc5c4)c3)CC2)=C(c2ccc(Cl)cc2)C1] | (R)-2-((1H-pyrrolo[2,3-b]pyridin-5-yl)oxy)-4-(4-((4'-chloro-5,5-dimethyl-3,4,5,6-tetra-hydro-[1,1'-biphenyl]-2-yl)methyl)piperazin-1-yl)-N-((2-((4-hydroxy-4-methylpiperidin-1-yl)methyl)-7-nitroindolin-5-yl)sulfonyl)benzamide | MS-ESI (m/z): 923 [M + 1]+ |
| 1-10 | 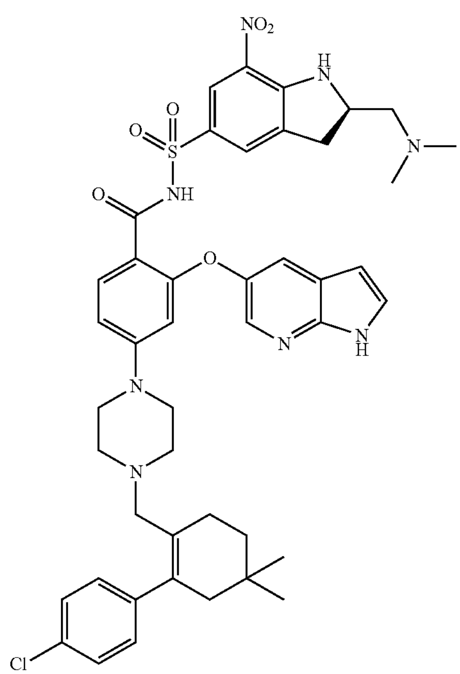 [SMILES: CN(C)C[C@H]1Cc2cc(S(=O)(=O)NC(=O)c3ccc(N4CCN(CC5=C(c6ccc(Cl)cc6)CC(C)(C)CC5)CC4)cc3Oc3cnc4[nH]ccc4c3)cc([N+](=O)[O-])c2N1] | (R)-2-((1H-pyrrolo[2,3-b]pyridin-5-yl)oxy)-4-(4-((4'-chloro-5,5-dimethyl-3,4,5,6-tetra-hydro-[1,1'-biphenyl]-2-yl)methyl)piperazin-1-yl)-N-((2-((dimethylamino)methyl)-7-nitroindolin-5-yl)sulfonyl)benzamide | MS-ESI (m/z): 853 [M + 1]+ |

TABLE 1-continued

| EXAMPLE | STRUCTURE | NAME | DATA |
|---|---|---|---|
| 1-11 | 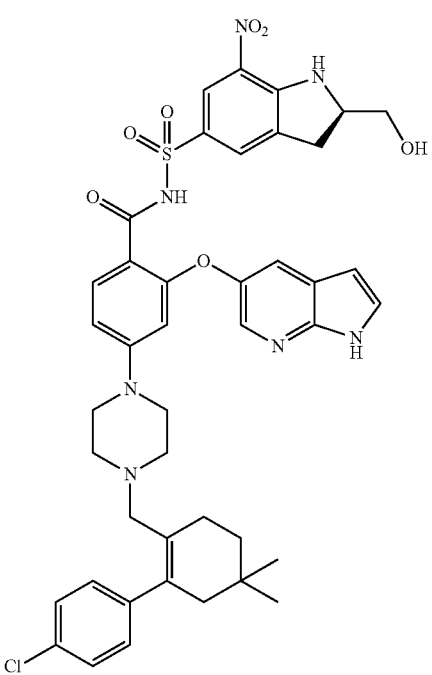 [SMILES: CC1(C)CCC(CN2CCN(c3ccc(C(=O)NS(=O)(=O)c4cc5c(c([N+](=O)[O-])c4)N[C@@H](CO)C5)c(Oc4cnc5[nH]ccc5c4)c3)CC2)=C(c2ccc(Cl)cc2)C1] | (R)-2-((1H-pyrrolo[2,3-b]pyridin-5-yl)oxy)-4-(4-((4'-chloro-5,5-dimethyl-3,4,5,6-tetra-hydro-[1,1'-biphenyl]-2-yl)methyl)piperazin-1-yl)-N-((2-(hydroxymethyl)-7-nitroindolin-5-yl)sulfonyl)benzamide | MS-ESI (m/z): 826 [M + 1]+ |
| 1-12 | 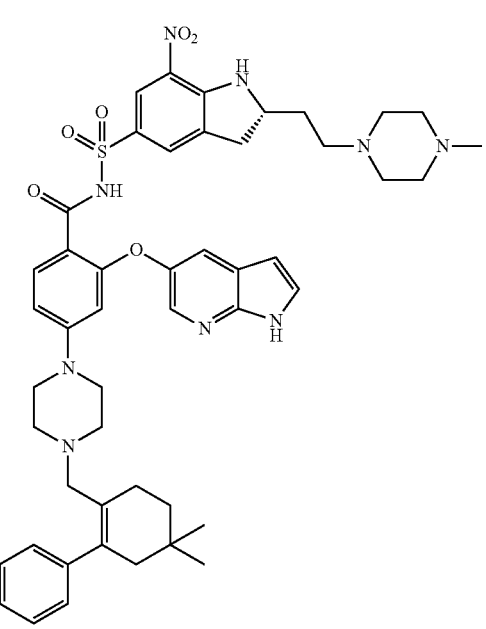 | (S)-2-((1H-pyrrolo[2,3-b]pyridin-5-yl)oxy)-4-(4-((4'-chloro-5,5-dimethyl-3,4,5,6-tetra-hydro-[1,1'-biphenyl]-2-yl)methyl)piperazin-1-yl)-N-((2-(2-(4-methylpiperazin-1-yl)ethyl)-7-nitroindolin-5-yl)sulfonyl)benzamide | MS-ESI (m/z): 922 [M + 1]+ |

| EXAMPLE | STRUCTURE | NAME | DATA |
|---|---|---|---|
| 1-13 | 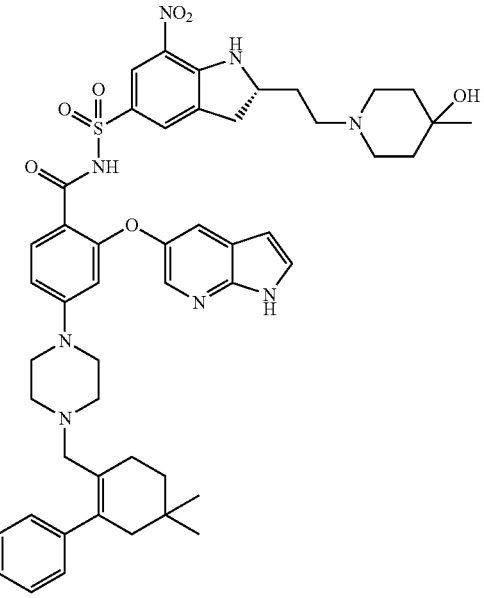 | (S)-2-((1H-pyrrolo[2,3-b]pyridin-5-yl)oxy)-4-(4-((4'-chloro-5,5-dimethyl-3,4,5,6-tetra-hydro-[1,1'-biphenyl]-2-yl)methyl)piperazin-1-yl)-N-((2-(2-(4-hydroxy-4-methylpiperidin-1-yl)ethyl)-7-nitroindolin-5-yl)sulfonyl)benzamide | MS-ESI (m/z): 937 [M + 1]+ |
| 1-14 | 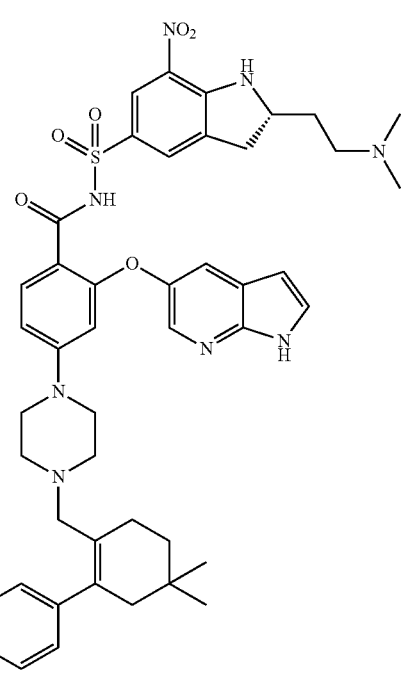 | (S)-2-((1H-pyrrolo[2,3-b]pyridin-5-yl)oxy)-4-(4-((4'-chloro-5,5-dimethyl-3,4,5,6-tetra-hydro-[1,1'-biphenyl]-2-yl)methyl)piperazin-1-yl)-N-((2-(2-(dimethylamino)ethyl)-7-nitroindolin-5-yl)sulfonyl)benzamide | MS-ESI (m/z): 867 [M + 1]+ |

TABLE 1-continued

| EXAMPLE | STRUCTURE | NAME | DATA |
|---|---|---|---|
| 1-15 | 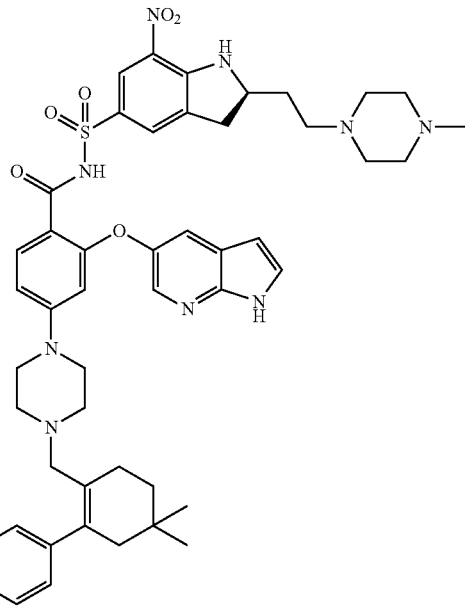 | (R)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((2-(2-(4-methylpiperazin-1-yl)ethyl)-7-nitroindolin-5-yl)sulfonyl)benzamide | MS-ESI (m/z): 922 [M + 1]$^+$ |
| 1-16 | 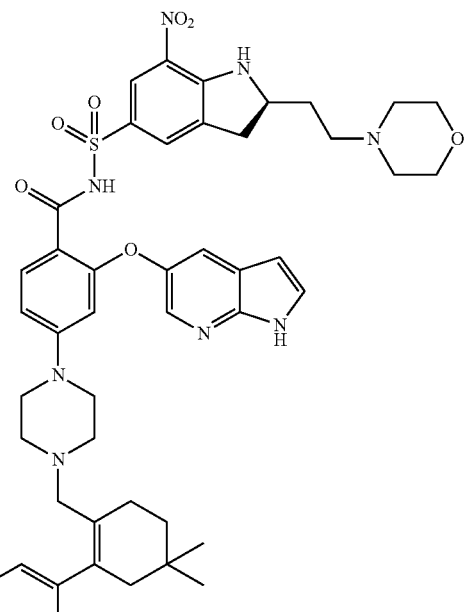 | (R)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((2-(2-morpholinoethyl)-7-nitroindolin-5-yl)sulfonyl)benzamide | MS-ESI (m/z): 909 [M + 1]$^+$ |

TABLE 1-continued

| EXAMPLE | STRUCTURE | NAME | DATA |
|---|---|---|---|
| 1-17 | 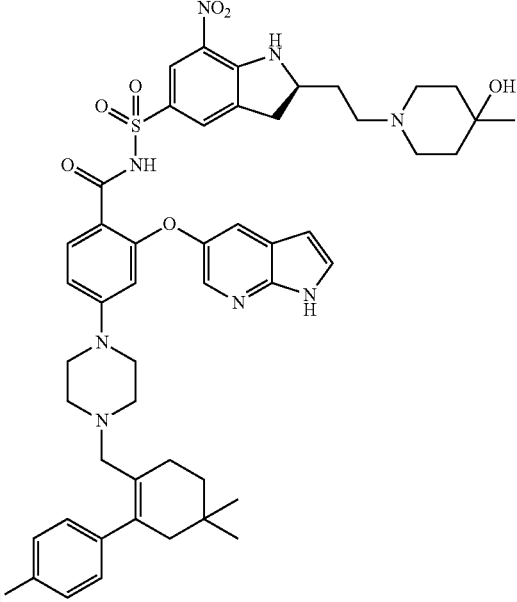 | (R)-2-((1H-pyrrolo[2,3-b]pyridin-5-yl)oxy)-4-(4-((4'-chloro-5,5-dimethyl-3,4,5,6-tetra-hydro-[1,1'-biphenyl]-2-yl)methyl)piperazin-1-yl)-N-((2-(2-(4-hydroxy-4-methylpiperidin-1-yl)ethyl)-7-nitroindolin-5-yl)sulfonyl)benzamide | MS-ESI (m/z): 937 [M + 1]$^+$ |
| 1-18 | 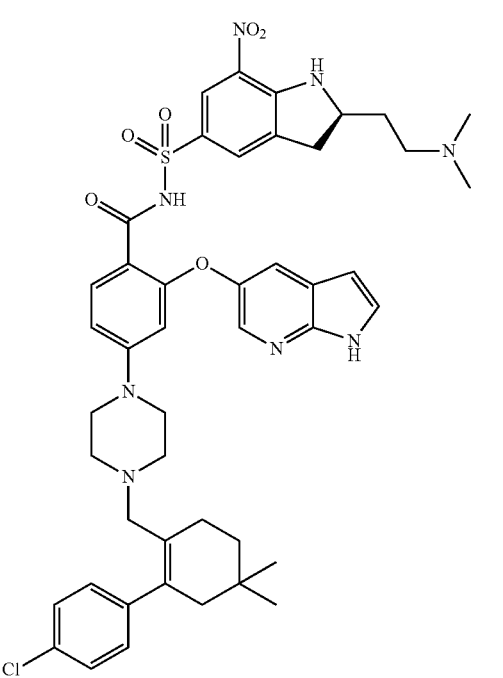 [SMILES: CN(C)CC[C@H]1Cc2cc(S(=O)(=O)NC(=O)c3ccc(N4CCN(CC5=C(c6ccc(Cl)cc6)CC(C)(C)CC5)CC4)cc3Oc3cnc4[nH]ccc4c3)cc([N+](=O)[O-])c2N1] | (R)-2-((1H-pyrrolo[2,3-b]pyridin-5-yl)oxy)-4-(4-((4'-chloro-5,5-dimethyl-3,4,5,6-tetra-hydro-[1,1'-biphenyl]-2-yl)methyl)piperazin-1-yl)-N-((2-(2-(dimethylamino)ethyl)-7-nitroindolin-5-yl)sulfonyl)benzamide | MS-ESI (m/z): 867 [M + 1]$^+$ |

TABLE 1-continued

| EXAMPLE | STRUCTURE | NAME | DATA |
|---|---|---|---|
| 1-19 | 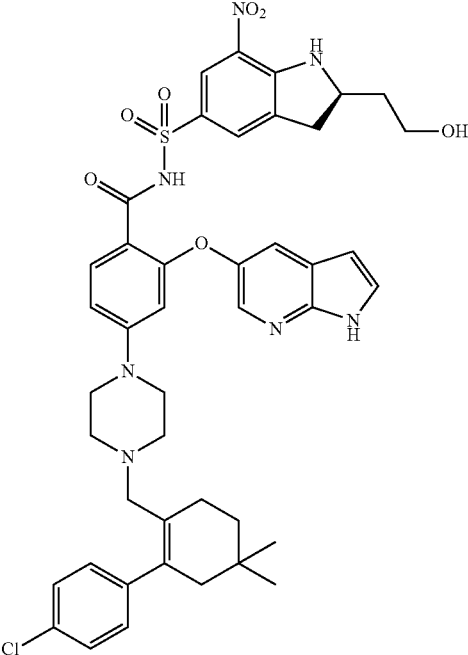 [SMILES: CC1(C)CCC(CN2CCN(c3ccc(C(=O)NS(=O)(=O)c4cc5c(c([N+](=O)[O-])c4)N[C@@H](CCO)C5)c(Oc4cnc5[nH]ccc5c4)c3)CC2)=C(c2ccc(Cl)cc2)C1] | (R)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((2-(2-hydroxyethyl)-7-nitroindolin-5-yl)sulfonyl)benzamide | MS-ESI (m/z): 840 [M + 1]$^+$ |
| 1-20 | 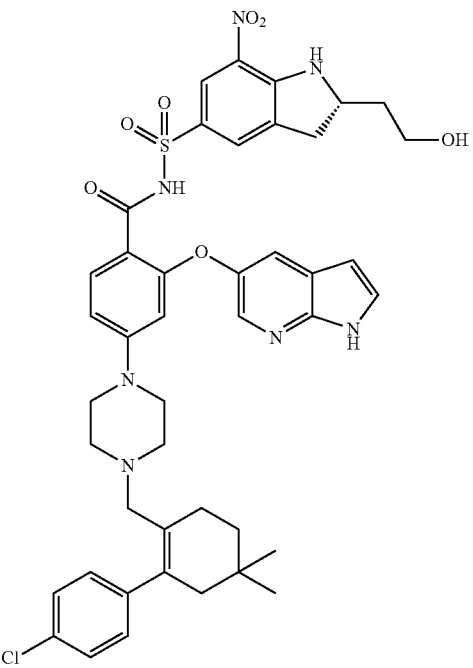 [SMILES: CC1(C)CCC(CN2CCN(c3ccc(C(=O)NS(=O)(=O)c4cc5c(c([N+](=O)[O-])c4)N[C@H](CCO)C5)c(Oc4cnc5[nH]ccc5c4)c3)CC2)=C(c2ccc(Cl)cc2)C1] | (S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((2-(2-hydroxyethyl)-7-nitroindolin-5-yl)sulfonyl)benzamide | MS-ESI (m/z): 840 [M + 1]$^+$ |

TABLE 1-continued

| EXAMPLE | STRUCTURE | NAME | DATA |
|---|---|---|---|
| 1-21 | 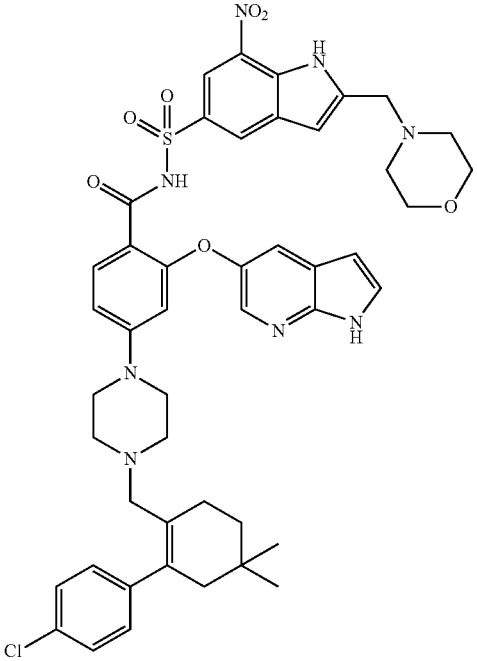 [SMILES: CC1(C)CCC(CN2CCN(c3ccc(C(=O)NS(=O)(=O)c4cc([N+](=O)[O-])c5[nH]c(CN6CCOCC6)cc5c4)c(Oc4cnc5[nH]ccc5c4)c3)CC2)=C(c2ccc(Cl)cc2)C1] | 2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((2-(morpholinomethyl)-7-nitro-1H-indol-5-yl)sulfonyl)benzamide | MS-ESI (m/z): 893 [M + 1]$^+$ |
| 1-22 | 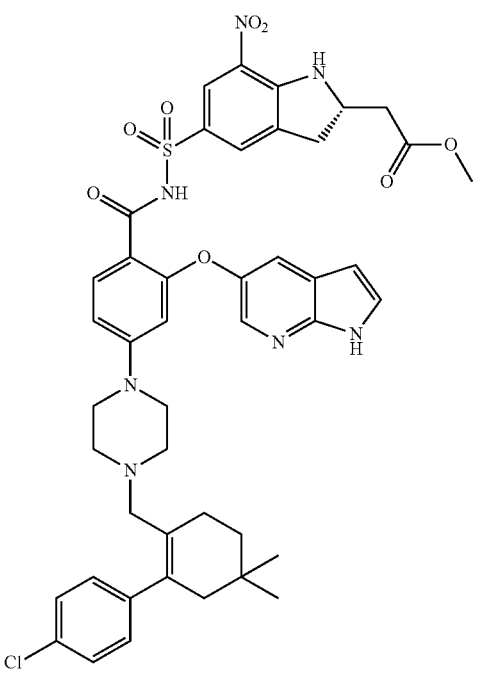 [SMILES: COC(=O)C[C@@H]1Cc2cc(S(=O)(=O)NC(=O)c3ccc(N4CCN(CC5=C(c6ccc(Cl)cc6)CC(C)(C)CC5)CC4)cc3Oc3cnc4[nH]ccc4c3)cc([N+](=O)[O-])c2N1] | methyl (S)-2-(5-(N-(2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)benzoyl)sulfamoyl)-7-nitroindolin-2-yl)acetate | MS-ESI (m/z): 868 [M + 1]$^+$ |

TABLE 1-continued

| EXAMPLE | STRUCTURE | NAME | DATA |
|---|---|---|---|
| 1-23 | 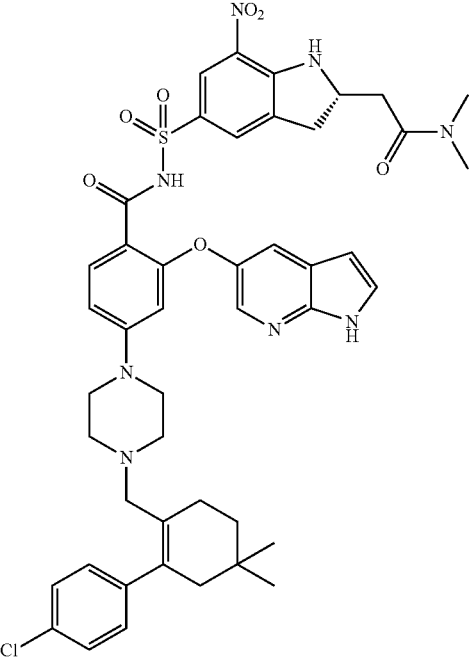 [SMILES: CN(C)C(=O)C[C@@H]1Cc2cc(S(=O)(=O)NC(=O)c3ccc(N4CCN(CC5=C(c6ccc(Cl)cc6)CC(C)(C)CC5)CC4)cc3Oc3cnc4[nH]ccc4c3)cc([N+](=O)[O-])c2N1] | (S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((2-(2-(dimethylamino)-2-oxoethyl)-7-nitroindolin-5-yl)sulfonyl)benzamide | MS-ESI (m/z): 881 [M + 1]$^+$ |
| 1-24 | 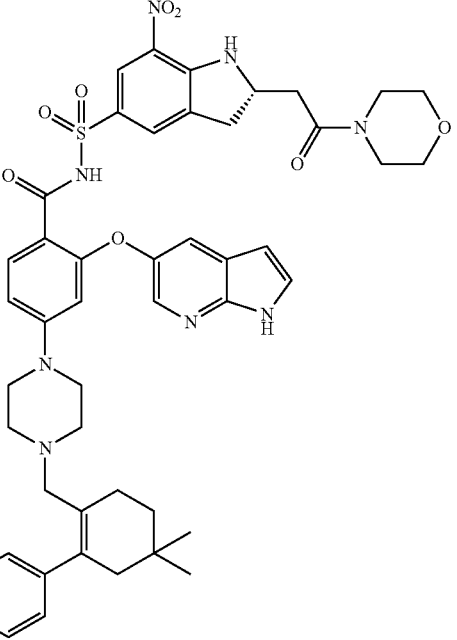 | (S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((2-(2-morpholino-2-oxoethyl)-7-nitroindolin-5-yl)sulfonyl)benzamide | MS-ESI (m/z): 923 [M + 1]$^+$ |

TABLE 1-continued

| EXAMPLE | STRUCTURE | NAME | DATA |
|---|---|---|---|
| 1-25 | 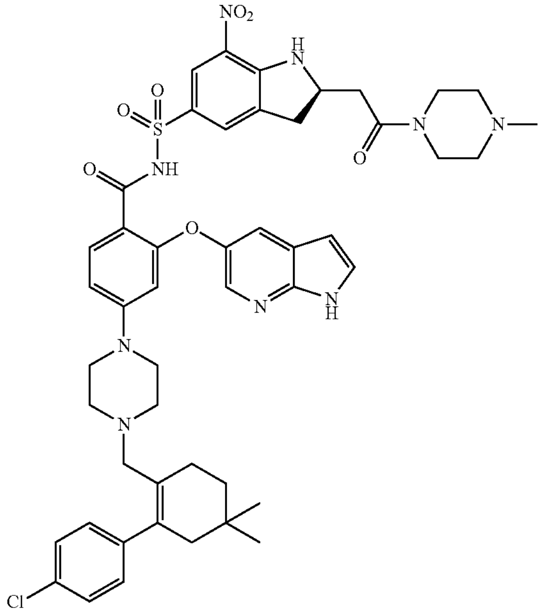 [SMILES: CN1CCN(C(=O)C[C@H]2Cc3cc(S(=O)(=O)NC(=O)c4ccc(N5CCN(CC6=C(c7ccc(Cl)cc7)CC(C)(C)CC6)CC5)cc4Oc4cnc5[nH]ccc5c4)cc([N+](=O)[O-])c3N2)CC1] | (R)-2-((1H-pyrrolo[2,3-b]pyridin-5-yl)oxy)-4-(4-((4'-chloro-5,5-dimethyl-3,4,5,6-tetra-hydro-[1,1'-biphenyl]-2-yl)methyl)piperazin-1-yl)-N-((2-(2-(4-methylpiperazin-1-yl)-2-oxoethyl)-7-nitroindolin-5-yl)sulfonyl)benzamide | MS-ESI (m/z): 936 [M + 1]+ |
| 1-26 | 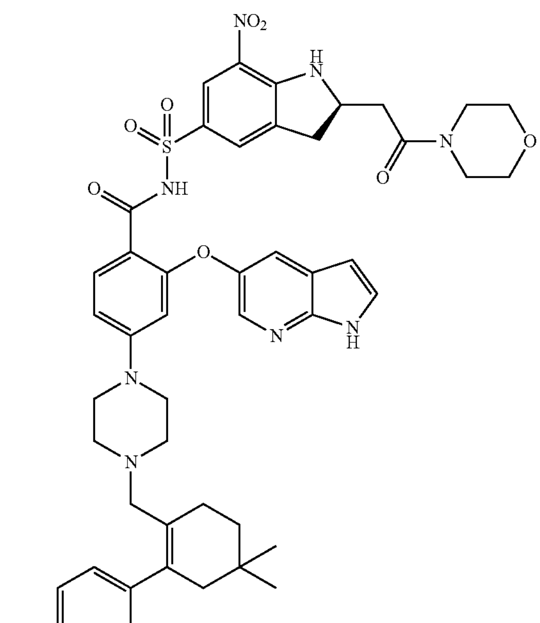 | (R)-2-((1H-pyrrolo[2,3-b]pyridin-5-yl)oxy)-4-(4-((4'-chloro-5,5-dimethyl-3,4,5,6-tetra-hydro-[1,1'-biphenyl]-2-yl)methyl)piperazin-1-yl)-N-((2-(2-morpholino-2-oxoethyl)-7-nitroindolin-5-yl)sulfonyl)benzamide | MS-ESI (m/z): 923 [M + 1]+ |

TABLE 1-continued
| EXAMPLE | STRUCTURE | NAME | DATA |
|---|---|---|---|
| 1-27 | 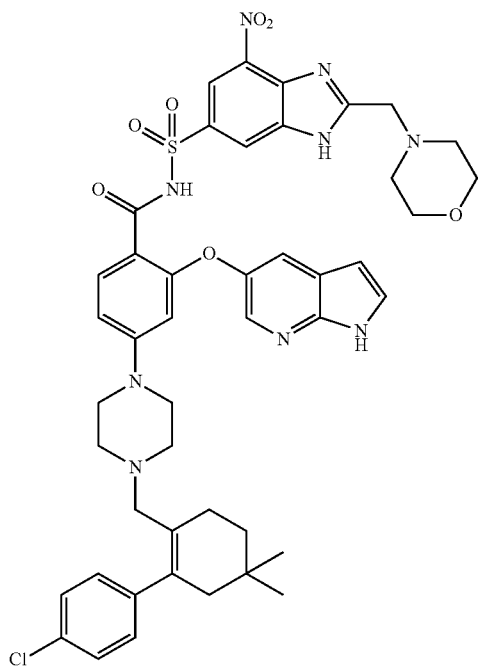 [SMILES: CC1(C)CCC(CN2CCN(c3ccc(C(=O)NS(=O)(=O)c4cc([N+](=O)[O-])c5nc(CN6CCOCC6)[nH]c5c4)c(Oc4cnc5[nH]ccc5c4)c3)CC2)=C(c2ccc(Cl)cc2)C1] | 2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((2-(morpholinomethyl)-4-nitro-1H-benzo[d]imidazol-6-yl)sulfonyl)benzamide | MS-ESI (m/z): 894 [M + 1]⁺ |

Example 2-1

(S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-((4-methylpiperazin-1-yl)methyl)-5-nitro-3,4-dihydro-2H-benzo[b][1,4]oxazin-7-yl)sulfonyl)benzamide (2-1)

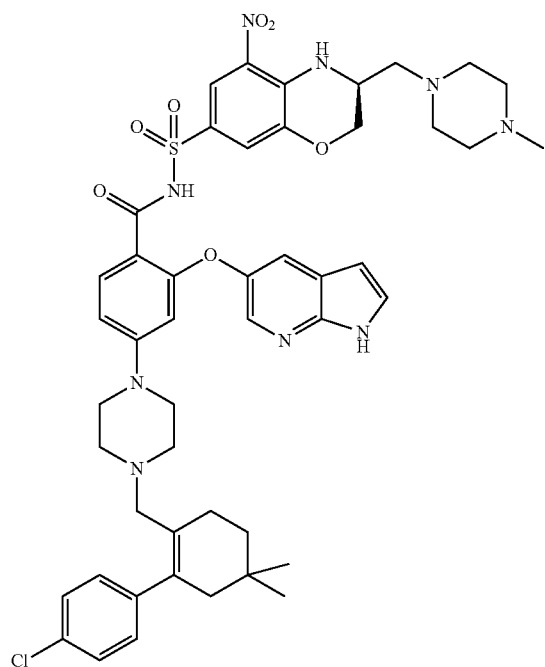

2-1

(S)-3-((4-methylpiperazin-1-yl)methyl)-5-nitro-3,4-dihydro-2H-benzo[b][1,4]oxazine-7-sulfonamide (2-1a)

A mixture of (R)-(5-nitro-7-sulfamoyl-3,4-dihydro-2H-benzo[b][1,4]oxazin-3-yl)methyl methanesulfonate (Intermediate C) (11.0 mg, 0.03 mmol), 1-methylpiperazine (12.0 mg, 0.12 mmol) and $K_2CO_3$ (20.7 mg, 0.15 mmol) in $CH_3CN$ (4 mL) was stirred at 80° C. for 1.5 h. The reaction was quenched by water and extracted with EtOAc (2×30 mL). The extracts were washed with brine (30 mL), dried with $Na_2SO_4$ and concentrated. The residue was purified by flash column chromatography on silica gel eluting with DCM/MeOH (10:1) to give the title compound (S)-3-((4-methylpiperazin-1-yl)methyl)-5-nitro-3,4-dihydro-2H-benzo[b][1,4]oxazine-7-sulfonamide (2-1a). MS-ESI (m/z): 372 [M+1]$^+$.

(S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-((4-methylpiperazin-1-yl)methyl)-5-nitro-3,4-dihydro-2H-benzo[b][1,4]oxazin-7-yl)sulfonyl)benzamide (2-1)

The title compound (S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-((4-methylpiperazin-1-yl)methyl)-5-nitro-3,4-dihydro-2H-benzo[b][1,4]oxazin-7-yl)sulfonyl)benzamide (2-1) was prepared according to the synthetic method of 1-1 by replacing (S)-2-(morpholinomethyl)-7-nitroindoline-5-sulfonamide (1-1a) with (S)-3-((4-methylpiperazin-1-yl)methyl)-5-nitro-3,4-dihydro-2H-benzo[b][1,4]oxazine-7-sulfonamide (2-1a). MS-ESI (m/z): 924 [M+1]$^+$.

Example 2-2

(R)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-(2-morphohnoethyl)-5-nitro-3,4-dihydro-2H-benzo[b][1,4]oxazin-7-yl)sulfonyl)benzamide (2-2)

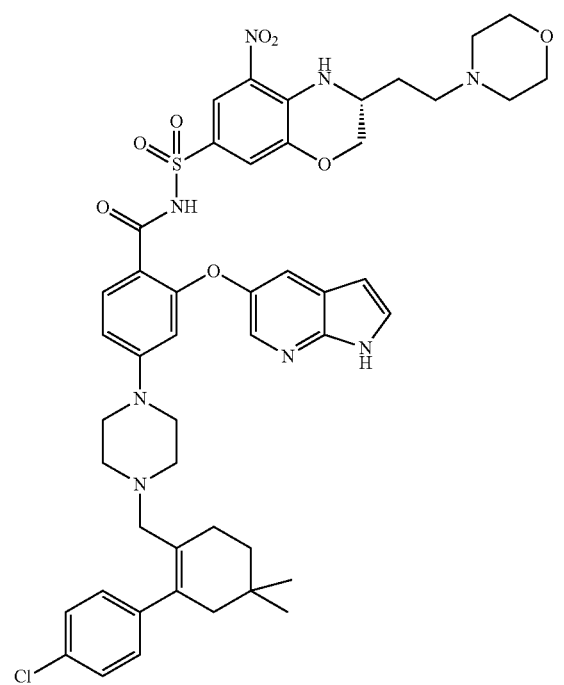

2-2

The title compound (R)-2-((1H-pyrrolo[2,3-b]pyridin-5-yl)oxy)-4-(4-((4'-chloro-5,5-dimethyl-3,4,5,6-tetrahydro-[1, 1'-biphenyl]-2-yl)methyl)piperazin-1-yl)-N-((3-(2-morpholinoethyl)-5-nitro-3,4-dihydro-2H-benzo[b][1,4]oxazin-7-yl)sulfonyl)benzamide (2-2) was prepared according to the synthetic method of 1-1 by replacing (S)-2-(iodomethyl)-7-nitroindoline-5-sulfonamide (Intermediate A) with (R)-3-(2-iodoethyl)-5-nitro-3,4-dihydro-2H-benzo[b][1,4]oxazine-7-sulfonamide (Intermediate E). MS-ESI (m/z): 925 [M+1]$^+$.

Example 2-3

(R)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-(4-hydroxy-4-methylcyclohexyl)-5-nitro-3,4-dihydro-2H-benzo[b][1,4]oxazin-7-yl)sulfonyl)benzamide (2-3-A and 2-3-B)

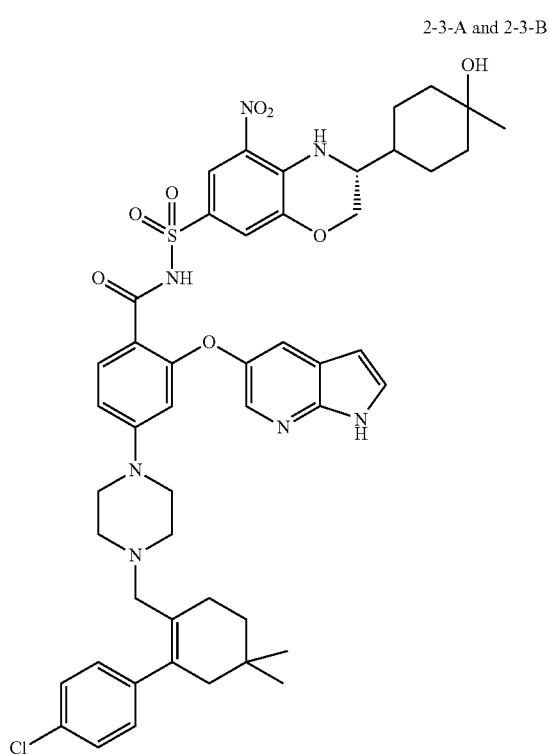 [SMILES: CC1(C)CCC(CN2CCN(c3ccc(C(=O)NS(=O)(=O)c4cc5c(c([N+](=O)[O-])c4)N[C@H](C4CCC(C)(O)CC4)CO5)c(Oc4cnc5[nH]ccc5c4)c3)CC2)=C(c2ccc(Cl)cc2)C1]

2-3-A and 2-3-B methyl(R)-2-amino-2-(4-hydroxyphenyl)acetate (2-3a)

To a solution of (R)-2-amino-2-(4-hydroxyphenyl)acetic acid (1.0 g, 6.0 mmol) in MeOH (10 mL) was added SOCl$_2$ (1.3 ml, 18.0 mmol) dropwise. The mixture was stirred at RT for 0.5 h. The mixture was concentrated to give the crude product of the title compound methyl(R)-2-amino-2-(4-hydroxyphenyl)acetate (2-3a). MS-ESI (m/z): 182 [M+1]$^+$.

methyl(R)-2-((tert-butoxycarbonyl)amino)-2-(4-hydroxyphenyl)acetate (2-3b)

To a suspension of methyl(R)-2-amino-2-(4-hydroxyphenyl)acetate (2-3a) (1.0 g, 5.5 mmol) in 1,4-dioxane (10 mL) was added K$_2$CO$_3$ (1.2 g, 8.8 mmol) and (Boc)$_2$O (1.3 g, 6.0 mmol). The mixture was stirred at RT overnight. The reaction mixture was diluted with water and extracted with EtOAc. The extracts were washed with brine, dried over Na$_2$SO$_4$ and concentrated. The residue was purified by recrystallized with PE/EtOAc to give title compound methyl (R)-2-((tert-butoxycarbonyl)amino)-2-(4-hydroxyphenyl)acetate (2-3b). MS-ESI (m/z): 282 [M+1]$^+$.

tert-butyl (R)-(2-hydroxy-1-(4-hydroxyphenyl)ethyl)carbamate (2-3c)

To a solution of methyl(R)-2-((tert-butoxycarbonyl)amino)-2-(4-hydroxyphenyl)acetate (2-3b) (1.0 g, 3.55 mmol) in THF (40 mL) was added LAH (445 mg, 11.7 mmol) in portions, and the mixture was stirred at 0° C. for 1 h. To the reaction mixture was added Na$_2$SO$_4$.10.H$_2$O at 0° C. The mixture was filtered through Celite, and filtrate was concentrated. The residue was purified by column chromatography on silica gel eluting to give title compound tert-butyl (R)-(2-hydroxy-1-(4-hydroxyphenyl)ethyl)carbamate (2-3c). MS-ESI (m/z): 254 [M+1]$^+$.

tert-butyl(R)-4-(4-hydroxyphenyl)-2,2-dimethyloxazolidine-3-carboxylate (2-3d)

A mixture of tert-butyl (R)-(2-hydroxy-1-(4-hydroxyphenyl)ethyl)carbamate (2-3c) (847 mg, 3.33 mmol), DMP (3.05 g, 29.34 mmol) and BF$_3$.Et$_2$O (40 μl, 0.33 mmol) in Acetone (3 mL) was stirred at RT for 4 h, The reaction was quenched by ice water and the mixture was extracted with EtOAc. The extracts were washed with brine, dried over Na$_2$SO$_4$ and concentrated. The residue was purified by column chromatography on silica gel eluting with PE/EtOAc (6:1) to give title compound tert-butyl(R)-4-(4-hydroxyphenyl)-2,2-dimethyloxazolidine-3-carboxylate (2-3d). MS-ESI (m/z): 294 [M+1]$^+$.

tert-butyl(R)-4-(4-hydroxycyclohexyl)-2,2-dimethyl-oxazolidine-3-carboxylate (2-3e)

A mixture of tert-butyl(R)-4-(4-hydroxyphenyl)-2,2-dimethyloxazolidine-3-carboxylate (2-3d) (760 mg, 2.55 mmol) and PtO$_2$ (100 mg) in IPA (60 mL) and HOAc (4 mL) was stirred at RT under H$_2$ atmosphere for 48 hours. The reaction mixture was filtered through celite and concentrated to give the crude product of title compound tert-butyl(R)-4-(4-hydroxycyclohexyl)-2,2-dimethyloxazolidine-3-carboxylate (2-3e) which was used directly for next step. MS-ESI (m/z): 300 [M+1]$^+$.

tert-butyl(R)-2,2-dimethyl-4-(4-oxocyclohexyl)oxazolidine-3-carboxylate (2-3f)

A mixture of tert-butyl(R)-4-(4-hydroxycyclohexyl)-2,2-dimethyloxazolidine-3-carboxylate (2-3e) (233 mg, 0.773 mmol) and DMP (424 mg, 2.18 mmol) in DCM (10 mL) was stirred at RT for 1.5 h. The reaction mixture was washed with saturated NaHCO$_3$ aqueous solution (30 mL), The organic layer was concentrated. The residue was purified by column chromatography on silica gel eluting to give title compound tert-butyl(R)-2,2-dimethyl-4-(4-oxocyclohexyl)oxazolidine-3-carboxylate (2-3f). MS-ESI (m/z): 298 [M+1]$^+$.

tert-butyl(R)-4-(4-hydroxy-4-methylcyclohexyl)-2,2-dimethyloxazolidine-3-carboxylate (2-3g)

To a solution of tert-butyl(R)-2,2-dimethyl-4-(4-oxocyclohexyl)oxazolidine-3-carboxylate (2-3f) (200 mg, 0.87 mmol) in THF (6 mL) was added MeLi (1.5 mL, 1.6 M) at −78~−40° C. The mixture was stirred at −78~−40° C. for 1 h, The reaction was quenched by saturated NH$_4$Cl aqueous solution and the mixture was extracted with EtOAc. The extracts were washed with brine (30 mL), dried over Na$_2$SO$_4$, and evaporated to give the crude product of tert-butyl(R)-4-(4-hydroxy-4-methylcyclohexyl)-2,2-dimethyloxazolidine-3-carboxylate (2-3g), which was used for next step directly. MS-ESI (m/z): 314 [M+1]$^+$.

(R)-4-(1-amino-2-hydroxyethyl)-1-methylcyclohexan-1-ol trifluoroacetate (2-3 h)

A mixture of tert-butyl(R)-4-(4-hydroxy-4-methylcyclohexyl)-2,2-dimethyloxazolidine-3-carboxylate (2-3g) (200 mg, 0.63 mmol) and TFA (0.5 mL, 5 mmol) in DCM (5 mL) was stirred at RT for 45 min. The reaction mixture was evaporated to give the crude product of (R)-4-(1-amino-2-hydroxyethyl)-1-methylcyclohexan-1-ol trifluoroacetate (2-3 h), which was used for next step directly. MS-ESI (m/z): 174 [M+1]$^+$.

(R)-3-bromo-4-((2-hydroxy-1-(4-hydroxy-4-methylcyclohexyl)ethyl)amino)-5-nitrobenzenesulfonamide (2-3i-A and 2-3i-B)

A mixture of (R)-4-(1-amino-2-hydroxyethyl)-1-methylcyclohexan-1-ol trifluoroacetate (2-3 h) (250 mg, 0.81 mmol), 3-bromo-4-chloro-5-nitrobenzenesulfonamide (C-1) (250 mg, 0.138 mmol) and DIPEA (500.0 mg, 3.815 mmol) in ACN (6 mL) was stirred at 80° C. overnight. The reaction mixture was cooled to RT and concentrated. The residue was purified by preparative TLC upper spot to give title compound (R)-3-bromo-4-((2-hydroxy-1-(4-hydroxy-4-methylcyclohexyl)ethyl)amino)-5-nitrobenzenesulfonamide (2-3i-A). And purified by preparative TLC lower spot to give title compound (R)-3-bromo-4-((2-hydroxy-1-(4-hydroxy-4-methylcyclohexyl)ethyl)amino)-5-nitrobenzenesulfonamide (2-3i-B) MS-ESI (m/z): 452 [M+1]$^+$.

(R)-3-(4-hydroxy-4-methylcyclohexyl)-5-nitro-3,4-dihydro-2H-benzo[b][1,4]-oxazine-7-sulfonamide (2-3j-A)

A mixture of (R)-3-bromo-4-((2-hydroxy-1-(4-hydroxy-4-methylcyclohexyl)-ethyl)amino)-5-nitrobenzenesulfonamide (2-3i-A) (50 mg, 0.11 mmol), Pd$_2$(dba)$_3$ (15 mg, 0.016 mmol), Xantphos (16 mg, 0.028 mmol) and Cs$_2$CO$_3$ (71 mg, 0. 22 mmol) in dioxane (5 mL) was stirred at 100° C. for 1.5 h. The mixture was cooled to RT. The mixture was filtered through Celite, and filtrate was concentrated. The residue was purified by preparative TLC (DCM/MeOH=15:1) to give title compound (R)-3-(4-hydroxy-4-methylcyclohexyl)-5-nitro-3,4-dihydro-2H-benzo[b][1,4]-oxazine-7-sulfonamide (2-3j-A). MS-ESI (m/z): 372 [M+1]$^+$.

(R)-3-(4-hydroxy-4-methylcyclohexyl)-5-nitro-3,4-dihydro-2H-benzo[b][1,4]-oxazine-7-sulfonamide (2-3j-B)

The title compound (R)-3-(4-hydroxy-4-methylcyclohexyl)-5-nitro-3,4-dihydro-2H-benzo[b][1,4]-oxazine-7-sulfonamide (2-3j-B) was prepared according to the synthetic method of 2-3j-A by replacing (R)-3-bromo-4-((2-hydroxy-1-(4-hydroxy-4-methylcyclohexyl)-ethyl)amino)-5-nitrobenzenesulfonamide (2-3i-A) with (R)-3-bromo-4-((2-hydroxy-1-(4-hydroxy-4-methylcyclohexyl)ethyl)amino)-5-nitrobenzenesulfonamide (2-3i-B). MS-ESI (m/z): 372 [M+1]$^+$.

(R)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-(4-hydroxy-4-methylcyclohexyl)-5-nitro-3,4-dihydro-2H-benzo[b][1,4]oxazin-7-yl)sulfonyl)benzamide (2-3-A and 2-3-B)

The title compound (R)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-(4-hydroxy-4-methylcyclohexyl)-5-nitro-3,4-dihydro-2H-benzo[b][1,4]oxazin-7-yl)sulfonyl)benzamide (2-3A and 2-3B) was prepared according to the synthetic method of 1-1 by replacing (S)-2-(morpholinomethyl)-7-nitroindoline-5-sulfonamide (1-1a) with (R)-3-(4-hydroxy-4-methylcyclohexyl)-5-nitro-3,4-dihydro-2H-benzo[b][1,4]-oxazine-7-sulfonamide (2-3j-A) or (R)-3-(4-hydroxy-4-methylcyclohexyl)-5-nitro-3,4-dihydro-2H-benzo[b][1,4]-oxazine-7-sulfonamide (2-3j-B). MS-ESI (m/z): 924 [M+1]$^+$.

Following essentially the same procedures described for Examples 2-1~2-3 or using similar synthetic methods or strategies, Examples 2-4~2-252 listed in Table 2 were prepared. The structures and names of Examples 2-4~2-252 are given in Table 2.

TABLE 2

| EXAMPLE | STRUCTURE | NAME | DATA |
|---|---|---|---|
| 2-4 | 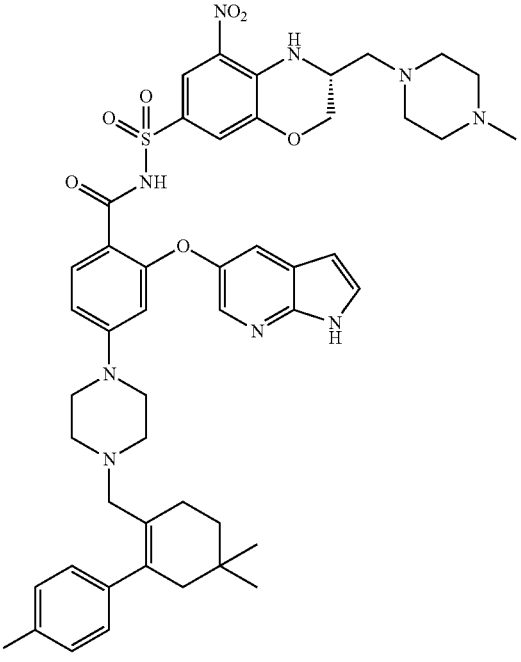 | (R)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-((4-methylpiperazin-1-yl)methyl)-5-nitro-3,4-dihydro-2H-benzo[b][1,4]oxazin-7-yl)sulfonyl)benzamide | MS-ESI (m/z): 924 [M + 1]+ |
| 2-5 | 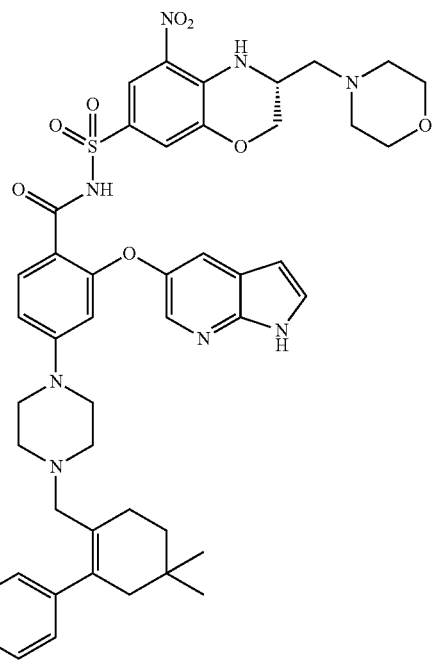 | (R)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-(morpholinomethyl)-5-nitro-3,4-dihydro-2H-benzo[b][1,4]oxazin-7-yl)sulfonyl)benzamide | MS-ESI (m/z): 911 [M + 1]+ |

TABLE 2-continued

| EXAMPLE | STRUCTURE | NAME | DATA |
|---|---|---|---|
| 2-6 | 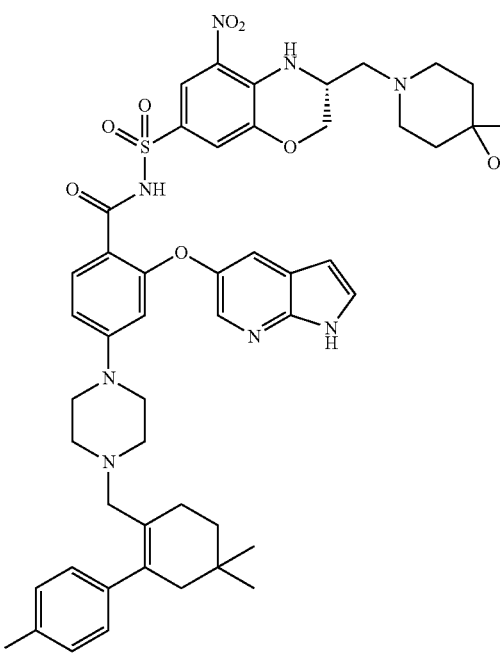 | (R)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-((4-hydroxy-4-methylpiperidin-1-yl)methyl)-5-nitro-3,4-dihydro-2H-benzo[b][1,4]oxazin-7-yl)sulfonyl)benzamide | MS-ESI (m/z): 939 [M + 1]$^+$ |
| 2-7 | 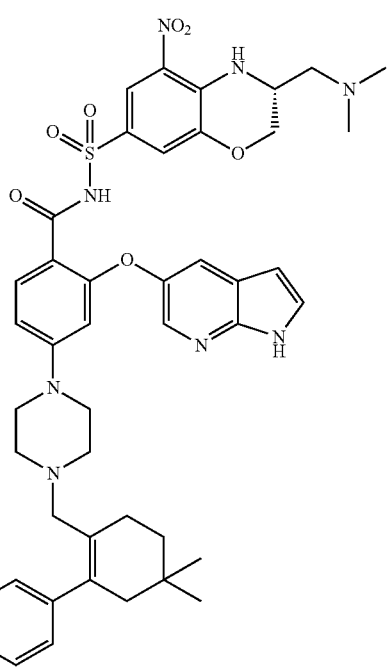 | (R)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-((dimethylamino)methyl)-5-nitro-3,4-dihydro-2H-benzo[b][1,4]oxazin-7-yl)sulfonyl)benzamide | MS-ESI (m/z): 869 [M + 1]$^+$ |

TABLE 2-continued

| EXAMPLE | STRUCTURE | NAME | DATA |
|---|---|---|---|
| 2-8 | 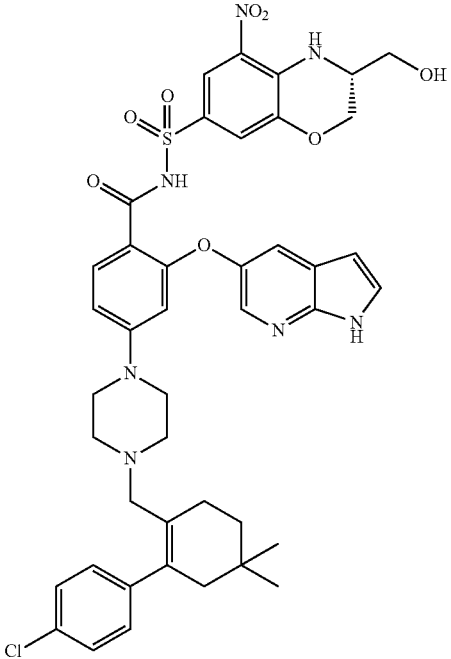 | (R)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-(hydroxymethyl)-5-nitro-3,4-dihydro-2H-benzo[b][1,4]oxazin-7-yl)sulfonyl)benzamide | MS-ESI (m/z): 842 [M + 1]+ |
| 2-9 | 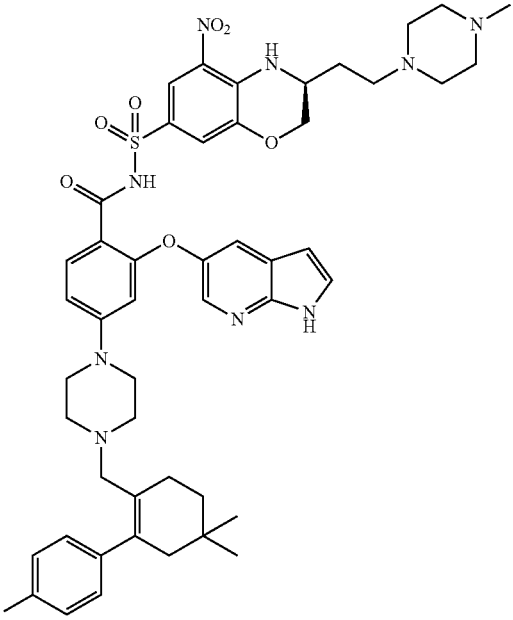 | (S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-(2-(4-methylpiperazin-1-yl)ethyl)-5-nitro-3,4-dihydro-2H-benzo[b][1,4]oxazin-7-yl)sulfonyl)benzamide | MS-ESI (m/z): 938 [M + 1]+ |

TABLE 2-continued

| EXAMPLE | STRUCTURE | NAME | DATA |
|---|---|---|---|
| 2-10 | 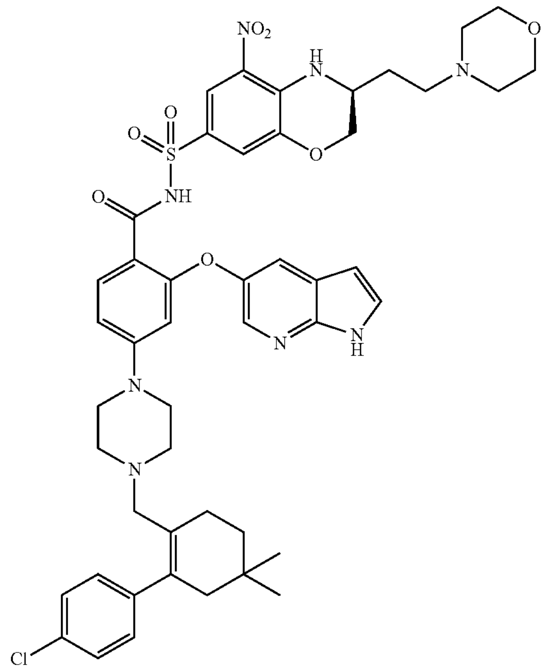 [SMILES: CC1(C)CCC(CN2CCN(c3ccc(C(=O)NS(=O)(=O)c4cc5c(c([N+](=O)[O-])c4)N[C@@H](CCN4CCOCC4)CO5)c(Oc4cnc5[nH]ccc5c4)c3)CC2)=C(c2ccc(Cl)cc2)C1] | (S)-2-((1H-pyrrolo[2,3-b]pyridin-5-yl)oxy)-4-(4-((4'-chloro-5,5-dimethyl-3,4,5,6-tetra-hydro-[1,1'-biphenyl]-2-yl)methyl)piperazin-1-yl)-N-((3-(2-morpholinoethyl)-5-nitro-3,4-dihydro-2H-benzo[b][1,4]oxazin-7-yl)sulfonyl)benzamide | MS-ESI (m/z): 925 [M + 1]+ |
| 2-11 | 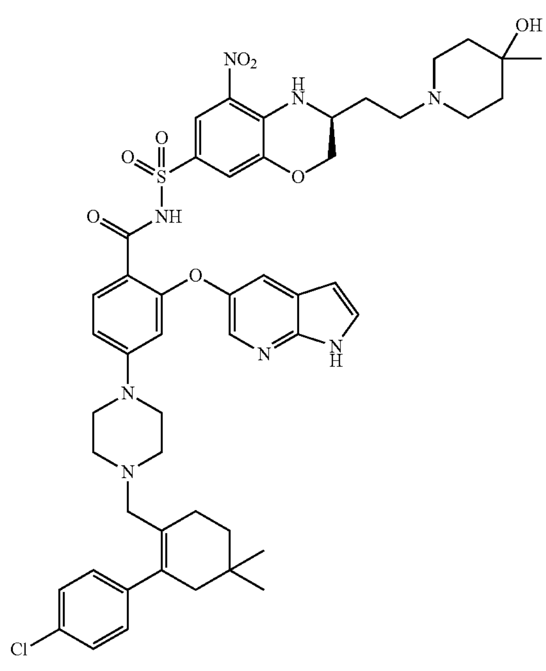 [SMILES: CC1(C)CCC(CN2CCN(c3ccc(C(=O)NS(=O)(=O)c4cc5c(c([N+](=O)[O-])c4)N[C@@H](CCN4CCC(C)(O)CC4)CO5)c(Oc4cnc5[nH]ccc5c4)c3)CC2)=C(c2ccc(Cl)cc2)C1] | (S)-2-((1H-pyrrolo[2,3-b]pyridin-5-yl)oxy)-4-(4-((4'-chloro-5,5-dimethyl-3,4,5,6-tetra-hydro-[1,1'-biphenyl]-2-yl)methyl)piperazin-1-yl)-N-((3-(2-(4-hydroxy-4-methylpiperidin-1-yl)ethyl)-5-nitro-3,4-dihydro-2H-benzo[b][1,4]oxazin-7-yl)sulfonyl)benzamide | MS-ESI (m/z): 953 [M + 1]+ |

TABLE 2-continued

| EXAMPLE | STRUCTURE | NAME | DATA |
|---|---|---|---|
| 2-12 | 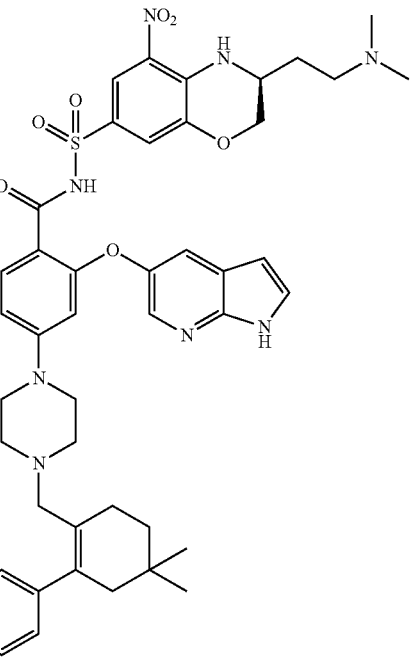 | (S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-(2-(dimethylamino)ethyl)-5-nitro-3,4-dihydro-2H-benzo[b][1,4]oxazin-7-yl)sulfonyl)benzamide | MS-ESI (m/z): 883 [M + 1]+ |
| 2-13 | 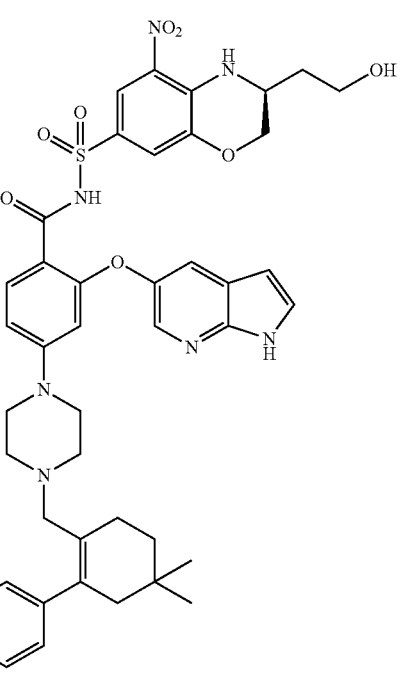 | (S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-(2-hydroxyethyl)-5-nitro-3,4-dihydro-2H-benzo[b][1,4]oxazin-7-yl)sulfonyl)benzamide | MS-ESI (m/z): 925 [M + 1]+ |

TABLE 2-continued

| EXAMPLE | STRUCTURE | NAME | DATA |
|---|---|---|---|
| 2-14 | 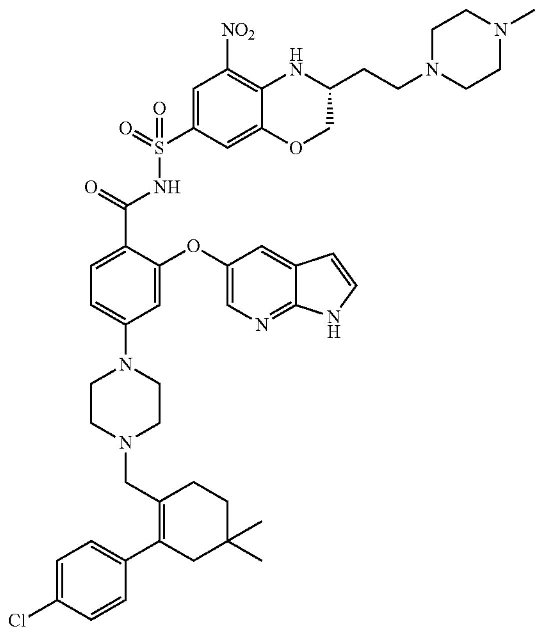 [SMILES: CN1CCN(CC[C@@H]2COc3cc(S(=O)(=O)NC(=O)c4ccc(N5CCN(CC6=C(c7ccc(Cl)cc7)CC(C)(C)CC6)CC5)cc4Oc4cnc5[nH]ccc5c4)cc([N+](=O)[O-])c3N2)CC1] | (R)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-(2-(4-methylpiperazin-1-yl)ethyl)-5-nitro-3,4-dihydro-2H-benzo[b][1,4]oxazin-7-yl)sulfonyl)benzamide | MS-ESI (m/z): 938 [M + 1]$^+$ |
| 2-15 | 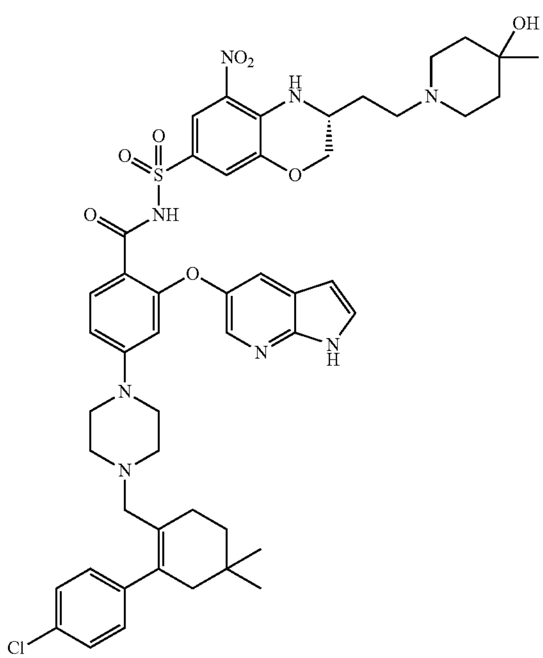 [SMILES: CC1(C)CCC(CN2CCN(c3ccc(C(=O)NS(=O)(=O)c4cc5c(c([N+](=O)[O-])c4)N[C@H](CCN4CCC(C)(O)CC4)CO5)c(Oc4cnc5[nH]ccc5c4)c3)CC2)=C(c2ccc(Cl)cc2)C1] | (R)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-(2-(4-hydroxy-4-methylpiperidin-1-yl)ethyl)-5-nitro-3,4-dihydro-2H-benzo[b][1,4]oxazin-7-yl)sulfonyl)benzamide | MS-ESI (m/z): 953 [M + 1]$^+$ |

TABLE 2-continued

| EXAMPLE | STRUCTURE | NAME | DATA |
|---|---|---|---|
| 2-16 | 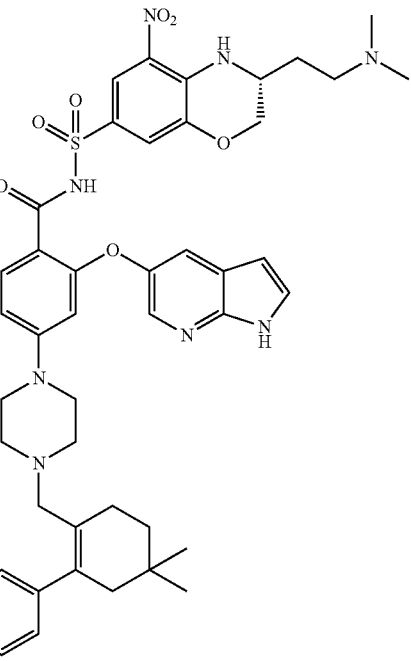 | (R)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-(2-(dimethylamino)ethyl)-5-nitro-3,4-dihydro-2H-benzo[b][1,4]oxazin-7-yl)sulfonyl)benzamide | MS-ESI (m/z): 883 [M + 1]+ |
| 2-17 | 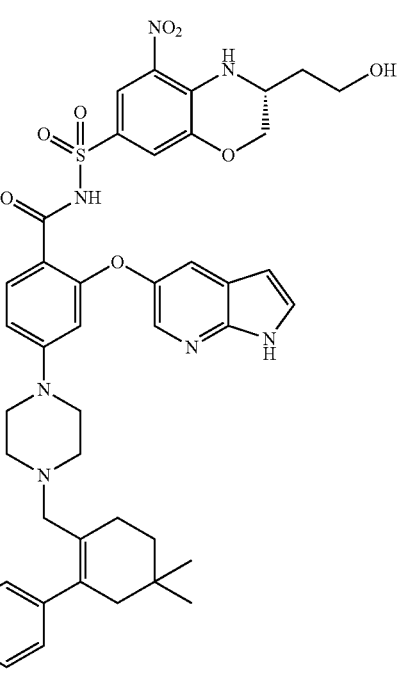 | (R)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-(2-hydroxyethyl)-5-nitro-3,4-dihydro-2H-benzo[b][1,4]oxazin-7-yl)sulfonyl)benzamide | MS-ESI (m/z): 856 [M + 1]+ |

TABLE 2-continued

| EXAMPLE | STRUCTURE | NAME | DATA |
|---|---|---|---|
| 2-18 | 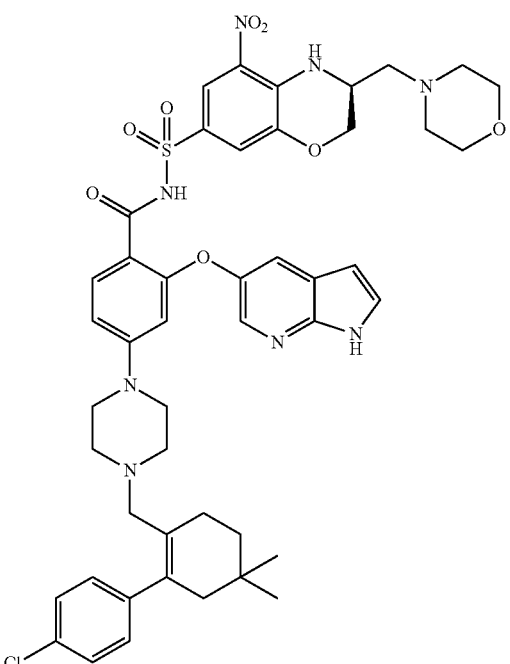 | (S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-(morpholinomethyl)-5-nitro-3,4-dihydro-2H-benzo[b][1,4]oxazin-7-yl)sulfonyl)benzamide | MS-ESI (m/z): 911 [M + 1]+ |
| 2-19 | 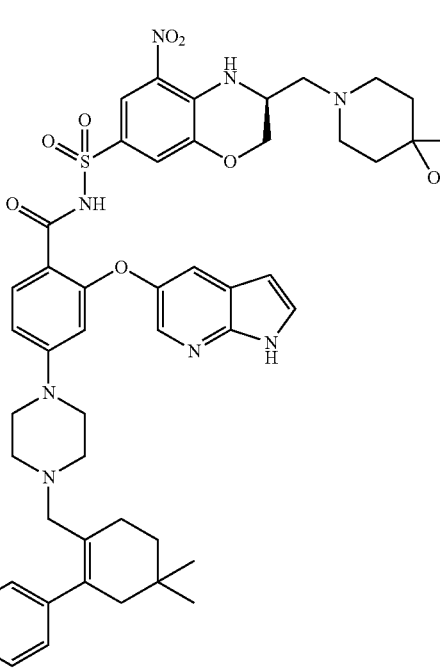 | (S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-((4-hydroxy-4-methylpiperidin-1-yl)methyl)-5-nitro-3,4-dihydro-2H-benzo[b][1,4]oxazin-7-yl)sulfonyl)benzamide | MS-ESI (m/z): 939 [M + 1]+ |

TABLE 2-continued

| EXAMPLE | STRUCTURE | NAME | DATA |
|---|---|---|---|
| 2-20 | 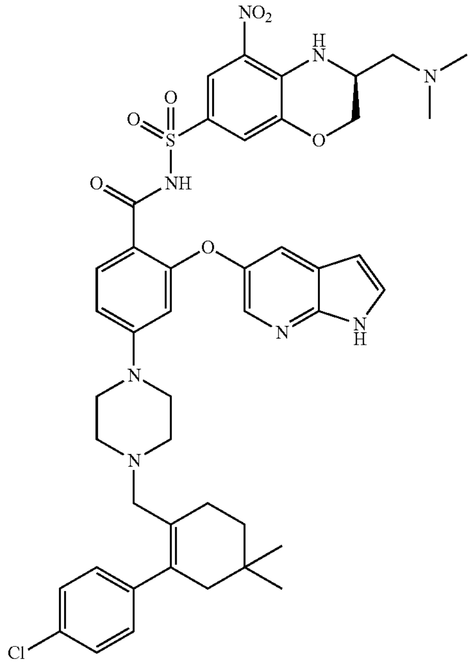 [SMILES: CN(C)C[C@H]1COc2cc(S(=O)(=O)NC(=O)c3ccc(N4CCN(CC5=C(c6ccc(Cl)cc6)CC(C)(C)CC5)CC4)cc3Oc3cnc4[nH]ccc4c3)cc([N+](=O)[O-])c2N1] | (S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-((dimethylamino)methyl)-5-nitro-3,4-dihydro-2H-benzo[b][1,4]oxazin-7-yl)sulfonyl)benzamide | MS-ESI (m/z): 869 [M + 1]+ |
| 2-21 | 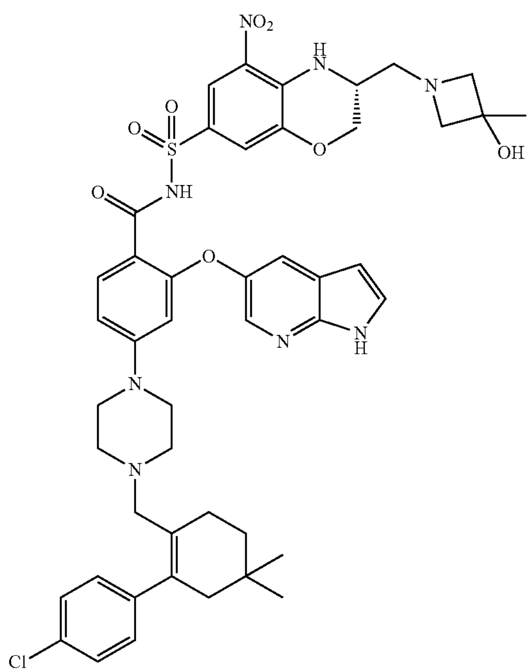 [SMILES: CC1(C)CCC(CN2CCN(c3ccc(C(=O)NS(=O)(=O)c4cc5c(c([N+](=O)[O-])c4)N[C@H](CN4CC(C)(O)C4)CO5)c(Oc4cnc5[nH]ccc5c4)c3)CC2)=C(c2ccc(Cl)cc2)C1] | (R)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-((3-hydroxy-3-methylazetidin-1-yl)methyl)-5-nitro-3,4-dihydro-2H-benzo[b][1,4]oxazin-7-yl)sulfonyl)benzamide | MS-ESI (m/z): 911 [M + 1]+ |

| EXAMPLE | STRUCTURE | NAME | DATA |
|---|---|---|---|
| 2-22 | 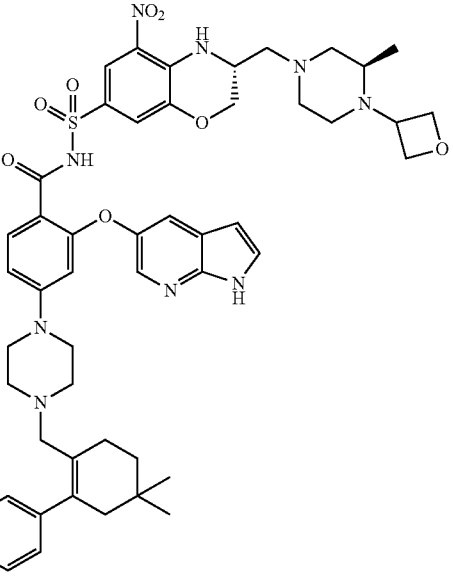 | 2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-(((R)-3-(((R)-3-methyl-4-(oxetan-3-yl)piperazin-1-yl)methyl)-5-nitro-3,4-dihydro-2H-benzo[b][1,4]oxazin-7-yl)sulfonyl)benzamide | MS-ESI (m/z): 980 [M + 1]⁺ |
| 2-23 | 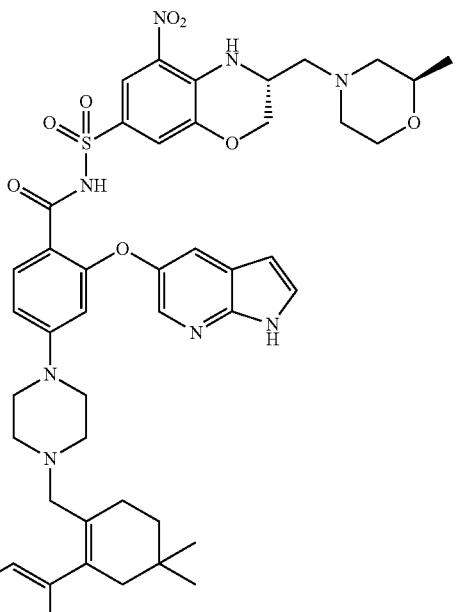 | 2-(1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-(((R)-3-(((R)-2-methylmorpholino)ethyl)-5-nitro-3,4-dihydro-2H-benzo[b][1,4]oxazin-7-yl)sulfonyl)benzamide | MS-ESI (m/z): 925 [M + 1]⁺ |

TABLE 2-continued

| EXAMPLE | STRUCTURE | NAME | DATA |
|---|---|---|---|
| 2-24 | 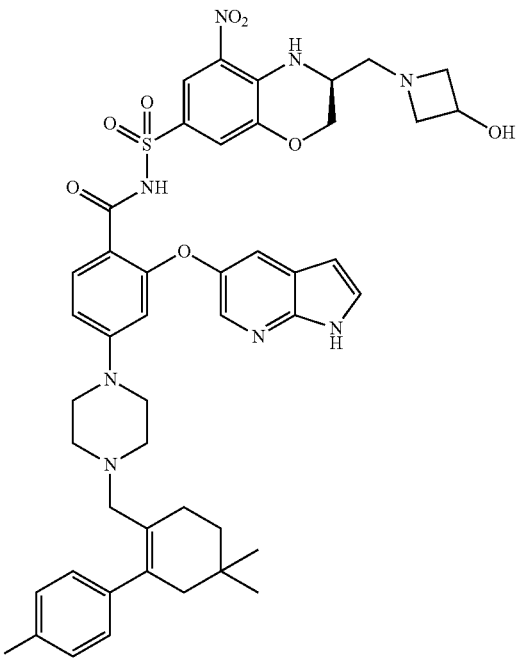 | (S)-2-((1H-pyrrolo[2,3-b]pyridin-5-yl)oxy)-4-(4-((4'-chloro-5,5-dimethyl-3,4,5,6-tetra-hydro-[1,1'-biphenyl]-2-yl)methyl)piperazin-1-yl)-N-((3-((3-hydroxyazetidin-1-yl)methyl)-5-nitro-3,4-dihydro-2H-benzo[b][1,4]oxazin-7-yl)sulfonyl)benzamide | MS-ESI (m/z): 897 [M + 1]$^+$ |
| 2-25 | 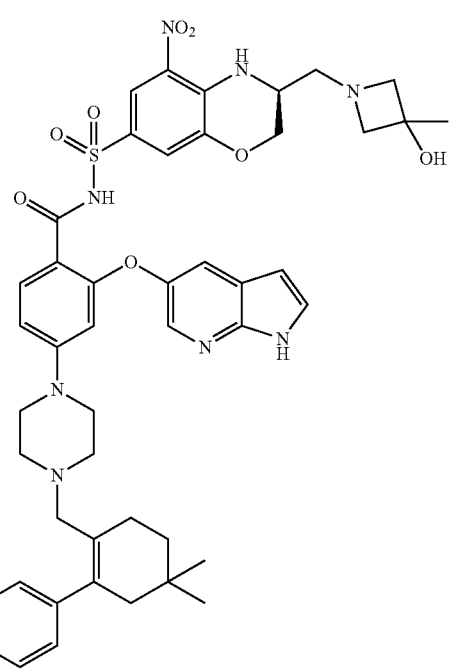 | (S)-2-((1H-pyrrolo[2,3-b]pyridin-5-yl)oxy)-4-(4-((4'-chloro-5,5-dimethyl-3,4,5,6-tetra-hydro-[1,1'-biphenyl]-2-yl)methyl)piperazin-1-yl)-N-((3-((3-hydroxy-3-methylazetidin-1-yl)methyl)-5-nitro-3,4-dihydro-2H-benzo[b][1,4]oxazin-7-yl)sulfonyl)benzamide | MS-ESI (m/z): 911 [M + 1]$^+$ |

TABLE 2-continued

| EXAMPLE | STRUCTURE | NAME | DATA |
|---|---|---|---|
| 2-26 | 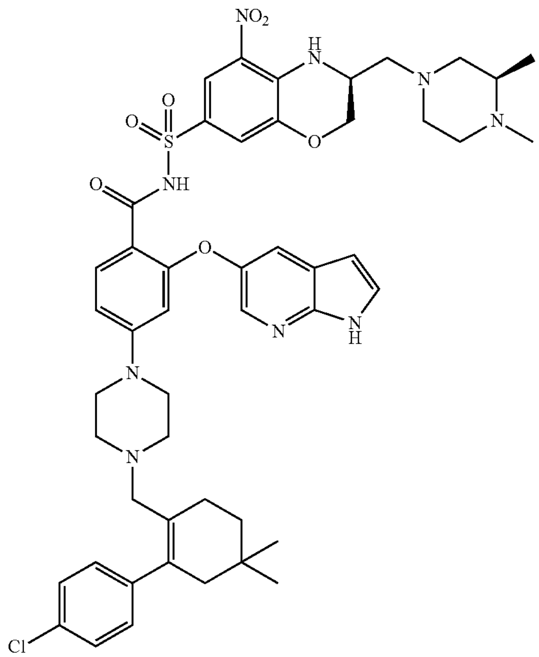 [SMILES: C[C@@H]1CN(C[C@H]2COc3cc(S(=O)(=O)NC(=O)c4ccc(N5CCN(CC6=C(c7ccc(Cl)cc7)CC(C)(C)CC6)CC5)cc4Oc4cnc5[nH]ccc5c4)cc([N+](=O)[O-])c3N2)CCN1C] | 2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-(((S)-3-(((R)-3,4-dimethylpiperazin-1-yl)methyl)-5-nitro-3,4-dihydro-2H-benzo[b][1,4]oxazin-7-yl)sulfonyl)benzamide | MS-ESI (m/z): 938 [M + 1]+ |
| 2-27 | 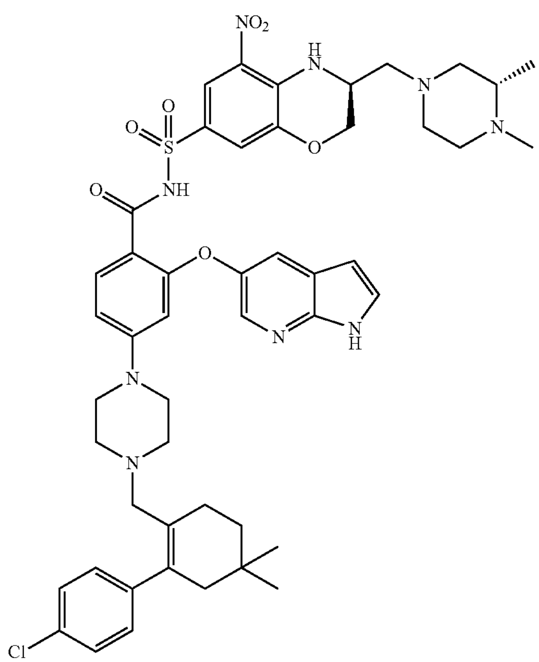 [SMILES: C[C@H]1CN(C[C@H]2COc3cc(S(=O)(=O)NC(=O)c4ccc(N5CCN(CC6=C(c7ccc(Cl)cc7)CC(C)(C)CC6)CC5)cc4Oc4cnc5[nH]ccc5c4)cc([N+](=O)[O-])c3N2)CCN1C] | 2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-(((S)-3-(((S)-3,4-dimethylpiperazin-1-yl)methyl)-5-nitro-3,4-dihydro-2H-benzo[b][1,4]oxazin-7-yl)sulfonyl)benzamide | MS-ESI (m/z): 938 [M + 1]+ |

TABLE 2-continued

| EXAMPLE | STRUCTURE | NAME | DATA |
|---|---|---|---|
| 2-28 | 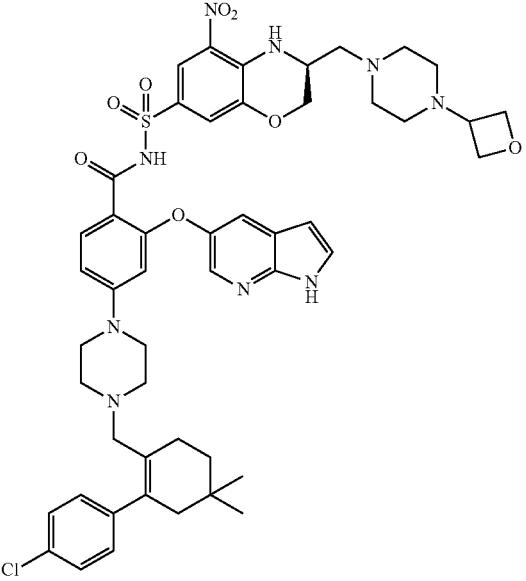 [SMILES: CC1(C)CCC(CN2CCN(c3ccc(C(=O)NS(=O)(=O)c4cc5c(c([N+](=O)[O-])c4)N[C@@H](CN4CCN(C6COC6)CC4)CO5)c(Oc4cnc5[nH]ccc5c4)c3)CC2)=C(c2ccc(Cl)cc2)C1] | (S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((5-nitro-3-((4-(oxetan-3-yl)piperazin-n-1-yl)methyl)-3,4-dihydro-2H-benzo[b][1,4]oxazin-7-yl)sulfonyl)benzamide | MS-ESI (m/z): 966 [M + 1]+ |
| 2-29 | 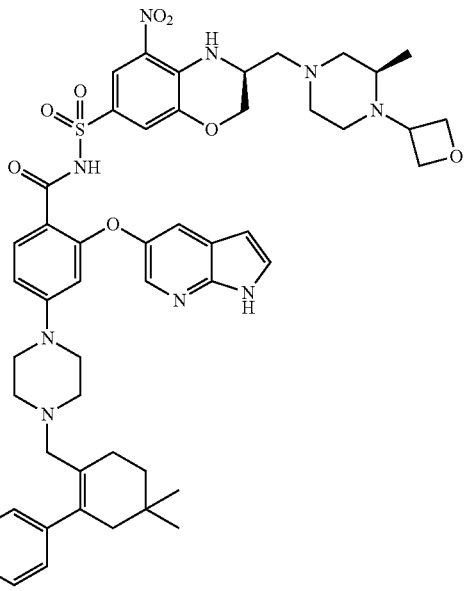 | 2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-(((S)-3-(((R)-3-methyl-4-(oxetan-3-yl)piperazin-1-yl)methyl)-5-nitro-3,4-dihydro-2H-benzo[b][1,4]oxazin-7-yl)sulfonyl)benzamide | MS-ESI (m/z): 980 [M + 1]+ |

TABLE 2-continued

| EXAMPLE | STRUCTURE | NAME | DATA |
|---|---|---|---|
| 2-30 | 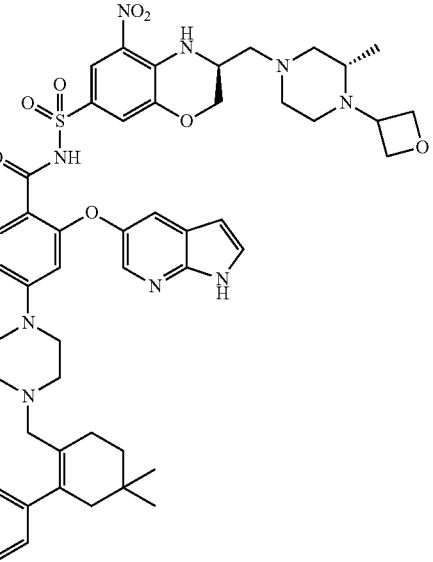 | 2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-(((S)-3-(((S)-3-methyl-4-(oxetan-3-yl)piperazin-1-yl)methyl)-5-nitro-3,4-dihydro-2H-benzo[b][1,4]oxazin-7-yl)sulfonyl)benzamide | MS-ESI (m/z): 980 [M + 1]+ |
| 2-31 | 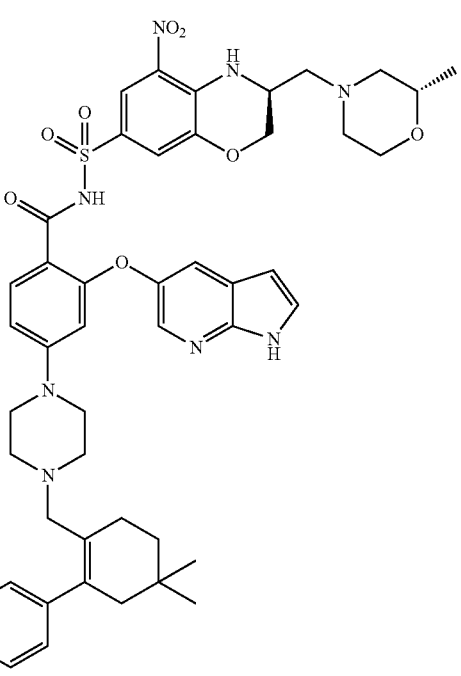 | 2-(1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-(((S)-3-(((S)-2-methylmorpholino)methyl)-5-nitro-3,4-dihydro-2H-benzo[b][1,4]oxazin-7-yl)sulfonyl)benzamide | MS-ESI (m/z): 925 [M + 1]+ |

TABLE 2-continued

| EXAMPLE | STRUCTURE | NAME | DATA |
|---|---|---|---|
| 2-32 | 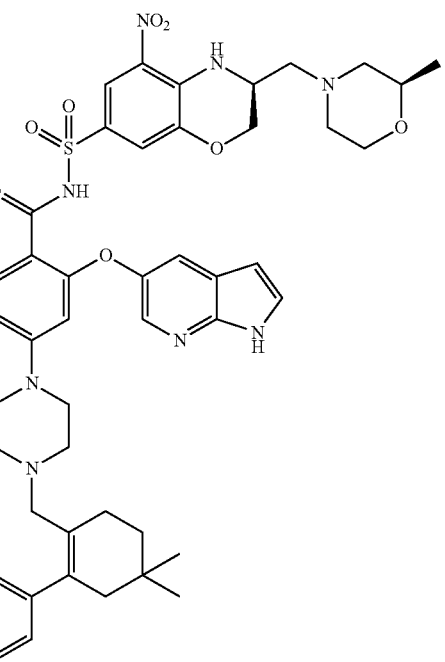 | 2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-(((S)-3-(((R)-2-methylmorpholino)methyl)-5-nitro-3,4-dihydro-2H-benzo[b][1,4]oxazin-7-yl)sulfonyl)benzamide | MS-ESI (m/z): 925 [M + 1]+ |
| 2-33 | 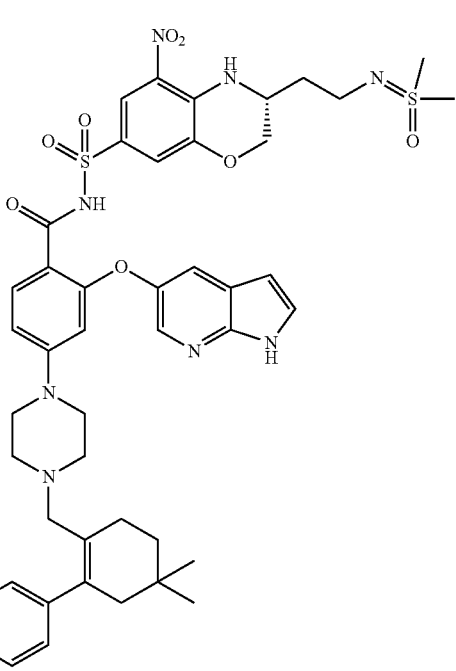 | (R)-2-((1H-pyrrolo[2,3-b]pyridin-5-yl)oxy)-4-(4-((4'-chloro-5,5-dimethy-3,4,5,6-tetra-hydro-[1,1'-biphenyl]-2-yl)methyl)piperazin-1-yl)-N-((3-(2-((dimethyl(oxo)-16-sulfan ylidene)amino)ethyl)-5-nitro-3,4-dihydro-2H-benzo[b][1,4]oxazin-7-yl)sulfonyl)benzamide | MS-ESI (m/z): 931 [M + 1]+ |

TABLE 2-continued

| EXAMPLE | STRUCTURE | NAME | DATA |
|---|---|---|---|
| 2-34 | 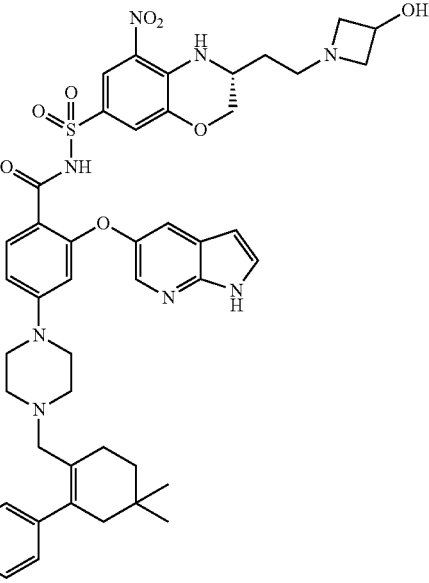 | (R)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-(2-(3-hydroxyazetidin-1-yl)ethyl)-5-nitro-3,4-dihydro-2H-benzo[b][1,4]oxazin-7-yl)sulfonyl)benzamide | MS-ESI (m/z): 911 [M + 1]+ |
| 2-35 | 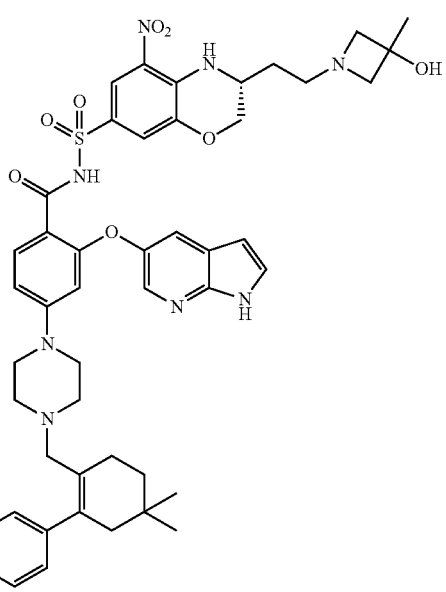 | (R)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-(2-(3-hydroxy-3-methylazetidin-1-yl)ethyl)-5-nitro-3,4-dihydro-2H-benzo[b][1,4]oxazin-7-yl)sulfonyl)benzamide | MS-ESI (m/z): 925 [M + 1]+ |

| EXAMPLE | STRUCTURE | NAME | DATA |
|---|---|---|---|
| 2-36 | 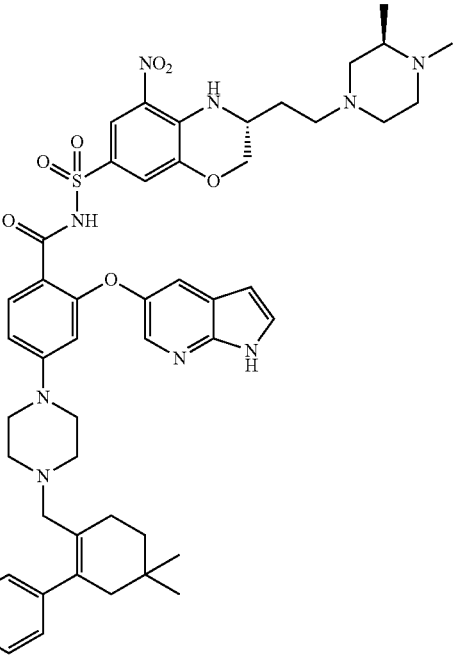 | 2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-(((R)-3-(2-((R)-3,4-dimethylpiperazin-1-yl)ethyl)-5-nitro-3,4-dihydro-2H-benzo[b][1,4]oxazin-7-yl)sulfonyl)benzamide | MS-ESI (m/z): 952 [M + 1]+ |
| 2-37 | 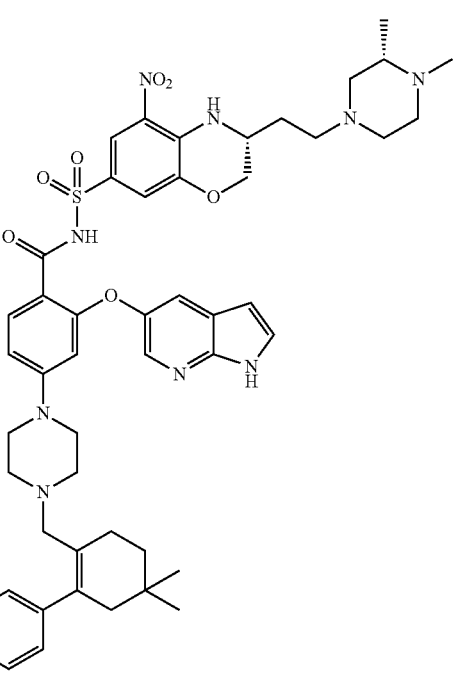 | 2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-(((R)-3-(2-((S)-3,4-dimethylpiperazin-1-yl)ethyl)-5-nitro-3,4-dihydro-2H-benzo[b][1,4]oxazin-7-yl)sulfonyl)benzamide | MS-ESI (m/z): 952 [M + 1]+ |

TABLE 2-continued

| EXAMPLE | STRUCTURE | NAME | DATA |
|---|---|---|---|
| 2-38 | 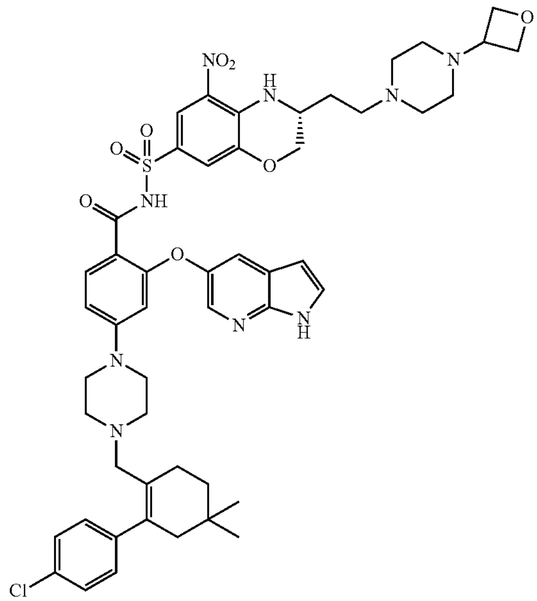 [SMILES: CC1(C)CCC(CN2CCN(c3ccc(C(=O)NS(=O)(=O)c4cc5c(c([N+](=O)[O-])c4)N[C@H](CCN4CCN(C6COC6)CC4)CO5)c(Oc4cnc5[nH]ccc5c4)c3)CC2)=C(c2ccc(Cl)cc2)C1] | (R)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((5-nitro-3-(2-(4-(oxetan-3-yl)piperazin-1-yl)ethyl)-3,4-dihydro-2H-benzo[b][1,4]oxazin-7-yl)sulfonyl)benzamide | MS-ESI (m/z): 980 [M + 1]⁺ |
| 2-39 | 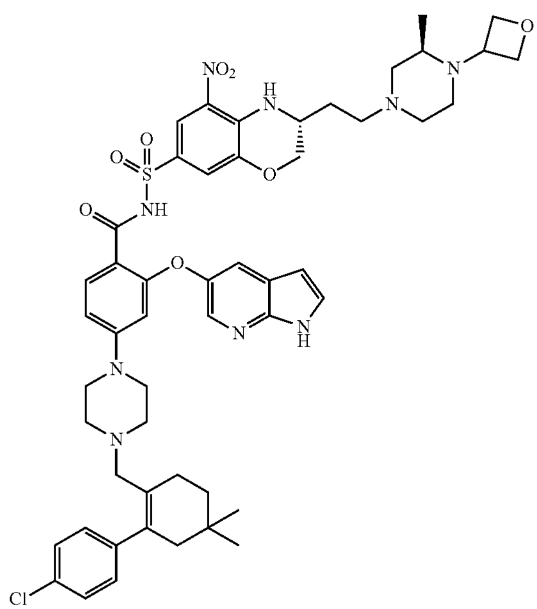 [SMILES: C[C@@H]1CN(CC[C@@H]2COc3cc(S(=O)(=O)NC(=O)c4ccc(N5CCN(CC6=C(c7ccc(Cl)cc7)CC(C)(C)CC6)CC5)cc4Oc4cnc5[nH]ccc5c4)cc([N+](=O)[O-])c3N2)CCN1C1COC1] | 2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-(((R)-3-(2-((R)-3-methyl-4-(oxetan-3-yl)piperazin-1-yl)ethyl)-5-nitro-3,4-dihydro-2H-benzo[b][1,4]oxazin-7-yl)sulfonyl)benzamide | MS-ESI (m/z): 994 [M + 1]⁺ |

TABLE 2-continued

| EXAMPLE | STRUCTURE | NAME | DATA |
|---|---|---|---|
| 2-40 | 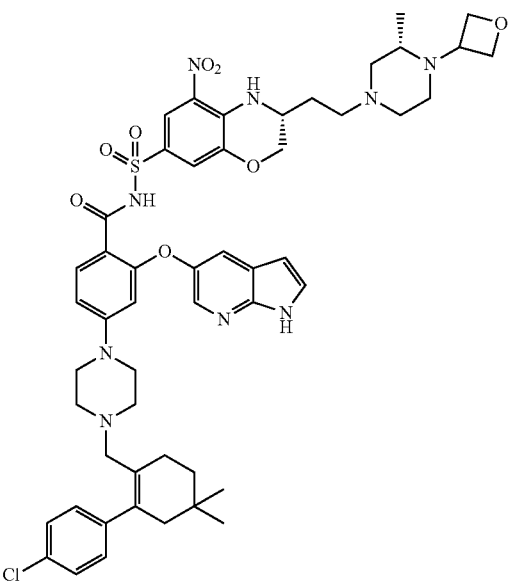 [SMILES: C[C@H]1CN(CC[C@@H]2COc3cc(S(=O)(=O)NC(=O)c4ccc(N5CCN(CC6=C(c7ccc(Cl)cc7)CC(C)(C)CC6)CC5)cc4Oc4cnc5[nH]ccc5c4)cc([N+](=O)[O-])c3N2)CCN1C1COC1] | 2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-(((R)-3-(2-((S)-3-methyl-4-(oxetan-3-yl)piperazin-1-yl)ethyl)-5-nitro-3,4-dihydro-2H-benzo[b][1,4]oxazin-7-yl)sulfonyl)benzamide | MS-ESI (m/z): 994 [M + 1]$^+$ |
| 2-41 | 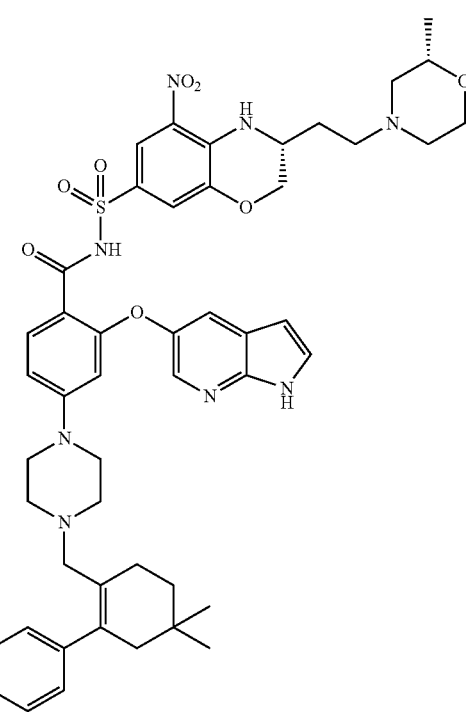 | 2-((1H-pyrrolo[2,3-b]pyridin-5-yl)oxy)-4-(4-((4'-chloro-5,5-dimethyl-3,4,5,6-tetrahydo-[1,1'-biphenyl]-2-yl)methyl)piperazin-1-yl)-N-(((R)-3-(2-((S)-2-methylmorpholino)ethyl)-5-nitro-3,4-dihydro-2H-benzo[b][1,4]oxazin-7-yl)sulfonyl)benzamide | MS-ESI (m/z): 939 [M + 1]$^+$ |

TABLE 2-continued

| EXAMPLE | STRUCTURE | NAME | DATA |
|---|---|---|---|
| 2-42 | 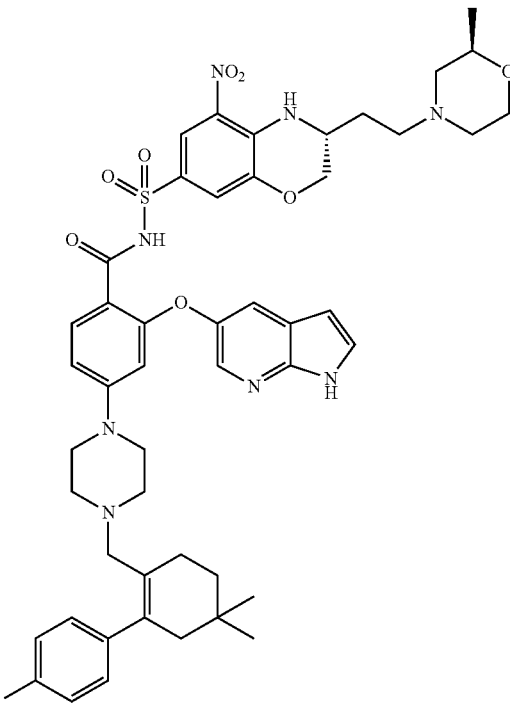 | 2-((1H-pyrrolo[2,3-b]pyridin-5-yl)oxy)-4-(4-((4'-chloro-5,5-dimethyl-3,4,5,6-tetrahydo-[1,1'-biphenyl]2-yl)methyl)piperazin-1-yl)-N-(((R)-3-(2-((R)-2-methylmorpholino)ethyl)-5-nitro-3,4-dihydro-2H-benzo[b][1,4]oxazin-7-yl)sulfonyl)benzamide | MS-ESI (m/z): 939 [M + 1]+ |
| 2-43 | 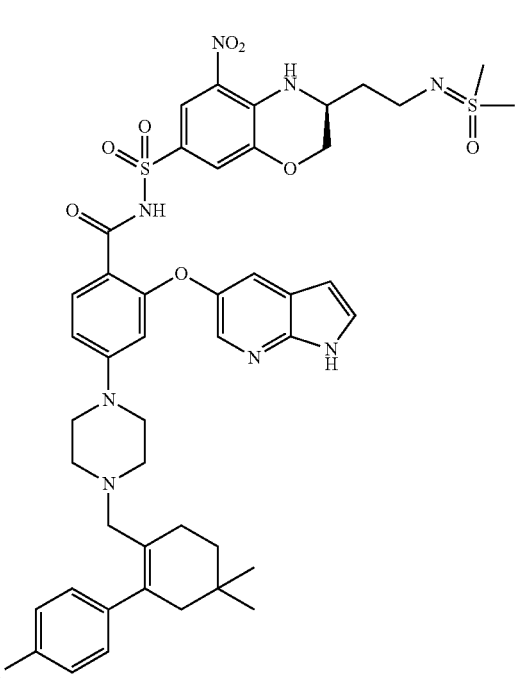 | (S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-(2-((dimethyl(oxo)-16-sulfanylidene)amino)ethyl)-5-nitro-3,4-dihydro-2H-benzo[b][1,4]oxazin-7-yl)sulfonyl)benzamide | MS-ESI (m/z): 931 [M + 1]+ |

TABLE 2-continued

| EXAMPLE | STRUCTURE | NAME | DATA |
|---|---|---|---|
| 2-44 | 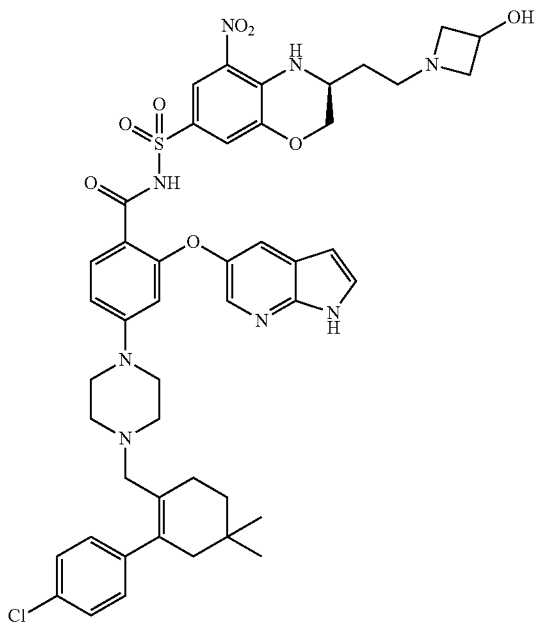 [SMILES: CC1(C)CCC(CN2CCN(c3ccc(C(=O)NS(=O)(=O)c4cc5c(c([N+](=O)[O-])c4)N[C@@H](CCN4CC(O)C4)CO5)c(Oc4cnc5[nH]ccc5c4)c3)CC2)=C(c2ccc(Cl)cc2)C1] | (S)-2-((1H-pyrrolo[2,3-b]pyridin-5-yl)oxy)-4-(4-((4'-chloro-5,5-dimethyl-3,4,5,6-tetra-hydro-[1,1'-biphenyl]-2-yl)methyl)piperazin-1-yl)-N-((3-(2-(3-hydroxyazetidin-1-yl)ethyl)-5-nitro-3,4-dihydro-2H-benzo[b][1,4]oxazin-7-yl)sulfonyl)benzamide | MS-ESI (m/z): 911 [M + 1]+ |
| 2-45 | 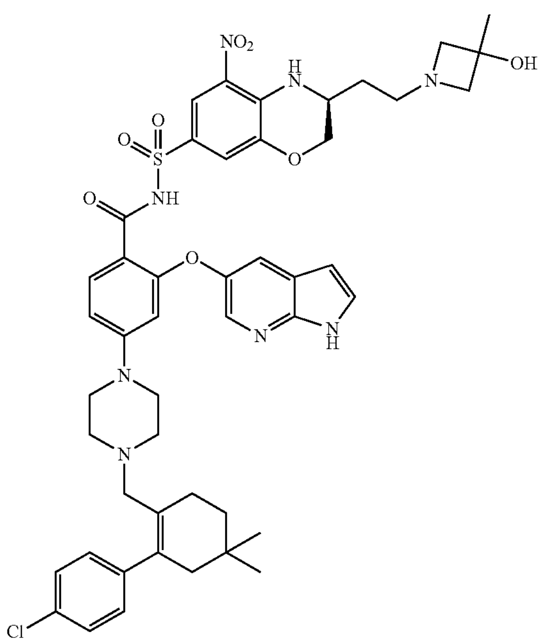 [SMILES: CC1(C)CCC(CN2CCN(c3ccc(C(=O)NS(=O)(=O)c4cc5c(c([N+](=O)[O-])c4)N[C@@H](CCN4CC(C)(O)C4)CO5)c(Oc4cnc5[nH]ccc5c4)c3)CC2)=C(c2ccc(Cl)cc2)C1] | (S)-2-((1H-pyrrolo[2,3-b]pyridin-5-yl)oxy)-4-(4-((4'-chloro-5,5-dimethyl-3,4,5,6-tetra-hydro-[1,1'-biphenyl]-2-yl)methyl)piperazin-1-yl)-N-((3-(2-(3-hydroxy-3-methylazetidin-1-yl)ethyl)-5-nitro-3,4-dihydro-2H-benzo[b][1,4]oxazin-7-yl)sulfonyl)benzamide | MS-ESI (m/z): 925 [M + 1]+ |

TABLE 2-continued

| EXAMPLE | STRUCTURE | NAME | DATA |
|---|---|---|---|
| 2-46 | 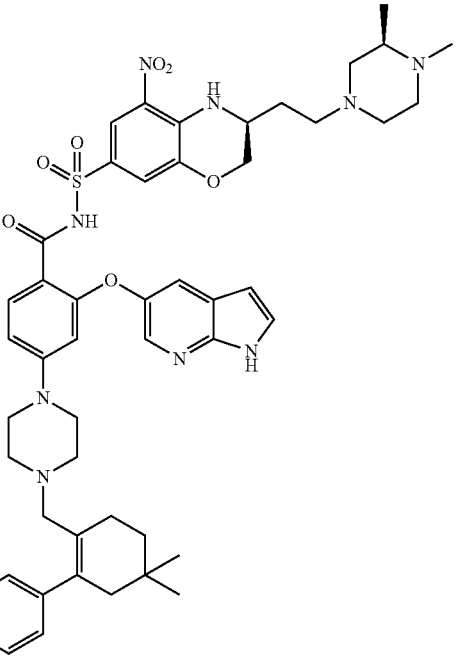 | 2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-(((S)-3-(2-((R)-3,4-dimethylpiperazin-1-yl)ethyl)-5-nitro-3,4-dihydro-2H-benzo[b][1,4]oxazin-7-yl)sulfonyl)benzamide | MS-ESI (m/z): 952 [M + 1]⁺ |
| 2-47 | 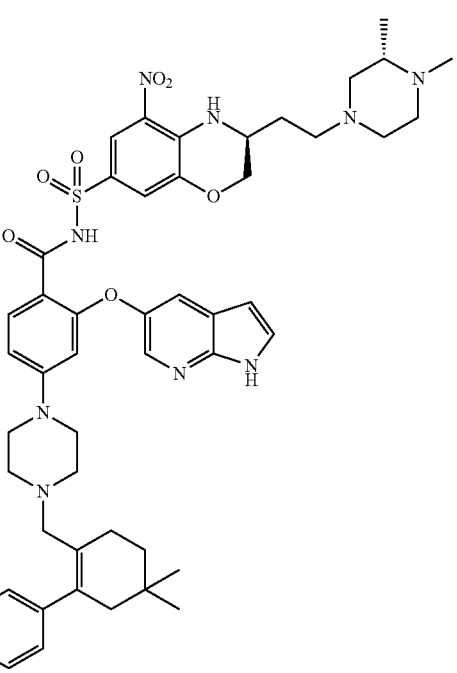 | 2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-(((S)-3-(2-((S)-3,4-dimethylpiperazin-1-yl)ethyl)-5-nitro-3,4-dihydro-2H-benzo[b][1,4]oxazin-7-yl)sulfonyl)benzamide | MS-ESI (m/z): 952 [M + 1]⁺ |

TABLE 2-continued

| EXAMPLE | STRUCTURE | NAME | DATA |
|---|---|---|---|
| 2-48 | 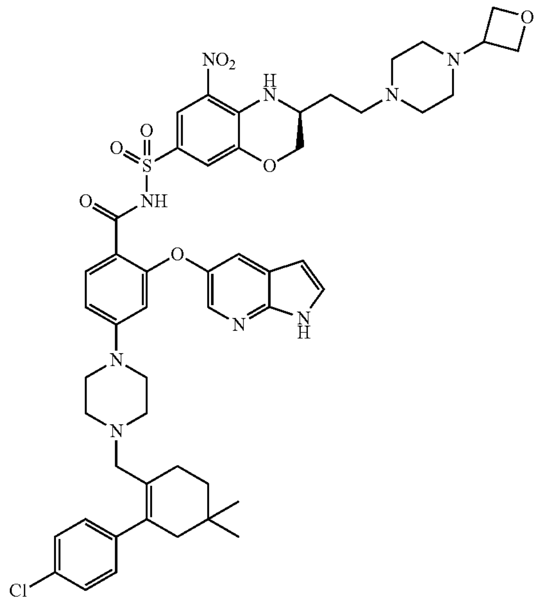 [SMILES: CC1(C)CCC(CN2CCN(c3ccc(C(=O)NS(=O)(=O)c4cc5c(c([N+](=O)[O-])c4)N[C@@H](CCN4CCN(C6COC6)CC4)CO5)c(Oc4cnc5[nH]ccc5c4)c3)CC2)=C(c2ccc(Cl)cc2)C1] | (S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((5-nitro-3-(2-(4-(oxetan-3-yl)piperazin-1-yl)ethyl)-3,4-dihydro-2H-benzo[b][1,4]oxazin-7-yl)sulfonyl)benzamide | MS-ESI (m/z): 980 [M + 1]$^+$ |
| 2-49 | 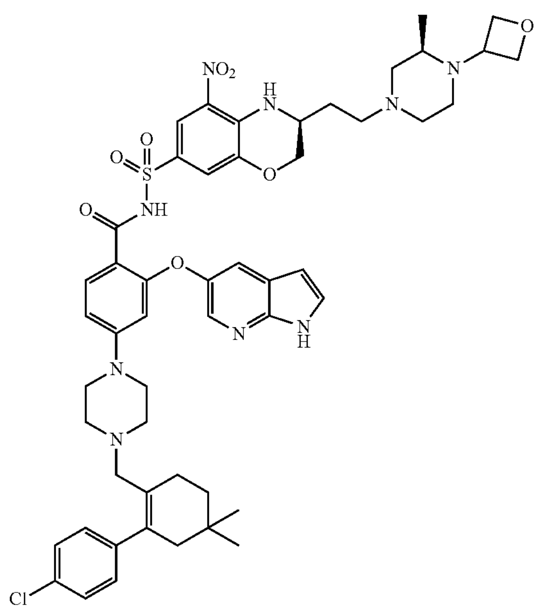 [SMILES: C[C@@H]1CN(CC[C@H]2COc3cc(S(=O)(=O)NC(=O)c4ccc(N5CCN(CC6=C(c7ccc(Cl)cc7)CC(C)(C)CC6)CC5)cc4Oc4cnc5[nH]ccc5c4)cc([N+](=O)[O-])c3N2)CCN1C1COC1] | 2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-(((S)-3-(2-((R)-3-methyl-4-(oxetan-3-yl)piperazin-1-yl)ethyl)-5-nitro-3,4-dihydro-2H-benzo[b][1,4]oxazin-7-yl)sulfonyl)benzamide | MS-ESI (m/z): 994 [M + 1]$^+$ |

TABLE 2-continued

| EXAMPLE | STRUCTURE | NAME | DATA |
|---|---|---|---|
| 2-50 | 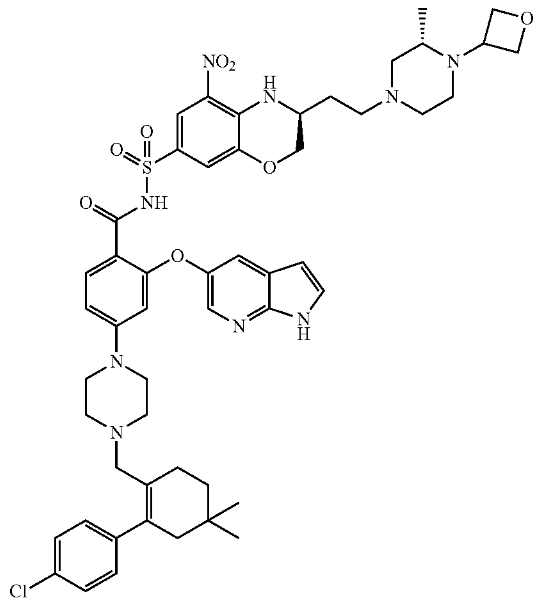 [SMILES: C[C@H]1CN(CC[C@H]2COc3cc(S(=O)(=O)NC(=O)c4ccc(N5CCN(CC6=C(c7ccc(Cl)cc7)CC(C)(C)CC6)CC5)cc4Oc4cnc5[nH]ccc5c4)cc([N+](=O)[O-])c3N2)CCN1C1COC1] | 2-((1H-pyrrolo[2,3b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-(((S)-3-(2-((S)-3-methyl-4-(oxetan-3-yl)piperazin-1-yl)ethyl)-5-nitro-3,4-dihydro-2H-benzo[b][1,4]oxazin-7-yl)sulfonyl)benzamide | MS-ESI (m/z): 994 [M + 1]+ |
| 2-51 | 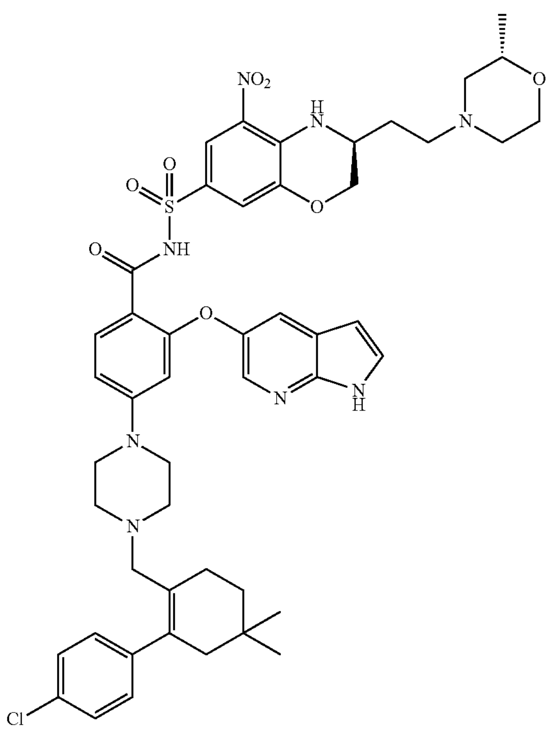 [SMILES: C[C@H]1CN(CC[C@H]2COc3cc(S(=O)(=O)NC(=O)c4ccc(N5CCN(CC6=C(c7ccc(Cl)cc7)CC(C)(C)CC6)CC5)cc4Oc4cnc5[nH]ccc5c4)cc([N+](=O)[O-])c3N2)CCO1] | 2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-(((S)-3-(2-((S)-2-methylmorpholino)ethyl)-5-nitro-3,4-dihydro-2H-benzo[b][1,4]oxazin-7-yl)sulfonyl)benzamide | MS-ESI (m/z): 939 [M + 1]+ |

TABLE 2-continued

| EXAMPLE | STRUCTURE | NAME | DATA |
|---|---|---|---|
| 2-52 | 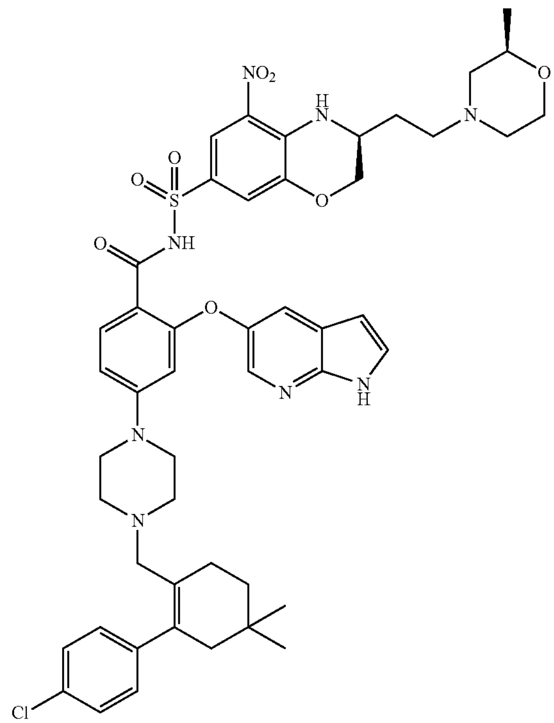 [SMILES: C[C@@H]1CN(CC[C@H]2COc3cc(S(=O)(=O)NC(=O)c4ccc(N5CCN(CC6=C(c7ccc(Cl)cc7)CC(C)(C)CC6)CC5)cc4Oc4cnc5[nH]ccc5c4)cc([N+](=O)[O-])c3N2)CCO1] | 2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-(((S)-3-(2-((R)-2-methylmorpholino)ethyl)-5-nitro-3,4-dihydro-2H-benzo[b][1,4]oxazin-7-yl)sulfonyl)benzamide | MS-ESI (m/z): 939 [M + 1]$^+$ |
| 2-53 | 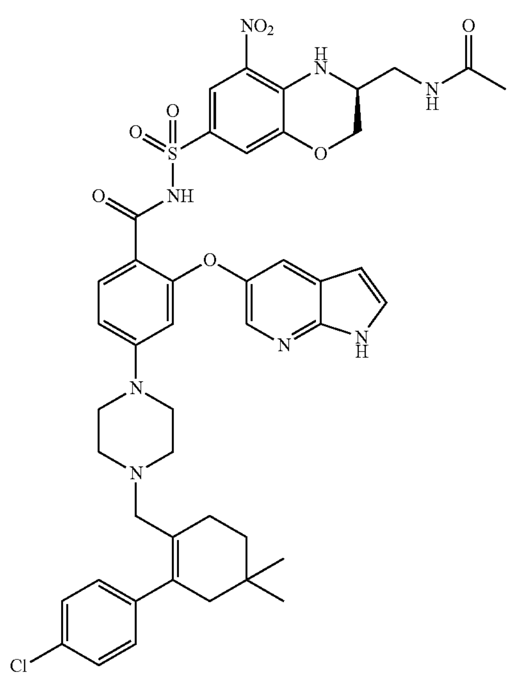 [SMILES: CC(=O)NC[C@H]1COc2cc(S(=O)(=O)NC(=O)c3ccc(N4CCN(CC5=C(c6ccc(Cl)cc6)CC(C)(C)CC5)CC4)cc3Oc3cnc4[nH]ccc4c3)cc([N+](=O)[O-])c2N1] | (S)-2-((1H-pyrrolo[2,3-b]pyridin-5-yl)oxy)-N-((3-(acetamidomethyl)-5-nitro-3,4-dihydro-2H-benzo[b][1,4]oxazin-7-yl)sulfonyl)-4-(4-((4'-chloro-5,5-dimethyl-3,4,5,6-tetrahydro-[1,1'-biphenyl]-2-yl)methyl)piperazin-1-yl)benzamide | MS-ESI (m/z): 883 [M + 1]$^+$ |

TABLE 2-continued

| EXAMPLE | STRUCTURE | NAME | DATA |
|---|---|---|---|
| 2-54 | 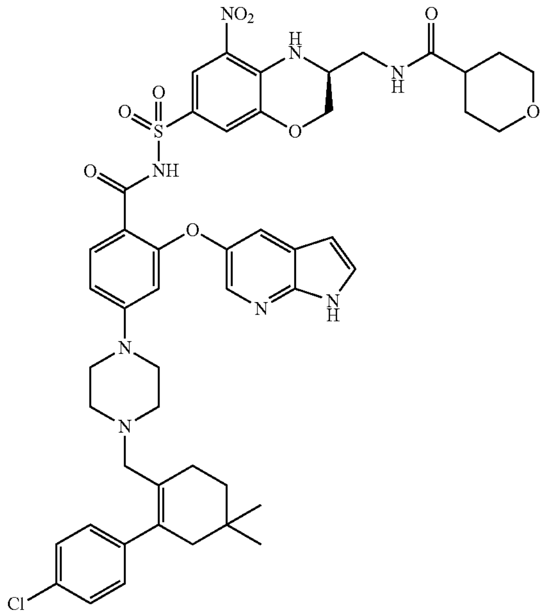 [SMILES: CC1(C)CCC(CN2CCN(c3ccc(C(=O)NS(=O)(=O)c4cc5c(c([N+](=O)[O-])c4)N[C@@H](CNC(=O)C4CCOCC4)CO5)c(Oc4cnc5[nH]ccc5c4)c3)CC2)=C(c2ccc(Cl)cc2)C1] | (S)-N-((7-(N-(2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)benzoyl)sulfamoyl)-5-nitro-3,4-dihydro-2H-benzo[b][1,4]oxazin-3-yl)methyl)tetrahydro-2H-pyran-4-carboxamide | MS-ESI (m/z): 953 [M + 1]+ |
| 2-55 | 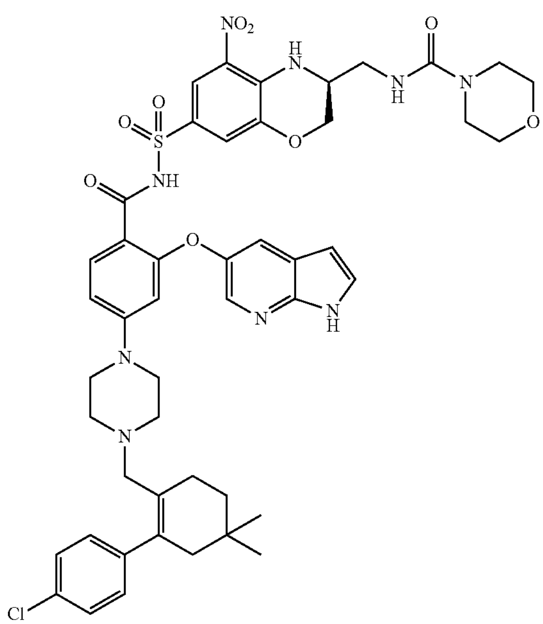 [SMILES: CC1(C)CCC(CN2CCN(c3ccc(C(=O)NS(=O)(=O)c4cc5c(c([N+](=O)[O-])c4)N[C@@H](CNC(=O)N4CCOCC4)CO5)c(Oc4cnc5[nH]ccc5c4)c3)CC2)=C(c2ccc(Cl)cc2)C1] | (S)-N-((7-(N-(2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)benzoyl)sulfamoyl)-5-nitro-3,4-dihydro-2H-benzo[b][1,4]oxazin-3-yl)methyl)morpholine-4-carboxamide | MS-ESI (m/z): 954 [M + 1]+ |

TABLE 2-continued

| EXAMPLE | STRUCTURE | NAME | DATA |
|---|---|---|---|
| 2-56 | 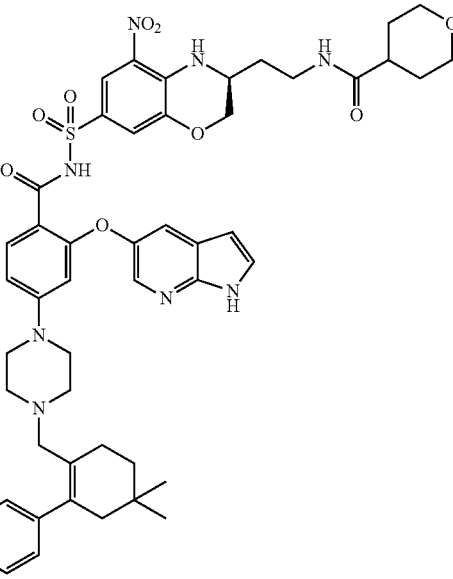 | (S)-N-(2-(7-(N-(2-((1H-pyrrolo[2,3-b]pyridrin-5-yl)oxy)-4-(4-((4'-chloro-5,5-dimethyl-3,4,5,6-tetrahydro-[1,1'-biphenyl]-2-yl)methyl)piperazin-1-yl)benzoyl)sulfamoyl)-5-nitro-3,4-dihydro-2H-benzo[b][1,4]oxazin-3-yl)ethyl)tetrahydro-2H-pyran-4-carboxamide | MS-ESI (m/z): 967 [M + 1]$^+$ |
| 2-57 | 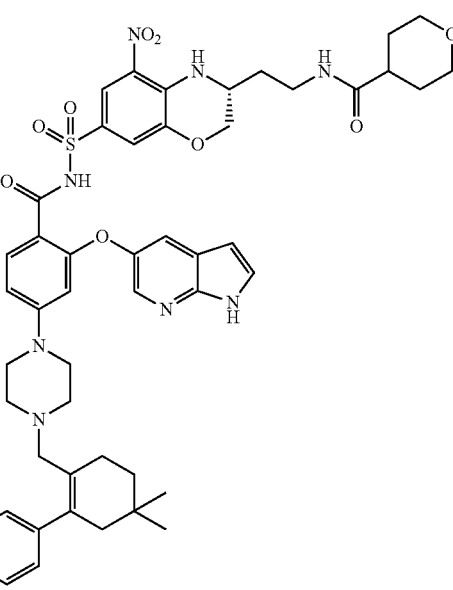 | (R)-N-(2-(7-(N-(2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)benzoyl)sulfamoyl)-5-nitro-3,4-dihydro-2H-benzo[b][1,4]oxazin-3-yl)ethyl)tetrahydro-2H-pyran-4-carboxamide | MS-ESI (m/z): 967 [M + 1]$^+$ |

TABLE 2-continued

| EXAMPLE | STRUCTURE | NAME | DATA |
|---|---|---|---|
| 2-58 | 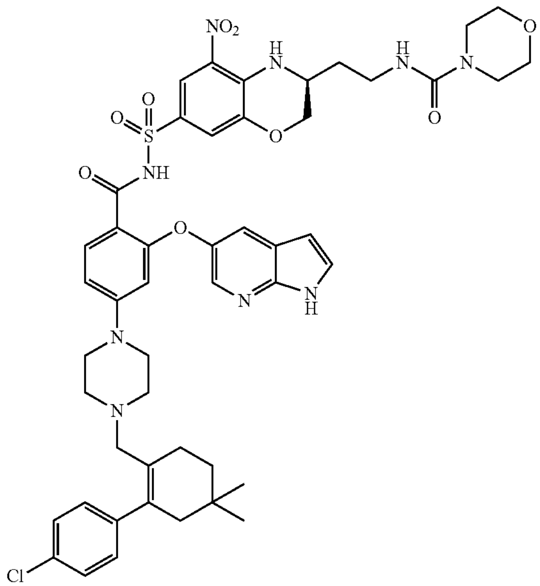 [SMILES: CC1(C)CCC(CN2CCN(c3ccc(C(=O)NS(=O)(=O)c4cc5c(c([N+](=O)[O-])c4)N[C@@H](CCNC(=O)N4CCOCC4)CO5)c(Oc4cnc5[nH]ccc5c4)c3)CC2)=C(c2ccc(Cl)cc2)C1] | (S)-N-(2-(7-(N-(2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)benzoyl)sulfamoyl)-5-nitro-3,4-dihydro-2H-benzo[b][1,4]oxazin-3-yl)ethyl)morpholine-4-carboxamide | MS-ESI (m/z): 968 [M + 1]$^+$ |
| 2-59 | 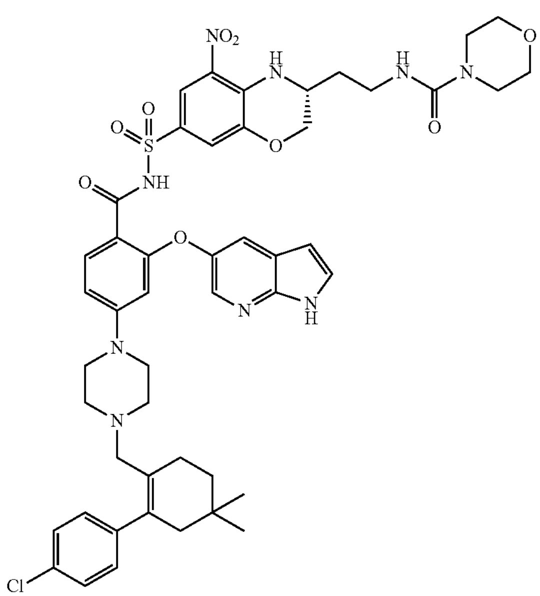 [SMILES: CC1(C)CCC(CN2CCN(c3ccc(C(=O)NS(=O)(=O)c4cc5c(c([N+](=O)[O-])c4)N[C@H](CCNC(=O)N4CCOCC4)CO5)c(Oc4cnc5[nH]ccc5c4)c3)CC2)=C(c2ccc(Cl)cc2)C1] | (R)-N-(2-(7-(N-(2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)benzoyl)sulfamoyl)-5-nitro-3,4-dihydro-2H-benzo[b][1,4]oxazin-3-yl)ethyl)morpholine-4-carboxamide | MS-ESI (m/z): 968 [M + 1]$^+$ |

TABLE 2-continued

| EXAMPLE | STRUCTURE | NAME | DATA |
|---|---|---|---|
| 2-60 | 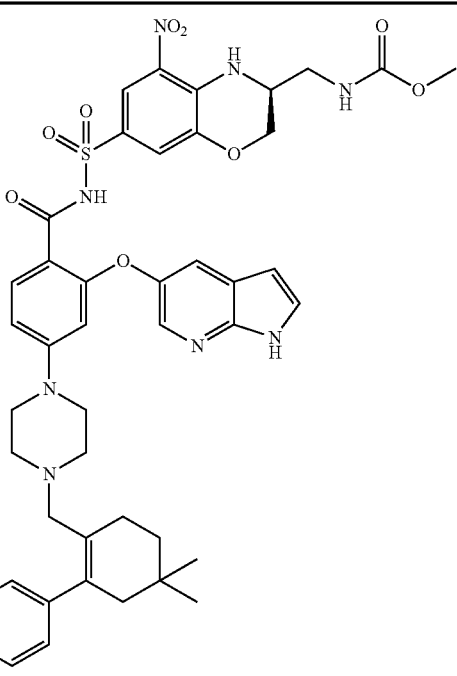 | methyl (S)-((7-(N-(2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)benzoyl)sulfamoyl)-5-nitro-3,4-dihydro-2H-benzo[b][1,4]oxazin-3-yl)methyl)carbamate | MS-ESI (m/z): 899 [M + 1]+ |
| 2-61 | 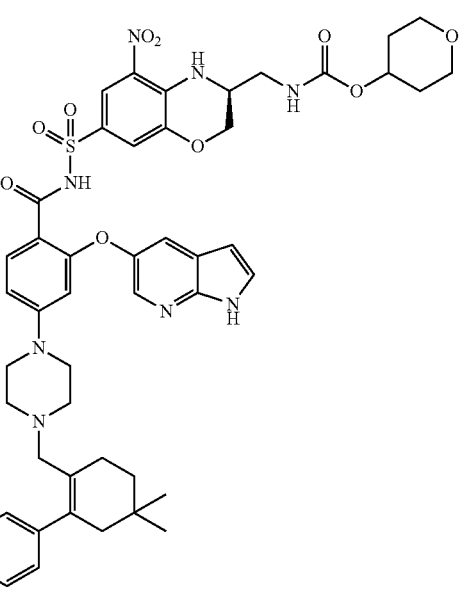 | tetrahydro-2H-pyran-4-yl (S)-((7-(N-(2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)benzoyl)sulfamoyl)-5-nitro-3,4-dihydro-2H-benzo[b][1,4]oxazin-3-yl)methyl)carbamate | MS-ESI (m/z): 969 [M + 1]+ |

TABLE 2-continued

| EXAMPLE | STRUCTURE | NAME | DATA |
|---|---|---|---|
| 2-62 | 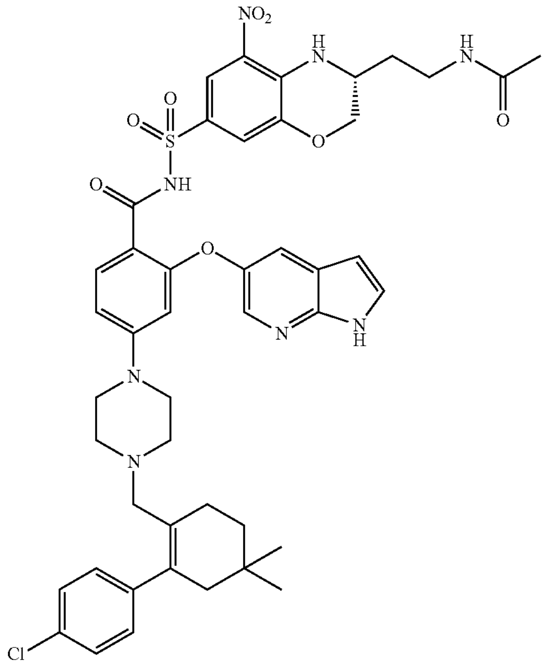 [SMILES: CC(=O)NCC[C@@H]1COc2cc(S(=O)(=O)NC(=O)c3ccc(N4CCN(CC5=C(c6ccc(Cl)cc6)CC(C)(C)CC5)CC4)cc3Oc3cnc4[nH]ccc4c3)cc([N+](=O)[O-])c2N1] | (R)-2-((1H-pyrrolo[2,3-b]pyridin-5-yl)oxy)-N-((3-(2-acetamidoethyl)-5-nitro-3,4-dihydro-2H-benzo[b][1,4]oxazin-7-yl)sulfonyl)-4-(4-((4'-chloro-5,5-dimethyl-3,4,5,6-tetrahydro-[1,1'-biphenyl]-2-yl)methyl)piperazin-1-yl)benzamide | MS-ESI (m/z): 897 [M + 1]+ |
| 2-63 | 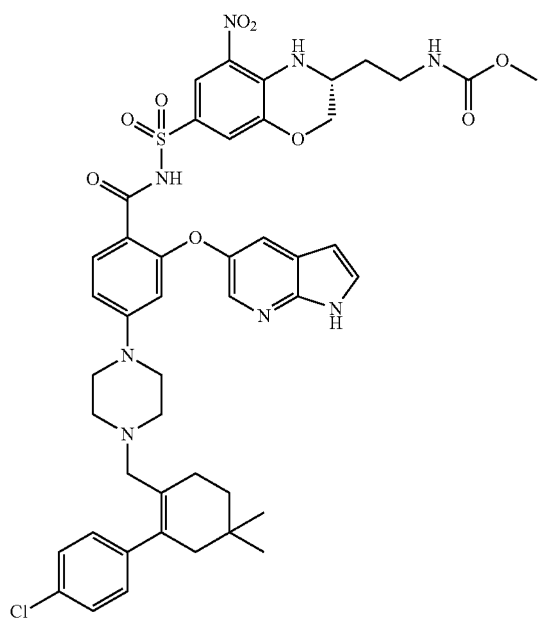 [SMILES: COC(=O)NCC[C@@H]1COc2cc(S(=O)(=O)NC(=O)c3ccc(N4CCN(CC5=C(c6ccc(Cl)cc6)CC(C)(C)CC5)CC4)cc3Oc3cnc4[nH]ccc4c3)cc([N+](=O)[O-])c2N1] | methyl (R)-(2-(7-(N-(2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)benzoyl)sulfamoyl)-5-nitro-3,4-dihydro-2H-benzo[b][1,4]oxazin-3-yl)ethyl)carbamate | MS-ESI (m/z): 913 [M + 1]+ |

TABLE 2-continued

| EXAMPLE | STRUCTURE | NAME | DATA |
|---|---|---|---|
| 2-64 | 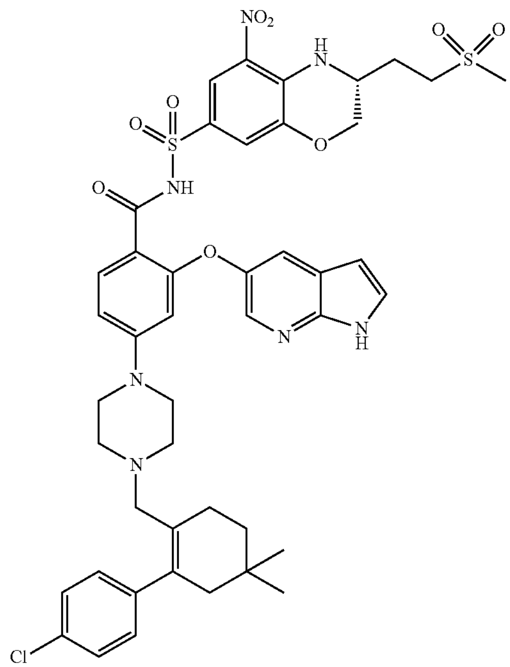 [SMILES: CC1(C)CCC(CN2CCN(c3ccc(C(=O)NS(=O)(=O)c4cc5c(c([N+](=O)[O-])c4)N[C@H](CCS(C)(=O)=O)CO5)c(Oc4cnc5[nH]ccc5c4)c3)CC2)=C(c2ccc(Cl)cc2)C1] | (R)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-(2-(methylsulfonyl)ethyl)-5-nitro-3,4-dihydro-2H-benzo[b][1,4]oxazin-7-yl)sulfonyl)benzamide | MS-ESI (m/z): 918 [M + 1]⁺ |
| 2-65 | 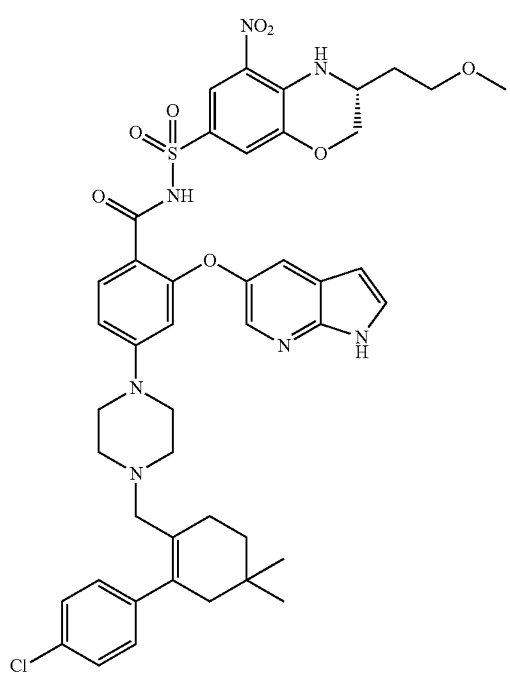 [SMILES: COCC[C@@H]1COc2cc(S(=O)(=O)NC(=O)c3ccc(N4CCN(CC5=C(c6ccc(Cl)cc6)CC(C)(C)CC5)CC4)cc3Oc3cnc4[nH]ccc4c3)cc([N+](=O)[O-])c2N1] | (R)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-(2-methoxyethyl)-5-nitro-3,4-dihydro-2H-benzo[b][1,4]oxazin-7-yl)sulfonyl)benzamide | MS-ESI (m/z): 870 [M + 1]⁺ |

TABLE 2-continued

| EXAMPLE | STRUCTURE | NAME | DATA |
|---|---|---|---|
| 2-66 | 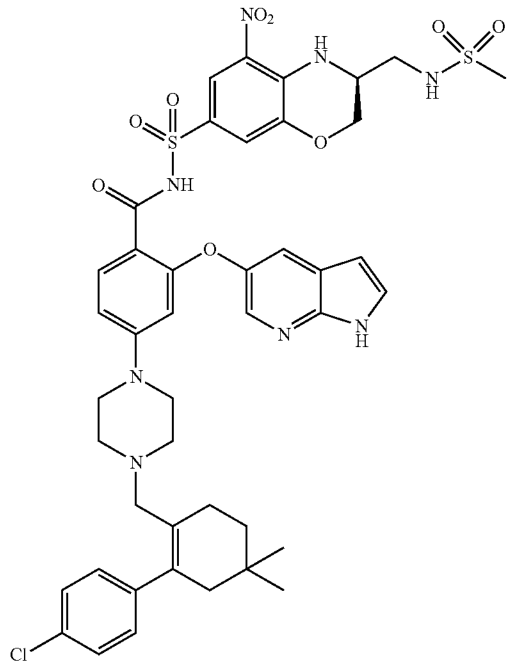 [SMILES: CC1(C)CCC(CN2CCN(c3ccc(C(=O)NS(=O)(=O)c4cc5c(c([N+](=O)[O-])c4)N[C@@H](CNS(C)(=O)=O)CO5)c(Oc4cnc5[nH]ccc5c4)c3)CC2)=C(c2ccc(Cl)cc2)C1] | (S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-(methylsulfonamidomethyl)-5-nitro-3,4-dihydro-2H-benzo[b][1,4]oxazin-7-yl)sulfonyl)benzamide | MS-ESI (m/z): 919 [M + 1]+ |
| 2-67 | 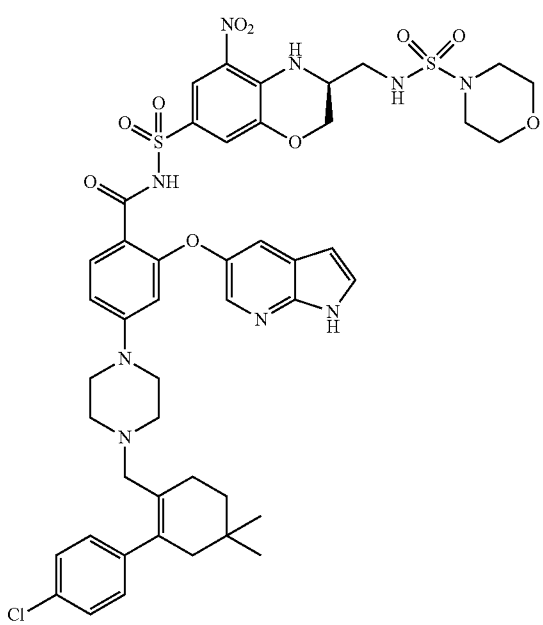 [SMILES: CC1(C)CCC(CN2CCN(c3ccc(C(=O)NS(=O)(=O)c4cc5c(c([N+](=O)[O-])c4)N[C@@H](CNS(=O)(=O)N4CCOCC4)CO5)c(Oc4cnc5[nH]ccc5c4)c3)CC2)=C(c2ccc(Cl)cc2)C1] | (S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-((morpholine-4-sulfonamido)methyl)-5-nitro-3,4-dihydro-2H-benzo[b][1,4]oxazin-7-yl)sulfonyl)benzamide | MS-ESI (m/z): 990 [M + 1]+ |

TABLE 2-continued

| EXAMPLE | STRUCTURE | NAME | DATA |
|---|---|---|---|
| 2-68 | 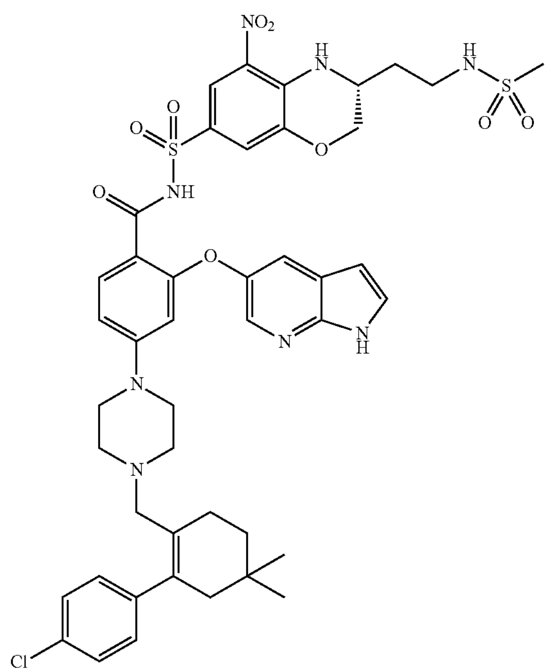 [SMILES: CC1(C)CCC(CN2CCN(c3ccc(C(=O)NS(=O)(=O)c4cc5c(c([N+](=O)[O-])c4)N[C@H](CCNS(C)(=O)=O)CO5)c(Oc4cnc5[nH]ccc5c4)c3)CC2)=C(c2ccc(Cl)cc2)C1] | (R)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-(2-(methylsulfonamido)ethyl)-5-nitro-3,4-dihydro-2H-benzo[b][1,4]oxazin-7-yl)sulfonyl)benzamide | MS-ESI (m/z): 933 [M + 1]$^+$ |
| 2-69 | 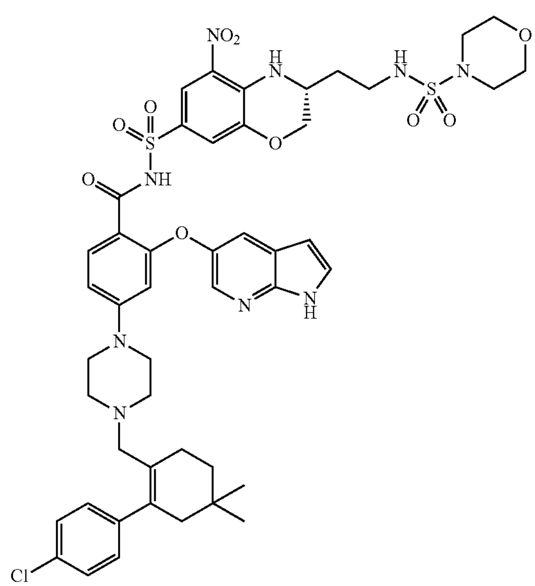 [SMILES: CC1(C)CCC(CN2CCN(c3ccc(C(=O)NS(=O)(=O)c4cc5c(c([N+](=O)[O-])c4)N[C@H](CCNS(=O)(=O)N4CCOCC4)CO5)c(Oc4cnc5[nH]ccc5c4)c3)CC2)=C(c2ccc(Cl)cc2)C1] | (R)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-(2-(morpholine-4-sulfonamido)ethyl)-5-nitro-3,4-dihydro-2H-benzo[b][1,4]oxazin-7-yl)sulfonyl)benzamide | MS-ESI (m/z): 1004 [M + 1]$^+$ |

| EXAMPLE | STRUCTURE | NAME | DATA |
|---|---|---|---|
| 2-70 | 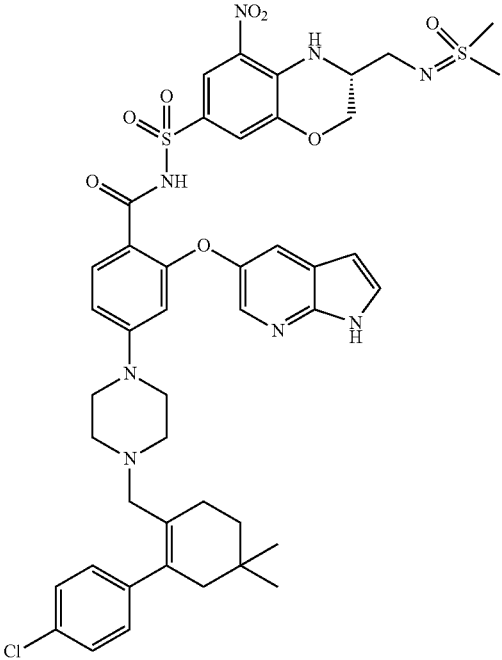 [SMILES: CC1(C)CCC(CN2CCN(c3ccc(C(=O)NS(=O)(=O)c4cc5c(c([N+](=O)[O-])c4)N[C@H](CN=S(C)(C)=O)CO5)c(Oc4cnc5[nH]ccc5c4)c3)CC2)=C(c2ccc(Cl)cc2)C1] | (R)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-(((dimethyl(oxo)-$\lambda^6$-sulfanylidene)amino)methyl)-5-nitro-3,4-dihydro-2H-benzo[b][1,4]oxazin-7-yl)sulfonyl)benzamide | MS-ESI (m/z): 917 [M + 1]$^+$ |
| 2-71 | 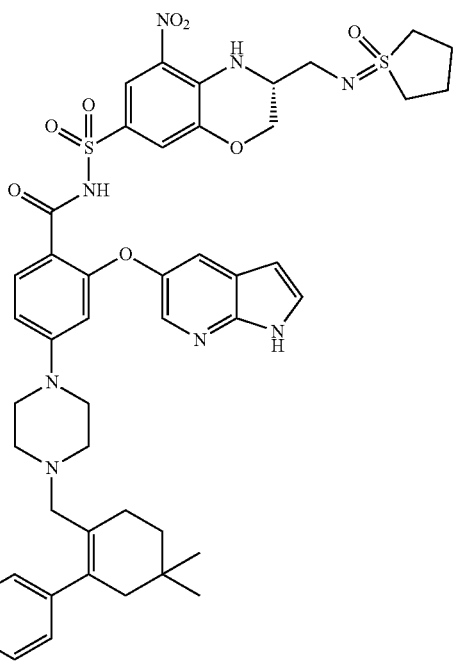 | (R)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((5-nitro-3-(((1-oxidotetrahydro-1$\lambda^6$-thiophen-1-ylidene)amino)methyl)-3,4-dihydro-2H-benzo[b][1,4]oxazin-7-yl)sulfonyl)benzamide | MS-ESI (m/z): 943 [M + 1]$^+$ |

| EXAMPLE | STRUCTURE | NAME | DATA |
|---|---|---|---|
| 2-72 | 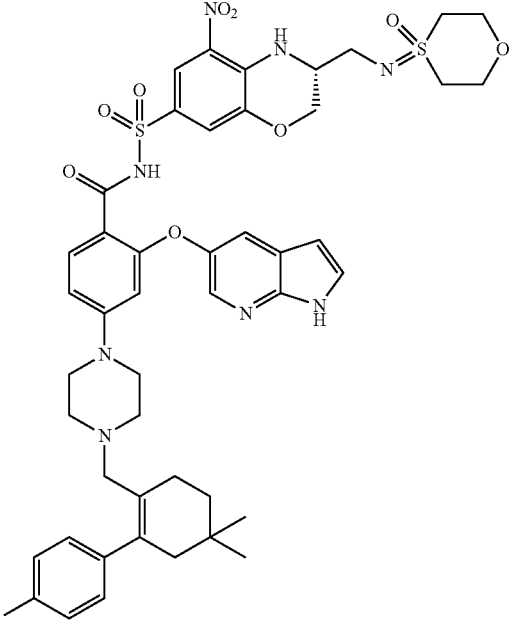 | (R)-2-((1H-pyrrolo[2,3-b]pyridin-5-yl)oxy)-4-(4-((4'-chloro-5,5-dimethyl-3,4,5,6-tetra-hydro-[1,1'-biphenyl]-2-yl)methyl)piperazin-1-yl)-N-((5-nitro-3-(((4-oxido-1,4$\lambda^6$-oxathian-4-ylidene)amino)methyl)-3,4-dihydro-2H-benzo[b][1,4]oxazin-7-yl)sulfonyl)benzamide | MS-ESI (m/z): 959 [M + 1]$^+$ |
| 2-73 | 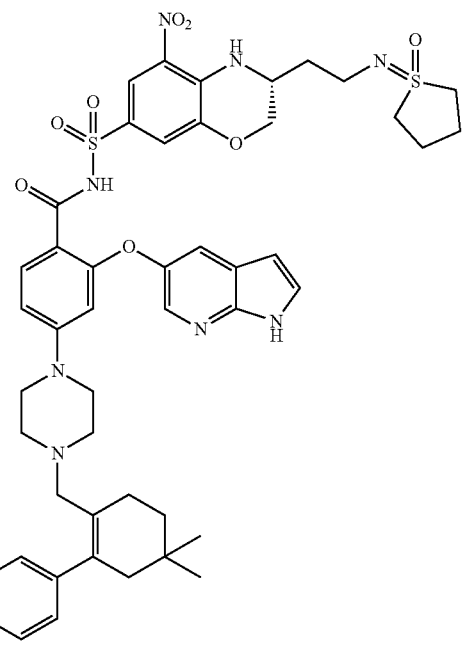 | (R)-2-((1H-pyrrolo[2,3-b]pyridin-5-yl)oxy)-4-(4-((4'-chloro-5,5-dimethyl-3,4,5,6-tetra-hydro-[1,1'-biphenyl]-2-yl)methyl)piperazin-1-yl)-N-((5-nitro-3-(2-((1-oxidotetrahydro-1$\lambda^6$-thiophen-1-ylidene)amino)ethyl)-3,4-dihydro-2H-benzo[b][1,4]oxazin-7-yl)sulfonyl)benzamide | MS-ESI (m/z): 957 [M + 1]$^+$ |

TABLE 2-continued

| EXAMPLE | STRUCTURE | NAME | DATA |
|---|---|---|---|
| 2-74 | 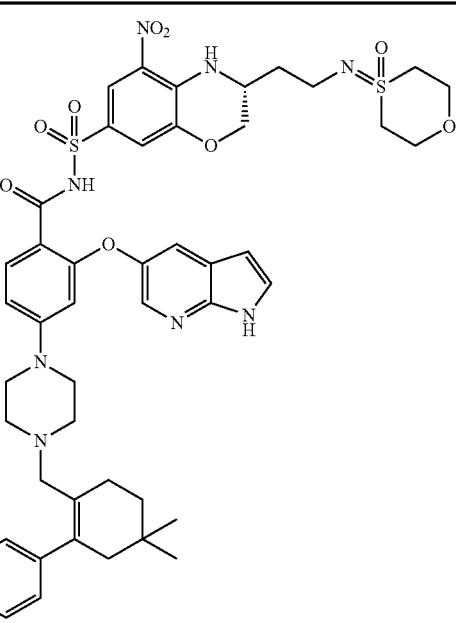 | (R)-2-((1H-pyrrolo[2,3-b]pyridin-5-yl)oxy)-4-(4-((4'-chloro-5,5-dimethyl-3,4,5,6-tetra-hydro-[1,1'-biphenyl]-2-yl)methyl)piperazin-1-yl)-N-((5-nitro-3-(2-((4-oxido-1,4λ6-oxathian-4-ylidene)amino)ethyl)-3,4-dihydro-2H-benzo[b][1,4]oxazin-7-yl)sulfonyl)benzamide | MS-ESI (m/z): 973 [M + 1]+ |
| 2-75 | 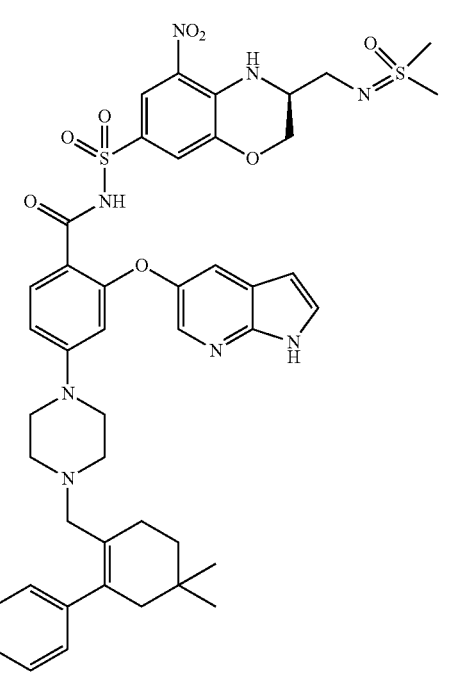 | (S)-2-((1H-pyrrolo[2,3-b]pyridin-5-yl)oxy)-4-(4-((4'-chloro-5,5-dimethyl-3,4,5,6-tetra-hydro-[1,1'-biphenyl]-2-yl)methyl)piperazin-1-yl)-N-((3-(((dimethyl(oxo)-λ6-sulfanylidene)amino)methyl)-5-nitro-3,4-dihydro-2H-benzo[b][1,4]oxazin-7-yl)sulfonyl)benzamide | MS-ESI (m/z): 917 [M + 1]+ |

| EXAMPLE | STRUCTURE | NAME | DATA |
|---|---|---|---|
| 2-76 | 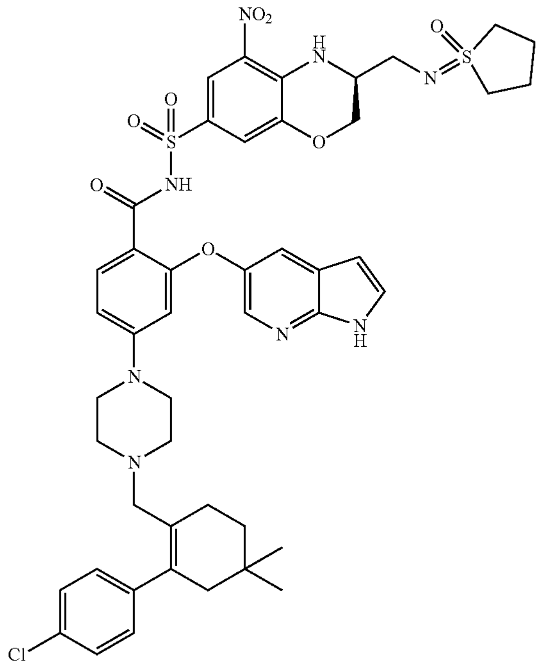 [SMILES: CC1(C)CCC(CN2CCN(c3ccc(C(=O)NS(=O)(=O)c4cc5c(c([N+](=O)[O-])c4)N[C@@H](CN=S4(=O)CCCC4)CO5)c(Oc4cnc5[nH]ccc5c4)c3)CC2)=C(c2ccc(Cl)cc2)C1] | (S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((5-nitro-3-(((1-oxidotetrahydro-1$\lambda^6$-thiophen-1-ylidene)amino)methyl)-3,4-dihydro-2H-benzo[b][1,4]oxazin-7-yl)sulfonyl)benzamide | MS-ESI (m/z): 943 [M + 1]$^+$ |
| 2-77 | 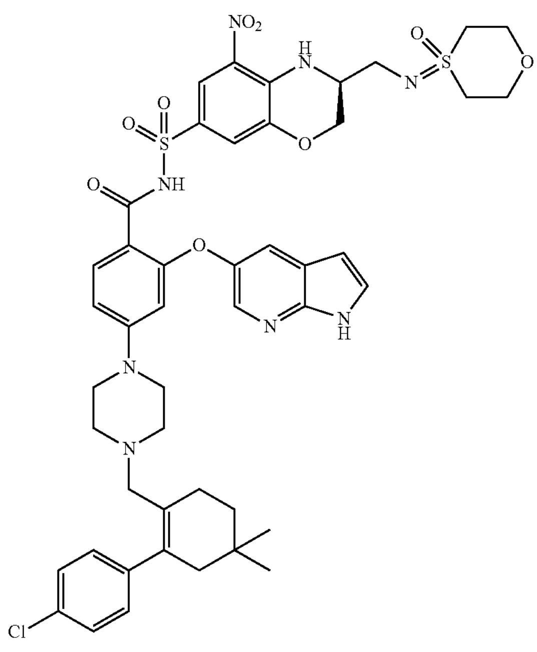 [SMILES: CC1(C)CCC(CN2CCN(c3ccc(C(=O)NS(=O)(=O)c4cc5c(c([N+](=O)[O-])c4)N[C@@H](CN=S4(=O)CCOCC4)CO5)c(Oc4cnc5[nH]ccc5c4)c3)CC2)=C(c2ccc(Cl)cc2)C1] | (S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((5-nitro-3-(((4-oxido-1,4$\lambda^6$-oxathian-4-ylidene)amino)methyl)-3,4-dihydro-2H-benzo[b][1,4]oxazin-7-yl)sulfonyl)benzamide | MS-ESI (m/z): 959 [M + 1]$^+$ |

| EXAMPLE | STRUCTURE | NAME | DATA |
|---|---|---|---|
| 2-78 | 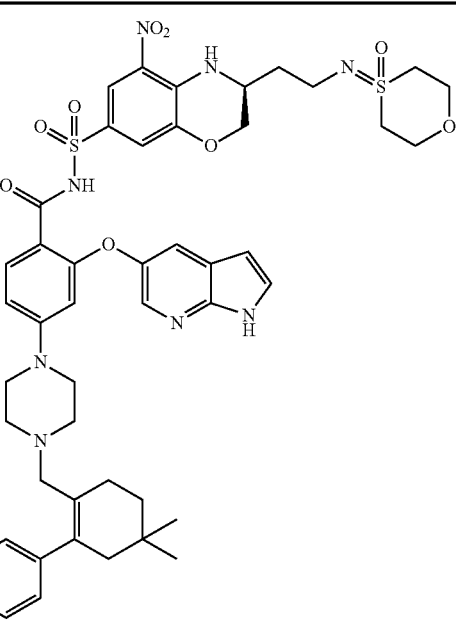 | (S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((5-nitro-3-(2-((4-oxido-1,4^6-oxathian-4-ylidene)amino)ethyl)-3,4-dihydro-2H-benzo[b][1,4]oxazin-7-yl)sulfonyl)benzamide | MS-ESI (m/z): 973 [M + 1]⁺ |
| 2-79 | 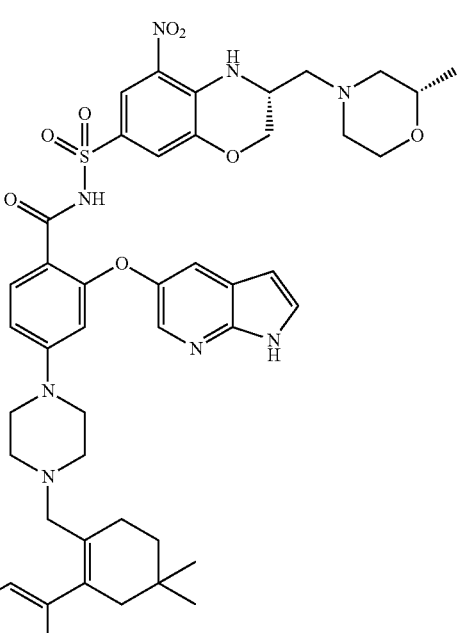 | 2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-(((R)-3-(((S)-2-methylmorpholino)methyl)-5-nitro-3,4-dihydro-2H-benzo[b][1,4]oxazin-7-yl)sulfonyl)benzamide | MS-ESI (m/z): 925 [M + 1]⁺ |

TABLE 2-continued

| EXAMPLE | STRUCTURE | NAME | DATA |
|---|---|---|---|
| 2-80 | 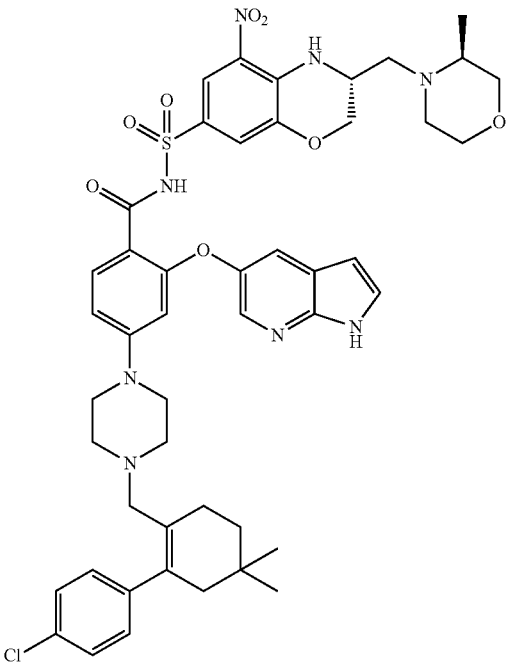 [SMILES: C[C@H]1COCCN1C[C@@H]1COc2cc(S(=O)(=O)NC(=O)c3ccc(N4CCN(CC5=C(c6ccc(Cl)cc6)CC(C)(C)CC5)CC4)cc3Oc3cnc4[nH]ccc4c3)cc([N+](=O)[O-])c2N1] | 2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-(((R)-3-(((S)-3-methylmorpholino)methyl)-5-nitro-3,4-dihydro-2H-benzo[b][1,4]oxazin-7-yl)sulfonyl)benzamide | MS-ESI (m/z): 925 [M + 1]+ |
| 2-81 | 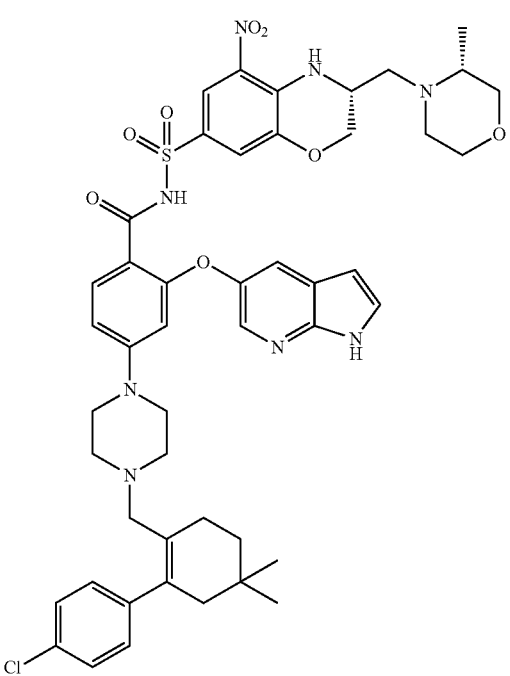 [SMILES: C[C@@H]1COCCN1C[C@@H]1COc2cc(S(=O)(=O)NC(=O)c3ccc(N4CCN(CC5=C(c6ccc(Cl)cc6)CC(C)(C)CC5)CC4)cc3Oc3cnc4[nH]ccc4c3)cc([N+](=O)[O-])c2N1] | 2-((1H-pyrrolo[2,3-b]pyridin-5-yl)oxy)-4-(4-((4'-chloro-5,5-dimethyl-3,4,5,6-tetrahydro-[1,1,'-biphenyl]-2-yl)methyl)piperazin-1-yl)-N-(((R)-3-(((R)-3-methylmorpholino)methyl)-5-nitro-3,4-dihydro-2H-benzo[b][1,4]oxazin-7-yl)sulfonyl)benzamide | MS-ESI (m/z): 925 [M + 1]+ |

TABLE 2-continued

| EXAMPLE | STRUCTURE | NAME | DATA |
|---|---|---|---|
| 2-82 | 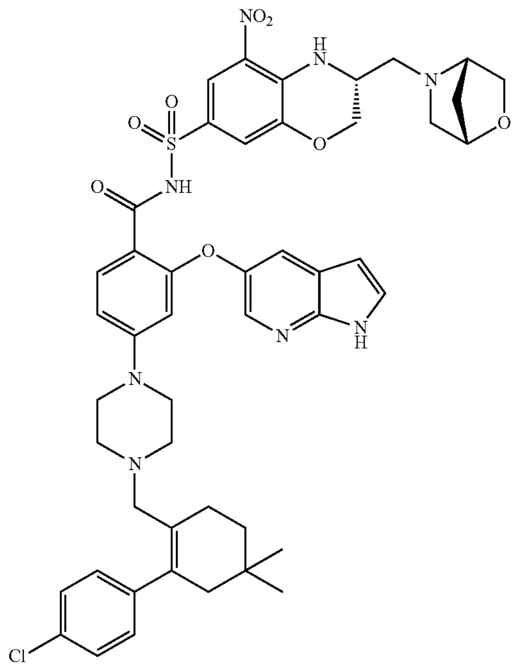 [SMILES: CC1(C)CCC(CN2CCN(c3ccc(C(=O)NS(=O)(=O)c4cc5c(c([N+](=O)[O-])c4)N[C@H](CN4C[C@@H]6C[C@H]4CO6)CO5)c(Oc4cnc5[nH]ccc5c4)c3)CC2)=C(c2ccc(Cl)cc2)C1] | 2-((1H-pyrrolo[2,3-b]pyridin-5-yl)oxy)-N-(((R)-3-(((1S,4S)-2-oxa-5-azabicyclo[2.2.1]heptan-5-yl)methyl)-5-nitro-3,4-dihydro-2H-benzo[b][1,4]oxazin-7-yl)sulfonyl)-4-(4-((4'-chloro-5,5-dimethyl-3,4,5,6-tetrahydro-[1,1'-biphenyl]-2-yl)methyl)piperazin-1-yl)benzamide | MS-ESI (m/z): 923 [M + 1]+ |
| 2-83 | 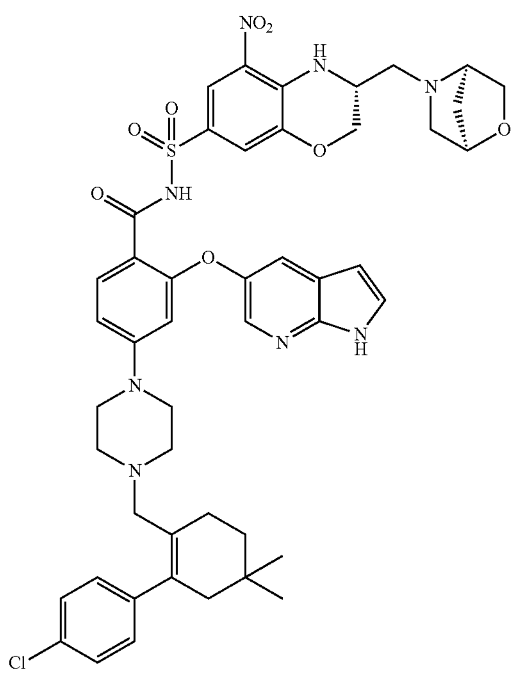 [SMILES: CC1(C)CCC(CN2CCN(c3ccc(C(=O)NS(=O)(=O)c4cc5c(c([N+](=O)[O-])c4)N[C@H](CN4C[C@H]6C[C@@H]4CO6)CO5)c(Oc4cnc5[nH]ccc5c4)c3)CC2)=C(c2ccc(Cl)cc2)C1] | 2-((1H-pyrrolo[2,3-b]pyridin-5-yl)oxy)-N-(((R)-3-(((1R,4R)-2-oxa-5-azabicyclo[2.2.1]heptan-5-yl)methyl)-5-nitro-3,4-dihydro-2H-benzo[b][1,4]oxazin-7-yl)sulfonyl)-4-(4-((4'-chloro-5,5-dimethyl-3,4,5,6-tetrahydro-[1,1'-biphenyl]-2-yl)methyl)piperazin-1-yl)benzamide | MS-ESI (m/z): 923 [M + 1]+ |

TABLE 2-continued

| EXAMPLE | STRUCTURE | NAME | DATA |
|---|---|---|---|
| 2-84 | 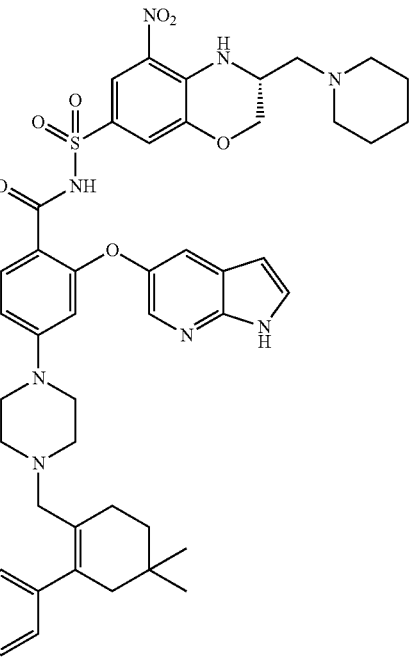 | (R)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((5-nitro-3-(piperidin-1-ylmethyl)-3,4-dihydro-2H-benzo[b][1,4]oxazin-7-yl)sulfonyl)benzamide | MS-ESI (m/z): 909 [M + 1]+ |
| 2-85 | 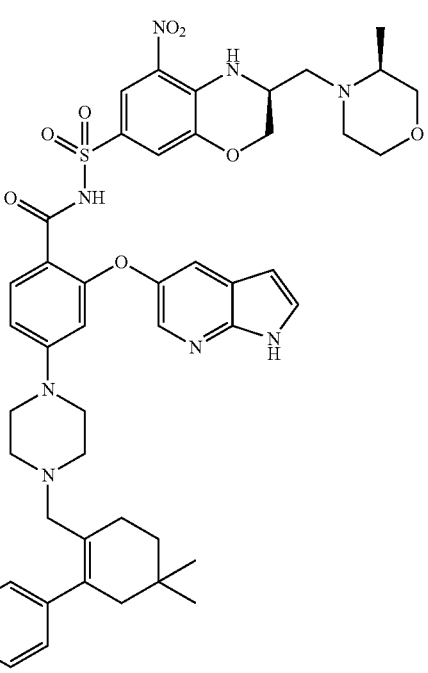 | 2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-(((S)-3-(((S)-3-methylmorpholino)methyl)-5-nitro-3,4-dihydro-2H-benzo[b][1,4]oxazin-7-yl)sulfonyl)benzamide | MS-ESI (m/z): 925 [M + 1]+ |

TABLE 2-continued

| EXAMPLE | STRUCTURE | NAME | DATA |
|---|---|---|---|
| 2-86 | 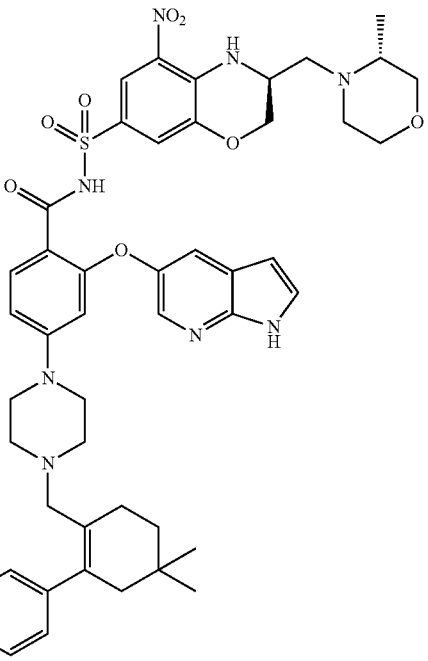 | 2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-(((S)-3-(((R)-3-methylmorpholino)methyl)-5-nitro-3,4-dihydro-2H-benzo[b][1,4]oxazin-7-yl)sulfonyl)benzamide | MS-ESI (m/z): 925 [M + 1]+ |
| 2-87 | 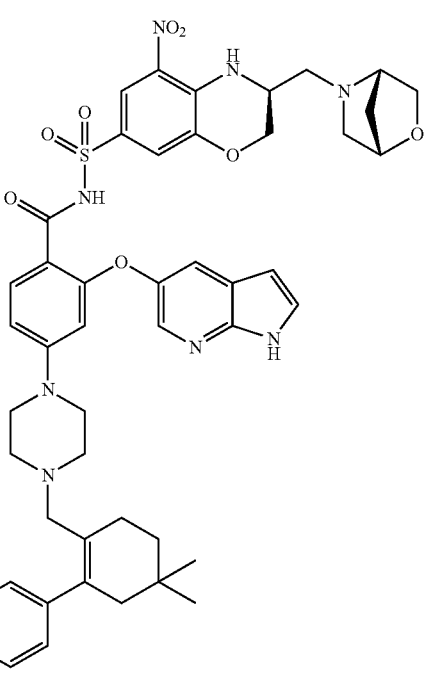 | 2-((1H-pyrrolo[2,3-b]pyridin-5-yl)oxy)-N-(((S)-3-(((1S,4S)-2-oxa-5-azabicyclo[2.2.1]heptan-5-yl)methyl)-5-nitro-3,4-dihydro-2H-benzo[b][1,4]oxazin-7-yl)sulfonyl)-4-(4-((4'-chloro-5,5-dimethyl-3,4,5,6-tetrahydro-[1,1'-biphenyl]-2-yl)methyl)piperazin-1-yl)benzamide | MS-ESI (m/z): 923 [M + 1]+ |

TABLE 2-continued

| EXAMPLE | STRUCTURE | NAME | DATA |
|---|---|---|---|
| 2-88 | 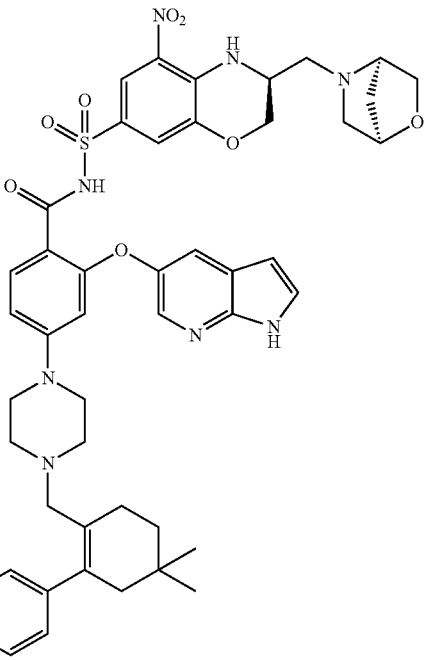 | 2-((1H-pyrrolo[2,3-b]pyridin-5-yl)oxy)-N-(((S)-3-(((1R,4R)-2-oxa-5-azabicyclo[2.2.1]heptan-5-yl)methyl)-5-nitro-3,4-dihydro-2H-benzo[b][1,4]oxazin-7-yl)sulfonyl)-4-(4-((4'-chloro-5,5-dimethyl-3,4,5,6-tetrahydro-[1,1'-biphenyl]-2-yl)methyl)piperazin-1-yl)benzamide | MS-ESI (m/z): 923 [M + 1]+ |
| 2-89 | 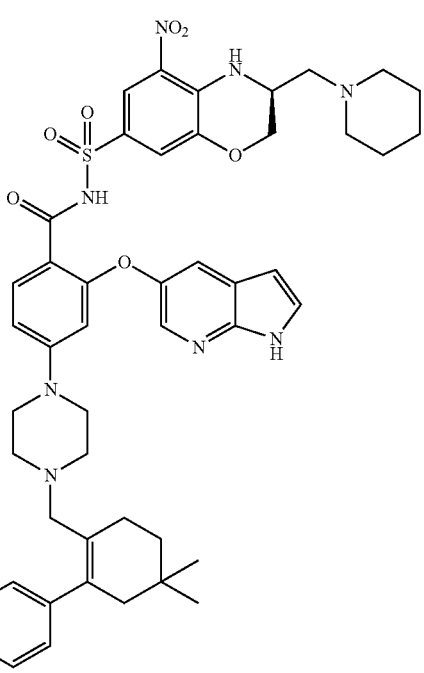 | (S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((5-nitro-3-(piperidin-1-ylmethyl)-3,4-dihydro-2H-benzo[b][1,4]oxazin-7-yl)sulfonyl)benzamide | MS-ESI (m/z): 909 [M + 1]+ |

TABLE 2-continued

| EXAMPLE | STRUCTURE | NAME | DATA |
|---|---|---|---|
| 2-90 | 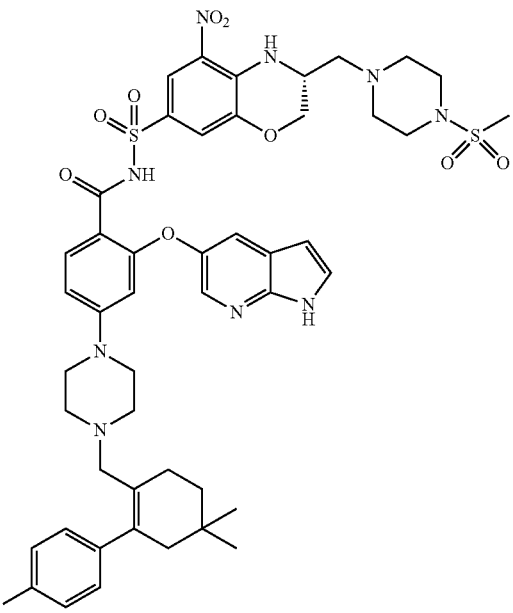 | (R)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-((4-(methylsulfonyl)piperazin-1-yl)methyl)-5-nitro-3,4-dihydro-2H-benzo[b][1,4]oxazin-7-yl)sulfonyl)benzamide | MS-ESI (m/z): 988 [M + 1]+ |
| 2-91 | 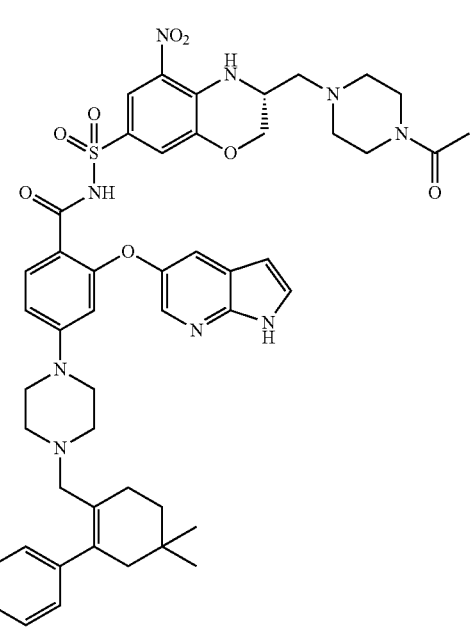 | (R)-2-((1H-pyrrolo[2,3-b]pyridin-5-yl)oxy)-N-((3-((4-acetylpiperazin-1-yl)methyl)-5-nitro-3,4-dihydro-2H-benzo[b][1,4]oxazin-7-yl)sulfonyl)-4-(4-((4'-chloro-5,5-dimethyl-3,4,5,6-tetrahydro-[1,1'-biphenyl]-2-yl)methyl)piperazin-1-yl)benzamide | MS-ESI (m/z): 952 [M + 1]+ |

TABLE 2-continued

| EXAMPLE | STRUCTURE | NAME | DATA |
|---|---|---|---|
| 2-92 | 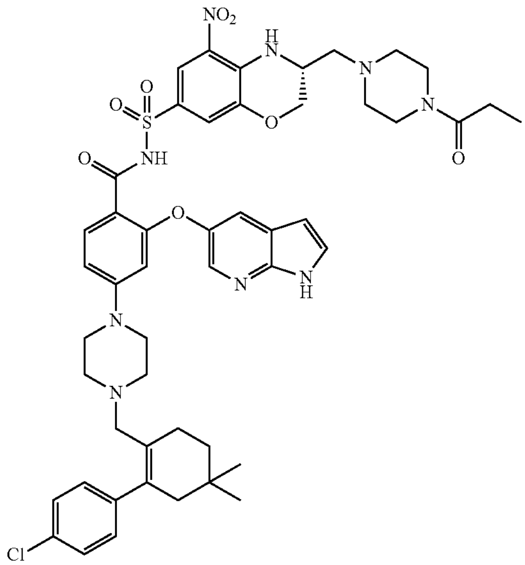 | (R)-2-((1H-pyrrolo[2,3-b]pyridin-5-yl)oxy)-(4-((4'-chloro-5,5-dimethyl-3,4,5,6-tetrahydro-[1,1'-biphenyl]-2-yl)methyl)piperazin-1-yl)-N-((5-nitro-3-((4-propionylpiperazin-1-yl)methyl)-3,4-dihydro-2H-benzo[b][1,4]oxazin-7-yl)sulfonyl)benzamide | MS-ESI (m/z): 966 [M + 1]$^+$ |
| 2-93 | 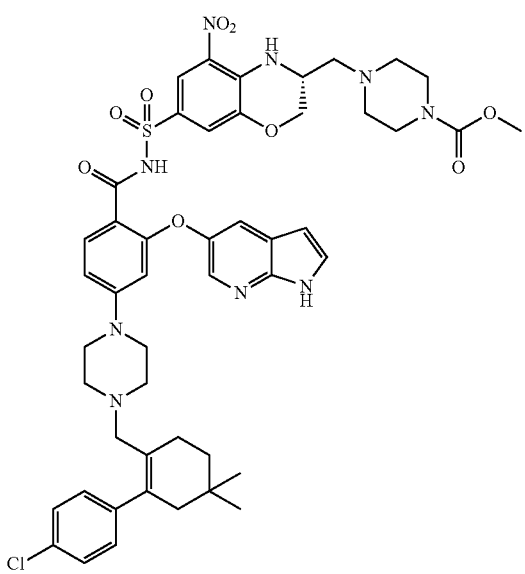 [SMILES: COC(=O)N1CCN(C[C@@H]2COc3cc(S(=O)(=O)NC(=O)c4ccc(N5CCN(CC6=C(c7ccc(Cl)cc7)CC(C)(C)CC6)CC5)cc4Oc4cnc5[nH]ccc5c4)cc([N+](=O)[O-])c3N2)CC1] | methyl (R)-4-((7-(N-(2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)benzoyl)sulfamoyl)-5-nitro-3,4-dihydro-2H-benzo[b][1,4]oxazin-3-yl)methyl)piperazin-1-carboxylate | MS-ESI (m/z): 968 [M + 1]$^+$ |

TABLE 2-continued

| EXAMPLE | STRUCTURE | NAME | DATA |
|---|---|---|---|
| 2-94 | 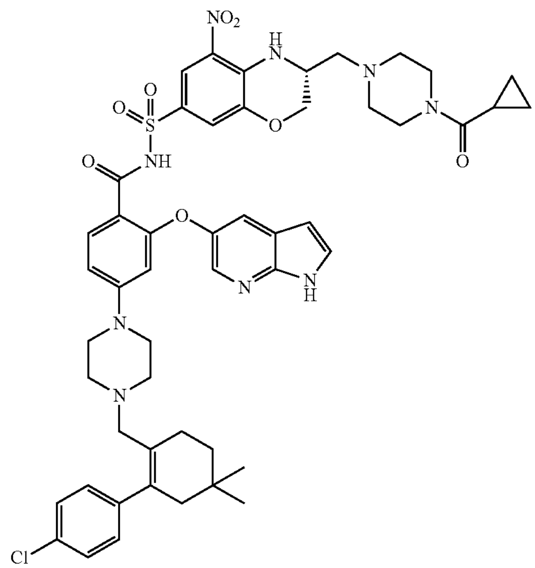 [SMILES: CC1(C)CCC(CN2CCN(c3ccc(C(=O)NS(=O)(=O)c4cc5c(c([N+](=O)[O-])c4)N[C@H](CN4CCN(C(=O)C6CC6)CC4)CO5)c(Oc4cnc5[nH]ccc5c4)c3)CC2)=C(c2ccc(Cl)cc2)C1] | (R)-2-((1H-pyrrolo[2,3-b]pyridin-5-yl)oxy)-4-(4-((4'-chloro-5,5-dimethyl-3,4,5,6-tetra-hydro-[1,1'-biphenyl]-2-yl)methyl)piperazin-1-yl)-N-((3-((4-(cyclopropanecarbonyl)piperazin-1-yl)methyl)-5-nitro-3,4-dihydro-2H-benzo[b][1,4]oxazin-7-yl)sulfonyl)benzamide | MS-ESI (m/z): 978 [M + 1]⁺ |
| 2-95 | 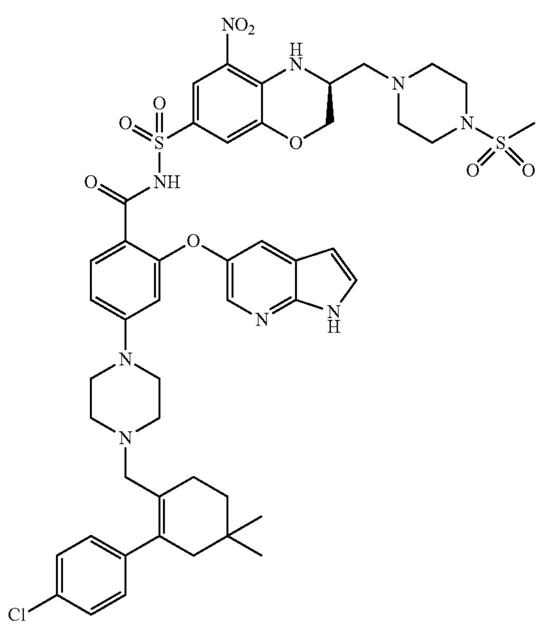 [SMILES: CC1(C)CCC(CN2CCN(c3ccc(C(=O)NS(=O)(=O)c4cc5c(c([N+](=O)[O-])c4)N[C@@H](CN4CCN(S(C)(=O)=O)CC4)CO5)c(Oc4cnc5[nH]ccc5c4)c3)CC2)=C(c2ccc(Cl)cc2)C1] | (S)-2-((1H-pyrrolo[2,3-b]pyridin-5-yl)oxy)-4-(4-((4'-chloro-5,5-dimethyl-3,4,5,6-tetra-hydro[1,1'-biphenyl]-2-yl)methyl)piperazin-1-yl)-N-((3-((4-(methylsulfonyl)piperazin-1-yl)methyl)-5-nitro-3,4-dihydro-2H-benzo[b][1,4]oxazin-7-yl)sulfonyl)benzamide | MS-ESI (m/z): 988 [M + 1]⁺ |

TABLE 2-continued

| EXAMPLE | STRUCTURE | NAME | DATA |
|---|---|---|---|
| 2-96 | 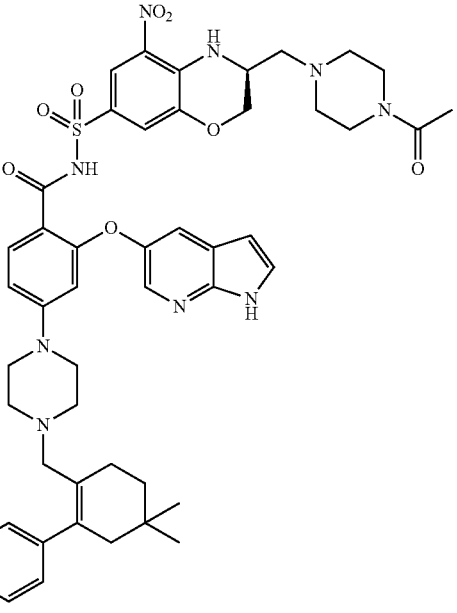 | (S)-2-((1H-pyrrolo[2,3-b]pyridin-5-yl)oxy)-N-((3-((4-acetylpiperazin-1-yl)methyl)-5-nitro-3,4-dihydro-2H-benzo[b][1,4]oxazin-7-yl)sulfonyl)-4-(4-((4'-chloro-5,5-dimethyl-3,4,5,6-tetrahydro-[1,1'-biphenyl]-2-yl)methyl)piperazin-1-yl)benzamide | MS-ESI (m/z): 952 [M + 1]+ |
| 2-97 | 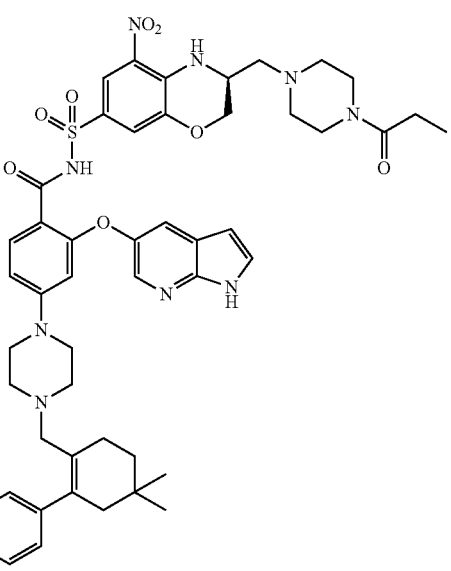 | (S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((5-nitro-3-((4-propionylpiperazin-1-yl)methyl)-3,4-dihydro-2H-benzo[b][1,4]oxazin-7-yl)sulfonyl)benzamide | MS-ESI (m/z): 966 [M + 1]+ |

TABLE 2-continued

| EXAMPLE | STRUCTURE | NAME | DATA |
|---|---|---|---|
| 2-98 | 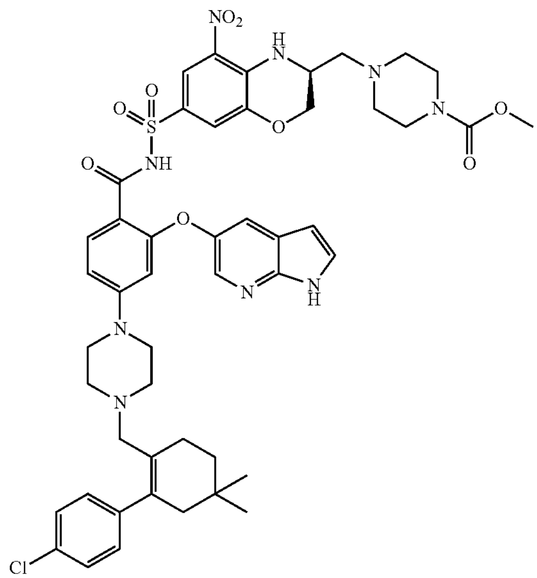 | methyl (S)-4-((7-(N-(2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)benzoyl)sulfamoyl)-5-nitro-3,4-dihydro-2H-benzo[b][1,4]oxazin-3-yl)methyl)piperazin-1-carboxylate | MS-ESI (m/z): 968 [M + 1]+ |
| 2-99 | 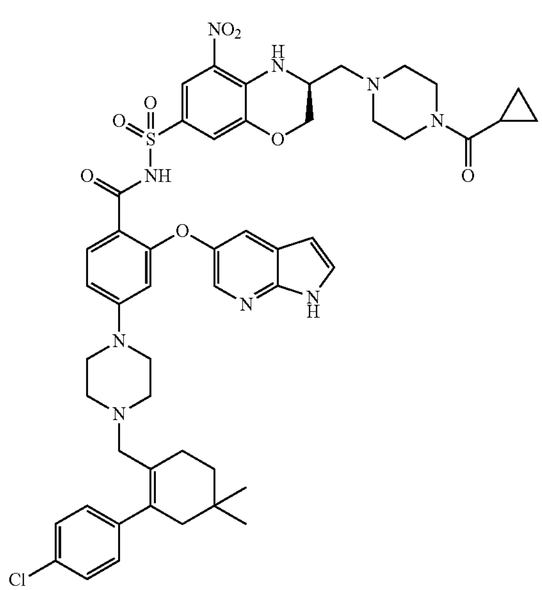 [SMILES: CC1(C)CCC(CN2CCN(c3ccc(C(=O)NS(=O)(=O)c4cc5c(c([N+](=O)[O-])c4)N[C@@H](CN4CCN(C(=O)C6CC6)CC4)CO5)c(Oc4cnc5[nH]ccc5c4)c3)CC2)=C(c2ccc(Cl)cc2)C1] | (S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-((4-(cyclopropanecarbonyl)piperazin-1-yl)methyl)-5-nitro-3,4-dihydro-2H-benzo[b][1,4]oxazin-7-yl)sulfonyl)benzamide | MS-ESI (m/z): 978 [M + 1]+ |

TABLE 2-continued

| EXAMPLE | STRUCTURE | NAME | DATA |
|---|---|---|---|
| 2-100 | 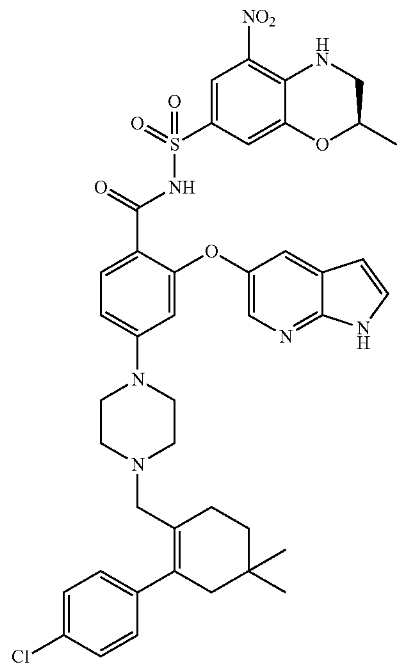 [SMILES: C[C@@H]1CNc2c(cc(S(=O)(=O)NC(=O)c3ccc(N4CCN(CC5=C(c6ccc(Cl)cc6)CC(C)(C)CC5)CC4)cc3Oc3cnc4[nH]ccc4c3)cc2[N+](=O)[O-])O1] | (R)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((2-methyl-5-nitro-3,4-dihydro-2H-benzo[b][1,4]oxazin-7-yl)sulfonyl)benzamide | MS-ESI (m/z): 826 [M + 1]+ |
| 2-101 | 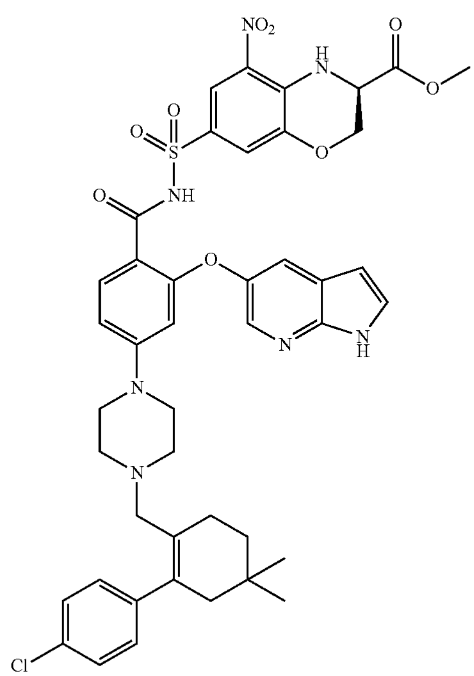 [SMILES: COC(=O)[C@H]1COc2cc(S(=O)(=O)NC(=O)c3ccc(N4CCN(CC5=C(c6ccc(Cl)cc6)CC(C)(C)CC5)CC4)cc3Oc3cnc4[nH]ccc4c3)cc([N+](=O)[O-])c2N1] | methyl (R)-7-(N-(2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)benzoyl)sulfamoyl)-5-nitro-3,4-dihydro-2H-benzo[b][1,4]oxazine-3-carboxylate | MS-ESI (m/z): 870 [M + 1]+ |

TABLE 2-continued

| EXAMPLE | STRUCTURE | NAME | DATA |
|---------|-----------|------|------|
| 2-102 | 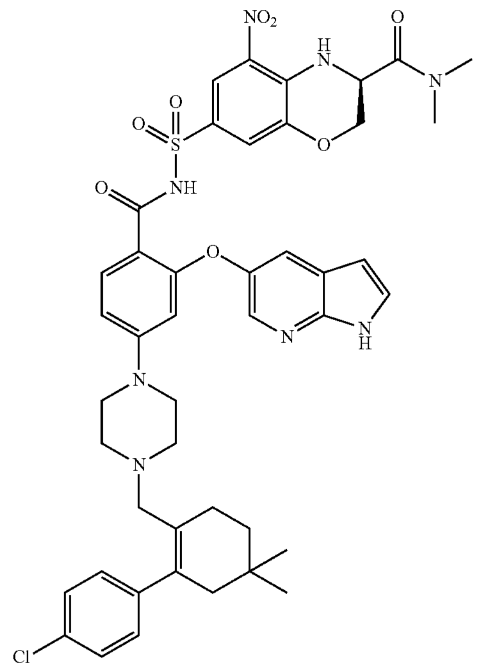 [SMILES: CN(C)C(=O)[C@H]1COc2cc(S(=O)(=O)NC(=O)c3ccc(N4CCN(CC5=C(c6ccc(Cl)cc6)CC(C)(C)CC5)CC4)cc3Oc3cnc4[nH]ccc4c3)cc([N+](=O)[O-])c2N1] | (R)-7-(N-(2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)benzoyl)sulfamoyl)-N,N-dimethyl-5-nitro-3,4-dihydro-2H-benzo[b][1,4]oxazine-3-carboxamide | MS-ESI (m/z): 883 [M + 1]+ |
| 2-103 | 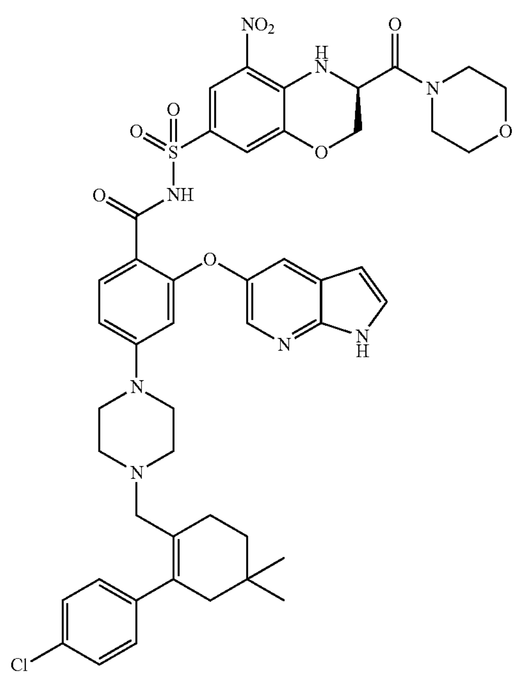 [SMILES: CC1(C)CCC(CN2CCN(c3ccc(C(=O)NS(=O)(=O)c4cc5c(c([N+](=O)[O-])c4)N[C@@H](C(=O)N4CCOCC4)CO5)c(Oc4cnc5[nH]ccc5c4)c3)CC2)=C(c2ccc(Cl)cc2)C1] | (R)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-(morpholine-4-carbonyl)-5-nitro-3,4-dihydro-2H-benzo[b][1,4]oxazin-7-yl)sulfonyl)benzamide | MS-ESI (m/z): 925 [M + 1]+ |

TABLE 2-continued

| EXAMPLE | STRUCTURE | NAME | DATA |
|---|---|---|---|
| 2-104 | 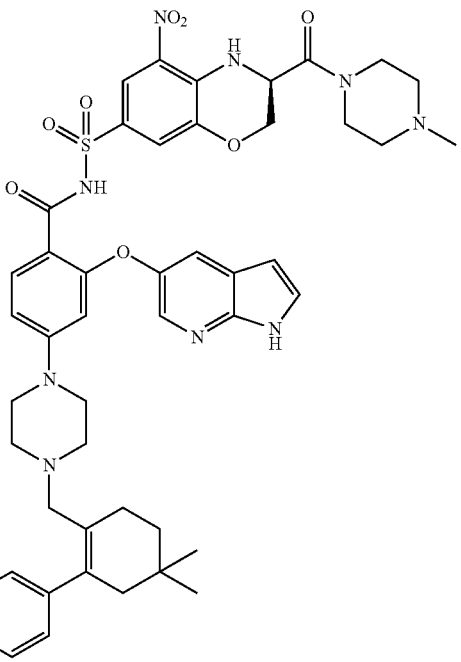 | (R)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-(4-methylpiperazin--1carbonyl)-5-nitro-3,4-dihydro-2H-benzo[b][1,4]oxazin-7-yl)sulfonyl)benzamide | MS-ESI (m/z): 938 [M + 1]+ |
| 2-105 | 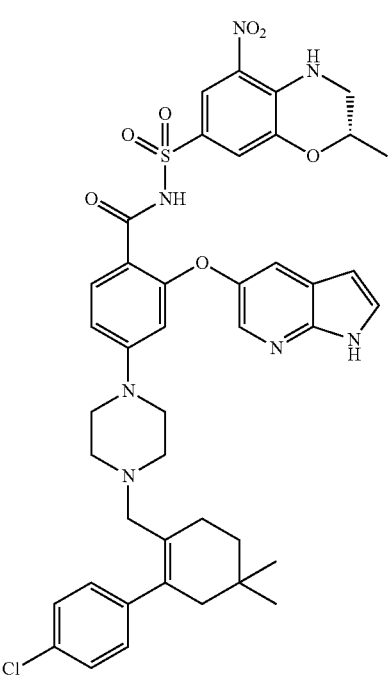 [SMILES: C[C@H]1CNc2c(cc(S(=O)(=O)NC(=O)c3ccc(N4CCN(CC5=C(c6ccc(Cl)cc6)CC(C)(C)CC5)CC4)cc3Oc3cnc4[nH]ccc4c3)cc2[N+](=O)[O-])O1] | (S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((2-methyl-5-nitro-3,4-dihydro-2H-benzo[b][1,4]oxazin-7-yl)sulfonyl)benzamide | MS-ESI (m/z): 826 [M + 1]+ |

TABLE 2-continued

| EXAMPLE | STRUCTURE | NAME | DATA |
|---|---|---|---|
| 2-106 | 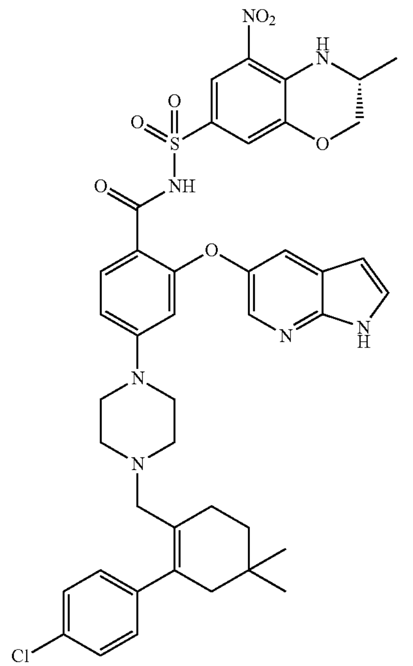 [SMILES: C[C@@H]1COc2cc(S(=O)(=O)NC(=O)c3ccc(N4CCN(CC5=C(c6ccc(Cl)cc6)CC(C)(C)CC5)CC4)cc3Oc3cnc4[nH]ccc4c3)cc([N+](=O)[O-])c2N1] | (R)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-methyl-5-nitro-3,4-dihydro-2H-benzo[b][1,4]oxazin-7-yl)sulfonyl)benzamide | MS-ESI (m/z): 826 [M + 1]+ |
| 2-107 | 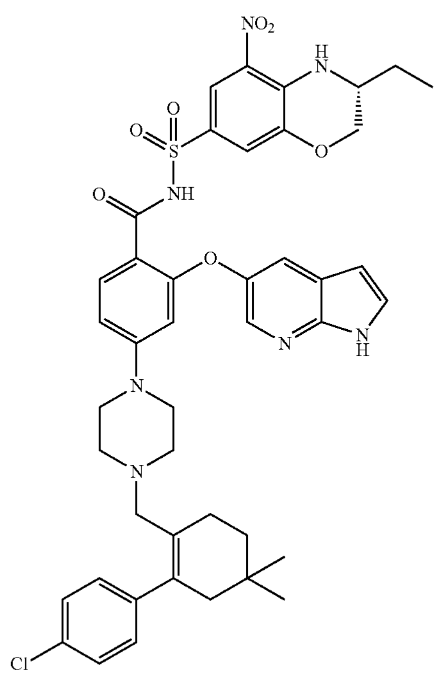 [SMILES: CC[C@@H]1COc2cc(S(=O)(=O)NC(=O)c3ccc(N4CCN(CC5=C(c6ccc(Cl)cc6)CC(C)(C)CC5)CC4)cc3Oc3cnc4[nH]ccc4c3)cc([N+](=O)[O-])c2N1] | (R)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-ethyl-5-nitro-3,4-dihydro-2H-benzo[b][1,4]oxazin-7-yl)sulfonyl)benzamide | MS-ESI (m/z): 840 [M + 1]+ |

TABLE 2-continued

| EXAMPLE | STRUCTURE | NAME | DATA |
|---|---|---|---|
| 2-108 | 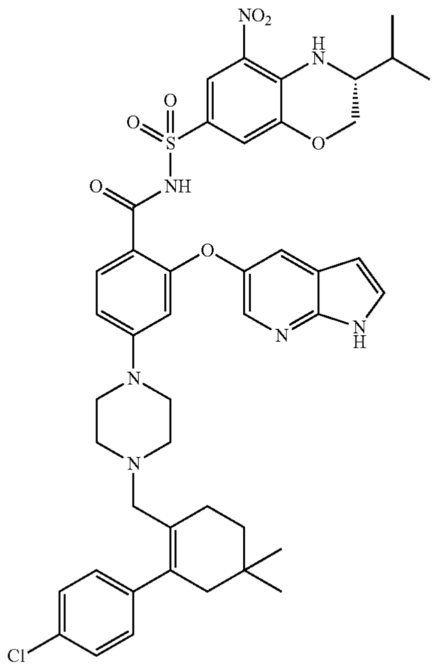 [SMILES: CC(C)[C@@H]1COc2cc(S(=O)(=O)NC(=O)c3ccc(N4CCN(CC5=C(c6ccc(Cl)cc6)CC(C)(C)CC5)CC4)cc3Oc3cnc4[nH]ccc4c3)cc([N+](=O)[O-])c2N1] | (R)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-isopropyl-5-nitro-3,4-dihydro-2H-benzo[b][1,4]oxazin-7-yl)sulfonyl)benzamide | MS-ESI (m/z): 854 [M + 1]+ |
| 2-109 | 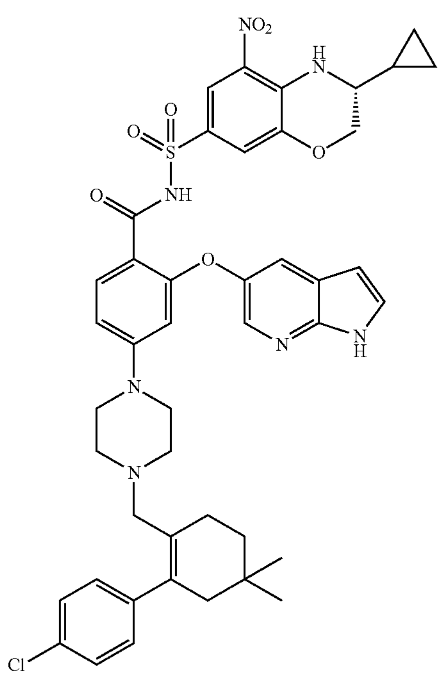 [SMILES: CC1(C)CCC(CN2CCN(c3ccc(C(=O)NS(=O)(=O)c4cc5c(c([N+](=O)[O-])c4)N[C@H](C4CC4)CO5)c(Oc4cnc5[nH]ccc5c4)c3)CC2)=C(c2ccc(Cl)cc2)C1] | (R)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-cyclopropyl-5-nitro-3,4-dihydro-2H-benzo[b][1,4]oxazin-7-yl)sulfonyl)benzamide | MS-ESI (m/z): 852 [M + 1]+ |

| EXAMPLE | STRUCTURE | NAME | DATA |
| --- | --- | --- | --- |
| 2-110 | 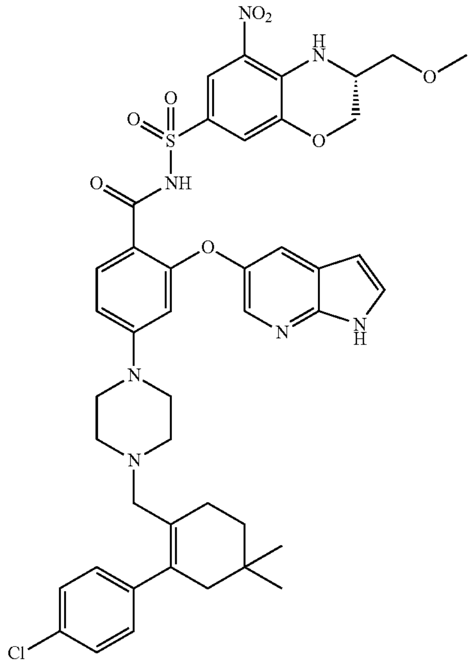 [SMILES: COC[C@@H]1COc2cc(S(=O)(=O)NC(=O)c3ccc(N4CCN(CC5=C(c6ccc(Cl)cc6)CC(C)(C)CC5)CC4)cc3Oc3cnc4[nH]ccc4c3)cc([N+](=O)[O-])c2N1] | (R)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-(methoxymethyl)-5-nitro-3,4-dihydro-2H-benzo[b][1,4]oxazin-7-yl)sulfonyl)benzamide | MS-ESI (m/z): 856 [M + 1]+ |
| 2-111 | 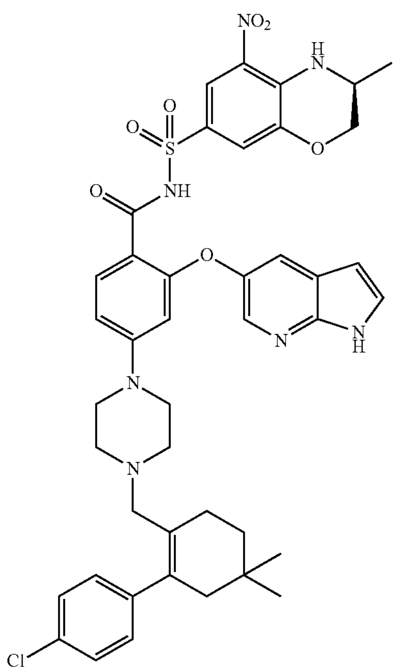 [SMILES: C[C@H]1COc2cc(S(=O)(=O)NC(=O)c3ccc(N4CCN(CC5=C(c6ccc(Cl)cc6)CC(C)(C)CC5)CC4)cc3Oc3cnc4[nH]ccc4c3)cc([N+](=O)[O-])c2N1] | (S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1yl)-N-((3-methyl-5-nitro-3,4-dihydro-2H-benzo[b][1,4]oxazin-7-yl)sulfonyl)benzamide | MS-ESI (m/z): 826 [M + 1]+ |

TABLE 2-continued

| EXAMPLE | STRUCTURE | NAME | DATA |
|---|---|---|---|
| 2-112 | 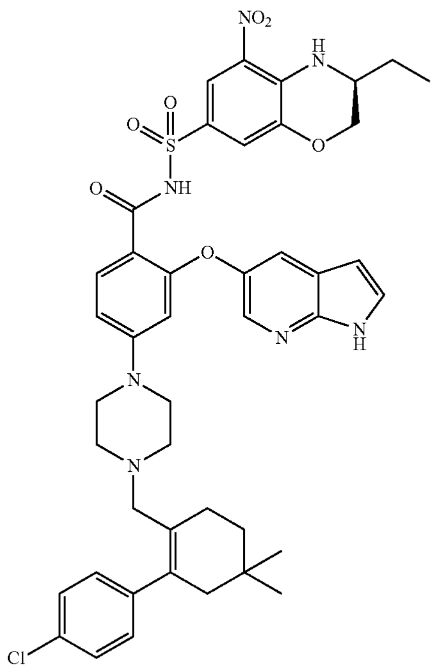 [SMILES: CC[C@H]1COc2cc(S(=O)(=O)NC(=O)c3ccc(N4CCN(CC5=C(c6ccc(Cl)cc6)CC(C)(C)CC5)CC4)cc3Oc3cnc4[nH]ccc4c3)cc([N+](=O)[O-])c2N1] | (S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-ethyl-5-nitro-3,4-dihydro-2H-benzo[b][1,4]oxazin-7-yl)sulfonyl)benzamide | MS-ESI (m/z): 840 [M + 1]+ |
| 2-113 | 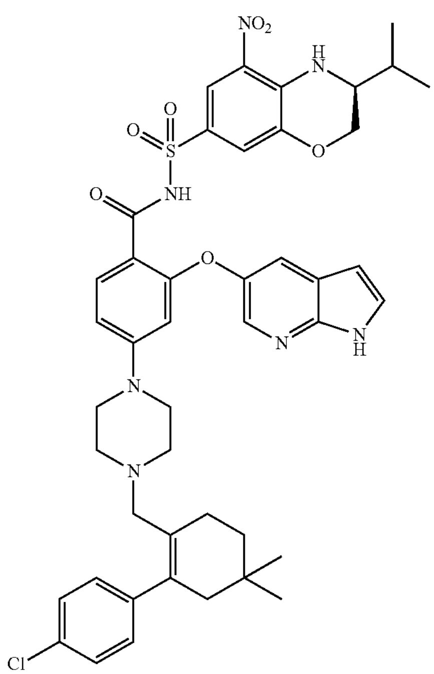 [SMILES: CC(C)[C@H]1COc2cc(S(=O)(=O)NC(=O)c3ccc(N4CCN(CC5=C(c6ccc(Cl)cc6)CC(C)(C)CC5)CC4)cc3Oc3cnc4[nH]ccc4c3)cc([N+](=O)[O-])c2N1] | (S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-isopropyl-5-nitro-3,4-dihydro-2H-benzo[b][1,4]oxazin-7-yl)sulfonyl)benzamide | MS-ESI (m/z): 854 [M + 1]+ |

TABLE 2-continued

| EXAMPLE | STRUCTURE | NAME | DATA |
|---|---|---|---|
| 2-114 | 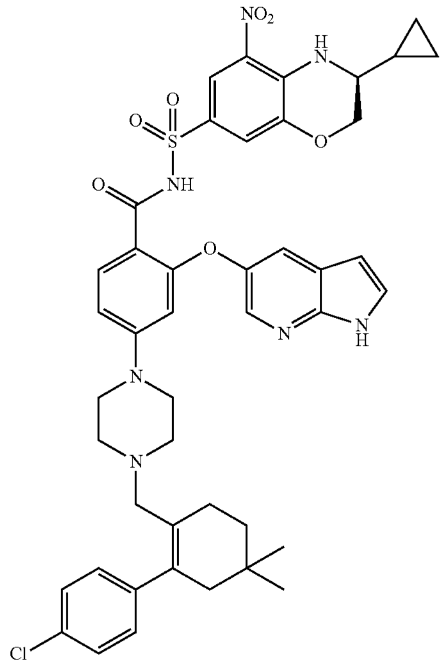 [SMILES: CC1(C)CCC(CN2CCN(c3ccc(C(=O)NS(=O)(=O)c4cc5c(c([N+](=O)[O-])c4)N[C@@H](C4CC4)CO5)c(Oc4cnc5[nH]ccc5c4)c3)CC2)=C(c2ccc(Cl)cc2)C1] | (S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-cyclopropyl-5-nitro-3,4-dihydro-2H-benzo[b][1,4]oxazin-7-yl)sulfonyl)benzamide | MS-ESI (m/z): 852 [M + 1]+ |
| 2-115 | 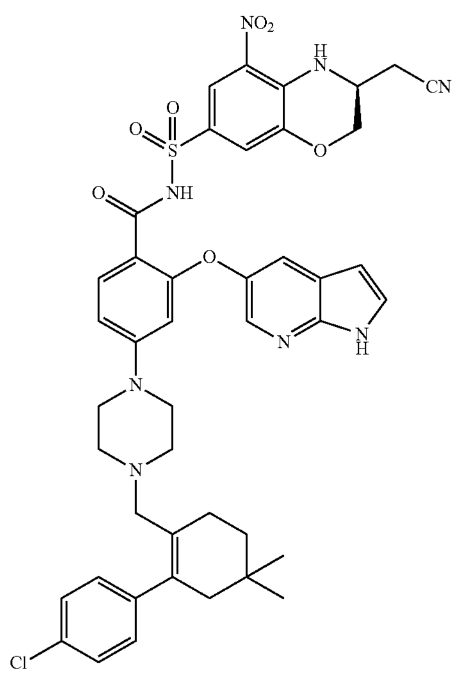 [SMILES: CC1(C)CCC(CN2CCN(c3ccc(C(=O)NS(=O)(=O)c4cc5c(c([N+](=O)[O-])c4)N[C@@H](CC#N)CO5)c(Oc4cnc5[nH]ccc5c4)c3)CC2)=C(c2ccc(Cl)cc2)C1] | (S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-(cyanomethyl)-5-nitro-3,4-dihydro-2H-benzo[b][1,4]oxazin-7-yl)sulfonyl)benzamide | MS-ESI (m/z): 851 [M + 1]+ |

TABLE 2-continued

| EXAMPLE | STRUCTURE | NAME | DATA |
|---|---|---|---|
| 2-116 | 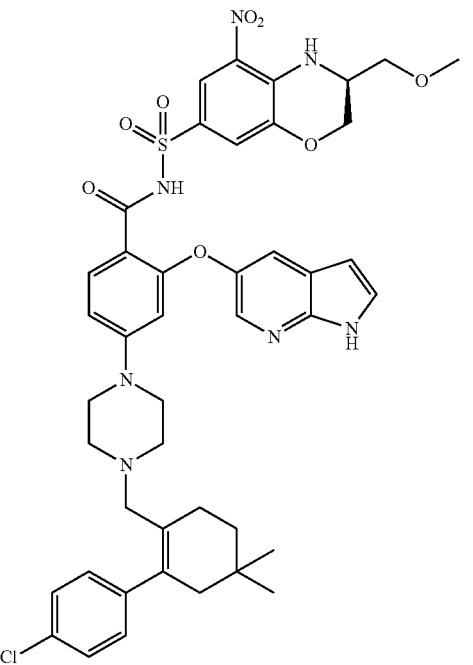 [SMILES: COC[C@H]1COc2cc(S(=O)(=O)NC(=O)c3ccc(N4CCN(CC5=C(c6ccc(Cl)cc6)CC(C)(C)CC5)CC4)cc3Oc3cnc4[nH]ccc4c3)cc([N+](=O)[O-])c2N1] | (S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-(methoxymethyl)-5-nitro-3,4-dihydro-2H-benzo[b][1,4]oxazin-7-yl)sulfonyl)benzamide | MS-ESI (m/z): 856 [M + 1]+ |
| 2-117 | 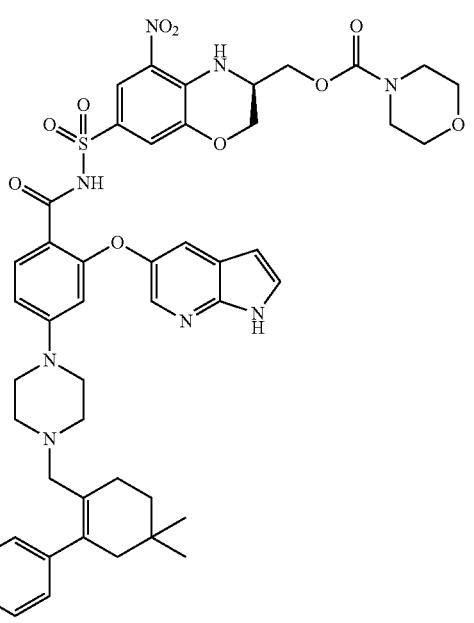 | (R)-(7-(N-(2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)benzoyl)sulfamoyl)-5-nitro-3,4-dihydro-2H-benzo[b][1,4]oxazin-3-yl)methyl morpholine-4-carboxylate | MS-ESI (m/z): 955 [M + 1]+ |

TABLE 2-continued

| EXAMPLE | STRUCTURE | NAME | DATA |
|---|---|---|---|
| 2-118 | 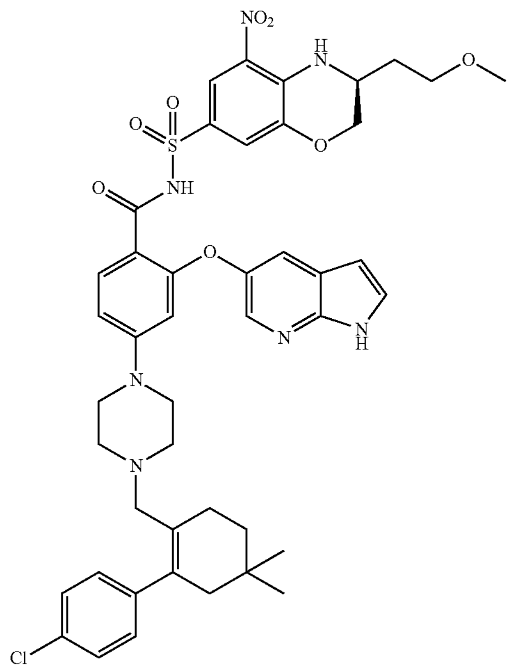 [SMILES: COCC[C@H]1COc2cc(S(=O)(=O)NC(=O)c3ccc(N4CCN(CC5=C(c6ccc(Cl)cc6)CC(C)(C)CC5)CC4)cc3Oc3cnc4[nH]ccc4c3)cc([N+](=O)[O-])c2N1] | (S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-(2-methoxyethyl)-5-nitro-3,4-dihydro-2H-benzo[b][1,4]oxazin-7-yl)sulfonyl)benzamide | MS-ESI (m/z): 870 [M + 1]+ |
| 2-119 | 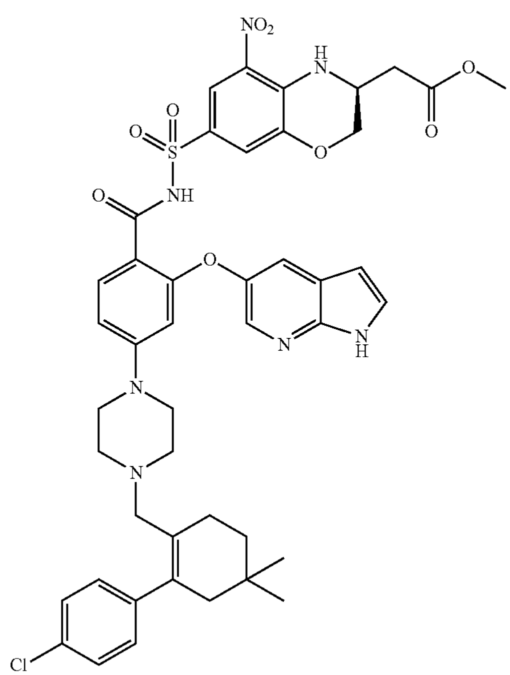 [SMILES: COC(=O)C[C@H]1COc2cc(S(=O)(=O)NC(=O)c3ccc(N4CCN(CC5=C(c6ccc(Cl)cc6)CC(C)(C)CC5)CC4)cc3Oc3cnc4[nH]ccc4c3)cc([N+](=O)[O-])c2N1] | methyl (S)-2-(7-(N-(2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)benzoyl)sulfamoyl)-5-nitro-3,4-dihydro-2H-benzo[b][1,4]oxazin-3-yl)acetate | MS-ESI (m/z): 884 [M + 1]+ |

TABLE 2-continued

| EXAMPLE | STRUCTURE | NAME | DATA |
|---|---|---|---|
| 2-120 | 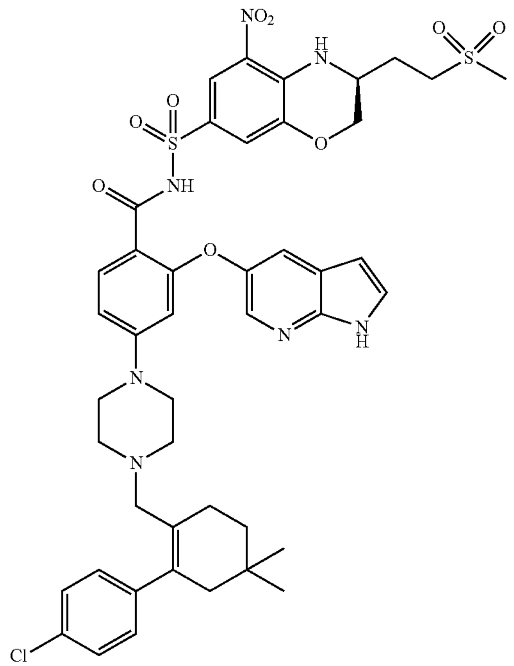 [SMILES: CC1(C)CCC(CN2CCN(c3ccc(C(=O)NS(=O)(=O)c4cc5c(c([N+](=O)[O-])c4)N[C@@H](CCS(C)(=O)=O)CO5)c(Oc4cnc5[nH]ccc5c4)c3)CC2)=C(c2ccc(Cl)cc2)C1] | (S)-2-((1H-pyrrolo[2,3-b]pyridin-5-yl)oxy)-4-(4-((4'-chloro-5,5-dimethyl-3,4,5,6-tetra-hydro-[1,1'-biphenyl]-2-yl)methyl)piperazin-1-yl)-N-((3-(2-(methylsulfonyl)ethyl)-5-nitro-3,4-dihydro-2H-benzo[b][1,4]oxazin-7-yl)sulfonyl)benzamide | MS-ESI (m/z): 918 [M + 1]⁺ |
| 2-121 | 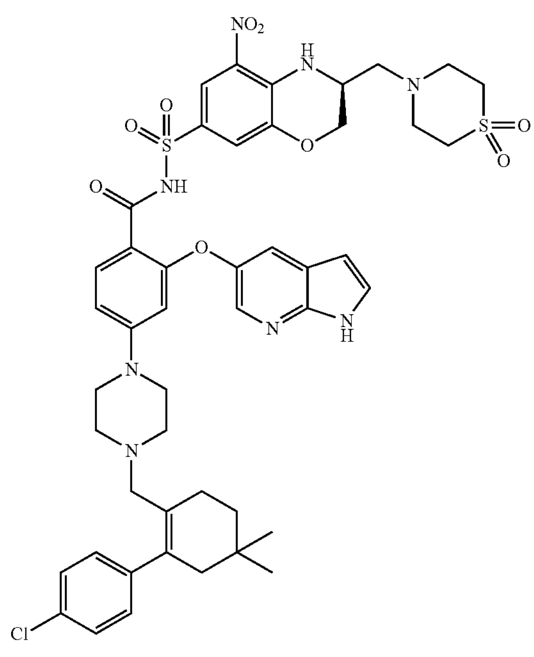 [SMILES: CC1(C)CCC(CN2CCN(c3ccc(C(=O)NS(=O)(=O)c4cc5c(c([N+](=O)[O-])c4)N[C@@H](CN4CCS(=O)(=O)CC4)CO5)c(Oc4cnc5[nH]ccc5c4)c3)CC2)=C(c2ccc(Cl)cc2)C1] | (S)-2-((1H-pyrrolo[2,3-b]pyridin-5-yl)oxy)-4-(4-((4'-chloro-5,5-dimethyl-3,4,5,6-tetra-hydro-[1,1'-biphenyl]-2-yl)methyl)piperazin-1-yl)-N-((3-((1,1-dioxidothiomorpholino)methyl)-5-nitro-3,4-dihydro-2H-benzo[b][1,4]oxazin-7-yl)sulfonyl)benzamide | MS-ESI (m/z): 959 [M + 1]⁺ |

TABLE 2-continued

| EXAMPLE | STRUCTURE | NAME | DATA |
|---|---|---|---|
| 2-122 | 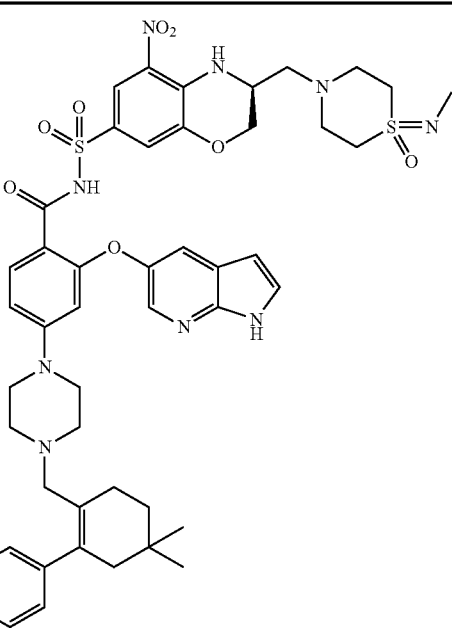 | (S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-((1-(methylimino)-1-oxido-1λ$^6$-thiomorpholino)methyl)-5-nitro-3,4-dihydro-2H-benzo[b][1,4]oxazin-7-yl)sulfonyl)benzamide | MS-ESI (m/z): 972 [M + 1]$^+$ |
| 2-123 | 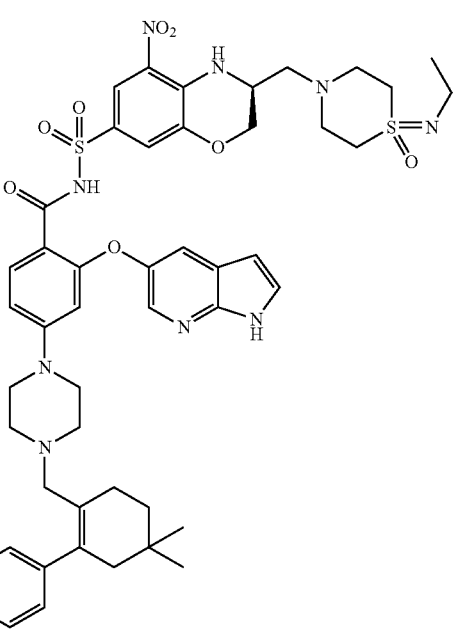 | (S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-((1-(ethylimino)-1-oxido-1λ$^6$-thiomorpholino)methyl)-5-nitro-3,4-dihydro-2H-benzo[b][1,4]oxazin-7-yl)sulfonyl)benzamide | MS-ESI (m/z): 986 [M + 1]$^+$ |

TABLE 2-continued

| EXAMPLE | STRUCTURE | NAME | DATA |
|---|---|---|---|
| 2-124 | 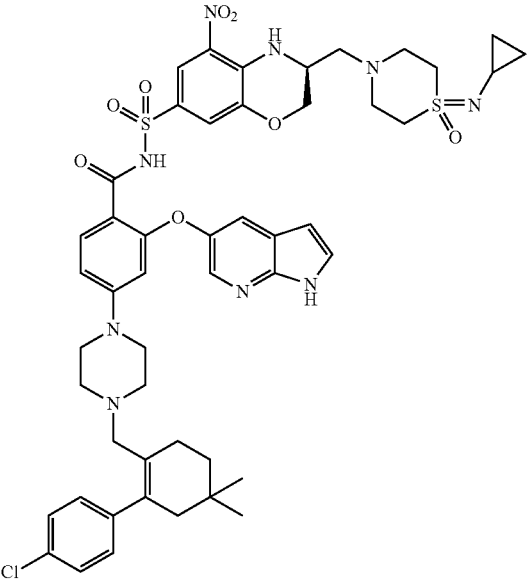 [SMILES: CC1(C)CCC(CN2CCN(c3ccc(C(=O)NS(=O)(=O)c4cc5c(c([N+](=O)[O-])c4)N[C@@H](CN4CCS(=O)(=NC6CC6)CC4)CO5)c(Oc4cnc5[nH]ccc5c4)c3)CC2)=C(c2ccc(Cl)cc2)C1] | (S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-((1-(cyclopropylimino)-1-oxido-1λ⁶-thiomorpholino)methyl)-5-nitro-3,4-dihydro-2H-benzo[b][1,4]oxazin-7-yl)sulfonyl)benzamide | MS-ESI (m/z): 998 [M + 1]⁺ |
| 2-125 | 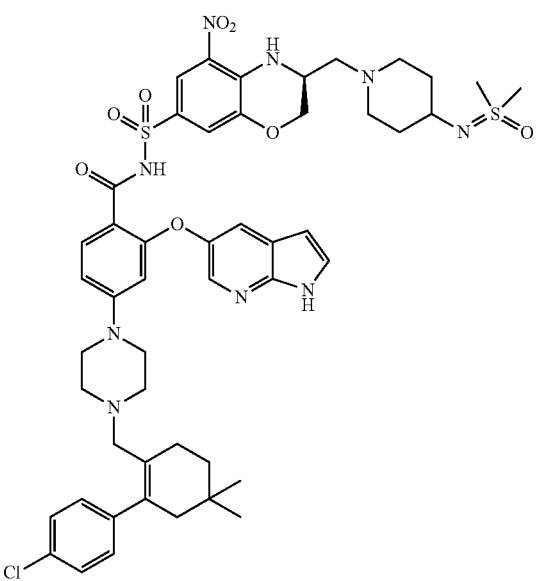 [SMILES: CC1(C)CCC(CN2CCN(c3ccc(C(=O)NS(=O)(=O)c4cc5c(c([N+](=O)[O-])c4)N[C@@H](CN4CCC(N=S(C)(C)=O)CC4)CO5)c(Oc4cnc5[nH]ccc5c4)c3)CC2)=C(c2ccc(Cl)cc2)C1] | (S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-((4-((dimethyl(oxo)-λ⁶-sulfanylidene)amino)piperidin-1-yl)methyl)-5-nitro-3,4-dihydro-2H-benzo[b][1,4]oxazin-7-yl)sulfonyl)benzamide | MS-ESI (m/z): 1000 [M + 1]⁺ |

TABLE 2-continued

| EXAMPLE | STRUCTURE | NAME | DATA |
|---|---|---|---|
| 2-126 | 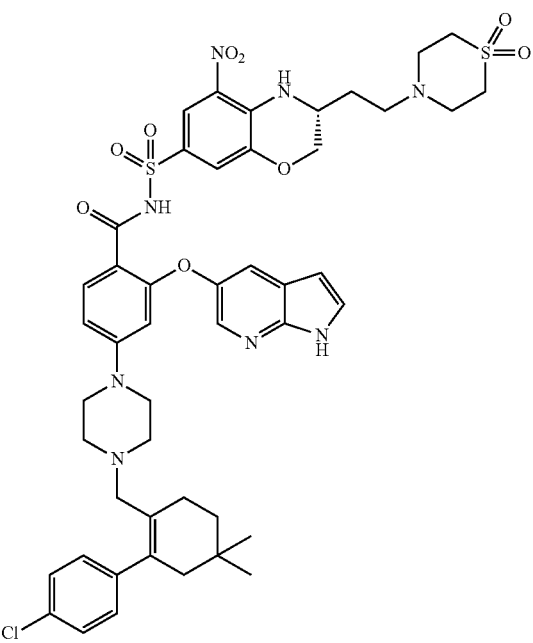 [SMILES: CC1(C)CCC(CN2CCN(c3ccc(C(=O)NS(=O)(=O)c4cc5c(c([N+](=O)[O-])c4)N[C@H](CCN4CCS(=O)(=O)CC4)CO5)c(Oc4cnc5[nH]ccc5c4)c3)CC2)=C(c2ccc(Cl)cc2)C1] | (R)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-(2-(1,1-dioxidothiomorpholino)ethyl)-5-nitro-3,4-dihydro-2H-benzo[b][1,4]oxazin-7-yl)sulfonyl)benzamide | MS-ESI (m/z): 973 [M + 1]+ |
| 2-127 | 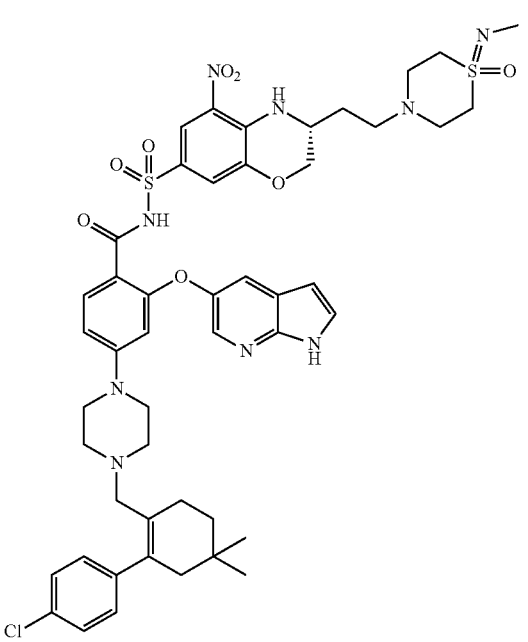 [SMILES: CN=S1(=O)CCN(CC[C@@H]2COc3cc(S(=O)(=O)NC(=O)c4ccc(N5CCN(CC6=C(c7ccc(Cl)cc7)CC(C)(C)CC6)CC5)cc4Oc4cnc5[nH]ccc5c4)cc([N+](=O)[O-])c3N2)CC1] | (R)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-(2-(1-(methylimino)-1-oxido-1λ6-thiomorpholino)ethyl)-5-nitro-3,4-dihydro-2H-benzo[b][1,4]oxazin-7-yl)sulfonyl)benzamide | MS-ESI (m/z): 986 [M + 1]+ |

TABLE 2-continued

| EXAMPLE | STRUCTURE | NAME | DATA |
|---|---|---|---|
| 2-128 | 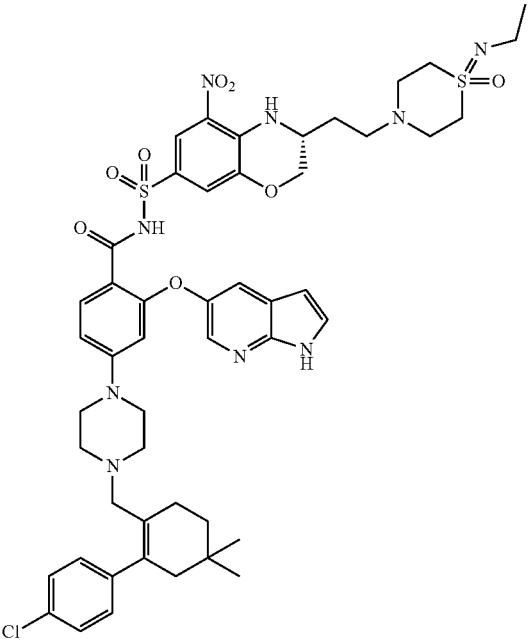 [SMILES: CCN=S1(=O)CCN(CC[C@@H]2COc3cc(S(=O)(=O)NC(=O)c4ccc(N5CCN(CC6=C(c7ccc(Cl)cc7)CC(C)(C)CC6)CC5)cc4Oc4cnc5[nH]ccc5c4)cc([N+](=O)[O-])c3N2)CC1] | (R)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-y)-N-((3-(2-(1-(ethylimino)-1-oxido-1λ⁶-thiomorpholino)ethyl)-5-nitro-3,4-dihydro-2H-benzo[b][1,4]oxazin-7-yl)sulfonyl)benzamide | MS-ESI (m/z): 1000 [M + 1]⁺ |
| 2-129 | 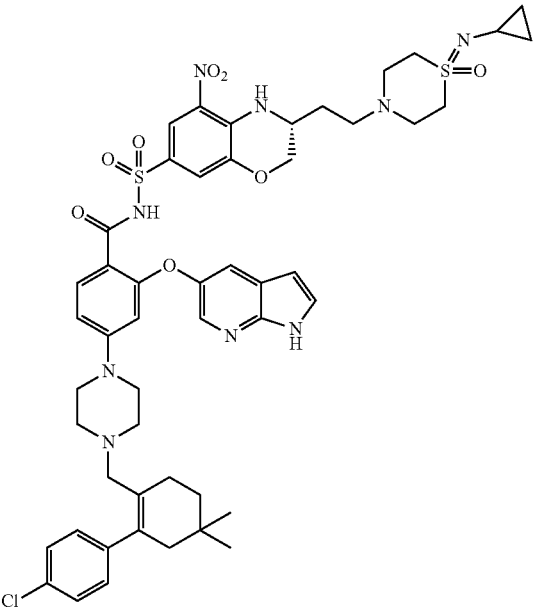 [SMILES: CC1(C)CCC(CN2CCN(c3ccc(C(=O)NS(=O)(=O)c4cc5c(c([N+](=O)[O-])c4)N[C@H](CCN4CCS(=O)(=NC6CC6)CC4)CO5)c(Oc4cnc5[nH]ccc5c4)c3)CC2)=C(c2ccc(Cl)cc2)C1] | (R)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-(2-(1-(cyclopropylimino)-1-oxido-1λ⁶-thiomorpholino)ethyl)-5-nitro-3,4-dihydro-2H-benzo[b][1,4]oxazin-7-yl)sulfonyl)benzamide | MS-ESI (m/z): 1012 [M + 1]⁺ |

TABLE 2-continued

| EXAMPLE | STRUCTURE | NAME | DATA |
|---|---|---|---|
| 2-130 | 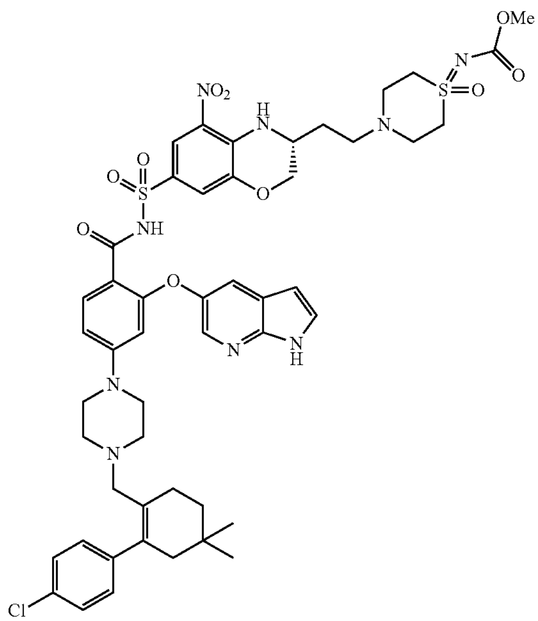 [SMILES: COC(=O)N=S1(=O)CCN(CC[C@@H]2COc3cc(S(=O)(=O)NC(=O)c4ccc(N5CCN(CC6=C(c7ccc(Cl)cc7)CC(C)(C)CC6)CC5)cc4Oc4cnc5[nH]ccc5c4)cc([N+](=O)[O-])c3N2)CC1] | methyl (R)-(4-(2-(7-(N-(2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)benzoyl)sulfamoyl)-5-nitro-3,4-dihydro-2H-benzo[b][1,4]oxazin-3-yl)ethyl)-1oxido-1λ⁶-thiomorpholin-1-ylidene)carbamate | MS-ESI (m/z): 1030 [M + 1]⁺ |
| 2-131 | 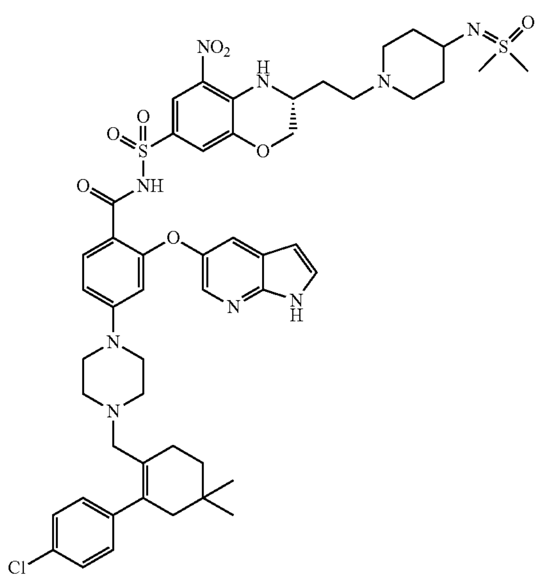 [SMILES: CC1(C)CCC(CN2CCN(c3ccc(C(=O)NS(=O)(=O)c4cc5c(c([N+](=O)[O-])c4)N[C@H](CCN4CCC(N=S(C)(C)=O)CC4)CO5)c(Oc4cnc5[nH]ccc5c4)c3)CC2)=C(c2ccc(Cl)cc2)C1] | (R)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-(2-(4-((dimethyl(oxo)-λ⁶-sulfanylidene)amino)piperidin-1-yl)ethyl)-5-nitro-3,4-dihydro-2H-benzo[b][1,4]oxazin-7-yl)sulfonyl)benzamide | MS-ESI (m/z): 1014 [M + 1]⁺ |

| EXAMPLE | STRUCTURE | NAME | DATA |
|---|---|---|---|
| 2-132 | 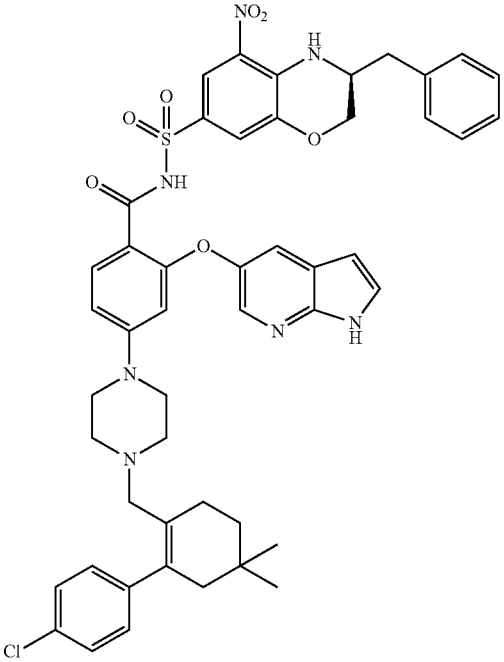 [SMILES: CC1(C)CCC(CN2CCN(c3ccc(C(=O)NS(=O)(=O)c4cc5c(c([N+](=O)[O-])c4)N[C@@H](Cc4ccccc4)CO5)c(Oc4cnc5[nH]ccc5c4)c3)CC2)=C(c2ccc(Cl)cc2)C1] | (S)-2-((1H-pyrrolo[2,3-b]pyridin-5-yl)oxy)-N-((3-benzyl-5-nitro-3,4-dihydro-2H-benzo[b][1,4]oxazin-7-yl)sulfonyl)-4-(4-((4'-chloro-5,5-dimethyl-3,4,5,6-tetrahydro-[1,1'-biphenyl]-2-yl)methyl)piperazin-1-yl)benzamide | MS-ESI (m/z): 902 [M + 1]+ |
| 2-133 | 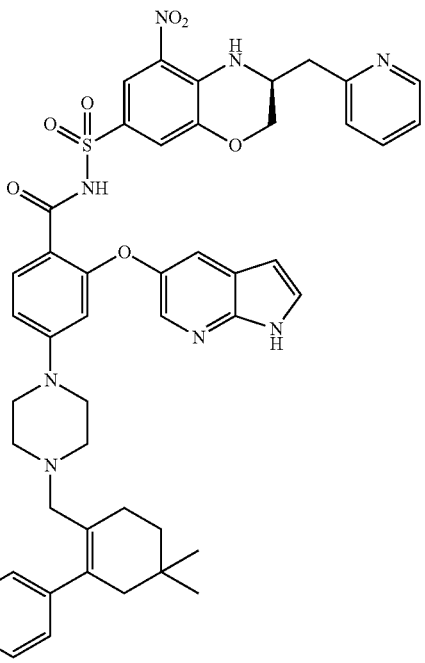 | (S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((5-nitro-3-(pyridin-2-ylmethyl)-3,4-dihydro-2H-benzo[b][1,4]oxazin-7-yl)sulfonyl)benzamide | MS-ESI (m/z): 903 [M + 1]+ |

TABLE 2-continued

| EXAMPLE | STRUCTURE | NAME | DATA |
|---|---|---|---|
| 2-134 | 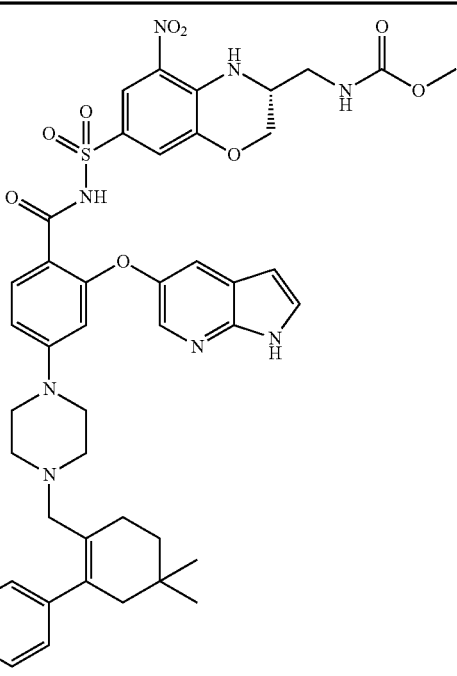 | methyl (R)-((7-(N-(2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)benzoyl)sulfamoyl)-5-nitro-3,4-dihydro-2H-benzo[b][1,4]oxazin-3-yl)methyl)carbamate | MS-ESI (m/z): 899 [M + 1]+ |
| 2-135 | 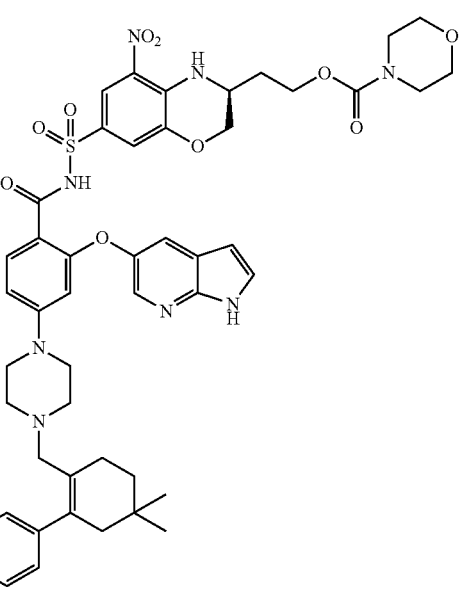 | (S)-2-(7-(N-(2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)benzoyl)sulfamoyl)-5-nitro-3,4-dihydro-2H-benzo[b][1,4]oxazin-3-yl)ethyl morpholine-4-carboxylate | MS-ESI (m/z): 969 [M + 1]+ |

TABLE 2-continued

| EXAMPLE | STRUCTURE | NAME | DATA |
|---|---|---|---|
| 2-136 | 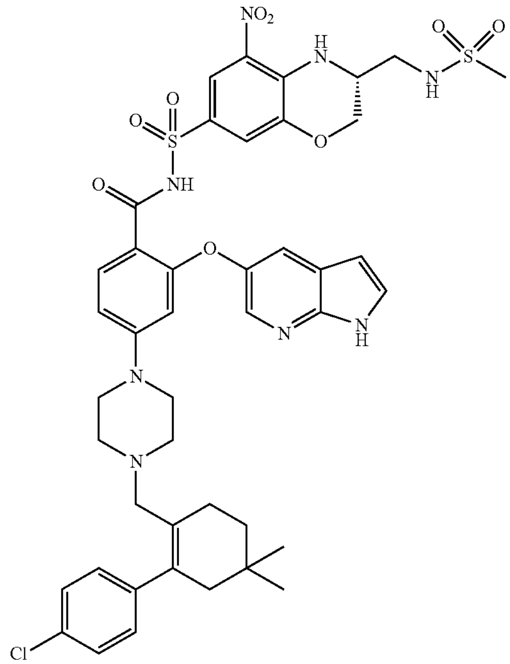 [SMILES: CC1(C)CCC(CN2CCN(c3ccc(C(=O)NS(=O)(=O)c4cc5c(c([N+](=O)[O-])c4)N[C@H](CNS(C)(=O)=O)CO5)c(Oc4cnc5[nH]ccc5c4)c3)CC2)=C(c2ccc(Cl)cc2)C1] | (R)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-(methylsulfonamidomethyl)-5-nitro-3,4-dihydro-2H-benzo[b][1,4]oxazin-7-yl)sulfonyl)benzamide | MS-ESI (m/z): 919 [M + 1]+ |
| 2-137 | 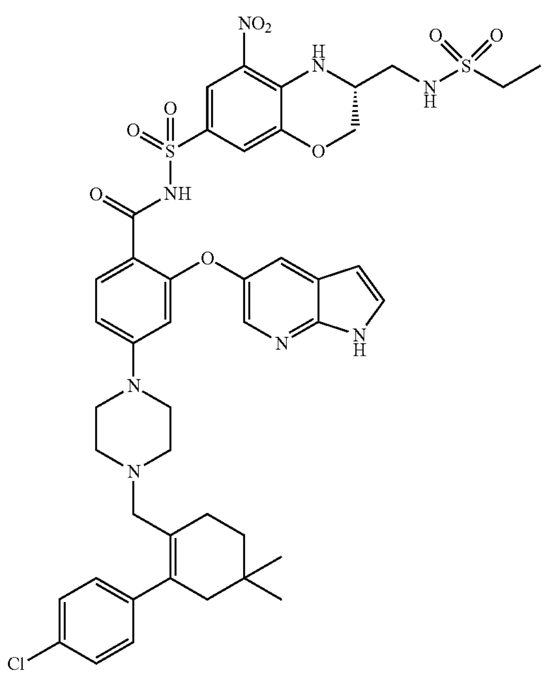 [SMILES: CCS(=O)(=O)NC[C@@H]1COc2cc(S(=O)(=O)NC(=O)c3ccc(N4CCN(CC5=C(c6ccc(Cl)cc6)CC(C)(C)CC5)CC4)cc3Oc3cnc4[nH]ccc4c3)cc([N+](=O)[O-])c2N1] | (R)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-(ethylsulfonamidomethyl)-5-nitro-3,4-dihydro-2H-benzo[b][1,4]oxazin-7-yl)sulfonyl)benzamide | MS-ESI (m/z): 933 [M + 1]+ |

| EXAMPLE | STRUCTURE | NAME | DATA |
|---|---|---|---|
| 2-138 | 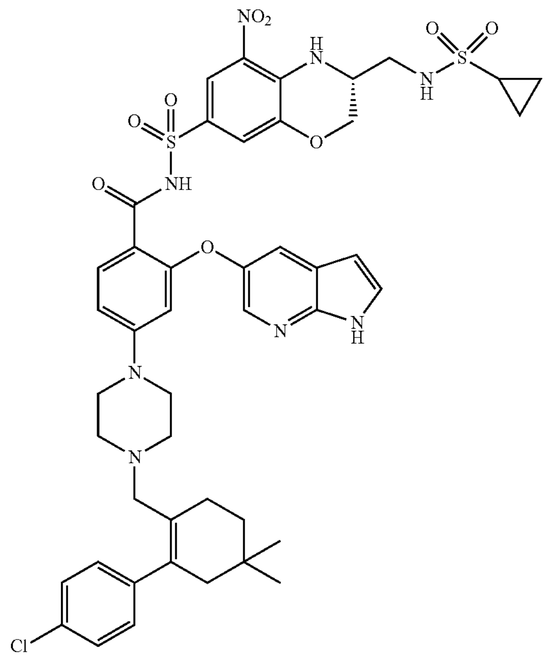 [SMILES: CC1(C)CCC(CN2CCN(c3ccc(C(=O)NS(=O)(=O)c4cc5c(c([N+](=O)[O-])c4)N[C@H](CNS(=O)(=O)C4CC4)CO5)c(Oc4cnc5[nH]ccc5c4)c3)CC2)=C(c2ccc(Cl)cc2)C1] | (R)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-(cyclopropanesulfonamidomethyl)-5-nitro-3,4-dihydro-2H-benzo[b][1,4]oxazin-7-yl)sulfonyl)benzamide | MS-ESI (m/z): 945 [M + 1]⁺ |
| 2-139 | 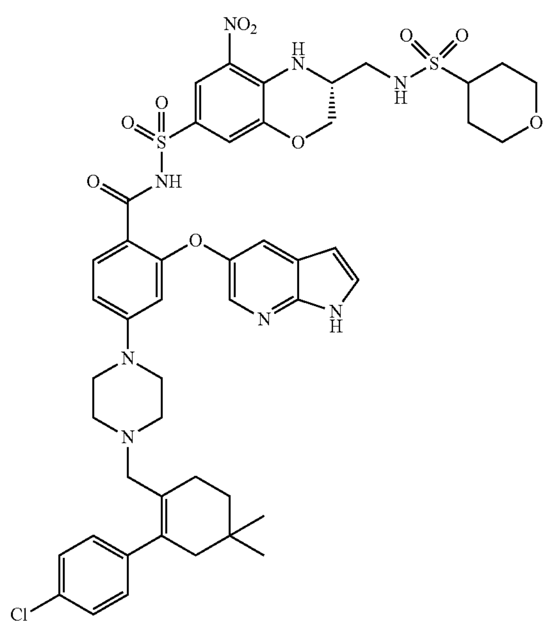 [SMILES: CC1(C)CCC(CN2CCN(c3ccc(C(=O)NS(=O)(=O)c4cc5c(c([N+](=O)[O-])c4)N[C@H](CNS(=O)(=O)C4CCOCC4)CO5)c(Oc4cnc5[nH]ccc5c4)c3)CC2)=C(c2ccc(Cl)cc2)C1] | (R)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((5-nitro-3-(((tetrahydro-2H-pyran)-4-sulfonamido)methyl)-3,4-dihydro-2H-benzo[b][1,4]oxazin-7-yl)sulfonyl)benzamide | MS-ESI (m/z): 989 [M + 1]⁺ |

| EXAMPLE | STRUCTURE | NAME | DATA |
|---|---|---|---|
| 2-140 | 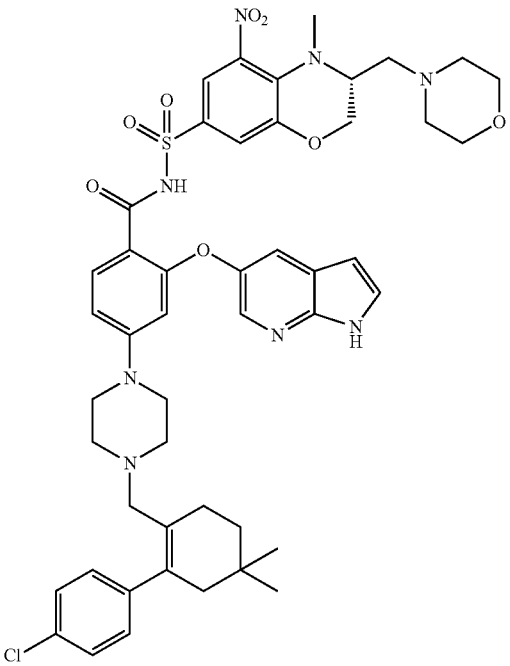 [SMILES: CN1c2c(cc(S(=O)(=O)NC(=O)c3ccc(N4CCN(CC5=C(c6ccc(Cl)cc6)CC(C)(C)CC5)CC4)cc3Oc3cnc4[nH]ccc4c3)cc2[N+](=O)[O-])OC[C@H]1CN1CCOCC1] | (R)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((4-methyl-3-(morpholinomethyl)-5-nitro-3,4-dihydro-2H-benzo[b][1,4]oxazin-7-yl)sulfonyl)benzamide | MS-ESI (m/z): 925 [M + 1]+ |
| 2-141 | 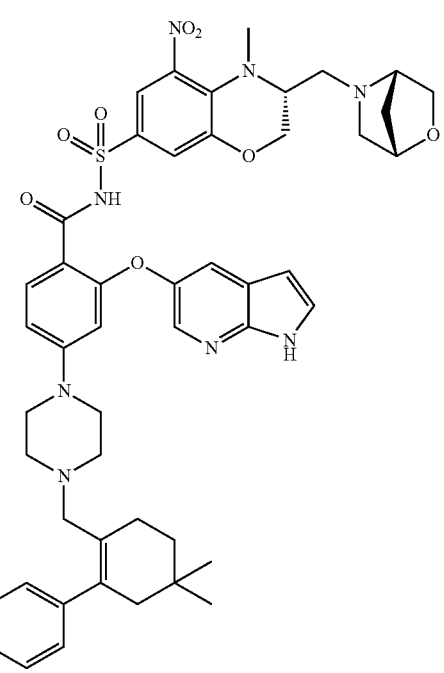 | 2-((1H-pyrrolo[2,3-b]pyridin-5-yl)oxy)-N-(((R)-3-(((1S,4S)-2-oxa-5-azabicyclo[2.2.1]heptan-5-yl)methyl)-4-methyl-5-nitro-3,4-dihydro-2H-benzo[b][1,4]oxazin-7-yl)sulfonyl)-4-(4-((4'-chloro-5,5-dimethyl-3,4,5,6-tetrahydro-[1,1'-biphenyl]-2-yl)methyl)piperazin-1-yl)benzamide | MS-ESI (m/z): 937 [M + 1]+ |

TABLE 2-continued

| EXAMPLE | STRUCTURE | NAME | DATA |
|---|---|---|---|
| 2-142 | 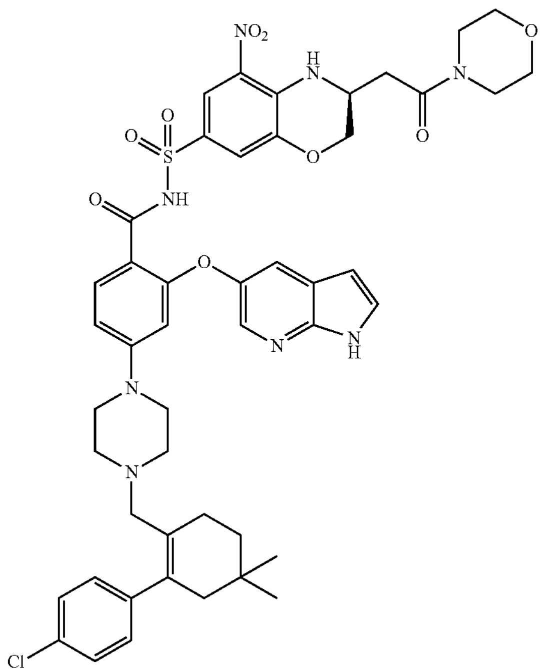 [SMILES: CC1(C)CCC(CN2CCN(c3ccc(C(=O)NS(=O)(=O)c4cc5c(c([N+](=O)[O-])c4)N[C@@H](CC(=O)N4CCOCC4)CO5)c(Oc4cnc5[nH]ccc5c4)c3)CC2)=C(c2ccc(Cl)cc2)C1] | (S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-(2-morpholino-2-oxoethyl)-5-nitro-3,4-dihydro-2H-benzo[b][1,4]oxazin-7-yl)sulfonyl)benzamide | MS-ESI (m/z): 939 [M + 1]⁺ |
| 2-143 | 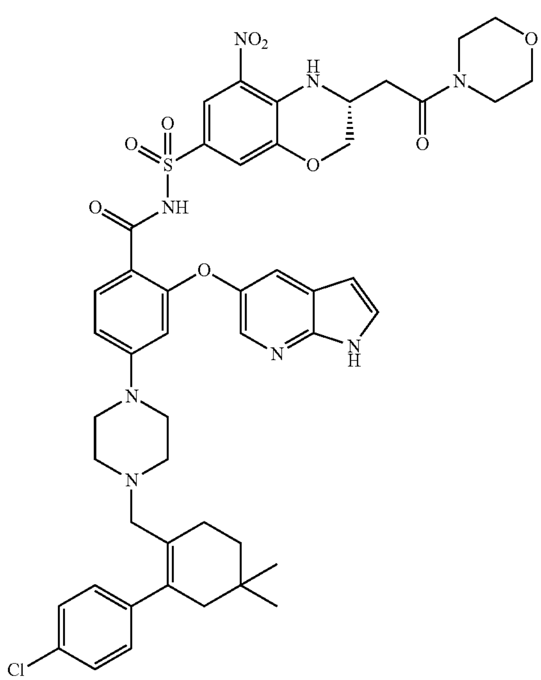 [SMILES: CC1(C)CCC(CN2CCN(c3ccc(C(=O)NS(=O)(=O)c4cc5c(c([N+](=O)[O-])c4)N[C@H](CC(=O)N4CCOCC4)CO5)c(Oc4cnc5[nH]ccc5c4)c3)CC2)=C(c2ccc(Cl)cc2)C1] | (R)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-(2-morpholino-2-oxoethyl)-5-nitro-3,4-dihydro-2H-benzo[b][1,4]oxazin-7-yl)sulfonyl)benzamide | MS-ESI (m/z): 939 [M + 1]⁺ |

TABLE 2-continued

| EXAMPLE | STRUCTURE | NAME | DATA |
|---|---|---|---|
| 2-144 | 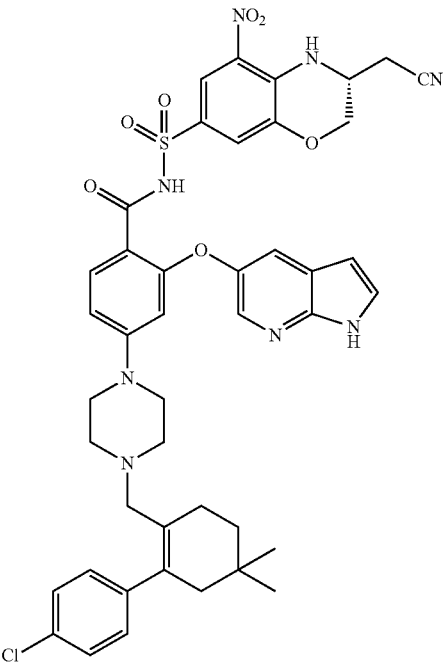 [SMILES: CC1(C)CCC(CN2CCN(c3ccc(C(=O)NS(=O)(=O)c4cc5c(c([N+](=O)[O-])c4)N[C@H](CC#N)CO5)c(Oc4cnc5[nH]ccc5c4)c3)CC2)=C(c2ccc(Cl)cc2)C1] | (R)-2-((1H-pyrrolo[2,3-b]pyridin-5-yl)oxy)-4-(4-((4'-chloro-5,5-dimethyl-3,4,5,6-tetra-hydro-[1,1'-biphenyl]-2-yl)methyl)piperazin-1-yl)-N-((3-(cyanomethyl)-5-nitro-3,4-dihydro-2H-benzo[b][1,4]oxazin-7-yl)sulfonyl)benzamide | MS-ESI (m/z): 851 [M + 1]+ |
| 2-145 | 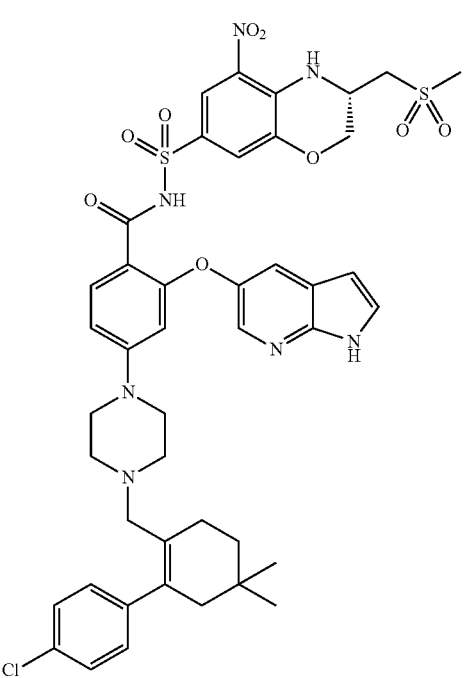 [SMILES: CC1(C)CCC(CN2CCN(c3ccc(C(=O)NS(=O)(=O)c4cc5c(c([N+](=O)[O-])c4)N[C@H](CS(C)(=O)=O)CO5)c(Oc4cnc5[nH]ccc5c4)c3)CC2)=C(c2ccc(Cl)cc2)C1] | (S)-2-((1H-pyrrolo[2,3-b]pyridin-5-yl)oxy)-4-(4-((4'-chloro-5,5-dimethyl-3,4,5,6-tetra-hydro-[1,1'-biphenyl]-2-yl)methyl)piperazin-1-yl)-N-((3-((methylsulfonyl)methyl)-5-nitro-3,4-dihydro-2H-benzo[b][1,4]oxazin-7-yl)sulfonyl)benzamide | MS-ESI (m/z): 904 [M + 1]+ |

TABLE 2-continued

| EXAMPLE | STRUCTURE | NAME | DATA |
|---|---|---|---|
| 2-146 | 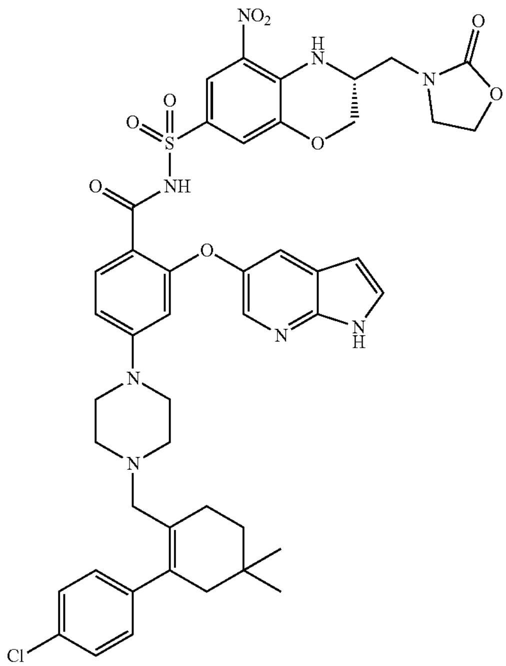 [SMILES: CC1(C)CCC(CN2CCN(c3ccc(C(=O)NS(=O)(=O)c4cc5c(c([N+](=O)[O-])c4)N[C@H](CN4CCOC4=O)CO5)c(Oc4cnc5[nH]ccc5c4)c3)CC2)=C(c2ccc(Cl)cc2)C1] | (R)-2-((1H-pyrrolo[2,3-b]pyridin-5-yl)oxy)-4-(4-((4'-chloro-5,5-dimethyl-3,4,5,6-tetra-hydro-[1,1'-biphenyl]-2-yl)methyl)piperazin-1-yl)-N-((5-nitro-3-((2-oxooxazolidin-3-yl)methyl)-3,4-dihydro-2H-benzo[b][1,4]oxazin-7-yl)sulfonyl)benzamide | MS-ESI (m/z): 911 [M + 1]+ |
| 2-147 | 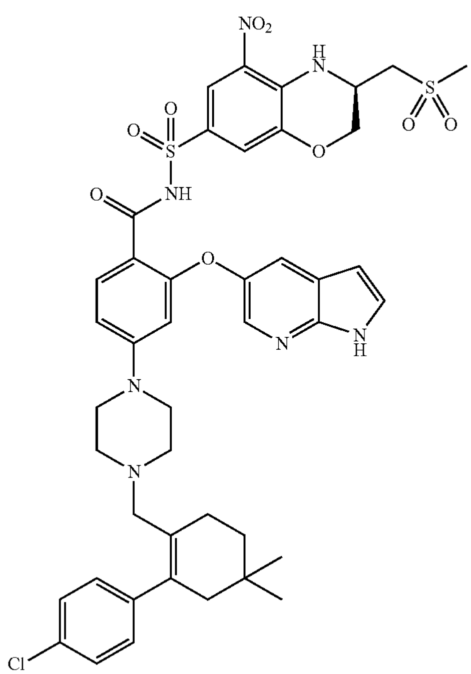 [SMILES: CC1(C)CCC(CN2CCN(c3ccc(C(=O)NS(=O)(=O)c4cc5c(c([N+](=O)[O-])c4)N[C@@H](CS(C)(=O)=O)CO5)c(Oc4cnc5[nH]ccc5c4)c3)CC2)=C(c2ccc(Cl)cc2)C1] | (R)-2-((1H-pyrrolo[2,3-b]pyridin-5-yl)oxy)-4-(4-((4'-chloro-5,5-dimethyl-3,4,5,6-tetra-hydro-[1,1'-biphenyl]-2-yl)methyl)piperazin-1-yl)-N-((3-((methylsulfonyl)methyl)-5-nitro-3,4-dihydro-2H-benzo[b][1,4]oxazin-7-yl)sulfonyl)benzamide | MS-ESI (m/z): 904 [M + 1]+ |

TABLE 2-continued

| EXAMPLE | STRUCTURE | NAME | DATA |
|---|---|---|---|
| 2-148 | 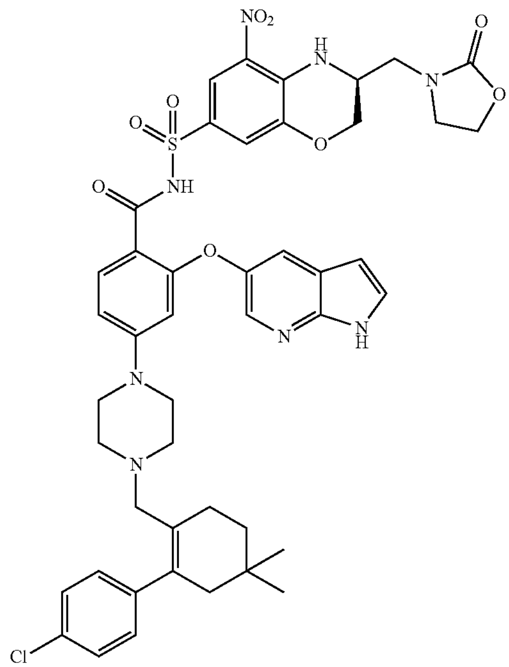 [SMILES: CC1(C)CCC(CN2CCN(c3ccc(C(=O)NS(=O)(=O)c4cc5c(c([N+](=O)[O-])c4)N[C@@H](CN4CCOC4=O)CO5)c(Oc4cnc5[nH]ccc5c4)c3)CC2)=C(c2ccc(Cl)cc2)C1] | (S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((5-nitro-3-((2-oxooxazolidin-3-yl)methyl)-3,4-dihydro-2H-benzo[b][1,4]oxazin-7-yl)sulfonyl)benzamide | MS-ESI (m/z): 911 [M + 1]+ |
| 2-149 | 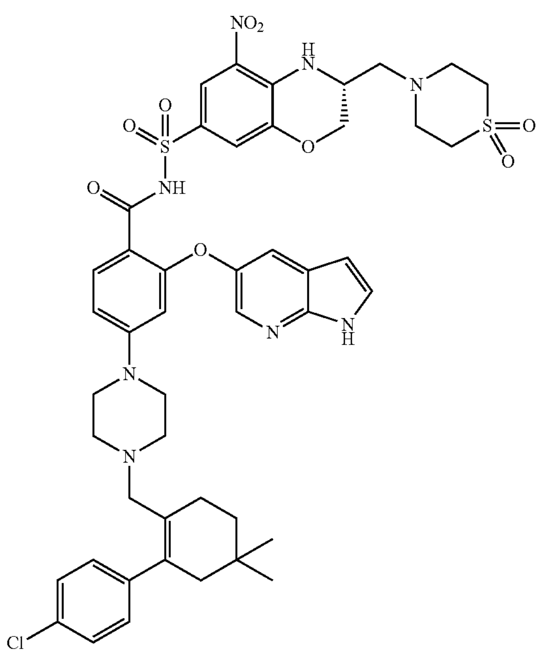 [SMILES: CC1(C)CCC(CN2CCN(c3ccc(C(=O)NS(=O)(=O)c4cc5c(c([N+](=O)[O-])c4)N[C@H](CN4CCS(=O)(=O)CC4)CO5)c(Oc4cnc5[nH]ccc5c4)c3)CC2)=C(c2ccc(Cl)cc2)C1] | (R)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-((1,1-dioxidothiomorpholino)methyl)-5-nitro-3,4-dihydro-2H-benzo[b][1,4]oxazin-7-yl)sulfonyl)benzamide | MS-ESI (m/z): 959 [M + 1]+ |

| EXAMPLE | STRUCTURE | NAME | DATA |
|---|---|---|---|
| 2-150 | 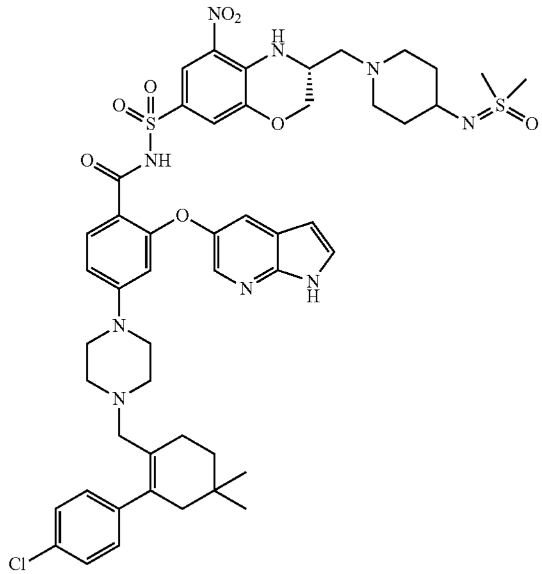 [SMILES: CC1(C)CCC(CN2CCN(c3ccc(C(=O)NS(=O)(=O)c4cc5c(c([N+](=O)[O-])c4)N[C@H](CN4CCC(N=S(C)(C)=O)CC4)CO5)c(Oc4cnc5[nH]ccc5c4)c3)CC2)=C(c2ccc(Cl)cc2)C1] | (R)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-((4-((dimethyl(oxo)-16-sulfanylidene)amino)piperidin-1-yl)methyl)-5-nitro-3,4-dihydro-2H-benzo[b][1,4]oxazin-7-yl)sulfonyl)benzamide | MS-ESI (m/z): 1000 [M + 1]+ |
| 2-151 | 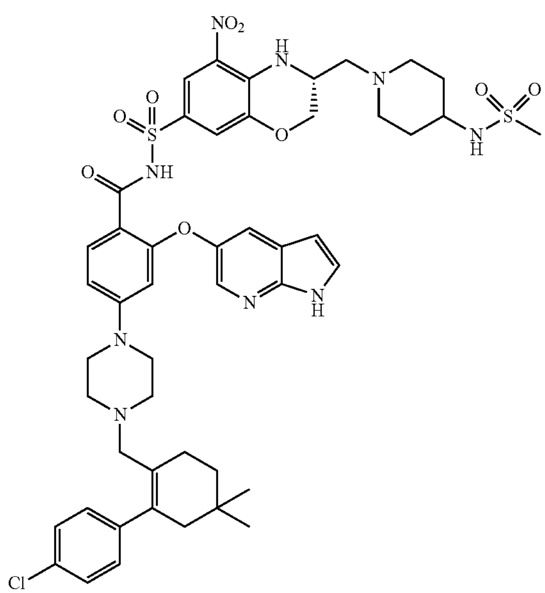 [SMILES: CC1(C)CCC(CN2CCN(c3ccc(C(=O)NS(=O)(=O)c4cc5c(c([N+](=O)[O-])c4)N[C@H](CN4CCC(NS(C)(=O)=O)CC4)CO5)c(Oc4cnc5[nH]ccc5c4)c3)CC2)=C(c2ccc(Cl)cc2)C1] | (R)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-((4-(methylsulfonamido)piperidin-1-yl)methyl)-5-nitro-3,4-dihydro-2H-benzo[b][1,4]oxazin-7-yl)sulfonyl)benzamide | MS-ESI (m/z): 1002 [M + 1]+ |

TABLE 2-continued

| EXAMPLE | STRUCTURE | NAME | DATA |
|---|---|---|---|
| 2-152 | 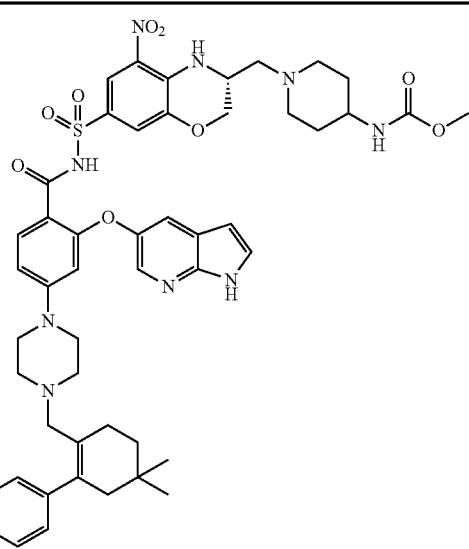 | methyl (R)-(1-((7-(N-(2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)benzoyl)sulfamoyl)-5-nitro-3,4-dihydro-2H-benzo[b][1,4]oxazin-3-yl)methyl)piperidin-4-yl)carbamate | MS-ESI (m/z): 982 [M + 1]$^+$ |
| 2-153 | 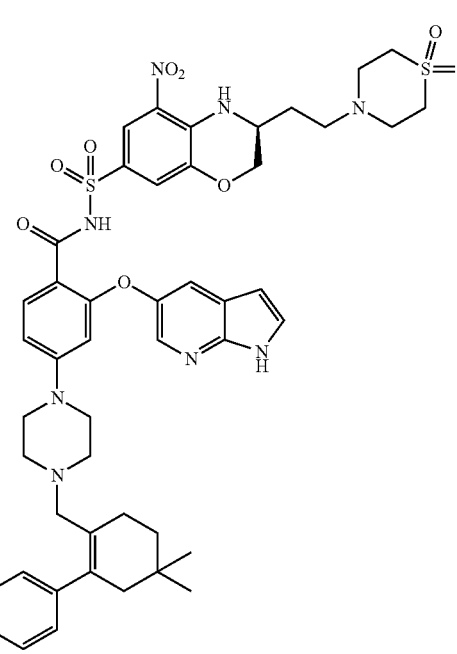 | (S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-(2-(1,1-dioxidothiomorpholino)ethyl)-5-nitro-3,4-dihydro-2H-benzo[b][1,4]oxazin-7-yl)sulfonyl)benzamide | MS-ESI (m/z): 973 [M + 1]$^+$ |

| EXAMPLE | STRUCTURE | NAME | DATA |
|---|---|---|---|
| 2-154 | 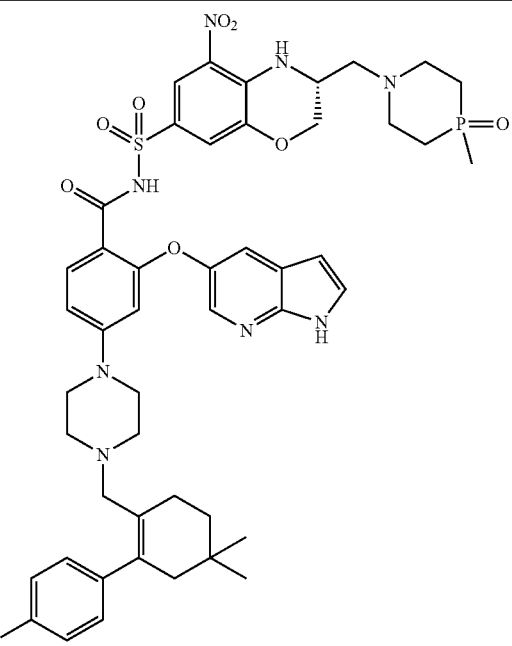 | (R)-2-((1H-pyrrolo[2,3-b]pyridin-5-yl)oxy)-4-(4-((4'-chloro-5,5-dimethyl-3,4,5,6-tetra-hydro-[1,1'-biphenyl]-2-yl)methyl)piperazin-1-yl)-N-((3-((4-methyl-4-oxido-1,4-azaphosphinan-1-yl)methyl)-5-nitro-3,4-dihydro-2H-benzo[b][1,4]oxazin-7-yl)sulfonyl)benzamide | MS-ESI (m/z): 957 [M + 1]+ |
| 2-155 | 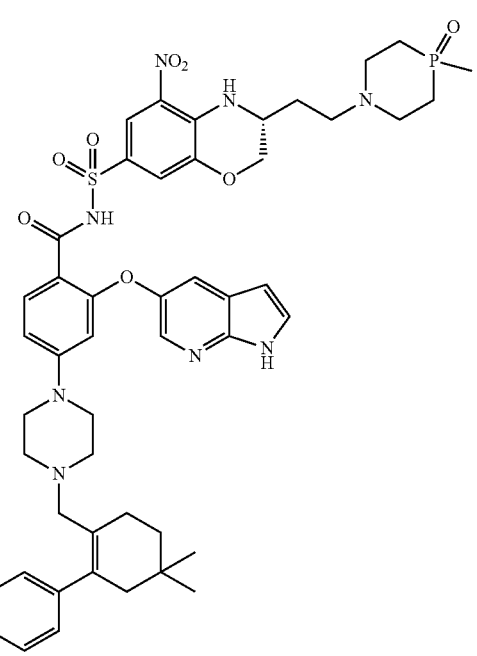 | (R)-2-((1H-pyrrolo[2,3-b]pyridin-5-yl)oxy)-4-(4-((4'-chloro-5,5-dimethyl-3,4,5,6-tetra-hydro-[1,1'-biphenyl]-2-yl)methyl)piperazin-1-yl)-N-((3-(2-(4-methyl-4-oxido-1,4-azaphosphinan-1-yl)ethyl)-5-nitro-3,4-dihydro-2H-benzo[b][1,4]oxazin-7-yl)sulfonyl)benzamide | MS-ESI (m/z): 971 [M + 1]+ |

TABLE 2-continued

| EXAMPLE | STRUCTURE | NAME | DATA |
|---|---|---|---|
| 2-156 | 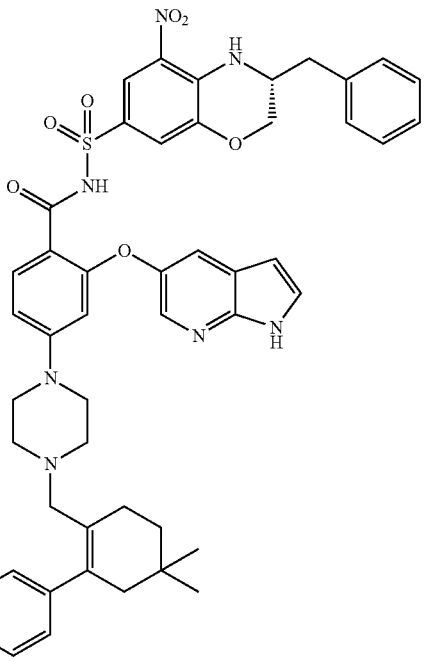 | (R)-2-((1H-pyrrolo[2,3-b]pyridin-5-yl)oxy)-N-((3-benzyl-5-nitro-3,4-dihydro-2H-benzo[b][1,4]oxazin-7-yl)sulfonyl)-4-(4-((4'-chloro-5,5-dimethyl-3,4,5,6-tetrahydro-[1,1'-biphenyl]-2-yl)methyl)piperazin-1-yl)benzamide | MS-ESI (m/z): 902 [M + 1]+ |
| 2-157 | 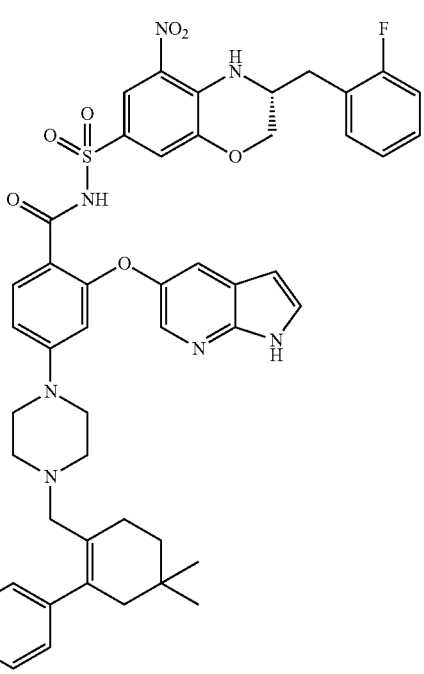 | (R)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-(2-fluorobenzyl)-5-nitro-3,4-dihydro-2H-benzo[b][1,4]oxazin-7-yl)sulfonyl)benzamide | MS-ESI (m/z): 920 [M + 1]+ |

TABLE 2-continued

| EXAMPLE | STRUCTURE | NAME | DATA |
|---|---|---|---|
| 2-158 | 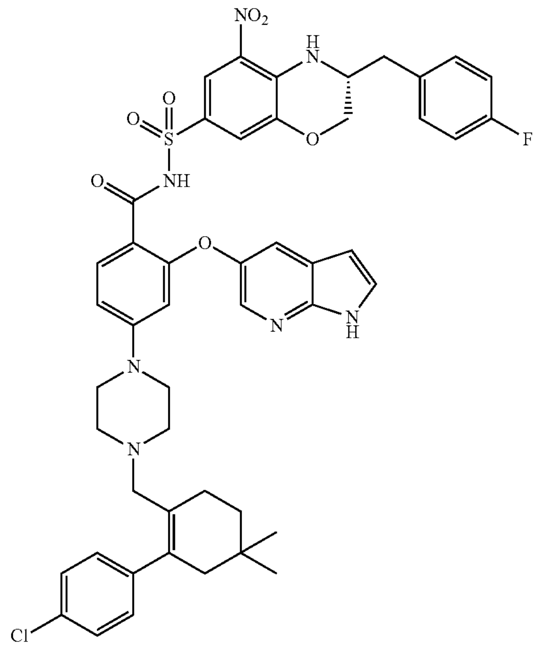 | (R)-2-((1H-pyrrolo[2,3-b]pyridin-5-yl)oxy)-4-(4-((4'-chloro-5,5-dimethyl-3,4,5,6-tetra-hydro-[1,1'-biphenyl]-2-yl)methyl)piperazin-1-yl)-N-((3-(4-fluorobenzyl)-5-nitro-3,4-dihydro-2H-benzo[b][1,4]oxazin-7-yl)sulfonyl)benzamide | MS-ESI (m/z): 920 [M + 1]+ |
| 2-159 | 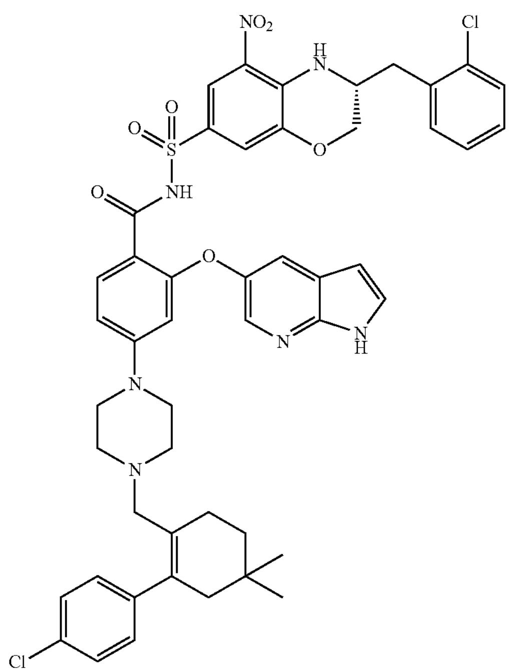 | (R)-2-((1H-pyrrolo[2,3-b]pyridin-5-yl)oxy)-4-(4-((4'-chloro-5,5-dimethyl-3,4,5,6-tetra-hydro-[1,1'-biphenyl]-2-yl)methyl)piperazin-1-yl)-N-((3-(2-chlorobenzyl)-5-nitro-3,4-dihydro-2H-benzo[b]+0[1,4]oxazin-7-yl)sulfonyl)benzamide | MS-ESI (m/z): 936 [M + 1]+ |

TABLE 2-continued

| EXAMPLE | STRUCTURE | NAME | DATA |
|---|---|---|---|
| 2-160 | 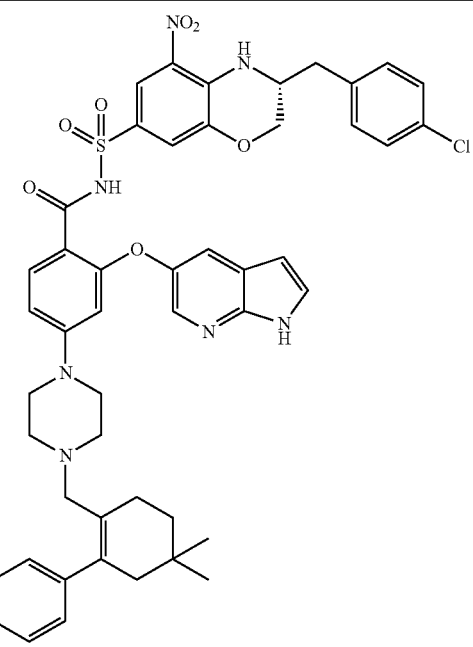 | (R)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-(4-chlorobenzyl)-5-nitro-3,4-dihydro-2H-benzo[b][1,4]oxazin-7-yl)sulfonyl)benzamide | MS-ESI (m/z): 936 [M + 1]+ |
| 2-161 | 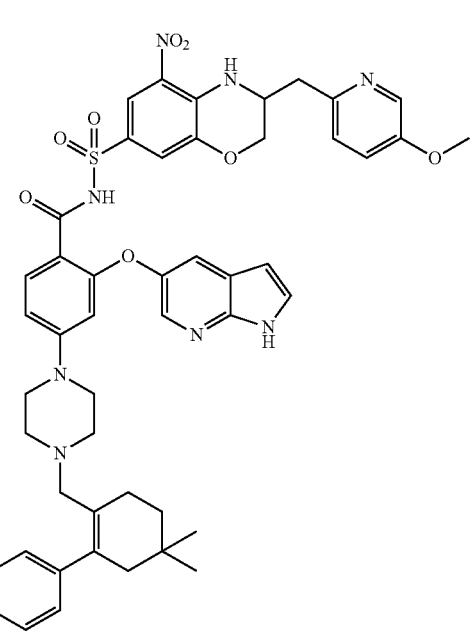 | 2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-((5-methoxypyridin-2-yl)methyl)-5-nitro-3,4-dihydro-2H-benzo[b][1,4]oxazin-7-yl)sulfonyl)benzamide | MS-ESI (m/z): 933 [M + 1]+ |

TABLE 2-continued

| EXAMPLE | STRUCTURE | NAME | DATA |
|---|---|---|---|
| 2-162 | 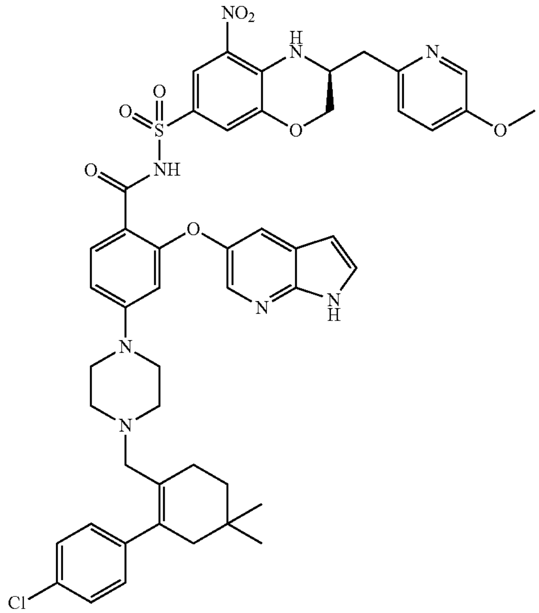 [SMILES: COc1ccc(C[C@H]2COc3cc(S(=O)(=O)NC(=O)c4ccc(N5CCN(CC6=C(c7ccc(Cl)cc7)CC(C)(C)CC6)CC5)cc4Oc4cnc5[nH]ccc5c4)cc([N+](=O)[O-])c3N2)nc1] | (S)-2-((1H-pyrrolo[2,3-b]pyridin-5-yl)oxy)-4-(4-((4'-chloro-5,5-dimethyl-3,4,5,6-tetra-hydro-[1,1'-biphenyl]-2-yl)methyl)piperazin-1-yl)-N-((3-((5-methoxypyridin-2-yl)methyl)-5-nitro-3,4-dihydro-2H-benzo[b][1,4]oxazin-7-yl)sulfonyl)benzamide | MS-ESI (m/z): 933 [M + 1]+ |
| 2-163 | 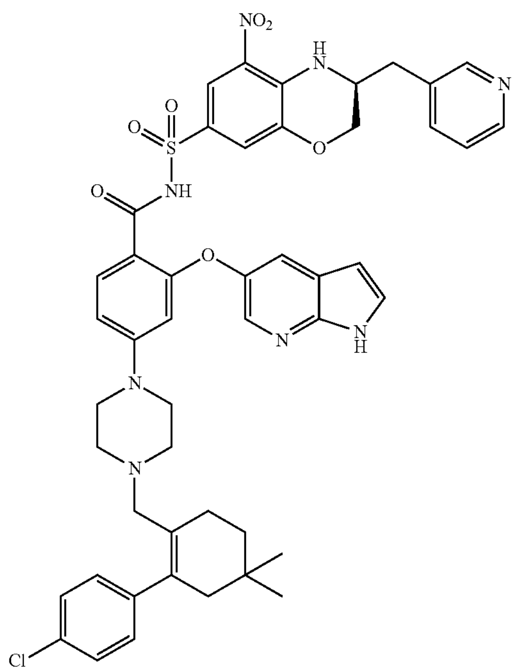 [SMILES: CC1(C)CCC(CN2CCN(c3ccc(C(=O)NS(=O)(=O)c4cc5c(c([N+](=O)[O-])c4)N[C@@H](Cc4cccnc4)CO5)c(Oc4cnc5[nH]ccc5c4)c3)CC2)=C(c2ccc(Cl)cc2)C1] | (S)-2-((1H-pyrrolo[2,3-b]pyridin-5-yl)oxy)-4-(4-((4'-chloro-5,5-dimethyl-3,4,5,6-tetra-hydro-[1,1'-biphenyl]-2-yl)methyl)piperazin-1-yl)-N-((5-nitro-3-(pyridin-3-ylmethyl)-3,4-dihydro-2H-benzo[b][1,4]oxazin-7-yl)sulfonyl)benzamide | MS-ESI (m/z): 903 [M + 1]+ |

TABLE 2-continued

| EXAMPLE | STRUCTURE | NAME | DATA |
|---|---|---|---|
| 2-164 | 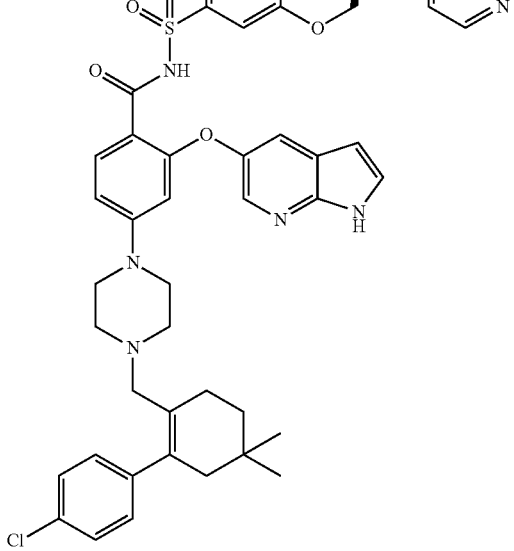 | (S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((5-nitro-3-(pyridin-4-ylmethyl)-3,4-dihydro-2H-benzo[b][1,4]oxazin-7-yl)sulfonyl)benzamide | MS-ESI (m/z): 903 [M + 1]+ |
| 2-165 | 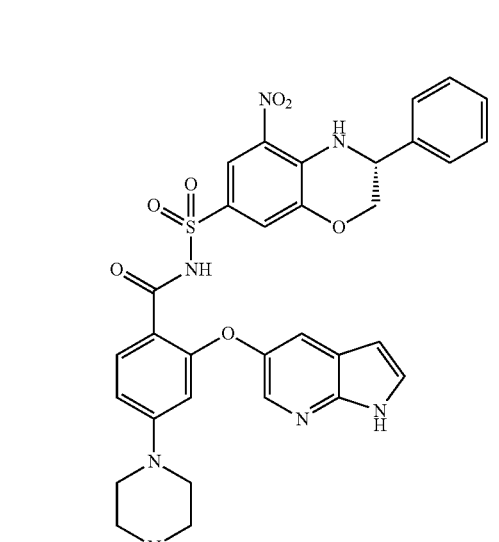 | (R)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((5-nitro-3-phenyl-3,4-dihydro-2H-benzo[b][1,4]oxazin-7-yl)sulfonyl)benzamide | MS-ESI (m/z): 888 [M + 1]+ |

TABLE 2-continued

| EXAMPLE | STRUCTURE | NAME | DATA |
|---|---|---|---|
| 2-166 | 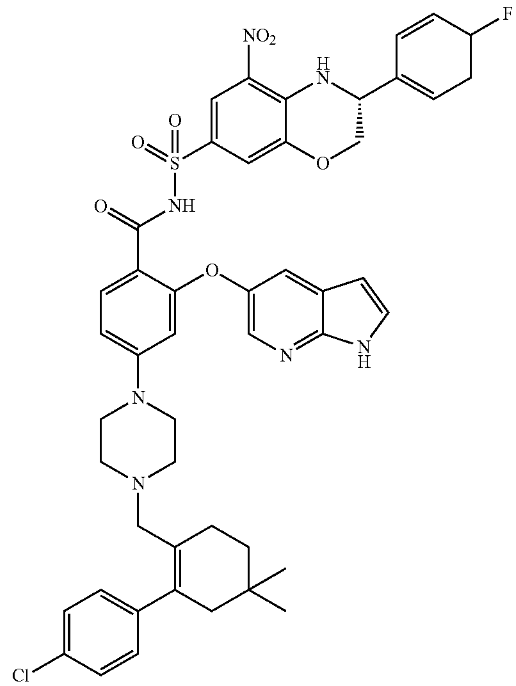 [SMILES: CC1(C)CCC(CN2CCN(c3ccc(C(=O)NS(=O)(=O)c4cc5c(c([N+](=O)[O-])c4)N[C@H](C4=CCC(F)C=C4)CO5)c(Oc4cnc5[nH]ccc5c4)c3)CC2)=C(c2ccc(Cl)cc2)C1] | (R)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-(4-fluorophenyl)-5-nitro-3,4-dihydro-2H-benzo[b][1,4]oxazin-7-yl)sulfonyl)benzamide | MS-ESI (m/z): 906 [M + 1]⁺ |
| 2-167 | 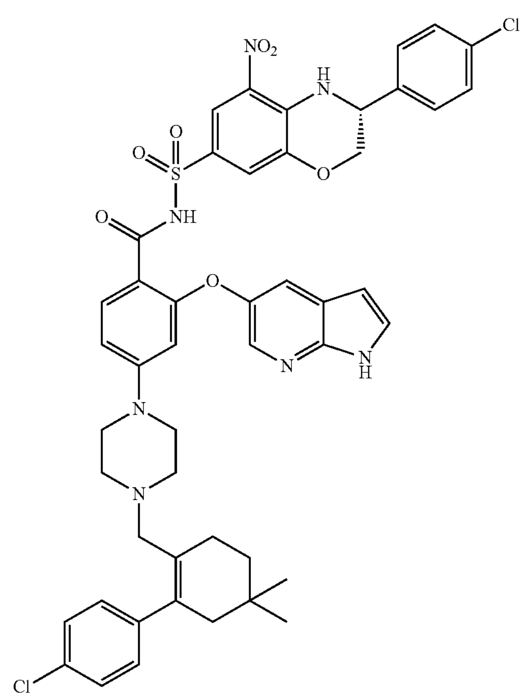 [SMILES: CC1(C)CCC(CN2CCN(c3ccc(C(=O)NS(=O)(=O)c4cc5c(c([N+](=O)[O-])c4)N[C@H](c4ccc(Cl)cc4)CO5)c(Oc4cnc5[nH]ccc5c4)c3)CC2)=C(c2ccc(Cl)cc2)C1] | (R)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-(4-chlorophenyl)-5-nitro-3,4-dihydro-2H-benzo[b][1,4]oxazin-7-yl)sulfonyl)benzamide | MS-ESI (m/z): 922 [M + 1]⁺ |

TABLE 2-continued

| EXAMPLE | STRUCTURE | NAME | DATA |
|---|---|---|---|
| 2-168 | 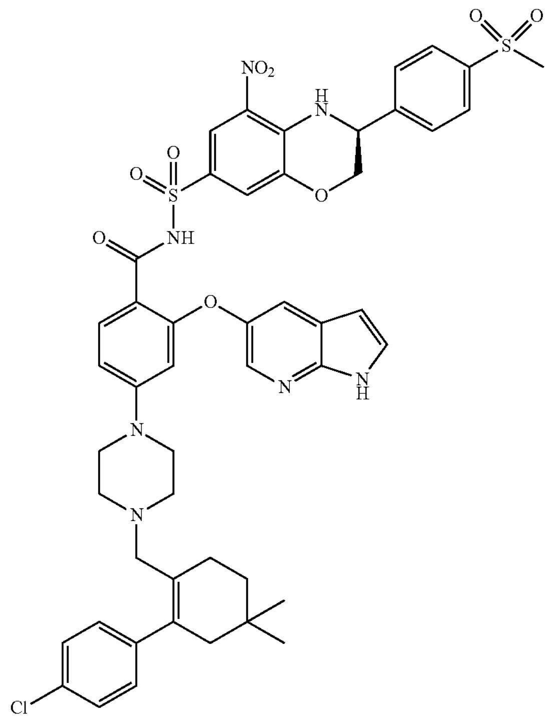 [SMILES: CC1(C)CCC(CN2CCN(c3ccc(C(=O)NS(=O)(=O)c4cc5c(c([N+](=O)[O-])c4)N[C@@H](c4ccc(S(C)(=O)=O)cc4)CO5)c(Oc4cnc5[nH]ccc5c4)c3)CC2)=C(c2ccc(Cl)cc2)C1] | (S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-(4-(methylsulfonyl)phenyl)-5-nitro-3,4-dihydro-2H-benzo[b][1,4]oxazin-7-yl)sulfonyl)benzamide | MS-ESI (m/z): 966 [M + 1]+ |
| 2-169 | 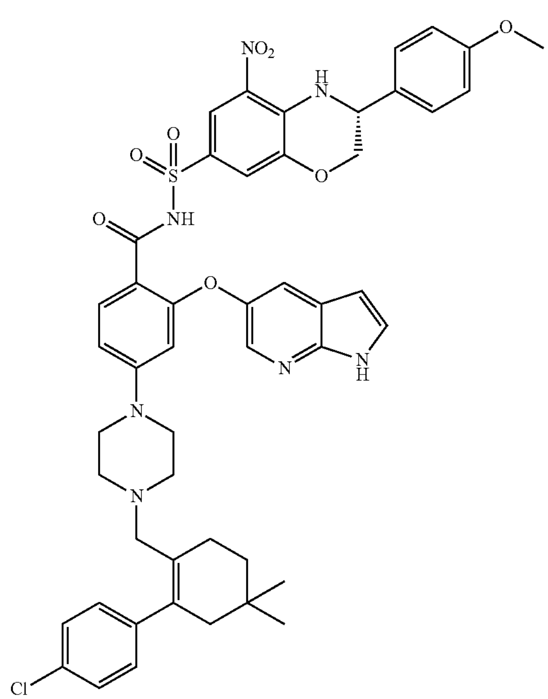 [SMILES: COc1ccc([C@@H]2COc3cc(S(=O)(=O)NC(=O)c4ccc(N5CCN(CC6=C(c7ccc(Cl)cc7)CC(C)(C)CC6)CC5)cc4Oc4cnc5[nH]ccc5c4)cc([N+](=O)[O-])c3N2)cc1] | (R)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-(4-methoxyphenyl)-5-nitro-3,4-dihydro-2H-benzo[b][1,4]oxazin-7-yl)sulfonyl)benzamide | MS-ESI (m/z): 918 [M + 1]+ |

TABLE 2-continued

| EXAMPLE | STRUCTURE | NAME | DATA |
|---|---|---|---|
| 2-170 | 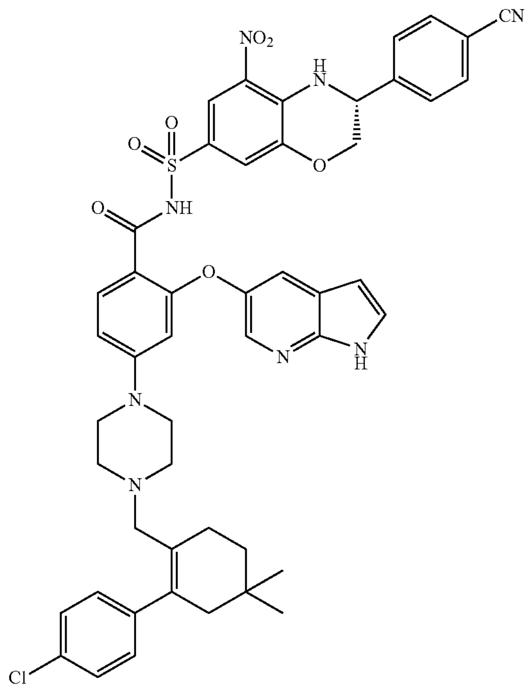 [SMILES: CC1(C)CCC(CN2CCN(c3ccc(C(=O)NS(=O)(=O)c4cc5c(c([N+](=O)[O-])c4)N[C@H](c4ccc(C#N)cc4)CO5)c(Oc4cnc5[nH]ccc5c4)c3)CC2)=C(c2ccc(Cl)cc2)C1] | (R)-2-((1H-pyrrolo[2,3-b]pyridin-5-yl)oxy)-4-(4-((4'-chloro-5,5-dimethyl-3,4,5,6-tetra-hydro-[1,1'-biphenyl]-2-yl)methyl)piperazin-1-yl)-N-((3-(4-cyanophenyl)-5-nitro-3,4-dihydro-2H-benzo[b][1,4]oxazin-7-yl)sulfonyl)benzamide | MS-ESI (m/z): 913 [M + 1]+ |
| 2-171 | 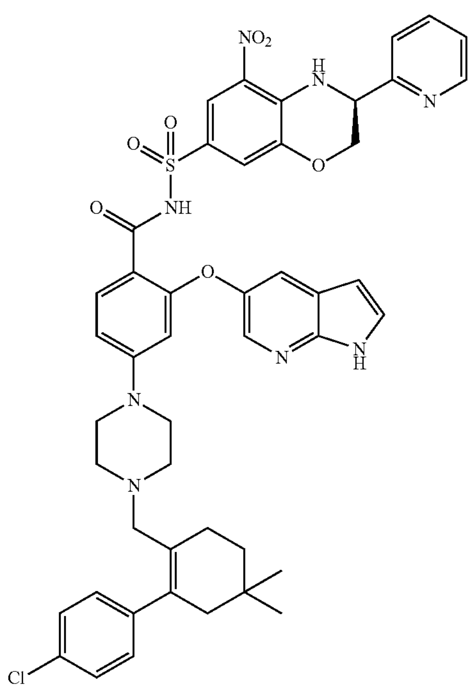 [SMILES: CC1(C)CCC(CN2CCN(c3ccc(C(=O)NS(=O)(=O)c4cc5c(c([N+](=O)[O-])c4)N[C@@H](c4ccccn4)CO5)c(Oc4cnc5[nH]ccc5c4)c3)CC2)=C(c2ccc(Cl)cc2)C1] | (S)-2-((1H-pyrrolo[2,3-b]pyridin-5-yl)oxy)-4-(4-((4'-chloro-5,5-dimethyl-3,4,5,6-tetra-hydro-[1,1'-biphenyl]-2-yl)methyl)piperazin-1-yl)-N-((5-nitro-3-(pyridin-2-yl)-3,4-dihydro-2H-benzo[b][1,4]oxazin-7-yl)sulfonyl)benzamide | MS-ESI (m/z): 889 [M + 1]+ |

TABLE 2-continued

| EXAMPLE | STRUCTURE | NAME | DATA |
|---|---|---|---|
| 2-172 | 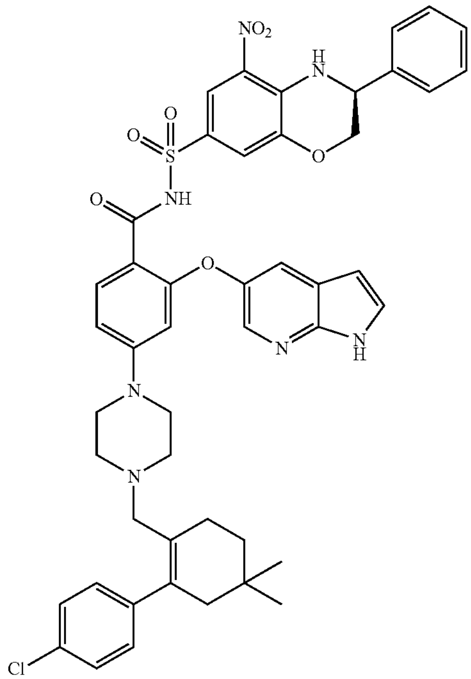 [SMILES: CC1(C)CCC(CN2CCN(c3ccc(C(=O)NS(=O)(=O)c4cc5c(c([N+](=O)[O-])c4)N[C@@H](c4ccccc4)CO5)c(Oc4cnc5[nH]ccc5c4)c3)CC2)=C(c2ccc(Cl)cc2)C1] | (S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((5-nitro-3-phenyl-3,4-dihydro-2H-benzo[b][1,4]oxazin-7-yl)sulfonyl)benzamide | MS-ESI (m/z): 888 [M + 1]⁺ |
| 2-173 | 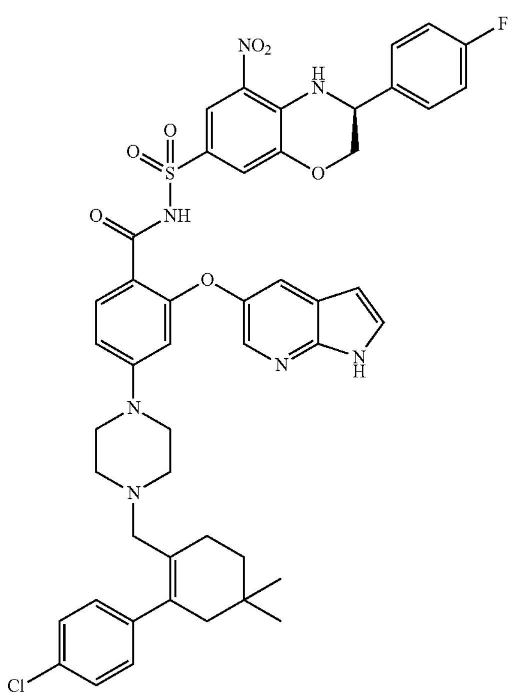 [SMILES: CC1(C)CCC(CN2CCN(c3ccc(C(=O)NS(=O)(=O)c4cc5c(c([N+](=O)[O-])c4)N[C@@H](c4ccc(F)cc4)CO5)c(Oc4cnc5[nH]ccc5c4)c3)CC2)=C(c2ccc(Cl)cc2)C1] | (S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-(4-fluorophenyl)-5-nitro-3,4-dihydro-2H-benzo[b][1,4]oxazin-7-yl)sulfonyl)benzamide | MS-ESI (m/z): 906 [M + 1]⁺ |

| EXAMPLE | STRUCTURE | NAME | DATA |
|---|---|---|---|
| 2-174 | 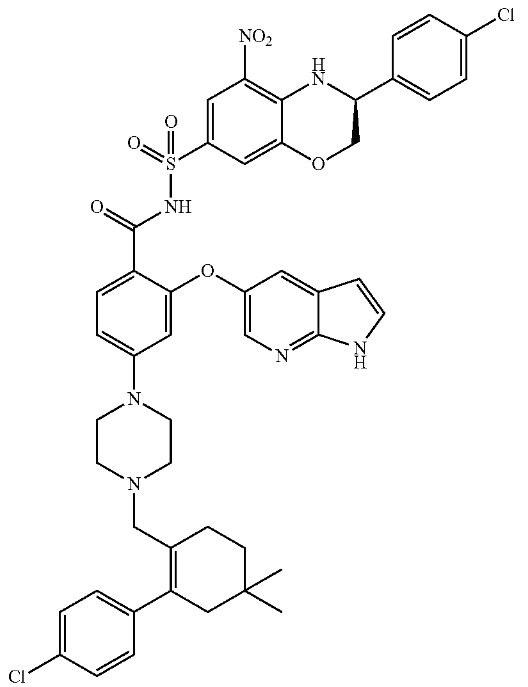 [SMILES: CC1(C)CCC(CN2CCN(c3ccc(C(=O)NS(=O)(=O)c4cc5c(c([N+](=O)[O-])c4)N[C@@H](c4ccc(Cl)cc4)CO5)c(Oc4cnc5[nH]ccc5c4)c3)CC2)=C(c2ccc(Cl)cc2)C1] | (S)-2-((1H-pyrrolo[2,3-b]pyridin-5-yl)oxy)-4-(4-((4'-chloro-5,5-dimethyl-3,4,5,6-tetra-hydro-[1,1'-biphenyl]-2-yl)methyl)piperazin-1-yl)-N-((3-(4-chlorophenyl)-5-nitro-3,4-dihydro-2H-benzo[b][1,4]oxazin-7-yl)sulfonyl)benzamide | MS-ESI (m/z): 922 [M + 1]+ |
| 2-175 | 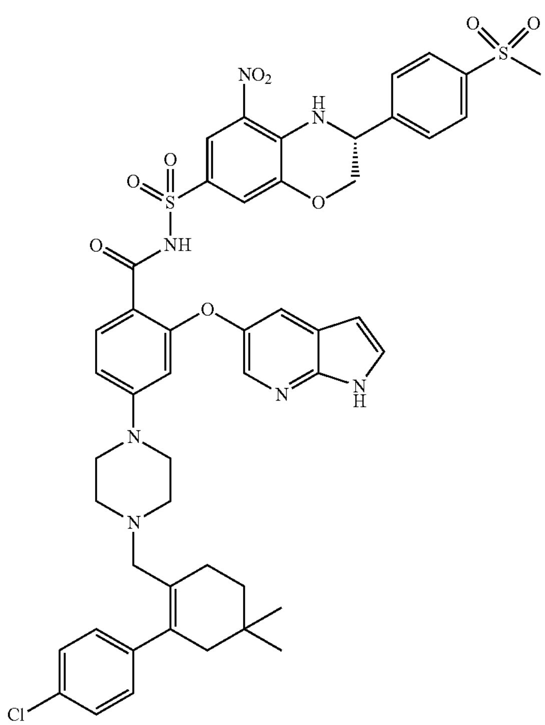 [SMILES: CC1(C)CCC(CN2CCN(c3ccc(C(=O)NS(=O)(=O)c4cc5c(c([N+](=O)[O-])c4)N[C@H](c4ccc(S(C)(=O)=O)cc4)CO5)c(Oc4cnc5[nH]ccc5c4)c3)CC2)=C(c2ccc(Cl)cc2)C1] | (R)-2-((1H-pyrrolo[2,3-b]pyridin-5-yl)oxy)-4-(4-((4'-chloro-5,5-dimethyl-3,4,5,6-tetra-hydro-[1,1'-biphenyl]-2-yl)methyl)piperazin-1-yl)-N-((3-(4-(methylsulfonyl)phenyl)-5-nitro-3,4-dihydro-2H-benzo[b][1,4]oxazin-7-yl)sulfonyl)benzamide | MS-ESI (m/z): 966 [M + 1]+ |

TABLE 2-continued

| EXAMPLE | STRUCTURE | NAME | DATA |
|---|---|---|---|
| 2-176 | 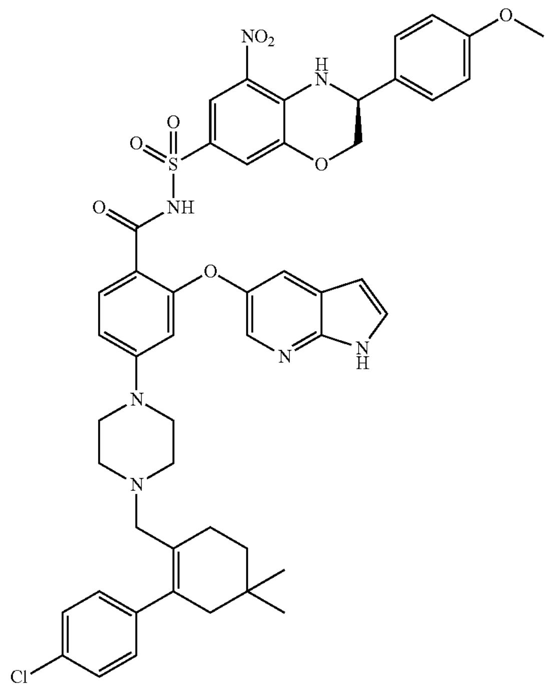 [SMILES: COc1ccc([C@H]2COc3cc(S(=O)(=O)NC(=O)c4ccc(N5CCN(CC6=C(c7ccc(Cl)cc7)CC(C)(C)CC6)CC5)cc4Oc4cnc5[nH]ccc5c4)cc([N+](=O)[O-])c3N2)cc1] | (S)-2-((1H-pyrrolo[2,3-b]pyridin-5-yl)oxy)-4-(4-((4'-chloro-5,5-dimethyl-3,4,5,6-tetra-hydro-[1,1'-biphenyl]-2-yl)methyl)piperazin-1-yl)-N-((3-(4-methoxyphenyl)-5-nitro-3,4-dihydro-2H-benzo[b][1,4]oxazin-7-yl)sulfonyl)benzamide | MS-ESI (m/z): 918 [M + 1]+ |
| 2-177 | 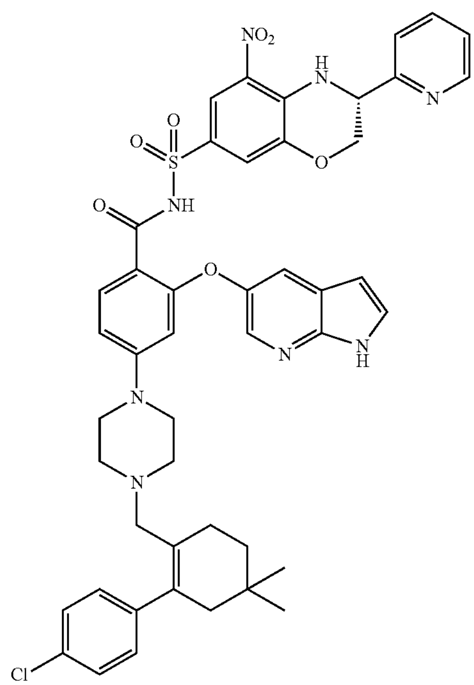 [SMILES: CC1(C)CCC(CN2CCN(c3ccc(C(=O)NS(=O)(=O)c4cc5c(c([N+](=O)[O-])c4)N[C@H](c4ccccn4)CO5)c(Oc4cnc5[nH]ccc5c4)c3)CC2)=C(c2ccc(Cl)cc2)C1] | (R)-2-((1H-pyrrolo[2,3-b]pyridin-5-yl)oxy)-4-(4-((4'-chloro-5,5-dimethyl-3,4,5,6-tetra-hydro-[1,1'-biphenyl]-2-yl)methyl)piperazin-1-yl)-N-((5-nitro-3-(pyridin-2-yl)-3,4-dihydro-2H-benzo[b][1,4]oxazin-7-yl)sulfonyl)benzamide | MS-ESI (m/z): 889 [M + 1]+ |

TABLE 2-continued

| EXAMPLE | STRUCTURE | NAME | DATA |
|---|---|---|---|
| 2-178 | 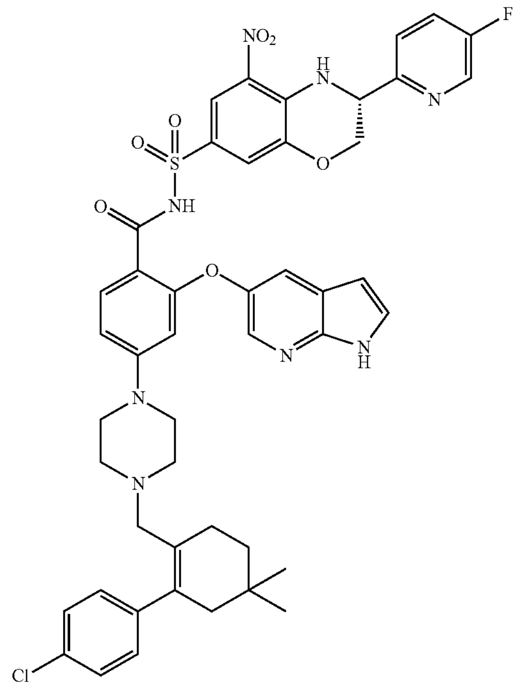 [SMILES: CC1(C)CCC(CN2CCN(c3ccc(C(=O)NS(=O)(=O)c4cc5c(c([N+](=O)[O-])c4)N[C@H](c4ccc(F)cn4)CO5)c(Oc4cnc5[nH]ccc5c4)c3)CC2)=C(c2ccc(Cl)cc2)C1] | (R)-2-((1H-pyrrolo[2,3-b]pyridin-5-yl)oxy)-4-(4-((4'-chloro-5,5-dimethyl-3,4,5,6-tetra-hydro-[1,1'-biphenyl]-2-yl)methyl)piperazin-1-yl)-N-((3-(5-fluoropyridin-2-yl)-5-nitro-3,4-dihydro-2H-benzo[b][1,4]oxazin-7-yl)sulfonyl)benzamide | MS-ESI (m/z): 907 [M + 1]⁺ |
| 2-179 | 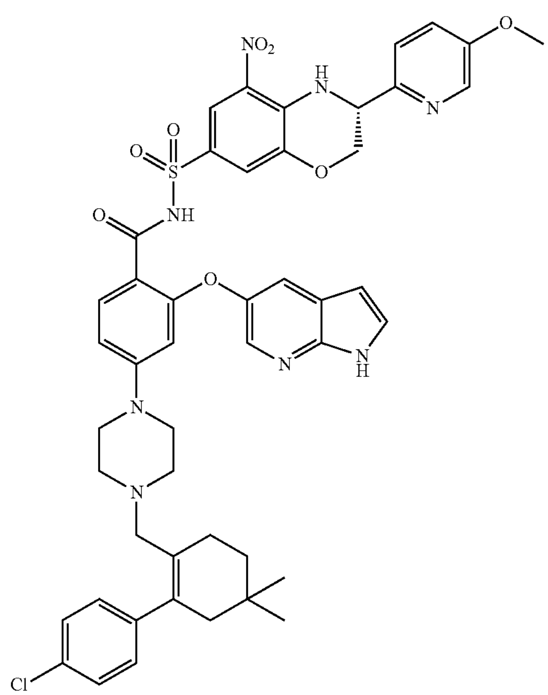 [SMILES: COc1ccc([C@@H]2COc3cc(S(=O)(=O)NC(=O)c4ccc(N5CCN(CC6=C(c7ccc(Cl)cc7)CC(C)(C)CC6)CC5)cc4Oc4cnc5[nH]ccc5c4)cc([N+](=O)[O-])c3N2)nc1] | (R)-2-((1H-pyrrolo[2,3-b]pyridin-5-yl)oxy)-4-(4-((4'-chloro-5,5-dimethyl-3,4,5,6-tetra-hydro-[1,1'-biphenyl]-2-yl)methyl)piperazin-1-yl)-N-((3-(5-methoxypyridin-2-yl)-5-nitro-3,4-dihydro-2H-benzo[b][1,4]oxazin-7-yl)sulfonyl)benzamide | MS-ESI (m/z): 919 [M + 1]⁺ |

TABLE 2-continued

| EXAMPLE | STRUCTURE | NAME | DATA |
|---|---|---|---|
| 2-180 | 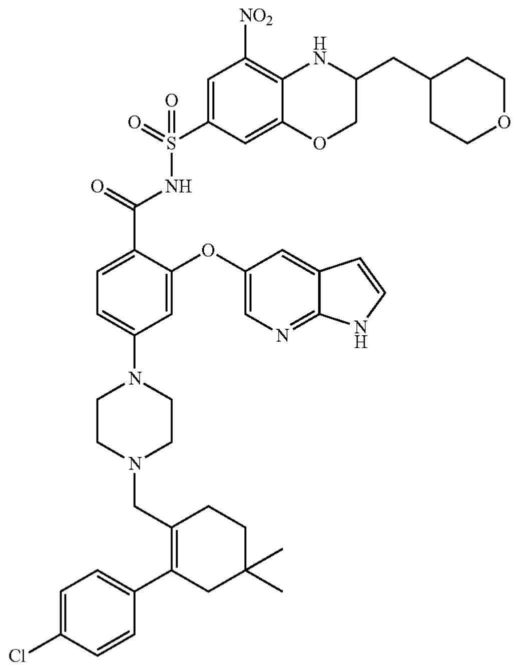 [SMILES: CC1(C)CCC(CN2CCN(c3ccc(C(=O)NS(=O)(=O)c4cc5c(c([N+](=O)[O-])c4)NC(CC4CCOCC4)CO5)c(Oc4cnc5[nH]ccc5c4)c3)CC2)=C(c2ccc(Cl)cc2)C1] | 2-((1H-pyrrolo[2,3b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((5-nitro-3-((tetrahydro-2H-pyran-4-yl)methyl)-3,4-dihydro-2H-benzo[b][1,4]oxazin-7-yl)sulfonyl)benzamide | MS-ESI (m/z): 910 [M + 1]+ |
| 2-181 | 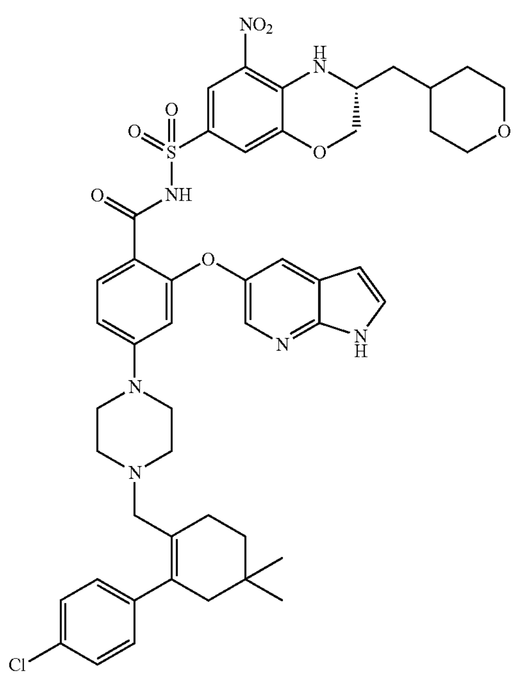 [SMILES: CC1(C)CCC(CN2CCN(c3ccc(C(=O)NS(=O)(=O)c4cc5c(c([N+](=O)[O-])c4)N[C@H](CC4CCOCC4)CO5)c(Oc4cnc5[nH]ccc5c4)c3)CC2)=C(c2ccc(Cl)cc2)C1] | (R)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((5-nitro-3-((tetrahydro-2H-pyran-4-yl)methyl)-3,4-dihydro-2H-benzo[b][1,4]oxazin-7-yl)sulfonyl)benzamide | MS-ESI (m/z): 910 [M + 1]+ |

TABLE 2-continued

| EXAMPLE | STRUCTURE | NAME | DATA |
|---|---|---|---|
| 2-182 | 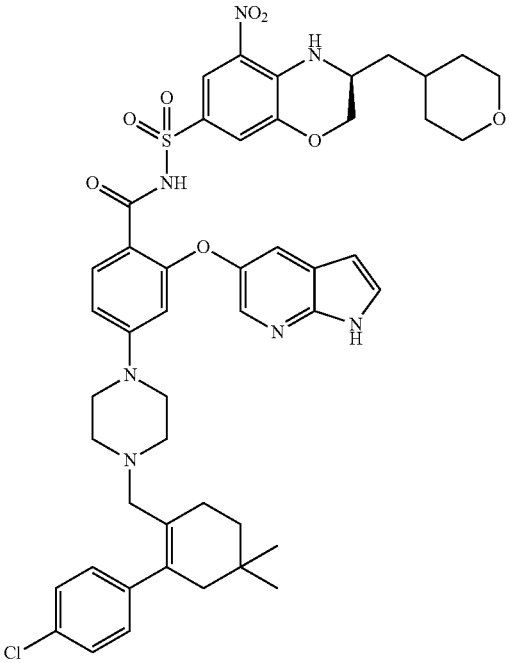 | (S)-2-((1H-pyrrolo[2,3-b]pyridin-5-yl)oxy)-4-(4-((4'-chloro-5,5-dimethyl-3,4,5,6-tetra-hydro-[1,1'-biphenyl]-2-yl)methyl)piperazin-1-yl)-N-((5-nitro-3-((tetrahydro-2H-pyran-4-yl)methyl)-3,4-dihydro-2H-benzo[b][1,4]oxazin-7-yl)sulfonyl)benzamide | MS-ESI (m/z): 910 [M + 1]+ |
| 2-183 | 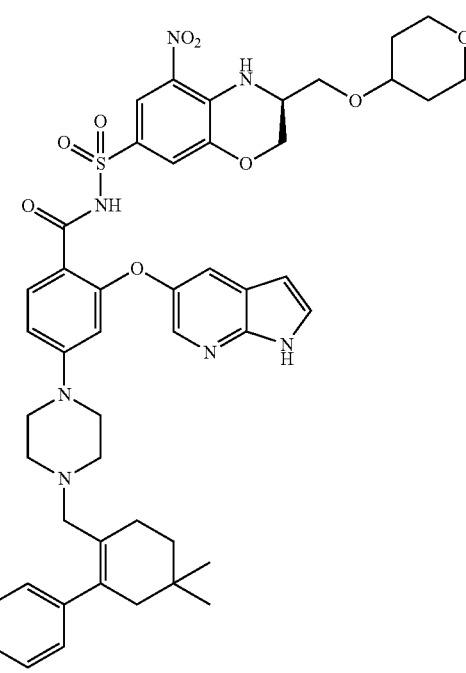 | (S)-2-((1H-pyrrolo[2,3-b]pyridin-5-yl)oxy)-4-(4-((4'-chloro-5,5-dimethyl-3,4,5,6-tetra-hydro-[1,1'-biphenyl]-2-yl)methyl)piperazin-1-yl)-N-((5-nitro-3-(((tetrahydro-2H-pyran-4-yl)oxy)methyl)-3,4-dihydro-2H-benzo[b][1,4]oxazin-7-yl)sulfonyl)benzamide | MS-ESI (m/z): 926 [M + 1]+ |

TABLE 2-continued

| EXAMPLE | STRUCTURE | NAME | DATA |
|---|---|---|---|
| 2-184 | 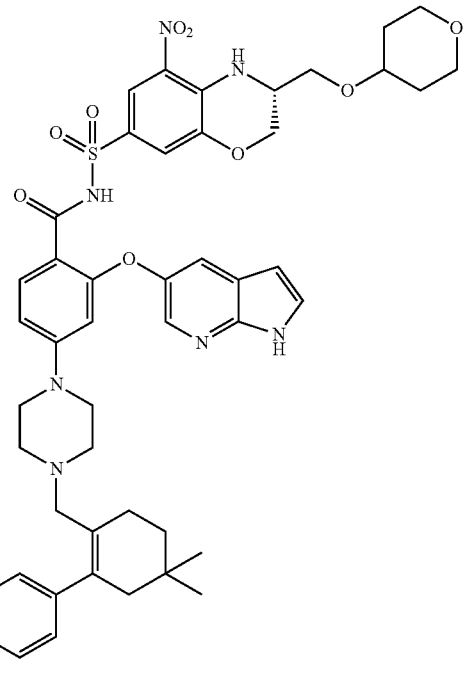 | (R)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((5-nitro-3-(((tetrahydro-2H-pyran-4-yl)oxy)methyl)-3,4-dihydro-2H-benzo[b][1,4]oxazin-7-yl)sulfonyl)benzamide | MS-ESI (m/z): 926 [M + 1]$^+$ |
| 2-185 | 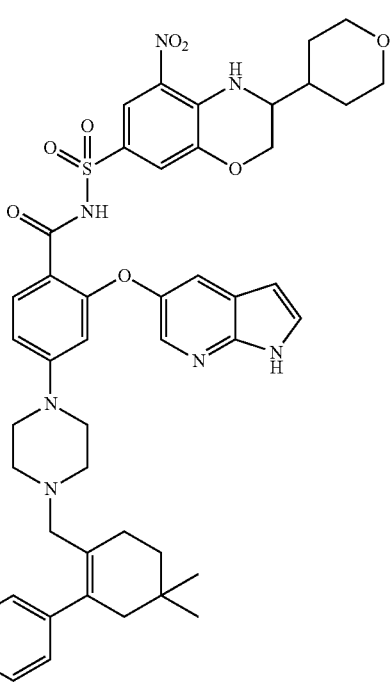 | 2-((1H-pyrrolo[2,3-b]pyridin-5-yl)oxy)-4-4-((4'-chloro-5,5-dimethyl-3,4,5,6-tetrahydro-[1,1'-biphenyl]-2-yl)methyl)piperazin-1-yl)-N-((5-nitro-3-(tetrahydro-2H-pyran-4-yl)-3,4-dihydro-2H-benzo[b][1,4]oxazin-7-yl)sulfonyl)benzamide | MS-ESI (m/z): 896 [M + 1]$^+$ |

TABLE 2-continued

| EXAMPLE | STRUCTURE | NAME | DATA |
|---|---|---|---|
| 2-186 | 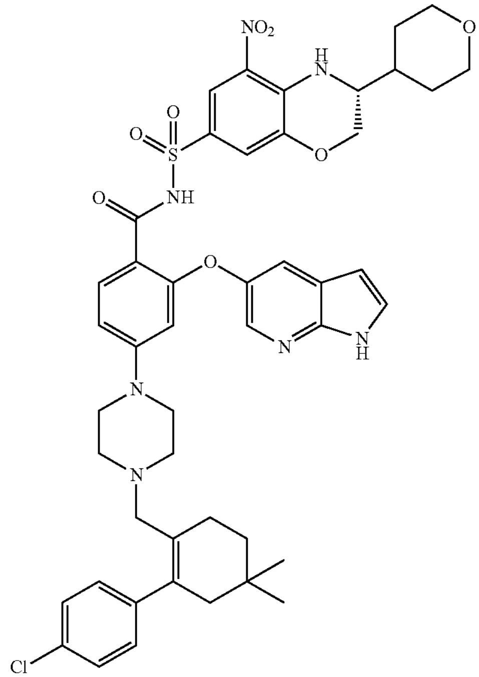 [SMILES: CC1(C)CCC(CN2CCN(c3ccc(C(=O)NS(=O)(=O)c4cc5c(c([N+](=O)[O-])c4)N[C@H](C4CCOCC4)CO5)c(Oc4cnc5[nH]ccc5c4)c3)CC2)=C(c2ccc(Cl)cc2)C1] | (R)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((5-nitro-3-(tetrahydro-2H-pyran-4-yl)-3,4-dihydro-2H-benzo[b][1,4]oxazin-7-yl)sulfonyl)benzamide | MS-ESI (m/z): 896 [M + 1]$^+$ |
| 2-187 | 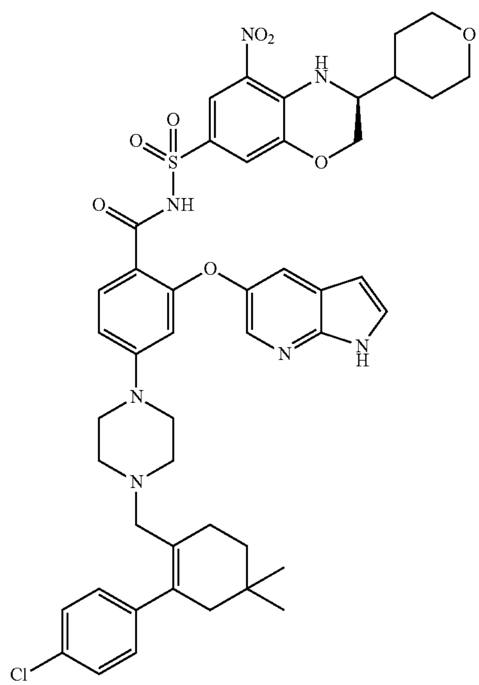 [SMILES: CC1(C)CCC(CN2CCN(c3ccc(C(=O)NS(=O)(=O)c4cc5c(c([N+](=O)[O-])c4)N[C@@H](C4CCOCC4)CO5)c(Oc4cnc5[nH]ccc5c4)c3)CC2)=C(c2ccc(Cl)cc2)C1] | (S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((5-nitro-3-(tetrahydro-2H-pyran-4-yl)-3,4-dihydro-2H-benzo[b][1,4]oxazin-7-yl)sulfonyl)benzamide | MS-ESI (m/z): 896 [M + 1]$^+$ |

TABLE 2-continued

| EXAMPLE | STRUCTURE | NAME | DATA |
|---|---|---|---|
| 2-188 | 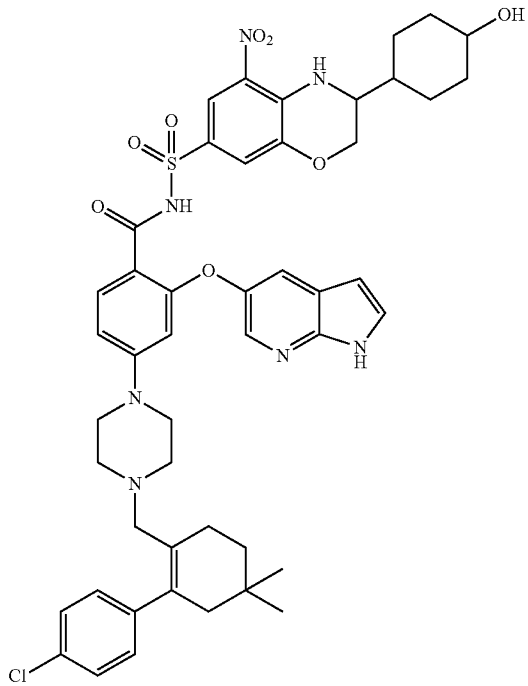 [SMILES: CC1(C)CCC(CN2CCN(c3ccc(C(=O)NS(=O)(=O)c4cc5c(c([N+](=O)[O-])c4)NC(C4CCC(O)CC4)CO5)c(Oc4cnc5[nH]ccc5c4)c3)CC2)=C(c2ccc(Cl)cc2)C1] | 2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-(4-hydroxycyclohexyl)-5-nitro-3,4-dihydro-2H-benzo[b][1,4]oxazin-7-yl)sulfonyl)benzamide | MS-ESI (m/z): 910 [M + 1]⁺ |
| 2-189 | 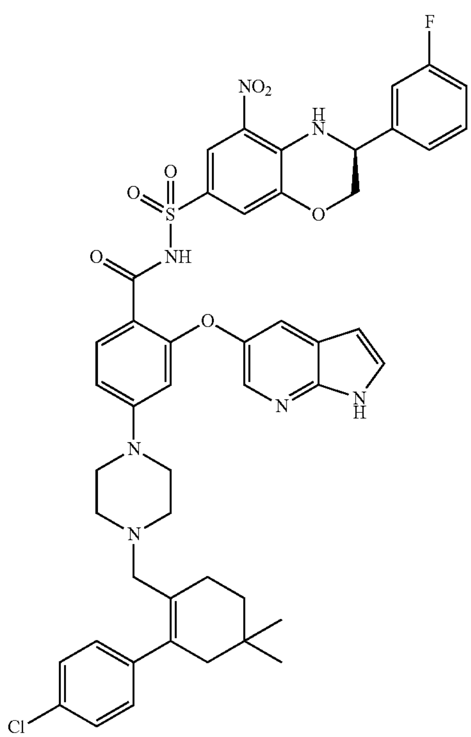 | (S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-(2-fluorobenzyl)-5-nitro-3,4-dihydro-2H-benzo[b][1,4]oxazin-7-yl)sulfonyl)benzamide | MS-ESI (m/z): 920 [M + 1]⁺ |

TABLE 2-continued

| EXAMPLE | STRUCTURE | NAME | DATA |
|---|---|---|---|
| 2-190 | 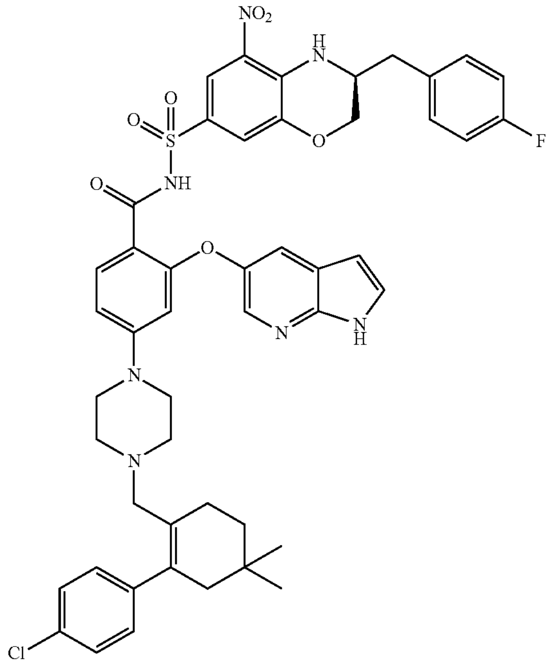 [SMILES: CC1(C)CCC(CN2CCN(c3ccc(C(=O)NS(=O)(=O)c4cc5c(c([N+](=O)[O-])c4)N[C@@H](Cc4ccc(F)cc4)CO5)c(Oc4cnc5[nH]ccc5c4)c3)CC2)=C(c2ccc(Cl)cc2)C1] | (S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-(4-fluorobenzyl)-5-nitro-3,4-dihydro-2H-benzo[b][1,4]oxazin-7-yl)sulfonyl)benzamide | MS-ESI (m/z): 920 [M + 1]$^+$ |
| 2-191 | 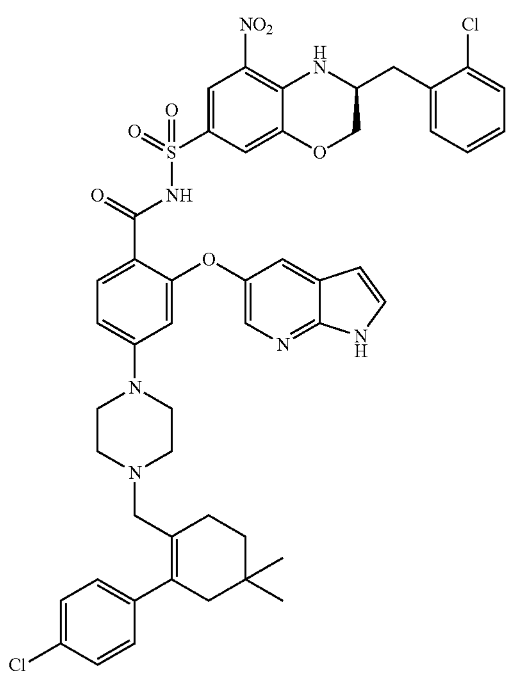 [SMILES: CC1(C)CCC(CN2CCN(c3ccc(C(=O)NS(=O)(=O)c4cc5c(c([N+](=O)[O-])c4)N[C@@H](Cc4ccccc4Cl)CO5)c(Oc4cnc5[nH]ccc5c4)c3)CC2)=C(c2ccc(Cl)cc2)C1] | (S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-(2-chlorobenzyl)-5-nitro-3,4-dihydro-2H-benzo[b][1,4]oxazin-7-yl)sulfonyl)benzamide | MS-ESI (m/z): 936 [M + 1]$^+$ |

TABLE 2-continued

| EXAMPLE | STRUCTURE | NAME | DATA |
|---|---|---|---|
| 2-192 | 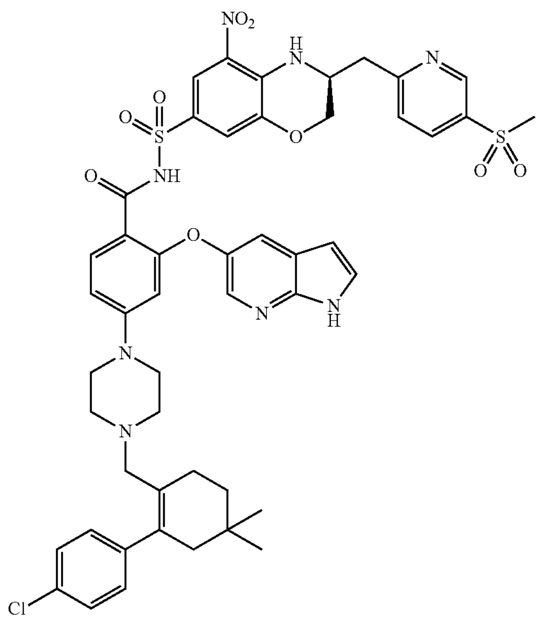 [SMILES: CC1(C)CCC(CN2CCN(c3ccc(C(=O)NS(=O)(=O)c4cc5c(c([N+](=O)[O-])c4)N[C@@H](Cc4ccc(S(C)(=O)=O)cn4)CO5)c(Oc4cnc5[nH]ccc5c4)c3)CC2)=C(c2ccc(Cl)cc2)C1] | (S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-((5-(methylsulfonyl)pyridin-2-yl)methyl)-5-nitro-3,4-dihydro-2H-benzo[b][1,4]oxazin-7-yl)sulfonyl)benzamide | MS-ESI (m/z): 981 [M + 1]+ |
| 2-193 | 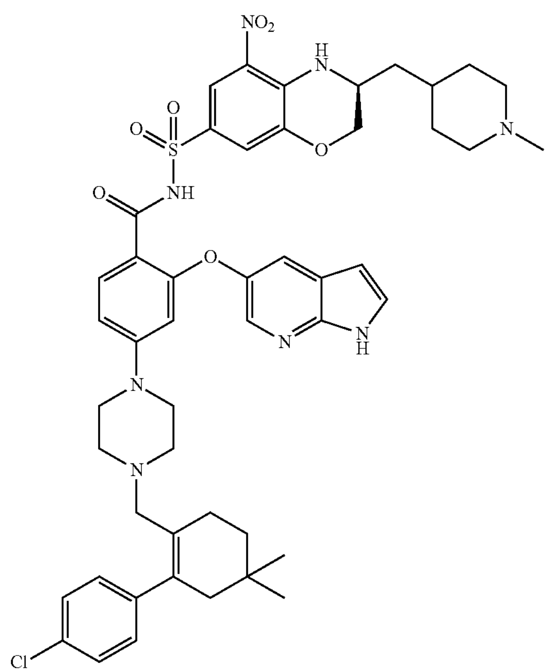 [SMILES: CN1CCC(C[C@H]2COc3cc(S(=O)(=O)NC(=O)c4ccc(N5CCN(CC6=C(c7ccc(Cl)cc7)CC(C)(C)CC6)CC5)cc4Oc4cnc5[nH]ccc5c4)cc([N+](=O)[O-])c3N2)CC1] | (S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-((1-methylpiperidin-4-yl)methyl)-5-nitro-3,4-dihydro-2H-benzo[b][1,4]oxazin-7-yl)sulfonyl)benzamide | MS-ESI (m/z): 923 |

TABLE 2-continued

| EXAMPLE | STRUCTURE | NAME | DATA |
|---|---|---|---|
| 2-194 | 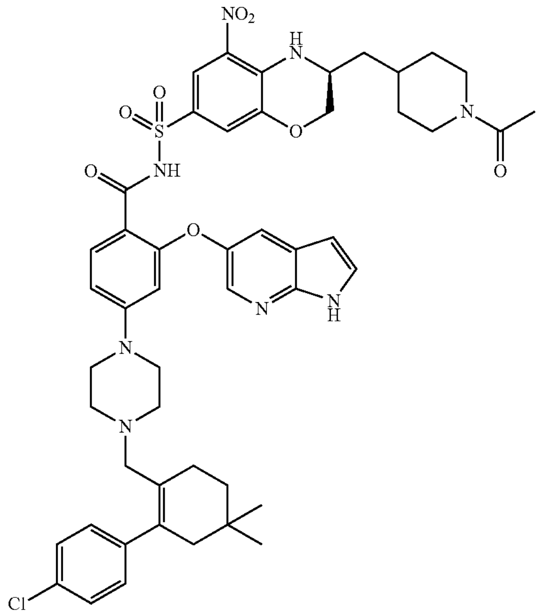 | (S)-2-((1H-pyrrolo[2,3-b]pyridin-5-yl)oxy)-N-((3-((1-acetylpiperidin-4-yl)methyl)-5-nitro-3,4-dihydro-2H-benzo[b][1,4]oxazin-7-yl)sulfonyl)-4-(4-((4'-chloro-5,5-dimethyl-3,4,5,6-tetrahydro-[1,1'-biphenyl]-2-yl)methyl)piperazin-1-yl)benzamide | MS-ESI (m/z): 951 [M + 1]⁺ |
| 2-195 | 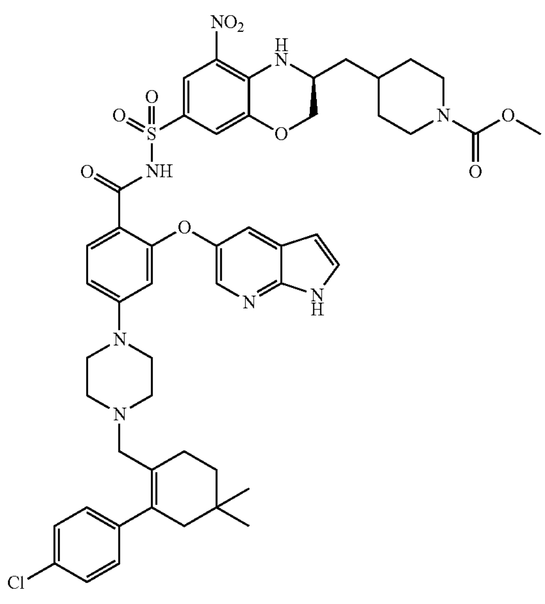 [SMILES: COC(=O)N1CCC(C[C@H]2COc3cc(S(=O)(=O)NC(=O)c4ccc(N5CCN(CC6=C(c7ccc(Cl)cc7)CC(C)(C)CC6)CC5)cc4Oc4cnc5[nH]ccc5c4)cc([N+](=O)[O-])c3N2)CC1] | methyl (S)-4-((7-(N-(2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)benzoyl)sulfamoyl)-5-nitro-3,4-dihydro-2H-benzo[b][1,4]oxazin-3-yl)methyl)piperidine-1-carboxylate | MS-ESI (m/z): 967 [M + 1]⁺ |

TABLE 2-continued

| EXAMPLE | STRUCTURE | NAME | DATA |
|---|---|---|---|
| 2-196 | 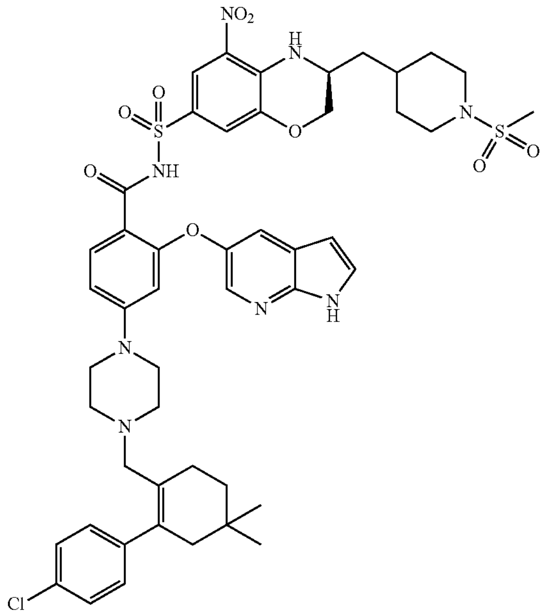 [SMILES: CC1(C)CCC(CN2CCN(c3ccc(C(=O)NS(=O)(=O)c4cc5c(c([N+](=O)[O-])c4)N[C@@H](CC4CCN(S(C)(=O)=O)CC4)CO5)c(Oc4cnc5[nH]ccc5c4)c3)CC2)=C(c2ccc(Cl)cc2)C1] | (S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-((1-(methylsulfonyl)piperidin-4-yl)methyl)-5-nitro-3,4-dihydro-2H-benzo[b][1,4]oxazin-7-yl)sulfonyl)benzamide | MS-ESI (m/z): 987 [M + 1]+ |
| 2-197 | 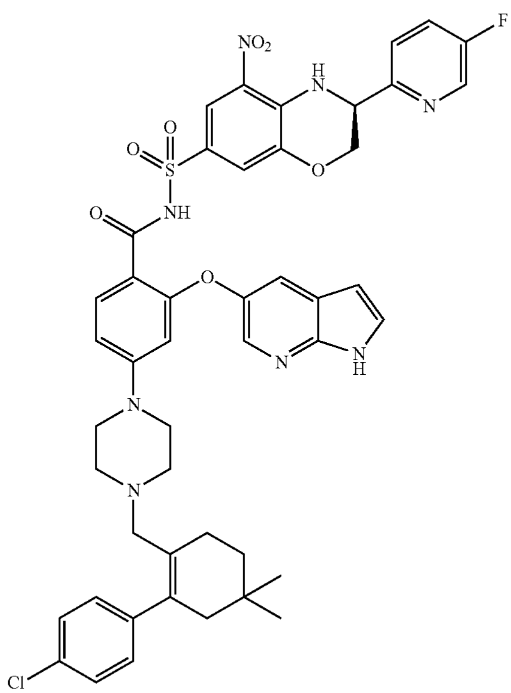 | (S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-(5-fluoropyridin-2-yl)-5-nitro-3,4-dihydro-2H-benzo[b][1,4]oxazin-7-yl)sulfonyl)benzamide | MS-ESI (m/z): 907 [M + 1]+ |

TABLE 2-continued

| EXAMPLE | STRUCTURE | NAME | DATA |
|---|---|---|---|
| 2-198-A | 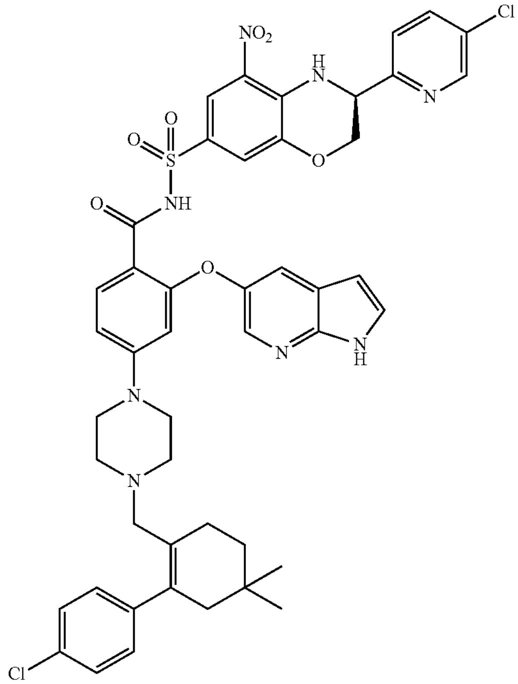 | (S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-(5-chloropyridin-2-yl)-5-nitro-3,4-dihydro-2H-benzo[b][1,4]oxazin-7-yl)sulfonyl)benzamide | MS-ESI (m/z): 923 [M + 1]+ |
| 2-198-B | 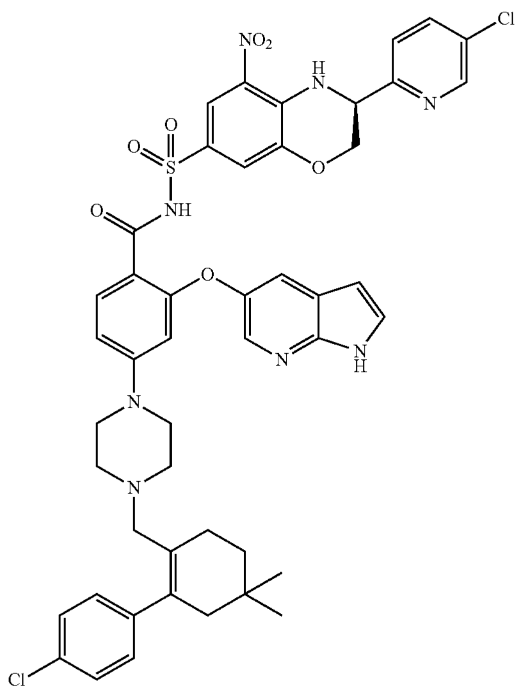 [SMILES: CC1(C)CCC(CN2CCN(c3ccc(C(=O)NS(=O)(=O)c4cc5c(c([N+](=O)[O-])c4)N[C@@H](c4ccc(Cl)cn4)CO5)c(Oc4cnc5[nH]ccc5c4)c3)CC2)=C(c2ccc(Cl)cc2)C1] | (S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-(5-chloropyridin-2-yl)-5-nitro-3,4-dihydro-2H-benzo[b][1,4]oxazin-7-yl)sulfonyl)benzamide | MS-ESI (m/z): 923 [M + 1]+ |

TABLE 2-continued

| EXAMPLE | STRUCTURE | NAME | DATA |
|---|---|---|---|
| 2-199 | 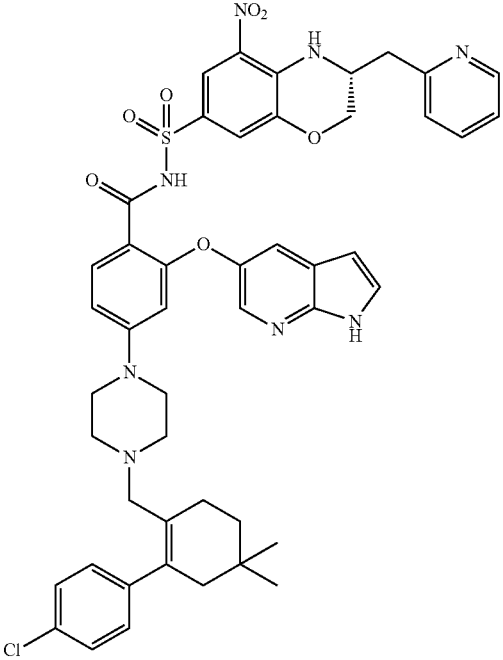 [SMILES: CC1(C)CCC(CN2CCN(c3ccc(C(=O)NS(=O)(=O)c4cc5c(c([N+](=O)[O-])c4)N[C@H](Cc4ccccn4)CO5)c(Oc4cnc5[nH]ccc5c4)c3)CC2)=C(c2ccc(Cl)cc2)C1] | (R)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((5-nitro-3-(pyridin-2-ylmethyl)-3,4-dihydro-2H-benzo[b][1,4]oxazin-7-yl)sulfonyl)benzamide | MS-ESI (m/z): 903 [M + 1]+ |
| 2-200 | 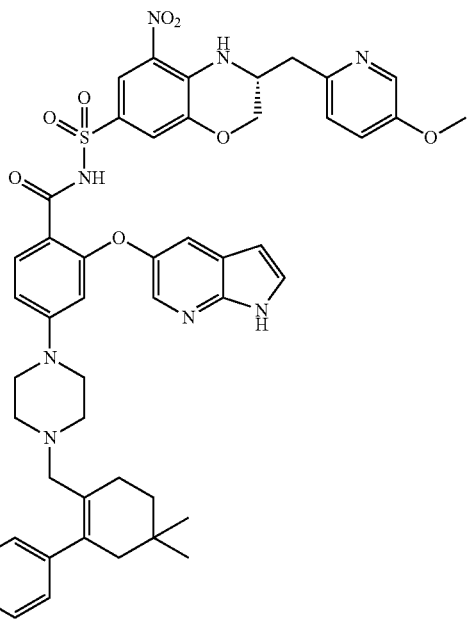 | (R)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-((5-methoxypyridin-2-yl)methyl)-5-nitro-3,4-dihydro-2H-benzo[b][1,4]oxazin-7-yl)sulfonyl)benzamide | MS-ESI (m/z): 933 [M + 1]+ |

TABLE 2-continued

| EXAMPLE | STRUCTURE | NAME | DATA |
|---|---|---|---|
| 2-201 | 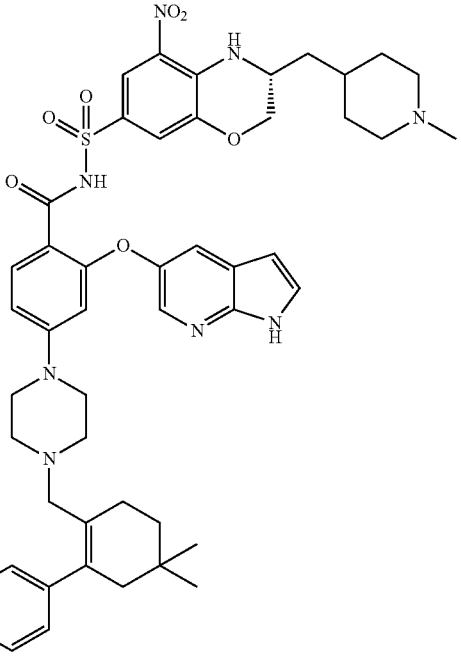 | (R)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-((1-methylpiperidin-4-yl)methyl)-5-nitro-3,4-dihydro-2H-benzo[b][1,4]oxazin-7-yl)sulfonyl)benzamide | MS-ESI (m/z): 923 [M + 1]⁺ |
| 2-202 | 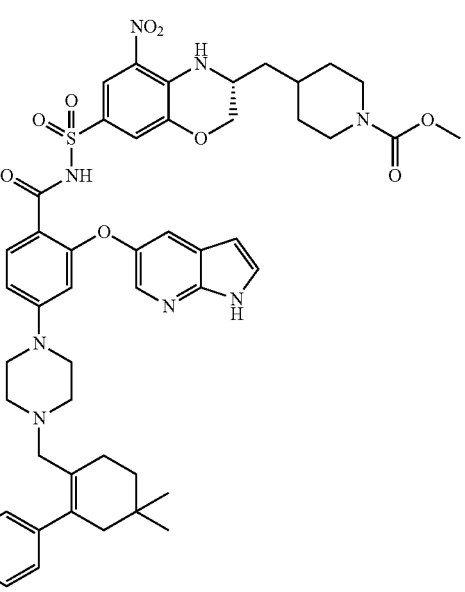 | methyl (R)-4-((7-(N-(2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)benzoyl)sulfamoyl)-5-nitro-3,4-dihydro-2H-benzo[b][1,4]oxazin-3-yl)methyl)piperidine-1-carboxylate | MS-ESI (m/z): 967 [M + 1]⁺ |

TABLE 2-continued

| EXAMPLE | STRUCTURE | NAME | DATA |
|---|---|---|---|
| 2-203 | 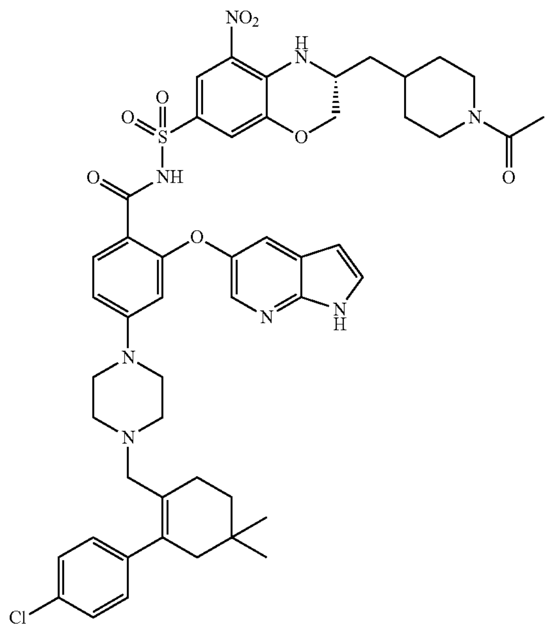 [SMILES: CC(=O)N1CCC(C[C@@H]2COc3cc(S(=O)(=O)NC(=O)c4ccc(N5CCN(CC6=C(c7ccc(Cl)cc7)CC(C)(C)CC6)CC5)cc4Oc4cnc5[nH]ccc5c4)cc([N+](=O)[O-])c3N2)CC1] | (R)-2-((1H-pyrrolo[2,3-b]pyridin-5-yl)oxy)-N-((3-((1-acetylpiperidin-4-yl)methyl)-5-nitro-3,4-dihydro-2H-benzo[b][1,4]oxazin-7-yl)sulfonyl)-4-(4-((4'-chloro-5,5-dimethyl-3,4,5,6-tetrahydro-[1,1'-biphenyl]-2-yl)methyl)piperazin-1-yl)benzamide | MS-ESI (m/z): 951 [M + 1]+ |
| 2-204 | 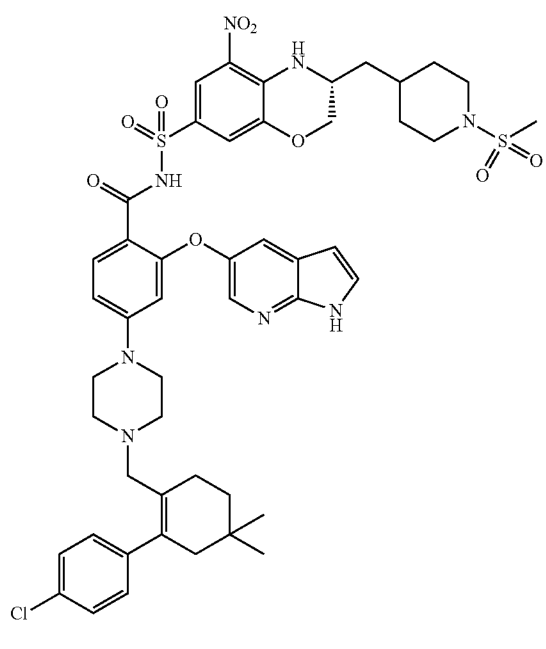 [SMILES: CC1(C)CCC(CN2CCN(c3ccc(C(=O)NS(=O)(=O)c4cc5c(c([N+](=O)[O-])c4)N[C@H](CC4CCN(S(C)(=O)=O)CC4)CO5)c(Oc4cnc5[nH]ccc5c4)c3)CC2)=C(c2ccc(Cl)cc2)C1] | (R)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-((1-(methylsulfonyl)piperidin-4-yl)methyl)-5-nitro-3,4-dihydro-2H-benzo[b][1,4]oxazin-7-yl)sulfonyl)benzamide | MS-ESI (m/z): 987 [M + 1]+ |

TABLE 2-continued

| EXAMPLE | STRUCTURE | NAME | DATA |
|---|---|---|---|
| 2-205 | 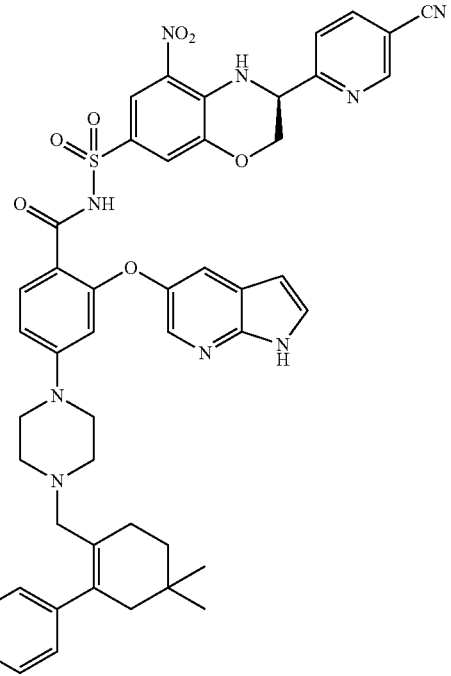 | (S)-2-((1H-pyrrolo[2,3-b]pyridin-5-yl)oxy)-4-(4-((4'-chloro-5,5-dimethyl-3,4,5,6-tetra-hydro-[1,1'-biphenyl]-2-yl)methyl)piperazin-1-yl)-N-((3-(5-cyanopyridin-2-yl)-5-nitro-3,4-dihydro-2H-benzo[b][1,4]oxazin-7-yl)sulfonyl)benzamide | MS-ESI (m/z): 914 [M + 1]+ |
| 2-206 | 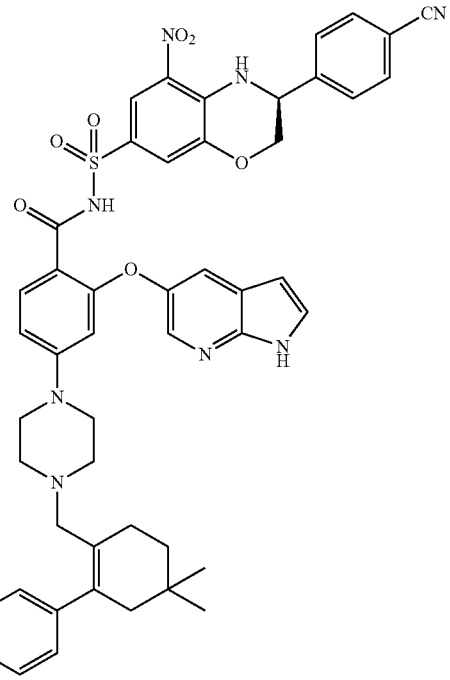 | (S)-2-((1H-pyrrolo[2,3-b]pyridin-5-yl)oxy)-4-(4-((4'-chloro-5,5-dimethyl-3,4,5,6-tetra-hydro-[1,1'-biphenyl]-2-yl)methyl)piperazin-1-yl)-N-((3-(4-cyanophenyl)-5-nitro-3,4-dihydro-2H-benzo[b][1,4]oxazin-7-yl)sulfonyl)benzamide | MS-ESI (m/z): 913 [M + 1]+ |

TABLE 2-continued

| EXAMPLE | STRUCTURE | NAME | DATA |
|---|---|---|---|
| 2-207 | 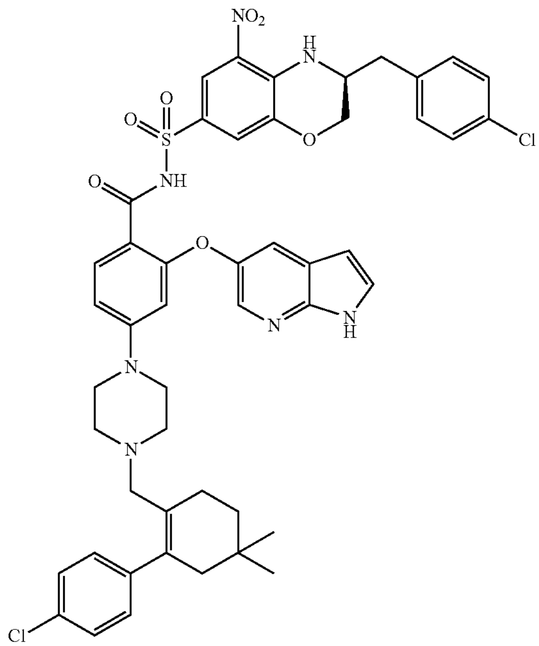 [SMILES: CC1(C)CCC(CN2CCN(c3ccc(C(=O)NS(=O)(=O)c4cc5c(c([N+](=O)[O-])c4)N[C@@H](Cc4ccc(Cl)cc4)CO5)c(Oc4cnc5[nH]ccc5c4)c3)CC2)=C(c2ccc(Cl)cc2)C1] | (S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-(4-chlorobenzyl)-5-nitro-3,4-dihydro-2H-benzo[b][1,4]oxazin-7-yl)sulfonyl)benzamide | MS-ESI (m/z): 936 [M + 1]+ |
| 2-208 | 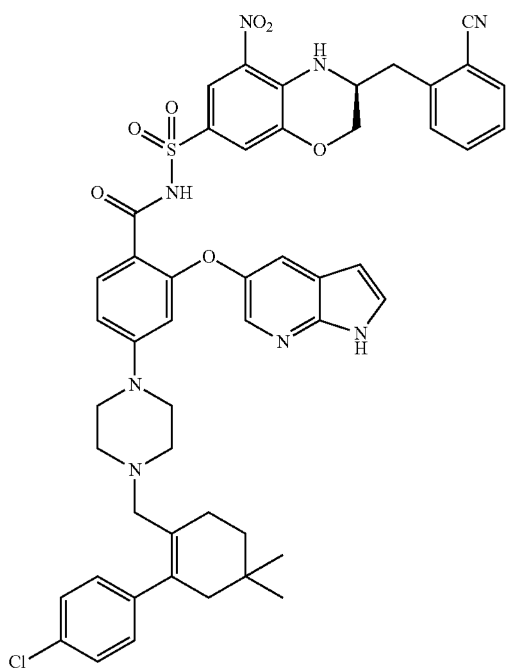 | (S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-(2-cyanobenzyl)-5-nitro-3,4-dihydro-2H-benzo[b][1,4]oxazin-7-yl)sulfonyl)benzamide | MS-ESI (m/z): 927 [M + 1]+ |

TABLE 2-continued

| EXAMPLE | STRUCTURE | NAME | DATA |
|---|---|---|---|
| 2-209 | 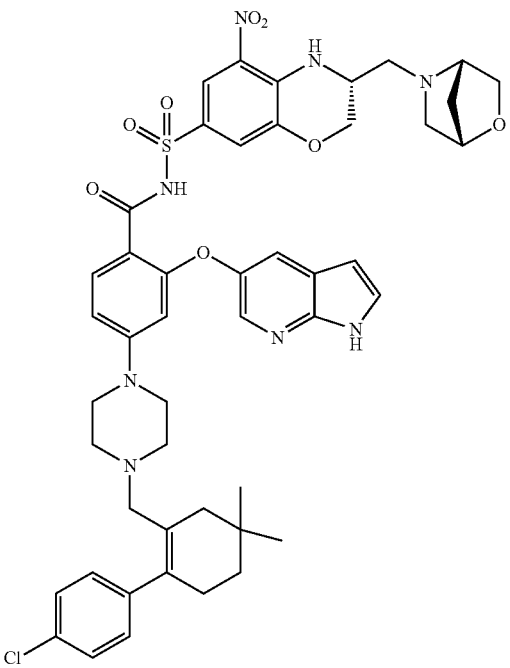 [SMILES: CC1(C)CCC(c2ccc(Cl)cc2)=C(CN2CCN(c3ccc(C(=O)NS(=O)(=O)c4cc5c(c([N+](=O)[O-])c4)N[C@H](CN4C[C@@H]6C[C@H]4CO6)CO5)c(Oc4cnc5[nH]ccc5c4)c3)CC2)C1] | 2-((1H-pyrrolo[2,3-b]pyridin-5-yl)oxy)-N-(((R)-3-(((1S,4S)-2-oxa-5-azabicyclo[2.2.1]heptan-5-yl)methyl)-5-nitro-3,4-dihydro-2H-benzo[b][1,4]oxazin-7-yl)sulfonyl)-4-(4-((4'-chloro-4,4-dimethyl-3,4,5,6-tetrahydro-1,1'-biphenyl]-2-yl)methyl)piperazin-1-yl)benzamide | MS-ESI (m/z): 923 [M + 1]+ |
| 2-210 | 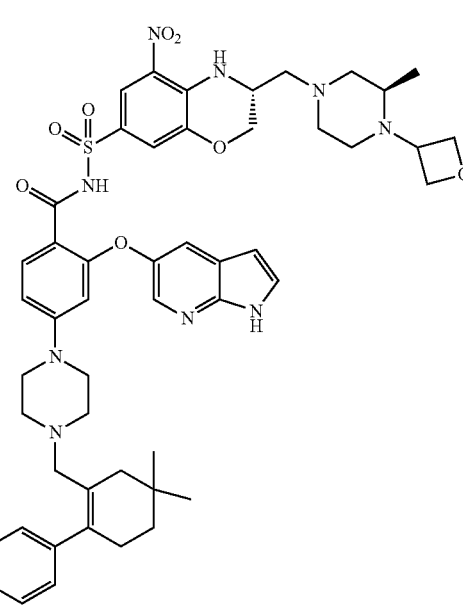 | 2-((1H-pyrrolo[2,3-b]pyridin-5-yl)oxy)-4-(4-((4'-chloro-4,4-dimethyl-3,4,5,6-tetrahydro-[1,1'-biphenyl]-2-yl)methyl)piperazin-1-yl)-N-(((R)-3-(((R)-3-methyl-4-(oxetan-3-yl)piperazin-1-yl)methyl)-5-nitro-3,4-dihydro-2H-benzo[b][1,4]oxazin-7-yl)sulfonyl)benzamide | MS-ESI (m/z): 980 [M + 1]+ |

TABLE 2-continued

| EXAMPLE | STRUCTURE | NAME | DATA |
|---|---|---|---|
| 2-211 | 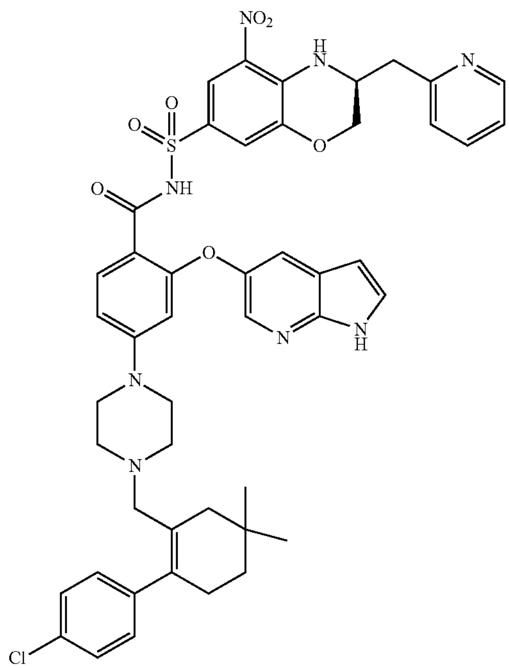 [SMILES: CC1(C)CCC(c2ccc(Cl)cc2)=C(CN2CCN(c3ccc(C(=O)NS(=O)(=O)c4cc5c(c([N+](=O)[O-])c4)N[C@@H](Cc4ccccn4)CO5)c(Oc4cnc5[nH]ccc5c4)c3)CC2)C1] | (S)-2-((1H-pyrrolo[2,3-b]pyridin-5-yl)oxy)-4-(4-((4'-chloro-4,4-dimethyl-3,4,5,6-tetra-hydro-[1,1'-biphenyl]-2-yl)methyl)piperazin-1-yl)-N-((5-nitro-3-(pyridin-2-ylmethyl)-3,4-dihydro-2H-benzo[b][1,4]oxazin-7-yl)sulfonyl)benzamide | MS-ESI (m/z): 903 [M + 1]+ |
| 2-212 | 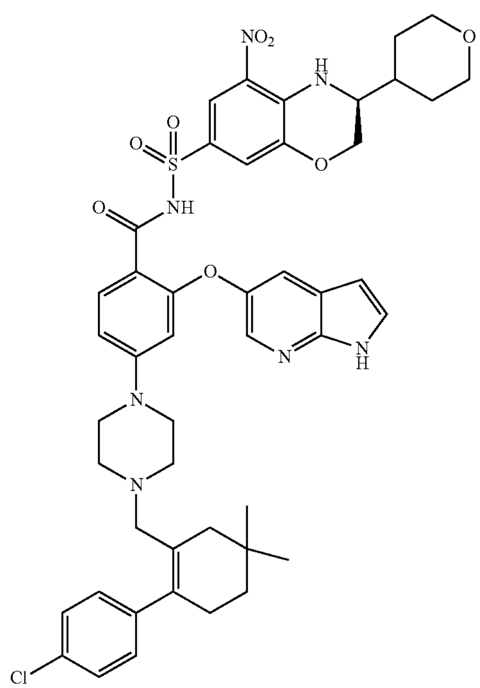 [SMILES: CC1(C)CCC(c2ccc(Cl)cc2)=C(CN2CCN(c3ccc(C(=O)NS(=O)(=O)c4cc5c(c([N+](=O)[O-])c4)N[C@@H](C4CCOCC4)CO5)c(Oc4cnc5[nH]ccc5c4)c3)CC2)C1] | (S)-2-((1H-pyrrolo[2,3-b]pyridin-5-yl)oxy)-4-(4-((4'-chloro-4,4-dimethyl-3,4,5,6-tetra-hydro-[1,1'-biphenyl]-2-yl)methyl)piperazin-1-yl)-N-((5-nitro-3-(tetrahydro-2H-pyran-4-yl)-3,4-dihydro-2H-benzo[b][1,4]oxazin-7-yl)sulfonyl)benzamide | MS-ESI (m/z): 896 [M + 1]+ |

TABLE 2-continued

| EXAMPLE | STRUCTURE | NAME | DATA |
|---|---|---|---|
| 2-213 | 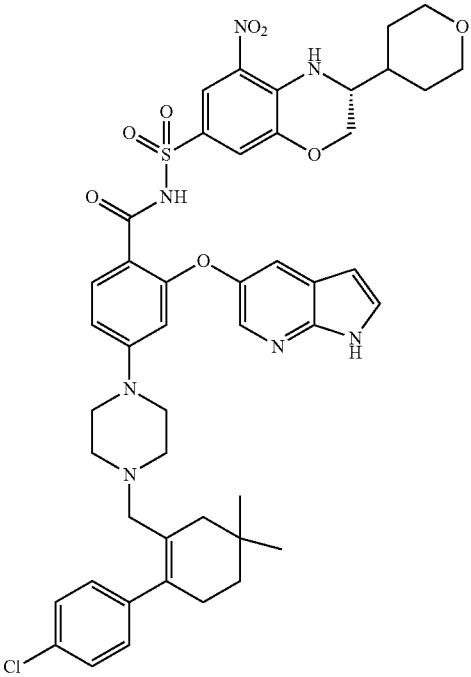 [SMILES: CC1(C)CCC(c2ccc(Cl)cc2)=C(CN2CCN(c3ccc(C(=O)NS(=O)(=O)c4cc5c(c([N+](=O)[O-])c4)N[C@H](C4CCOCC4)CO5)c(Oc4cnc5[nH]ccc5c4)c3)CC2)C1] | (R)-2-((1H-pyrrolo[2,3-b]pyridin-5-yl)oxy)-4-(4-((4'-chloro-4,4-dimethyl-3,4,5,6-tetrahydro-[1,1'-biphenyl]-2-yl)methyl)piperazin-1-yl)-N-((5-nitro-3-(tetrahydro-2H-pyran-4-yl)-3,4-dihydro-2H-benzo[b][1,4]oxazin-7-yl)sulfonyl)benzamide | MS-ESI (m/z): 896 [M + 1]+ |
| 2-214 | 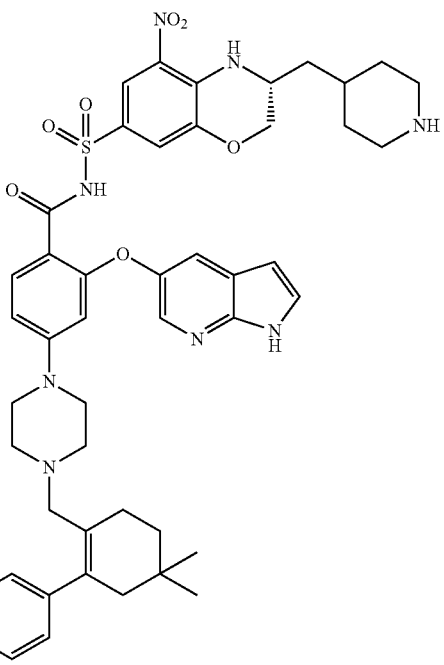 | (R)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((5-nitro-3-(piperidin-4-ylmethyl)-3,4-dihydro-2H-benzo[b][1,4]oxazin-7-yl)sulfonyl)benzamide | MS-ESI (m/z): 909 [M + 1]+ |

| EXAMPLE | STRUCTURE | NAME | DATA |
|---|---|---|---|
| 2-215 | 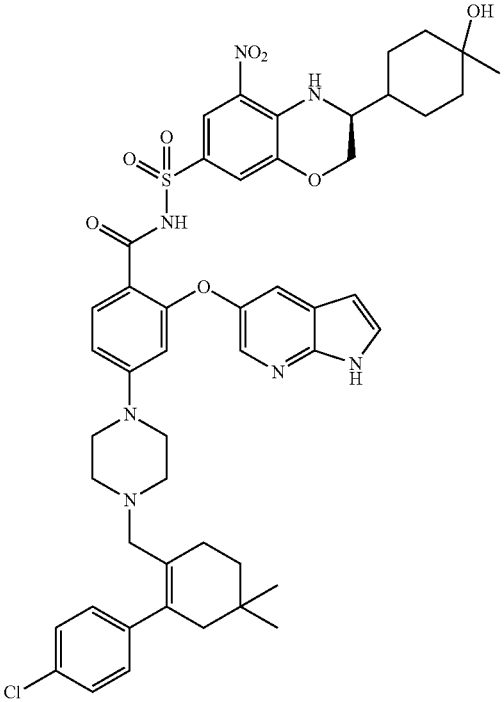 [SMILES: CC1(C)CCC(CN2CCN(c3ccc(C(=O)NS(=O)(=O)c4cc5c(c([N+](=O)[O-])c4)N[C@@H](C4CCC(C)(O)CC4)CO5)c(Oc4cnc5[nH]ccc5c4)c3)CC2)=C(c2ccc(Cl)cc2)C1] | (S)-2-((1H-pyrrolo[2,3-b]pyridin-5-yl)oxy)-4-(4-((4'-chloro-5,5-dimethyl-3,4,5,6-tetra-hydro-[1,1'-biphenyl]-2-yl)methyl)piperazin-1-yl)-N-((3-(4-hydroxy-4-methylcyclohexyl)-5-nitro-3,4-dihydro-2H-benzo[b][1,4]oxazin-7-yl)sulfonyl)benzamide | MS-ESI (m/z): 924 [M + 1]⁺ |
| 2-216 | 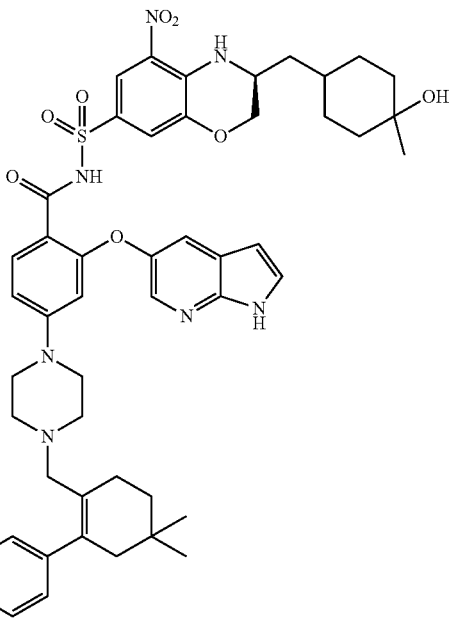 | (S)-2-((1H-pyrrolo[2,3-b]pyridin-5-yl)oxy)-4-(4-((4'-chloro-5,5-dimethyl-3,4,5,6-tetra-hydro-[1,1'-biphenyl]-2-yl)methyl)piperazin-1-yl)-N-((3-((4-hydroxy-4-methylcyclohexyl)methyl)-5-nitro-3,4-dihydro-2H-benzo[b][1,4]oxazin-7-yl)sulfonyl)benzamide | MS-ESI (m/z): 938 [M + 1]⁺ |

| EXAMPLE | STRUCTURE | NAME | DATA |
|---|---|---|---|
| 2-217 | 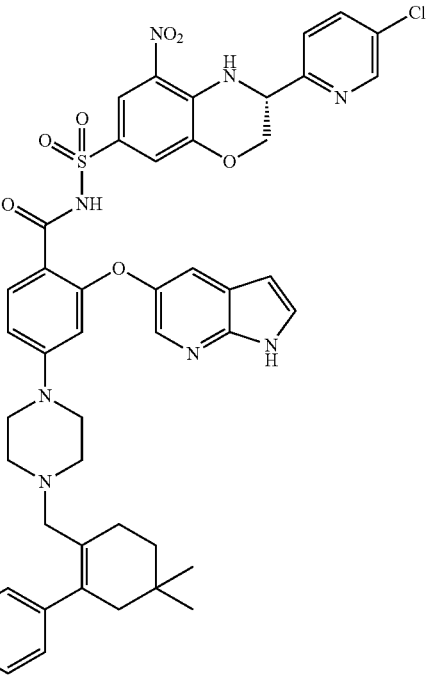 | (R)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-(5-chloropyridin-2-yl)-5-nitro-3,4-dihydro-2H-benzo[b][1,4]oxazin-7-yl)sulfonyl)benzamide | MS-ESI (m/z): 923 [M + 1]+ |
| 2-218 | 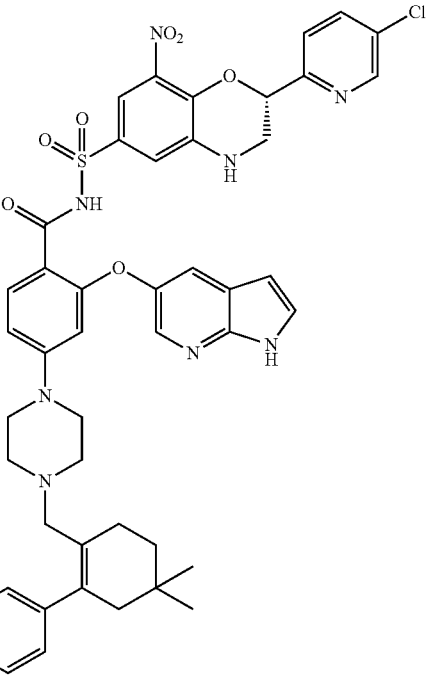 | (S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((2-(5-chloropyridin-2-yl)-8-nitro-3,4-dihydro-2H-benzo[b][1,4]oxazin-6-yl)sulfonyl)benzamide | MS-ESI (m/z): 923 [M + 1]+ |

TABLE 2-continued

| EXAMPLE | STRUCTURE | NAME | DATA |
| --- | --- | --- | --- |
| 2-219 | 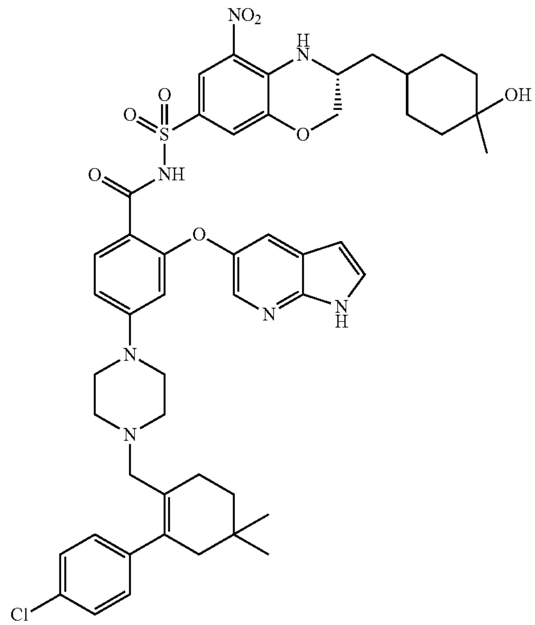 [SMILES: CC1(C)CCC(CN2CCN(c3ccc(C(=O)NS(=O)(=O)c4cc5c(c([N+](=O)[O-])c4)N[C@H](CC4CCC(C)(O)CC4)CO5)c(Oc4cnc5[nH]ccc5c4)c3)CC2)=C(c2ccc(Cl)cc2)C1] | (R)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-((4-hydroxy-4-methylcyclohexyl)methyl)-5-nitro-3,4-dihydro-2H-benzo[b][1,4]oxazin-7-yl)sulfonyl)benzamide | MS-ESI (m/z): 938 [M + 1]$^+$ |
| 2-220 | 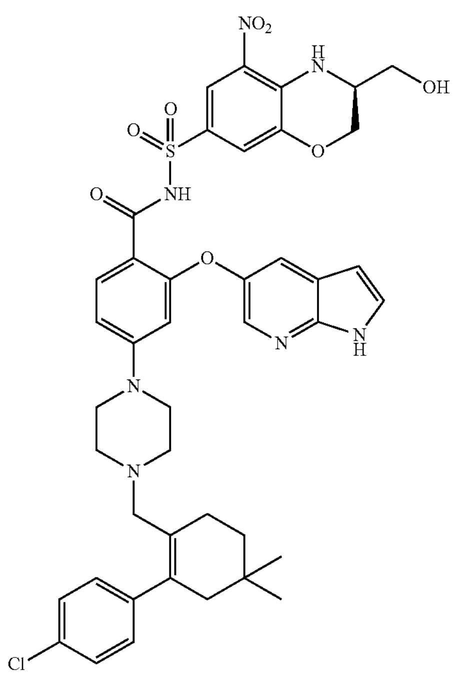 | (S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-(hydroxymethyl)-5-nitro-3,4-dihydro-2H-benzo[b][1,4]oxazin-7-yl)sulfonyl)benzamide | MS-ESI (m/z): 842 [M + 1]$^+$ |

TABLE 2-continued

| EXAMPLE | STRUCTURE | NAME | DATA |
|---|---|---|---|
| 2-221 | 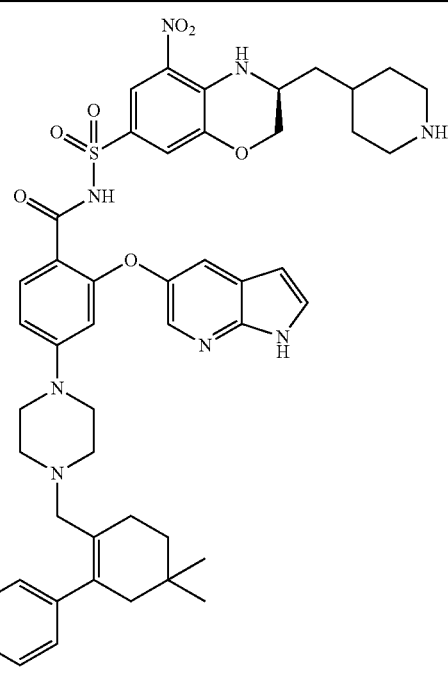 | (S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((5-nitro-3-(piperidin-4-ylmethyl)-3,4-dihydro-2H-benzo[b][1,4]oxazin-7-yl)sulfonyl)benzamide | MS-ESI (m/z): 909 [M + 1]$^+$ |
| 2-222 | 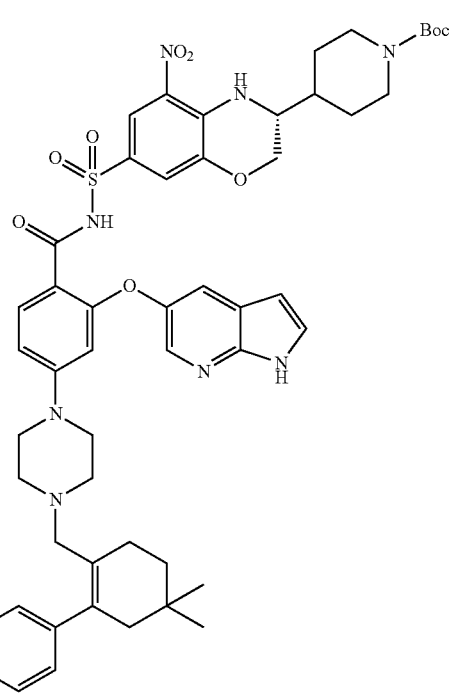 | tert-butyl (R)-4-(7-(N-(2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)benzoyl)sulfamoyl)-5-nitro-3,4-dihydro-2H-benzo[b][1,4]oxazin-3-yl)piperidine-1-carboxylate | MS-ESI (m/z): 995 [M + 1]$^+$ |

TABLE 2-continued

| EXAMPLE | STRUCTURE | NAME | DATA |
|---|---|---|---|
| 2-223 | 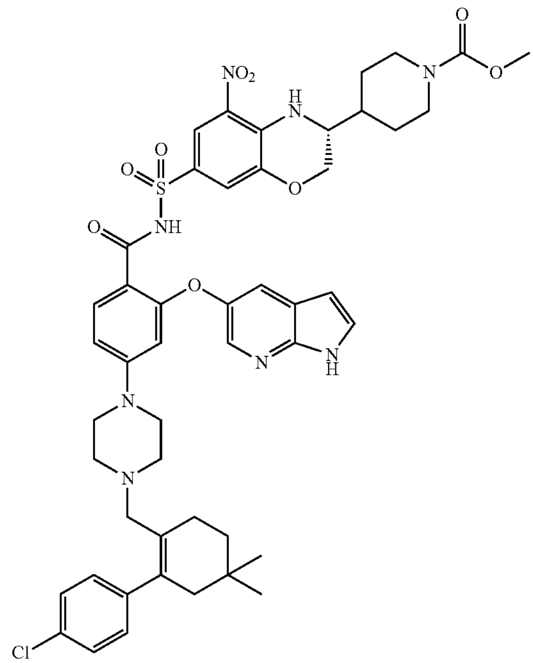 [SMILES: COC(=O)N1CCC([C@@H]2COc3cc(S(=O)(=O)NC(=O)c4ccc(N5CCN(CC6=C(c7ccc(Cl)cc7)CC(C)(C)CC6)CC5)cc4Oc4cnc5[nH]ccc5c4)cc([N+](=O)[O-])c3N2)CC1] | methyl (R)-4-(7-(N-(2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)benzoyl)sulfamoyl)-5-nitro-3,4-dihydro-2H-benzo[b]+0[1,4]oxazin-3-yl)piperidine-1-carboxylate | MS-ESI (m/z): 953 [M + 1]+ |
| 2-224 | 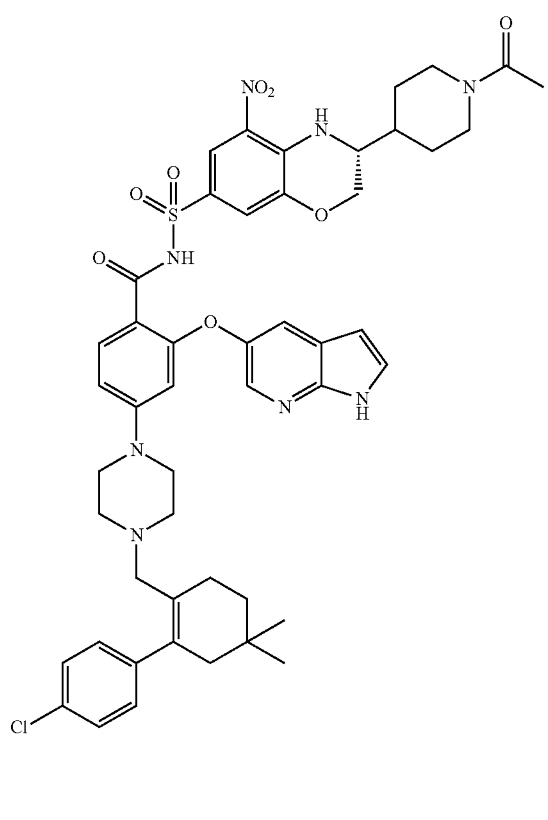 [SMILES: CC(=O)N1CCC([C@@H]2COc3cc(S(=O)(=O)NC(=O)c4ccc(N5CCN(CC6=C(c7ccc(Cl)cc7)CC(C)(C)CC6)CC5)cc4Oc4cnc5[nH]ccc5c4)cc([N+](=O)[O-])c3N2)CC1] | (R)-2-((1H-pyrrolo[2,3-b]pyridin-5-yl)oxy)-N-((3-(1-acetylpiperidin-4-yl)-5-nitro-3,4-dihydro-2H-benzo[b][1,4]oxazin-7-yl)sulfonyl)-4-(4-((4'-chloro-5,5-dimethyl-3,4,5,6-tetrahydro-[1,1'-biphenyl]-2-yl)methyl)piperazin-1-yl)benzamide | MS-ESI (m/z): 937 [M + 1]+ |

TABLE 2-continued

| EXAMPLE | STRUCTURE | NAME | DATA |
|---|---|---|---|
| 2-225 | 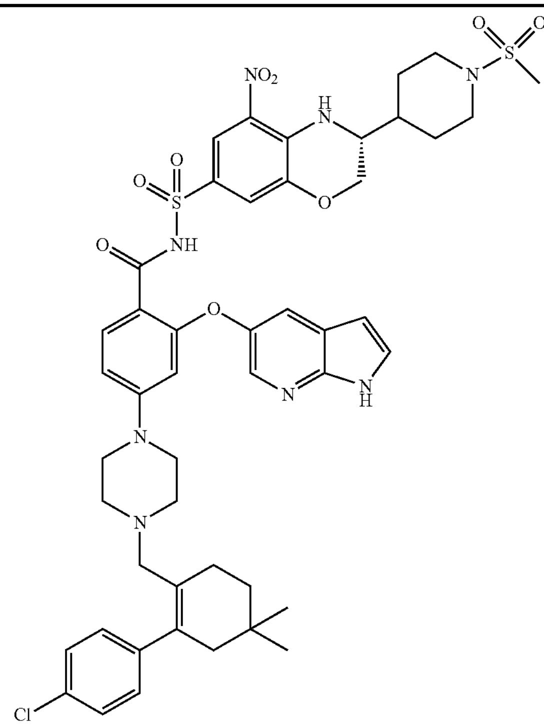 | (R)-2-((1H-pyrrolo[2,3-b]pyridin-5-yl)oxy)-4-(4-((4'-chloro-5,5-dimethyl-3,4,5,6-tetra-hydro-[1,1'-biphenyl]-2-yl)methyl)piperazin-1-yl)-N-((3-(1-(methylsulfonyl)piperidin-4-yl)-5-nitro-3,4-dihydro-2H-benzo[b][1,4]oxazin-7-yl)sulfonyl)benzamide | MS-ESI (m/z): 973 [M + 1]⁺ |
| 2-226 | 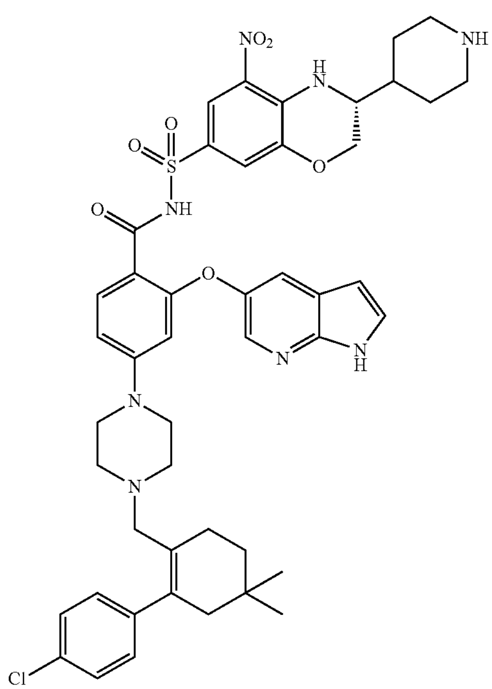 [SMILES: CC1(C)CCC(CN2CCN(c3ccc(C(=O)NS(=O)(=O)c4cc5c(c([N+](=O)[O-])c4)N[C@H](C4CCNCC4)CO5)c(Oc4cnc5[nH]ccc5c4)c3)CC2)=C(c2ccc(Cl)cc2)C1] | (R)-2-((1H-pyrrolo[2,3-b]pyridin-5-yl)oxy)-4-(4-((4'-chloro-5,5-dimethyl-3,4,5,6-tetra-hydro-[1,1'-biphenyl]-2-yl)methyl)piperazin-1-yl)-N-((5-nitro-3-(piperidin-4-yl)-3,4-dihydro-2H-benzo[b][1,4]oxazin-7-yl)sulfonyl)benzamide | MS-ESI (m/z): 895 [M + 1]⁺ |

TABLE 2-continued

| EXAMPLE | STRUCTURE | NAME | DATA |
|---|---|---|---|
| 2-227 | 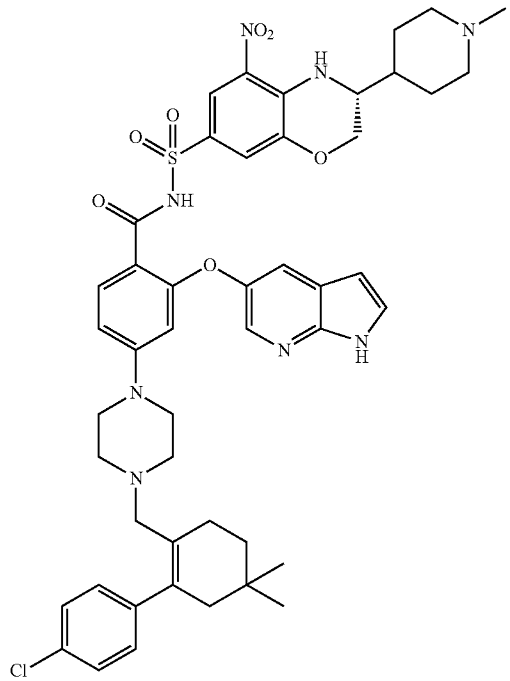 [SMILES: CN1CCC([C@@H]2COc3cc(S(=O)(=O)NC(=O)c4ccc(N5CCN(CC6=C(c7ccc(Cl)cc7)CC(C)(C)CC6)CC5)cc4Oc4cnc5[nH]ccc5c4)cc([N+](=O)[O-])c3N2)CC1] | (R)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-(1-methylpiperidin-4-yl)-5-nitro-3,4-dihydro-2H-benzo[b][1,4]oxazin-7-yl)sulfonyl)benzamide | MS-ESI (m/z): 909 [M + 1]+ |
| 2-228 | 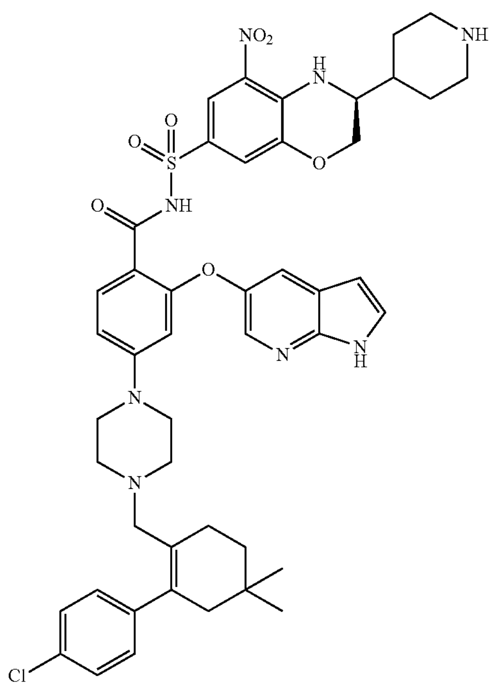 [SMILES: CC1(C)CCC(CN2CCN(c3ccc(C(=O)NS(=O)(=O)c4cc5c(c([N+](=O)[O-])c4)N[C@@H](C4CCNCC4)CO5)c(Oc4cnc5[nH]ccc5c4)c3)CC2)=C(c2ccc(Cl)cc2)C1] | (S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((5-nitro-3-(piperidin-4-yl)-3,4-dihydro-2H-benzo[b][1,4]oxazin-7-yl)sulfonyl)benzamide | MS-ESI (m/z): 895 [M + 1]+ |

TABLE 2-continued

| EXAMPLE | STRUCTURE | NAME | DATA |
|---|---|---|---|
| 2-229 | 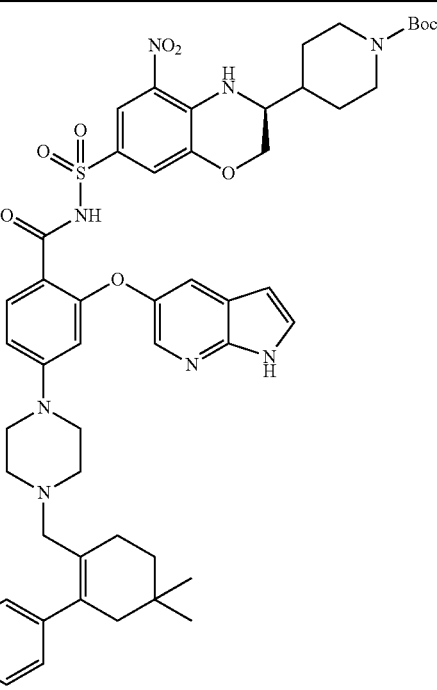 | tert-butyl (S)-4-(7-(N-(2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)benzoyl)sulfamoyl)-5-nitro-3,4-dihydro-2H-benzo[b][1,4]oxazin-3-yl)piperidine-1-carboxylate | MS-ESI (m/z): 995 [M + 1]+ |
| 2-230 | 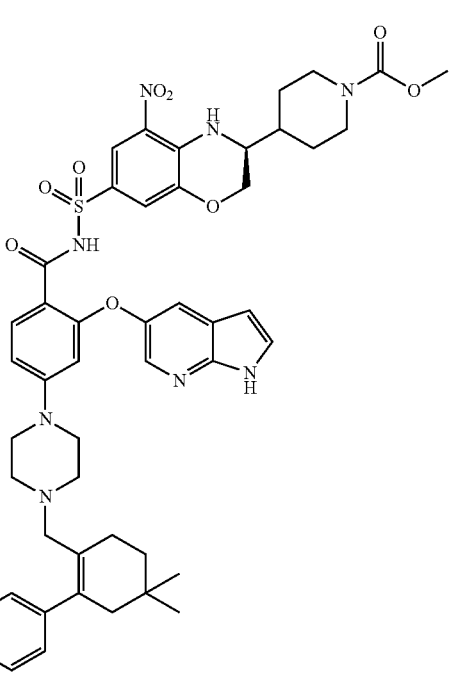 | methyl (S)-4-(7-(N-(2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)benzoyl)sulfamoyl)-5-nitro-3,4-dihydro-2H-benzo[b][1,4]oxazin-3-yl)piperidine-1-carboxylate | MS-ESI (m/z): 953 [M + 1]+ |

TABLE 2-continued

| EXAMPLE | STRUCTURE | NAME | DATA |
|---|---|---|---|
| 2-231 | 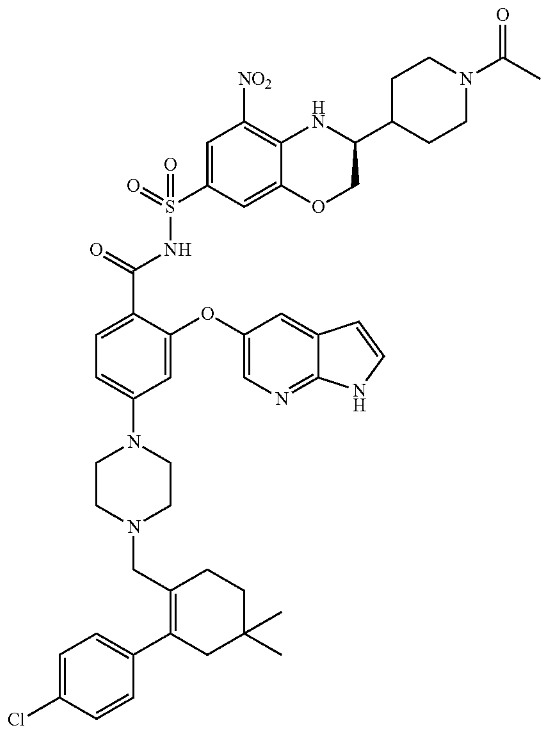 [SMILES: CC(=O)N1CCC([C@H]2COc3cc(S(=O)(=O)NC(=O)c4ccc(N5CCN(CC6=C(c7ccc(Cl)cc7)CC(C)(C)CC6)CC5)cc4Oc4cnc5[nH]ccc5c4)cc([N+](=O)[O-])c3N2)CC1] | (S)-2-((1H-pyrrolo[2,3-b]pyridin-5-yl)oxy)-N-((3-(1-acetylpiperidin-4-yl)-5-nitro-3,4-dihydro-2H-benzo[b][1,4]oxazin-7-yl)sulfonyl)-4-(4-((4'-chloro-5,5-dimethyl-3,4,5,6-tetrahydro-[1,1'-biphenyl]-2-yl)methyl)piperazin-1-yl)benzamide | MS-ESI (m/z): 937 [M + 1]+ |
| 2-232 | 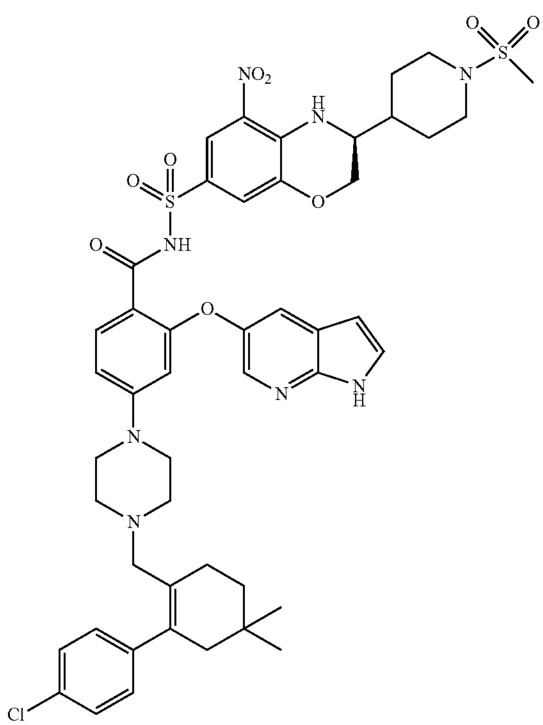 [SMILES: CC1(C)CCC(CN2CCN(c3ccc(C(=O)NS(=O)(=O)c4cc5c(c([N+](=O)[O-])c4)N[C@@H](C4CCN(S(C)(=O)=O)CC4)CO5)c(Oc4cnc5[nH]ccc5c4)c3)CC2)=C(c2ccc(Cl)cc2)C1] | (S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-(1-(methylsulfonyl)piperidin-4-yl)-5-nitro-3,4-dihydro-2H-benzo[b][1,4]oxazin-7-yl)sulfonyl)benzamide | MS-ESI (m/z): 973 [M + 1]+ |

TABLE 2-continued

| EXAMPLE | STRUCTURE | NAME | DATA |
|---|---|---|---|
| 2-233 | 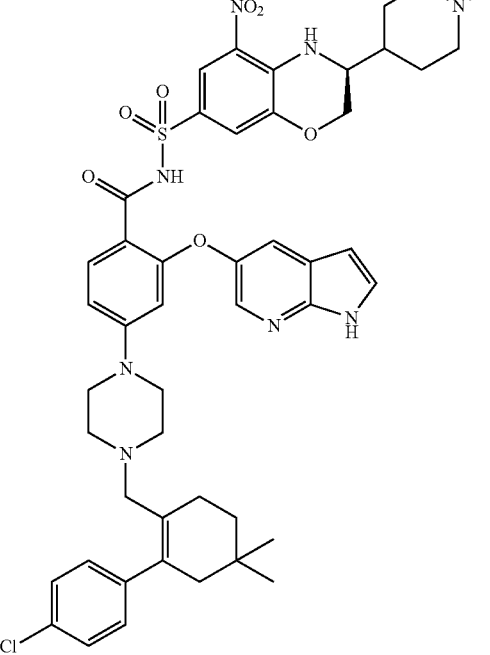 | (S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-(1-methylpiperidin-4-yl)-5-nitro-3,4-dihydro-2H-benzo[b][1,4]oxazin-7-yl)sulfonyl)benzamide | MS-ESI (m/z): 909 [M + 1]+ |
| 2-234 | 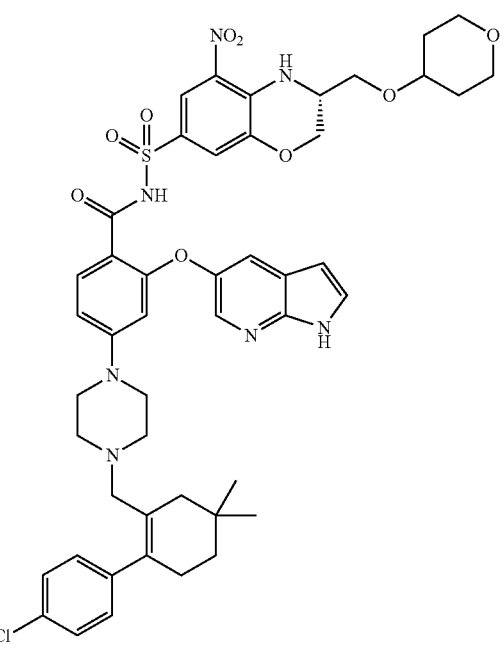 | (R)-2-((1H-pyrrolo[2,3-b]pyridin-5-yl)oxy)-4-(4-((4'-chloro-4,4-dimethyl-3,4,5,6-tetrahydro-[1,1'-biphenyl]-2-yl)methyl)piperazin-1-yl)-N-((5-nitro-3-(((tetrahydro-2H-pyra 4-yl)oxy)methyl)-3,4-dihydro-2H-benzo[b][1,4]oxazin-7-yl)sulfonyl)benzamide | MS-ESI (m/z): 926 [M + 1]+ |

TABLE 2-continued

| EXAMPLE | STRUCTURE | NAME | DATA |
|---|---|---|---|
| 2-235 | 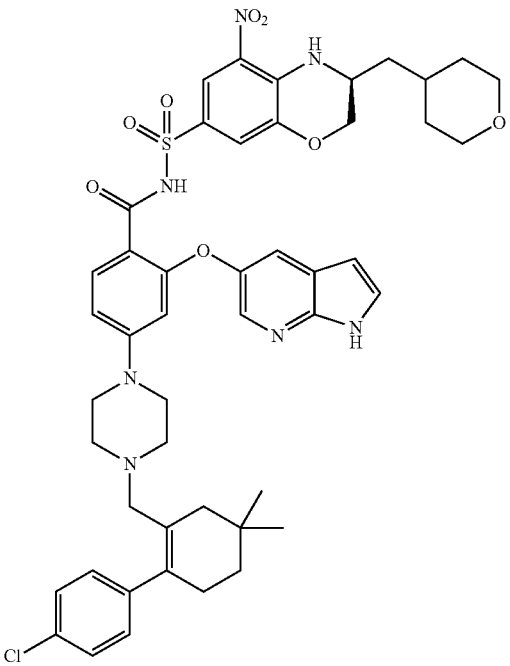 [SMILES: CC1(C)CCC(c2ccc(Cl)cc2)=C(CN2CCN(c3ccc(C(=O)NS(=O)(=O)c4cc5c(c([N+](=O)[O-])c4)N[C@@H](CC4CCOCC4)CO5)c(Oc4cnc5[nH]ccc5c4)c3)CC2)C1] | (S)-2-((1H-pyrrolo[2,3-b]pyridin-5-yl)oxy)-4-(4-((4'-chloro-4,4-dimethyl-3,4,5,6-tetrahydro-[1,1'-biphenyl]-2-yl)methyl)piperazin-1-yl)-N-((5-nitro-3-((tetrahydro-2H-pyran-4-yl)methyl)-3,4-dihydro-2H-benzo[b][1,4]oxazin-7-yl)sulfonyl)benzamide | MS-ESI (m/z): 910 [M + 1]+ |
| 2-236 | 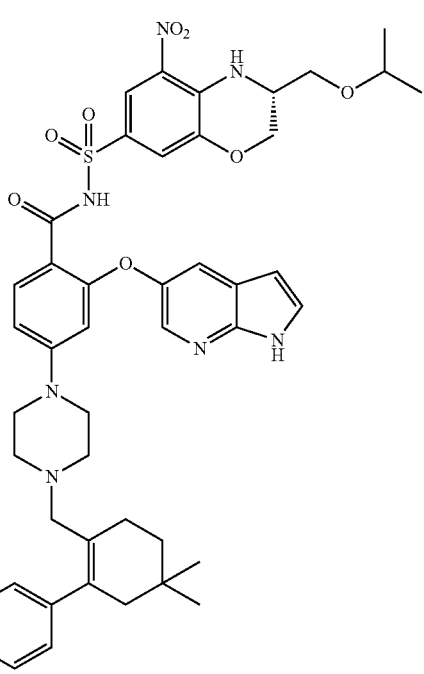 | (R)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-(isopropoxymethyl)-5-nitro-3,4-dihydro-2H-benzo[b][1,4]oxazin-7-yl)sulfonyl)benzamide | MS-ESI (m/z): 884 [M + 1]+ |

TABLE 2-continued

| EXAMPLE | STRUCTURE | NAME | DATA |
| --- | --- | --- | --- |
| 2-237 | 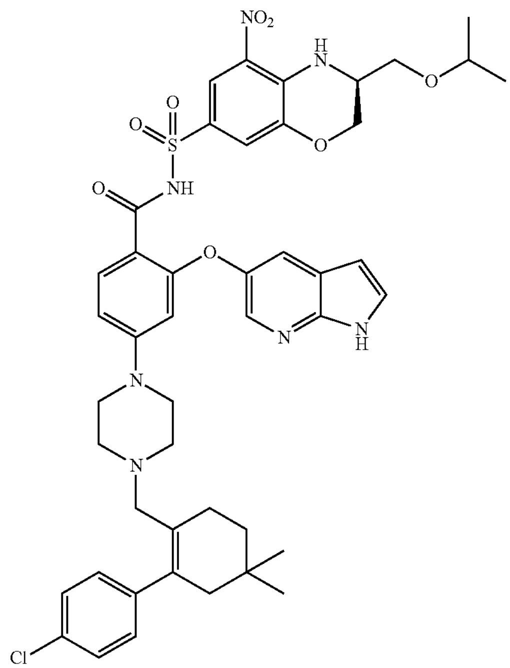 [SMILES: CC(C)OC[C@H]1COc2cc(S(=O)(=O)NC(=O)c3ccc(N4CCN(CC5=C(c6ccc(Cl)cc6)CC(C)(C)CC5)CC4)cc3Oc3cnc4[nH]ccc4c3)cc([N+](=O)[O-])c2N1] | (S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-(isopropoxymethyl)-5-nitro-3,4-dihydro-2H-benzo[b][1,4]oxazin-7-yl)sulfonyl)benzamide | MS-ESI (m/z): 884 [M + 1]+ |
| 2-238 | 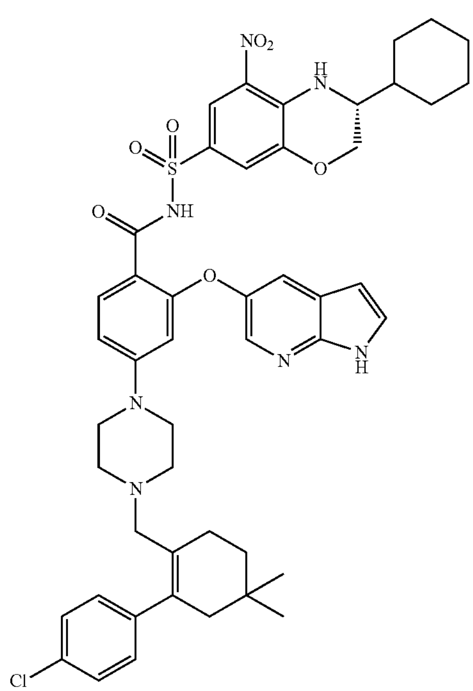 [SMILES: CC1(C)CCC(CN2CCN(c3ccc(C(=O)NS(=O)(=O)c4cc5c(c([N+](=O)[O-])c4)N[C@H](C4CCCCC4)CO5)c(Oc4cnc5[nH]ccc5c4)c3)CC2)=C(c2ccc(Cl)cc2)C1] | (R)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-cyclohexyl-5-nitro-3,4-dihydro-2H-benzo[b][1,4]oxazin-7-yl)sulfonyl)benzamide | MS-ESI (m/z): 894 [M + 1]+ |

TABLE 2-continued

| EXAMPLE | STRUCTURE | NAME | DATA |
|---|---|---|---|
| 2-239A | 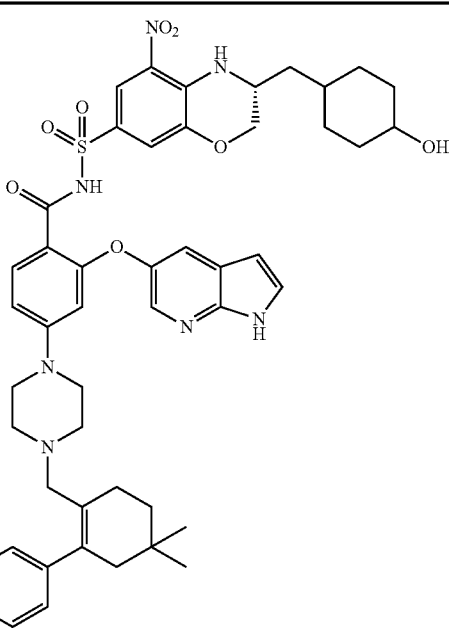 | (R)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-((4-hydroxycyclohexyl)methyl)-5-nitro-3,4-dihydro-2H-benzo[b][1,4]oxazin-7-yl)sulfonyl)benzamide | MS-ESI (m/z): 924 [M + 1]+ |
| 2-239B | 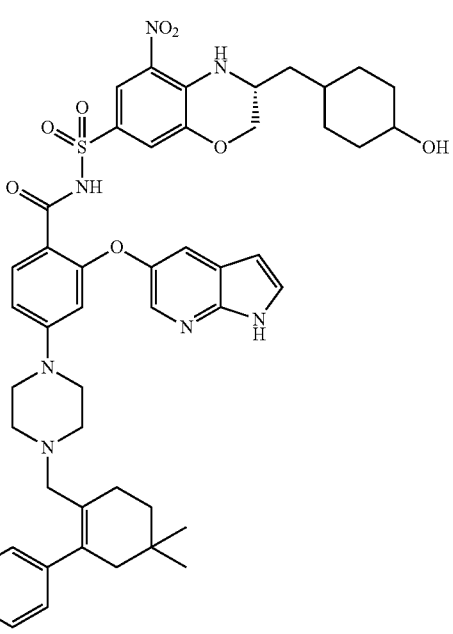 | (R)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-((4-hydroxycyclohexyl)methyl)-5-nitro-3,4-dihydro-2H-benzo[b][1,4]oxazin-7-yl)sulfonyl)benzamide | MS-ESI (m/z): 924 [M + 1]+ |

TABLE 2-continued

| EXAMPLE | STRUCTURE | NAME | DATA |
|---|---|---|---|
| 2-240A | 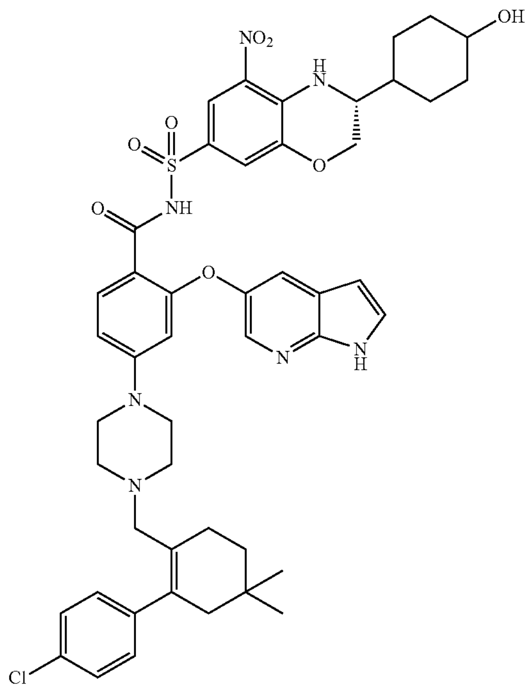 [SMILES: CC1(C)CCC(CN2CCN(c3ccc(C(=O)NS(=O)(=O)c4cc5c(c([N+](=O)[O-])c4)N[C@H](C4CCC(O)CC4)CO5)c(Oc4cnc5[nH]ccc5c4)c3)CC2)=C(c2ccc(Cl)cc2)C1] | (R)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-(4-hydroxycyclohexyl)-5-nitro-3,4-dihydro-2H-benzo[b][1,4]oxazin-7-yl)sulfonyl)benzamide | MS-ESI (m/z): 910 [M + 1]+ |
| 2-240B | 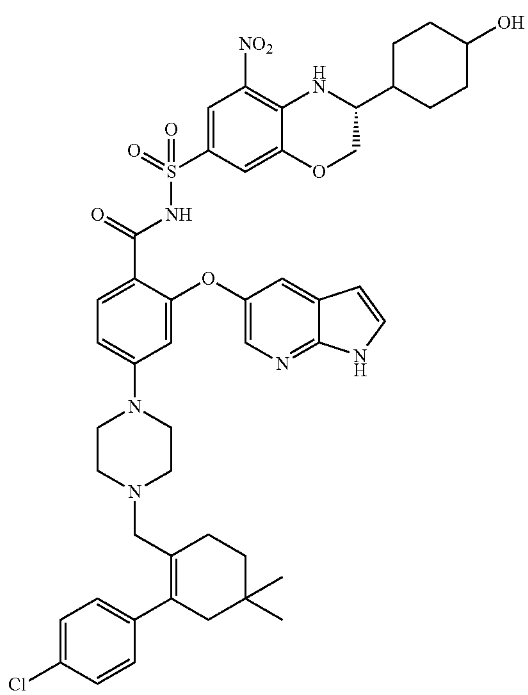 | (R)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-(4-hydroxycyclohexyl)-5-nitro-3,4-dihydro-2H-benzo[b][1,4]oxazin-7-yl)sulfonyl)benzamide | MS-ESI (m/z): 910 [M + 1]+ |

TABLE 2-continued

| EXAMPLE | STRUCTURE | NAME | DATA |
|---|---|---|---|
| 2-241 | 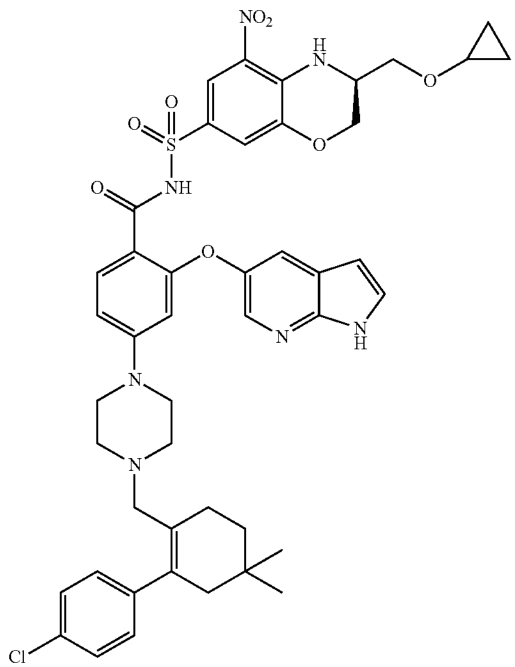 [SMILES: CC1(C)CCC(CN2CCN(c3ccc(C(=O)NS(=O)(=O)c4cc5c(c([N+](=O)[O-])c4)N[C@@H](COC4CC4)CO5)c(Oc4cnc5[nH]ccc5c4)c3)CC2)=C(c2ccc(Cl)cc2)C1] | (S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-(cyclopropoxymethyl)-5-nitro-3,4-dihydro-2H-benzo[b][1,4]oxazin-7-yl)sulfonyl)benzamide | MS-ESI (m/z): 882 [M + 1]⁺ |
| 2-242 | 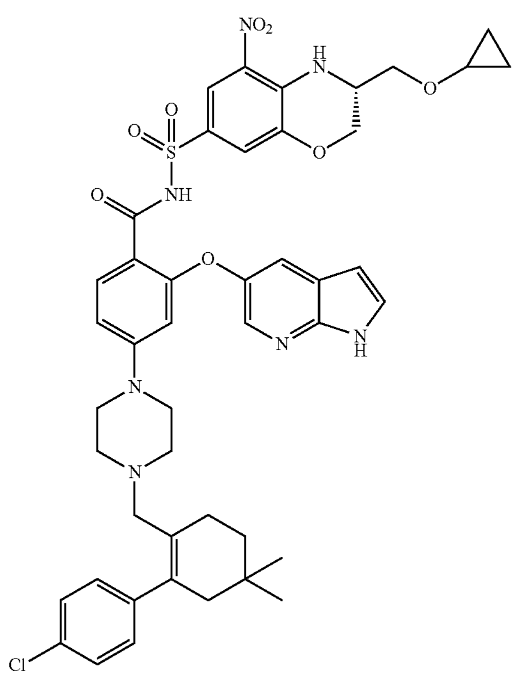 [SMILES: CC1(C)CCC(CN2CCN(c3ccc(C(=O)NS(=O)(=O)c4cc5c(c([N+](=O)[O-])c4)N[C@H](COC4CC4)CO5)c(Oc4cnc5[nH]ccc5c4)c3)CC2)=C(c2ccc(Cl)cc2)C1] | (R)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-(cyclopropoxymethyl)-5-nitro-3,4-dihydro-2H-benzo[b][1,4]oxazin-7-yl)sulfonyl)benzamide | MS-ESI (m/z): 882 [M + 1]⁺ |

TABLE 2-continued

| EXAMPLE | STRUCTURE | NAME | DATA |
|---|---|---|---|
| 2-243 | 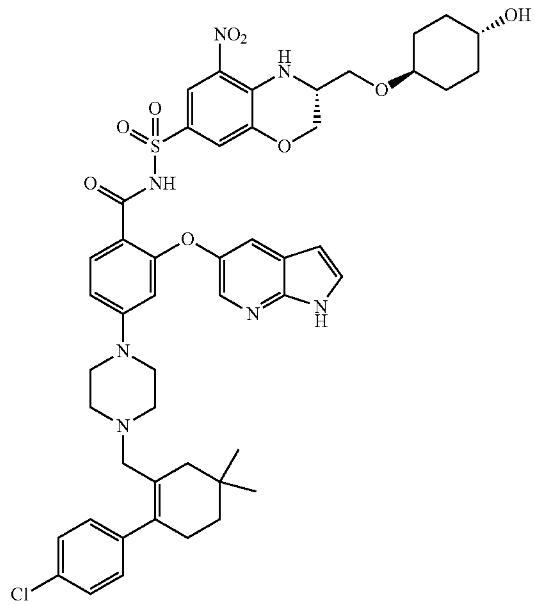 [SMILES: CC1(C)CCC(c2ccc(Cl)cc2)=C(CN2CCN(c3ccc(C(=O)NS(=O)(=O)c4cc5c(c([N+](=O)[O-])c4)N[C@H](CO[C@H]4CC[C@H](O)CC4)CO5)c(Oc4cnc5[nH]ccc5c4)c3)CC2)C1] | 2-((1H-pyrrolo[2,3-b]pyridin-5-yl)oxy)-4-(4-((4'-chloro-4,4-dimethyl-3,4,5,6-tetrahydro-[1,1'-biphenyl]-2-yl)methyl)piperazin-1-yl)-N-(((R)-3-((((1r,4R)-4-hydroxycyclohexyl)oxy)methyl)-5-nitro-3,4-dihydro-2H-benzo[b][1,4]oxazin-7-yl)sulfonyl)benzamide | MS-ESI (m/z): 940 [M + 1]$^+$ |
| 2-244A | 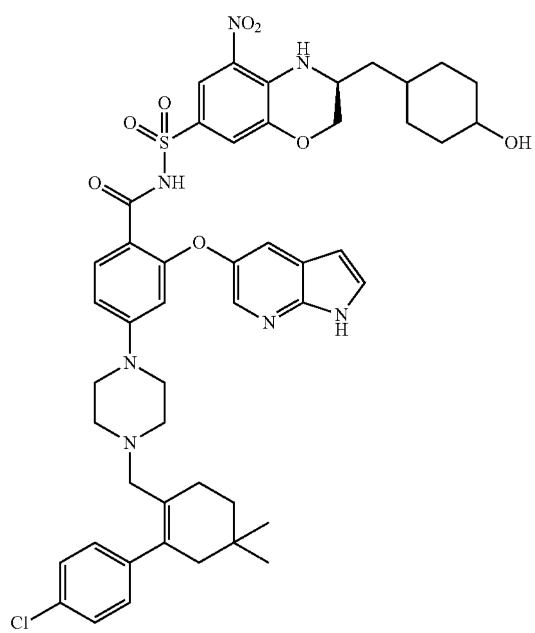 [SMILES: CC1(C)CCC(CN2CCN(c3ccc(C(=O)NS(=O)(=O)c4cc5c(c([N+](=O)[O-])c4)N[C@@H](CC4CCC(O)CC4)CO5)c(Oc4cnc5[nH]ccc5c4)c3)CC2)=C(c2ccc(Cl)cc2)C1] | (S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-((4-hydroxycyclohexyl)methyl)-5-nitro-3,4-dihydro-2H-benzo[b][1,4]oxazin-7-yl)sulfonyl)benzamide | MS-ESI (m/z): 924 [M + 1]$^+$ |

| EXAMPLE | STRUCTURE | NAME | DATA |
|---|---|---|---|
| 2-244B | 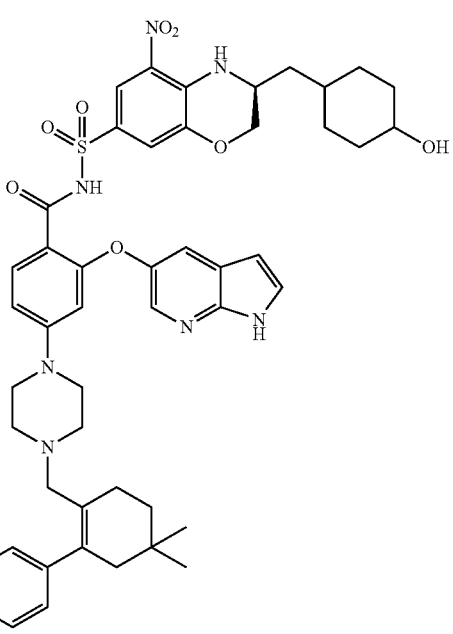 | (S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-((4-hydroxycyclohexyl)methyl)-5-nitro-3,4-dihydro-2H-benzo[b][1,4]oxazin-7-yl)sulfonyl)benzamide | MS-ESI (m/z): 924 [M + 1]⁺ |
| 2-245A | 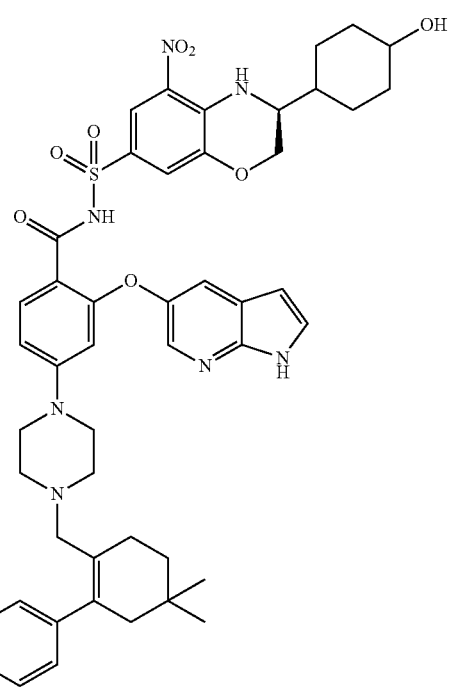 | (S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-(4-hydroxycyclohexyl)-5-nitro-3,4-dihydro-2H-benzo[b][1,4]oxazin-7-yl)sulfonyl)benzamide | MS-ESI (m/z): 910 [M + 1]⁺ |

TABLE 2-continued

| EXAMPLE | STRUCTURE | NAME | DATA |
| --- | --- | --- | --- |
| 2-245B | 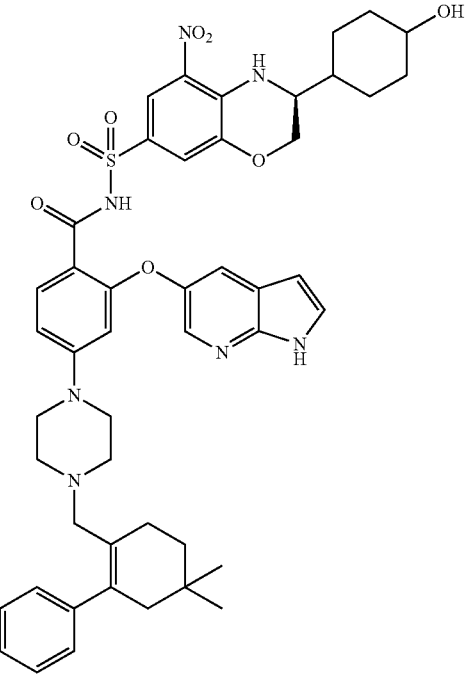 | (S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-(4-hydroxycyclohexyl)-5-nitro-3,4-dihydro-2H-benzo[b][1,4]oxazin-7-yl)sulfonyl)benzamide | MS-ESI (m/z): 910 [M + 1]$^+$ |
| 2-246A | 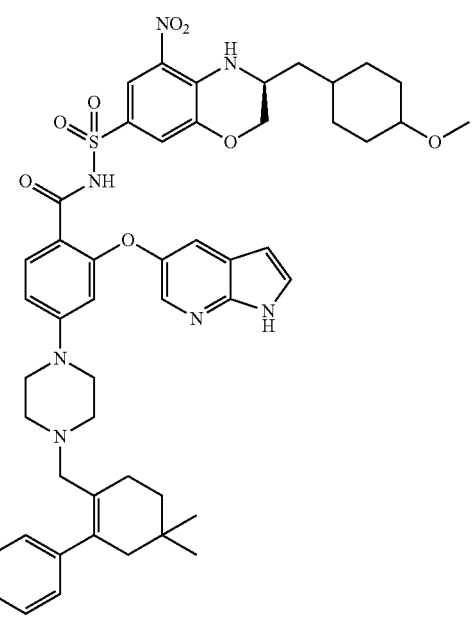 | (S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-((4-methoxycyclohexyl)methyl)-5-nitro-3,4-dihydro-2H-benzo[b][1,4]oxazin-7-yl)sulfonyl)benzamide | MS-ESI (m/z): 938 [M + 1]$^+$ |

TABLE 2-continued

| EXAMPLE | STRUCTURE | NAME | DATA |
|---|---|---|---|
| 2-246B | 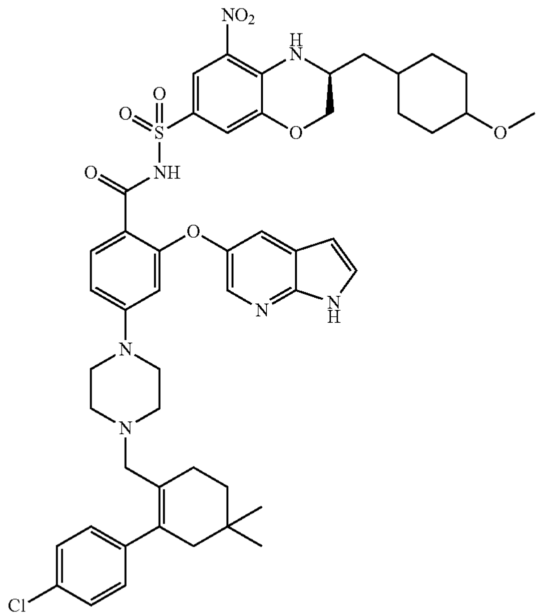 [SMILES: COC1CCC(C[C@H]2COc3cc(S(=O)(=O)NC(=O)c4ccc(N5CCN(CC6=C(c7ccc(Cl)cc7)CC(C)(C)CC6)CC5)cc4Oc4cnc5[nH]ccc5c4)cc([N+](=O)[O-])c3N2)CC1] | (S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-((4-methoxycyclohexyl)methyl)-5-nitro-3,4-dihydro-2H-benzo[b][1,4]oxazin-7-yl)sulfonyl)benzamide | MS-ESI (m/z): 938 [M + 1] $^+$ |
| 2-247A | 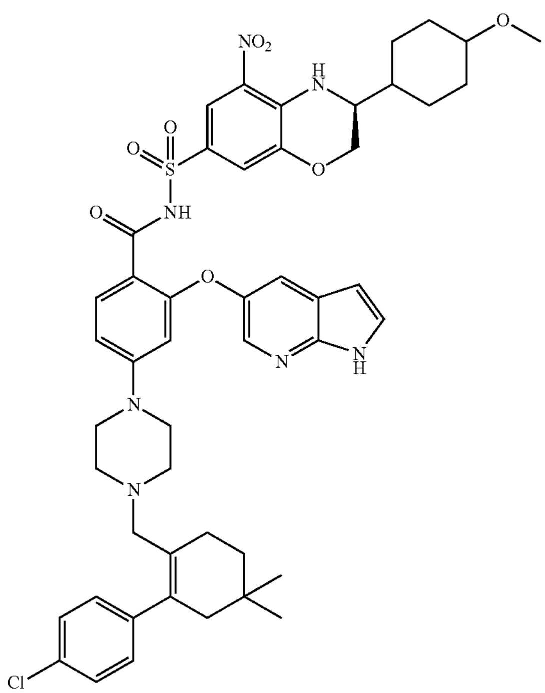 [SMILES: COC1CCC([C@H]2COc3cc(S(=O)(=O)NC(=O)c4ccc(N5CCN(CC6=C(c7ccc(Cl)cc7)CC(C)(C)CC6)CC5)cc4Oc4cnc5[nH]ccc5c4)cc([N+](=O)[O-])c3N2)CC1] | (S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-(4-methoxycyclohexyl)-5-nitro-3,4-dihydro-2H-benzo[b][1,4]oxazin-7-yl)sulfonyl)benzamide | MS-ESI (m/z): 924 [M + 1] $^+$ |

TABLE 2-continued

| EXAMPLE | STRUCTURE | NAME | DATA |
|---|---|---|---|
| 2-247B | 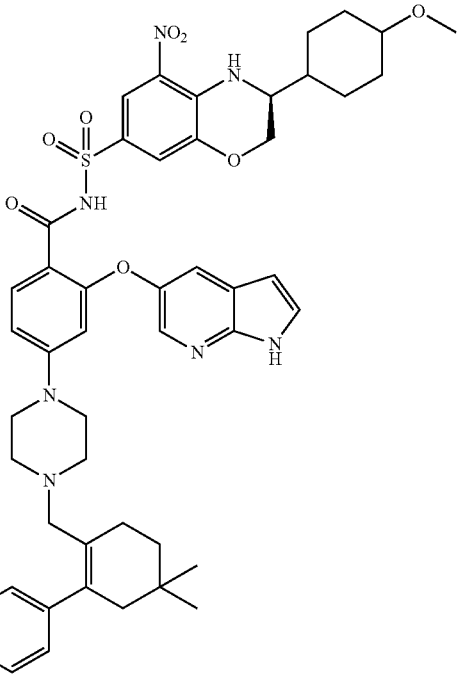 | (S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-(4-methoxycyclohexyl)-5-nitro-3,4-dihydro-2H-benzo[b][1,4]oxazin-7-yl)sulfonyl)benzamide | MS-ESI (m/z): 924 [M + 1]⁺ |
| 2-248A | 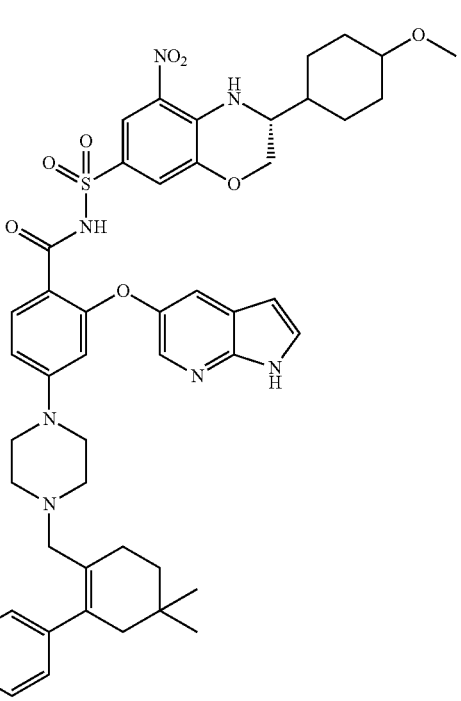 | (R)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-(4-methoxycyclohexyl)-5-nitro-3,4-dihydro-2H-benzo[b][1,4]oxazin-7-yl)sulfonyl)benzamide | MS-ESI (m/z): 924 [M + 1]⁺ |

TABLE 2-continued

| EXAMPLE | STRUCTURE | NAME | DATA |
|---|---|---|---|
| 2-248B | 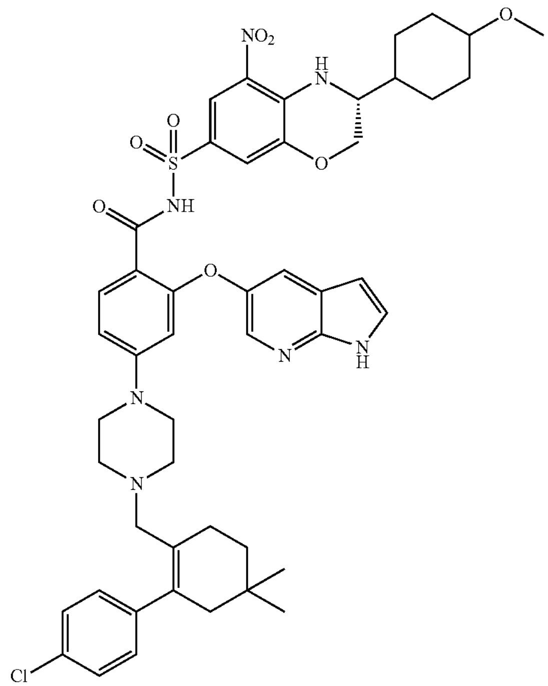 [SMILES: COC1CCC([C@@H]2COc3cc(S(=O)(=O)NC(=O)c4ccc(N5CCN(CC6=C(c7ccc(Cl)cc7)CC(C)(C)CC6)CC5)cc4Oc4cnc5[nH]ccc5c4)cc([N+](=O)[O-])c3N2)CC1] | (R)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-(4-methoxycyclohexyl)-5-nitro-3,4-dihydro-2H-benzo[b][1,4]oxazin-7-yl)sulfonyl)benzamide | MS-ESI (m/z): 924 [M + 1]⁺ |
| 2-249A | 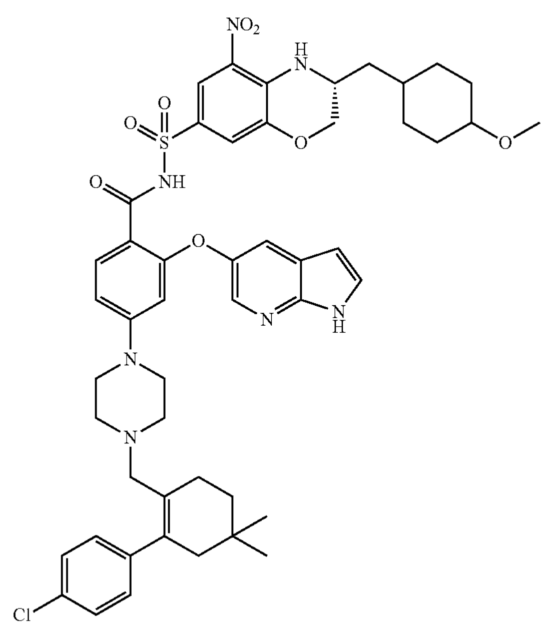 [SMILES: COC1CCC(C[C@@H]2COc3cc(S(=O)(=O)NC(=O)c4ccc(N5CCN(CC6=C(c7ccc(Cl)cc7)CC(C)(C)CC6)CC5)cc4Oc4cnc5[nH]ccc5c4)cc([N+](=O)[O-])c3N2)CC1] | (R)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-((4-methoxycyclohexyl)methyl)-5-nitro-3,4-dihydro-2H-benzo[b][1,4]oxazin-7-yl)sulfonyl)benzamide | MS-ESI (m/z): 938 [M + 1]⁺ |

TABLE 2-continued

| EXAMPLE | STRUCTURE | NAME | DATA |
|---|---|---|---|
| 2-249B | 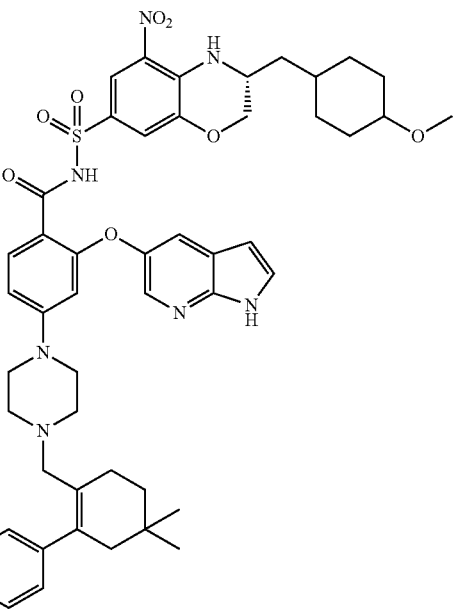 | (R)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-((4-methoxycyclohexyl)methyl)-5-nitro-3,4-dihydro-2H-benzo[b][1,4]oxazin-7-yl)sulfonyl)benzamide | MS-ESI (m/z): 938 [M + 1] $^+$ |
| 2-250 | 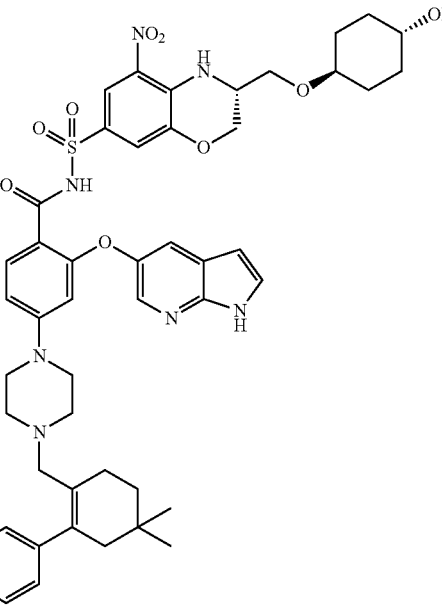 | 2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-(((R)-3-((((1r,4R)-4-hydroxycyclohexyl)oxy)methyl)-5-nitro-3,4-dihydro-2H-benzo[b][1,4]oxazin-7-yl)sulfonyl)benzamide | MS-ESI (m/z): 940 [M + 1] $^+$ |

TABLE 2-continued

| EXAMPLE | STRUCTURE | NAME | DATA |
|---|---|---|---|
| 2-251 | 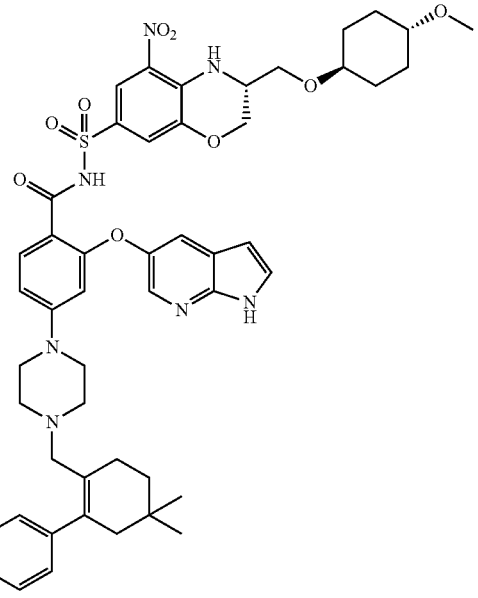 | 2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-(((R)-3-((((1r,4R)-4-methoxycyclohexyl)oxy)methyl)-5-nitro-3,4-dihydro-2H-benzo[b][1,4]oxazin-7-yl)sulfonyl)benzamide | MS-ESI (m/z): 954 [M + 1]$^+$ |
| 2-252 | 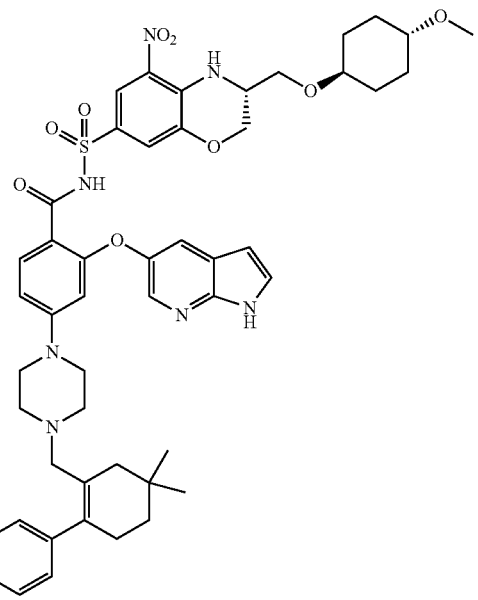 | 2-((1H-pyrrolo[2,3-b]pyridin-5-yl)oxy)-4-(4-((4'-chloro-4,4-dimethyl-3,4,5,6-tetrahydro-[1,1'-biphenyl]-2-yl)methyl)piperazin-1-yl)-N-(((R)-3-((((1r,4R)-4-methoxycyclohexyl)oxy)methyl)-5-nitro-3,4-dihydro-2H-benzo[b][1,4]oxazin-7-yl)sulfonyl)benzamide | MS-ESI (m/z): 954 [M + 1]$^+$ |

Example 3-1

(R)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-((4-methylpiperazin-1-yl)methyl)-5-nitro-3,4-dihydro-2H-benzo[b][1,4]thiazin-7-yl)sulfonyl)benzamide (3-1)

Example 3-2

(R)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-(2-morphohnoethyl)-5-nitro-3,4-dihydro-2H-benzo[b][1,4]thiazin-7-yl)sulfonyl)benzamide (3-2)

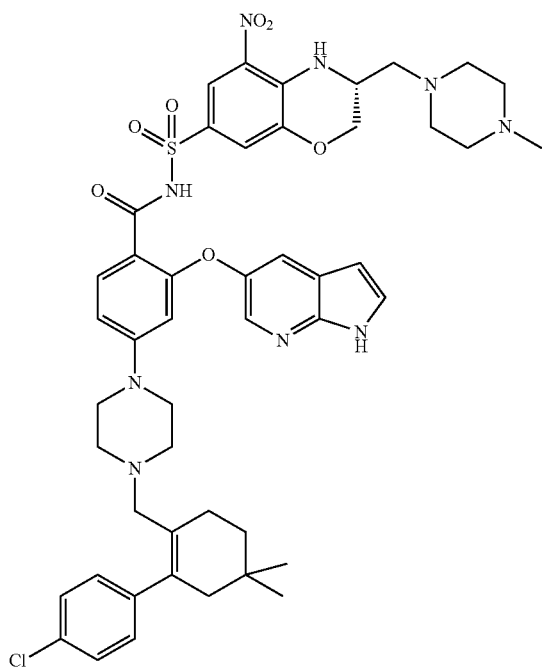

3-1

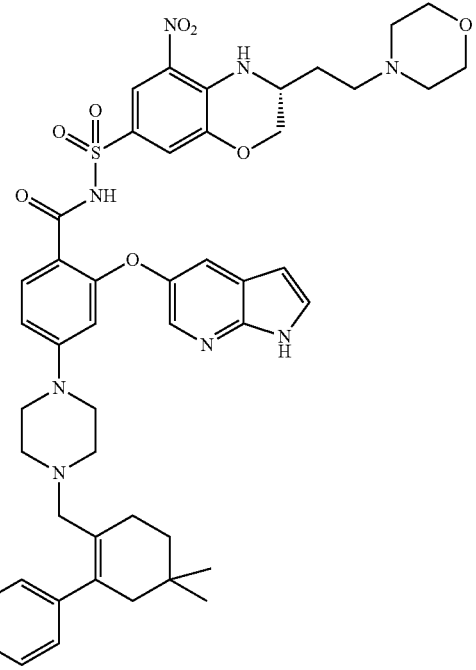

3-2

The title compound (R)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-((4-methylpiperazin-1-yl)methyl)-5-nitro-3,4-dihydro-2H-benzo[b][1,4]thiazin-7-yl)sulfonyl)benzamide (3-1) was prepared according to the synthetic method of 2-1 by replacing (S)-2-(iodomethyl)-7-nitroindoline-5-sulfonamide (Intermediate C) with (R)-(5-nitro-7-sulfamoyl-3,4-dihydro-2H-benzo[b][1,4]thiazin-3-yl)methyl methanesulfonate (Intermediate G). MS-ESI (m/z): 940 [M+1]$^+$.

The title compound (R)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-(2-morpholinoethyl)-5-nitro-3,4-dihydro-2H-benzo[b][1,4]thiazin-7-yl)sulfonyl)benzamide (3-2) was prepared according to the synthetic method of 2-1 by replacing 1-methylpiperazine and (R)-(5-nitro-7-sulfamoyl-3,4-dihydro-2H-benzo[b][1,4]oxazin-3-yl)methyl methanesulfonate (Intermediate C) with morpholine and (R)-2-(5-nitro-7-sulfamoyl-3,4-dihydro-2H-benzo[b][1,4]thiazin-3-yl)ethyl methanesulfonate (Intermediate H). MS-ESI (m/z): 941 [M+1]$^+$.

Following essentially the same procedures described for Examples 3-1~3-2 or or using similar synthetic methods or strategies, Examples 3-3~3-20 listed in Table 3 were prepare. The structures and names of Examples 3-3~3-20 are given in Table 3.

TABLE 3

| EXAMPLE | STRUCTURE | NAME | DATA |
|---|---|---|---|
| 3-3 | 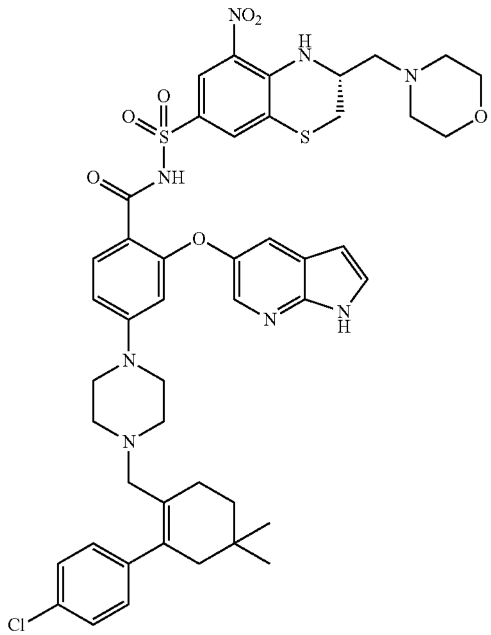 | (R)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-(morpholinomethyl)-5-nitro-3,4-dihydro-2H-benzo[b][1,4]thiazin-7-yl)sulfonyl)benzamide | MS-ESI (m/z): 927 [M + 1]⁺ |
| 3-4 | 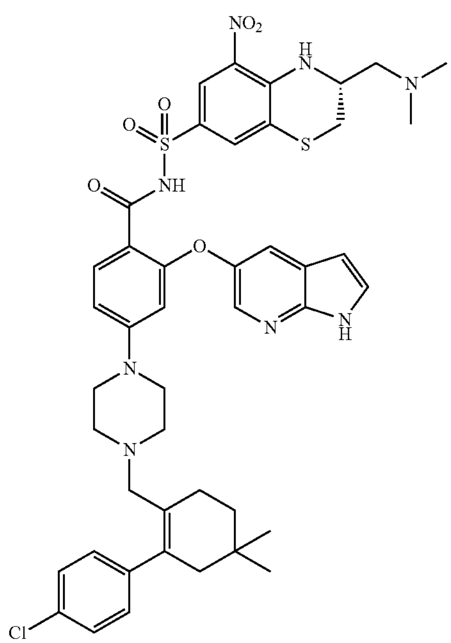 [SMILES: CN(C)C[C@@H]1CSc2cc(S(=O)(=O)NC(=O)c3ccc(N4CCN(CC5=C(c6ccc(Cl)cc6)CC(C)(C)CC5)CC4)cc3Oc3cnc4[nH]ccc4c3)cc([N+](=O)[O-])c2N1] | (R)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-((dimethylamino)methyl)-5-nitro-3,4-dihydro-2H-benzo[b][1,4]thiazin-7-yl)sulfonyl)benzamide | MS-ESI (m/z): 885 [M + 1]⁺ |

TABLE 3-continued

| EXAMPLE | STRUCTURE | NAME | DATA |
|---|---|---|---|
| 3-5 | 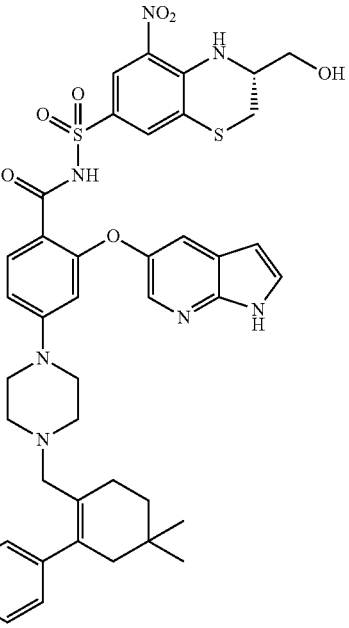 | (R)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-(hydroxymethyl)-5-nitro-3,4-dihydro-2H-benzo[b][1,4]thiazin-7-yl)sulfonyl)benzamide | MS-ESI (m/z): 858 [M + 1]+ |
| 3-6 | 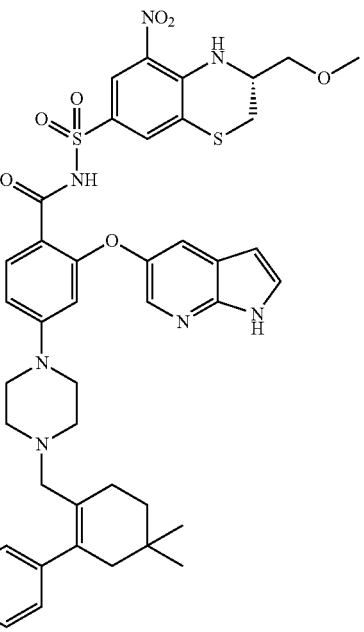 | (R)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-(methoxymethyl)-5-nitro-3,4-dihydro-2H-benzo[b][1,4]thiazin-7-yl)sulfonyl)benzamide | MS-ESI (m/z): 872 [M + 1]+ |

TABLE 3-continued

| EXAMPLE | STRUCTURE | NAME | DATA |
|---|---|---|---|
| 3-7 | 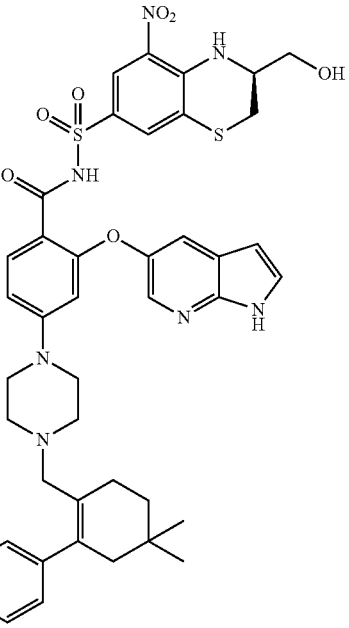 | (S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-(hydroxymethyl)-5-nitro-3,4-dihydro-2H-benzo[b][1,4]thiazin-7-yl)sulfonyl)benzamide | MS-ESI (m/z): 858 [M + 1]+ |
| 3-8 | 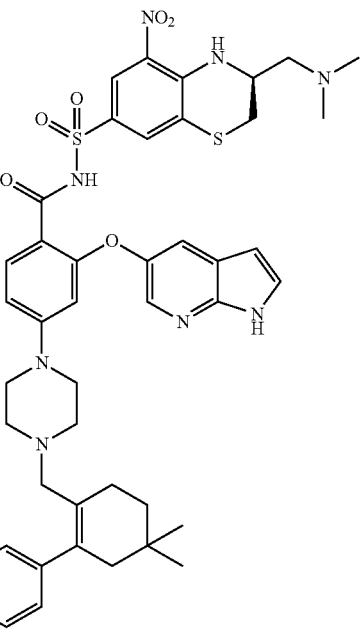 | (S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-((dimethylamino)methyl)-5-nitro-3,4-dihydro-2H-benzo[b][1,4]thiazin-7-yl)sulfonyl)benzamide | MS-ESI (m/z): 885 [M + 1]+ |

TABLE 3-continued

| EXAMPLE | STRUCTURE | NAME | DATA |
|---|---|---|---|
| 3-9 | 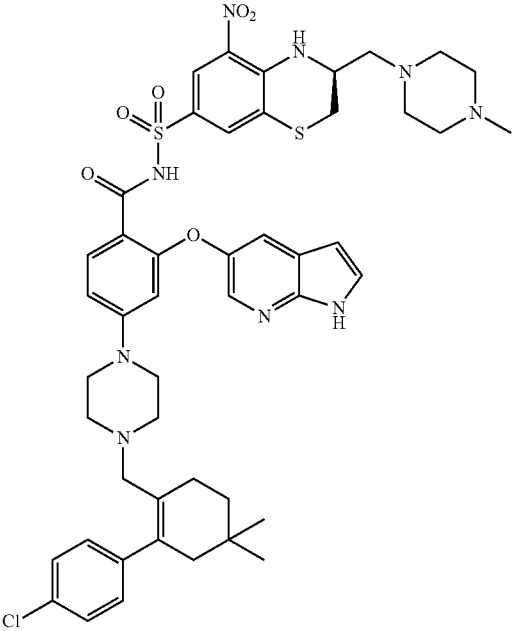 | (S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-((4-methylpiperazin-1-yl)methyl)-5-nitro-3,4-dihydro-2H-benzo[b][1,4]thiazin-7-yl)sulfonyl)benzamide | MS-ESI (m/z): 940 [M + 1]⁺ |
| 3-10 | 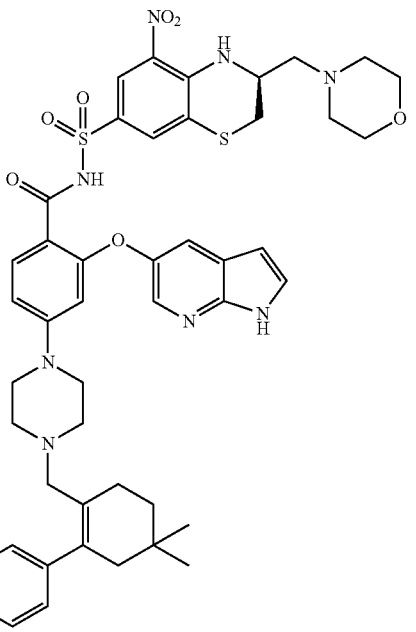 | (S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-(morpholinomethyl)-5-nitro-3,4-dihydro-2H-benzo[b][1,4]thiazin-7-yl)sulfonyl)benzamide | MS-ESI (m/z): 927 [M + 1]⁺ |

TABLE 3-continued

| EXAMPLE | STRUCTURE | NAME | DATA |
|---|---|---|---|
| 3-11 | 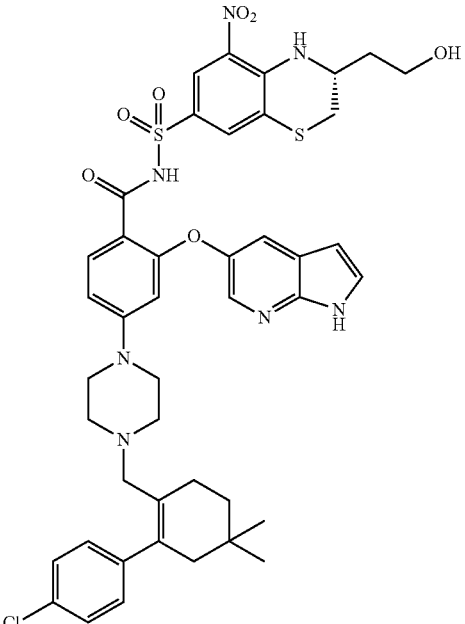 | (R)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-(2-hydroxyethyl)-5-nitro-3,4-dihydro-2H-benzo[b][1,4]thiazin-7-yl)sulfonyl)benzamide | MS-ESI (m/z): 872 [M + 1]+ |
| 3-12 | 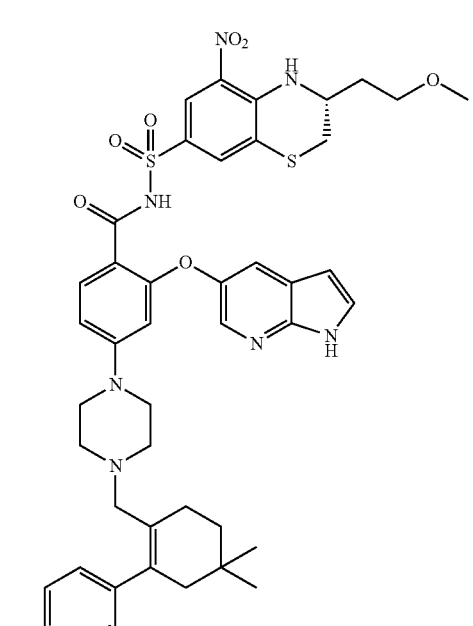 | (R)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-(2-methoxyethyl)-5-nitro-3,4-dihydro-2H-benzo[b][1,4]thiazin-7-yl)sulfonyl)benzamide | MS-ESI (m/z): 886 [M + 1]+ |

TABLE 3-continued

| EXAMPLE | STRUCTURE | NAME | DATA |
|---|---|---|---|
| 3-13 | 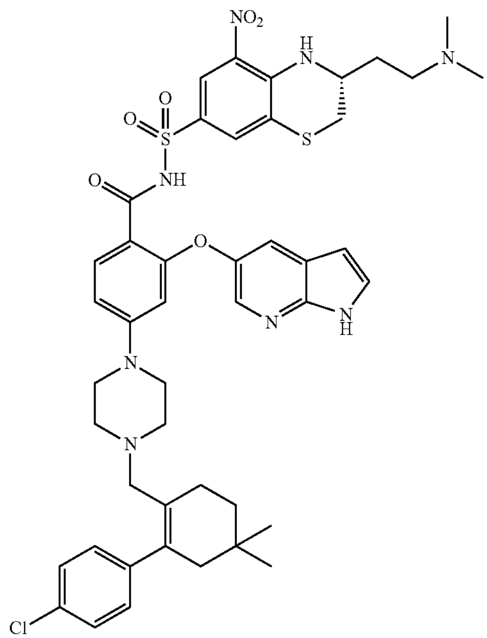 [SMILES: CN(C)CC[C@@H]1CSc2cc(S(=O)(=O)NC(=O)c3ccc(N4CCN(CC5=C(c6ccc(Cl)cc6)CC(C)(C)CC5)CC4)cc3Oc3cnc4[nH]ccc4c3)cc([N+](=O)[O-])c2N1] | (R)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-(2-(dimethylamino)ethyl)-5-nitro-3,4-dihydro-2H-benzo[b][1,4]thiazin-7-yl)sulfonyl)benzamide | MS-ESI (m/z): 899 [M + 1]$^+$ |
| 3-14 | 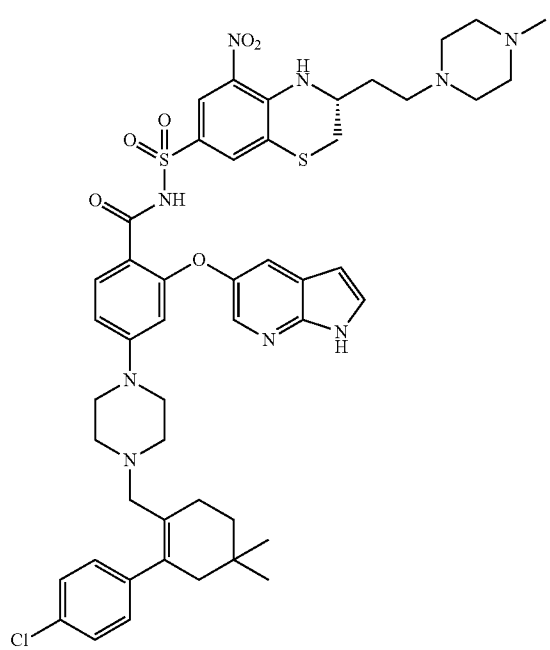 | (R)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-(2-(4-methylpiperazin-1-yl)ethyl)-5-nitro-3,4-dihydro-2H-benzo[b][1,4]thiazin-7-yl)sulfonyl)benzamide | MS-ESI (m/z): 954 [M + 1]$^+$ |

TABLE 3-continued

| EXAMPLE | STRUCTURE | NAME | DATA |
|---|---|---|---|
| 3-15 | 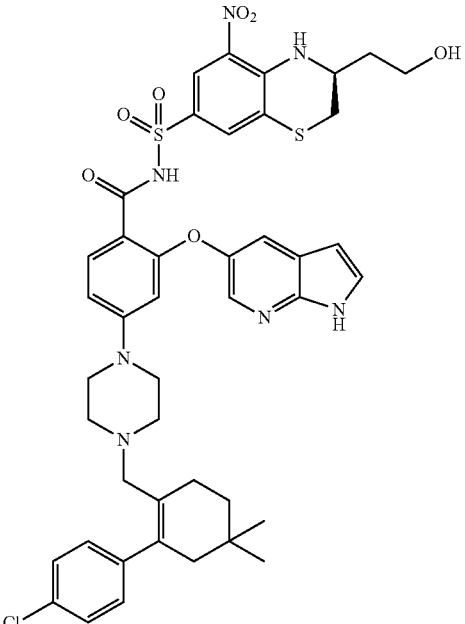 [SMILES: CC1(C)CCC(CN2CCN(c3ccc(C(=O)NS(=O)(=O)c4cc5c(c([N+](=O)[O-])c4)N[C@@H](CCO)CS5)c(Oc4cnc5[nH]ccc5c4)c3)CC2)=C(c2ccc(Cl)cc2)C1] | (S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-(2-hydroxyethyl)-5-nitro-3,4-dihydro-2H-benzo[b][1,4]thiazin-7-yl)sulfonyl)benzamide | MS-ESI (m/z): 872 [M + 1]+ |
| 3-16 | 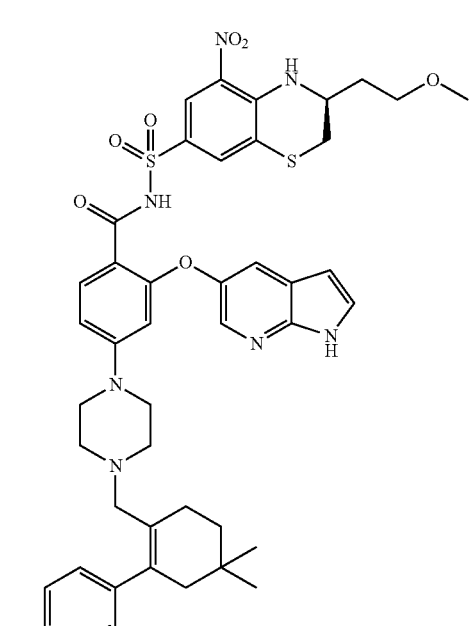 | (S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-(2-methoxyethyl)-5-nitro-3,4-dihydro-2H-benzo[b][1,4]thiazin-7-yl)sulfonyl)benzamide | MS-ESI (m/z): 886 [M + 1]+ |

TABLE 3-continued

| EXAMPLE | STRUCTURE | NAME | DATA |
|---|---|---|---|
| 3-17 | 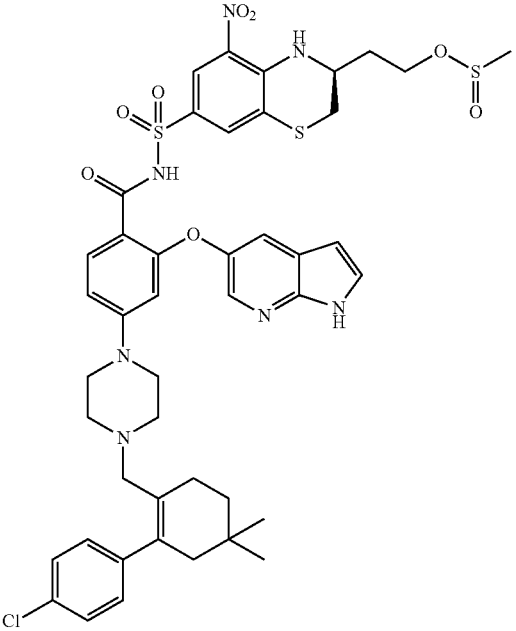 [SMILES: CS(=O)OCC[C@H]1CSc2cc(S(=O)(=O)NC(=O)c3ccc(N4CCN(CC5=C(c6ccc(Cl)cc6)CC(C)(C)CC5)CC4)cc3Oc3cnc4[nH]ccc4c3)cc([N+](=O)[O-])c2N1] | 2-((S)-7-(N-(2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)benzoyl)sulfamoyl)-5-nitro-3,4-dihydro-2H-benzo[b][1,4]thiazin-3-yl)ethyl methanesulfinate | MS-ESI (m/z): 934 [M + 1]+ |
| 3-18 | 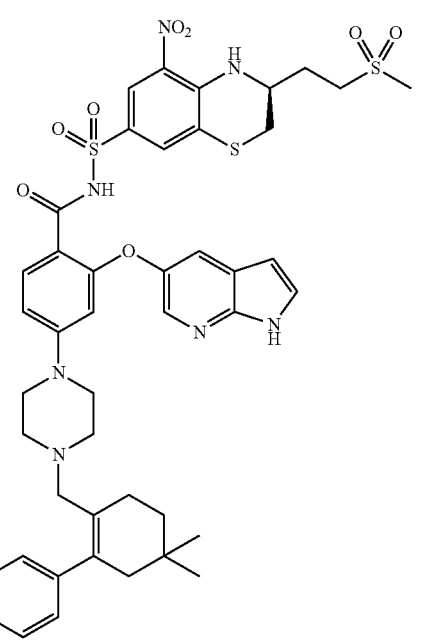 | (S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-(2-(methylsulfonyl)ethyl)-5-nitro-3,4-dihydro-2H-benzo[b][1,4]thiazin-7-yl)sulfonyl)benzamide | MS-ESI (m/z): 934 [M + 1]+ |

TABLE 3-continued

| EXAMPLE | STRUCTURE | NAME | DATA |
|---|---|---|---|
| 3-19 | 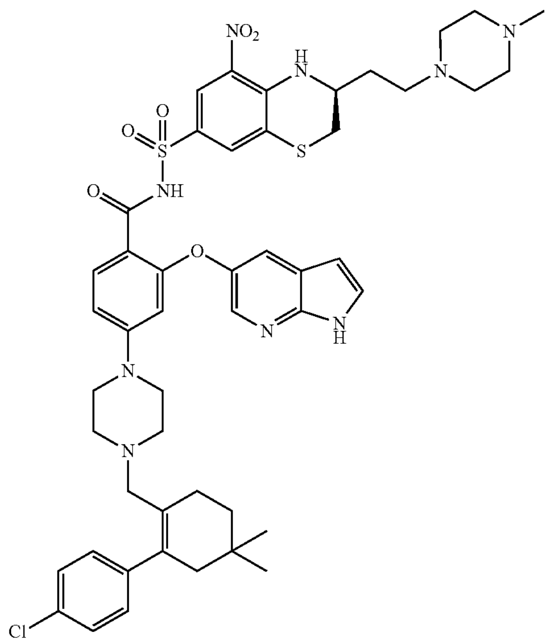 | (S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-(2-(4-methylpiperazin-1-yl)ethyl)-5-nitro-3,4-dihydro-2H-benzo[b][1,4]thiazin-7-yl)sulfonyl)benzamide | MS-ESI (m/z): 954 [M + 1]+ |
| 3-20 | 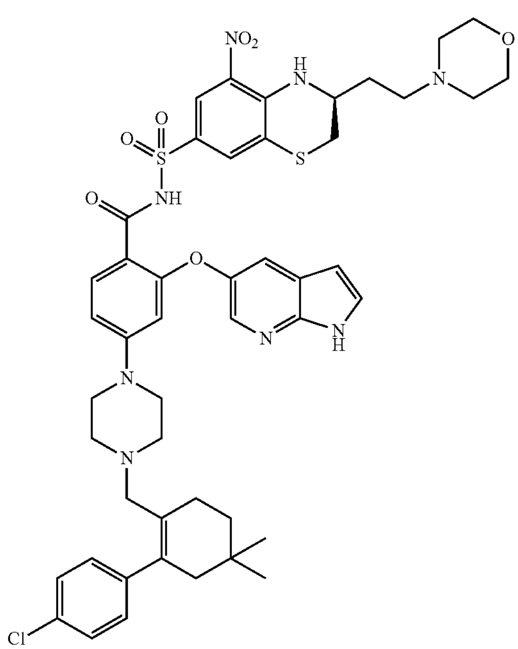 | (S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-(2-morpholinoethyl)-5-nitro-3,4-dihydro-2H-benzo[b][1,4]thiazin-7-yl)sulfonyl)benzamide | MS-ESI (m/z): 941 [M + 1]+ |

Example 4-1

(S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((2-((4-methylpiperazin-1-yl)methyl)-8-nitro-1,2,3,4-tetrahydroquinoxalth-6-yl)sulfonyl)benzamide (4-1)

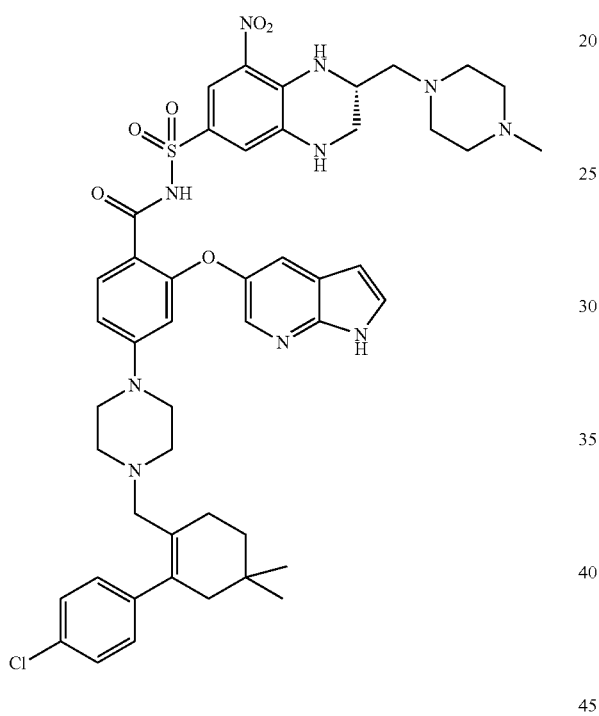

4-1

The title compound (S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((2-((4-methylpiperazin-1-yl)methyl)-8-nitro-1,2,3,4-tetrahydroquinoxalin-6-yl)sulfonyl)benzamide (4-1) was prepared according to the synthetic method of 2-1 by replacing (R)-(5-nitro-7-sulfamoyl-3,4-dihydro-2H-benzo[b][1,4]oxazin-3-yl)methyl methanesulfonate (Intermediate C) with (S)-(8-nitro-6-sulfamoyl-1,2,3,4-tetrahydroquinoxalin-2-yl)methyl methanesulfonate (Intermediate I). MS-ESI (m/z): 923 [M+1]$^+$.

Following essentially the same procedures described for Examples 4-1 or using similar synthetic strategies or methods, Examples 4-2~4-5 listed in Table 4 was prepared. The structures and names of Examples 4-2~4-5 is given in Table 4.

TABLE 4

| EXAMPLE | STRUCTURE | NAME | DATA |
| --- | --- | --- | --- |
| 4-2 | 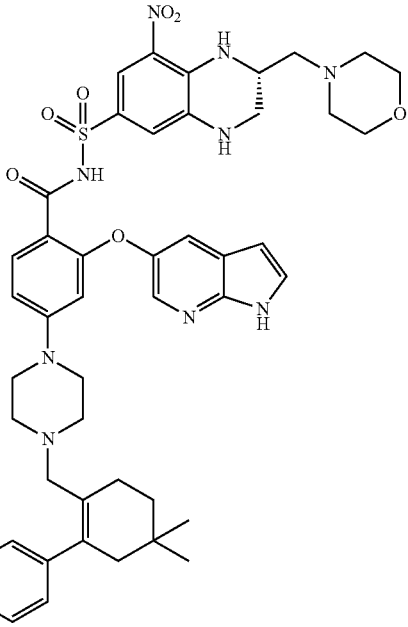 | (S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((2-(morpholinomethyl)-8-nitro-1,2,3,4-tetrahydroquinoxalin-6-yl)sulfonyl)benzamide | MS-ESI (m/z): 910 [M + 1]+ |
| 4-3 | 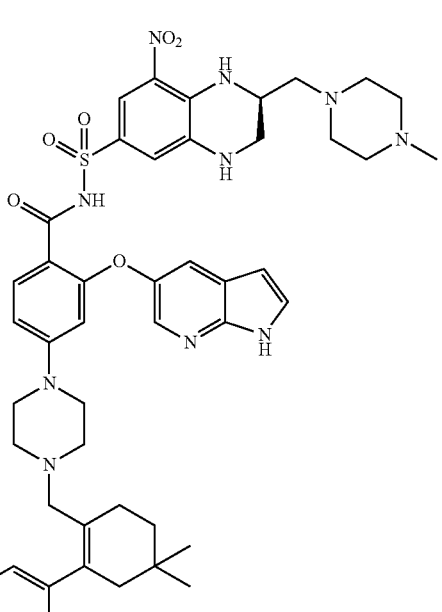 | (R)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((2-((4-methylpiperazin-1-yl)methyl)-8-nitro-1,2,3,4-tetrahydroquinoxalin-6-yl)sulfonyl)benzamide | MS-ESI (m/z): 923 [M + 1]+ |

TABLE 4-continued

| EXAMPLE | STRUCTURE | NAME | DATA |
|---|---|---|---|
| 4-4 | 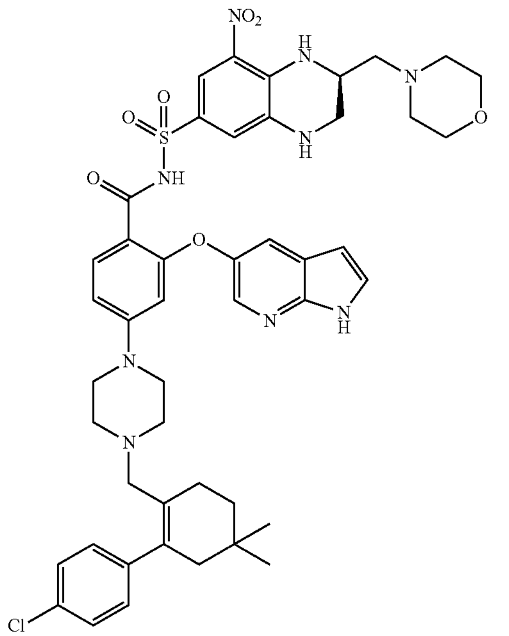 | (R)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((2-(morpholinomethyl)-8-nitro-1,2,3,4-tetrahydroquinoxalin-6-yl)sulfonyl)benzamide | MS-ESI (m/z): 910 [M + 1]+ |
| 4-5 | 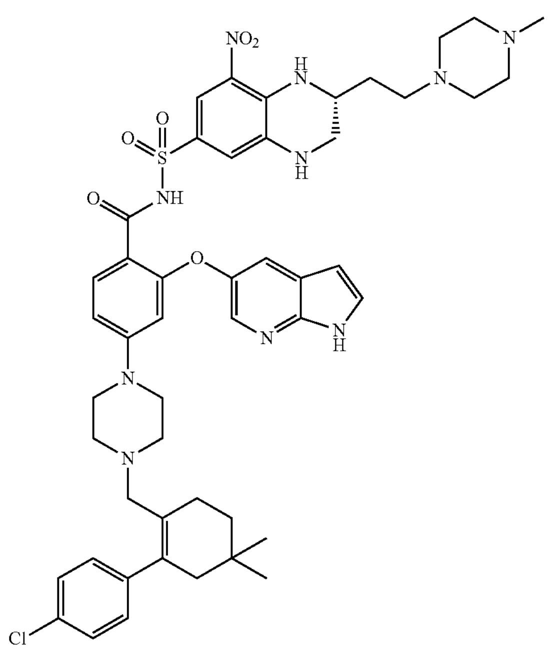 [SMILES: CN1CCN(CC[C@@H]2CNc3cc(S(=O)(=O)NC(=O)c4ccc(N5CCN(CC6=C(c7ccc(Cl)cc7)CC(C)(C)CC6)CC5)cc4Oc4cnc5[nH]ccc5c4)cc([N+](=O)[O-])c3N2)CC1] | (R)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((2-(2-(4-methylpiperazin-1-yl)ethyl)-8-nitro-1,2,3,4-tetrahydroquinoxalin-6-yl)sulfonyl)benzamide | MS-ESI (m/z): 937 [M + 1]+ |

Example 5-1

(S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((2-(morpholinomethyl)-8-nitro-2,3-dihydrobenzo[b][1,4]dioxin-6-yl)sulfonyl)benzamide (5-1)

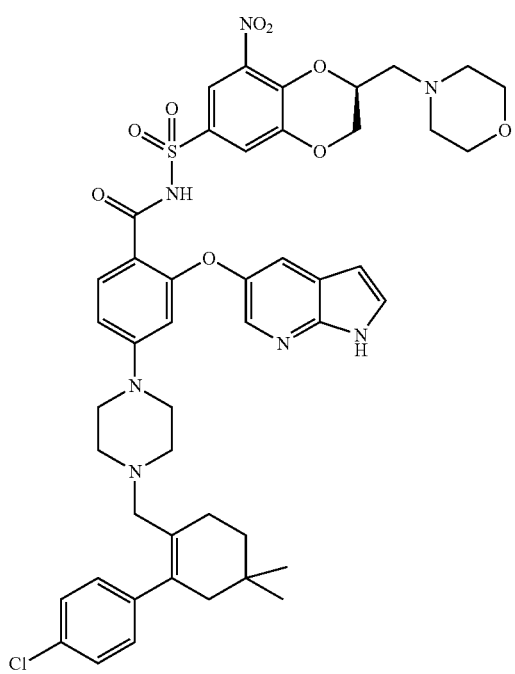

5-1

3-nitrobenzene-1,2-diol (5-1a)

The title compound 3-nitrobenzene-1,2-diol (5-1a) was prepared according to the method described in WO2012/92880.

(R)-(2,2-dimethyl-1,3-dioxolan-4-yl)methyl methanesulfonate (5-1b)

The title compound (R)-(2,2-dimethyl-1,3-dioxolan-4-yl)methyl methanesulfonate (5-1b) was prepared according to the method described in US2006/63814.

(S)-2-((2,2-dimethyl-1,3-dioxolan-4-yl)methoxy)-6-nitrophenol (5-1c)

To a solution of 3-nitrobenzene-1,2-diol (5-1a) (0.10 g, 0.65 mmol) in DMSO (1.5 mL) was added NaOH(52 g, 1.3 mmol) at 25° C. The mixture was stirred at 25° C. for 15 min. Then (R)-(2,2-dimethyl-1,3-dioxolan-4-yl)methyl methanesulfonate (5-1b) was added to the mixture at 25° C. and stirred at 80° C. for 12 h. The mixture was poured into ice water (20 mL) at 0° C. The mixture was extracted by EtOAc, washed with brine (15 mL), dried over $Na_2SO_4$ and concentrated to give the crude product of (S)-2-((2,2-dimethyl-1,3-dioxolan-4-yl)methoxy)-6-nitrophenol (5-1c), which was used for next step directly.

(S)-(8-nitro-2,3-dihydrobenzo[b][1,4]dioxin-2-yl)methanol (5-1d)

To a solution of (S)-2((2,2-dimethyl-1,3-dioxolan-4-yl)methoxy)-6-nitrophenol (5-1d) (0.17 g, 0.63 mmol) in HOAc (0.7 mL) was added HBr (35% in HOAc, 0.45 mL) at 25° C. The mixture was stirred at 25° C. for 2 h. Then EtOH (3.0 mL) and NaOH(50% in $H_2O$, 1.4 mL) was added to the mixture at 25° C. and stirred at 25° C. for 12 h. Then Con.HCl (1.4 mL) was added to the mixture at 25° C. The mixture was extracted by EtOAc, washed with brine (15 mL), dried over $Na_2SO_4$ and concentrated. The residue was purified by column chromatography on silica gel eluting with EtOAc/PE (1:4) to give title compound (S)-(8-nitro-2,3-dihydrobenzo[b][1,4]dioxin-2-yl)methanol (5-1d).

(R)-(8-nitro-2,3-dihydrobenzo[b][1,4]dioxin-2-yl)methyl methanesulfonate (5-1e)

The title compound (R)-(8-nitro-2,3-dihydrobenzo[b][1,4]dioxin-2-yl)methyl methanesulfonate (5-1e) was prepared according to the synthetic method of (R)-(5-nitro-7-sulfamoyl-3,4-dihydro-2H-benzo[b][1,4]oxazin-3-yl)methyl methanesulfonate (Intermediate C) by replacing (S)-3-(hydroxymethyl)-5-nitro-3,4-dihydro-2H-benzo[b][1,4]-oxazine-7-sulfonamide (C-6) with (S)-(8-nitro-2,3-dihydrobenzo[b][1,4]dioxin-2-yl)methanol (5-1d).

(R)-(6-(chlorosulfonyl)-8-nitro-2,3-dihydrobenzo[b][1,4]dioxin-2-yl)methyl methanesulfonate (5-1f)

To a solution of PCl₅ (0.27 g, 1.3 mmol) in sulfurochloridic acid (1.0 mL) was added (R)-(8-nitro-2,3-dihydrobenzo[b][1,4]dioxin-2-yl)methyl methanesulfonate (5-1e) (0.19 g, 0.67 mmol) at 25° C. The mixture was stirred at 25° C. for 1 h. The mixture was poured into ice water (20 mL) at 0° C. The mixture was extracted by EtOAc, washed with brine (15 mL), dried over Na₂SO₄ and concentrated to give the crude product of (R)-(6-(chlorosulfonyl)-8-nitro-2,3-dihydrobenzo[b][1,4]dioxin-2-yl)methyl methanesulfonate (5-1f), which was used for next step directly.

(R)-(8-nitro-6-sulfamoyl-2,3-dihydrobenzo[b][1,4]dioxin-2-yl)methyl methanesulfonate (5-1g)

To a solution of (R)-(6-(chlorosulfonyl)-8-nitro-2,3-dihydrobenzo[b][1,4]dioxin-2-yl)methyl methanesulfonate (5-10 (0.21 g, 0.57 mmol) in EtOAc (3.0 mL) was added NH₃·H₂O (0.2 mL) at 25° C. The mixture was stirred at 25° C. for 10 min. The mixture was poured into ice water (10 mL) at 0° C. The mixture was extracted by EtOAc, washed with brine (15 mL), dried over Na₂SO₄ and concentrated to give the crude product of (R)-(8-nitro-6-sulfamoyl-2,3-dihydrobenzo[b][1,4]dioxin-2-yl)methyl methanesulfonate (5-1g), which was used for next step directly.

(S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((2-(morpholinomethyl)-8-nitro-2,3-dihydrobenzo[b][1,4]dioxin-6-yl)sulfonyl)benzamide (5-1)

The title compound (S)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((2-(morpholinomethyl)-8-nitro-2,3-dihydrobenzo [b][1,4]dioxin-6-yl)sulfonyl)benzamide (5-1) was prepared according to the synthetic method of 2-1 by replacing (R)-(5-nitro-7-sulfamoyl-3,4-dihydro-2H-1-benzo [b][1,4]oxazin-3-yl)methyl methanesulfonate (Intermediate C) with (R)-(8-nitro-6-sulfamoyl-2,3-dihydrobenzo[b][1,4]dioxin-2-yl)methyl methanesulfonate (5-1g). MS-ESI (m/z): 912 [M+1]⁺.

Following essentially the same procedures described for Examples 5-1 or using similar synthetic methods or strategies, Examples 5-2~5-4 listed in Table 5 was prepared. The structures and names of Examples 5-2~5-4 is given in Table 5.

TABLE 5

| EXAMPLE | STRUCTURE | NAME | DATA |
| --- | --- | --- | --- |
| 5-2 | 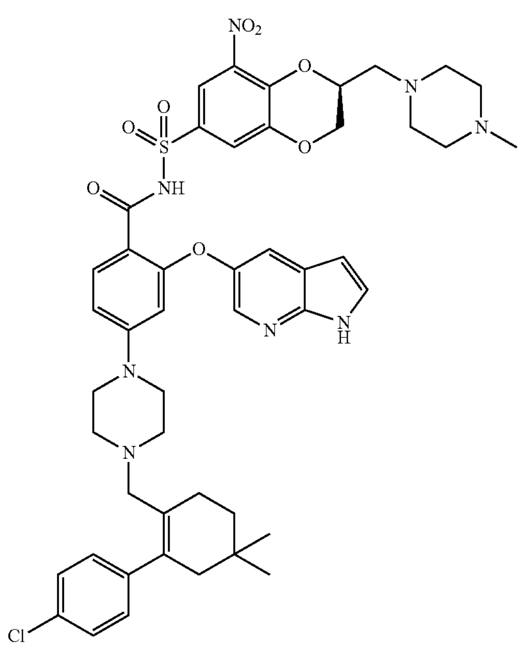 [SMILES: CN1CCN(C[C@H]2COc3cc(S(=O)(=O)NC(=O)c4ccc(N5CCN(CC6=C(c7ccc(Cl)cc7)CC(C)(C)CC6)CC5)cc4Oc4cnc5[nH]ccc5c4)cc([N+](=O)[O-])c3O2)CC1] | (R)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-(4-hydroxycyclohexyl)-5-nitro-3,4-dihydro-2H-benzo[b][1,4]oxazin-7-yl)sulfonyl)benzamide | MS-ESI (m/z): 925 [M + 1]⁺ |

TABLE 5-continued

| EXAMPLE | STRUCTURE | NAME | DATA |
|---|---|---|---|
| 5-3 | 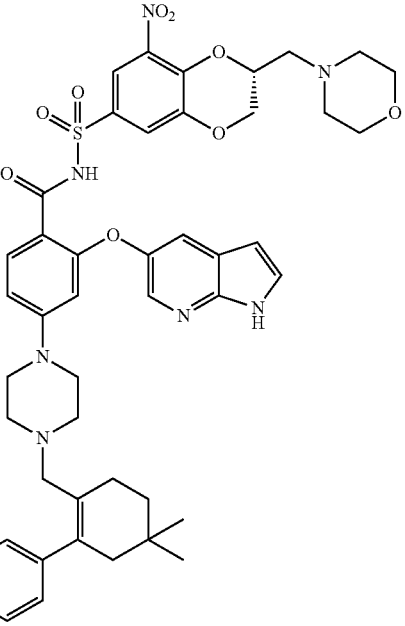 | (R)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((2-(morpholinomethyl)-8-nitro-2,3-dihydrobenzo[b][1,4]dioxin-6-yl)sulfonyl)benzamide | MS-ESI (m/z): 912 [M + 1]+ |
| 5-4 | 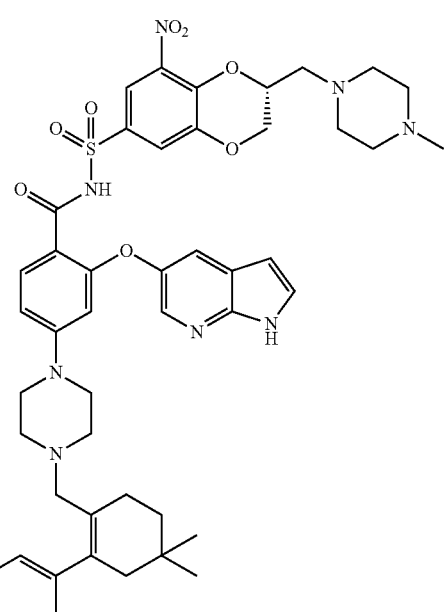 | (R)-2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((2-((4-methylpiperazin-1-yl)methyl)-8-nitro-2,3-dihydrobenzo[b][1,4]dioxin-6-yl)sulfonyl)benzamide | MS-ESI (m/z): 925 [M + 1]+ |

Example 6-1

N-(((R)-3-(((1S,4S)-2-oxa-5-azabicyclo[2.2.1]heptan-5-yl)methyl)-5-nitro-3,4-dihydro-2H-benzo[b][1,4]oxazin-7-yl)sulfonyl)-4-(4-((4'-chloro-5,5-dimethyl-3,4,5,6-tetrahydro-[1,1'-biphenyl]-2-yl)methyl)piperazin-1-yl)-2-(pyrazolo[4,3-b]pyrrolo[3,2-e]pyridin-1(5H)-yl)benzamide (6-1)

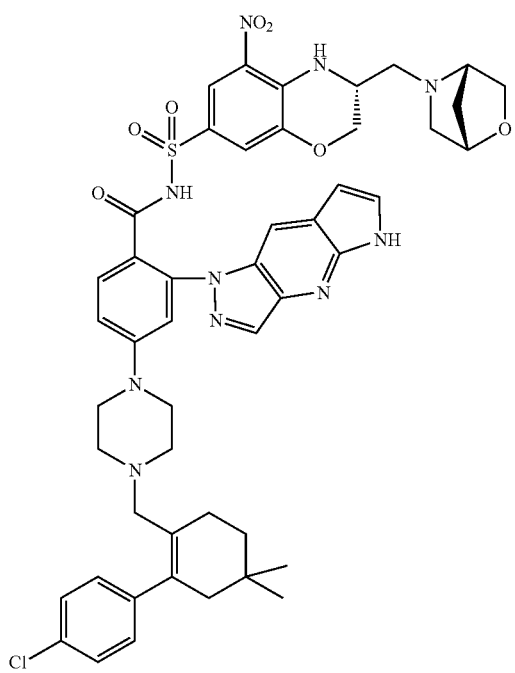

6-1

4-(4-((4'-chloro-5,5-dimethyl-3,4,5,6-tetrahydro-[1,1'-biphenyl]-2-yl)methyl)piperazin-1-yl)-2-(pyrazolo[4,3-b]pyrrolo[3,2-e]pyridin-1(5H)-yl)benzoic acid (6-1a)

4-(4-((4'-chloro-5,5-dimethyl-3,4,5,6-tetrahydro-[1,1'-biphenyl]-2-yl)methyl)piperazin-1-yl)-2-(pyrazolo[4,3-b]pyrrolo[3,2-e]pyridin-1(5H)-yl)benzoic acid (6-1a) was prepared according to the method described in WO2017/132474.

(R)-3-(((1 S,4S)-2-oxa-5-azabicyclo[2.2.1]heptan-5-yl)methyl)-5-nitro-3,4-dihydro-2H-benzo[b][1,4]oxazine-7-sulfonamide (6-1b)

The title compound (R)-3-(((1S,4S)-2-oxa-5-azabicyclo[2.2.1]heptan-5-yl)-methyl)-5-nitro-3,4-dihydro-2H-benzo[b][1,4]oxazine-7-sulfonamide (6-1b) was prepared according to the synthetic method of 2-1a by replacing methyl O-(tert-butyldimethylsilyl)-L-serinate (C-2) and 1-methylpiperazine with methyl O-(tert-butyldimethylsilyl)-D-serinate and (1S,4S)-2-oxa-5-azabicyclo[2.2.1]heptane. MS-ESI (m/z): 371 [M+1]$^+$.

N-(((R)-3-(((1S,4S)-2-oxa-5-azabicyclo[2. 2.1]heptan-5-yl)methyl)-5-nitro-3,4-dihydro-2H-benzo[b][1,4]oxazin-7-yl)sulfonyl)-4-(4-((4'-chloro-5,5-dimethyl-3,4,5,6-tetrahydro-[1,1'-biphenyl]-2-yl)methyl)piperazin-1-yl)-2-(pyrazolo[4,3-b]pyrrolo[3,2-e]pyridin-1(5H)-yl)benzamide (6-1)

The title compound N-(((R)-3-(((1S,4S)-2-oxa-5-azabicyclo[2.2.1]heptan-5-yl)-methyl)-5-nitro-3,4-dihydro-2H-benzo[b][1,4]oxazin-7-yl)sulfonyl)-4-(4-((4'-chloro-5,5-dimethyl-3,4,5,6-tetrahydro-[1,1'-biphenyl]-2-yl)methyl)piperazin-1-yl)-2-(pyrazolo[4,3-b]pyrrolo[3,2-e]pyridin-1(5H)-yl)benzamide (6-1) was prepared according to the synthetic method of 1-1 by replacing (S)-2-(morpholinomethyl)-7-nitroindoline-5-sulfonamide (1-1a) and 2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)benzoic acid (1-1b) with (R)-3-(((1S,4S)-2-oxa-5-azabicyclo[2.2.1]heptan-5-yl)methyl)-5-nitro-3,4-dihydro-2H-benzo[b][1,4]oxazine-7-sulfonamide (6-1b) and 4-(4-((4'-chloro-5,5-dimethyl-3,4,5,6-tetrahydro-[1,1'-biphenyl]-2-yl)methyl)-piperazin-1-yl)-2-(pyrazolo[4,3-b]pyrrolo[3,2-e]pyridin-1(5H)-yl)benzoic acid (6-1a). MS-ESI (m/z): 947 [M+1]$^+$.

Following essentially the same procedures described for Examples 6-1 or using similar synthetic methods or strategies, Examples 6-2~6-3 listed in Table 5 was prepared. The structures and names of Examples 6-2~6-3 is given in Table 6.

TABLE 6

| EXAMPLE | STRUCTURE | NAME | DATA |
|---|---|---|---|
| 6-2 | 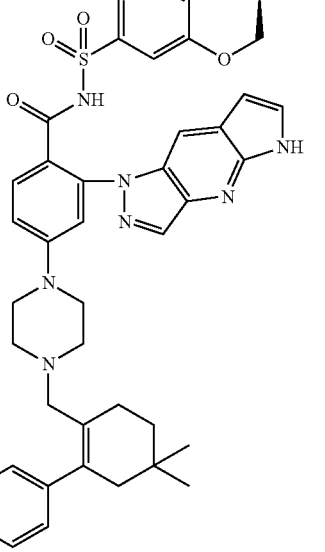 | (S)-4-(4-((4'-chloro-5,5-dimethyl-3,4,5,6-tetrahydro-[1,1'-biphenyl]-2-yl)methyl)piperazin-1-yl)-N-((3-cyclopropyl-5-nitro-3,4-dihydro-2H-benzo[b][1,4]oxazin-7-yl)sulfonyl)-2-(pyrazolo[4,3-b]pyrrolo[3,2-e]pyridin-1(5H)-yl)benzamide | MS-ESI (m/z): 876 [M + 1]+ |
| 6-3 | 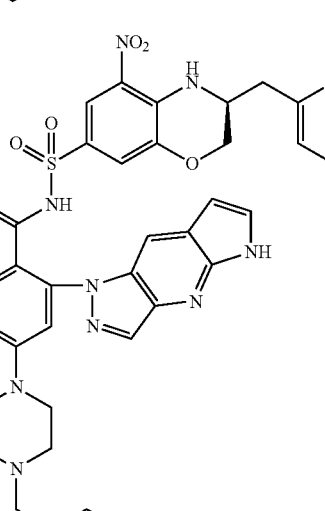 | (S)-4-(4-((4'-chloro-5,5-dimethyl-3,4,5,6-tetrahydro-[1,1'-biphenyl]-2-yl)methyl)piperazin-1-yl)-N-((5-nitro-3-(pyridin-2-ylmethyl)-3,4-dihydro-2H-benzo[b][1,4]oxazin-7-yl)sulfonyl)-2-(pyrazolo[4,3-b]pyrrolo[3,2-e]pyridin-1(5H)-yl)benzamide | MS-ESI (m/z): 927 [M + 1]+ |

Cell Proliferation Assays

MTS testing kit was purchased from Promega. The RPMI-1640, Fetal bovine serum and Penicillin-Streptomycin were purchased from Gibco. Dimethyl sulfoxide (DMSO) was purchased from Sigma.

To investigate whether a compound is able to inhibit the activity of BCL-2 in cells, a mechanism-based assay using DOHH2 (DSMZ No.® ACC 47) and RS4;11 (ATCC® CRL-1873™) cell was developed. In this assay, inhibition of Bcl-2 was detected by the inhibition of DOHH2 cells proliferation. DOHH2 cells were cultured in culture flasks to 40-80% confluence in RPMI-1640 plus 10% fetal bovine serum. Cells were collected and plated onto 96-well plates at desired cell density (5000 cells/well). Plates were incubated overnight at 37° C., with 5% $CO_2$ to adhere. Compounds were added to the plates, and the final compound concentrations were 10000, 3333, 1111, 270, 124, 41, 14, 4.6 and 1.5 nM. Plates plated with DOHH2 or RS4;11 cells were placed at 37° C., with 5% $CO_2$ for 120 h (DOHH2) or 72 h (RS4;11) respectively. 20 μl MTS/100 μl medium mixture solution were added to each well and incubate the plates for exactly 2 hours. The reaction was stopped by adding 25 μl 10% SDS per well. Measure absorbance at 490 nm and 650 nm (reference wavelength). $IC_{50}$ was calculated using GraphPad Prism 5.0.

Select compounds prepared as described above were assayed according to the biological procedures described herein. The results are given in the table 7.

| Example | DOHH2 IC$_{50}$ (nM) | RS4; 11 IC$_{50}$ (nM) |
|---|---|---|
| 1-1 | 80 | 48 |
| 1-2 | 79 | 38 |
| 1-3 | 20 | 8 |
| 1-4 | 308 | / |
| 1-5 | 211 | 51 |
| 1-6 | 221 | / |
| 1-7 | 26 | 3 |
| 1-8 | 27 | 1 |
| 1-9 | 66 | 80 |
| 1-10 | 33 | 16 |
| 1-11 | 154 | 69 |
| 1-12 | 299 | 58 |
| 1-13 | 91 | 74 |
| 1-14 | 57 | 52 |
| 1-15 | 50 | 15 |
| 1-16 | 73 | 16 |
| 1-17 | 61 | 56 |
| 1-18 | 5 | 18 |
| 1-19 | 96 | 93 |
| 1-20 | 170 | / |
| 1-21 | 12 | 1 |
| 1-22 | 175 | 47 |
| 1-23 | 57 | 20 |
| 1-24 | 41 | 73 |
| 1-25 | 6 | 6 |
| 1-26 | 102 | 12 |
| 1-27 | 51 | / |
| 2-1 | 6 | 1 |
| 2-2 | 8 | 2 |
| 2-3A | 16 | 1 |
| 2-3B | 33 | 8 |
| 2-4 | 139 | / |
| 2-5 | 12 | 3 |
| 2-6 | 18 | 2 |
| 2-7 | 95 | 72 |
| 2-8 | 67 | 14 |
| 2-9 | 33 | 10 |
| 2-10 | 28 | 9 |
| 2-11 | 53 | 12 |
| 2-12 | 19 | 1 |
| 2-13 | 33 | 9 |
| 2-14 | 15 | 4 |
| 2-15 | 50 | 20 |
| 2-16 | 34 | 4 |
| 2-17 | 20 | 8 |
| 2-18 | 9 | 4 |
| 2-19 | 70 | 36 |
| 2-20 | 59 | 29 |
| 2-21 | 8 | 1 |
| 2-22 | 2 | 1 |
| 2-23 | 33 | 7 |
| 2-24 | 115 | 72 |
| 2-25 | 10 | 8 |
| 2-26 | 19 | 6 |
| 2-27 | 12 | 1 |
| 2-28 | 1 | 1 |
| 2-29 | 7 | 1 |
| 2-30 | 8 | 1 |
| 2-31 | 18 | 7 |
| 2-32 | 34 | 18 |
| 2-33 | 25 | 11 |
| 2-34 | 41 | 14 |
| 2-35 | 30 | 5 |
| 2-36 | 33 | 7 |
| 2-37 | 25 | 1 |
| 2-38 | 27 | 1 |
| 2-39 | 33 | 9 |
| 2-40 | 36 | 22 |
| 2-41 | 23 | 2 |
| 2-42 | 38 | 6 |
| 2-43 | 10 | 1 |
| 2-44 | 51 | 46 |
| 2-45 | 17 | 12 |
| 2-46 | 7 | 1 |
| 2-47 | 12 | 22 |
| 2-48 | 9 | 14 |
| 2-49 | 12 | 16 |
| 2-50 | 22 | 9 |
| 2-51 | 13 | 10 |
| 2-52 | 31 | 25 |
| 2-53 | 543 | 53 |
| 2-54 | 134 | 61 |
| 2-56 | 571 | 41 |
| 2-57 | 392 | / |
| 2-58 | 868 | / |
| 2-59 | 730 | / |
| 2-60 | 82 | 1 |
| 2-61 | 444 | 48 |
| 2-62 | 230 | / |
| 2-63 | 64 | 12 |
| 2-64 | 70 | 25 |
| 2-65 | 14 | 20 |
| 2-66 | 13 | 18 |
| 2-67 | 1316 | / |
| 2-68 | 83 | 26 |
| 2-70 | 28 | 5 |
| 2-71 | 43 | 58 |
| 2-72 | 24 | 6 |
| 2-73 | 69 | 79 |
| 2-74 | 108 | 64 |
| 2-75 | 64 | 1 |
| 2-76 | 120 | / |
| 2-77 | 602 | 50 |
| 2-78 | 15 | 6 |
| 2-79 | 55 | 7 |
| 2-80 | 49 | 7 |
| 2-81 | 14 | 3 |
| 2-82 | 9 | 1 |
| 2-83 | 13 | 1 |
| 2-84 | 82 | 26 |
| 2-85 | 434 | / |
| 2-86 | 648 | / |
| 2-87 | 26 | 7 |
| 2-88 | 14 | 2 |
| 2-89 | 55 | 50 |
| 2-90 | 22 | 8 |
| 2-91 | 49 | 5 |
| 2-92 | 79 | 5 |
| 2-93 | 16 | 40 |
| 2-94 | 1 | 20 |
| 2-95 | 19 | 45 |
| 2-96 | 85 | 72 |
| 2-97 | 23 | 23 |
| 2-98 | 38 | 17 |
| 2-99 | 20 | 8 |
| 2-100 | 31 | 22 |
| 2-102 | 95 | 10 |
| 2-103 | 490 | 16 |
| 2-104 | 173 | 7 |
| 2-105 | 51 | 35 |
| 2-106 | 19 | 9 |
| 2-107 | 22 | 8 |
| 2-108 | 51 | 16 |
| 2-109 | 56 | 11 |
| 2-110 | 96 | 2 |
| 2-111 | 26 | 28 |
| 2-112 | 15 | 11 |
| 2-113 | 20 | 6 |
| 2-114 | 48 | 1 |
| 2-115 | 38 | 6 |
| 2-116 | 83 | 16 |
| 2-117 | 41 | 44 |
| 2-118 | 649 | 11 |
| 2-121 | 48 | 36 |
| 2-122 | 660 | / |
| 2-124 | 649 | / |
| 2-125 | 43 | 19 |
| 2-126 | 11 | 5 |
| 2-127 | 42 | 23 |

| Example | DOHH2 IC$_{50}$ (nM) | RS4; 11 IC$_{50}$ (nM) |
| --- | --- | --- |
| 2-128 | 28 | 20 |
| 2-129 | 16 | 9 |
| 2-130 | 26 | 14 |
| 2-131 | 39 | 9 |
| 2-132 | 28 | 2 |
| 2-133 | 8 | 1 |
| 2-134 | 39 | 2 |
| 2-135 | 186 | / |
| 2-136 | 378 | / |
| 2-137 | 139 | / |
| 2-138 | 166 | 72 |
| 2-139 | 338 | 88 |
| 2-142 | 28 | 3 |
| 2-143 | 35 | 35 |
| 2-144 | 14 | 3 |
| 2-145 | 87 | 1 |
| 2-146 | 160 | / |
| 2-147 | 135 | 16 |
| 2-149 | 247 | 50 |
| 2-150 | 67 | 45 |
| 2-151 | 2 | 1 |
| 2-152 | 1 | 1 |
| 2-153 | 8 | 1 |
| 2-154 | 201 | 24 |
| 2-155 | 459 | 66 |
| 2-156 | 6 | 19 |
| 2-157 | 39 | 10 |
| 2-158 | 135 | 43 |
| 2-159 | 47 | 29 |
| 2-160 | 168 | 95 |
| 2-161 | 20 | 17 |
| 2-162 | 325 | 43 |
| 2-163 | 53 | 29 |
| 2-164 | 16 | 34 |
| 2-165 | 77 | / |
| 2-166 | 300 | 82 |
| 2-167 | 29 | / |
| 2-168 | 32 | 33 |
| 2-169 | 39 | / |
| 2-170 | 464 | / |
| 2-171 | 302 | / |
| 2-172 | 14 | / |
| 2-173 | 24 | / |
| 2-174 | 23 | / |
| 2-175 | 139 | 53 |
| 2-176 | 547 | 64 |
| 2-177 | 119 | 13 |
| 2-178 | 28 | / |
| 2-179 | 380 | 18 |
| 2-180 | 15 | 8 |
| 2-181 | 84 | 45 |
| 2-182 | 16 | 3 |
| 2-183 | 20 | 4 |
| 2-184 | 11 | 3 |
| 2-185 | 3 | 1 |
| 2-186 | 13 | 1 |
| / | / | / |
| 2-187 | 14 | 2 |
| 2-188 | 19 | 1 |
| 2-189 | 148 | 78 |
| 2-190 | 25 | 8 |
| 2-191 | 153 | / |
| 2-192 | 143 | 5 |
| 2-193 | 28 | 1 |
| 2-194 | 74 | 5 |
| 2-195 | 138 | 4 |
| 2-196 | 94 | 6 |
| 2-197 | 412 | / |
| 2-198B | 444 | / |
| 2-199 | 55 | 18 |
| 2-200 | 218 | 3 |
| 2-201 | 145 | 22 |
| 2-202 | 63 | 36 |
| 2-203 | 96 | 20 |
| 2-204 | 17 | 26 |
| 2-206 | 312 | 21 |
| 2-207 | 402 | / |
| 2-208 | 110 | 17 |
| 2-209 | 35 | 1 |
| 2-210 | 35 | 7 |
| 2-211 | 92 | 35 |
| 2-212 | 27 | 8 |
| 2-213 | 41 | 8 |
| 2-214 | 465 | 16 |
| 2-215 | 65 | 3 |
| 2-216 | 268 | 13 |
| 2-217 | 715 | / |
| 2-218 | 507 | / |
| 2-219 | 662 | / |
| 2-220 | 36 | 8 |
| 2-221 | 474 | 30 |
| 2-222 | 3 | 25 |
| 2-223 | 11 | 1 |
| 2-224 | 3 | 4 |
| 2-225 | 15 | 2 |
| 2-226 | 48 | 10 |
| 2-227 | 6 | 1 |
| 2-228 | 48 | / |
| 2-229 | 1 | 38 |
| 2-230 | 2 | 1 |
| 2-231 | 5 | 1 |
| 2-232 | 1 | 6 |
| 2-233 | 13 | 17 |
| 2-234 | 6 | 14 |
| 2-235 | 23 | 10 |
| 2-236 | 6 | 1 |
| 2-237 | 3 | 14 |
| 2-238 | 18 | 9 |
| 2-239A | 5 | 1 |
| 2-239B | 1 | 1 |
| 2-240A | 5 | 1 |
| 2-240B | 1 | 1 |
| 2-241 | 11 | 4 |
| 2-243 | 1 | 9 |
| 2-244A | 7 | 3 |
| 2-244B | 1 | 3 |
| 2-245A | 1 | 1 |
| 2-245B | 1 | 1 |
| 2-246B | 13 | 29 |
| 2-247A | 19 | 24 |
| 2-247B | 36 | 45 |
| 2-248A | 27 | 35 |
| 2-248B | 14 | 64 |
| 2-250 | 7 | 1 |
| 2-251 | 44 | 1 |
| 2-252 | 83 | 29 |
| 3-1 | 3 | 1 |
| 3-2 | 13 | 3 |
| 3-3 | 58 | 35 |
| 3-4 | 41 | 12 |
| 3-5 | 12 | 8 |
| 3-6 | 14 | 8 |
| 3-7 | 31 | 10 |
| 3-8 | 67 | 17 |
| 3-9 | 24 | 13 |
| 3-10 | 32 | 11 |
| 3-11 | 16 | 11 |
| 3-12 | 120 | 84 |
| 3-13 | 2 | 2 |
| 3-14 | 9 | 4 |
| 3-15 | 48 | 13 |
| 3-16 | 132 | 33 |
| 3-17 | 49 | 19 |
| 3-18 | 54 | 20 |
| 3-19 | 6 | 1 |
| 3-20 | 9 | 2 |
| 4-1 | 13 | 1 |
| 4-2 | 29 | 9 |
| 4-3 | 38 | 46 |
| 4-4 | 28 | 14 |
| 4-5 | 232 | / |
| 5-1 | 17 | 9 |

-continued

| Example | DOHH2 IC$_{50}$ (nM) | RS4; 11 IC$_{50}$ (nM) |
|---|---|---|
| 5-2 | 25 | 1 |
| 5-3 | 12 | 4 |
| 5-4 | 13 | 34 |
| 6-1 | 73 | 2 |
| 6-2 | 264 | / |
| 6-3 | 185 | / |
| / | / | / |
| / | / | / |

What is claimed is:

1. A compound of formula (I),

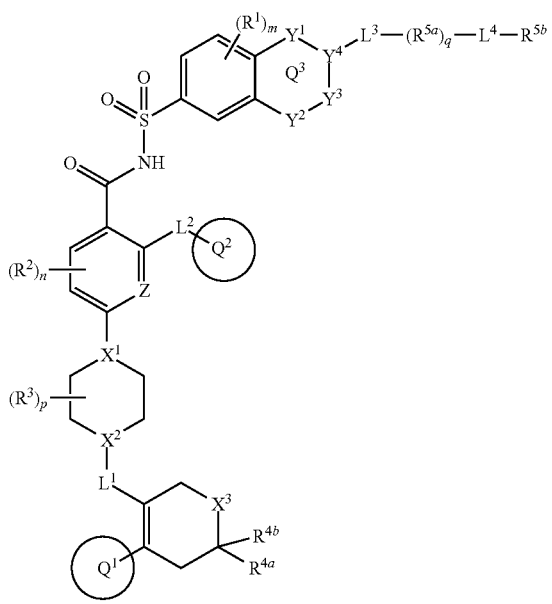

or a pharmaceutically acceptable salt thereof, wherein $Q^1$ is

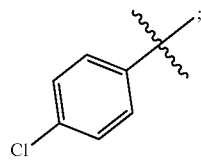 [SMILES: *c1ccc(Cl)cc1]

$Q^2$ is selected from

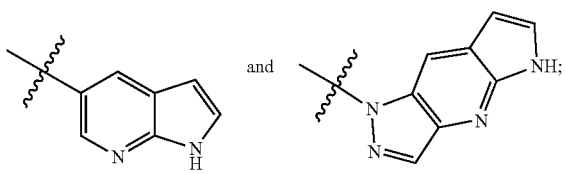 [SMILES: *c1cnc2[nH]ccc2c1 ; *n1ncc2nc3[nH]ccc3cc21]

$L^1$ is —CH$_2$—;
$L^2$ is a bond or —O—;
$X^1$ is N;
$X^2$ is N;
$X^3$ is —CH$_2$—;
Z is C;
$R^1$ is NO$_2$ or SO$_2$CF$_3$;
$R^2$ is hydrogen;
$R^3$ is hydrogen;
m is 1;
n is 1;
p is 1;
$R^{4a}$ and $R^{4b}$ are independently selected from hydrogen and methyl;
$Q^3$ is heterocyclyl, wherein heterocyclyl is unsubstituted or substituted with at least one substituent independently selected from $R^X$;
$Y^1$ is NH;
$Y^2$ is O;
$Y^3$ is CR$^{6a}$R$^{6b}$;
$Y^4$ is C;
$L^3$ is selected from —(CR$^C$R$^D$)$_u$—, —(CR$^C$R$^D$)$_u$O(CR$^C$R$^D$)$_t$—, —(CR$^C$R$^D$)$_u$C(O)(CR$^C$R$^D$)$_t$—, —(CR$^C$R$^D$)$_u$OC(O)(CR$^C$R$^D$)$_t$—, —(CR$^C$R$^D$)$_u$C(O)O(CR$^C$R$^D$)$_t$—, —(CR$^C$R$^D$)$_u$NR$^A$C(O)(CR$^C$R$^D$)$_t$—, —(CR$^C$R$^D$)$_u$C(O)NR$^A$(CR$^C$R$^D$)$_t$—, —(CR$^C$R$^D$)$_u$NR$^A$C(O)O(CR$^C$R$^D$)$_t$—, —(CR$^C$R$^D$)$_u$S(O)$_r$(CR$^C$R$^D$)$_t$— and —(CR$^{C5}$R$^{D5}$)$_u$NR$^A$S(O)$_r$(CR$^C$R$^D$)$_t$—;
each $R^{5a}$ is independently selected from C$_{1-10}$ alkyl, C$_{3-10}$ cycloalkyl, heterocyclyl, aryl and heteroaryl, wherein alkyl, cycloalkyl and heterocyclyl are each unsubstituted or substituted with at least one substituent independently selected from $R^X$;
$L^4$ is selected from —(CR$^C$R$^D$)$_u$—;
$R^{5b}$ is selected from hydrogen, halogen, C$_{1-10}$ alkyl, C$_{3-10}$ cycloalkyl, C$_{3-10}$ heterocyclyl, CN, —OR$^{A5}$, —NR$^{A5}$R$^{B5}$, —NR$^{A5}$C(O)OR$^{B5}$, —N=S(O)R$^{A5}$R$^{B5}$, —C(O)R$^{A5}$, —C(O)OR$^{A5}$, —C(O)NR$^{A5}$R$^{B5}$ and —S(O)$_r$R$^{A5}$;
each $R^{6a}$ and $R^{6b}$ are independently selected from hydrogen, halogen, C$_{1-10}$ alkyl, C$_{2-10}$ alkenyl, C$_{2-10}$ alkynyl, C$_{3-10}$ cycloalkyl, C$_{3-10}$ cycloalkyl-C$_{1-4}$ alkyl, heterocyclyl, heterocyclyl-C$_{1-4}$ alkyl, aryl, aryl-C$_{1-4}$ alkyl, heteroaryl, heteroaryl-C$_{1-4}$ alkyl, CN, NO$_2$, —NR$^{A6}$R$^{B6}$, —OR$^{A6}$, —C(O)R$^{A6}$, —C(=NR$^{E6}$)R$^{A6}$, —C(=N—OR$^{B6}$)R$^{A6}$, —C(O)OR$^{A6}$, —OC(O)R$^{A6}$, —C(O)NR$^{A6}$R$^{B6}$, —NR$^{A6}$C(O)R$^{B6}$, —C(=NR$^{E6}$)NR$^{A6}$R$^{B6}$, —NR$^{A6}$C(=NR$^{E6}$)R$^{B6}$, —OC(O)NR$^{A6}$R$^{B6}$, —NR$^{A6}$C(O)$_r$OR$^{B6}$, —NR$^{A6}$C(O)NR$^{A6}$R$^{B6}$, —NR$^{A6}$C(S)NR$^{A6}$R$^{B6}$, —NR$^{A6}$C(=NR$^{E6}$)NR$^{A6}$R$^{B6}$, —S(O)$_r$R$^{A6}$, —S(O)(=NR$^{E6}$)R$^{B6}$, —N=S(O)R$^{A6}$R$^{B6}$, —S(O)$_2$OR$^{A6}$, —OS(O)$_2$R$^{A6}$, —NR$^{A6}$S(O)$_r$R$^{B6}$, —NR$^{A6}$S(O)(=NR$^{E6}$)R$^{B6}$, —S(O)$_r$NR$^{A6}$R$^{B6}$, —S(O)(=NR$^{E6}$)NR$^{A6}$R$^{B6}$, —NR$^{A6}$S(O)$_2$NR$^{A6}$R$^{B6}$, —NR$^{A6}$S(O)(=NR$^{E6}$)NR$^{A6}$R$^{B6}$, —P(O)R$^{A6}$R$^{B6}$ and —P(O)(OR$^{A6}$)(OR$^{B6}$), wherein alkyl, alkenyl, alkynyl, cycloalkyl, heterocyclyl, aryl and heteroaryl are each unsubstituted or substituted with at least one substituent independently selected from $R^X$;
or $R^{6a}$ and $R^{6b}$ together with the carbon atoms to which they are attached form a 3-7 membered ring containing 0, 1, 2 or 3 heteroatoms independently selected from oxygen, sulfur, nitrogen, and phosphorus, and optionally substituted with 1, 2 or 3 $R^X$ groups;
each $R^A$, $R^{A5}$, $R^{A6}$, $R^{B5}$ and $R^{B6}$ are independently selected from hydrogen, C$_{1-10}$ alkyl, C$_{2-10}$ alkenyl, C$_{2-10}$ alkynyl, C$_{3-10}$ cycloalkyl, C$_{3-10}$ cycloalkyl-C$_{1-4}$ alkyl, heterocyclyl, heterocyclyl-C$_{1-4}$ alkyl, aryl, aryl-C$_{1-4}$ alkyl, heteroaryl, and heteroaryl-C$_{1-4}$ alkyl, wherein alkyl, alkenyl, alkynyl, cycloalkyl, heterocyclyl, aryl and heteroaryl are each unsubstituted or substituted with at least one substituent independently selected from $R^X$;

or each "$R^{A5}$ and $R^{B5}$" and "$R^{A6}$ and $R^{B6}$" together with the atom(s) to which they are attached form a heterocyclic ring of 4 to 12 members containing 0, 1, or 2 additional heteroatoms independently selected from oxygen, sulfur, nitrogen and phosphorus, and optionally substituted with 1, 2 or 3 R groups;

each $R^C$ and $R^D$ are independently selected from hydrogen, halogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl and heteroaryl-$C_{1-4}$ alkyl, wherein alkyl, alkenyl, alkynyl, cycloalkyl, heterocyclyl, aryl and heteroaryl are each unsubstituted or substituted with at least one substituent independently selected from $R^X$;

each $R^{E6}$ is independently selected from hydrogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, heteroaryl-$C_{1-4}$ alkyl, CN, NO$_2$, OR$^{a1}$, SR$^{a1}$, —S(O)$_r$R$^{a1}$, —C(O)R$^{a1}$, C(O)OR$^{a1}$, —C(O)NR$^{a1}$R$^{b1}$ and —S(O)$_r$NR$^{a1}$R$^{b1}$, wherein alkyl, alkenyl, alkynyl, cycloalkyl, heterocyclyl, aryl and heteroaryl are each unsubstituted or substituted with at least one substituent independently selected from $R^Y$;

each $R^X$ is independently selected from hydrogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, heteroaryl-$C_{1-4}$ alkyl, halogen, CN, NO$_2$, —(CR$^{c1}$R$^{d1}$)$_t$NR$^{a1}$R$^{b1}$, —(CR$^{c1}$R$^{d1}$)$_t$OR$^{b1}$, —(CR$^{c1}$R$^{d1}$)$_t$C(O)R$^{a1}$, —(CR$^{c1}$R$^{d1}$)$_t$C(=NR$^{c1}$)R$^{a1}$, —(CR$^{c1}$R$^{d1}$)$_t$C(=N—OR$^{b1}$)R$^{a1}$, —(CR$^{c1}$R$^{d1}$)$_t$C(O)OR$^{b1}$, —(CR$^{c1}$R$^{d1}$)$_t$OC(O)R$^{b1}$, —(CR$^{c1}$R$^{d1}$)$_t$C(O)NR$^{a1}$R$^{b1}$, —(CR$^{c1}$R$^{d1}$)$_t$NR$^{a1}$C(O)R$^{b1}$, —(CR$^{c1}$R$^{d1}$)$_t$C(=NR$^{c1}$)NR$^{a1}$R$^{b1}$, —(CR$^{c1}$R$^{d1}$)$_t$NR$^{a1}$C(=NR$^{c1}$)R$^{b1}$, —(CR$^{c1}$R$^{d1}$)$_t$OC(O)NR$^{a1}$R$^{b1}$, —(CR$^{c1}$R$^{d1}$)$_t$NR$^{a1}$C(O)OR$^{b1}$, —(CR$^{c1}$R$^{d1}$)$_t$NR$^{a1}$C(O)NR$^{a1}$R$^{b1}$, —(CR$^{c1}$R$^{d1}$)$_t$NR$^{a1}$C(S)NR$^{a1}$R$^{b1}$, —(CR$^{c1}$R$^{d1}$)$_t$NR$^{a1}$C(=NR$^{c1}$)NR$^{a1}$R$^{b1}$, —(CR$^{c1}$R$^{d1}$)$_t$S(O)$_r$R$^{b1}$, —(CR$^{c1}$R$^{d1}$)$_t$S(O)(=NR$^{c1}$)R$^{b1}$, —(CR$^{c1}$R$^{d1}$)$_t$N=S(O)R$^{a1}$R$^{b1}$, —(CR$^{c1}$R$^{d1}$)$_t$S(O)$_2$OR$^{b1}$, —(CR$^{c1}$R$^{d1}$)$_t$OS(O)$_2$R$^{b1}$, —(CR$^{c1}$R$^{d1}$)$_t$NR$^{a1}$S(O)$_r$R$^{b1}$, —(CR$^{c1}$R$^{d1}$)$_t$NR$^{a1}$S(O)(=NR$^{e1}$)R$^{b1}$, —(CR$^{c1}$R$^{d1}$)$_t$S(O)$_r$NR$^{a1}$R$^{b1}$, —(CR$^{c1}$R$^{d1}$)$_t$S(O)(=NR$^{e1}$)NR$^{a1}$R$^{b1}$, —(CR$^{c1}$R$^{d1}$)$_t$NR$^{a1}$S(O)$_2$NR$^{a1}$R$^{b1}$, —(CR$^{c1}$R$^{d1}$)$_t$NR$^{a1}$S(O)(=NR$^{e1}$)NR$^{a1}$R$^{b1}$, —(CR$^{c1}$R$^{d1}$)$_t$P(O)R$^{a1}$R$^{b1}$ and —(CR$^{c1}$R$^{d1}$)$_t$P(O)(OR$^{a1}$)(OR$^{b1}$), wherein alkyl, alkenyl, alkynyl, cycloalkyl, heterocyclyl, aryl and heteroaryl are each unsubstituted or substituted with at least one substituent independently selected from $R^Y$;

each $R^{a1}$ and each $R^{b1}$ are independently selected from hydrogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl and heteroaryl-$C_{1-4}$ alkyl, wherein alkyl, alkenyl, alkynyl, cycloalkyl, heterocyclyl, aryl and heteroaryl are each unsubstituted or substituted with at least one substituent independently selected from $R^Y$;

or $R^{a1}$ and $R^{b1}$ together with the atom(s) to which they are attached form a heterocyclic ring of 4 to 12 members containing 0, 1 or 2 additional heteroatoms independently selected from oxygen, sulfur, nitrogen and phosphorus, and optionally substituted with 1, 2 or 3 $R^Y$ groups;

each $R^{c1}$ and each $R^{d1}$ are independently selected from hydrogen, halogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl and heteroaryl-$C_{1-4}$ alkyl, wherein alkyl, alkenyl, alkynyl, cycloalkyl, heterocyclyl, aryl and heteroaryl are each unsubstituted or substituted with at least one substituent independently selected from $R^Y$;

or $R^{c1}$ and $R^{d1}$ together with the carbon atom(s) to which they are attached form a ring of 3 to 12 members containing 0, 1 or 2 heteroatoms independently selected from oxygen, sulfur and nitrogen, and optionally substituted with 1, 2 or 3 $R^Y$ groups;

each $R^{e1}$ is independently selected from hydrogen, $C_{1-10}$ alkyl, $C_{3-10}$ cycloalkyl, $C_{3-10}$ cycloalkyl-$C_{1-4}$ alkyl, CN, NO$_2$, —OR$^{a2}$, —SR$^{a2}$, —S(O)$_r$R$^{a2}$, —C(O)R$^{a2}$, —C(O)OR$^{a2}$, —S(O)$_r$NR$^{a2}$R$^{b2}$ and —C(O)NR$^{a2}$R$^{b2}$;

each $R^Y$ is independently selected from $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, heteroaryl-$C_{1-4}$ alkyl, halogen, CN, NO$_2$, —(CR$^{c2}$R$^{d2}$)$_t$NR$^{a2}$R$^{b2}$, —(CR$^{c2}$R$^{d2}$)$_t$OR$^{b2}$, —(CR$^{c2}$R$^{d2}$)$_t$C(O)R$^{a2}$, —(CR$^{c2}$R$^{d2}$)$_t$C(=NR$^{c2}$)R$^{a2}$, —(CR$^{c2}$R$^{d2}$)$_t$C(=N—OR$^{b2}$)R$^{a2}$, —(CR$^{c2}$R$^{d2}$)$_t$C(O)OR$^{b2}$, —(CR$^{c2}$R$^{d2}$)$_t$OC(O)R$^{b2}$, —(CR$^{c2}$R$^{d2}$)$_t$C(O)NR$^{a2}$R$^{b2}$, —(CR$^{c2}$R$^{d2}$)$_t$NR$^{a2}$C(O)R$^{b2}$, —(CR$^{c2}$R$^{d2}$)$_t$C(=NR$^{e2}$)NR$^{a2}$R$^{b2}$, —(CR$^{c2}$R$^{d2}$)$_t$NR$^{a2}$C(=NR$^{e2}$)R$^{b2}$, —(CR$^{c2}$R$^{d2}$)$_t$OC(O)NR$^{a2}$R$^{b2}$, —(CR$^{c2}$R$^{d2}$)$_t$NR$^{a2}$C(O)NR$^{a2}$R$^{b2}$, —(CR$^{c2}$R$^{d2}$)$_t$NR$^{a2}$C(O)OR$^{b2}$, —(CR$^{c2}$R$^{d2}$)$_t$NR$^{a2}$C(S)NR$^{a2}$R$^{b2}$, (CR$^{c2}$R$^{d2}$)$_t$NR$^{a2}$C(=NR$^{e2}$)NR$^{a2}$R$^{b2}$, —(CR$^{c2}$R$^{d2}$)$_t$S(O)$_r$R$^{b2}$, —(CR$^{c2}$R$^{d2}$)$_t$S(O)(=NR$^{e2}$)R$^{b2}$, —(CR$^{c2}$R$^{d2}$)$_t$N=S(O)R$^{a2}$R$^{b2}$, —(CR$^{c2}$R$^{d2}$)$_t$S(O)$_2$OR$^{b2}$, —(CR$^{c2}$R$^{d2}$)$_t$OS(O)$_2$R$^{b2}$, —(CR$^{c2}$R$^{d2}$)$_t$NR$^{a2}$S(O)$_r$R$^{b2}$, —(CR$^{c2}$R$^{d2}$)$_t$NR$^{a2}$S(O)(—NR$^{e2}$)R$^{b2}$, —(CR$^{c2}$R$^{d2}$)$_t$S(O)$_r$NR$^{a2}$R$^{b2}$, —(CR$^{c2}$R$^{d2}$)$_t$S(O)(=NR$^{e2}$)NR$^{a2}$R$^{b2}$, —(CR$^{c2}$R$^{d2}$)$_t$NR$^{a2}$S(O)$_2$NR$^{a2}$R$^{b2}$, —(CR$^{c2}$R$^{d2}$)$_t$NR$^{a2}$S(O)(=NR$^{e2}$)NR$^{a2}$R$^{b2}$, —(CR$^{c2}$R$^{d2}$)$_t$P(O)R$^{a2}$R$^{b2}$ and —(CR$^{c2}$R$^{d2}$)$_t$P(O)(OR$^{a2}$)(OR$^{b2}$), wherein alkyl, alkenyl, alkynyl, cycloalkyl, heterocyclyl, aryl and heteroaryl are each unsubstituted or substituted with at least one substituent independently selected from OH, CN, amino, halogen, $C_{1-10}$ alkyl, $C_{2-10}$ alkenyl, $C_{2-10}$ alkynyl, $C_{3-10}$ cycloalkyl, $C_{1-10}$ alkoxy, $C_{3-10}$ cycloalkoxy, $C_{1-10}$ alkylthio, $C_{3-10}$ cycloalkylthio, $C_{1-10}$ alkylamino, $C_{3-10}$ cycloalkylamino and di($C_{1-10}$ alkyl)amino;

each $R^{a2}$ and each $R^{b2}$ are independently selected from hydrogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, $C_{1-10}$ alkoxy, $C_{3-10}$ cycloalkoxy, $C_{1-10}$ alkylthio, $C_{3-10}$ cycloalkylthio, $C_{1-10}$ alkylamino, $C_{3-10}$ cycloalkylamino, di($C_{1-10}$ alkyl)amino, heterocyclyl, heterocyclyl-$C_{1-4}$ alkyl, aryl, aryl-$C_{1-4}$ alkyl, heteroaryl and heteroaryl-$C_{1-4}$ alkyl, wherein alkyl, alkenyl, alkynyl, cycloalkyl, alkoxy, cycloalkoxy, alkylthio, cycloalkylthio, alkylamino, cycloalkylamino, heterocyclyl, aryl and heteroaryl are each unsubstituted or substituted with at least one substituent independently selected from halogen, CN, $C_{1-10}$ alkyl, $C_{2-10}$ alkenyl, $C_{2-10}$ alkynyl, $C_{3-10}$ cycloalkyl, OH, $C_{1-10}$ alkoxy, $C_{3-10}$ cycloalkoxy, $C_{1-10}$ alkylthio, $C_{3-10}$ cycloalkylthio, amino, $C_{1-10}$ alkylamino, $C_{3-10}$ cycloalkylamino and di($C_{1-10}$ alkyl)amino;

or $R^{a2}$ and $R^{b2}$ together with the atom(s) to which they are attached form a heterocyclic ring of 4 to 12 members containing 0, 1 or 2 additional heteroatoms independently selected from oxygen, sulfur, nitrogen and phosphorus, and optionally substituted with 1 or 2 substituents, independently selected from halogen, CN, $C_{1-10}$ alkyl, $C_{2-10}$ alkenyl, $C_{2-10}$ alkynyl, $C_{3-10}$ cycloalkyl, OH, $C_{1-10}$ alkoxy, $C_{3-10}$ cycloalkoxy, $C_{1-10}$ alkylthio, $C_{3-10}$ cycloalkylthio, amino, $C_{1-10}$ alkylamino, $C_{3-10}$ cycloalkylamino and di($C_{1-10}$ alkyl)amino;

each $R^{c2}$ and each $R^{d2}$ are independently selected from hydrogen, halogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, $C_{1-10}$ alkoxy, $C_{3-10}$ cycloalkoxy, $C_{1-10}$ alkylthio, $C_{3-10}$ cycloalkylthio, $C_{1-10}$ alkylamino, $C_{3-10}$ cycloalkylamino, di($C_{1-10}$ alkyl)amino, heterocyclyl, heterocyclyl-$C_{1-4}$ alkyl, aryl, aryl-$C_{1-4}$ alkyl, heteroaryl and heteroaryl-$C_{1-4}$ alkyl, wherein alkyl, alkenyl, alkynyl, cycloalkyl, alkoxy, cycloalkoxy, alkylthio, cycloalkylthio, alkylamino, cycloalkylamino, heterocyclyl, aryl and heteroaryl are each unsubstituted or substituted with at least one substituent independently selected from halogen, CN, $C_{1-10}$ alkyl, $C_{2-10}$ alkenyl, $C_{2-10}$ alkynyl, $C_{3-10}$ cycloalkyl, OH, $C_{1-10}$ alkoxy, $C_{3-10}$ cycloalkoxy, $C_{1-10}$ alkylthio, $C_{3-10}$ cycloalkylthio, amino, $C_{1-10}$ alkylamino, $C_{3-10}$ cycloalkylamino and di($C_{1-10}$ alkyl)amino;

or $R^{c2}$ and $R^{d2}$ together with the carbon atom(s) to which they are attached form a ring of 3 to 12 members containing 0, 1 or 2 heteroatoms independently selected from oxygen, sulfur and nitrogen, and optionally substituted with 1 or 2 substituents, independently selected from halogen, CN, $C_{1-10}$ alkyl, $C_{2-10}$ alkenyl, $C_{2-10}$ alkynyl, $C_{3-10}$ cycloalkyl, OH, $C_{1-10}$ alkoxy, $C_{3-10}$ cycloalkoxy, $C_{1-10}$ alkylthio, $C_{3-10}$ cycloalkylthio, amino, $C_{1-10}$ alkylamino, $C_{3-10}$ cycloalkylamino and di($C_{1-10}$ alkyl)amino;

each $R^{e2}$ is independently selected from hydrogen, CN, $NO_2$, $C_{1-10}$ alkyl, $C_{3-10}$ cycloalkyl, $C_{3-10}$ cycloalkyl-$C_{1-4}$ alkyl, $C_{1-10}$ alkoxy, $C_{3-10}$ cycloalkoxy, —C(O)$C_{1-4}$ alkyl, —C(O)$C_{3-10}$ cycloalkyl, —C(O)O$C_{1-4}$ alkyl, —C(O)O$C_{3-10}$ cycloalkyl, —C(O)N($C_{1-4}$ alkyl)$_2$, —C(O)N($C_{3-10}$ cycloalkyl)$_2$, —S(O)$_2C_{1-4}$ alkyl, —S(O)$_2C_{3-10}$ cycloalkyl, —S(O)$_2$N($C_{1-4}$ alkyl)$_2$ and —S(O)$_2$N($C_{3-10}$ cycloalkyl)$_2$;

q is selected from 0 and 1;
each r is independently selected from 0, 1 and 2;
each t is independently selected from 0 and 1; and
each u is independently selected from 0, 1 and 2.

2. The compound of claim 1, wherein $Q^2$ is

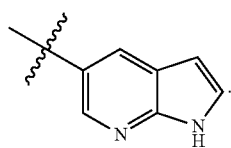 [SMILES: *c1cnc2[nH]ccc2c1]

3. The compound of claim 1, wherein $Q^2$ is

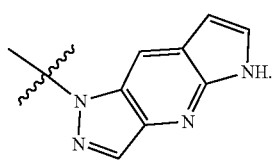 [SMILES: *n1ncc2nc3[nH]ccc3cc21]

4. The compound of claim 1, wherein $L^2$ is —O—.
5. The compound of claim 1, wherein $R^1$ is $NO_2$.
6. The compound of claim 1, wherein $R^1$ is $SO_2CF_3$.
7. The compound of claim 1, wherein $R^{4a}$ and $R^{4b}$ are each methyl.
8. The compound of claim 1, wherein $L^3$ is selected from a bond, —$CH_2$—, —($CH_2$)$_2$—, —$CH_2$O—, —($CH_2$)$_2$O—, —($CH_2$)$_2$OC(O)—, —C(O)—, —C(O)O—, —$CH_2$C(O)—, —$CH_2$C(O)O—, —$CH_2$OC(O)—, —C(O)NCH$_3$—, —$CH_2$NHC(O)—, —$CH_2$NHC(O)O—, —($CH_2$)$_2$NHC(O)—, ($CH_2$)$_2$NHC(O)O, —($CH_2$)$_2$SO$_2$—, and —$CH_2$NHSO$_2$—.
9. The compound of claim 1, wherein q is 0.
10. The compound of claim 1, wherein q is 1.
11. The compound of claim 1, wherein $R^{5a}$ is selected from phenyl, pyridinyl,

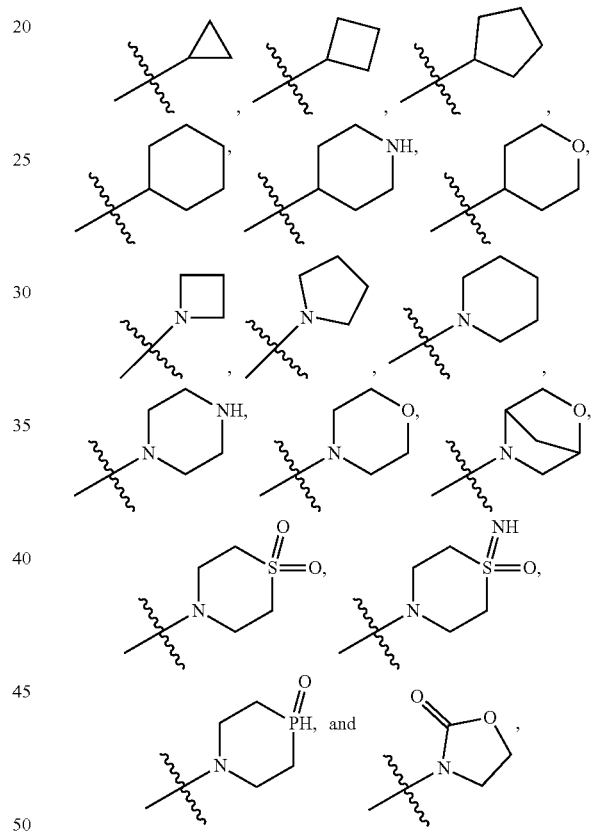

which are unsubstituted or substituted with at least one substituent independently selected from $R^X$.

12. The compound of claim 1, wherein $R^{5b}$ is selected from hydrogen, fluoro, methyl, ethyl, isopropyl, cyclopropyl, oxetanyl, CN, OH, —OCH$_2$, —N(CH$_3$)$_2$, —N=S(O)(CH$_3$), —NHC(O)OCH$_3$, —C(O) CH$_3$, —C(O)C$_2$H$_5$, —C(O)—C$_3$H$_7$, —C(O)OCH$_3$, —C(O)OC(CH$_3$)$_3$, —C(O)N(CH$_3$)$_2$, —SOCH$_3$, and —S(O)$_2$CH$_3$.

13. The compound of claim 1, wherein $R^{5b}$ is selected from —NR$^{A5}$R$^{B5}$ and —N=S(O)R$^{A5}$R$^{B5}$, wherein $R^{A5}$ and $R^{B5}$ together with the atom to which they are attached form a heterocyclic ring of 4 to 12 members containing 0, 1, or 2 additional heteroatoms independently selected from oxygen, sulfur, nitrogen and phosphorus and optionally substituted with 1, 2, or 3 $R^X$ groups.

14. A pharmaceutical composition, comprising a compound of claim 1, or a pharmaceutically acceptable salt thereof, and at least one pharmaceutically acceptable carrier.

15. A method for treating a cell-proliferative disorder, comprising administering to a subject in need thereof an effective amount of the compound of claim 1 or a pharmaceutically acceptable salt thereof.

16. The method of claim 15, wherein the cell-proliferative disorder is selected from lymphoma, osteosarcoma, melanoma, or a breast, renal, prostate, colorectal, thyroid, ovarian, pancreatic, neuronal, lung, uterine, or gastrointestinal tumor.

* * * * *

UNITED STATES PATENT AND TRADEMARK OFFICE
CERTIFICATE OF CORRECTION

| | | |
|---|---|---|
| PATENT NO. | : 12,312,349 B2 | Page 1 of 1 |
| APPLICATION NO. | : 17/376963 | |
| DATED | : May 27, 2025 | |
| INVENTOR(S) | : Hongbin Liu et al. | |

It is certified that error appears in the above-identified patent and that said Letters Patent is hereby corrected as shown below:

On the Title Page

Item (73) Second Assignee: "Shanghai Fosun Pharmaceutical Industrial Development Co,, Ltd."
should be replaced with --Shanghai Fosun Pharmaceutical Industrial Development Co., Ltd.--

Signed and Sealed this
Tenth Day of February, 2026

John A. Squires
*Director of the United States Patent and Trademark Office*